(12) United States Patent
Abe et al.

(10) Patent No.: US 7,317,009 B2
(45) Date of Patent: *Jan. 8, 2008

(54) PYRROLOPYRIDAZINE DERIVATIVES

(75) Inventors: Yoshito Abe, Osaka (JP); Makoto Inoue, Osaka (JP); Tsuyoshi Mizutani, Osaka (JP); Kozo Sawada, Osaka (JP); Kazuhiko Ohne, Osaka (JP); Mitsuaki Okumura, Osaka (JP); Yuki Sawada, Osaka (JP); Kenichiro Imamura, Osaka (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/500,293

(22) Filed: Aug. 8, 2006

(65) Prior Publication Data

US 2006/0270678 A1   Nov. 30, 2006

Related U.S. Application Data

(63) Continuation of application No. 10/747,079, filed on Dec. 30, 2003, now Pat. No. 7,153,854.

(30) Foreign Application Priority Data

Jan. 9, 2003   (AU) ............................... 2003900189
Jul. 14, 2003  (AU) ............................... 2003903628

(51) Int. Cl.
C07D 487/04   (2006.01)
A61K 31/5025  (2006.01)

(52) U.S. Cl. ................... 514/234.5; 544/116; 544/235; 514/248

(58) Field of Classification Search ............. 544/116, 544/235; 514/248, 234.5
See application file for complete search history.

(56) References Cited

U.S. PATENT DOCUMENTS 6,472,389 B1   10/2002   Ohtani et al.

FOREIGN PATENT DOCUMENTS

| FR | 2 792 938 | 11/2000 |
| WO | WO 91/18903 | 12/1991 |
| WO | WO 9118903 A1 * | 12/1991 |
| WO | 03/082208 | 10/2003 |

OTHER PUBLICATIONS

Cecil Textbook of Medicine (20th Edition, vol. 2), 1996, pp. 1739-1747.*

Aoki et al. The Journal of Pharmacology and Experimental Therapeutics, vol. 298, No. 3, pp. 1142-1149.*
Duan et al. (abstract of Chin J. Hepatol., Aug. 2003, vol. 11, No. 8, 493-496).*
Ichiyama et al, Scand. J. Infect. Dis., 35:59-61 (2003).*
Kawada et al, J. Infect. Dis. 2003, 188(5): 690-698).*
Landellls et al. British Journal of Pharmacology (2001) 133, 722-729.*
W. Flitsch, et al., Tetrahedron Letters, vol. 12, XP-002273465, pp. 1479-1484, "Synthesen und Reaktionen von 5-Aza-Indolizinen und 5-Aza-Cycl(3.2.2)Azin-Derivaten", 1968.
Cecil Textbook of Medicine (20th Edition, vol. 2), 1996, pp. 1739-1747.
Flitsch et al. Tetrahedron Letters (1968), (12), 1479-84.
Takashi Ichiyama, et al., "Cerebrospinal Fluid and Serum Levels of Cytokines and Soluble Tumor Necrosis Factor Receptor Influenza Virus-associated Enciphalopathy", Scand J Infect Dis, Taylor & Francis Healthsciences, vol. 35, pp. 59-61.
Jun-Ichi Kawada, et al., "Systemic Cytokine Responses in Patients with Influenza-Associated Enciphalopathy", Major Article, Sep. 1, 2003, pp. 690-698.
Duan Zhong-Ping, et al., "Clinical Characteristics and Mechanism of Liver Injury in Patients with Severe Acute Respiratory Syndrome", Chin J. Hepatol, vol. 11, No. 8, Aug. 2003, pp. 493-496.
Landellls et al., British Journal of Pharmacology (2001) 133, 722-729.
STN Search Printout (p. 66-70), from wo 91/18903, 1991.
Mark Glembycz, Current Opinion in Pharmacology, 2005, 5:238-244.

* cited by examiner

*Primary Examiner*—Kahsay Habte
(74) *Attorney, Agent, or Firm*—Oblon, Spivak, McClelland, Maier & Neustadt, P.C.

(57) ABSTRACT

The invention relates to compound of the formula (I) or its salt, in which $R^1$, $R^2$, $R^3$ and $R^4$ are as defined in the description, their use of as medicament, the process for their preparation and use for the treatment of PDE-IV or TNF-α mediated diseases (I)

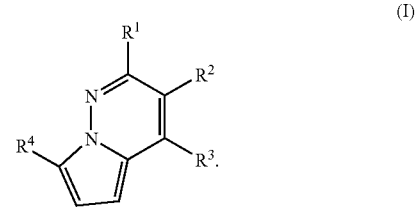

5 Claims, No Drawings

PYRROLOPYRIDAZINE DERIVATIVES

TECHNICAL FIELD

This invention relates to new pyrrolopyridazine derivatives and pharmaceutically acceptable salts thereof which inhibit enzymatic activity of phosphodiesterase IV (PDE IV) and production of tumor necrosis factor-α (TNF-α).

BACKGROUND ART

Cyclic adenosine monophosphate (adenosine 3',5'-cyclic monophosphate, "cAMP" or "cyclic AMP") is known as an intracellular second messenger, which is intermediated by a first messenger (hormone, neurotransmitter or autacoid) and the cellar responses. The first messenger stimulates the enzyme responsible for synthesis of cAMP, and then the cAMP intervenes in many functions such as metabolic, contractile or secretory. The effect of cAMP end when it is degraded by cyclic nucleotide phosphodiesterases, in particular phosphosiesterase-4 (PDE4 or PDE-IV), which is specific for cAMP. PDE-IV have been identified in many tissues including the central nervous systems, the heart, vascular smooth muscle, airway smooth muscle, myeloid lines, lymphoid, and the like. Evaluation of cAMP level by using the PDE-IV inhibitor would produce beneficial effect on inappropriate activation of airway smooth muscle and a wide variety of inflammatory cells.

A major concern with the use of PDE-IV inhibitors is the side effect of emesis which has been observed for several candidate compounds as described in C. Burnouf et al., (Ann. Rep. In Med. Chem., 33:91-109(1998)). Burnouf describe the wide variation of the severity of the undesirable side effects exhibited by various compounds.

Some condensed heterocyclic derivatives having the inhibitory activity of PDE-IV have been known, for example in WO03/016279, WO03/018579, WO0.3/000679 and the like. However, there remains a need for novel compounds that inhibit PDE-TV with minimal side effects. Although some pyrrolopyridazine derivatives having the inhibitory activity of hydroxymethylglutaryl (HMG) CoA reductase have been known, for example, in WO91/18903, pyrrolopyridazine derivatives having the inhibitory activity of PDE-IV have not been known.

DISCLOSURE OF INVENTION

This invention relates to new pyrrolopyridazine derivatives.

The compounds of this invention inhibit cAMP phosphodiesterase enzymes, in particular phosphodiesterase-4 enzyme, and also inhibit the production of tumor necrosis factor-α (TNF-α), a serum glycoprotein.

Accordingly, one object of this invention is to provide the new and useful pyrrolopyridazine derivatives and pharmaceutically acceptable salts thereof which possess a strong phosphodiesterase-4 (PDE IV)-inhibitory activity and a strong inhibitory activity on the production of tumor necrosis factor (TNF).

Another object of this invention is to provide processes for preparation of the pyrrolopyridazine derivatives and salts thereof.

A further object of this invention is to provide a pharmaceutical composition comprising said pyrrolopyridazine derivatives or a pharmaceutically acceptable salt thereof.

Still further object of this invention is to provide a use of said pyrrolopyridazine derivatives or a pharmaceutically acceptable salt thereof as a medicament for prophylactic and therapeutic treatment of PDE-IV and TNF mediated diseases such as chronic inflammatory diseases, specific autoimmune diseases, sepsis-induced organ injury, and the like in human being and animals.

The object pyrrolopyridazine derivatives of the present invention are novel and can be represented by the following general formula (I):

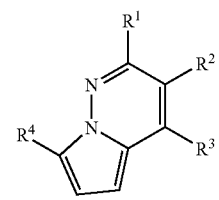

(I)

in which
$R^1$ is (1) carboxy or protected carboxy,
  (2) —$CONR^5R^6$,
  (3) hydroxy or lower alkoxy,
  (4) amino, cyclo(lower)alkylamino or mono- or di(lower)alkylamino optionally substituted by lower alkoxy,
  (5) trihalo(lower)alkyl,
  (6) trihalo(lower)alkylsulfonyloxy or arylsulfonylamino,
  (7) substituted or unsubstituted lower alkyl,
  (8) substituted or unsubstituted aryl, or
  (9) substituted or unsubstituted heterocyclic group,
$R^2$ is $R^7$ or -($A^1$)p-X-$A^2$-$R^7$,
  wherein
  p is integer of 0 or 1;
  $A^1$ is ($C_1$-$C_2$)alkylene or —CH=CH—;
  $A^2$ is —($C_1$-$C_2$)n- or —(CH=CH)m- [wherein n is integer which may range from 1 to 6 and m is integer which may range from 1 to 3];
  X is single bond, —O—, —$NR^8$—, —C(=O)—, —C(=$NR^9$)— or hydroxy($C_1$-$C_2$)alkylene [wherein $R^8$ is hydrogen or lower alkyl, and $R^9$ is substituted or unsubstituted N-containing heterocyclic group]; and
  $R^7$ is
  (1) hydrogen,
  (2) substituted or unsubstituted aryl,
  (3) substituted or unsubstituted heterocyclic group,
  (4) carboxy, protected carboxy or $CONR^{10}R^{11}$,
  (5) acyl or halocarbonyl,
  (6) cyano,
  (7) amino, protected amino, or mono- or di(lower)alkylamino,
  (8) hydroxy, aryloxy, acyloxy or lower alkoxy optionally substituted by hydroxy or acyloxy,
  (9) lower alkylthio, lower alkylsulfinyl or lower alkylsulfonyl, or
  (10) —O—$R^{12}$,
  or
$R^1$ and $R^2$ are combined together to form lower alkylene or lower alkenylen group, which is optionally interrupted by amino or sulfonyl and optionally fuse with benzene ring, and also is optionally substituted by the group consisting of lower alkyl, hydroxy, oxo and lower alkoxy,
$R^3$ is substituted or unsubstituted aryl, or substituted or unsubstituted heterocyclic group,
$R^4$ is hydrogen, halogen, cyano, carbamoyl, acyl, thiocyanate, lower alkylthio, lower alkenyl, hydroxyl(lower)alkyl, trihalo(lower)alkyl or lower alkyl, $R^5$, $R^6$, $R^{10}$ and $R^{11}$ each independently represents hydrogen, lower alkylsulfonyl, heterocyclic group or lower alkyl optionally substituted by hydroxy, alkoxy, sulfo, carboxy, protected carboxy or —$R^{17}$, or alternatively $R^5$ and $R^6$ or $R^{10}$ and $R^{11}$, together with the nitrogen atom to which they are attached, represent N-containing heterocyclic group, and $R^{12}$ and $R^{17}$ are each independently a group derived from protected or unprotected sugar by removal of the hydroxy group therefrom, or a pharmaceutically acceptable salt thereof, or prodrug thereof.

Suitable pharmaceutically acceptable salts of the object compound (I) are conventional non-toxic salts and may include a salt with a base or an acid addition salt such as a salt with an inorganic base, for example, an alkali metal salt (e.g., sodium salt, potassium salt, etc.), an alkaline earth metal salt (e.g., calcium salt, magnesium salt, etc.), an ammonium salt; a salt with an organic base, for example, an organic amine salt (e.g., triethylamine salt, pyridine salt, picoline salt, ethanolamine salt, triethanolamine salt, dicyclohexylamine salt, N,N'-dibenzylethylenediamine salt, etc.); an inorganic acid addition salt (e.g., hydrochloride, hydrobromide, sulfate, phosphate, etc.); an organic carboxylic or sulfonic acid addition salt (e.g., formate, acetate, trifluoroacetate, maleate, tartrate, fumarate, methanesulfonate, benzenesulfonate, toluenesulfonate, etc.); a salt with a basic or acidic amino acid (e.g., arginine, aspartic acid, glutamic acid, etc.).

The "prodrug" means the derivatives of the object compound (I) having a chemically or metabolically degradable group, which became pharmaceutically active after chemo- or biotransformation.

Preferred embodiments of the object compound (I) are as follows.

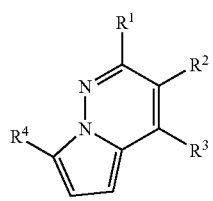

(I)

in which $R^1$ is (1) carboxy or esterified carboxy (more preferably, ethoxycarbonyl), (2) —$CONR^5R^6$ [wherein $R^5$ and $R^6$ each independently represents lower alkyl, or alternatively $R^5$ and $R^6$, together with nitrogen atom to which they are attached represents saturated 5- or 6-membered heteromonocyclic group containing 1 to 2 nitrogen atom(s).] (more preferably, dimethylcarbamoyl or 1-pyrrolidinylcarbonyl), (3) hydroxy or lower alkoxy, (4) amino, cyclo(lower)alkylamino, or mono- or di(lower)alkylamino optionally substituted by lower alkoxy, (5) trihalo(lower)alkyl, (6) trihalo(lower)alkylsulfonyloxy or arylsulfonylamino, (7) lower alkyl optionally substituted by (i) halogen; (ii) carboxy; (iii) protected carboxy; (iv) cyano; (v) carbamoyl; (vi) —$OCONR^{15}R^{16}$ [wherein $R^{15}$ and $R^{16}$ each independently represents hydrogen, aryl or lower alkyl optionally substituted by aryl, or $R^{15}$ and $R^{16}$, together with the nitrogen atom to which they are attached, represents saturated 5- or 6-membered heteromonocyclic group containing 1 to 2 nitrogen atom(s) and also optionally containing oxygen atom.] (more preferably, dimethylcarbamoyloxy, methyl-phenylcarbamoyloxy, morpholinylcarbonyloxy or pyrrolidinylcarbonyloxy); (vii) lower alkylthio; (viii) lower alkylsulfonyl; (ix) lower alkylsulfonyloxy; (x) lower alkylsulfonylamino; (xi) mono- or di(lower)alkylamino optionally substituted by hydroxy, lower alkoxy, aryloxy, or substituted or unsubstituted aryl; (xii) amino; (xiii) acylamino (more preferably, lower alkanoylamino such as acetylamino, aroylamino such as benzoylamino, or heterocycliccarbonylamino such as pyrazinylcarbonylamino); (xiv) protected amino such as phthalimide, benzylamino or lower alkoxycarbonylamino; (xv) hydroxy; (xvi) acyloxy (more preferably, lower alkanoyloxy such as acetyloxy); (xvii) cyclo(lower)alkyloxy; (xviii) aryloxy; (xix) substituted or unsubstituted aryl (more preferably, phenyl); (xx) saturated or unsaturated 5- or 6-membered heteromonocyclic group containing 1 to 3 nitrogen atom(s) and also optionally containing oxygen atom or sulfur atom (more preferably, piperazinyl, morpholinyl, oxazolidinyl, thiomorpholinyl, piperidinyl, pyrrolidinyl or triazolyl) optionally substituted by lower alkyl, hydroxy (lower)alkyl, aryl or oxo; or (xxi) lower alkoxy optionally substituted by carboxy, protected carboxy, hydroxy, protected hydroxy, lower alkoxy, cyclo(lower)alkyl, substituted or unsubstituted aryl (more preferably, phenyl optionally substituted by cyano, carboxy, protected carboxy or carbamoyl), saturated or unsaturated 5- or 6-membered heteromonocyclic group containing 1 to 2 nitrogen atom(s) (more preferably, pyridinyl, pyrazinyl or piperazinyl) optionally substituted by lower alkyl, or —$CONR^{13}R^{14}$ [wherein $R^{13}$ and $R^{14}$ each independently represents hydrogen or lower alkyl optionally substituted by aryl, or $R^{13}$ and $R^{14}$, together with the nitrogen atom to which they are attached, represents saturated 5- or 6-membered heteromonocyclic group containing 1 to 2 nitrogen atom(s) and also optionally containing oxygen atom.] (more preferably, carbamoyl, methylcarbamoyl, benzylcarbamoyl or morpholinylcarbonyl), (8) aryl (more preferably, phenyl) optionally substituted by the substituent(s) selected from the group consisting of halogen, or (9) saturated or unsaturated 5- or 6-membered heteromonocyclic group (more preferably, pyrrolidinyl, pyrrolyl, oxazolyl, isooxazolyl, thiazolyl, furanyl, thienyl, pyridinyl) optionally substituted by lower alkyl or halogen, $R^2$ is $R^7$ or -($A^1$)p-X-$A^2$-$R^7$ wherein p is 0 or 1, $A^1$ is ($C_1$-$C_2$)alkylene or —CH=CH—;

$A^2$ is —($CH_2$)n- or —CH=CH)m- [wherein n is integer which may range from 1 to 6 and m is integer which may range from 1 to 3];

X is single bond, —O—, —$NR^8$—, —C(=O)—, —C(=$NR^9$)— or hydroxy($C_1$-$C_2$)alkylene;

[wherein $R^8$ is hydrogen or lower alkyl, and $R^9$ is substituted or unsubstituted pyrrolyl such as 2-ethyl-5-(4-fluorobenzoyl)pyrrolyl]

$R^7$ is (1) hydrogen, (2) aryl (more preferably, phenyl) optionally substituted by lower alkoxy, (3) unsaturated heteromonocyclic group containing 1 to 2 nitrogen atom(s), (more preferably, pyridinyl), (4) carboxy, esterified carboxy (more preferably, lower alkoxycarbonyl) or $-CONR^{10}R^{11}$ [wherein $R^{10}$ and $R^{11}$ each independently represents hydrogen, lower alkylsulfonyl, unsaturated heteromonocyclic group containing 1 to 2 nitrogen atom(s) such as pyridinyl or lower alkyl optionally substituted by hydroxy, alkoxy, carboxy, protected carboxy, sulfo or $-R^{17}$, or alternatively $R^{10}$ and $R^{11}$, together with the nitrogen atom to which they are attached, represents saturated 5- or 6-membered heteromonocyclic group containing 1 to 2 nitrogen atom(s) and also optionally containing oxygen atom such as morpholinyl.], (5) acyl (e.g. lower alkanoyl such as formyl or acetyl, and heterocycliccarbonyl such as pyridinylcarbonyl) or halocarbonyl, (6) cyano, (7) amino, protected amino such as lower alkoxycarbonylamino, or mono- or di(lower)alkylamino, (8) hydroxy, aryloxy, acyloxy or lower alkoxy optionally substituted by hydroxy or acyloxy (e.g. lower alkanoyloxy), (9) lower alkylthio, lower alkylsulfinyl or lower alkylsulfonyl, or

(10) $-O-R^{12}$, or $R^1$ and $R^2$ are combined together to form lower alkylene or lower alkenylen group which is optionally interrupted by amino or sulfonyl and also is optionally substituted by the group consisting of lower alkyl, hydroxy, oxo and lower alkoxy, which is represented by the following formula:

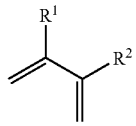

that may include the following ones;

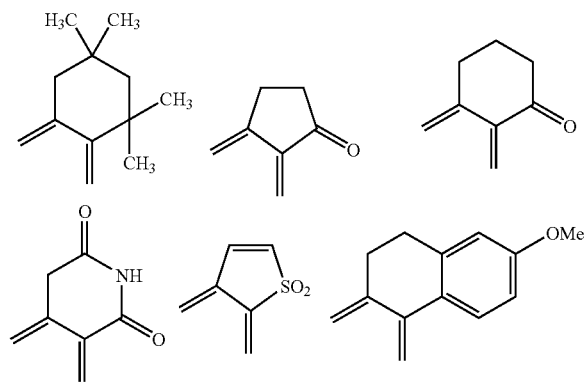

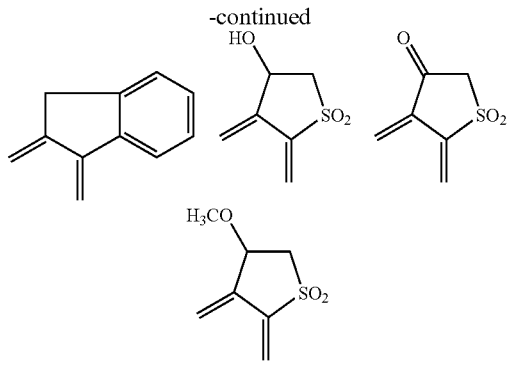

$R^3$ is (1) aryl (more preferably, phenyl or naphthyl) optionally substituted by at least one substituent(s) selected from the group consisting of (i) halogen, (ii) carboxy, (iii) protected carboxy, (iv) cyano, (v) $-CONR^{15}R^{16}$ [wherein $R^{15}$ and $R^{16}$ each independently represents hydrogen, lower alkyl optionally substituted by hydroxy], (vi) lower alkyl, (vii) cyclo(lower)alkyl, (viii) hydroxy (lower)alkyl, (ix) lower alkoxy, (x) trihalo(lower)alkyl, (xi) unsaturated 5- or 6-membered heteromonocyclic group containing 1 to 2 oxygen atom(s) and 1 to 2 nitrogen atom(s) such as oxazolyl, (xii) lower alkylsulfonyl, (xiii) nitro, (xiv) sulfamoyl, and (xv) protected sulfamoyl; or (2) heterocyclic group selected from the group consisting of pyridinyl, pyrazinyl, oxazolyl, isooxazolyl, furanyl, thienyl, quinolyl, benzofuranyl and benzothienyl, wherein said heterocyclic group is optionally substituted by at least one substituent(s) selected from the group consisting of (i) lower alkyl, (ii) cyclo(lower) alkyl, (iii) lower alkoxy, (iv) acyl such as lower alkanoyl, (v) amino, (vi) mono- or di(lower)alkylamino, (vii) protected amino such as lower alkoxycarbonylamino, (viii) cyano, (ix) carboxy, (x) protected carboxy such as ethoxycarbonyl or methoxycarbonyl, (xi) $-CONR^{15}R^{16}$ [wherein $R^{15}$ and $R^{16}$ each independently represents hydrogen, lower alkyl optionally substituted by hydroxy], (xii) lower alkenyl optionally substituted by lower alkoxy, (xiii) halogen, (xiv) lower alkylthio and (xv) hydroxy;

$R^4$ is hydrogen, halogen, cyano, carbamoyl, lower alkanoyl, thiocyanate, lower alkylthio, lower alkenyl, hydroxyl (lower)alkyl, trihalo(lower)alkyl or lower alkyl, and $R^{12}$ and $R^{17}$ are each independently a group derived from protected or unprotected sugar such as galactose by removal of the hydroxy group therefrom, or a pharmaceutically acceptable salt thereof.

More preferred compounds of formula (I) are those in which:

$R^1$ is (1) mono- or di(lower)alkylamino, (2) aryl such as phenyl, (3) saturated or unsaturated 5 to 6 membered heteromonocyclic group containing 1 to 2 hetero atom(s) selected from nitrogen, oxygen or sulfur atom(s) (more preferably, pyrrolidinyl, pyrrolyl, oxazolyl, isooxazolyl, thiazolyl, furanyl, thienyl, pyridinyl, etc), or (4) lower alkyl optionally substituted by lower alkoxy or saturated 5- or 6-membered heteromonocyclic group containing 1 to 2 nitrogen atom(s) and also optionally containing oxygen atom (more preferably, piperazinyl or morpholinyl), wherein lower alkoxy is optionally substituted by cyclo(lower)alkyl or unsaturated 5 to 6 membered heteromonocyclic group containing 1 to 2 nitrogen atom(s) (more preferably, pyridinyl), R² is R⁷ or -A²-R⁷, wherein
A² is —(CH₂)n- or —(CH═CH)m- [wherein n is integer which may range 2 to 6 and
m is integer of 1 or 2, and
R⁷ is hydrogen, lower alkylsulfonyl, carboxy, protected carboxy or unsaturated 5 to 6 membered heteromonocyclic group containing 1 to 2 nitrogen atom(s) (more preferably, pyridinyl), R³ is (1) aryl optionally substituted by lower alkyl, cyclo (lower)alkyl, halogen, cyano or carbamoyl; or
(2) unsaturated condensed heterocyclic group containing 1 to 2 nitrogen atom(s) (more preferably, quinolinyl); or unsaturated 5 to 6 membered heteromonocyclic group containing at least one nitrogen atom(s) (more preferably, 3-pyridinyl and 4-pyridinyl) substituted by lower alkyl, cyclo(lower)alkyl or halogen, and R⁴ is lower alkyl.

Most preferred compounds of formula (I) are those in which:

R¹ is phenyl, saturated or unsaturated 5 to 6 membered heteromonocyclic group containing 1 to 2 hetero atom(s) selected from nitrogen, oxygen or sulfur atom(s) (more preferably, pyrrolyl, isooxazolyl, furanyl, thienyl, etc.) or lower alkyl optionally substituted by lower alkoxy or saturated or saturated 5- or 6-membered heteromonocyclic group containing 1 to 2 nitrogen atom(s) and also optionally containing oxygen atom (more preferably, piperazinyl or morpholinyl), wherein lower alkoxy is optionally substituted by cyclo(lower)alkyl or unsaturated 5 to 6 membered heteromonocyclic group containing at least one nitrogen atom(s) (more preferably, pyridinyl), R² is —(CH₂)n-R⁷, wherein n is integer which may range 2 to 5, and R⁷ is carboxy or protected carboxy, R³ is (1) phenyl optionally substituted by lower alkyl, cyclo(lower)alkyl, lower alkoxy, halogen, cyano or carbamoyl; or (2) unsaturated 5 to 6 membered heteromonocyclic group containing at least one nitrogen atom(s) (more preferably, 3-pyridinyl and 4-pyridinyl) substituted by lower alkyl, cyclo(lower)alkyl, lower alkoxy, carbamoyl or halogen, and R⁴ is lower alkyl.

Preferred concrete compound of formula (I) is:
(1) 3-[7-Ethyl-2-methyl-3-(4-pyridinyl)-pyrrolo[1,2-b]pyridazin-4-yl]benzonitrile,
(2) 3-[7-Ethyl-2-(2-furyl)pyrrolo[1,2-b]pyridazin-4-yl]benzonitrile,
(3) 4-[7-Ethyl-2-methyl-3-(methylsulfonyl)-pyrrolo[1,2-b]pyridazin-4-yl]benzonitrile,
(4) 3-[7-Ethyl-2-(2-furyl)pyrrolo[1,2-b]pyridazin-4-yl]benzamide,
(5) Ethyl 5-[4-(3-cyanophenyl)-7-ethyl-2-methylpyrrolo[1,2-b]pyridazin-3-yl]pentanoate,
(6) 2-{[4-(3-Chlorophenyl)-7-ethyl-2-methylpyrrolo[1,2-b]pyridazin-3-yl]methyl}-1,3-propanediol,
(7) 3-[4-(3-Chlorophenyl)-7-ethyl-2-phenyl-pyrrolo[1,2-b]pyridazin-3-yl]propanoic acid,
(8) 5-[7-Ethyl-2-methyl-4-(6-quinolinyl)pyrrolo[1,2-b]pyridazin-3-yl]pentanoic acid,
(9) 5-[4-(2-Chloro-4-pyridinyl)-7-ethyl-2-methylpyrrolo[1,2-b]pyridazin-3-yl]pentanoic acid,
(10) 5-[7-Ethyl-2-(methoxymethyl)-4-(5-methyl-3-pyridinyl)pyrrolo[1,2-b]pyridazin-3-yl]pentanoic acid,
(11) 5-[4-(5-Bromo-3-pyridinyl)-7-ethyl-2-(methoxymethyl)pyrrolo[1,2-b]pyridazin-3-yl]pentanoic acid,
(12) 3-[7-Ethyl-2-(methoxymethyl)-4-(5-methyl-3-pyridinyl)pyrrolo[1,2-b]pyridazin-3-yl]propanoic acid,
(13) 5-[4-(5-Bromo-3-pyridinyl)-7-ethyl-2-(4-morpholinylmethyl)pyrrolo[1,2-b]pyridazin-3-yl]pentanoic acid,
(14) Ethyl (2E)-3-[7-chloro-4-(4-fluorophenyl)-2-isopropylpyrrolo[1,2-b]pyridazin-3-yl]-2-propenoate,
(15) 6-{4-[4-(aminocarbonyl)phenyl]-7-ethyl-2-methylpyrrolo[1,2-b]pyridazin-3-yl}hexanoic acid
(16) 3-[4-(5-bromo-3-pyridinyl)-7-ethyl-2-(methoxymethyl)pyrrolo[1,2-b]pyridazin-3-yl]propanoic acid,
(17) 4-[4-(5-bromo-3-pyridinyl)-7-ethyl-2-(methoxymethyl)pyrrolo[1,2-b]pyridazin-3-yl]butanoic acid,
(18) 5-[2-[(cyclohexylmethoxy)methyl]-7-ethyl-4-(5-methyl-3-pyridinyl)pyrrolo[1,2-b]pyridazin-3-yl]pentanoic acid,
(19) 5-{7-ethyl-4-(5-methyl-3-pyridinyl)-2-[(4-pyridinylmethoxy)methyl]pyrrolo[1,2-b]pyridazin-3-yl}pentanoic acid.
(20) 4-{4-(5-chloro-3-pyridinyl)-7-ethyl-2-[(4-pyridinylmethoxy)methyl]pyrrolo[1,2-b]pyridazin-3-yl}butanoic acid,
(21) 4-[4-(5-chloro-3-pyridinyl)-7-ethyl-2-(4-morpholinylmethyl)pyrrolo[1,2-b]pyridazin-3-yl]butanoic acid,
(22) 4-[4-(5-chloro-3-pyridinyl)-7-ethyl-2-(methoxymethyl)pyrrolo[1,2-b]pyridazin-3-yl]butanoic acid,
(23) 5-[4-(5-chloro-3-pyridinyl)-7-ethyl-2-(methoxymethyl)pyrrolo[1,2-b]pyridazin-3-yl]pentanoic acid, or
(24) 5-{4-(3-cyanophenyl)-7-ethyl-2-[(4-pyridinylmethoxy)methyl]pyrrolo[1,2-b]pyridazin-3-yl}pentanoic acid, or a pharmaceutically acceptable salt thereof.

More preferred concrete compound of formula (I) is:
(1) Ethyl 5-[4-(3-cyanophenyl)-7-ethyl-2-methylpyrrolo[1,2-b]pyridazin-3-yl]pentanoate,
(2) 3-[4-(3-Chlorophenyl)-7-ethyl-2-phenyl-pyrrolo[1,2-b]pyridazin-3-yl]propanoic acid,
(3) 5-[4-(2-Chloro-4-pyridinyl)-7-ethyl-2-methylpyrrolo[1,2-b]pyridazin-3-yl]pentanoic acid,
(4) 5-[7-Ethyl-2-(methoxymethyl)-4-(5-methyl-3-pyridinyl)pyrrolo[1,2-b]pyridazin-3-yl]pentanoic acid,
(5) 5-[4-(5-Bromo-3-pyridinyl)-7-ethyl-2-(methoxymethyl)pyrrolo[1,2-b]pyridazin-3-yl]pentanoic acid,
(6) 3-[7-Ethyl-2-(methoxymethyl)-4-(5-methyl-3-pyridinyl)pyrrolo[1,2-b]pyridazin-3-yl]propanoic acid,
(7) 5-[4-(5-Bromo-3-pyridinyl)-7-ethyl-2-(4-morpholinylmethyl)pyrrolo[1,2-b]pyridazin-3-yl]pentanoic acid,
(8) 6-{4-[4-(aminocarbonyl)phenyl]-7-ethyl-2-methylpyrrolo[1,2-b]pyridazin-3-yl}hexanoic acid
(9) 3-[4-(5-bromo-3-pyridinyl)-7-ethyl-2-(methoxymethyl)pyrrolo[1,2-b]pyridazin-3-yl]propanoic acid,
(10) 4-[4-(5-bromo-3-pyridinyl)-7-ethyl-2-(methoxymethyl)pyrrolo[1,2-b]pyridazin-3-yl]butanoic acid,
(11) 5-[2-[(cyclohexylmethoxy)methyl]-7-ethyl-4-(5-methyl-3-pyridinyl)pyrrolo[1,2-b]pyridazin-3-yl]pentanoic acid, and
(12) 5-{7-ethyl-4-(5-methyl-3-pyridinyl)-2-[(4-pyridinylmethoxy)methyl]pyrrolo[1,2-b]pyridazin-3-yl}pentanoic acid,
(13) 4-[4-(5-chloro-3-pyridinyl)-7-ethyl-2-(methoxymethyl)pyrrolo[1,2-b]pyridazin-3-yl]butanoic acid, or
(14) 5-[4-(5-chloro-3-pyridinyl)-7-ethyl-2-(methoxymethyl)pyrrolo[1,2-b]pyridazin-3-yl]pentanoic acid, or a pharmaceutically acceptable salt thereof.

The object compound (I) of the present invention can be prepared by the following processes.

Process 1

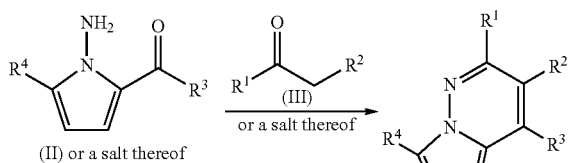

(II) or a salt thereof → (I-I) or a salt thereof

Process 2

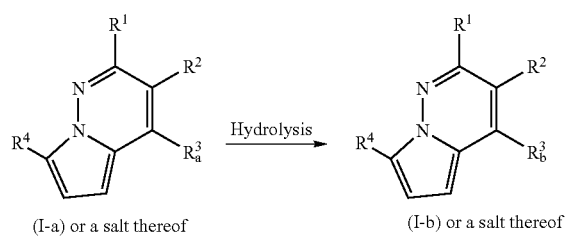

(I-a) or a salt thereof → Hydrolysis → (I-b) or a salt thereof

Process 3

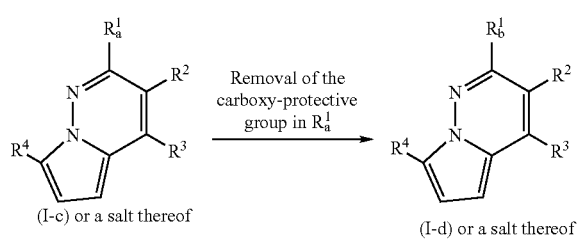

(I-c) or a salt thereof → Removal of the carboxy-protective group in $R_a^1$ → (I-d) or a salt thereof Process 4

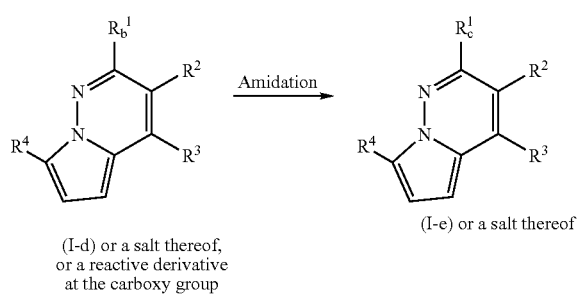

(I-d) or a salt thereof, or a reactive derivative at the carboxy group → Amidation → (I-e) or a salt thereof Process 5

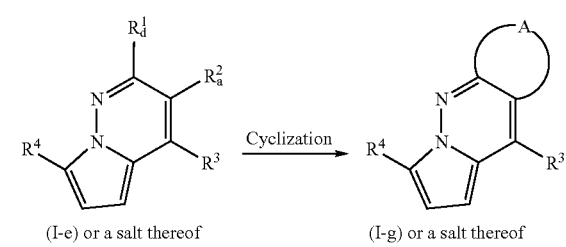

(I-e) or a salt thereof → Cyclization → (I-g) or a salt thereof

Process 6

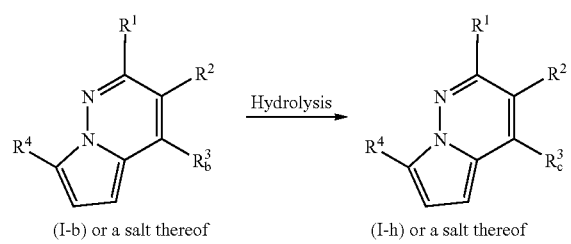

(I-b) or a salt thereof → Hydrolysis → (I-h) or a salt thereof

Process 7

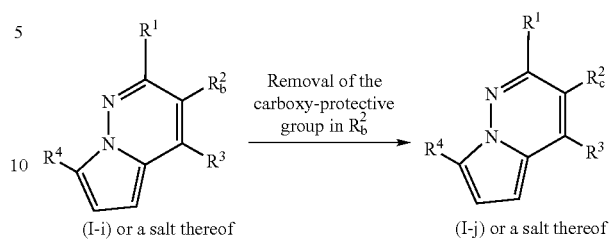

(I-i) or a salt thereof → Removal of the carboxy-protective group in $R_b^2$ → (I-j) or a salt thereof Process 8

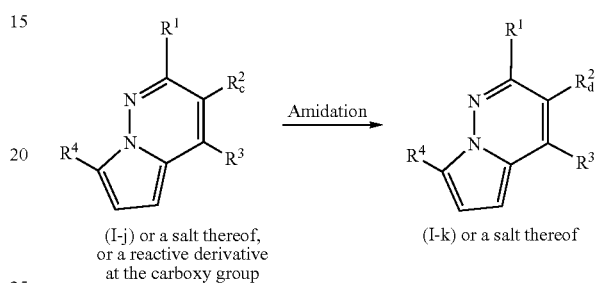

(I-j) or a salt thereof, or a reactive derivative at the carboxy group → Amidation → (I-k) or a salt thereof Process 9

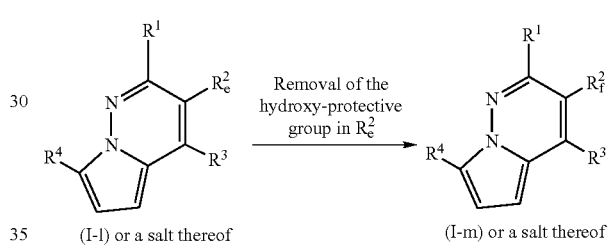

(I-l) or a salt thereof → Removal of the hydroxy-protective group in $R_e^2$ → (I-m) or a salt thereof Process 10

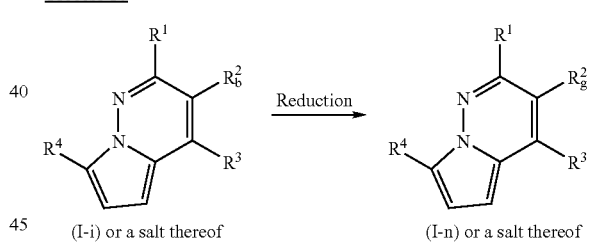

(I-i) or a salt thereof → Reduction → (I-n) or a salt thereof

Process 11

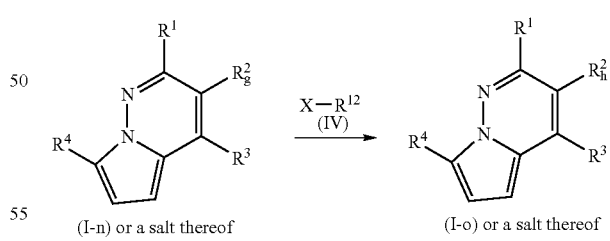

(I-n) or a salt thereof → X—R$^{12}$ (IV) → (I-o) or a salt thereof

Process 12

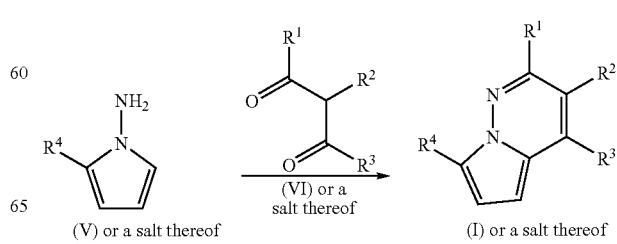

(V) or a salt thereof + (VI) or a salt thereof → (I) or a salt thereof

Process 13

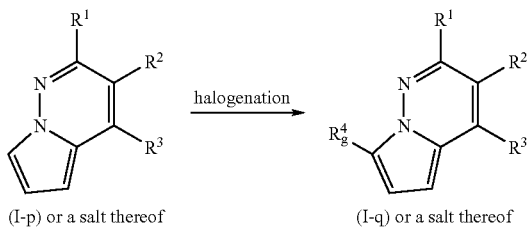

(I-p) or a salt thereof → halogenation → (I-q) or a salt thereof

Process 14

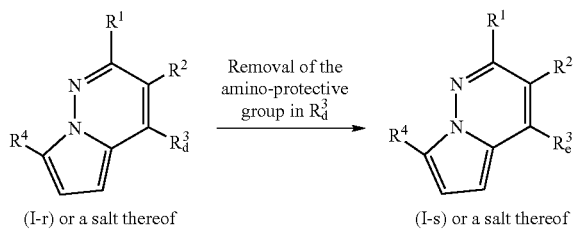

(I-r) or a salt thereof → Removal of the amino-protective group in $R_d^3$ → (I-s) or a salt thereof Process 15

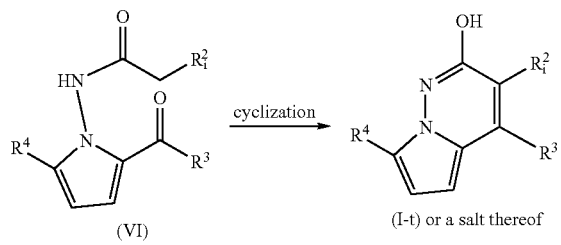

(VI) → cyclization → (I-t) or a salt thereof

Process 16

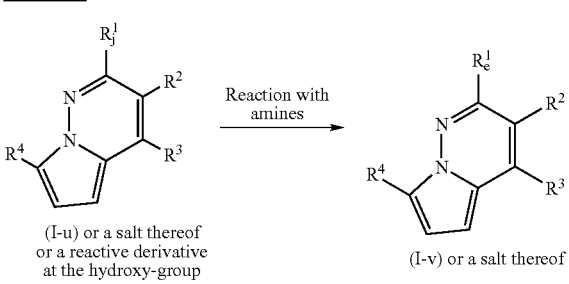

(I-u) or a salt thereof or a reactive derivative at the hydroxy-group → Reaction with amines → (I-v) or a salt thereof Process 17

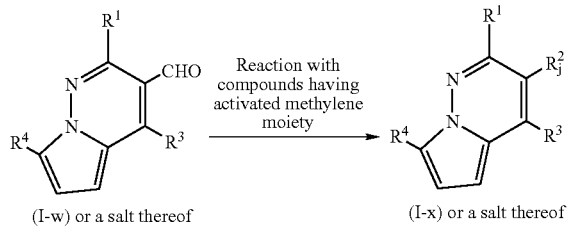

(I-w) or a salt thereof → Reaction with compounds having activated methylene moiety → (I-x) or a salt thereof Process 18

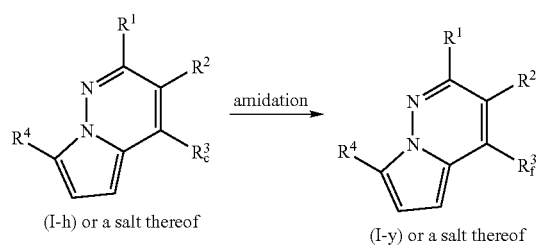

(I-h) or a salt thereof → amidation → (I-y) or a salt thereof

Process 19

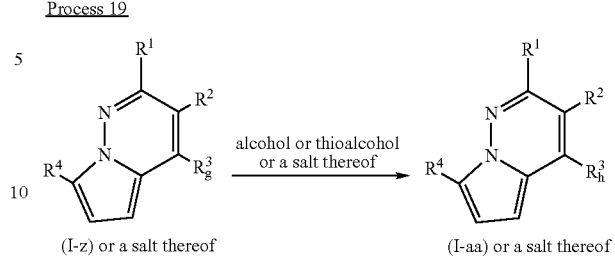

(I-z) or a salt thereof → alcohol or thioalcohol or a salt thereof → (I-aa) or a salt thereof Process 20

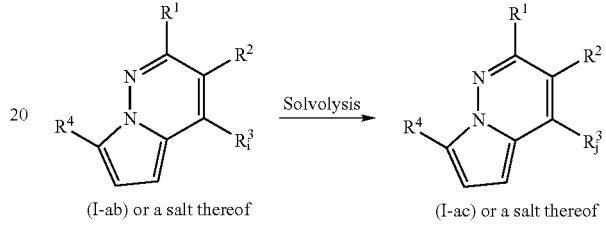

(I-ab) or a salt thereof → Solvolysis → (I-ac) or a salt thereof

Process 21

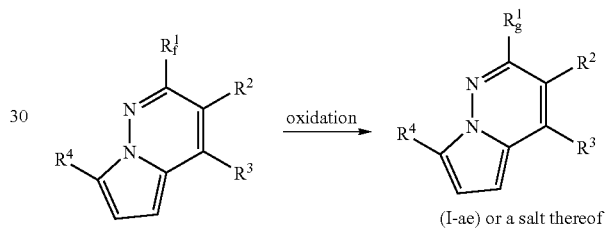

(I-ad) or a salt thereof → oxidation → (I-ae) or a salt thereof

Process 22

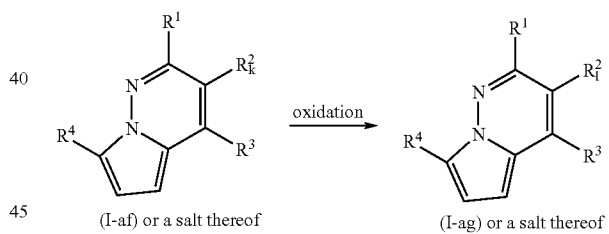

(I-af) or a salt thereof → oxidation → (I-ag) or a salt thereof

Process 23

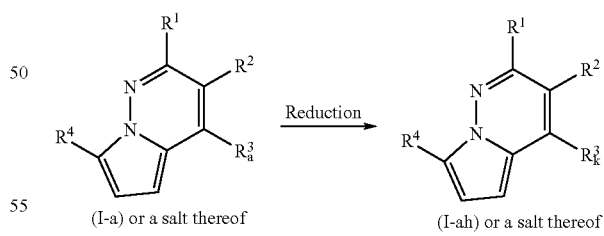

(I-a) or a salt thereof → Reduction → (I-ah) or a salt thereof

Process 24

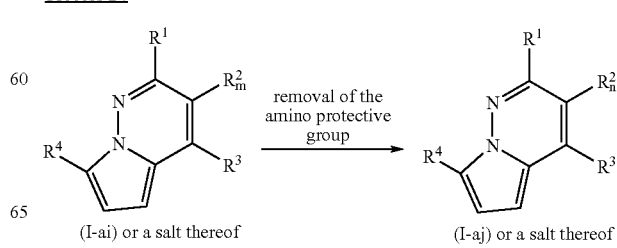

(I-ai) or a salt thereof → removal of the amino protective group → (I-aj) or a salt thereof Process 25

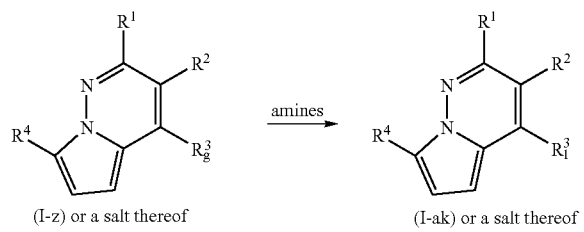

(I-z) or a salt thereof → (I-ak) or a salt thereof

Process 26

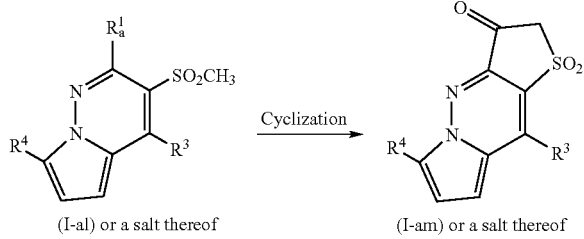

(I-al) or a salt thereof → (I-am) or a salt thereof

Process 27

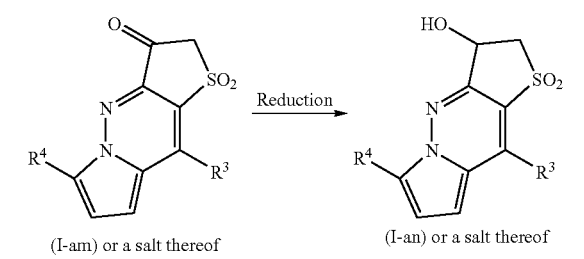

(I-am) or a salt thereof → (I-an) or a salt thereof

Process 28

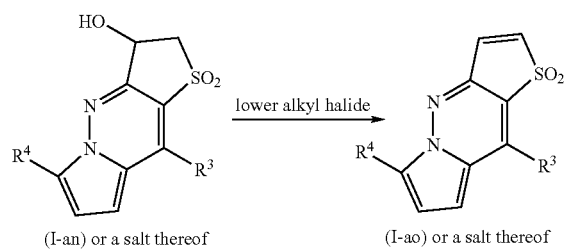

(I-an) or a salt thereof → (I-ao) or a salt thereof

Process 29

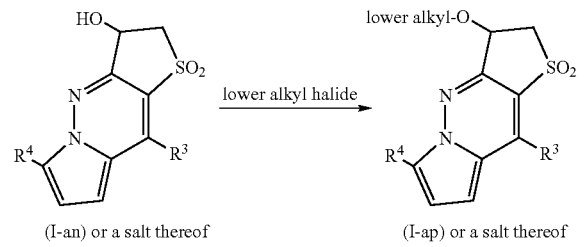

(I-an) or a salt thereof → (I-ap) or a salt thereof

Process 30

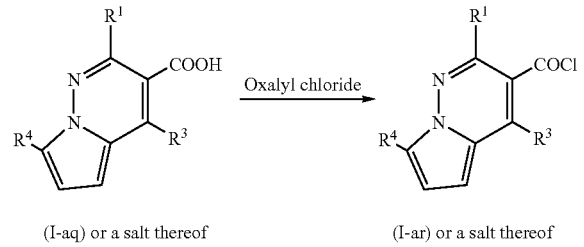

(I-aq) or a salt thereof → (I-ar) or a salt thereof

Process 31

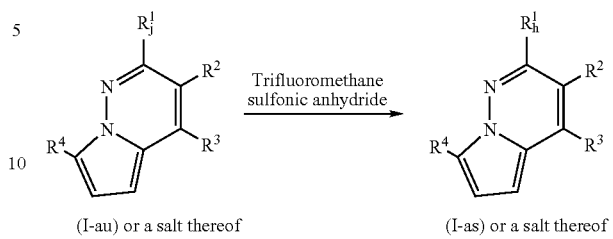

(I-au) or a salt thereof → (I-as) or a salt thereof

Process 32

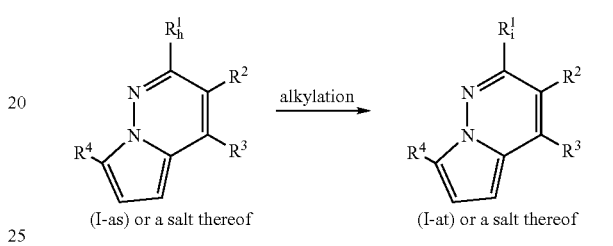

(I-as) or a salt thereof → (I-at) or a salt thereof

Process 33

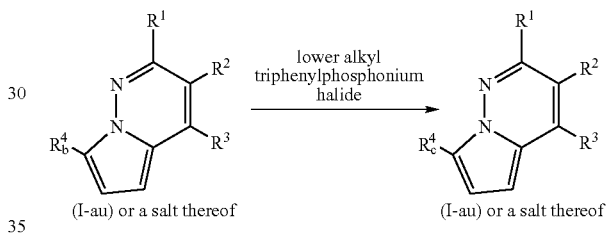

(I-au) or a salt thereof → (I-au) or a salt thereof

Process 34

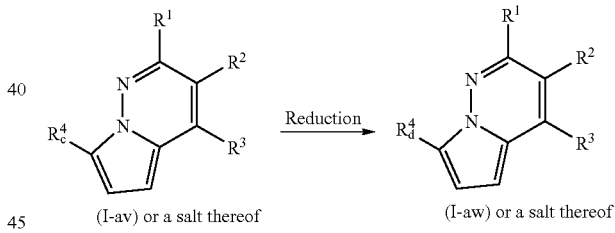

(I-av) or a salt thereof → (I-aw) or a salt thereof

Process 35

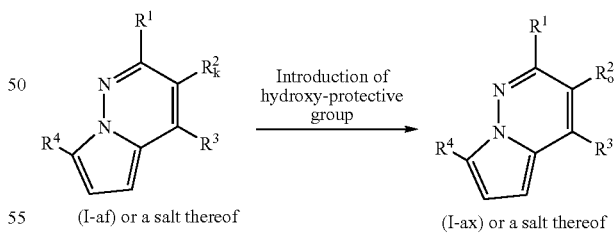

(I-af) or a salt thereof → (I-ax) or a salt thereof

Process 36

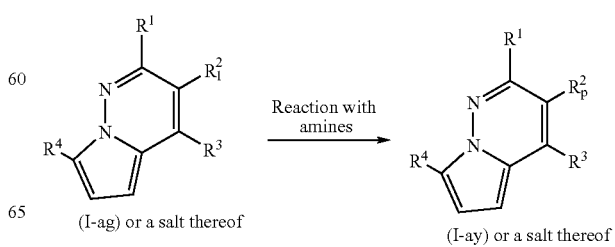

(I-ag) or a salt thereof → (I-ay) or a salt thereof

-continued

Process 37

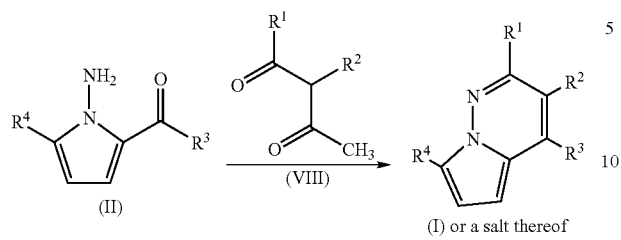

(I) or a salt thereof

Process 38

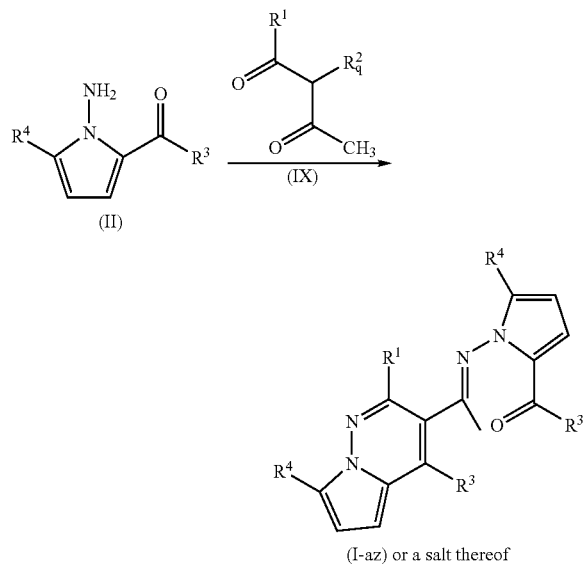

(I-az) or a salt thereof

Process 39

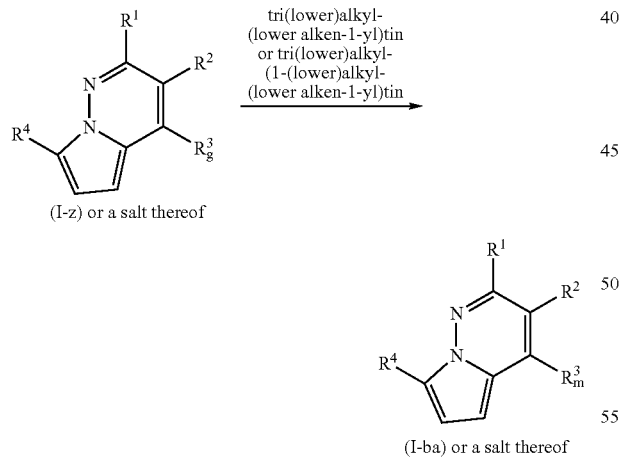

(I-ba) or a salt thereof

Process 40

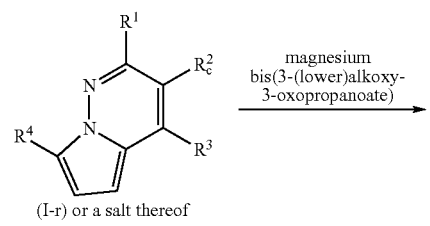

-continued

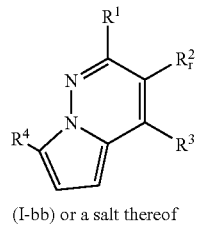

(I-bb) or a salt thereof wherein $R^1$, $R^2$, $R^3$ and $R^4$ are each as defined above,
 $R^1_a$ is the same as above $R^1$ having protected carboxy moiety,
 $R^1_b$ is the same as above $R^1$ having carboxy moiety,
 $R^1_c$ is —$CONR^5R^6$,
 $R^1_d$ is carbamoyl(lower)alkyl,
 $R^1_e$ is amino, mono- or di(lower)alkylamino-, lower alkoxy(lower)alkylamino, nitrogen-containing heterocyclic group, amino(lower)alkyl, mono- or di(lower)alkylamino(lower)alkyl, lower alkoxy(lower)alkylamino(lower)alkyl, nitrogen-containing heterocyclic (lower)alkyl,
 $R^1_f$ is lower alkylthio(lower)alkyl,
 $R^1_g$ is lower alkylsulfonyl(lower)alkyl,
 $R^1_h$ is trifluoromethanesulfonyloxy or trifluoromethanesulfonyloxy(lower)alkyl,
 $R^1_i$ is lower alkoxy or lower alkoxy(lower)alkyl,
 $R^1_j$ is hydroxy or hydroxy(lower)alkyl,
 $R^2_a$ is lower alkoxycarbonyl,
 $R^2_b$ is the same as above $R^2$ having protected carboxy moiety,
 $R^2_c$ is the same as above $R^2$ having carboxy moiety,
 $R^2_d$ is the same as above $R^2$ having carbamoyl moiety,
 $R^2_e$ is the same as above $R^2$ having protected hydroxy moiety,
 $R^2_f$ is the same as above $R^2$ having hydroxy moiety,
 $R^2_g$ is the same as above $R^2$ having hydroxymethyl moiety,
 $R^2_h$ is —$OR^{12}$,
 $R^2_i$ is lower alkoxycarbonyl or lower alkylsulfonyl,
 $R^2_j$ is substituted or unsubstituted lower alkenyl as mentioned in the above $R^2$, wherein said lower alkenyl is lower 1-alken-1-yl,
 $R^2_k$ is the same as above $R^2$ having hydroxy(lower)alkyl moiety,
 $R^2_l$ is the same as above $R^2$ having oxo(lower)alkyl moiety,
 $R^2_m$ is the same as above $R^2$ having protected amino moiety,
 $R^2_n$ is the same as above $R^2$ having amino moiety,
 $R^2_o$ is the same as above $R^2$ having protected hydroxy moiety,
 $R^2_p$ is the same as above $R^2$ having hydroxy(lower)alkylamino(lower)alkyl moiety,
 $R^2_q$ is the same as above $R^2$ having lower alkoxycarbonyl(lower)alkyl moiety,
 $R^2_r$ is the same as above $R^2$ having lower alkoxycarbonylmethylcarbonyl moiety,
 $R^3_a$ is the same as above $R^3$ having cyano moiety,
 $R^3_b$ is the same as above $R^3$ having carbamoyl moiety,
 $R^3_c$ is the same as above $R^3$ having carboxy moiety,
 $R^3_d$ is the same as above $R^3$ having protected sulfamoyl moiety, $R^3_e$ is the same as above $R^3$ having sulfamoyl moiety,
$R^3_f$ is the same as above $R^3$ having —$CONR^{10}R^{11}$ moiety,
$R^3_g$ is the same as above $R^3$ having haloheterocyclic moiety,
$R^3_h$ is the same as above $R^3$ having alkoxyheterocyclic, thioalkoxyheterocyclic or hydroxy moiety,
$R^3_i$ is the same as above $R^3$ having 1-(lower)alkoxy (lower)alken-1-ylheterocyclic moiety,
$R^3_j$ is the same as above $R^3$ having lower alkanoylheterocyclic moiety,
$R^3_k$ is the same as above $R^3$ having aminomethylheterocyclic moiety,
$R^3_l$ is the same as above $R^3$ having mono- or di(lower)alkylaminoheterocyclic moiety,
$R^3_m$ is the same as above $R^3$ having (lower)alken-1-ylheterocyclic group or 1-(lower)alkoxy-1-(lower)alken-1-yl-heterocyclic moiety,
$R^4_a$ is halogen,
$R^4_b$ is formyl,
$R^4_c$ is lower 1-alken-1-yl,
$R^4_d$ is lower alkyl,
$R^{12}$ is lower alkyl or a group derived from protected or unprotected sugar by removal of the hydroxy group therefrom,
X is a leaving group, and
a group of the formula:

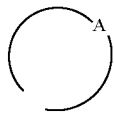

is lower alkylene interrupted by imino moiety and substituted by oxo groups.

The starting compound (II) of the present invention can be prepared according to a conventional manner or in a similar manner as described in the following Preparations and/or Examples.

Another point to be noted is that the pyrrolopyridazine moiety of the compound (I) can also exist in the tautomeric form, and such tautomeric equilibrium can be represented, for example, by the following formula.

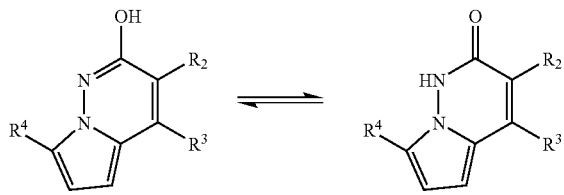

wherein $R^1$ $R^2$, $R^3$ and $R^4$ are each as defined above.

Both of the above tautomeric isomers are included within the scope of the present invention, and in the present specification and claims, however, the object compound (I) is represented for convenience' sake by one expression of the possible tautomeric forms of pyrrolopyridazine ring.

In the above and subsequent descriptions of the present specification, suitable examples and illustration of the various definitions which the present invention intends to include within the scope thereof are explained in detail as follows.

The term "lower" is used to intend a group having 1 to 6, preferably 1 to 4, carbon atom(s), unless otherwise provided.

Suitable "lower alkyl" and "lower alkyl moiety" may include straight or branched one having 1 to 6 carbon atom(s), such as methyl, ethyl, propyl, isopropyl, butyl, isobutyl, sec-butyl, tert-butyl, pentyl, tert-pentyl, hexyl, and the like, and in which more preferable example may be $C_1$-$C_4$ alkyl.

Suitable "lower alkenyl" may include vinyl(ethenyl), 1-(or 2-)propenyl, 1-(or 2- or 3-)butenyl, 1-(or 2- or 3- or 4-)pentenyl, 1-(or 2- or 3- or 4- or 5-)hexenyl, 1-methylvinyl, 1-ethylvinyl, 1-(or 2-)methyl-1-(or 2-)propenyl, 1-(or 2-)ethyl-1-(or 2-)propenyl, 1-(or 2- or 3-)methyl-1-(or 2- or 3-)butenyl, and the like, in which more preferable example may be $C_2$-$C_4$ alkenyl.

Suitable "lower alkynyl" may include ethynyl, 1-propynyl, propargyl, 1-methylpropargyl, 1 or 2 or 3-butynyl, 1 or 2 or 3 or 4-pentynyl, 1 or 2 or 3 or 4 or 5-hexynyl, and the like.

Suitable "lower alkylene" may include straight or branched one such as methylene, ethylene, trimethylene, tetramethylene, pentamethylene, hexamethylene, methylmethylene, ethylethylene, propylene, and the like, in which more preferable example may be $C_1$-$C_4$ alkylene and the most preferable one may be methylene.

Example of hydroxy($C_1$-$C_2$)alkylene is hydroxymethylene, (hydroxymethyl)methylene or 1-(or 2-)hydroxyethylene.

Suitable "lower alkoxy" may include methoxy, ethoxy, propoxy, isopropoxy, butoxy, isobutoxy, t-butoxy, pentyloxy, t-pentyloxy, hexyloxy and the like.

Suitable "halogen" and "halogen moiety" may include fluorine, bromine, chlorine and iodine.

Suitable "trihalo(lower)alkyl" may include trichloromethyl, trifluoromethyl, trichloroethyl, tribromoethyl, and the like.

Suitable "mono- or di(lower)alkylamino" may include amino group substituted by one or two lower alkyl such as methylamino, ethylamino, dimethylamino, and the like.

Example of "mono- or di(lower)alkylamino substituted by lower alkoxy" may be methoxymetylamino, methoxyethylamino, methoxyethyl(methyl)amino, methoxyethyl(ethyl)amino, di(methoxyethyl)amino, ethoxymethylamino, ethoxyethylamino, and the like.

Suitable "lower alkylthio" may include conventional ones such as methylthio, ethylthio, propylthio, butylthio, and the like.

Suitable "lower alkylsulfinyl" may include conventional ones such as methylsulfinyl, ethylsulfinyl, propylsulfinyl, butylsulfinyl, and the like.

Suitable "lower alkylsulfonyl" may include conventional ones such as methylsulfonyl, ethylsulfonyl, propylsulfonyl, bytylsulfonyl, and the like.

Suitable "trihalo(lower)alkylsulfonyloxy" may include sulfonyloxy group substituted by trihalo(lower)alkyl such as trifluoromethylsulfonyloxy, trifluoroethylsulfonyloxy, trichloromethylsulfonyloxy, and the like.

Suitable "protected carboxy" and "protected carboxy moiety" may include esterified carboxy and the like.

And suitable example of said ester may be the ones such as
lower alkyl ester (e.g., methyl ester, ethyl ester, propyl ester, isopropyl ester, butyl ester, isobutyl ester, t-butyl ester, pentyl ester, t-pentyl ester, hexyl ester, etc.);
lower alkenyl ester (e.g., vinyl ester, allyl ester, etc.);
lower alkynyl ester (e.g. ethynyl ester, propynyl ester, etc.);

lower alkoxy(lower)alkyl ester (e.g., methoxymethyl ester, ethoxymethyl ester, isopropoxymethyl ester, 1-methoxyethyl ester, 1-ethoxyethyl ester, etc.);

lower alkylthio(lower)alkyl ester (e.g., methylthiomethyl ester, ethylthiomethyl ester, ethylthioethyl ester, isopropoxythiomethyl ester, etc.);

mono(or di or tri)halo(lower)alkyl ester (e.g., 2-iodoethyl ester, 2,2,2-trichloroethyl ester, etc.);

lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 1-acetoxyethyl ester, 2-acetoxyethyl ester, 2-propionyloxyethyl ester, etc.);

lower alkoxycarbonyloxy(lower)alkyl ester (e.g., methoxycarbonyloxymethyl ester, ethoxycarbonyloxymethyl ester, propoxycarbonyloxymethyl ester, 1-(or 2-)-[methoxycarbonyloxy]ethyl ester, 1-(or 2-)-[ethoxycarbonyloxy]ethyl ester, 1-(or 2-)-[propoxycarbonyloxy]ethyl ester, 1-(or 2-)-[isopropoxycarbonyloxy]ethyl ester, etc.);

lower alkanesulfonyl(lower)alkyl ester (e.g., mesylmethyl ester, 2-mesylethyl ester, etc.);

lower alkoxycarbonyloxy(lower)alkyl ester (e.g., methoxycarbonyloxymethyl ester, ethoxycarbonyloxymethyl ester, propoxycarbonyloxymethyl ester, t-butoxycarbonyloxymethyl ester, 1-(or 2-)methoxycarbonyloxyethyl ester, 1-(or 2-)-ethoxycarbonyloxyethyl ester, 1-(or 2-)-isopropoxycarbonyloxyethyl ester, etc.);

phthalidylidene(lower)alkyl ester;

(5-lower alkyl-2-oxo-1,3-dioxol-4-yl)(lower)alkyl ester [e.g., (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.];

mono(or di or tri)aryl(lower)alkyl ester, for example, mono (or di or tri)phenyl(lower)alkyl ester which may have one or more suitable substituent(s) (e.g., benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.);

aryl ester which may have one or more suitable substituent(s) such as substituted or unsubstituted phenyl ester (e.g., phenyl ester, tolyl ester, t-butylphenyl ester, xylyl ester, mesityl ester, cumenyl ester, 4-chlorophenyl ester, 4-methoxyphenyl ester, etc.);

tri(lower)alkylsilyl ester (e.g. trimethylsilyl ester, triethylsilyl ester, etc.);

tri(lower)alkylsilyl(lower)alkyl ester (e.g. 2-trimethylsilylethyl ester, etc.);

and the like, in which more preferable example may be lower alkyl ester, i.e., lower alkoxycarbonyl (e.g. ethoxycarbonyl, etc.).

The term "protected amino" means an amino group bonded to the amino-protecting group. Example of such amino-protecting group include lower alkoxycarbonyl (e.g. methoxycarbonyl, ethoxycarbonyl, t-butoxycarbonyl, etc.); lower alkenyloxycarbonyl (e.g. vinyloxycarbonyl, allyloxycarbonyl, etc.); optionally substituted aryl(lower)alkoxycarbonyl (e.g. benzyloxycarbonyl, etc.); phthalimide; and the like. Further example of amino-protecting group are well-known in organic synthesis and are described by T. W. Greene and P. G. M. Wuts, "Protective Groups in Organic Synthesis," Second Edition, John Wiley and Sons, New York, N.Y., which is herein incorporated by reference.

The term "protected sulfamoyl" means sulfamoyl group having the amino-protecting group mentioned above on the nitrogen atom. A preferred amino-protecting group is aryl (lower)alkoxycarbonyl (e.g. benzyloxycarbonyl, etc.); and the like.

Suitable "acyl" and "acyl moiety" may include aliphatic acyl group, and acyl group containing an aromatic ring, which is referred to as aromatic acyl, or heterocyclic ring, which is referred to as heterocyclic acyl.

Suitable example of said acyl may be illustrated as follows:

Aliphatic acyl such as lower or higher alkanoyl (e.g., formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.); in which preferable "lower alkanoyl" may include straight or branched one such as formyl, acetyl, propionyl, butyryl, and the like.

lower or higher alkenoyl (e.g., acryloyl, 2-(or 3-)-butenoyl, 2-(or 3- or 4-)pentenoyl, 2-(or 3- or 4- or 5-)-hexenoyl, etc.);

lower alkadienoyl (e.g., heptadienoyl, hexadienoyl, etc.);

cyclo(lower)alkylcarbonyl (e.g., cyclopropylcarbonyl, cyclopentylcarbonyl, cyclohexylcarbonyl, etc.);

lower alkylglyoxyloyl (e.g., methylglyoxyloyl, ethylglyoxyloyl, propylglyoxyloyl, etc.);

lower alkoxyglyoxyloyl (e.g., methoxyglyoxyloyl, ethoxyglyoxyloyl, propoxyglyoxyloyl, etc.);

or the like;

Aromatic acyl such as aroyl (e.g., benzoyl, toluoyl, naphthoyl, etc.);

ar(lower)alkanoyl [e.g., phenyl(lower)alkanoyl (e.g., phenylacetyl, phenylpropanoyl, phenylbutanoyl, phenylisobutanoyl, phenylpentanoyl, phenylhexanoyl, etc.), naphthyl (lower)alkanoyl (e.g., naphthylacetyl, naphthylpropanoyl, naphthylbutanoyl, etc.), etc.];

ar(lower)alkenoyl [e.g., phenyl(lower)alkenoyl (e.g., phenylpropenoyl, phenylbutenoyl, phenylmethacryloyl, phenylpentenoyl, phenylhexenoyl, etc.), naphthyl(lower)alkenoyl (e.g., naphthylpropenoyl, naphthylbutenoyl, etc.), etc.];

aryloxy(lower)alkanoyl (e.g., phenoxyacetyl, phenoxypropionyl, etc.);

arylglyoxyloyl (e.g., phenylglyoxyloyl, naphthylglyoxyloyl, etc.);

heterocyclic acyl such as heterocycliccarbonyl;

heterocyclic(lower)alkanoyl (e.g., heterocyclicacetyl, heterocyclicpropanoyl, heterocyclicbutanoyl, heterocyclicpentanoyl, heterocyclichexanoyl, etc.);

heterocyclic(lower)alkenoyl(e.g., heterocyclicpropenoyl, heterocyclicbutenoyl, heterocyclicpentenoyl, heterocyclichexenoyl, etc.);

heterocyclicglyoxyloyl; heterocyclicoxycarbonyl; or the like;

in which suitable "heterocyclic moiety" may include saturated or unsaturated, monocyclic or polycyclic heterocyclic group containing at least one hetero-atom such as an oxygen, sulfur, nitrogen atom and the like, as mentioned below and preferable "heterocyclic-carbonyl" may include carbonyl group substituted by heterocyclic group as mentioned below such as pyrrolidinylcarbonyl, pyridinylcarbonyl, pyrazinylcarbonyl, and the like.

Suitable "halocarbonyl" may include chlorocarbonyl, bromocarbonyl, and the like.

Suitable "cyclo(lower)alkyl" and "cyclo(lower)alkyl moeity" may include one having 3 to 7 carbon atoms such as cyclopropyl, cyclobutyl, cyclopentyl, cyclohexyl, and the like.

Suitable "aryl" and "aryl moiety" may include $C_6$-$C_{10}$ aryl such as phenyl, naphthyl and the like.

Suitable "heterocyclic moiety" may include saturated or unsaturated, monocyclic or polycyclic heterocyclic group containing at least one hetero-atom such as an oxygen, sulfur, nitrogen atom and the like.

Preferable heterocyclic group may be heterocyclic group such as
(1) unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridinyl, dihydropyridinyl, pyrimidinyl, pyrazinyl, pyridazinyl, triazolyl (e.g., 1H-1,2,4-triazolyl, 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;
(2) saturated 3 to 8-membered (more preferably 5 or 6-membered) heteromonocyclic group containing 1 to 4 nitrogen atom(s), for example, pyrrolidinyl, imidazolidinyl, piperidyl, piperazinyl, etc.;
(3) unsaturated condensed heterocyclic group containing 1 to 4 nitrogen atom(s), for example, indolyl, isoindolyl, indolinyl, indolizinyl, benzimidazolyl, quinolyl, tetrahydroquinolyl (e.g., 1,2,3,4-tetrahydroquinolyl, etc.), isoquinolyl, indazolyl, benzotriazolyl, benzopyrimidinyl (e.g., benzo[b]pyrimidinyl, etc.), etc.;
(4) unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;
(5) saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;
(6) unsaturated condensed heterocyclic group containing 1 to 2 oxygen atom(s) and 1 to 3 nitrogen atom(s), for example, benzoxazolyl, benzoxadiazolyl, etc.;
(7) unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;
(8) saturated 3 to 8-membered (more preferably 5 or 6-membered) heteromonocyclic group containing 1 to 2 sulfur atom(s) and 1 to 3 nitrogen atom(s), for example, thiazolidinyl, etc.;
(9) unsaturated 3 to 8-membered (more preferably 5 or 6-membered) heteromonocyclic group containing 1 to 2 sulfur atom(s), for example, thienyl, dihydrodithiinyl, dihydrodithionyl, etc.;
(10) unsaturated condensed heterocyclic group containing 1 to 2 sulfur atom(s) and 1 to 3 nitrogen atom(s), for example, benzothiazolyl, benzothiadiazolyl, etc.;
(11) unsaturated 3 to 8-membered (more preferably 5 or 6-membered) heteromonocyclic group containing an oxygen atom, for example, furanyl, etc.;
(12) unsaturated condensed heterocyclic group containing 1 to 2 oxygen atom(s), for example, benzodioxolyl (e.g. methylenedioxyphenyl, etc.), benzofuranyl, etc.;
(13) unsaturated 3 to 8-membered (more preferably 5 or 6-membered) heteromonocyclic group containing an oxygen atom and 1 to 2 sulfur atom(s), for example, dihydrooxathiinyl, etc.;
(14) unsaturated condensed heterocyclic group containing 1 to 2 sulfur atom(s), for example, benzothienyl (e.g., benzo[b]thienyl, etc.), benzodithiinyl, etc.;
(15) unsaturated condensed heterocyclic group containing an oxygen atom and 1 to 2 sulfur atom(s), for example, benzoxathiinyl, etc.; and the like.

Suitable "heterocyclic group" and "heterocyclic moiety" in the terms "heterocycliccarbonyl" can be referred to the ones as mentioned above.

Suitable "N-containing heterocyclic group" and "N-containing heterocyclic moiety" can be referred to the ones as mentioned above, wherein the heterocyclic group is containing at least one nitrogen atom such as 1-pyrrolidinyl, morpholinyl and the like.

A group derived from a sugar may be the group derived from, for example, glyceraldehydes; an aldose such as erythrose, threose, arabinose, ribose, xylose, lyxose, glucose, mannose or galactose; a ketose such as fructose or sorbose; or a discccharide such as maltose, lactose or sucrose.

Protecting groups for the hydroxy group of the abovementioned sugars are an aliphatic acyl group, such as formyl, or acetyl; a cyclic ether group such as tetrahydro-2-furanyl or tetrahydro-2-pyranyl; a 1-alkoxyethyl group such as 1-methoxyethyl or 1-ethoxyethyl; and a silyl group such as trimethylsilyl, triethylsilyl or t-butyldimethylsilyl.

Suitable "substituted or unsubstituted lower alkyl" for $R^1$ may include straight or branched lower alkyl (e.g. methyl, isopropyl, neopentyl, etc.) optionally substituted by; (1) halogen (e.g. fluoro, bromo, etc.), (2) carboxy, (3) protected carboxy (e.g. esterified carboxy such as ethoxycarbonyl, etc.), (4) cyano, (5) carbamoyl, (6) —OCONR$^{15}$R$^{16}$ [wherein R$^{15}$ and R$^{16}$ each independently represents hydrogen, aryl or lower alkyl optionally substituted by aryl, or R$^{13}$ and R$^{14}$, together with the nitrogen atom to which they are attached, represents saturated 5- or 6-membered heteromonocyclic group containing 1 to 2 nitrogen atom(s) and also optionally containing oxygen atom.] (more preferably, dimethylcarbamoyloxy, methyl-phenylcarbamoyloxy, morpholinylcarbonyloxy, pyrrolidinylcarbonyloxy, etc); (7) lower alkylthio (e.g. methylthio, etc.), (8) lower alkylsulfonyl (e.g. methylsulfonyl, etc.), (9) lower alkylsulfonyloxy (e.g. methylsulfonyoxyl, etc.), (10) lower alkylsulfonylamino (e.g. methylsulfonylamino, etc.), (11) mono- or di(lower)alkylamino optionally substituted by hydroxy, lower alkoxy, acyloxy (e.g. phenoxy, etc.), or substituted or unsubstituted aryl (e.g. benzylamino, etc.), (12) amino; (13) acylamino (more preferably, lower alkanoylamino such as acetylamino, aroylamino such as benzoylamino, or heterocycliccarbonylamino such as pyrazinylcarbonylamino, or the like), (14) protected amino (e.g., methoxycarbonylamino, phthalimide, etc.), (15) hydroxy, (16) acyloxy (more preferably, lower alkanoyloxy such as acetyloxy, or the like), (17) cyclo(lower)alkyloxy, (18) aryloxy (e.g. phenoxy, etc.) (19) substituted or unsubstituted aryl (more preferably, phenyl), (20) saturated or unsaturated 5- or 6-membered heteromonocyclic group containing 1 to 3 nitrogen atom(s) and also optionally containing oxygen atom or sulfur atom (more preferably, piperazinyl, morpholinyl, oxazolidinyl, thiomorpholinyl, piperidinyl, pyrrolidinyl or triazolyl) optionally substituted by lower alkyl, hydroxy(lower)alkyl, aryl or oxo, (21) lower alkoxy (e.g. methoxy, ethoxy, iso-propoxy, etc.) optionally substituted by carboxy, protected carboxy (e.g.

tert-butoxycarbonyl, etc.), hydroxy, protected hydroxy (e.g. tetrahydro-2H-pyran-2-yloxy, etc.), cyclo(lower)alkyl (e.g. cyclopropyl, cyclohexyl, etc.), substituted or unsubstituted aryl (e.g. phenyl optionally substituted by cyano, carboxy, protected carboxy or carbamoyl, such as phenyl, 2-, 3- or 4-cyanophenyl, 2-, 3- or 4-carboxyphenyl, 2-, 3- or 4-(methoxycarbonyl)phenyl, 2-, 3- or 4-carbamoylphenyl, etc.), saturated or unsaturated 5- or 6-membered heterocyclic group containing 1 to 2 nitrogen atom(s) optionally substituted by lower (more preferably, 2-, 3- or 4-pyridinyl, pyrazinyl or 4-methylpiperazinyl)(e.g. 2-, 3- or 4-pyridinyl, pyrazinyl, etc.), or —CONR$^{13}$R$^{14}$ [wherein R$^{13}$ and R$^{14}$ each independently hydrogen or lower alkyl optionally substituted by aryl, or R$^{13}$ and R$^{14}$, together with the nitrogen atom to which they are attached, represents N-containing heterocyclic group] (e.g. morpholinocarbonyl, dimethylcarbamoyl, etc.), and the like.

Suitable "substituted or unsubstituted aryl" may include $C_6$-$C_{10}$ aryl (e.g. phenyl, naphthyl, etc.) optionally substituted by the substituent(s) selected from the group consisting of (1) halogen (e.g. fluoro, chloro, etc.), (2) carboxy, (3) protected carboxy, (4) cyano, (5) —CONR$^{15}$R$^{16}$ [wherein R$^{15}$ and R$^{16}$ are each independently represents hydrogen, lower alkyl optionally substituted by hydroxy] (e.g. carbamoyl, hydroxyethylcarbamoyl, etc.), (6) lower alkyl (e.g. methyl, etc.), (7) cyclo(lower)alkyl (e.g. cyclopropyl, etc) (8) lower alkoxy (e.g. methoxy, etc.), (9) trihalo(lower)alkyl (e.g. trifluoromethyl, etc.), (10) heterocyclic group such as oxazolyl, (11) lower alkylsulfonyl (e.g. methylsulfonyl, etc.), (12) nitro, (13) amino, (14) sulfamoyl, and (15) protected sulfamoyl such as ar(lower)alkoxycarbonylsulfamoyl, and the like.

In which,
preferable example of "substituted or unsubstituted aryl" for R$^1$ is aryl optionally substituted by the substituent(s) selected from the group consisting of halogen (e.g. phenyl, 4-fluorophenyl, etc.);
preferable example of "substituted or unsubstituted aryl" for R$^3$ is aryl optionally substituted by the substituent(s) selected from the group consisting of (1) halogen, (2) carboxy, (3) protected carboxy such as esterified carboxy (e.g. benzyloxycarbonyl, etc,), (4) cyano, (5) —CONR$^{15}$R$^{16}$ [wherein R$^{15}$ and R$^{16}$ are each independently represents hydrogen, lower alkyl optionally substituted by hydroxy], (6) lower alkyl, (7) cyclo(lower) alkyl, (8) lower alkoxy, (9) trihalo(lower)alkyl, (10) heterocyclic group, (11) lower alkylsulfonyl, (12) nitro, (13) amino, (14) sulfamoyl, and (15) protected sulfamoyl, and the like. (e.g. phenyl, 2-naphthyl, 2- or 3-chlorophenyl, 2,3-, 2,4-, 3,4- or 3,5-dichlorophenyl, 3- or 4-fluorophenyl, 3- or 4-cyanophenyl, 3- or 4-carbamoylphenyl, 4-sulfamoylphenyl, 4-(benzyloxycarbonylsulfamoyl)phenyl, 3-carboxyphenyl, 3-(N-(2-hydroxyethyl)carbamoyl) phenyl, 3-nitrophenyl, 3-trifluoromethylphenyl, 3-methylsulfonylphenyl, 3-(5-oxazolyl)phenyl, 3-methoxyphenyl, 3-methylphenyl, etc.); and
preferable example of "substituted or unsubstituted aryl" for R$^7$ is aryl optionally substituted by lower alkoxy (e.g. phenyl, 2-, 3- or 4-methoxyphenyl, etc.).

Suitable "substituted or unsubstituted heterocyclic group" may include heterocyclic group mentioned above (more preferably, pyridinyl, pyrazinyl, oxazolyl, isooxazolyl, furanyl, thienyl, quinolinyl, benzofuranyl and benzothienyl), which is optionally substituted by the substituent(s) selected from the group consisting of (1) lower alkyl (e.g. methyl, etc.), (2) cyclo(lower)alkyl (e.g. cyclopropyl, etc.) (3) lower alkoxy (e.g. methoxy, etc.), (4) acyl (e.g. lower alkanoyl such as acetyl, etc.), (5) amino, (6) mono- or di(lower) alkylamino (e.g. dimethylamino, etc.), (7) protected amino (e.g. lower alkoxycarbonylamino such as tert-butoxycarbonylamino, etc.), (8) cyano, (9) carboxy, (10) protected carboxy (e.g. benzyloxycarbonyl, etc.), (11) —CONR$^{15}$R$^{16}$ [wherein R$^{15}$ and R$^{16}$ are each independently represents hydrogen, lower alkyl optionally substituted by hydroxy] (e.g. carbamoyl, hydroxyethylcarbamoyl, etc.), (12) lower alkenyl optionally substituted by lower alkoxy (e.g. vinyl, 1-ethoxyvinyl, etc.), (13) halogen (e.g. chloro, bromo, etc.), (14) lower alkylthio, (15) hydroxy, and the like.

In which,
preferable example of "substituted or unsubstituted heterocyclic group" for R$^1$ is heterocyclic group optionally substituted by lower alkyl or halogen (e.g. 2-pyridinyl, 5-blomo-3-pyridinyl, 1-methyl-2-pyrrolyl, 1-pyrrolyl, 1-pyrrolidinyl, 3-methyl-2-thienyl, 2-thienyl, 2- or 3-furanyl, 2-thiazolyl, 5-oxazolyl, 5-methyl-isooxazolyl, 3,5-dimethyl-4-isoxazolyl, etc.); and
preferable example of "substituted or unsubstituted heterocyclic group" for R$^3$ is heterocyclic group optionally substituted by at least one substituent(s) selected from the group consisting of (1) lower alkyl, (2) cyclo(lower)alkyl, (3) lower alkoxy, (4) acyl such as lower alkanoyl, (5) amino, (6) mono- or di(lower)alkylamino, (7) protected amino such as lower alkoxycarbonylamino, (8) cyano, (9) carboxy, (10) protected carboxy such as esterified carboxy (e.g. benzyloxycarbonyl), (11) carbamoyl, (12) lower alkenyl optionally substituted by lower alkoxy, (13) halogen, (14) lower alkylthio, and (15) hydroxy (e.g. 3- or 4-pyridyl, 2-pyrazinyl, 6-methoxy-2-pyrazinyl, 4- or 5-oxazolyl, 2-benzofuranyl, 2-benzothienyl, 3- or 6-quinolinyl, 2-chloro-4-pyridyl, 5-bromo-3-pyridyl, 5-chloro-2-thienyl, 5,6-dichloro-2-pyridinyl, 4-chloro-2-pyridyl, 5-cyano-3-pyridyl, 5-carboxy-3-pyridinyl, 5-carbamoyl-3-pyridyl, 5-(benzyloxycarbonyl)-3-pyridyl, 5-(tert-butoxycarbonylamino)-3-pyridinyl, 5-amino-3-pyridinyl, 2-methoxy-4-pyridyl, 3-methoxy-5-isoxazolyl, 2-methylthio-4-pyridinyl, 2-hydroxy-4-pyridyl, 5-methyl-3-pyridyl, 5-ethyl-3-pyridyl, 5-methyl-3-isoxazolyl, 5-vinyl-3-pyridyl, 2-vinyl-4-pyridyl, 5-acetyl-3-pyridyl, 2-dimethylamino-4-pyridinyl, 5-(1-ethoxyvinyl)-3-pyridyl, 2-oxo-1,2-dihydro-4-pyridyl, or 2-methylthio-4-pyridyl, etc.).

R$^1$ and R$^2$ are combined together to form lower alkylene or lower alkenylen group which is optionally interrupted by amino or sulfonyl and also is optionally substituted by the group consisting of lower alkyl, hydroxy, oxo and lower alkoxy, which is represented by the following formula:

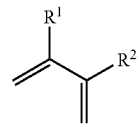

The above formula may include following ones;

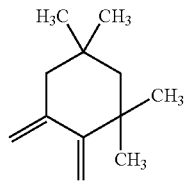 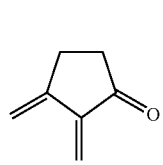 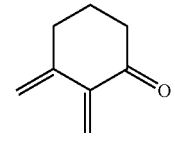

-continued

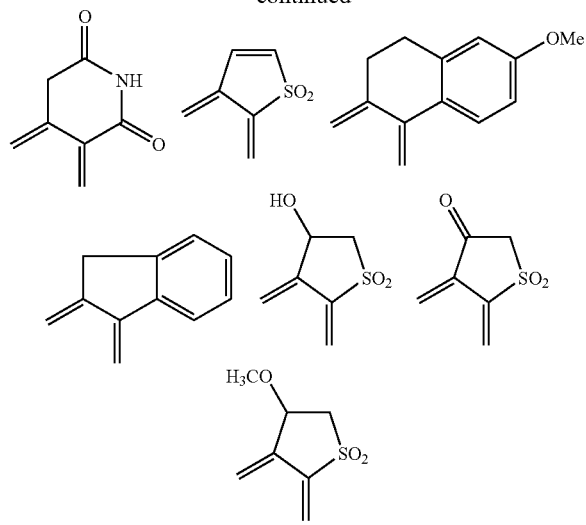

Suitable "substituted or unsubstituted aryl(lower)alkenyl" may include $C_6$-$C_{10}$ aryl(lower)alkenyl which is optionally substituted by halogen (e.g. 2-phenylvinyl, 2-(2- or 3-chlorophenyl)vinyl, etc.).

Suitable "leaving group" may include acid residue, lower alkoxy as exemplified above, and the like.

The above Processes can be carried out according to a conventional manner such as the one described in Preparations and/or Examples, or in a similar manner thereto. Among the above Processes, fused heterocyclic ring forming processes (such as Process 1 and Process 12) are important for carrying out of this invention and are explained in more detail.

According to the Process 1, pyrrolopyridazine derivatives (I) can be prepared by reacting the 1-amino-2-acylpyrrole derivative (II) or a salt thereof and the compound (III) or a salt thereof in the presence of a catalytic amount of acid catalyst in an inert solvent, preferably with concomitant removal of the water being produced by physical (e.g. Dean-Stark trap) or chemical (e.g. molecular sieves) means. Suitable acid catalyst is, for example p-toluenesulfonic acid, methanesulfonic acid, hydrochloric acid, trifluoroacetic acid and so on. Suitable inert solvent is, for example, benzene, toluene, tetrahydrofuran and the like.

Another ring forming process is described in Process 12, in this process pyrrolopyridazine derivatives (I) can be also prepared reacting 1-aminopyrole derivative (V) or a salt thereof and β-diketone derivative or a salt thereof under the similar condition before mentioned Process 1, and therefore the reaction conditions can be referred to those of the Process 1.

The compounds of the present invention can be purified by any conventional purification methods employed for purifying organic compounds, such as re-crystallization, column chromatography, thin-layer chromatography, high-performance liquid chromatography and the like. The compounds can be identified by conventional methods such as NMR spectrography, mass spectrography, IR spectrography, elemental analysis, and measurement of melting point.

Suitable salts of the object and the starting compounds in Processes 1 to 40 can be referred to the ones as exemplified for the compound (I).

The new pyrrolopyridazine derivatives (I) and pharmaceutically acceptable salts thereof hardly possess a strong inhibitory activity against phosphodiesterase III (PDE III), but possess a strong inhibitory activity against phosphodiesterase IV (PDE IV) and a strong inhibitory activity on the tumor necrosis factor (TNF).

That is, the pyrrolopyridazine derivatives (I) and pharmaceutically acceptable salts thereof are selective inhibitors of phosphodiesterase IV (PDE IV) and inhibitors on the production of tumor necrosis factor (TNF).

Accordingly, the new pyrrolopyridazine derivatives (I) and a pharmaceutically acceptable salt thereof can be used for prophylactic and therapeutic treatment of PDE-IV and TNF mediated diseases such as chronic inflammatory diseases (e.g., rheumatoid arthritis, osteoarthritis, emphysema, chronic bronchiolitis, allergic rhinitis, etc.), osteoporosis, rejection by transplantation, asthma, chronic obstructive pulmonary disease (COPD), eosinophilia, fibrotic disease (e.g., cystic fibrosis, pulmonary fibrosis, hepatic fibrosis, renal fibrosis, etc.), (viral alcoholic, drug-induced) acute and fulminant hepatitis, hepatic steatosis (alcoholic and non-alcoholic steato-hepatitis), chronic (viral and non-viral) hepatitis, hepatic cirrhosis, autoimmune hepatitis, pancreatitis, nephritis, endotoxin shock, specific autoimmune diseases [e.g., ankylosing spondylitis, autoimmune encephalomyelitis, autoimmune hematological disorders (e.g., hemolytic anemia, aplastic anemia, pure red cell anemia, idiopathic thrombocytopenia, etc.), systemic lupus erythematosus (SLE), polychondritis, scleroderma, Wegener granulomatosis, dermatomyositis, chronic active hepatitis (Wilson's disease, etc.), myasthenia gravis, idiopathic sprue, autoimmune inflammatory bowel disease (e.g., ulcerative colitis, Crohn's disease, etc.), endocrine ophthalmopathy, Grave's disease, sarcoidosis, multiple sclerosis, primary biliary cirrhosis, juvenile diabetes (diabetes mellitus type I), Reiter's syndrome, non infection uveitis, autoimmune keratitis (e.g., keratoconjunctivitis sicca, vernal keratoconjunctivitis, etc.), interstitial lung fibrosis, psoriatic arthritis, etc.], dermatological disorders associated with PDE-IV enzyme (such as psoriasis and other benign or malignant proliferative skin diseases, atopic dermatitis, and urticaria), neurodegenerative disorders such as Parkinson disease, Alzheimer's disease, acute and chronic multiple sclerosis, cancer cachexia, viral infection, AIDS cachexia, thrombosis, and the like.

For therapeutic administration, the compound (I), or its prodrug, or a salt thereof can be administered alone or in the form of a mixture, preferably, with a pharmaceutical vehicle or carrier.

The active ingredient of this invention can be used in the form of a pharmaceutical preparation, for example, in solid, semisolid or liquid form, which contains a compound (I), as an active ingredient, in admixture with an organic or inorganic carrier or excipient suitable for external (topical), enteral, intravenous, intramuscular, parenteral or intra-mucous applications. The active ingredient can be formulated, for example, with the conventional non-toxic, pharmaceutically acceptable carriers for ointment, cream, plaster, tablets, pellets, capsules, suppositories, solution (saline, for example), emulsion, suspension (olive oil, for example), aerosols, pills, powders, syrups, injections, troches, cataplasms, aromatic waters, lotions, buccal tablets, sublingual tablets, nasal drops and any other form suitable for use. The carriers which can be used are water, wax, glucose, lactose, gum acacia, gelatin, mannitol, starch paster, magnesium trisilicate, talc, corn starch, keratin, paraffin, colloidal silica, potato starch, urea and other carriers suitable for use in manufacturing preparations, in solid, semisolid, or liquid form, and in addition auxiliary, stabilizing, thickening and coloring agents and perfumes may be used. The active compound is included in a pharmaceutical composition in an effective amount sufficient to produce the desired effect upon the process or condition of the diseases.

The active ingredient can be formulated into, for example, preparations for oral application, preparations for injection, preparations for external application, preparations for inhalation, and preparations for application to mucous membranes.

Further, the compound of this invention can be used in combination with other therapeutic compounds. In particular, the combinations of the PDE4 inhibiting compound of this invention can be advantageously used in combination with i) Leukotriene receptor antagonists, ii) Leukotriene biosynthesis inhibitors, iii) COX-2 selective inhibitors, iv) statins, v) NSAIDs, vi) M2/M3 antagonists, vii) corticosteroids, viii) Hi (histamine) receptor antagonists, ix) beta 2 adrenoceptor agonist, x) interferon, xi) antiviral drugs for hepatitis C virus (HCV) such as protease inhibitor, helicase inhibitor, polymerase inhibitor, or the like, xii) antiviral drug for hepatitis B virus such as lamivudine, xiii) ursodesoxycholic acid, xiv) glycyrrhizin, xv) human grouth factor (HGF), xvi) aminosalicylic acid such as salazosulfapyridine, mesalazin, or the like, xvii) steroids such as prednisolone farnesylate, xviii) immunosuppressant such as azathioprine, 6-mercaptopurine, tacrolimus, and the like.

Mammals which may be treated by the present invention include livestock mammals such as cows, horses, etc., domestic animals such as dogs, cats, rats, etc. and humans, preferably humans.

While the dosage of therapeutically effective amount of the compound (I) will vary depending upon the age and condition of each individual patient, an average single dose to a human patient of about 0.01 mg, 0.1 mg, 1 mg, 10 mg, 50 mg, 100 mg, 250 mg, 500 mg, and 1000 mg of the compound (I) may be effective for treating the above-mentioned diseases. In general, amounts between 0.01 mg/body and about 1,000 mg/body may be administered per day.

In order to show the utilities of the pyrrolopyridazine derivatives (I) and a pharmaceutically acceptable salt thereof of the present invention, pharmacological test data of the representative compound of the pyrrolopyridazine derivatives (I) are illustrated in the following.

(a) Inhibition of U937 Phosphodiesterase IV (PDE IV)

1. Test Method:

Cultured U937 cells were washed twice and harvested with phosphate-buffered saline (PBS) by cell-scraper. After centrifugation, the cell pellet was suspended in homogenizing buffer (0.5% deoxycholate [DOC], 5 mM 2-mercaptoethanol, 1 μM leupeptin, 100 μM PMSF, 20 μM p-tosyl-L-lysine-chloromethyl ketone [TLCK] in PBS). The cell suspension was then sonicated for a couple of minutes and homogenized by a glass-Teflon homogenizer with twenty strokes. The homogenate was centrifuged at 200 g for 30 minutes, and the supernatant was further ultra-centrifuged at 100,000×g for 90 minutes (4° C.). The final supernatant was dialyzed against dialysis buffer, which was the same component as homogenizing buffer without DOC. The dialysate of enzyme preparation was stored at −20° C. until assay.

PDE4, activity was estimated with a Phosphodiesterase [$^3$H]cAMP SPA Enzyme Assay System (Amersham Pharmacia Biotech), using a 96 well Opti-plate. Reactions were initiated by addition of 0.025 μCi/well of [$^3$H]cAMP to the enzyme mixture containing 50 mM Tris-HCl (pH 7.5), 8.3 mM $MgCl_2$, 1.7 mM EGTA, and various concentrations of the test compound or vehicle. CI-930 (10 μM in final), a specific PDE3, inhibitor, was also added in the reaction mixture. After incubation at 30° C. for 15 minutes, 50 μL of SPA beads suspension was added to each well. The well-plate was then shaken for 20 minutes by a plate mixer. Radio-activity in each well was counted by a Top Counter.

Test compounds were dissolved in 100% dimethylsulfoxide (DMSO) and diluted into respective concentrations with the final solution containing 1% v/v of DMSO.

$IC_{50}$ values of test compounds for the enzyme activity of PDE4 was determined from regression analysis for log-logit conversion values of percent inhibition in the compound-treated tubes compared to that of the control. Percent inhibition was calculated with the following equation: Inhibition (%)={1−(C−B)/(A−B)}×100; in which A, B and C means mean values of radio-activity counts (dpm) of control, blank and the compound-treated tubes, respectively.

2. Test Results

The following table illustrates the inhibitory activity on PDE-IV of the representative compound of formula (I):

| Example | Compound name | IC50 (μM) |
|---|---|---|
| 198 | 6-{4-[4-(aminocarbonyl)phenyl]-7-ethyl-2-methylpyrrolo[1,2-b]pyridazin-3-yl}hexanoic acid | <1 |

(b) Inhibition on TNF-alpha Production in Human Mononuclear Cells

1. Test Method (1) Human Peripheral Blood Mononuclear Cells (PBMCs) Preparation

Blood (30 ml for each person) was collected from the median cubital vein of healthy volunteer was divided 15 mL each in heparin containing conical tube and the same volume of RPMI1640 was added to each tube. Diluted blood was then piled up to 20 mL of Ficoll-Paque PLUS (Amersham Pharmacia Biotech) in polystyrene centrifuge tube. After centrifugation at 1,600 rpm for 30 minutes, cells gathering in the center area of the gradient were collected by capillary and washed with 40 mL of RPMI1640 in several times with centrifugation at 1,200 rpm for 10 minutes. PBMC finally precipitated were suspended in RPMI1640 containing 1% fetal bovine serum and antibiotics. After cell counting, final suspension at $3 \times 10^6$ cells/mL in culture medium was prepared.

(2) TNF-alpha Production from Stimulated PBMCs

Human PBMCs prepared by the density gradient method using Ficoll-Paque PLUS were suspended in the culture medium mentioned above with the concentration of $3 \times 10^6$ cells/mL and 0.5 mL of the suspension was sowed into each well of a 24-well culture plate. Cells were incubated in the $CO_2$ incubator for 24 hours with 0.25 mL of LPS in addition of 0.25 mL of concentrations of drugs or vehicle at the start of the incubation. Final concentration of LPS in the incubation medium was 1 μg/mL. After 24 hours, the supernatant of each well by centrifugation at 1,700 rpm for 10 minutes was stored at −80° C. until assay. TNF-alpha levels in the medium were measured by ELISA.

The $IC_{50}$ values of drugs on cytokine productions in LPS stimulated PBMC were estimated by the regression analysis for the relative values of cytokine level in the drug-treated wells compared to those of the vehicle-treated ones.

2. Test Results

| Example | Compound name | IC50 (nM) |
|---|---|---|
| 198 | 6-{4-[4-(aminocarbonyl)phenyl]-7-ethyl-2-methylpyrrolo[1,2-b]pyridazin-3-yl}hexanoic acid | <100 |

BEST MODE FOR CARRYING OUT THE INVENTION

The following examples are provided to further illustrate details for the preparation of the compounds of the present invention. The examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds.

The starting materials and intermediates are prepared by the application or adaptation of known methods, for example methods as described in the Reference Examples or their obvious chemical equivalents.

The abbreviations, symbols and terms used in the Preparations, Examples and Formulae have the following meanings.

DMF N,N-dimethylformamide
EtOAc or AcOEt Ethyl acetate
THF Tetrahydrofuran
Et3N Triethylamine
MeOH Methanol
EtOH Ethanol
BuOH Butanol
DCM Dichloromethane
Pd/C Palladium on carbon powder Preparation 1

To a suspension of 2-pyridinethiol (17 g) in tetrahydrofuran (200 mL) was added triethylamine (15.5 g) in an ice-water bath under $N_2$. To this was added a solution of 4-cyanobenzoyl chloride (25.3 g) in tetrahydrofuran (80 mL) below 10° C. over 30 minutes. After 15 minutes, the bath was removed and the mixture was stirred overnight at ambient temperature. The mixture was concentrated in vacuo. The residue was partitioned between chloroform and water. The organic layer was washed with saturated sodium bicarbonate and brine, dried over magnesium sulfate, and evaporated in vacuo. The residue (38 g) was triturated with isopropyl ether to give S-(2-pyridinyl) 4-cyanobenzenecarbothioate (325 g) as a pale brown solid.

S-(2-Pyridinyl) 4-cyanobenzenecarbothioate

NMR (CDCl$_3$, δ): 7.38 (1H, t, J=7 Hz), 7.72 (1H, d, J=8 Hz), 7.75-7.87 (3H, m), 8.11 (2H, d, J=8 Hz), 8.71 (1H, d, J=2 Hz) MS (ESI$^+$): m/z 241 (M+H)

The following compound(s) was (were) obtained in substantially the same manner as that of Preparation 1.

Preparation 2

S-(2-Pyridinyl) 2-chloro-4-pyridinecarbothioate

NMR (CDCl$_3$, δ): 7.40 (1H, m), 7.65-7.75 (2H, m), 7.75-7.90 (2H, m), 8.62 (1H, d, J=5 Hz), 8.70 (1H, m)

Preparation 4

S-(2-Pyridinyl) 3-cyanobenzenecarbothioate

NMR (CDCl$_3$, δ): 7.39 (1H, m), 7.66 (1H, t, J=8 Hz), 7.72 (1H, t, J=8 Hz), 7.83 (1H, m), 7.91 (1H, d, J=8 Hz), 8.24 (1H, d, J=8 Hz), 8.29 (1H, s), 8.71 (1H, m) MS (ESI$^+$): m/z 241 (M+H)

Preparation 5

S-(2-Pyridinyl) 3-methoxybenzenecarbothioate

NMR (CDCl$_3$, δ): 3.87 (3H, s), 7.16 (1H, m), 7.32-7.44 (2H, m), 7.51 (1H, m), 7.63 (1H, d, J=8 Hz), 7.71-7.83 (2H, m), 8.69 (1H, m)

Preparation 6

S-(2-Pyridinyl) 4-pyridinecarbothioate

NMR (CDCl$_3$, δ): 7.35-7.43 (1H, m), 7.73 (1H, d, J=8 Hz), 7.77-7.88 (3H, m), 8.70 (1H, d, J=7 Hz), 8.85 (2H, d, J=8 Hz) MS (ESI$^+$): m/z 217

Preparation 7

S-(2-Pyridinyl) 2-pyrazinecarbothioate

NMR (CDCl$_3$, δ): 7.38 (1H, m), 7.71 (1H, d, J=8 Hz), 7.82 (1H, m), 8.73 (2H, m), 8.86 (1H, m), 9.17 (1H, s)

Preparation 8

S-(2-Pyridinyl) 3-pyridinecarbothioate

NMR (CDCl$_3$, δ): 7.37 (1H, m), 7.46 (1H, m), 7.73 (1H, m), 7.83 (1H, m), 8.27 (1H, m), 8.68 (1H, m), 8.84 (1H, m), 9.23 (1H, m)

Preparation 9

To a solution of 2-ethyl-1H-pyrrole in toluene (120 mL) was added dropwise 1M methylmagnesium bromide in tetrahydrofuran (170 mL) in a dry ice-acetone bath below −60° C. over 30 minutes. Then the mixture was stirred in an ice-water bath for 40 minutes. To this reaction mixture was added S-(2-pyridinyl) 4-cyanobenzenecarbothioate (15.2 g) portionwise over 10 minutes in a dryice-acetone bath. After 1.5 hours stirring, saturated ammonium chloride (100 mL) was added therein and the reaction mixture was allowed to ambient temperature. The mixture was partitioned between ethyl acetate and water. The organic layer was washed with 1N sodium hydroxide (100 mL) twice, water, and brine, dried over magnesium sulfate, and evaporated in vacuo. The residue was triturated with isopropyl ether to give 4-[(5-ethyl-1H-pyrrol-2-yl)carbonyl]benzonitrile (12.7 g) as a pale yellow solid.

4-[(5-Ethyl-1H-pyrrol-2-yl)carbonyl]benzonitrile

NMR (CDCl$_3$, δ): 1.32 (3H, t, J=8 Hz), 2.75 (2H, q, J=8 Hz), 6.11 (1H, d, J=5 Hz), 6.76 (1H, d, J=5 Hz), 7.77 (2H, d, J=8 Hz), 7.94 (2H, d, J=8 Hz), 9.49 (1H, br s) MS (ESI$^+$): m/z 225 (M+H)

The following compound was obtained in substantially the same manner as that of Preparation 9.

Preparation 10

(2E)-1-(5-Ethyl-1H-pyrrol-2-yl)-3-phenyl-2-propen-1-one

NMR (CDCl$_3$, δ): 1.31 (3H, t, J=7 Hz), 2.73 (2H, q, J=7 Hz), 6.10 (1H, m), 7.02 (1H, m), 7.27 (1H, d, J=16 Hz), 7.35-7.43 (3H, m), 7.63 (2H, m), 7.79 (1H, d, J=16 Hz) MS (ESI$^+$): m/z 226 (M+H)

Preparation 11

To a solution of 4-[(5-ethyl-1H-pyrrol-2-yl)carbonyl]-benzonitrile (12.5 g) in N,N-dimethylformamide (63 mL) was added 60% sodium hydride in oil (2.68 g) in an ice-water bath under N$_2$. After 30 minutes, to the mixture was added 1-(aminooxy)-2,4-dinitrobenzene (13.3 g). After 2 hours, the mixture was partitioned between ethyl acetate and water. The aqueous layer was extracted with ethyl acetate. The combined organic layer was washed with water (100 mL) 3 times, 1N sodium hydroxide (100 mL), and brine, dried over magnesium sulfate, and evaporated in vacuo. The residue was purified by flash silica gel chromatography (silica gel, 500 mL) eluted with hexane-chloroform=1-2, 1-5, and 1-10 followed by triturated with isopropyl ether to give 4-[(1-amino-5-ethyl-1H-pyrrol-2-yl)carbonyl]benzonitrile (8.1 g, 60.7%) as an yellow solid. The mixed fraction and the mother layer (7 g) were repurified by flash silica gel chromatography (silica gel, 200 mL) eluted with hexane-chloroform=2-1 and 1-1 followed by triturated with isopropyl ether to give 4-[(1-amino-5-ethyl-1H-pyrrol-2-yl)carbonyl]benzonitrile (2.0 g, 15%) as a pale yellow solid.

4-[(1-Amino-5-ethyl-1H-pyrrol-2-yl)carbonyl]-benzonitrile

NMR (CDCl$_3$, δ): 1.29 (3H, t, J=8 Hz), 2.77 (2H, q, J=8 Hz), 5.75 (2H, br s), 5.94 (1H, d, J=5 Hz), 6.59 (1H, d, J=5 Hz), 7.76 (2H, d, J=8 Hz), 7.85 (2H, d, J=8 Hz) MS (ESI$^+$): m/z 240 (M+H)

The following compounds were obtained in substantially the same manner as that of Preparation 11.

Preparation 12

(1-Amino-5-ethyl-1H-pyrrol-2-yl)(2-chloro-4-pyridinyl)methanone

NMR (CDCl$_3$, δ): 1.29 (3H, t, J=7 Hz), 2.77 (2H, q, J=7 Hz), 5.71 (2H, s), 5.96 (1H, d, J=4 Hz), 6.63 (1H, d, J=4 Hz), 7.50 (1H, d, J=4 Hz), 7.61 (1H, s), 8.52 (1H, d, J=4 Hz) MS: (m/z) 250 (M+H)

Preparation 13

3-[(1-Amino-5-ethyl-1H-pyrrol-2-yl)carbonyl]-benzonitrile

NMR (CDCl$_3$, δ): 1.29 (3H, t, J=7 Hz), 2.77 (2H, q, J=7 Hz), 5.74 (2H, s), 5.94 (1H, d, J=5 Hz), 6.59 (1H, d, J=5 Hz), 7.59 (1H, t, J=8 Hz), 7.82 (1H, d, J=8 Hz), 8.00 (1H, d, J=8 Hz), 8.06 (1H, s)

Preparation 14

(2E)-1-(1-Amino-5-ethyl-1H-pyrrol-2-yl)-3-phenyl-2-propen-1-one

NMR (CDCl$_3$, δ): 1.28 (3H, t, J=7 Hz), 2.73 (2H, q, J=7 Hz), 5.93 (1H, d, J=5 Hz), 6.99 (1H, d, J=5 Hz), 7.30 (1H, d, J=16 Hz), 7.37-7.43 (3H, m), 7.62 (2H, m), 7.74 (1H, d, J=16 Hz) MS (ESI$^+$): m/z 241 (M+H)

Preparation 15

(1-Amino-5-ethyl-1H-pyrrol-2-yl)(3-methoxyphenyl)-methanone

NMR (CDCl$_3$, δ): 1.26 (3H, t, J=7 Hz), 2.75 (2H, q, J=7 Hz), 3.86 (3H, s), 5.79 (2H, s), 5.89 (1H, d, J=4 Hz), 6.67 (1H, d, J=4 Hz), 7.07 (1H, m), 7.29-7.40 (3H, m) MS (ESI$^+$): m/z 245

Preparation 16

(1-Amino-5-ethyl-1H-pyrrol-2-yl)(4-pyridinyl)methanone

NMR (CDCl$_3$, δ): 1.29 (3H, t, J=7 Hz), 2.77 (2H, q, J=7 Hz), 5.76 (2H, s), 5.94 (1H, d, J=4 Hz), 6.63 (1H, d, J=4 Hz), 7.58 (2H, d, J=7 Hz), 8.75 (2H, d, J=7 Hz) MS (ESI$^+$): m/z 216

Preparation 17

(1-Amino-5-ethyl-1H-pyrrol-2-yl)(2-pyrazinyl)methanone

NMR (CDCl$_3$, δ): 1.29 (3H, t, J=7 Hz), 2.77 (2H, q, J=7 Hz), 5.79 (2H, s), 5.98 (1H, d, J=4 Hz), 7.27 (1H, d, J=4 Hz), 8.63 (1H, m), 8.71 (1H, m), 9.17 (1H, m)

Preparation 18

(1-Amino-5-ethyl-1H-pyrrol-2-yl)(3-pyridinyl)methanone

NMR (CDCl$_3$, δ): 1.29 (3H, t, J=7 Hz), 2.77 (2H, q, J=7 Hz), 5.78 (2H, s), 5.94 (1H, d, J=4 Hz), 6.65 (1H, d, J=4 Hz), 7.39 (1H, m), 8.06 (1H, m), 8.74 (1H, m), 8.99 (1H, m)

Preparation 19

(1-Amino-5-ethyl-1H-pyrrol-2-yl)(5-bromo-3-pyridinyl)-methanone

NMR (CDCl$_3$, δ): 1.29 (3H, t, J=7 Hz), 2.76 (2H, q, J=7 Hz), 5.72 (2H, s), 5.96 (1H, m), 6.65 (1H, m), 8.19 (1H, m), 8.70 (1H, m), 8.89 (1H, m)

Preparation 20

To a solution of tert-butyl 3-oxobutanoate (20.0 g) in tetrahydrofuran (200 mL) was added 60% sodium hydride in oil (556 g) portionwise over 20 minutes in an ice-water bath under N₂. After 40 minutes, to the mixture was added ethyl 5-iodopentanoate (35.6 g) at the temperature. After 15 minutes, the mixture was stirred at ambient temperature. After 1 hour, the reaction mixture was heated at 50° C. for 24 hours. The cooled mixture was partitioned between ethyl acetate and water. The aqueous layer was extracted with ethyl acetate. The combined organic layer was washed with water and brine, dried over magnesium sulfate, and evaporated in vacuo. The residue was purified by flash silica gel chromatography (silica gel, 1 L) eluting with hexane-ethyl acetate=50-1, 20-1, 10-1, and 8-1 to give 1-tert-butyl 7-ethyl 2-acetylheptanedioate (27.3 g, 75.4%) as colorless oil.

1-tert-Butyl 7-ethyl 2-acetylheptanedioate

NMR (CDCl₃, δ): 1.20-1.38 (5H, m), 1.46 (9H, s), 1.54-1.71 (2H, m), 1.75-1.87 (2H, m), 2.12 (3H, s), 2.30 (2H, t, J=8 Hz), 3.30 (12H, t, J=8 Hz), 4.11 (2H, q, J=8 Hz)

The following compounds were obtained in substantially the same manner as that of Preparation 20.

Preparation 21

1-tert-Butyl 9-ethyl 2-acetylnonanedioate

NMR (CDCl₃, δ): 1.23-1.33 (9H, m), 1.46 (9H, s), 1.55 (2H, m), 1.77 (2H, m), 2.21 (3H, s), 2.28 (2H, t, J=7 Hz), 3.27 (1H, t, J=7 Hz), 4.12 (2H, q, J=7 Hz) MS (ESI⁺): m/z 315 (M+H)

Preparation 22 tert-Butyl 2-acetylhexanoate

NMR (CDCl₃, δ): 0.90 (3H, t, J=8 Hz), 1.28-1.40 (4H, m), 1.46 (9H, s), 1.73-1.89 (2H, m), 2.22 (3H, s), 3.30 (1H, t, J=8 Hz)

Preparation 23

1-tert-Butyl 8-ethyl 2-acetyloctanedioate

NMR (CDCl₃, δ): 1.21-1.33 (7H, m), 1.46 (9H, s), 1.54-1.69 (2H, m), 1.74-1.85 (2H, m), 2.21 (3H, s), 2.28 (2H, t, J=8 Hz), 3.29 (1H, t, J=8 Hz), 4.12 (2H, q, J=8 Hz)

Preparation 24

To a suspension of magnesium chloride (1.33 g) in dichloromethane (40 mL) was added 1-tert-butyl 7-ethyl 2-acetylheptanedioate (4.0 g) at ambient temperature under N₂.

To this mixture was added dropwise pyridine (2.26 mL) in an ice-water bath. Then the mixture was stirred at ambient temperature for 40 minutes. To the reaction mixture was added a solution of 3-cyanobenzoyl chloride (3.01 g) in dichloromethane (6 mL) dropwise over 2 minutes. The reaction mixture was stirred at ambient temperature for 2 hours. To the mixture was added 1N hydrogen chloride and ethyl acetate in an ice-water bath. The organic layer was washed with 1N hydrogen chloride, water, and brine, dried over magnesium sulfate, and evaporated in vacuo to give a solid. The residue was purified by flash silica gel chromatography (silica gel, 300 mL) eluting with hexane-ethyl acetate=10-1, 8-1, 5-1, and 3-1 to give 1-tert-butyl 7-ethyl 2-acetyl-2-(3-cyanobenzoyl)heptanedioate (4.23 g, 72.9%) as colorless oil.

1-tert-Butyl 7-ethyl 2-acetyl-2-(3-cyanobenzoyl)-heptanedioate

NMR (CDCl₃, δ): 1.25 (3H, t, J=8 Hz), 1.28-1.40 (11H, m), 1.63-1.75 (2H, m), 2.19-2.28 (2H, m), 2.32 (2H, t, J=8 Hz), 2.45 (3H, s), 4.11 (2H, q, J=8 Hz), 7.56 (1H, t, J=8 Hz), 7.80 (2H, dd, J=8, 1 Hz), 7.95 (2H, dd, J=8, 1 Hz), 8.06 (1H, br s) MS (ESI⁺): m/z 416 (M+H)

The following compounds were obtained in substantially the same manner as that of Preparation 24.

Preparation 25

Ethyl 2-isobutyryl-4-methyl-3-oxopentanoate

NMR (300 MHz, CDCl₃, δ): 1.10-1.23 (12H, m), 1.30-1.43 (3H, m), 2.91-3.10 (2H, m), 4.21-4.36 (2H, m)

Preparation 26

Ethyl 2-(2-chlorobenzoyl)-4-methyl-3-oxopentanoate

NMR (300 MHz, CDCl₃, δ): 0.79 (3H, t, J=75 Hz), 1.22 (6H, d, J=75 Hz), 3.36-3.54 (1H, m), 3.88 (2H, q, J=75 Hz), 7.26-7.44 (4H, m)

Preparation 27

Ethyl 4-methyl-2-(2-naphthoyl)-3-oxopentanoate

NMR (300 MHz, CDCl₃, δ): 0.76-1.03 (3H, m), 1.10-1.30 (6H, m), 2.56-2.71 (½H, m), 2.88-3.04 (⅙H, m), 3.20-3.35 (⅓H, m), 3.72-4.336 (3H, m), 7.50-7.68 (2+⅓H, m), 7.82-8.01 (3+⅔H, m), 8.09 (⅓H, s), 8.35 (½H, s), 8.41 (⅙H, s) MS (ES+): m/e 313.45

Preparation 28

1-tert-Butyl 7-ethyl 2-acetyl-2-[3-(trifluoromethyl)benzoyl]heptanedioate

NMR (CDCl₃, δ): 1.24 (3H, t, J=7 Hz), 1.32 (9H, s), 1.36-1.75 (4H, m), 2.15-2.36 (4H, m), 2.45 (3H, s), 4.11 (2H, q, J=7 Hz), 7.56 (1H, t, J=8 Hz), 7.79 (1H, d, J=8 Hz), 7.93 (1H, d, J=8 Hz), 8.04 (1H, s)

Preparation 29

1-tert-Butyl 7-ethyl 2-acetyl-2-[(5-methyl-3-pyridinyl)carbonyl]heptanedioate

NMR (CDCl₃, δ): 1.24 (3H, t, J=7 Hz), 1.27-1.42 (2H, m), 1.34 (9H, s), 1.65-1.77 (2H, m), 2.16-2.35 (4H, m), 2.39 (3H, s), 2.43 (3H, s), 4.10 (2H, q, J=7 Hz), 7.87 (1H, s), 8.56 (1H, s), 8.73 (1H, s) MS (ESI⁺): m/z 406 (M+H)

Preparation 30

1-tert-Butyl 7-ethyl 2-(methoxyacetyl)-2-[(3-methoxy-5isoxazolyl)carbonyl]heptanedioate NMR (CDCl₃, δ): 1.25 (3H, t, J=7 Hz), 1.39 (9H, s), 1.35-1.50 (2H, m), 1.64-1.75 (2H, m), 2.15-2.23 (2H, m), 2.32 (2H, t, J=7 Hz), 3.40 (3H, s), 4.01 (3H, s), 4.12 (2H, q, J=7 Hz), 4.57 (2H, s), 6.54 (1H, s)

Preparation 31

1-tert-Butyl 7-ethyl 2-acetyl-2-[3-(1,3-oxazol-5-yl)benzoyl]heptanedioate

NMR (CDCl$_3$, δ): 1.23 (3H, t, J=7 Hz), 1.33 (9H, s), 1.30-1.43 (2H, m), 1.62-1.76 (2H, m), 2.17-2.35 (4H, m), 2.44 (3H, s), 4.09 (2H, q, J=7 Hz), 7.42 (1H, s), 7.48 (1H, t, J=8 Hz), 7.69 (1H, d, J=8 Hz), 7.82 (1H, d, J=8 Hz), 7.94 (1H, s), 8.09 (1H, m)

Preparation 32

1-tert-Butyl 7-ethyl 2-acetyl-2-(3,4-dichlorobenzoyl)heptanedioate

NMR (CDCl$_3$, δ): 1.23 (3H, t, J=7 Hz), 1.30-1.43 (2H, m), 1.35 (9H, s), 1.63-1.74 (2H, m), 2.15-2.34 (4H, m), 2.41 (3H, s), 4.10 (2H, q, J=7 Hz), 7.48 (1H, d, J=8 Hz), 7.56 (1H, dd, J=2, 8 Hz), 7.88 (1H, d, J=2 Hz)

Preparation 33

1-tert-Butyl 7-ethyl 2-acetyl-2-[(4-chloro-2-pyridinyl)carbonyl]heptanedioate

NMR (CDCl$_3$, δ): 1.23-1.30 (3H, m), 1.25 (9H, s), 1.40-1.58 (2H, m), 1.65-1.77 (2H, m), 2.10-2.21 (2H, m), 2.35 (2H, t, J=7 Hz), 2.61 (3H, s), 4.12 (2H, q, J=7 Hz), 7.39 (1H, m), 8.04 (1H, m), 8.43 (1H, d, J=5 Hz) MS (ESI$^+$): m/z 426 (M+H)

Preparation 34

1-tert-Butyl 7-ethyl 2-[(5-chloro-2-thienyl)carbonyl]-2-(methoxyacetyl)heptanedioate NMR (CDCl$_3$, δ): 1.23 (3H, t, J=7 Hz), 1.25-1.40 (2H, m), 1.41 (9H, s), 1.62-1.74 (2H, m), 2.26-2.37 (4H, m), 3.37 (3H, s), 4.11 (2H, q, J=7 Hz), 4.30 (1H, d, J=17 Hz), 4.42 (1H, d, J=17 Hz), 6.92 (1H, d, J=4 Hz), 7.39 (1H, d, J=4 Hz)

Preparation 35

1-tert-Butyl 7-ethyl 2-acetyl-2-[(6-methoxy-2-pyrazinyl)carbonyl]heptanedioate

NMR (CDCl$_3$, δ): 1.24 (3H, t, J=7 Hz), 1.26 (9H, s), 1.38-1.49 (2H, m), 1.66-1.80 (2H, m), 2.14-2.26 (2H, m), 2.33 (2H, t, J=7 Hz), 2.57 (3H, s), 3.90 (3H, s), 4.12 (2H, q, J=7 Hz), 8.37 (1H, s), 8.83 (1H, s)

Preparation 36

1-tert-Butyl 7-ethyl 2-acetyl-2-(1-benzofuran-2-ylcarbonyl)heptanedioate

NMR (CDCl$_3$, δ): 1.23 (3H, t, J=7 Hz), 1.33 (9H, s), 1.38-1.55 (2H, m), 1.64-1.77 (2H, m), 2.23-2.36 (4H, m), 2.49 (3H, s), 4.08 (2H, q, J=7 Hz), 7.32 (1H, m), 7.46 (2H, m), 7.54 (1H, s), 7.71 (1H, d, J=8 Hz)

Preparation 37

1-tert-Butyl 7-ethyl 2-acetyl-2-(1-benzothien-2-ylcarbonyl)heptanedioate

NMR (CDCl$_3$, δ): 1.23 (3H, t, J=7 Hz), 1.30-1.45 (2H, m), 1.39 (9H, s), 1.62-1.75 (2H, m), 2.25-2.38 (4H, m), 2.40 (3H, s), 4.10 (2H, q, J=7 Hz), 7.36-7.51 (2H, m), 7.76 (1H, s), 7.82-7.88 (2H, m)

Preparation 38

1-tert-Butyl 7-ethyl 2-acetyl-2-(1,3-oxazol-5-ylcarbonyl)heptanedioate

NMR (CDCl$_3$, δ): 1.24 (3H, t, J=7 Hz), 1.30-1.45 (2H, m), 1.38 (9H, s), 1.63-1.77 (2H, m), 2.15-2.27 (2H, m), 2.30 (2H, t, J=7 Hz), 2.43 (3H, s), 4.10 (2H, q, J=7 Hz), 7.80 (1H, s), 7.93 (1H, s)

Preparation 39

1-tert-Butyl 7-ethyl 2-acetyl-2-benzoylheptanedioate

NMR (CDCl$_3$, δ): 1.26 (3H, t, J=7 Hz), 1.20-1.40 (2H, m), 1.32 (9H, s), 1.60-1.73 (2H, m), 2.26-2.38 (4H, m), 2.40 (3H, s), 4.12 (2H, q, J=7 Hz), 7.36-7.78 (5H, m)

Preparation 40

1-tert-Butyl 7-ethyl 2-acetyl-2-(6-quinolinylcarbonyl)heptanedioate

NMR (CDCl$_3$, δ): 1.21 (3H, t, J=7 Hz), 1.30 (9H, s), 1.32-1.47 (2H, m), 1.64-1.77 (2H, m), 2.26-2.38 (4H, m), 2.46 (3H, s), 4.08 (2H, q, J=7 Hz), 7.48 (1H, m), 8.04 (1H, dd, J=2 Hz, 8 Hz), 8.13 (1H, d, J=8 Hz), 8.23 (1H, d, J=8 Hz), 8.28 (1H, d, J=2 Hz), 9.00 (1H, m) MS (ESI$^+$): m/z 442 (M+H)

Preparation 41

1-tert-Butyl 9-ethyl 2-acetyl-2-[4-({[(benzyloxy)carbonyl]amino}sulfonyl)benzoyl]-nonanedioate NMR (CDCl$_3$, δ): 1.23-1.37 (11H, m), 1.60 (9H, s), 2.15-2.31 (4H, m), 2.46 (3H, s), 4.12 (2H, q, J=7 Hz), 5.10 (2H, s), 7.26-7.40 (5H, m), 7.65 (1H, s, br), 7.84 (2H, d, J=9 Hz), 8.06 (2H, d, J=9 Hz)

Preparation 42

1-tert-Butyl 7-ethyl 2-acetyl-2-(2-chloroisonicotinoyl)heptanedioate

NMR (CDCl$_3$, δ): 1.20-1.40 (14H, m), 1.61-1.75 (2H, m), 2.19-2.28 (2H, m), 2.20 (2H, t, J=8 Hz), 2.31 (2H, t, J=8 Hz), 2.46 (3H, s), 4.11 (2H, q, J=8 Hz), 7.41 (1H, dd, J=7, 1 Hz), 7.55 (1H, d, J=1 Hz), 8.50 (1H, d, J=7 Hz)

Preparation 43

1-tert-Butyl 7-ethyl 2-acetyl-2-[3-(methylsulfonyl)benzoyl]heptanedioate

NMR (CDCl$_3$, δ): 1.24 (3H, t, J=8 Hz), 1.27-1.40 (11H, m), 1.61-1.75 (2H, m), 2.19-2.35 (4H, m), 2.46 (3H, s), 3.07 (3H, s), 4.10 (2H, q, J=8 Hz), 7.65 (1H, t, J=8 Hz), 7.99 (1H, dd, J=8, 1 Hz), 8.09 (2H, br d, J=8 Hz), 8.34 (1H, br s)

Preparation 44

1-tert-Butyl 7-ethyl 2-acetyl-2-(3-nitrobenzoyl)heptanedioate

NMR (CDCl$_3$, δ): 1.30-1.39 (12H, m), 1.61-1.75 (2H, m), 2.19-2.35 (4H, m), 2.47 (3H, s), 4.10 (2H, q, J=8 Hz), 7.63 (1H, t, J=8 Hz), 8.09 (1H, br d, J=8 Hz), 8.39 (1H, br d, J=8 Hz), 8.60 (1H, br s)

Preparation 45 tert-Butyl 2-acetyl-2-(4-cyanobenzoyl)hexanoate

NMR (CDCl$_3$, δ): 0.90 (3H, t, J=8 Hz), 1.20-1.44 (13H, m), 2.15-2.25 (2H, m), 2.45 (3H, s), 7.70 (2H, d, J=8 Hz), 7.83 (2H, d, J=8 Hz)

Preparation 46

1-tert-Butyl 7-ethyl 2-acetyl-2-[(5-bromo-3-pyridinyl)carbonyl]heptanedioate

NMR (CDCl$_3$, δ): 1.25 (3H, t, J=7 Hz), 1.36 (9H, s), 1.32-1.45 (2H, m), 1.65-1.77 (2H, m), 2.18-2.28 (2H, m), 2.32 (2H, t, J=7 Hz), 2.45 (3H, s), 4.11 (2H, q, J=7 Hz), 8.20 (1H, m), 8.80 (2H, m) MS: (m/z) 470, 472 (M+H)

Preparation 47

1-tert-Butyl 7-ethyl 2-(2-chloroisonicotinoyl)-2-[(methylthio)acetyl]heptanedioate NMR (CDCl$_3$, δ): 1.24 (3H, t, J=7 Hz), 1.37 (9H, s), 1.23-1.45 (2H, m), 1.63-1.77 (2H, m), 2.05 (3H, s), 2.16-2.28 (2H, m), 2.32 (2H, t, J=7 Hz), 3.16 (1H, d, J=17 Hz), 4.07 (1H, d, J=17 Hz), 4.11 (2H, q, J=7 Hz), 7.68 (1H, d, J=5 Hz), 7.87 (1H, s), 8.49 (1H, d, J=5 Hz)

Preparation 48

Ethyl 2-(4-fluorobenzoyl)-3-oxobutanoate

NMR (CDCl$_3$, δ): (mixture of tautomers) 0.97 and 1.02 (3H, t, J=7 Hz), 2.07 and 2.42 (3H, s), 4.01 and 4.13 (2H, q, J=7 Hz), 7.06-7.18, 7.56, and 7.85 (4H, m) MS (ESI$^+$): m/z 275 (M+H)

Preparation 49

1-tert-Butyl 8-ethyl 2-acetyl-2-(3-cyanobenzoyl)octanedioate

NMR (CDCl$_3$, δ): 1.21-1.46 (16H, m), 1.56-1.70 (2H, m), 2.15-2.25 (2H, m), 2.29 (2H, t, J=8 Hz), 2.45 (3H, s), 4.12 (2H, q, J=8 Hz), 7.56 (1H, t, J=8 Hz), 7.80 (2H, dd, J=8, 1 Hz), 7.95 (2H, dd, J=8, 1 Hz), 8.05 (1H, br s)

Preparation 50

1-tert-Butyl 7-ethyl 2-acetyl-2-[(6-chloro-2-pyridinyl)carbonyl]heptanedioate

NMR (CDCl$_3$, δ): 1.25 (3H, t, J=7 Hz), 1.27 (9H, s), 1.20-1.78 (4H, m), 2.08 (2H, t, J=7 Hz), 2.26-2.40 (2H, m), 2.69 (3H, s), 4.12 (2H, q, J=7 Hz), 7.43 (1H, d, J=8 Hz), 7.81 (1H, t, J=8 Hz), 7.96 (1H, d, J=8 Hz) MS (ESI$^+$): m/z 426

Preparation 51

1-tert-Butyl 7-ethyl 2-acetyl-2-(3-methoxybenzoyl)heptanedioate

NMR (CDCl$_3$, δ): 1.25 (3H, m), 1.34 (9H, s), 1.20-1.92 (4H, m), 2.10-2.38 (4H, m), 2.41 (3H, s), 3.84 (3H, s), 4.04-4.22 (2H, m), 7.08 (1H, br), 7.23-7.40 (3H, m)

Preparation 52

1-tert-Butyl 7-ethyl 2-acetyl-2-(3,5-dichlorobenzoyl)heptanedioate

NMR (CDCl$_3$, δ): 1.24 (3H, t, J=7 Hz), 1.26-1.40 (2H, m), 1.36 (9H, s), 1.63-1.76 (2H, m), 2.15-2.36 (4H, m), 2.43 (3H, s), 4.10 (2H, q, J=7 Hz), 7.51 (1H, m), 7.60 (2H, m)

Preparation 53

1-tert-Butyl 7-ethyl 2-acetyl-2-[(5-chloro-2-thienyl)carbonyl]heptanedioate

NMR (CDCl$_3$, δ): 1.23 (3H, t, J=7 Hz), 1.40 (9H, s), 1.30-1.90 (4H, m), 2.20-2.35 (4H, m), 2.38 (3H, s), 4.11 (2H, q, J=7 Hz), 6.91 (1H, d, J=4 Hz), 7.32 (1H, d, J=4 Hz)

Preparation 54

1-tert-Butyl 7-ethyl 2-acetyl-2-(3-fluorobenzoyl)heptanedioate

NMR (CDCl$_3$, δ): 1.23 (3H, t, J=7 Hz), 1.35 (9H, s), 1.35-1.45 (2H, m), 1.64-1.74 (2H, m), 2.16-2.35 (4H, m), 2.42 (3H, s), 4.09 (2H, q, J=7 Hz), 7.24 (1H, m), 7.35-7.43 (1H, m), 7.46-7.53 (2H, m)

Preparation 55

1-tert-Butyl 7-ethyl 2-acetyl-2-(3-quinolinylcarbonyl)heptanedioate

NMR (CDCl$_3$, δ): 1.22 (3H, t, J=7 Hz), 1.33 (9H, s), 1.33-1.53 (2H, m), 1.65-1.78 (2H, m), 2.25-2.43 (4H, m), 2.47 (3H, s), 4.08 (2H, q, J=7 Hz), 7.63 (1H, t, J=8 Hz), 7.81-7.87 (1H, t, J=8 Hz), 7.91 (1H, d, J=8 Hz), 8.56 (1H, m), 9.24 (1H, m) MS (ESI$^+$): m/z 442

Preparation 56

1-tert-Butyl 7-ethyl 2-acetyl-2-isonicotinoylheptanedioate

NMR (CDCl$_3$, δ): 1.23 (3H, t, J=7 Hz), 1.31 (9H, s), 1.30-1.45 (2H, m), 1.65-1.76 (2H, m), 2.18-2.28 (2H, m), 2.31 (2H, t, J=7 Hz), 2.45 (3H, s), 4.10 (2H, q, J=7 Hz), 7.52 (2H, d, J=7 Hz), 8.75 (2H, d, J=7 Hz)

Preparation 57

1-tert-Butyl 7-ethyl 2-acetyl-2-[(3-methoxy-5-isoxazolyl)carbonyl]heptanedioate

NMR (CDCl$_3$, δ): 1.25 (3H, t, J=7 Hz), 1.39 (9H, s), 1.35-1.50 (2H, m), 1.62-1.75 (2H, m), 2.11-2.23 (2H, m), 2.33 (2H, t, J=7 Hz), 2.49 (3H, s), 4.01 (3H, s), 4.11 (2H, q, J=7 Hz), 6.53 (1H, s)

Preparation 58

1-tert-Butyl 7-ethyl 2-acetyl-2-[(5-methyl-3-isoxazolyl)carbonyl]heptanedioate

NMR (CDCl$_3$, δ): 1.24 (3H, t, J=7 Hz), 1.31-1.48 (2H, m), 1.37 (9H, s), 1.63-1.75 (2H, m), 2.18-2.26 (2H, m), 2.31 (2H, t, J=7 Hz), 2.47 (3H, s), 2.50 (3H, s), 4.11 (2H, q, J=7 Hz), 6.38 (1H, s)

Preparation 59

1-tert-Butyl 7-ethyl 2-(2-chloroisonicotinoyl)-2-(methoxyacetyl)heptanedioate

NMR (CDCl₃, δ): 1.24 (3H, t, J=7 Hz), 1.32-1.45 (2H, m), 1.36 (9H, s), 1.64-1.78 (2H, m), 2.16-2.28 (2H, m), 2.31 (2H, t, J=7 Hz), 3.36 (3H, s), 4.11 (2H, q, J=7 Hz), 4.25 (1H, d, J=17 Hz), 4.39 (1H, d, J=17 Hz), 7.39 (1H, d, J=5 Hz), 7.54 (1H, s), 8.50 (1H, d, J=5 Hz) MS (ESI⁺): m/z 456

Preparation 60

1-tert-Butyl 7-ethyl 2-(methoxyacetyl)-2-(3-methoxybenzoyl)heptanedioate

NMR (CDCl₃, δ): 1.22 (3H, t, J=7 Hz), 1.25-1.33 (2H, m), 1.34 (9H, s), 1.60-1.75 (2H, m), 2.15-2.40 (4H, m), 3.38 (3H, s), 3.83 (3H, s), 4.08 (2H, q, J=7 Hz), 4.39 (1H, d, J=17 Hz), 4.55 (1H, d, J=17 Hz), 7.07 (1H, m), 7.26-7.34 (3H, m) MS (ESI⁺): m/z 451

Preparation 61

1-tert-Butyl 7-ethyl 2-(methoxyacetyl)-2-(6-quinolinylcarbonyl)heptanedioate

NMR (CDCl₃, δ): 1.25 (3H, t, J=7 Hz), 1.32 (9H, s), 1.30-1.50 (2H, m), 1.65-1.78 (2H, m), 2.26-2.44 (4H, m), 3.38 (3H, s), 4.11 (2H, q, J=7 Hz), 4.38 (1H, d, J=17 Hz), 4.57 (1H, d, J=17 Hz), 7.47 (1H, m), 8.03 (1H, d, J=8 Hz), 8.13 (1H, d, J=8 Hz), 8.28 (1H, d, J=8 Hz), 8.27 (1H, s), 9.01 (1H, m) MS (ESI⁺): m/z 472

Preparation 62

1-tert-Butyl 7-ethyl 2-(methoxyacetyl)-2-(3-pyridinylcarbonyl)heptanedioate

NMR (CDCl₃, δ): 1.23 (3H, 1, J=7 Hz), 1.30-1.47 (2H, m), 1.35 (9H, s), 1.63-1.78 (2H, m), 2.22-2.38 (4H, m), 3.37 (3H, s), 4.10 (2H, q, J=7 Hz), 4.32 (1H, d, J=17 Hz), 4.45 (1H, d, J=17 Hz), 7.37 (1H, m), 8.03 (1H, m), 8.73 (1H, m), 8.92 (1H, m)

Preparation 63

1-tert-Butyl 7-ethyl 2-(3-chlorobenzoyl)-2-(methoxyacetyl)heptanedioate

NMR (CDCl₃, δ): 1.25 (3H, t, J=7 Hz), 1.35 (9H, s), 1.20-1.50 (2H, m), 1.60-1.73 (2H, m), 2.25-2.35 (4H, m), 3.37 (3H, s), 4.12 (2H, q, J=7 Hz), 4.35 (1H, d, J=17 Hz), 4.50 (1H, d, J=17 Hz), 7.34 (1H, m), 7.48 (1H, d, J=8 Hz), 7.59 (1H, d, J=8 Hz), 7.73 (1H, m)

Preparation 64

1-tert-Butyl 7-ethyl 2-acetyl-2-(3-methylbenzoyl)heptanedioate

NMR (CDCl₃, δ): 1.25 (3H, t, J=7 Hz), 1.30-1.40 (2H, m), 1.33 (9H, s), 1.60-1.72 (2H, m), 2.10-2.38 (4H, m), 2.21 (3H, s), 2.39 (3H, s), 4.10 (2H, q, J=7 Hz), 7.26-7.36 (2H, m), 7.48-7.62 (2H, m) MS (ESI⁺): m/z 405

Preparation 67

1-tert-Butyl 7-ethyl 2-(methoxyacetyl)-2-[(5-methyl-3-pyridinyl)carbonyl]heptanedioate NMR (CDCl₃, δ): 1.25 (3H, t, J=7 Hz), 1.36 (9H, s), 1.30-1.45 (2H, m), 1.62-1.76 (2H, m), 2.20-2.36 (4H, m), 2.40 (3H, s), 3.38 (3H, s), 4.10 (2H, q, J=7 Hz), 4.34 (1H, d, J=17 Hz), 4.49 (1H, d, J=17 Hz), 7.86 (1H, s), 8.56 (1H, s), 8.73 (1H, s) MS (ESI⁺): m/z 436

Preparation 68

1-tert-Butyl 7-ethyl 2-acetyl-2-[(5-bromo-3-pyridinyl)carbonyl]heptanedioate

NMR (CDCl₃, δ): 1.25 (3H, t, J=7 Hz), 1.36 (9H, s), 1.32-1.45 (2H, m), 1.65-1.77 (2H, m), 2.18-2.28 (2H, m), 2.32 (2H, t, J=7 Hz), 2.45 (3H, s), 4.11 (2H, q, J=7 Hz), 8.20 (1H, m), 8.80 (2H, m) MS (ESI⁺): m/z 470, 472

Preparation 69

1-tert-Butyl 7-ethyl 2-[(5-bromo-3-pyridinyl)carbonyl]-2-(methoxyacetyl)heptanedioate NMR (CDCl₃, δ): 1.24 (3H, t, J=7 Hz), 1.30-1.44 (2H, m), 1.37 (9H, s), 1.65-1.77 (2H, m), 2.18-2.36 (4H, m), 3.36 (3H, s), 4.10 (2H, q, J=7 Hz), 4.28 (1H, d, J=17 Hz), 4.40 (1H, d, J=17 Hz), 8.18 (1H, m), 8.80 (2H, m) MS (ESI⁺): m/z 500, 502

Preparation 70

1-tert-Butyl 7-ethyl 2-acetyl-2-[(5,6-dichloro-3-pyridinyl)carbonyl]heptanedioate NMR (CDCl₃, δ): 1.24 (3H, t, J=7 Hz), 1.25-1.40 (2H, m), 1.38 (9H, s), 1.65-1.75 (2H, m), 2.18-2.27 (2H, m), 2.28-2.37 (2H, m), 2.44 (3H, s), 4.12 (2H, q, J=7 Hz), 8.13 (1H, d, J=2 Hz), 8.57 (1H, d, J=2 Hz)

Preparation 71

1-tert-Butyl 6-ethyl 2-(methoxyacetyl)-2-[(5-methyl-3-pyridinyl)carbonyl]hexanedioate NMR (CDCl₃, δ): 1.24 (3H, t, J=7 Hz), 1.36 (9H, s), 1.60-1.80 (2H, m), 2.20-2.45 (4H, m), 2.39 (3H, s), 3.38 (3H, s), 4.12 (2H, q, J=7 Hz), 4.38 (1H, d, J=18 Hz), 4.50 (1H, d, J=18 Hz), 7.87 (1H, s), 8.55 (1H, s), 8.73 (1H, s) MS (ESI⁺): m/z 422

Preparation 72

1-tert-Butyl 5-ethyl 2-(methoxyacetyl)-2-[(5-methyl-3-pyridinyl)carbonyl]pentanedioate NMR (CDCl₃, δ): 1.24 (3H, t, J=7 Hz), 1.37 (9H, s), 2.23-2.70 (4H, m), 2.39 (3H, s), 3.37 (3H, s), 4.12 (2H, q, J=7 Hz), 4.32 (1H, d, J=18 Hz), 4.43 (1H, d, J=18 Hz), 7.84 (1H, s), 8.55 (1H, s), 8.73 (1H, s) MS (ESI⁺): m/z 408

Preparation 73

1-tert-Butyl 6-ethyl 2-acetyl-2-[(5-methyl-3-pyridinyl)carbonyl]hexanedioate

NMR (CDCl₃, δ): 1.24 (3H, t, J=7 Hz), 1.34 (9H, s), 1.60-1.75 (2H, m), 2.20-2.39 (4H, m), 2.39 (3H, s), 2.46 (3H, s), 4.11 (2H, q, J=7 Hz), 7.87 (1H, s), 8.56 (1H, s), 8.73 (1H, s) MS (ESI⁺): m/z 392

Preparation 74

1-tert-Butyl 5-ethyl 2-acetyl-2-[(5-methyl-3-pyridinyl)carbonyl]pentanedioate

NMR (CDCl₃, δ): 1.24 (3H, t, J=7 Hz), 1.36 (9H, s), 2.39 (3H, s), 2.44 (3H, s), 2.35-2.47 (2H, m), 2.56-2.70 (2H, m), 4.11 (2H, q, J=7 Hz), 7.88 (1H, s), 8.56 (1H, s), 8.74 (1H, s) MS (ESI⁺): m/z 378

Preparation 75

1-tert-Butyl 5-ethyl 2-acetyl-2-[(5-bromo-3-pyridinyl)carbonyl]pentanedioate

NMR (CDCl₃, δ): 1.24 (3H, t, J=7 Hz), 1.37 (9H, s), 2.40 (2H, t, J=7 Hz), 2.59 (2H, t, J=7 Hz), 2.46 (3H, s), 4.13 (2H, q, J=7 Hz), 8.20 (1H, t, J=3 Hz), 8.81 (2H, dd, J=7, 3 Hz)

Preparation 76

1-tert-Butyl 7-ethyl 2-(3-cyanobenzoyl)-2-(methoxyacetyl)heptanedioate

NMR (CDCl₃, δ): 1.20-1.41 (14H, m), 1.60-1.74 (2H, m), 2.27-2.34 (4H, m), 3.37 (83H, s), 4.10 (2H, q, J=8 Hz), 4.29 (1H, d, J=16 Hz), 4.46 (1H, d, J=16 Hz), 7.55 (1H, t, J=8 Hz), 7.80 (1H, dd, J=8, 1 Hz), 7.93 (1H, dd, J=8, 1 Hz), 8.04 (1H, br s)

Preparation 77

1-tert-Butyl 7-ethyl 2-[(acetyloxy)acetyl]-2-[(5-bromo-3-pyridinyl)carbonyl]heptanedioate NMR (CDCl₃, δ): 1.22-1.28 (5H, m), 1.36 (9H, s), 1.68 (2H, m), 2.14 (3H, s), 2.32 (2H, m), 4.11 (2H, q, J=7 Hz), 5.07 (1H, d, J=18 Hz), 5.34 (1H, d, J=18 Hz), 8.21 (1H, m), 8.81 (2H, m)

Preparation 78

To 1-tert-butyl 7-ethyl 2-acetyl-2-(3-cyanobenzoyl)-heptanedioate (4.2 g) was added trifluoroacetic acid (20 mL) in an ice-water bath. After 30 minutes, the bath was removed and the reaction mixture was stirred at ambient temperature. After 1 hour, the mixture was concentrated. The residue was dissolved in toluene and was evaporated in vacuo to give ethyl 6-(3-cyanobenzoyl)-7-oxooctanoate (3.20 g, 100.4%) as colorless oil.

Ethyl 6-(3-cyanobenzoyl)-7-oxooctanoate

NMR (CDCl₃, δ): 1.25 (3H, t, J=8 Hz), 1.28-1.40 (2H, m), 1.60-1.74 (2H, m), 1.91-2.14 (2H, m), 2.17 (3H, s), 2.31 (2H, t, J=8 Hz), 4.11 (2H, q, J=8 Hz), 4.39 (1H, t, J=8 Hz), 7.64 (1H, t, J=8 Hz), 7.87 (2H, dd, J=8, 1 Hz), 8.20 (2H, dd, J=8, 1 Hz), 8.26 (1H, br s) MS (ESI⁻): m/z 314 (M−H)

The following compounds were obtained in substantially the same manner as that of Preparation 78.

Preparation 79

Ethyl 7-oxo-6-[3-(trifluoromethyl)benzoyl]octanoate

NMR (CDCl₃, δ): 1.24 (3H, t, J=7 Hz), 1.32-1.43 (2H, m), 1.62-1.77 (2H, m), 1.96-2.17 (2H, m), 2.17 (3H, s), 2.30 (2H, t, J=7 Hz), 4.11 (2H, q, J=7 Hz), 4.44 (1H, t, J=7 Hz), 7.64 (1H, t, J=8 Hz), 7.86 (1H, d, J=8 Hz), 8.15 (1H, d, J=8 Hz), 8.24 (1H, s)

Preparation 80

Ethyl 6-[(5-methyl-3-pyridinyl)carbonyl]-7-oxooctanoate

NMR (CDCl₃, δ): 1.26 (3H, t, J=7 Hz), 1.27-1.44 (2H, m), 1.65-1.75 (2H, m), 1.90-2.12 (2H, m), 2.17 (3H, s), 2.25-2.34 (2H, m), 2.43 (3H, s), 4.10 (2H, q, J=7 Hz), 4.42 (1H, t, J=7 Hz), 8.03 (1H, s), 8.63 (1H, s), 8.98 (1H, s) MS (ESI⁺): m/z 306 (M+H)

Preparation 81

Ethyl 8-methoxy-6-[(3-methoxy-5-isoxazolyl)carbonyl]-7-oxooctanoate

NMR (CDCl₃, δ): 1.25 (3H, t, J=7 Hz), 1.34-1.47 (2H, m), 1.65-1.74 (2H, m), 1.83-2.03 (2H, m), 2.29 (2H, t, J=7 Hz), 3.31 (3H, s), 4.05 (5H, s), 4.11 (2H, q, J=7 Hz), 4.51 (1H, t, J=7 Hz), 6.56 (1H, s) MS (ESI⁺): m/z 342 (M+H)

Preparation 82

Ethyl 6-[3-(1,3-oxazol-5-yl)benzoyl]-7-oxooctanoate

NMR (CDCl₃, δ): 1.23 (3H, t, J=7 Hz), 1.33-1.46 (2H, m), 1.63-1.77 (2H, m), 1.95-2.17 (2H, m), 2.17 (3H, s), 2.30 (2H, t, J=7 Hz), 4.12 (2H, q, J=7 Hz), 4.46 (1H, t, J=7 Hz), 7.47 (1H, s), 7.56 (1H, t, J=8 Hz), 7.85-7.96 (2H, m), 7.98 (1H, s), 8.27 (1H, m)

Preparation 83

Ethyl 6-(3,4-dichlorobenzoyl)-7-oxooctanoate

NMR (CDCl₃, δ): 1.24 (3H, t, J=7 Hz), 1.30-1.43 (2H, m), 1.60-1.74 (2H, m), 1.91-2.14 (2H, m), 2.14 (3H, s), 2.30 (2H, t, J=7 Hz), 4.11 (2H, q, J=7 Hz), 4.34 (1H, t, J=7 Hz), 7.57 (1H, d, J=8 Hz), 7.78 (1H, dd, J=2, 8 Hz), 8.06 (1H, d, J=2 Hz)

Preparation 84

Ethyl 6-[(4-chloro-2-pyridinyl)carbonyl]-7-oxooctanoate

NMR (CDCl₃, δ): 1.25 (3H, t, J=7 Hz), 1.34-1.48 (2H, m), 1.62-1.77 (2H, m), 1.80-2.10 (2H, m), 2.31 (2H, t, J=7 Hz), 2.34 (3H, s), 4.12 (2H, q, J=7 Hz), 4.83-4.92 (1H, m), 7.49 (1H, dd, J=2 Hz, 5 Hz), 8.04 (1H, d, J=2 Hz), 8.57 (1H, d, J=5 Hz) MS (ESI⁺): m/z 326 (M+H)

Preparation 85

Ethyl 6-[(5-chloro-2-thienyl)carbonyl]-8-methoxy-7-oxooctanoate

NMR (CDCl₃, δ): 1.24 (3H, t, J=7 Hz), 1.32-1.42 (2H, m), 1.60-1.73 (2H, m), 1.84-2.06 (2H, m), 2.28 (2H, t, J=7 Hz), 3.30 (3H, s), 3.97 (1H, d, J=17 Hz), 4.06 (1H, d, J=17 Hz), 4.11 (2H, q, J=7 Hz), 4.40 (1H, t, J=7 Hz), 6.99 (1H, d, J=4 Hz), 7.56 (1H, d, J=4 Hz)

Preparation 86

Ethyl 6-[(6-methoxy-2-pyrazinyl)carbonyl]-7-oxooctanoate

NMR (CDCl$_3$, δ): 1.25 (3H, t, J=7 Hz), 1.34-1.48 (2H, m), 1.60-1.78 (2H, m), 1.88-2.08 (2H, m), 2.31 (3H, s), 2.32 (2H, t, J=7 Hz), 4.01 (3H, s), 4.11 (2H, q, J=7 Hz), 4.62 (1H, t, J=7 Hz), 8.44 (1H, s), 8.81 (1H, s) MS (ESI$^+$): m/z 323 (M+H)

Preparation 87

Ethyl 6-(1-benzofuran-2-ylcarbonyl)-7-oxooctanoate

NMR (CDCl$_3$, δ): 1.23 (3H, t, J=7 Hz), 1.34-1.48 (2H, m), 1.62-1.76 (2H, m), 1.93-2.19 (2H, m), 2.24 (3H, s), 2.30 (2H, t, J=7 Hz), 4.10 (2H, q, J=7 Hz), 4.37 (1H, t, J=7 Hz), 7.34 (1H, t, J=8 Hz), 7.51 (1H, t, J=8 Hz), 7.56-7.65 (2H, m), 7.73 (1H, d, J=8 Hz) MS (ESI$^+$): m/z 895 (M+H)

Preparation 88

Ethyl 6-(1-benzothien-2-ylcarbonyl)-7-oxooctanoate

NMR (CDCl$_3$, δ): 1.23 (3H, t, J=7 Hz), 1.35-1.48 (2H, m), 1.60-1.80 (2H, m), 1.95-2.17 (2H, m), 2.19 (3H, s), 2.30 (2H, t, J=7 Hz), 4.10 (2H, q, J=7 Hz), 4.36 (1H, t, J=7 Hz), 7.38-7.53 (2H, m), 7.82-7.93 (2H, m), 8.05 (1H, s)

Preparation 89

Ethyl 6-(1,3-oxazol-5-ylcarbonyl)-7-oxooctanoate

NMR (CDCl$_3$, δ): 1.25 (3H, t, J=7 Hz), 1.30-1.43 (2H, m), 1.65-1.78 (2H, m), 1.92-2.10 (2H, m), 2.21 (3H, s), 2.32 (2H, t, J=7 Hz), 4.11 (3H, m), 7.88 (1H, s), 8.05 (1H, s)

Preparation 90

Ethyl 6-benzoyl-7-oxooctanoate

NMR (CDCl$_3$, δ): 1.24 (3H, t, J=7 Hz), 1.29-1.42 (2H, m), 1.60-1.75 (2H, m), 1.92-2.12 (2H, m), 2.14 (3H, s), 2.29 (2H, t, J=7 Hz), 4.10 (2H, q, J=7 Hz), 4.43 (1H, t, J=7 Hz), 7.42-7.53 (2H, m), 7.55-7.64 (1H, m), 7.98 (2H, d, J=8 Hz)

Preparation 91

Ethyl 7-oxo-6-(6-quinolinylcarbonyl)octanoate

NMR (CDCl$_3$, δ): 1.23 (3H, t, J=7 Hz), 1.36-1.48 (2H, m), 1.65-1.78 (2H, m), 2.00-2.18 (2H, m), 2.18 (3H, s), 2.30 (2H, t, J=7 Hz), 4.10 (2H, q, J=7 Hz), 4.58 (1H, t, J=8 Hz), 7.54 (1H, m), 8.18 (1H, d, J=8 Hz), 8.28 (1H, dd, J=2 Hz, 8 Hz), 8.32 (1H, d, J=8 Hz), 8.51 (1H, d, J=2 Hz), 9.05 (1H, m) MS (ESI$^+$): m/z 342 (M+H)

Preparation 92

Ethyl 8-[4-({[(benzyloxy)carbonyl]amino}sulfonyl)benzoyl]-9-oxodecanoate

NMR (CDCl$_3$, δ): 1.23-1.37 (9H, m), 1.55-1.68 (1H, s), 2.01 (2H, m), 2.18 (3H, s), 2.29 (2H, t, J=7 Hz), 4.12 (2H, q, J=7 Hz), 4.39 (1H, t, J=7 Hz), 5.11 (2H, s), 7.30-7.49 (5H, m), 7.74 (1H, s, br), 8.04-8.13 (4H, m) MS (ESI$^-$): m/z 530 (M−H)

Preparation 93

Ethyl 7-(1,3-oxazol-5-yl)-7-oxoheptanoate

NMR (CDCl$_3$, δ): 1.25 (3H, t, J=7 Hz), 1.41 (2H, m), 1.76 (2H, m), 2.03 (2H, m), 2.31 (2H, m), 3.20 (2H, m), 4.10 (2H, q, J=7 Hz), 7.94 (1H, s), 8.10 (1H, s)

Preparation 94

Ethyl 6-[3-(methylsulfonyl)benzoyl]-7-oxooctanoate

NMR (CDCl$_3$, δ): 1.24 (3H, t, J=8 Hz), 1.59-1.64 (2H, m), 1.91-2.15 (2H, m), 2.18 (3H, s), 2.30 (2H, t, J=8 Hz), 3.11 (3H, s), 4.10 (2H, q, J=8 Hz), 4.45 (1H, t, J=8 Hz), 7.23 (1H, t, J=8 Hz), 8.17 (1H, dd, J=8, 1 Hz), 8.25 (2H, br d, J=8 Hz), 8.53 (1H, br s) MS (ESI$^+$): m/z 369 (M+H)

Preparation 95

Ethyl 6-(2-chloroisonicotinoyl)-7-oxooctanoate

NMR (CDCl$_3$, δ): 1.25 (3H, t, J=8 Hz), 1.30-1.40 (2H, m), 1.60-1.71 (2H, m), 1.90-2.14 (2H, m), 2.27 (3H, s), 2.25-2.74 (2H, m), 4.11 (2H, q, J=8 Hz), 4.32 (1H, t, J=8 Hz), 7.15 (1H, dd, J=7, 1 Hz), 7.76 (1H, d, J=1 Hz), 8.09 (1H, d, J=7 Hz) MS (ESI$^+$): m/z 326 (M+H)

Preparation 96

Ethyl 6-(3-nitrobenzoyl)-7-oxooctanoate

NMR (CDCl$_3$, δ): 1.24 (3H, t, J=8 Hz), 1.29-1.41 (2H, m), 1.60-1.74 (2H, m), 1.91-2.16 (2H, m), 2.19 (3H, s), 2.30 (2H, t, J=8 Hz), 4.11 (2H, q, J=8 Hz), 4.46 (1H, t, J=8 Hz), 7.71 (1H, t, J=8 Hz), 8.30 (1H, br d, J=8 Hz), 8.45 (4H, br d, J=8 Hz), 8.80 (1H, br s) MS (ESI$^+$): m/z 337 (M+H)

Preparation 97

4-(2-Acetylhexanoyl)benzonitrile

NMR (CDCl$_3$, δ): 0.90 (3H, t, J=8 Hz), 1.18-1.44 (4H, m), 1.90-2.12 (2H, m), 2.17 (3H, s), 4.40 (1H, t, J=8 Hz), 7.80 (2H, d, J=8 Hz), 8.08 (2H, d, J=8 Hz) MS (ESI$^-$): m/z 242 (M−H)

Preparation 98

Ethyl 6-[(5-bromo-3-pyridinyl)carbonyl]-7-oxooctanoate

NMR (CDCl$_3$, δ): 1.25 (3H, t, J=7 Hz), 1.32-1.43 (2H, m), 1.60-1.76 (2H, m), 1.96-2.15 (2H, m), 2.19 (3H, s), 2.30 (2H, t, J=7 Hz), 4.12 (2H, q, J=7 Hz), 4.36 (1H, t, J=7 Hz), 8.37 (1H, s), 8.87 (1H, br), 9.07 (1H, br) MS: (m/z) 370, 372 (M+H)

Preparation 99

Ethyl 6-(2-chloroisonicotinoyl)-8-(methylthio)-7-oxooctanoate

NMR (CDCl$_3$, δ): 1.24 (3H, t, J=7 Hz), 1.34-1.47 (2H, m), 1.60-1.77 (2H, m), 1.92 (3H, s), 1.93-2.05 (2H, m), 2.30 (2H, t, J=7 Hz), 3.19 (1H, d, J=17 Hz), 3.26 (1H, d, J=17 Hz), 4.11 (2H, q, J=7 Hz), 4.68 (1H, t, J=7 Hz), 7.72 (1H, d, J=5 Hz), 7.86 (1H, s), 8.57 (1H, d, J=5 Hz) MS: (m/z) 370 (M−H), 372 (M+H)

Preparation 100

Ethyl 7-(3-cyanobenzoyl)-8-oxononanoate

NMR (CDCl$_3$, δ): 1.21-1.44 (7H, m), 1.55-1.69 (2H, m), 1.89-2.15 (2H, m), 2.17 (3H, s), 2.29 (2H, t, J=8 Hz), 4.12 (2H, q, J=8 Hz), 4.39 (1H, t, J=8 Hz), 7.64 (1H, t, J=8 Hz), 7.87 (1H, dd, J=8, 1 Hz), 8.20 (1H, dd, J=8, 1 Hz), 8.27 (1H, br s) MS (ESI$^+$): m/z 330 (M+H)

Preparation 101

Ethyl 6-[(6-chloro-2-pyridinyl)carbonyl]-7-oxooctanoate

NMR (CDCl$_3$, δ): 1.26 (3H, t, J=7 Hz), 1.36-1.52 (2H, m), 1.63-1.75 (2H, m), 1.77-2.06 (2H, m), 2.29 (2H, t, J=7 Hz), 2.45 (3H, s), 4.12 (2H, q, J=7 Hz), 4.82 (1H, t, J=7 Hz), 7.51 (1H, d, J=8 Hz), 7.82 (1H, t, J=8 Hz), 7.97 (1H, d, J=8 Hz) MS (ESI$^+$): m/z 326

Preparation 102

Ethyl 6-(3-methoxybenzoyl)-7-oxooctanoate

NMR (CDCl$_3$, δ): 1.25 (3H, t, J=7 Hz), 1.30-1.43 (2H, m), 1.60-1.77 (2H, m), 1.92-2.12 (2H, m), 2.15 (3H, s), 2.31 (2H, t, J=7 Hz), 3.88 (3H, s), 4.12 (2H, q, J=7 Hz), 4.42 (1H, t, J=7 Hz), 7.14 (1H, dd, J=2 Hz, 8 Hz), 7.40 (1H, t, J=8 Hz), 7.46-7.58 (2H, m) MS (ESI$^+$): m/z 321

Preparation 103

Ethyl 6-(3,5-dichlorobenzoyl)-7-oxooctanoate

NMR (CDCl$_3$, δ): 1.23 (3H, t, J=7 Hz), 1.32-1.42 (2H, m), 1.63-1.75 (2H, m), 1.90-2.12 (2H, m), 2.16 (3H, s), 2.30 (2H, t, J=7 Hz), 4.12 (2H, q, J=7 Hz), 4.32 (1H, t, J=7 Hz), 7.58 (1H, m), 7.82 (2H, m)

Preparation 104

Ethyl 6-[(5-chloro-2-thienyl)carbonyl]-7-oxooctanoate

NMR (CDCl$_3$, δ): 1.24 (3H, t, J=7 Hz), 1.30-1.40 (2H, m), 1.62-1.74 (2H, m), 1.90-2.12 (2H, m), 2.16 (3H, s), 2.29 (2H, t, J=7 Hz), 4.13 (2H, q, J=7 Hz), 4.14 (1H, m), 6.98 (1H, d, J=4 Hz), 7.58 (1H, d, J=4 Hz)

Preparation 105

Ethyl 6-(3-fluorobenzoyl)-7-oxooctanoate

NMR (CDCl$_3$, δ): 1.24 (3H, t, J=7 Hz), 1.28-1.42 (2H, m), 1.60-1.75 (2H, m), 1.90-2.13 (2H, m), 2.14 (3H, s), 2.29 (2H, t, J=7 Hz), 4.11 (2H, q, J=7 Hz), 4.37 (1H, t, J=7 Hz), 7.26-7.33 (1H, m), 7.43-7.52 (1H, m), 7.63-7.68 (1H, m), 7.76 (1H, d, J=8 Hz) MS (ESI$^+$): m/z 309

Preparation 106

Ethyl 7-oxo-6-(3-quinolinylcarbonyl)octanoate

NMR (CDCl$_3$, δ): 1.23 (3H, t, J=7 Hz), 1.35-1.47 (2H, m), 1.63-1.77 (2H, m), 1.98-2.18 (2H, m), 2.20 (3H, s), 2.31 (2H, t, J=7 Hz), 4.10 (2H, q, J=7 Hz), 4.55 (1H, t, J=7 Hz), 7.66 (1H, t, J=8 Hz), 7.87 (1H, t, J=8 Hz), 7.97 (1H, d, J=8 Hz), 8.18 (1H, d, J=8 Hz), 8.78 (1H, d, J=2 Hz), 9.43 (1H, d, J=2 Hz) MS (ESI$^+$): m/z 342

Preparation 107

Ethyl 6-isonicotinoyl-7-oxooctanoate

NMR (CDCl$_3$, δ): 1.24 (3H, t, J=7 Hz), 1.26-1.45 (2H, m), 1.60-1.75 (2H, m), 1.94-2.07 (2H, m), 2.17 (3H, s), 2.27-2.35 (2H, m), 4.11 (2H, q, J=7 Hz), 4.38 (1H, t, J=7 Hz), 7.74 (2H, m), 8.83 (2H, m)

Preparation 108

Ethyl 6-[(3-methoxy-5-isoxazolyl)carbonyl]-7-oxooctanoate

NMR (CDCl$_3$, δ): 1.25 (3H, t, J=7 Hz), 1.33-1.45 (2H, m), 1.60-1.80 (2H, m), 1.88-2.05 (2H, m), 2.28 (3H, s), 2.30-2.45 (2H, m), 4.03 (3H, s), 4.11 (2H, q, J=7 Hz), 4.33 (1H, t, J=7 Hz), 6.56 (1H, s) MS (ESI$^+$): m/z 312

Preparation 109

Ethyl 6-[(5-methyl-3-isoxazolyl)carbonyl]-7-oxooctanoate

NMR (CDCl$_3$, δ): 1.24 (3H, t, J=7 Hz), 1.32-1.44 (2H, m), 1.61-1.74 (2H, m), 1.85-2.07 (2H, m), 2.26-2.38 (2H, m), 2.29 (3H, s), 2.49 (3H, s), 4.11 (2H, q, J=7 Hz), 4.64 (1H, m), 6.39 (1H, s) MS (ESI$^+$): m/z 296

Preparation 110

Ethyl 6-(2-chloroisonicotinoyl)-8-methoxy-7-oxooctanoate

NMR (CDCl$_3$, δ): 1.24 (3H, t, J=7 Hz), 1.28-1.43 (2H, m), 1.66 (2H, t, J=7 Hz), 1.73-1.86 (1H, m), 1.93-2.07 (1H, m), 2.73 (2H, t, J=7 Hz), 3.23 (3H, s), 3.89 (1H, d, J=17 Hz), 4.00 (1H, d, J=17 Hz), 4.10 (2H, q, J=7 Hz), 4.58 (1H, t, J=7 Hz), 7.66 (1H, d, J=5 Hz), 7.78 (1H, s), 8.60 (1H, d, J=5 Hz) MS (ESI$^+$): m/z 356, MS (ESI$^-$): m/z 354

Preparation 111

Ethyl 8-methoxy-6-(3-methoxybenzoyl)-7-oxooctanoate

NMR (CDCl$_3$, δ): 1.24 (3H, t, J=7 Hz), 1.30-1.43 (2H, m), 1.60-1.73 (2H, m), 1.79-2.04 (2H, m), 2.28 (2H, t, J=7 Hz), 3.27 (3H, s), 3.87 (3H, s), 4.00 (2H, m), 4.12 (2H, q, J=7 Hz), 4.66 (1H, t, J=7 Hz), 7.13 (1H, m), 7.39 (1H, m), 7.45-7.55 (2H, m)

Preparation 112

Ethyl 8-methoxy-7-oxo-6-(6-quinolinylcarbonyl)octanoate

NMR (CDCl$_3$, δ): 1.24 (3H, t, J=7 Hz), 1.34-1.47 (2H, m), 1.60-1.75 (2H, m), 1.86-2.10 (2H, m), 2.27 (2H, t, J=7 Hz), 3.24 (3H, s), 4.02-4.10 (2H, m), 4.12 (2H, q, J=7 Hz), 4.83 (1H, t, J=7 Hz), 7.48-7.55 (1H, m), 8.16-8.33 (3H, m), 8.49 (1H, m), 9.02 (1H, m) MS (ESI$^+$): m/z 372

Preparation 113

Ethyl 8-methoxy-7-oxo-6-(3-pyridinylcarbonyl)octanoate

NMR (CDCl$_3$, δ): 1.23 (3H, t, J=7 Hz), 1.31-1.45 (2H, m), 1.60-1.73 (2H, m), 1.75-2.08 (2H, m), 2.28 (2H, t, J=7 Hz), 3.24 (3H, s), 3.94 (1H, d, J=17 Hz), 4.00 (1H, d, J=17 Hz), 4.10 (2H, q, J=7 Hz), 4.67 (1H, t, J=7 Hz), 7.44 (1H, m), 8.22 (1H, m), 8.81 (1H, d, J=5 Hz), 9.18 (1H, m) MS (ESI$^+$): m/z 322

Preparation 114

Ethyl 6-(3-chlorobenzoyl)-8-methoxy-7-oxooctanoate

NMR (CDCl$_3$, δ): 1.23 (3H, t, J=7 Hz), 1.30-1.44 (2H, m), 1.60-1.74 (2H, m), 1.75-1.92 (1H, m), 1.94-2.10 (1H, m), 2.28 (2H, t, J=7 Hz), 3.25 (3H, s), 3.93 (1H, d, J=17 Hz), 4.02 (1H, d, J=17 Hz), 4.12 (2H, q, J=7 Hz), 4.63 (1H, t, J=7 Hz), 7.43 (1H, t, J=8 Hz), 7.57 (1H, d, J=8 Hz), 7.83 (1H, d, J=8 Hz), 7.94 (1H, s)

Preparation 115

Ethyl 6-(3-methylbenzoyl)-7-oxooctanoate

NMR (CDCl$_3$, δ): 1.24 (3H, t, J=7 Hz), 1.29-1.42 (2H, m), 1.60-1.73 (2H, m), 1.90-2.06 (2H, m), 2.13 (3H, s), 2.28 (2H, t, J=7 Hz), 2.42 (3H, s), 4.10 (2H, q, J=7 Hz), 4.42 (1H, t, J=7 Hz), 7.31-7.43 (2H, m), 7.73-7.78 (2H, m)

Preparation 118

Ethyl 8-methoxy-6-[(5-methyl-3-pyridinyl)carbonyl]-7-oxooctanoate

NMR (CDCl$_3$, δ): 1.23 (3H, t, J=7 Hz), 1.30-1.47 (2H, m), 1.60-1.74 (2H, m), 1.75-1.93 (1H, m), 1.93-2.08 (1H, m), 2.26 (2H, t, J=7 Hz), 2.43 (3H, s), 3.25 (3H, s), 3.95 (1H, d, J=17 Hz), 4.03 (1H, d, J=17 Hz), 4.12 (2H, q, J=7 Hz), 4.67 (1H, t, J=7 Hz), 8.03 (1H, s), 8.63 (1H, s), 8.98 (1H, s) MS (ESI$^+$): m/z 336

Preparation 119

Ethyl 6-[(5-bromo-3-pyridinyl)carbonyl]-7-oxooctanoate

NMR (CDCl$_3$, δ): 1.25 (3H, t, J=7 Hz), 1.32-1.43 (2H, m), 1.60-1.76 (2H, m), 1.96-2.15 (2H, m), 2.19 (3H, s), 2.30 (2H, t, J=7 Hz), 4.12 (2H, q, J=7 Hz), 4.36 (1H, t, J=7 Hz), 8.37 (1H, s), 8.87 (1H, br), 9.07 (1H, br) MS (ESI$^+$): m/z 370, 372

Preparation 120

Ethyl 6-[(5-bromo-3-pyridinyl)carbonyl]-8-methoxy-7-oxooctanoate

NMR (CDCl$_3$, δ): 1.23 (3H, t, J=7 Hz), 1.30-1.47 (2H, m), 1.60-1.72 (2H, m), 1.75-1.93 (1H, m), 1.95-2.08 (1H, m), 2.27 (2H, t, J=7 Hz), 3.25 (3H, s), 3.93 (1H, d, J=17 Hz), 4.02 (1H, d, J=17 Hz), 4.10 (2H, q, J=7 Hz), 4.63 (1H, t, J=7 Hz), 8.38 (1H, m), 8.88 (1H, m), 9.07 (1H, m) MS (ESI$^+$): m/z 400, 402

Preparation 121

Ethyl 6-[(5,6-dichloro-3-pyridinyl)carbonyl]-7-oxooctanoate

NMR (CDCl$_3$, δ): 1.24 (3H, t, J=7 Hz), 1.30-1.43 (2H, m), 1.60-1.77 (2H, m), 1.95-2.17 (2H, m), 2.19 (3H, s), 2.30 (2H, t, J=7 Hz), 4.11 (2H, q, J=7 Hz), 4.32 (1H, t, J=7 Hz), 8.31 (1H, d, J=2 Hz), 8.82 (1H, d, J=2 Hz)

Preparation 122

Ethyl 7-methoxy-5-[(5-methyl-3-pyridinyl)carbonyl]-6-oxoheptanoate

NMR (CDCl$_3$, δ): 1.23 (3H, t, J=7 Hz), 1.60-1.75 (2H, m), 1.78-1.95 (1H, m), 1.95-2.12 (1H, m), 2.32 (2H, t, J=7 Hz), 2.44 (3H, s), 3.25 (3H, s), 3.94 (1H, d, J=18 Hz), 4.02 (1H, d, J=18 Hz), 4.12 (2H, q, J=7 Hz), 4.69 (1H, t, J=7 Hz), 8.04 (1H, s), 8.63 (1H, s), 9.00 (1H, s) MS (ESI$^+$): m/z 322

Preparation 123

Ethyl 6-methoxy-4-[(5-methyl-3-pyridinyl)carbonyl]-5-oxohexanoate

NMR (CDCl$_3$, δ): 1.24 (3H, t, J=7 Hz), 2.08-2.55 (4H, m), 2.44 (3H, s), 3.23 (3H, s), 3.94 (1H, d, J=18 Hz), 4.01 (1H, d, J=18 Hz), 4.12 (2H, q, J=7 Hz), 4.88 (1H, m), 8.12 (1H, s), 8.64 (1H, s), 9.04 (1H, s) MS (ESI$^+$): m/z 308

Preparation 124

Ethyl 5-[(5-methyl-3-pyridinyl)carbonyl]-6-oxoheptanoate

NMR (CDCl$_3$, δ): 1.25 (3H, t, J=7 Hz), 1.60-1.75 (2H, m), 1.96-2.13 (2H, m), 2.18 (3H, s), 2.36 (2H, t, J=7 Hz), 2.43 (3H, s), 4.12 (2H, q, J=7 Hz), 4.43 (1H, t, J=7 Hz), 8.04 (1H, s), 8.63 (1H, s), 8.97 (1H, s) MS (ESI$^+$): m/z 292

Preparation 125

Ethyl 4-[(5-methyl-3-pyridinyl)carbonyl]-5-oxohexanoate

NMR (CDCl$_3$, δ): 1.25 (3H, t, J=7 Hz), 2.20 (3H, s), 2.26-2.48 (4H, m), 2.43 (3H, s), 4.13 (2H, q, J=7 Hz), 4.62 (1H, t, J=7 Hz), 8.08 (1H, s), 8.64 (1H, s), 9.02 (1H, s) MS (ESI$^+$): m/z 278

Preparation 126

Ethyl 4-[(5-bromo-3-pyridinyl)carbonyl]-5-oxohexanoate

NMR (CDCl$_3$, δ): 1.25 (3H, t, J=7 Hz), 2.26 (3H, s), 2.30 (2H, t, J=7 Hz), 2.43 (2H, t, J=7 Hz), 4.15 (2H, q, J=7 Hz), 8.65 (1H, s), 8.94 (1H, s), 9.22 (1H, s)

Preparation 127

Ethyl 6-(3-cyanobenzoyl)-8-methoxy-7-oxooctanoate

NMR (CDCl$_3$, δ): 1.19-1.43 (12H, m), 1.57-1.70 (2H, m), 1.80 (1H, m), 1.99 (1H, m), 2.28 (2H, t, J=8 Hz), 3.24 (3H, s), 3.91 (1H, d, J=16 Hz), 4.01 (1H, d, J=16 Hz), 4.09 (2H, q, J=8 Hz), 4.65 (1H, t, J=8 Hz), 7.64 (1H, t, J=8 Hz), 7.87 (1H, dd, J=8, 1 Hz), 8.18 (1H, dd, J=8, 1 Hz), 8.25 (1H, br s)

Preparation 128

Ethyl 8-(acetyloxy)-6-[(5-bromo-3-pyridinyl)carbonyl]-7-oxooctanoate

NMR (CDCl$_3$, δ): 1.25 (3H, t, J=7 Hz), 1.37 (2H, m), 1.67 (2H, m), 1.98-2.06 (5H, m), 2.30 (2H, t, J=7 Hz), 4.11 (2H, q, J=7 Hz), 4.47 (1H, t, J=7 Hz), 4.66 (d, J=17 Hz), 4.74 (d, J=17 Hz), 8.37 (1H, m), 8.88 (1H, m), 9.06 (1H, m)

Preparation 129

To a solution of Meldrum's acid (30 g, 0.208 mol) in dichloromethane (420 mL) was added pyridine (33.7 mL, 0.416 mol) over 3 minutes in an ice-methanol bath under nitrogen atmosphere (−9° C.). To this mixture was added dropwise a solution of methoxyacetyl chloride (24.8 g) in dichloromethane (180 mL) over 1 hour period at the temperature. After addition, the reaction mixture was stirred at the temperature for 1 hour and at ambient temperature for 2 hours. The mixture was quenched with 1N hydrochoric acid (600 mL). The organic layer was separated and the aqueous layer was extracted with dichloromethane. The combined organic layer was washed with brine, dried over magnesium sulfate, and evaporated in vacuo to give 5-(methoxyacetyl)-2,2-dimethyl-1,3-dioxane-4,6-dione as dark orange oil (38.1 g, 84.7%).

5-(Methoxyacetyl)-2,2-dimethyl-1,3-dioxane-4,6-dione

NMR (CDCl$_3$, δ): 1.75 (6H, s), 3.53 (3H, s), 4.87 (2H, s)

Preparation 130

A solution of 5-(methoxyacetyl)-2,2-dimethyl-1,3-dioxane-4,6-dione (38 g) in tert-butanol (120 mL) and toluene (120 mL) was refluxed for 2 hours under nitrogen atmosphere. The mixture was evaporated in vacuo to give brown oil (325 g). The residue was dissolved in hexane-ethyl acetate=2-1 (200 mL) and was added silica gel (65 g) therein. After stirring for 30 minutes at ambient temperature, the mixture was filtered and washed with hexane-ethyl acetate=2-1 (200 mL). The filtrate was concentrated in vacuo to give tert-butyl 4-methoxy-3-oxobutanoate as pale yellow oil (30.1 g, 91.0%).

tert-Butyl 4-methoxy-3-oxobutanoate

NMR (CDCl$_3$, δ): 150 (9H, s), 3.41 (2H, s), 3.43 (3H, s), 4.08 (2H, s)

Preparation 131

To a mixture of 3-formylbenzoic acid (500 mg) and p-toluenesulfonylmethyl isocyanide (715 mg) in methanol (20 mL) was added potassium carbonate (1.38 g) and the mixture was heated under reflux for 2 hours. After evaporation of solvent, the residue was partitioned between ethyl acetate and water. The aqueous layer was separated and acidified with 1N hydrochloric acid. The resulting precipitates were collected and washed with water, methanol and ether to give 3-(1,3-oxazol-5-yl)benzoic acid as a colorless amorphous powder (484 mg).

3-(1,3-Oxazol-5-yl)benzoic acid

NMR (DMSO-d$_6$, δ): 7.63 (1H, t, J=8 Hz), 7.84 (1H, s), 7.89-8.02 (2H, m), 8.25 (1H, m), 8.50 (1H, s), 13.22 (1H, br)
MS (ESI$^+$): m/z 188 (M−H)

Preparation 132

A mixture of 1-(3-chlorophenyl)-1,3-butanedione (500 mg), 5-(iodomethyl)-2,2-dimethyl-1,3-dioxane (716 mg), and potassium carbonate (351 mg) in dimethylsulfoxide (2.5 mL) was stirred for 14 hours at room temperature and 2 hours at 40° C. The mixture was partitioned between ethyl acetate (20 mL) and water (10 mL). The organic layer was washed with water (10×2 mL) and brine, dried over magnesium sulfate, and evaporated to give a brown oil. Flash silica gel column chromatography eluting with ethyl acetate-hexane=1-10 to 2-5 afforded 1-(3-chlorophenyl)-2-[(2,2-dimethyl-1,3-dioxan-5-yl)methyl]-1,3-butanedione as an yellow oil (614 mg).

1-(3-Chlorophenyl)-2-[(2,2-dimethyl-1,3-dioxan-5-yl)methyl]-1,3-butanedione

NMR (CDCl$_3$, δ): 1.39 (6H, s), 1.70 (1H, m), 1.91-2.15 (2H, m), 2.16 (3H, s), 3.61 (2H, m), 3.88 (2H, m), 4.46 (1H, t, J=7 Hz), 7.44 (1H, t, J=9 Hz), 7.57 (1H, m), 7.86 (1H, d, J=9 Hz), 7.96 (1H, m)

The following compounds were obtained in substantially the same manner as that of Preparation 132.

Preparation 133

1-tert-Butyl 7-ethyl 2-(1,3-oxazol-5-ylcarbonyl)heptanedioate

NMR (CDCl$_3$, δ): 1.26 (3H, t, J=7 Hz), 1.32-1.38 (11H, m), 1.67 (2H, m), 1.97 (2H, m), 2.30 (2H, m), 3.86 (1H, t, J=7 Hz), 4.11 (2H, q, J=7 Hz), 7.86 (1H, s), 8.03 (1H, s)

Preparation 134

1-tert-Butyl 7-ethyl 2-[(3,5-dimethyl-4-isoxazolyl)carbonyl]heptanedioate

NMR (CDCl$_3$, δ): 1.25 (3H, t, J=7 Hz), 1.33-1.41 (11H, m), 1.64 (2H, m), 1.93 (2H, m), 2.30 (2H, m), 2.47 (3H, s), 2.69 (2H, s), 3.79 (1H, t, J=7 Hz), 4.12 (2H, q, J=7 Hz)

Preparation 135

To a suspension of magnesium chloride (1.46 g) in tetrahydrofuran (10 ml) was added a solution of ethyl 3-oxo-4-phenylbutanoate (2.0 g) in tetrahydrofuran (10 ml) and the mixture was cooled to 0° C., then pyridine (25 ml) was added. The mixture was stirred at 20° C. for 30 minutes, then a solution of 4-fluorobenzoyl chloride (2.44 g) in tetrahydrofuran (10 ml) was added at 0° C. After stirring at 20° C. for 2 hours, the mixture was partitioned between 0.5N hydrochloric acid and ethyl acetate. The organic layer was separated, washed with water and brine, dried over magnesium sulfate, and evaporated. The residue was chromatographed on silica gel eluting with a mixture of ethyl acetate and hexane (1:5) to give ethyl 2-(4-fluorobenzoyl)-3-oxo-4-phenylbutanoate (2.15 g) as an oil.

Ethyl 2-(4-fluorobenzoyl)-3-oxo-4-phenylbutanoate (mixture of tautomers, too complicated to be assigned)

Preparation 136

A mixture of 1-(4-fluorophenyl)butane-1,3-dione (1.0 g), potassium carbonate (3.42 g), and tetrabutylammonium bromide (20 mg) in toluene (10 ml) was refluxed for 3 hours. After cooling to 20° C., ethyl bromoacetate (0.74 ml) was added to the mixture. After being allowed to stand at 20° C. overnight, the mixture was partitioned between ethyl acetate and 0.5N hydrochloric acid. The organic layer was separated, washed with water and brine, dried over magnesium sulfate, and evaporated. The residue was chromatographed on silica gel eluting with a mixture of ethyl acetate and hexane (1:5) to give ethyl 3-(4-fluorobenzoyl)-4-oxopentanoate (964 mg) as an oil.

Ethyl 3-(4-fluorobenzoyl)-4-oxopentanoate

NMR (CDCl$_3$, δ): 1.23 (3H, t, J=7 Hz), 2.18 (3H, s), 3.01 (2H, d, J=7 Hz), 4.12 (2H, q, J=7 Hz), 4.95 (1H, d, J=7 Hz), 7.18 (2H, dt, J=2, 7 Hz), 8.07 (2H, ddd, J=2, 5, 7 Hz)

Preparation 137

A mixture of 1-(4-fluorophenyl)butane-1,3-dione (1.0 g), potassium carbonate (3.84 g), and tetrabutylammonium bromide (90 mg) in toluene (20 ml) was refluxed for 3 hours, then ethyl 6-bromohexanoate (1.18 ml) was added. After stirring at 100° C. for 3 hours, the mixture was partitioned between ethyl acetate and 0.5N hydrochloric acid. The organic layer was separated, washed with water and brine, dried over magnesium sulfate, and evaporated. The residue was chromatographed on silica gel eluting with a mixture of ethyl acetate and hexane (1:5) to give ethyl 7-(4-fluorobenzoyl)-8-oxononanoate (983 mg) as an oil.

Ethyl 7-(4-fluorobenzoyl)-8-oxononanoate

NMR (CDCl$_3$, δ): 1.24 (3H, t, J=7 Hz), 1.25-1.45 (4H, m), 1.55-1.70 (2H, m), 1.90-2.10 (2H, m), 2.13 (3H, s), 2.27 (2H, t, J=7 Hz), 4.11 (2H, q, J=7 Hz), 4.37 (1H, t, J=7 Hz), 7.16 (2H, t, J=9 Hz), 8.02 (2H, dd, J=5, 9 Hz)

Preparation 138

A mixture of pentane-2,4-dione (5.0 g), ethyl 7-bromoheptanoate (11.1 g), potassium carbonate (13.8 g), and cesium carbonate (1.63 g) in a mixture of acetonitrile (150 ml) and dimethylsulfoxide (30 ml) was stirred at 20° C. overnight, then pentane-2,4-dione (5 g) was added. After stirring at 20° C. overnight, the mixture was partitioned between ethyl acetate and 0.5N hydrochloric acid. The organic layer was separated, washed with water and brine, dried over magnesium sulfate, and evaporated. The residue was chromatographed on silica gel eluting with a mixture of ethyl acetate and hexane (1:5) to give ethyl 8-acetyl-9-oxodecanoate (55 g) as an oil.

Ethyl 7-acetyl-8-oxononanoate (mixture of tautomers, too complicated to be assigned)

Preparation 139

To a mixture of ethyl 7-acetyl-8-oxononanoate (4.0 g) and magnesium chloride (1.27 g) in dichloromethane (70 ml) was added pyridine (2.15 ml) at 0° C. The mixture was stirred at 20° C. for 1 hour, then a solution of 4-cyanobenzoyl chloride (2.87 g) in dichloromethane (10 ml) was added. After stirring for 3 hours at 20° C., the mixture was partitioned between ether and 1N hydrochloric acid. The organic layer was separated, washed with water and brine, dried over magnesium sulfate, and evaporated. The residue was chromatographed on silica gel eluting with a mixture of ethyl acetate and hexane (1:5) to give ethyl 7-acetyl-7-(4-cyanobenzoyl)-8-oxononanoate (352 g) as an oil.

1-tert-Butyl 8-ethyl 2-acetyl-2-(4-cyanobenzoyl)octanedioate

NMR (CDCl$_3$, δ): 1.24 (3H, t, J=7 Hz), 1.25-1.45 (4H, m), 1.30 (9H, s), 1.55-1.70 (2H, m), 2.20 (2H, t, J=7 Hz), 2.28 (2H, t, J=7 Hz), 2.44 (3H, s), 4.12 (2H, q, J=7 Hz), 7.72 (2H, t, J=9 Hz), 7.83 (2H, d, J=9 Hz)

Preparation 140

Ethyl 7-acetyl-7-(4-cyanobenzoyl)-8-oxononanoate (3.5 g) was dissolved in trifluoroacetic acid (12.6 ml) and the mixture was stirred at 20° C. for 15 minutes. The mixture was partitioned between ethyl acetate and water. The organic layer was separated, washed with water, aqueous sodium bicarbonate and brine, dried over MgSO$_4$ (magnesium sulfate), and evaporated to give ethyl 7-(4-cyanobenzoyl)-8-oxononanoate (2.25 g) as an oil.

Ethyl 7-(4-cyanobenzoyl)-8-oxononanoate

NMR (CDCl$_3$, δ): 1.25 (3H, t, J=7 Hz), 1.25-1.45 (4H, m), 1.55-1.70 (2H, m), 1.80-2.10 (2H, m), 2.16 (3H, s), 2.28 (2H, t, J=7 Hz), 4.12 (2H, q, J=7 Hz), 4.40 (1H, t, J=7 Hz), 7.80 (2H, t, J=9 Hz), 8.07 (2H, d, J=9 Hz)

Preparation 141

A mixture of methyl 4-(aminosulfonyl)benzoate (5.10 g) and potassium carbonate (655 g) in dimethoxyethane (50 mL) was refluxed for 5 minutes. After cooling the mixture, a solution of benzyl chloridocarbonate (5.25 g) in dimethoxyethane (30 mL), and the resulting mixture was refluxed for 1 hour. The reaction was quenched by adding 1N hydrochloric acid (100 mL). The mixture was extracted with ethyl acetate (200 mL), and the organic layer was washed with brine, dried over magnesium sulfate, and evaporated to give a pale yellow oil, which was solidified upon standing. The solid was triturated in diisopropyl ether (30 mL) to give methyl 4-({[(benzyloxy)carbonyl]amino}sulfonyl)benzoate as a white powder (3.38 g).

Methyl 4-({[(benzyloxy)carbonyl]amino}sulfonyl)benzoate

NMR (CDCl$_3$, δ): 3.98 (3H, s), 5.10 (2H, s), 7.22 (2H, m), 7.34 (3H, m), 7.64 (1H, s, br), 8.08 (2H, d, J=9 Hz), 8.16 (2H, d, J=9 Hz)

Preparation 142

A suspension of methyl 4-({[(benzyloxy)carbonyl]amino}sulfonyl)benzoate (3.38 g) and 85% pottasium hydroxide (1.28 g) in methanol (40 mL) was stirred for 35 minutes. Methanol was evaporated off, and to the mixture was added 1N hydrochloric acid (20 mL). A white crystal was formed, which was collected by filtration and washed with water and diisopropyl ether, and dried under vacuum. 4-({[(Benzyloxy)carbonyl]amino}sulfonyl)benzoic acid was obtained as a white crystal (2.92 g).

4-({[(Benzyloxy)carbonyl]amino}sulfonyl)benzoic acid

NMR (DMSO-d$_6$, δ): 5.06 (2H, s), 7.25 (2H, m), 7.33 (3H, m), 8.00 (2H, d, J=9 Hz), 8.15 (2H, d, J=9 Hz) MS (ESI$^-$): m/z 334 (M–H)

Preparation 143

To a suspension of S-(2-pyridinyl) 3-cyanobenzenecarbothioate (2.40 g) in toluene (10 mL) was added titanium chloride (1.99 g) under an ice-methanol bath over 5 minutes (–7 to –2° C.). After stirring for 10 minutes, a solution of 2-ethyl-1H-pyrrole (1.00 g) in toluene (10 mL) was added over 5 minutes (–4 to 0° C.). The resulting heterogeneous mixture was stirred for 15 hours at room temperature. Ethyl acetate (20 mL) and water (20 mL) were added, and the mixture was filtered through celite. The filtrate was diluted with ethyl acetate (80 mL) and water (30 mL), and organic extract was washed with water (30 mL), 1N sodium hydroxide (50 mL), and brine (50 mL), dried over magnesium sulfate, and evaporated to give a dark colored crystal (2.46 g). The crystal was triturated in diisopropyl ether (10 mL) to give 3-[(5-ethyl-1H-pyrrol-2-yl)carbonyl]benzonitrile as a brown crystal (157 g, 70.1%).

3-[(5-Ethyl-1H-pyrrol-2-yl)carbonyl]benzonitrile

NMR (CDCl$_3$, δ): 1.33 (3H, t, J=7 Hz), 2.75 (2H, q, J=7 Hz), 6.12 (1H, m), 6.78 (1H, m), 7.60 (1H, t, J=8 Hz), 7.82 (1H, d, J=8 Hz), 8.07 (1H, d, J=8 Hz), 8.14 (1H, s), 9.50 (1H, s, br)

Preparation 144

To a suspension of magnesium chloride (3.01 g) in tetrahydrofuran (30 mL) was added tert-butyl 3-oxobutanoate (5.00 g). The mixture was cooled under an ice-bath. Then, pyridine (5.00 g) was added over 15 minutes. After stirring for 1 hour at room temperature, the resulting mixture was cooled under the ice-bath. A solution of 2-chlorobenzoyl chloride (4.98 g) in tetrahydrofuran (30 mL) was added over 15 minutes. The mixture was stirred for 1 hour at room temperature. The reaction was quenched by adding 1N hydrochloric acid (65 mL). The mixture was filtered, and the solvent was evaporated off. The residue was extracted with ethyl acetate (150 mL). The extract was washed with water (100 mL), saturated sodium bicarbonate (100 mL), and brine, dried over magnesium sulfate, and evaporated to give tert-butyl 2-(3-chlorobenzoyl)-3-oxobutanoate as an yellow oil (8.82 g).

tert-Butyl 2-(3-chlorobenzoyl)-3-oxobutanoate

NMR (CDCl$_3$, δ): mixture of tautomers: 1.20 and 1.27 (9H, s), 2.16 and 2.44 (3H, s), 7.33-7.71 (4H, m), 13.66 (1H, s)

Preparation 145

A solution of tert-butyl 2-(3-chlorobenzoyl)-3-oxobutanoate (8.82 g) in trifluoroacetic acid (40 mL) was stirred for 1 hour under an ice-bath. The volatile was removed in vacuo, and the residue was partitioned between ethyl acetate (150 mL) and saturated sodium bicarbonate. The organic layer was washed with brine, dried over magnesium sulfate, and evaporated to give 1-(3-chlorophenyl)-1,3-butanedione as a pale orange crystal (533 g).

1-(3-Chlorophenyl)-1,3-butanedione

NMR (CDCl$_3$, δ): 2.21 (3H, s), 6.14 (1H, s), 7.38 (1H, t, J=9 Hz), 7.48 (1H, d, J=9 Hz), 7.75 (1H, d, J=9 Hz), 7.85 (1H, s)

Preparation 146

To a mixture of 2-(trimethylsilyl)ethanol (20.5 g) and pyridine (18.7 g) in dichloromethane (40 mL) was added a solution of ethanedioyl dichloride (10.0 g) in dichloromethane (20 mL) over 30 minutes under an ice-bath (6 to 20° C.). The bath was removed, and the mixture was stirred for 0.5 hour. The mixture was filtered, and the filtrate was partitioned between ethyl acetate (200 mL) and 1N hydrochloric acid (200 mL). The organic layer was washed with saturated sodium bicarbonate and brine, dried over magnesium sulfate, and evaporated to give bis[2-(trimethylsilyl)ethyl]oxalate as a pale yellow oil (25.1 g).

bis[2-(Trimethylsilyl)ethyl]oxalate

NMR (CDCl$_3$, δ): 0.08 (18H, s), 1.12 (4H, m), 4.38 (4H, m)

Preparation 147

To a suspension of dimethyl sulfone (7.00 g) in diethyl ether (50 mL) was added potassium tert-butoxide (8.76 g). To the resulting mixture was added bis[2-(trimethylsilyl)ethyl]oxalate (23.8 g). The resulting mixture was stirred for 36 hours at room temperature. The mixture was partitioned between ethyl acetate (100 mL) and 1N hydrochloric acid (50 mL). The organic layer was washed with brine, dried over magnesium sulfate, and evaporated to give a dark orange oil. Flash silica gel column chromatography eluting with ethyl acetate-hexane=1-25 to 8-5 afforded 2-(trimethylsilyl)ethyl 3-(methylsulfonyl)-2-oxopropanoate as a pale brown oil (8.37 g).

2-(Trimethylsilyl)ethyl 3-(methylsulfonyl)-2-oxopropanoate

NMR (CDCl$_3$, δ): 0.08 (9H, s), 1.14 (2H, m), 3.11 (3H, s), 4.43 (4H, m), 4.56 (2H, s) MS (ESI$^-$): m/z 265 (M–H)

Preparation 148

A mixture of 4-oxo-4-phenylbutanoic acid (5.00 g), ethanol (2.59 g), 1-(3-dimethylaminopropyl)-3-ethylcarbodiimide hydrochloride (6.46 g), and 4-(dimethylamino)pyridine (171 mg) in N,N-dimethylformamide (25 mL) was stirred for 1.5 hours at room temperature. The mixture was partitioned between ethyl acetate (100 mL) and 1N hydrochloric acid (75 mL), and the organic layer was washed with water (75×3 mL), saturated sodium bicarbonate (75 mL), and brine (75 mL), dried over magnesium sulfate, and evaporated to give ethyl 4-oxo-4-phenylbutanoate as a colorless oil (4.19 g).

Ethyl 4-oxo-4-phenylbutanoate

NMR (CDCl$_3$, δ): 1.27 (3H, t, J=7 Hz), 2.76 (2H, t, J=7 Hz), 3.32 (2H, t, J=7 Hz), 4.16 (2H, q, J=7 Hz), 7.47 (2H, t, J=9 Hz), 7.55 (1H, d, J=9 Hz), 7.98 (2H, d, J=9 Hz) MS (ESI$^+$): m/Z 207 (M+H)

The following compound was obtained in substantially the same manner as that of Preparation 148.

Preparation 149

Ethyl 5-oxo-5-phenylpentanoate

NMR (CDCl$_3$, δ): 1.26 (3H, t, J=7 Hz), 2.08 (2H, m), 2.44 (2H, t, J=7 Hz), 3.06 (2H, t, J=7 Hz), 4.14 (2H, q, J=7 Hz), 7.46 (2H, t, J=9 Hz), 7.56 (1H, d, J=9 Hz), 7.97 (2H, d, J=9 Hz) MS (ESI$^+$): m/z 221 (M+H)

Preparation 150

A mixture of 2-benzoylcyclohexanone (1.00 g), sodium ethoxide (404 mg) in ethanol (5 mL) was stirred for 3.5 hours at room temperature. The reaction was quenched by adding 1N hydrochloric acid (1 mL). The solvent was evaporated off, and the residue was partitioned between ethyl acetate and water. The organic layer was washed with brine, dried over magnesium sulfate, and evaporated to give ethyl 7-oxo-7-phenylheptanoate as a brown oil (1.33 g).

Ethyl 7-oxo-7-phenylheptanoate

NMR (CDCl$_3$, δ): 1.25 (3H, t, J=7 Hz), 1.42 (2H, m), 1.63-1.81 (4H, m), 2.32 (2H, t, J=7 Hz), 2.98 (2H, t, J=7 Hz), 4.12 (2H, q, J=7 Hz), 7.47 (2H, t, J=9 Hz), 7.54 (1H, d, J=7 Hz), 7.95 (2H, d, J=9 Hz)

Preparation 151

To a solution of ethyl 7-chloro-7-oxoheptanoate (1.31 g) in dichloromethane (25 mL) was added a solution of 2-(trimethylsilyl)-1,3-thiazole (500 mg) in dichloromethane (5 mL) under nitrogen. After stirring for 3 hours, the reaction was quenched by adding saturated sodium bicarbonate (5 mL). The mixture was partitioned between ethyl acetate (30 mL) and saturated sodium bicarbonate (30 mL), and the organic layer was washed with brine, dried over magnesium sulfate, and evaporated to give a colorless oil. Flash silica gel column chromatography eluting with ethyl acetate-hexane=1-10 to 2-5 afforded ethyl 7-oxo-7-(1,3-thiazol-2-yl)heptanoate as a colorless oil (778 mg).

Ethyl 7-oxo-7-(1,3-thiazol-2-yl)heptanoate

NMR (CDCl$_3$, δ): 1.25 (3H, t, J=7 Hz), 1.44 (2H, m), 1.64-1.85 (4H, m), 2.32 (2H, t, J=7 Hz), 3.17 (2H, t, J=7 Hz), 4.12 (2H, q, J=7 Hz), 7.66 (1H, d, J=3 Hz), 8.00 (1H, d, J=3 Hz) MS (ESI$^+$): m/z 256 (M+H)

Preparation 152

To a solution of 7-methoxy-7-oxoheptanoic acid (1.00 g) in dichloromethane (10 mL) was added a solution of trifluoroacetic anhydride (1.33 g) in dichloromethane (2 mL). After stirring for 0.5 hour, a solution of 1-methyl-1H-pyrrole (1.49 g) in dichloromethane (2 mL) was added. The mixture was stirred for 2 hours 40 minutes at room temperature and 2 hours at 35° C. The mixture was partitioned between ethyl acetate and saturated sodium bicarbonate. The organic layer was washed with brine, dried over magnesium sulfate, and evaporated to give a brown oil. Flash silica gel column chromatography eluting with ethyl acetate-hexane=1-20 to 4-5 afforded methyl 7-(1-methyl-1H-pyrrol-2-yl)-7-oxoheptanoate as a colorless oil (615 mg).

Methyl 7-(1-methyl-1H-pyrrol-2-yl)-7-oxoheptanoate

NMR (CDCl$_3$, δ): 1.34 (2H, m), 1.61-1.77 (4H, m), 2.32 (2H, t, J=7 Hz), 2.77 (2H, t, J=7 Hz), 3.66 (3H, s), 3.94 (3H, s), 6.13 (1H, m), 6.79 (1H, m), 6.93 (1H, m) MS (ESI$^+$): m/z 238 (M+H)

Preparation 153

To a suspension of 4-({[(benzyloxy)carbonyl]amino}-sulfonyl)benzoic acid (2.90 g) in dichloromethane (30 mL) was added N,N-dimethylformamide (19.0 mg) and followed by oxalyl chloride (1.15 g) under an ice-bath. The mixture was stirred for 0.5 hour at room temperature and refluxed for 1 hour. The resulting mixture was refluxed further for 5 minutes after adding oxalyl chloride (439 mg). The volatile was evaporated off to give a white solid. The solid was triturated in diisopropyl ether to give benzyl [4-(chlorocarbonyl)phenyl]sulfonylcarbamate as a white powder (2.40 g), which was used for the next reaction without further purification.

Benzyl [4-(chlorocarbonyl)phenyl]sulfonylcarbamate

Preparation 154

To a solution of tert-butyl 4-(methylthio)-3-oxobutanoate (5.00 g) and potassium carbonate (3.72 g) in dimethylformamide (25 mL) was added ethyl 5-iodopentanoate (6.89 g) and the mixture was stirred at ambient temperature for 15 hours. The mixture was partitioned between ethyl acetate and water. The organic layer was separated, washed with water and brine, dried over magnesium sulfate, and evaporated in vacuo. The residue was purified by silica gel column chromatography eluting with a mixture of hexane and ethyl acetate (20:1-10:1) to give 1-tert-butyl 7-ethyl 2-[(methylthio)acetyl]heptanedioate as colorless oil (5.88 g).

1-tert-butyl 7-ethyl 2-[(methylthio)acetyl]heptanedioate

NMR (CDCl$_3$, δ): 1.25 (3H, t, J=7 Hz), 1.30-1.42 (2H, m), 1.45 (9H, s), 1.63-1.74 (2H, m), 1.81-1.93 (2H, m), 2.05 (3H, s), 2.30 (2H, t, J=7 Hz), 3.23 (1H, d, J=17 Hz), 3.38 (1H, d, J=17 Hz), 3.74 (1H, t, J=7 Hz), 4.11 (2H, q, J=7 Hz)

Preparation 155

To a suspension of hydroxylamine hydrochloride (29.4 g) in dichloromethane (200 mL) was added diisopropylethylamine (54.6 g) over 3 minutes in a methanol-ice bath under a nitrogen atmosphere. A white precipitate was formed upon the addition. After stirring for 1 hour under the bath, a solution of diphenylphosphinic chloride (20.0 g) in dichloromethane (20 mL) was added over 60 minutes. A white crystal was formed upon the addition. The mixture was warmed to 0° C. over 1 hour with stirring. The reaction was quenched by adding water (200 mL) over 3 minutes. After stirring the mixture for 0.5 hour, the crystal was collected by filtration. The crystal was washed with water (50×3 mL) followed by diisopropyl ether (50×3 mL). The collected crystal was dried overnight in the air and 3 hours under a reduced pressure with slight warming (4° C.) to give a crude product. The crude product was triturated in EtOH (ethanol) to give (aminooxy)(diphenyl)phosphine oxide as a white crystal (15.3 g).

(Aminooxy)(diphenyl)phosphine oxide

NMR (CDCl$_3$, δ): 7.54-7.58 (6H, m), 7.74-7.83 (4H, m), 8.20-8.33 (2H, m)

Preparation 156

To a solution of 1-(1H-pyrrol-2-yl)ethanone (5.00 g) in tetrahydrofuran (100 mL) was added potassium tert-butoxide (6.17 g) in a water bath under a nitrogen atmosphere. After stirring for 1 hour, (aminooxy)(diphenyl)phosphine oxide (12.8 g) was added over 2 hours. After stirring for 2 hours at room temperature, water (4 mL) was added over 3 minutes to give a clear solution. The solvent was evaporated off, and the residue was partitioned between ethyl acetate (50 mL) and water (50 mL). The aqueous layer was extracted with ethyl acetate (25×5 mL), and the combined organic extract was washed with brine, dried over anhydrous magnesium sulfate, and evaporated to give a brown oil (6.01 g). The oil was dissolved in diisopropyl ether (30 mL), and to the solution was added hexane (15 mL) to afford a pale yellow crystal. After stirring for 1 hour, the crystal was removed by filtration. The filtrate was evaporated to give a brown oil (5.69 g). The oil was dissolved in ethyl acetate (45.5 mL), the solution was cooled under an ice-bath. To the cooled solution was added 4N hydrogen chloride in ethyl acetate (115 mL) over 15 minutes to afford a pale brown precipitate. After stirring the mixture for 0.5 hour under the bath, the precipitate was collected by filtration and washed with ethyl acetate (5×3 mL) to give a pale brown powder (5.33 g). The powder was suspended in ethyl acetate (37 mL) and warmed to 3° C. The suspension was stirred for 1 hour at room temperature. The powder was collected by filtration and washed with ethyl acetate (5×3 mL) to give 1-(1-amino-1H-pyrrol-2-yl)ethanone hydrochloride as a pale brown powder (5.25 g).

1-(1-Amino-1H-pyrrol-2-yl)ethanone hydrochloride

NMR (CDCl$_3$, δ): 2.37 (3H, s), 5.22 (2H, s, br), 6.07 (1H, m), 6.99 (1H, m), 7.15 (1H, m)

Preparation 157

Under a nitrogen atmosphere, hydrazine monohydrate (530 g) was added to ethanol (1.7 L) over 55 minutes. To the mixture was added 1-(1-amino-1H-pyrrol-2-yl)ethanone hydrochloride (170 g) over 20 minutes. The mixture was stirred for 10 minutes at room temperature and heated to refluxing temperature over 55 minutes, and refluxed for 15 minutes. After cooling the mixture under a water bath, water (1.7 L) was added to the mixture (30 to 31° C.). Ethanol was evaporated off, and the resulting mixture was extracted with chloroform (0.85×4 mL). The combined organic extract was washed with brine (1.3 L). The brine was extracted with chloroform (0.85 L). The combined organic extract was dried over anhydrous magnesium sulfate, and evaporated to give (1E)-1-(1-amino-1H-pyrrol-2-yl)ethanone hydrazone as a brown crystal (112 g).

(1E)-1-(1-Amino-1H-pyrrol-2-yl)ethanone hydrazone

NMR (CDCl$_3$, δ): 2.10 (3H, s), 5.11 (2H, s, br), 5.83 (2H, s, br), 5.98 (1H, m), 6.25 (1H, m), 6.79 (1H, m) MS (ESI$^+$): m/z 139 (M+H)

Preparation 158

To a suspension of (1E)-1-(1-amino-1H-pyrrol-2-yl)ethanone hydrazone (110 g) in toluene (1.1 L) was added potassium tert-butoxide (93.8 g) over 5 minutes under a nitrogen atmosphere, and the mixture was heated to refluxing temperature over 45 minutes. After refluxing for 15 minutes, the mixture was cooled to room temperature and partitioned between ethyl acetate (1.1 L) and water (1.1 L). The aqueous layer was extracted with ethyl acetate (1.1 L) again. The combined organic extract was was washed with brine (1.1 L), and the brine was extracted with ethyl acetate (0.5 L). All the organic layer was combined, dried over anhydrous magnesium sulfate, and evaporated to give 2-ethyl-1H-pyrrol-1-amine as a brown oil (94.4 g).

2-Ethyl-1H-pyrrol-1-amine

NMR (CDCl$_3$, δ): 1.26 (3H, t, J=7 Hz), 21.62 (2H, q, J=7 Hz), 4.53 (2H, s, br), 5.80 (1H, m), 5.99 (1H, m), 6.67 (1H, m)

Preparation 159

To a suspension of tert-butyl 4-methoxy-3-oxobutanoate (3.09 g) and potassium carbonate (2.50 g) in dimethylformamide (20 mL) was added ethyl 5-iodopentanoate (4.62 g) and the mixture was stirred at ambient temperature for 15 hours. The mixture was partitioned between ethyl acetate and water. The organic layer was separated, washed with water and brine, dried over magnesium sulfate, and evaporated in vacuo. The residue was purified by silica gel column chromatography eluting with a mixture of hexane and ethyl acetate (20:1-5:1) to give 1-tert-butyl 7-ethyl 2-(methoxyacetyl)heptanedioate as colorless oil (4.33 g).

1-tert-Butyl 7-ethyl 2-(methoxyacetyl)heptanedioate

NMR (CDCl$_3$, δ): 1.25 (3H, t, J=7 Hz), 1.30-1.44 (2H, m), 1.45 (9H, s), 1.60-1.73 (2H, m), 1.80-1.93 (2H, m), 2.29 (2H, t, J=7 Hz), 3.41 (3H, s), 3.47 (1H, t, J=7 Hz), 4.02 (4H, m) MS: (m/z) 317 (M+H)

The following compounds were obtained in substantially the same manner as that of Preparation 159.

Preparation 160

1-tert-Butyl 6-ethyl 2-(methoxyacetyl)hexanedioate

NMR (CDCl$_3$, δ): 1.25 (3H, t, J=7 Hz), 1.46 (9H, s), 1.52-1.73 (2H, m), 1.82-1.94 (2H, m), 2.33 (2H, t, J=7 Hz), 3.42 (3H, s), 3.50 (1H, t, J=7 Hz), 4.10 (2H, s), 4.12 (2H, q, J=7 Hz)

Preparation 161

1-tert-Butyl 5-ethyl 2-(methoxyacetyl)pentanedioate

NMR (CDCl$_3$, δ): 1.26 (3H, t, J=7 Hz), 1.47 (9H, s), 2.10-2.25 (2H, m), 2.37 (2H, t, J=7 Hz), 3.42 (3H, s), 3.62 (1H, t, J=7 Hz), 4.12 (2H, s), 4.13 (2H, q, J=7 Hz)

Preparation 162

1-tert-Butyl 6-ethyl 2-acetylhexanedioate

NMR (CDCl$_3$, δ): 1.26 (3H, t, J=7 Hz), 1.47 (9H, s), 1.57-1.75 (2H, m), 1.79-1.93 (2H, m), 2.23 (3H, s), 2.33 (2H, t, J=7 Hz), 3.33 (1H, t, J=7 Hz), 4.12 (2H, q, J=7 Hz) MS (ESI$^+$): m/z 273

Preparation 163

1-tert-Butyl 5-ethyl 2-acetylpentanedioate

NMR (CDCl$_3$, δ): 1.26 (3H, t, J=7 Hz), 1.47 (9H, s), 2.08-2.22 (2H, m), 2.24 (3H, s), 2.33-2.42 (2H, m), 3.45 (1H, t, J=7 Hz), 4.13 (2H, q, J=7 Hz)

Preparation 164

To a solution of 2-ethyl-1H-pyrrole (7.00 g) in tetrahydrofuran (14 mL) was added 0.93 M ethyl magnesium bromide (198 mL) under an ice-bath. The mixture was stirred for 1 hour at room temperature. Then the resulting solution was added to a suspension of 5-bromonicotinoyl chloride (22.3 g) in tetrahydrofuran (110 mL) over 50 minutes under an ice-bath. After stirring for 15 minutes under the bath, the reaction was quenched by adding saturated ammonium chloride (30 mL). The mixture was partitioned between ethyl acetate (350 mL) and water (350 mL). The organic layer was washed with saturated sodium bicarbonate and brine, dried over magnesium sulfate, and evaporated to give a dark colored gum (33.9 g). The gum was dispersed in ethyl acetate/hexane (1:3, 150 mL) in the presence of silica gel (150 mL). The mixture was filtered, and the filtrate was concentrated to give an yellow crystal (20.6 g). Flash silica gel column chromatography eluting with ethyl acetate-hexane=1-20 to 4-5 afforded (5-bromo-3-pyridinyl)(5-ethyl-1H-pyrrol-2-yl)methanone as a pale yellow solid (7.11 g).

(5-Bromo-3-pyridinyl)(5-ethyl-1H-pyrrol-2-yl)methanone

NMR (CDCl$_3$, δ): 1.33 (3H, t, J=7 Hz), 2.75 (2H, q, J=7 Hz), 6.14 (1H, m), 6.83 (1H, m), 8.27 (1H, m), 8.82 (1H, m), 8.98 (1H, m) MS (ESI$^+$): m/z 279 (M+H)

Preparation 165

To a solution of tert-butyl 4-(acetyloxy)-3-oxobutanoate (30.0 g) and ethyl 5-iodopentanoate (35.5 g) in N,N-dimethylformamide (150 mL) was added potassium carbonate (19.2 g) at room temperature. After stirring for 4 hours, the mixture was quenched by adding 1N hydrochloric acid (140 mL) under an ice-bath. The mixture was partitioned between ethyl acetate (450 mL) and water (300 mL). The organic extract was washed with water (500 mL, three times) and brine, dried over magnesium sulfate, and evaporated to give a brown oil containing 1-tert-butyl 7-ethyl 2-[(acetyloxy)acetyl]heptanedioate (63.4 g, 43% wt purity).

1-tert-Butyl 7-ethyl 2-[(acetyloxy)acetyl]heptanedioate

NMR (CDCl$_3$, δ): 1.20-1.37 (5H, m), 1.46 (9H, s), 1.63 (2H, m), 1.85 (2H, m), 2.17 (3H, s), 2.30 (2H, t, J=7 Hz), 3.39 (1H, t, J=7 Hz), 4.11 82H, q, J=7 Hz), 4.73 (1H, d, J=17 Hz), 4.82 (1H, d, J=17 Hz)

Preparation 166

To a solution of ethyl thiophene (2.00 g) and ethyl 7-chloro-7-oxoheptanoate (5.39 g) in dichloromethane (20 mL) was added 1 M tin chloride in dichloromethane (38.9 mL) over 0.5 hour under an ice-bath (5 to 8° C.). After stirring for 0.5 hour, the mixture was stirred for 0.5 hour at room temperature. The mixture was poured into ice-water (100 mL), and extracted with ethyl acetate (100 mL). The organic extract was washed with water (100 mL) and brine, dried over magnesium sulfate, and evaporated to give a brown oil. Flash silica gel column chromatography eluting with ethyl acetate-hexane=1-10 to 3-10 afforded ethyl 7-oxo-7-(2-thienyl)heptanoate as a brown oil (5.79 g).

Ethyl 7-oxo-7-(2-thienyl)heptanoate

NMR (CDCl$_3$, δ): 1.25 (3H, t, J=7 Hz), 1.42 (2H, m), 1.63-1.72 (4H, m), 2.31 (2H, t, J=7 Hz), 2.91 (2H, t, J=7 Hz), 4.12 (2H, q, J=7 Hz), 7.13 (1H, m), 7.612 (1H, m), 7.70 (1H, m)

The following compounds were obtained in substantially the same manner as those of Preparations 129 and 130.

Preparation 167 tert-Butyl 3-(3,5-dimethyl-4-isoxazolyl)-3-oxopropanoate

NMR (CDCl$_3$, δ): 1.47 (9H, s), 2.46 (3H, s), 2.68 (3H, s), 3.68 (2H, s)

Preparation 168

Ethyl 4-methyl-3-oxopentanoate

NMR (CDCl$_3$, δ): 1.14 (6H, d, J=7 Hz), 1.28 (3H, t, J=7 Hz), 2.71 (1H, quintet, J=7 Hz), 3.50 (s, 2H), 4.19 (2H, q, J=7 Hz), 7.06-7.18, 7.56, and 7.85 (4H, m)

Preparation 169 tert-Butyl 4-(methylthio)-3-oxobutanoate

NMR (CDCl$_3$, δ): 1.47 (9H, s), 2.07 (3H, s), 3.31 (2H, s), 3.58 (2H, s)

Preparation 170 tert-Butyl 3-(1,3-oxazol-5-yl)-3-oxopropanoate

NMR (CDCl$_3$, δ): (a mixture of keto- and enol-form); keto-form: 1.45 (9H, s), 3.77 (2H, s), 7.85 (1H, s), 8.04 (1H, s); enol-form: d 1.45 (9H, s), 5.54 (1H, s), 7.53 (1H, s), 7.91 (1H, s)

The following compounds were obtained in substantially the same manner as that of Preparation 143.

Preparation 171

(2-Chloro-4-pyridinyl)(5-ethyl-1H-pyrrol-2-yl)methanone

NMR (CDCl$_3$, δ): 1.32 (3H, t, J=7 Hz), 2.74 (2H, q, J=7 Hz), 6.13 (1H, m), 6.79 (1H, m), 7.56 (1H, d, J=5 Hz), 7.69 (1H, s), 8.54 (1H, d, J=5 Hz), 9.40 (1H, br)

Preparation 172

(5-Ethyl-1H-pyrrol-2-yl)(3-methoxyphenyl)methanone

NMR (CDCl$_3$, δ): 1.32 (3H, t, J=7 Hz), 2.74 (2H, q, J=7 Hz), 3.87 (3H, s), 6.08 (1H, m), 6.83 (1H, m), 7.08 (1H, dd, J=2 Hz, 8 Hz), 7.33-7.42 (2H, m), 7.47 (1H, d, J=8 Hz), 9.58 (1H, br) MS (ESI$^+$): m/z 230

Preparation 173

(5-Ethyl-1H-pyrrol-2-yl)(4-pyridinyl)methanone

NMR (CDCl$_3$, δ): 1.32 (3H, t, J=7 Hz), 2.72 (2H, q, J=7 Hz), 6.13 (1H, m), 6.81 (1H, m), 7.65 (2H, d, J=7 Hz), 8.77 (2H, d, J=7 Hz), 9.39 (1H, br)

Preparation 174

(5-Ethyl-1H-pyrrol-2-yl)(2-pyrazinyl)methanone

NMR (CDCl$_3$, δ): 1.33 (3H, t, J=7 Hz), 2.77 (2H, q, J=7 Hz), 6.14 (1H, m), 7.51 (1H, m), 8.65 (1H, m), 8.74 (1H, m), 9.36 (1H, br)

Preparation 175

(5-Ethyl-1H-pyrrol-2-yl)(3-pyridinyl)methanone

NMR (CDCl$_3$, δ): 1.33 (3H, t, J=7 Hz), 2.76 (2H, q, J=7 Hz), 6.12 (1H, m), 6.81 (1H, m), 7.42 (1H, m), 8.13 (1H, m), 8.76 (1H, m), 9.08 (1H, m), 9.36 (1H, br)

Preparation 176

A mixture of 3-[(1-amino-5-ethyl-1H-pyrrol-2-yl)carbonyl]benzonitrile (300 mg), methanesulfonylacetic acid (208 mg), 1-(3-dimethylaminopropyl)-3-ethylcarbodiimide hydrochloride (361 mg), and 1-hydroxybenzotriazole (254 mg) in N,N-dimethylformamide (1 mL) was stirred for 1.5 hours. The mixture was partitioned between ethyl acetate and water. The organic layer was washed with water two times, saturated sodium bicarbonate, and brine, dried over magnesium sulfate, and evaporated to give a pale brown solid. Flash silica gel column chromatography eluting with ethyl acetate-hexane=½ to ⅙ afforded N-[2-(3-cyanobenzoyl)-5-ethyl-1H-pyrrol-1-yl]-2-(methylsulfonyl)acetamide as a pale brown foam, which was solidified upon standing (505 mg).

N-[2-(3-Cyanobenzoyl)-5-ethyl-1H-pyrrol-1-yl]-2-(methylsulfonyl)acetamide

NMR (CDCl$_3$, δ): 1.29 (3H, t, J=7 Hz), 2.62 (2H, q, J=7 Hz), 3.28 (3H, s), 4.15 (2H, s), 6.12 (1H, d, J=5 Hz), 6.75 (1H, d, J=5 Hz), 7.58 (1H, t, J=9 Hz), 7.82 (1H, d, J=9 Hz), 8.01 (1H, d, J=9 Hz), 8.06 (1H, s)

The following compound was obtained in substantially the same manner as that of Preparation 176.

Preparation 177

Ethyl 3-{[2-(4-cyanobenzoyl)-5-ethyl-1H-pyrrol-1-yl]amino}-3-oxopropanoate

NMR (CDCl$_3$, δ): 1.20-1.37 (6H, m), 2.56 (2H, q, J=7 Hz), 3.57 (2H, s), 4.30 (2H, q, J=7 Hz), 6.06 (1H, d, J=5 Hz), 6.68 (1H, d, J=5 Hz), 7.54 (2H, d, J=9 Hz), 7.84 (2H, d, J=9 Hz)

EXAMPLE 1

To a solution of 4-[(1-amino-5-ethyl-1H-pyrrol-2-yl)carbonyl]benzonitrile (100 mg) in toluene (1 mL) were added 1-(4-methoxyphenyl)acetone (103 mg) and p-toluene-sulfonic acid monohydrate (16 mg) at ambient temperature. The reaction mixture was heated at 80° C. for 3 hours. The mixture was evaporated in vacuo. The residue was purified by flash silica gel column chromatography eluting with hexane-ethyl acetate 20-1 and 15-1 to give 4-[7-ethyl-3-(4-methoxyphenyl)-2-methylpyrrolo[1,2-b]pyridazin-4-yl]benzonitrile (31 mg, 20.2%) as an yellow solid.

4-[7-Ethyl-3-(4-methoxyphenyl)-2-methylpyrrolo[1,2-b]pyridazin-4-yl]benzonitrile NMR (CDCl$_3$, δ): 1.40 (3H, t, J=8 Hz), 2.31 (3H, s), 3.16 (2H, q, J=8 Hz), 3.77 (3H, s), 6.10 (1H, d, J=5 Hz), 6.60 (1H, d, J=5 Hz), 6.75 (2H, d, J=8 Hz), 6.93 (2H, d, J=8 Hz), 7.33 (2H, d, J=8 Hz), 7.53 (2H, d, J=8 Hz) MS (ESI$^+$): m/z 368 (M+H)

The following compounds were obtained in substantially the same manner as that of Example 1.

EXAMPLE 2

Ethyl 4-(4-cyanophenyl)-2-(2-ethoxy-2-oxoethyl)-7-ethylpyrrolo[1,2-b]pyridazine-3-carboxylate NMR (CDCl$_3$, δ): 0.84 (3H, t, J=7 Hz), 1.28 (3H, t, J=7 Hz), 1.37 (3H, t, J=7 Hz), 3.04 (2H, q, J=7 Hz), 3.93 (2H, q, J=7 Hz), 4.13 (3H, s), 4.19 (2H, q, J=7 Hz), 6.24 (1H, d, J=5 Hz), 6.62 (1H, d, J=5 Hz), 7.13 (2H, d, J=9 Hz), 7.76 (2H, d, J=9 Hz)

EXAMPLE 3

Ethyl 4-(4-cyanophenyl)-7-ethyl-2-(trifluoromethyl)pyrrolo[1,2-b]pyridazine-3-carboxylate NMR (CDCl$_3$, δ): 1.08 (3H, t, J=7 Hz), 1.41 (3H, t, J=7 Hz), 3.11 (2H, q, J=7 Hz), 4.11 (2H, q, J=7 Hz), 6.43 (1H, d, J=5 Hz), 6.93 (1H, d, J=5 Hz), 7.62 (2H, d, J=9 Hz), 7.80 (2H, d, J=9 Hz)

EXAMPLE 4

4-[7-Ethyl-2-methyl-3-(3-pyridinylcarbonyl)pyrrolo[1,2-b]pyridazin-4-yl]benzonitrile NMR (CDCl$_3$, δ): 1.43 (t, J=7 Hz, 3H), 2.47 (s, 3H), 3.09 (q, J=7 Hz, 2H), 6.35 (d, J=5 Hz, 1H), 6.74 (d, J=5 Hz, 1H), 7.23 (1H, m), 7.48 (2H, d, J=9 Hz), 7.55 (2H, d, J=9 Hz), 7.93 (1H, m), 8.62 (1H, m), 8.74 (1H, m)

EXAMPLE 5

3-[7-Ethyl-2-methyl-3-(4-pyridinyl)pyrrolo[1,2-b]pyridazin-4-yl]benzonitrile

NMR (CDCl$_3$, δ): 1.42 (3H, t, J=7 Hz), 2.32 (3H, s), 3.08 (2H, q, J=7 Hz), 6.15 (1H, d, J=5 Hz), 6.67 (1H, d, J=5 Hz), 7.00 (2H, d, J=9 Hz), 7.37 (2H, m), 7.57 (2H, m), 8.50 (2H, d, J=9 Hz)

EXAMPLE 6

4-(3-Benzyl-7-ethyl-2-methylpyrrolo[1,2-b]pyridazin-4-yl)benzonitrile

NMR (CDCl$_3$, δ): 1.40 (3H, t, J=8 Hz), 2.35 (3H, s), 3.04 (2H, q, J=8 Hz), 3.83 (3H, s), 5.94 (1H, d, J=5 Hz), 6.57 (1H, d, J=5 Hz), 6.98 (2H, d, J=8 Hz), 7.14-7.30 (3H, m), 7.46 (2H, d, J=8 Hz), 7.68 (2H, d, J=8 Hz) MS (ESI$^+$): m/z 352 (M+H)

EXAMPLE 7

4-(3-Chlorophenyl)-7-ethyl-2-phenylpyrrolo[1,2-b]pyridazine-3-carbonitrile mp: 172-173° C. NMR (CDCl$_3$, δ): 1.41 (3H, t, J=8 Hz), 3.10 (2H, q, J=8 Hz), 6.65 (1H, d, J=5 Hz), 6.88 (1H, d, J=5 Hz), 7.47-7.64 (6H, m), 7.70 (1H, br s), 7.81-7.90 (2H, m)

EXAMPLE 8

3-(3-Ethyl-7,7,9,9-tetramethyl-6,7,8,9-tetrahydropyrrolo[1,2-b]cinnolin-10-yl)benzonitrile NMR (CDCl$_3$, δ): 1.00-1.15 (12H, m), 1.37 (3H, t, J=8 Hz), 2.81 (3H, s), 3.00 (2H, q, J=8 Hz), 3.82 (2H, t, J=5 Hz), 5.46 (1H, d, J=5 Hz), 6.46 (1H, d, J=5 Hz), 7.50-7.65 (3H, m), 7.72 (1H, m)

EXAMPLE 9

3-(3-Ethyl-9-oxo-6,7,8,9-tetrahydropyrrolo[1,2-b]cinnolin-10-yl)benzonitrile

NMR (CDCl$_3$, δ): 1.40 (3H, t, J=8 Hz), 2.08-2.22 (2H, m), 2.60 (2H, t, J=7 Hz), 3.00-3.15 (4H, m), 6.26 (1H, d, J=5 Hz), 6.74 (1H, d, J=5 Hz), 7.49-7.61 (3H, m), 7.74 (1H, m) MS (ESI$^+$): m/z 316 (M+H)

EXAMPLE 10

3-(6-Ethyl-1-oxo-2,3-dihydro-1H-cyclopenta[e]pyrrolo[1,2-b]pyridazin-9-yl)benzonitrile mp: 150-154° C. NMR (CDCl$_3$, δ): 1.43 (3H, t, J=8 Hz), 2.75 (2H, t, J=7 Hz), 3.10 (2H, q, J=8 Hz), 3.24 (2H, t, J=7 Hz), 6.67 (1H, d, J=5 Hz), 6.87 (1H, d, J=5 Hz), 7.60 (1H, t, J=8 Hz), 7.75-7.90 (3H, m) MS (ESI$^+$): m/z 324 (M+Na)

EXAMPLE 11

3-(7-Ethyl-2-neopentylpyrrolo[1,2-b]pyridazin-4-yl)benzonitrile

NMR (CDCl$_3$, δ): 1.05 (9H, s), 1.39 (3H, t, J=8 Hz), 2.68 (2H, s), 3.04 (2H, q, J=8 Hz), 6.36 (1H, s), 6.48 (1H, d, J=5 Hz), 6.67 (1H, d, J=5 Hz), 7.51 (1H, t, J=8 Hz), 7.75 (1H, br d, J=8 Hz), 7.92-8.01 (2H, m) MS (ESI$^+$): m/z 318 (M+H)

EXAMPLE 12

3-[7-Ethyl-2-(2-furyl)pyrrolo[1,2-b]pyridazin-4-yl]benzonitrile

NMR (CDCl$_3$, δ): 1.44 (3H, t, J=8 Hz), 3.11 (2H, q, J=8 Hz), 6.52-6.60 (2H, m), 6.74 (1H, d, J=5 Hz), 6.98 (1H, s), 7.09 (1H, d, J=5 Hz), 7.56-7.68 (2H, m), 7.78 (1H, dd, J=8, 1 Hz), 7.96-8.08 (2H, m) MS (ESI$^+$): m/z 314 (M+H)

EXAMPLE 13

4-[7-Ethyl-2-methyl-3-(methylsulfonyl)pyrrolo[1,2-b]pyridazin-4-yl]benzonitrile

NMR (CDCl$_3$, δ): 1.38 (3H, t, J=8 Hz), 2.89 (3H, s), 3.00-3.11 (5H, m), 6.09 (1H, d, J=5 Hz), 6.73 (1H, d, J=5 Hz), 7.45 (2H, d, J=8 Hz), 7.76 (2H, d, J=8 Hz) MS (ESI$^+$): m/z 340 (M+H)

EXAMPLE 13-2

4-{7-Ethyl-2-[(methylsulfonyl)methyl]pyrrolo[1,2-b]pyridazin-4-yl}benzonitrile

NMR (CDCl$_3$, δ): 1.39 (3H, t, J=8 Hz), 2.96-3.09 (5H, m), 4.44 (2H, s), 6.63 (1H, d, J=5 Hz), 6.71 (1H, s), 6.81 (1H, d, J=5 Hz), 7.79 (2H, d, J=8 Hz), 7.85 (2H, d, J=8 Hz) MS (ESI$^+$): m/z 340 (M+H)

EXAMPLE 15

3-[7-Ethyl-2-methyl-3-(methylsulfonyl)pyrrolo[1,2-b]pyridazin-4-yl]benzonitrile

NMR (CDCl$_3$, δ): 1.39 (3H, t, J=8 Hz), 2.89 (3H, s), 3.00-3.11 (5H, m), 6.09 (1H, d, J=5 Hz), 6.73 (1H, d, J=5 Hz), 7.54-7.63 (3H, m), 7.77 (1H, m)

EXAMPLE 16

To a solution of 4-[7-ethyl-3-(4-methoxyphenyl)-2-methylpyrrolo[1,2-b]pyridazin-4-yl]benzonitrile (22 mg) in N,N-dimethylformamide (1 mL) were added 1N sodium hydroxide (0.12 mL) and 30% hydrogen peroxide (0.07 mL) at ambient temperature. After 1 hour stirring, the reaction mixture was partitioned between ethyl acetate and water. The organic layer was washed with water three times and brine, dried over magnesium sulfate, and evaporated in vacuo. The residue was purified by flash silica gel column chromatography (silica gel, 30 mL) eluting with hexane-ethyl acetate=5-1 and 0-1 to give 4-[7-ethyl-3-(4-methoxyphenyl)-2-methylpyrrolo[1,2-b]pyridazin-4-yl]benzamide (18 mg, 78.0%) as an yellow solid.

4-[7-Ethyl-3-(4-methoxyphenyl)-2-methylpyrrolo[1,2-b]pyridazin-4-yl]benzamide

NMR (CDCl$_3$, δ): 1.41 (3H, t, J=8 Hz), 2.31 (3H, s), 3.17 (2H, q, J=8 Hz), 3.77 (3H, s), 5.61 (0.2H, br s), 6.02 (0.4H, br s), 6.13 (1H, d, J=5 Hz), 6.60 (1H, d, J=5 Hz), 6.75 (2H, d, J=8 Hz), 6.95 (2H, d, J=8 Hz), 7.31 (2H, d, J=8 Hz), 7.68 (2H, d, J=8 Hz) MS (ESI$^+$): m/z 386 (M+H)

The following compound was obtained in substantially the same manner as that of Example 16.

EXAMPLE 17

[2-(Dimethylamino)-7-ethyl-3-(methylsulfonyl)pyrrolo[1,2-b]pyridazin-4-yl]benzamide NMR (CDCl$_3$, δ): 1.32 (3H, t, J=7 Hz), 2.90 (6H, s), 2.95 (2H, q, J=7 Hz), 3.36 (3H, s), 6.21 (1H, d, J=5 Hz), 6.79 (1H, d, J=5 Hz), 7.44 (1H, s, br), 7.52-7.56 (2H, m), 7.90 (1H, s), 7.94-8.06 (2H, m) MS (ESI$^+$): m/z 387 (M+H)

EXAMPLE 18

3-(7-Ethyl-2-neopentylpyrrolo[1,2-b]pyridazin-4-yl)benzamide

NMR (CDCl$_3$, δ): 1.05 (9H, s), 1.39 (3H, t, J=8 Hz), 2.68 (2H, s), 3.04 (2H, q, J=8 Hz), 5.70 (1H, br s), 6.11 (1H, br s), 6.41 (1H, s), 6.52 (1H, d, J=5 Hz), 6.65 (1H, d, J=5 Hz), 7.59 (1H, t, J=8 Hz), 7.85-7.93 (2H, m), 8.15 (1H, br s) MS (ESI$^+$): m/z 336 (M+H)

EXAMPLE 19

3-[7-Ethyl-2-(2-furyl)pyrrolo[1,2-b]pyridazin-4-yl]benzamide

NMR (CDCl$_3$, δ): 1.43 (3H, t, J=8 Hz), 3.10 (2H, q, J=8 Hz), 5.70 (1H, br s), 6.13 (1H, br s), 6.53-6.60 (2H, m), 6.71 (1H, d, J=5 Hz), 7.02 (1H, s), 7.06 (1H, d, J=5 Hz), 7.55-7.65 (2H, m), 7.79-7.98 (2H, m), 8.02 (1H, br s) MS (ESI$^+$): m/z 332 (M+H)

EXAMPLE 20

5-[2-({[4-(Aminocarbonyl)benzyl,]oxy}methyl)-4-(5-bromo-3-pyridinyl)-7-ethylpyrrolo[1,2-b]pyridazin-3-yl]pentanoic acid NMR (DMSO-d$_6$, δ): 1.27-1.45 (7H, m), 1.99 (2H, m), 2.96 (2H, m), 3.40 (2H, m), 4.67 (2H, s), 4.72 (2H, s), 5.88 (1H, d, J=5 Hz), 6.67 (1H, d, J=5 Hz), 7.35 (1H, s, br), 7.44 (2H, d, J=8 Hz), 7.86 (2H, d, J=8 Hz), 7.96 (1H, s, br), 8.21 (1H, m), 8.60 (1H, m), 8.86 (1H, m)

EXAMPLE 21

To a solution of ethyl 6-(3-cyanobenzoyl)-7-oxooctanoate (3.18 g) in toluene (30 mL) was added 2-ethyl-1H-pyrrol- 1-amine (1.17 g) and p-toluenesulfonic acid monohydrate (96 mg) at ambient temperature. The reaction mixture was refluxed for 1 hour. The mixture was evaporated in vacuo. The residue was purified by flash silica gel chromatography (silica gel, 200 mL) eluting with hexane-ethyl acetate=20-1, 15-1, and 10-1 to give ethyl 5-[4-(3-cyanophenyl)-7-ethyl-2-methylpyrrolo[1,2-b]pyridazin-3-yl]pentanoate (3.29 g, 83.8%) as an yellow oil.

Ethyl 5-[4-(3-cyanophenyl)-7-ethyl-2-methylpyrrolo[1,2-b]pyridazin-3-yl]pentanoate NMR (CDCl$_3$, δ): 1.23 (3H, t, J=8 Hz), 1.32-1.58 (7H, m), 2.18 (2H, t, J=8 Hz), 2.35-2.45 (2H, m), 3.01 (2H, q, J=8 Hz), 4.10 (2H, q, J=8 Hz), 5.79 (1H, d, J=5 Hz), 6.51 (1H, d, J=5 Hz), 7.57-7.67 (3H, m), 7.75 (1H, m)

The following compounds were obtained in substantially the same manner as that of Example 21.

EXAMPLE 22

Ethyl 2,4-diisopropylpyrrolo[1,2-b]pyridazine-3-carboxylate

NMR (300 MHz, CDCl$_3$, δ): 1.32 (6H, d, J=7.5 Hz), 1.39 (3H, t, J=75 Hz), 1.46 (6H, d, J=75 Hz), 2.91-3.05 (1H, m), 3.05-3.20 (1H, m), 4.38 (2H, q, J=75 Hz), 6.64-6.68 (1H, m), 6.76-6.80 (1H, m), 7.65-7.68 (1H, m) MS (ES+) m/e 275.33

EXAMPLE 23

Ethyl 4-(2-chlorophenyl)-2-isopropylpyrrolo[1,2-b]pyridazine-3-carboxylate

NMR (300 MHz, CDCl$_3$, δ): 0.89 (3H, t, J=7.5 Hz), 1.30-1.40 (6H, m), 3.36-3.51 (1H, m), 4.00 (2H, q, J=7.5 Hz), 6.10-6.18 (1H, m), 6.75-6.84 (1H, m), 7.28-7.45 (3H, m), 7.45-7.55 (1H, m), 7.75-7.81 (1H, m)

EXAMPLE 24

Ethyl 2-isopropyl-4-(2-naphthyl)pyrrolo[1,2-b]pyridazine-3-carboxylate

NMR (300 MHz, CDCl$_3$, δ): 0.78 (3H, t, J=7.5 Hz), 1.38 (6H, d, J=75 Hz), 3.24-3.35 (1H, m), 3.95 (2H, q, J=7.5 Hz), 6.36-6.40 (1H, m), 6.80-6.85 (1H, m), 7.50-7.54 (3H, m), 7.78-7.82 (1H, m), 7.82-8.00 (4H, m) MS (ES+) m/e 359.56

EXAMPLE 25

Ethyl 5-{7-ethyl-2-methyl-4-[3-(trifluoromethyl)phenyl]pyrrolo[1,2-b]pyridazin-3-yl}pentanoate NMR (CDCl$_3$, δ): 1.22 (3H, t, J=7 Hz), 1.37 (3H, t, J=7 Hz), 1.40-1.59 (4H, m), 2.14 (2H, t, J=7 Hz), 2.38-2.46 (2H, m), 2.55 (3H, s), 3.01 (2H, q, J=7 Hz), 4.10 (2H, q, J=7 Hz), 5.83 (1H, d, J=4 Hz), 6.51 (1H, d, J=4 Hz), 7.53-7.64 (3H, m), 7.71 (1H, d, J=8 Hz) MS (ESI$^+$): m/z 433 (M+H)

EXAMPLE 26

Ethyl 5-[7-ethyl-2-methyl-4-(5-methyl-3-pyridinyl)pyrrolo[1,2-b]pyridazin-3-yl]pentanoate NMR (CDCl$_3$, δ): 1.23 (3H, t, J=7 Hz), 1.37 (3H, t, J=7 Hz), 1.38-1.60 (4H, m), 2.18 (2H, t, J=7 Hz), 2.42 (3H, s), 2.38-2.50 (2H, m), 2.55 (3H, s), 3.00 (2H, q, J=7 Hz), 4.09 (2H, q, J=7 Hz), 5.87 (1H, d, J=4 Hz), 6.51 (1H, d, J=4 Hz), 7.50 (1H, s), 8.39 (1H, s), 8.53 (1H, s) MS (ESI$^+$): m/z 380 (M+H)

EXAMPLE 27

Ethyl 5-[7-ethyl-4-(3-methoxy-5-isoxazolyl)-2-(methoxymethyl)pyrrolo[1,2-b]pyridazin-3-yl]pentanoate NMR (CDCl$_3$, δ): 1.25 (3H, t, J=7 Hz), 1.36 (3H, t, J=7 Hz), 1.55-1.64 (2H, m), 1.64-1.80 (2H, m), 2.33 (2H, t, J=7 Hz), 2.74-2.85 (2H, m), 3.03 (2H, q, J=7 Hz), 3.43 (3H, s), 4.08 (3H, s), 4.12 (2H, q, J=7 Hz), 4.62 (2H, s), 6.28 (1H, s), 6.38 (1H, d, J=4 Hz), 6.65 (1H, d, J=4 Hz) MS (ESI$^+$): m/z 416 (M+H)

EXAMPLE 28

Ethyl 5-{7-ethyl-2-methyl-4-[3-(1,3-oxazol-5-yl)phenyl]pyrrolo[1,2-b]pyridazin-3-yl}pentanoate NMR (CDCl$_3$, δ): 1.20 (3H, t, J=7 Hz), 1.35 (3H, t, J=7 Hz), 1.40-1.63 (4H, m), 2.17 (2H, t, J=7 Hz), 2.44-2.57 (2H, m), 2.56 (3H, s), 3.02 (2H, q, J=7 Hz), 4.05 (2H, q, J=7 Hz), 5.89 (1H, d, J=4 Hz), 6.50 (1H, d, J=4 Hz), 7.33 (1H, d, J=8 Hz), 7.39 (1H, s), 7.53 (1H, t, J=8 Hz), 7.66 (1H, m), 7.74 (1H, d, J=8 Hz), 7.93 (1H, s)

EXAMPLE 29

Ethyl 5-[4-(3,4-dichlorophenyl)-7-ethyl-2-methylpyrrolo[1,2-b]pyridazin-3-yl]pentanoate NMR (CDCl$_3$, δ): 1.24 (3H, t, J=7 Hz), 1.37 (3H, t, J=7 Hz), 1.38-1.48 (2H, m), 1.50-1.65 (2H, m), 2.20 (2H, t, J=7 Hz), 2.38-2.47 (2H, m), 2.54 (3H, s), 3.00 (2H, q, J=7 Hz), 4.12 (2H, q, J=7 Hz), 5.87 (1H, d, J=4 Hz), 6.51 (1H, d, J=4 Hz), 7.19 (1H, dd, J=2 Hz, 8 Hz), 7.46 (1H, d, J=2 Hz), 7.56 (1H, d, J=8 Hz) MS (ESI$^+$): m/z 433 (M+H)

EXAMPLE 30

Ethyl 5-[4-(4-chloro-2-pyridinyl)-7-ethyl-2-methylpyrrolo[1,2-b]pyridazin-3-yl]pentanoate NMR (CDCl$_3$, δ): 1.24 (3H, t, J=7 Hz), 1.37 (3H, t, J=7 Hz), 1.44-1.67 (4H, m), 2.15-2.26 (2H, m), 2.42-2.56 (2H, m), 2.56 (3H, s), 3.01 (2H, q, J=7 Hz), 4.10 (2H, q, J=7 Hz), 5.95 (1H, d, J=3 Hz), 6.54 (1H, d, J=3 Hz), 7.40 (1H, dd, J=2 Hz, 4 Hz), 7.54 (1H, d, J=2 Hz), 8.67 (1H, d, J=4 Hz) MS (ESI$^+$): m/z 400 (M+H)

EXAMPLE 31

Ethyl 5-[4-(5-chloro-2-thienyl)-7-ethyl-2-(methoxymethyl)pyrrolo[1,2-b]pyridazin-3-yl]pentanoate NMR (CDCl$_3$, δ): 1.25 (3H, t, J=7 Hz), 1.36 (3H, t, J=7 Hz), 1.48-1.74 (4H, m), 2.28 (2H, t, J=7 Hz), 2.68-2.77 (2H, m), 3.02 (2H, q, J=7 Hz), 3.44 (3H, s), 4.12 (2H, q, J=7 Hz), 4.60 (2H, s), 6.25 (1H, d, J=4 Hz), 6.60 (1H, d, J=4 Hz), 6.97 (2H, m) MS (ESI$^+$): m/z 435 (M+H)

EXAMPLE 32

Ethyl 5-[7-ethyl-4-(6-methoxy-2-pyrazinyl)-2-methylpyrrolo[1,2-b]pyridazin-3-yl]pentanoate NMR (CDCl$_3$, δ): 1.23 (3H, t, J=7 Hz), 1.37 (3H, t, J=7 Hz), 1.52-1.68 (4H, m), 2.23 (2H, t, J=7 Hz), 2.48-2.55 (2H, m), 2.56 (3H, s), 3.02 (2H, q, J=7 Hz), 3.98 (3H, s), 4.09 (2H, q, J=7 Hz), 6.03 (1H, d, J=4 Hz), 6.55 (1H, d, J=4 Hz), 8.30 (1H, s), 8.33 (1H, s) MS (ESI$^+$): m/z 397 (M+H)

EXAMPLE 33

Ethyl 5-[4-(1-benzofuran-2-yl)-7-ethyl-2-methylpyrrolo[1,2-b]pyridazin-3-yl]pentanoate NMR (CDCl$_3$, δ): 1.23 (3H, t, J=7 Hz), 1.38 (3H, t, J=7 Hz), 1.62-1.83 (4H, m), 2.33 (2H, t, J=7 Hz), 2.57 (3H, s), 2.69-2.78 (2H, m), 3.03 (2H, q, J=7 Hz), 4.12 (2H, q, J=7 Hz), 6.48 (1H, d, J=4 Hz), 6.59 (1H, d, J=4 Hz), 7.15 (1H, s), 7.26-7.42 (2H, m), 7.57 (1H, d, J=8 Hz), 7.68 (1H, d, J=8 Hz) MS (ESI$^+$): m/z 405 (M+H)

EXAMPLE 34

Ethyl 5-[4-(1-benzothien-2-yl)-7-ethyl-2-methylpyrrolo[1,2-b]pyridazin-3-yl]pentanoate NMR (CDCl$_3$, δ): 1.21 (3H, t, J=7 Hz), 1.35 (3H, t, J=7 Hz), 1.52-1.69 (4H, m), 2.23 (2H, t, J=7 Hz), 2.56 (3H, s), 2.61-2.70 (2H, m), 3.02 (2H, q, J=7 Hz), 4.07 (2H, q, J=7 Hz), 6.21 (1H, d, J=4 Hz), 6.53 (1H, d, J=4 Hz), 7.35-7.43 (3H, m), 7.81-7.92 (2H, m)

EXAMPLE 35

Ethyl 5-[7-ethyl-2-methyl-4-(1,3-oxazol-5-yl)pyrrolo[1,2-b]pyridazin-3-yl]pentanoate NMR (CDCl$_3$, δ): 1.25 (3H, t, J=7 Hz), 1.36 (3H, t, J=7 Hz), 1.53-1.66 (2H, m), 1.66-1.83 (2H, m), 2.34 (2H, t, J=7 Hz), 2.56 (3H, s), 2.62-2.73 (2H, m), 3.02 (2H, q, J=7 Hz), 4.13 (2H, q, J=7 Hz), 6.42 (1H, d, J=4 Hz), 6.58 (1H, d, J=4 Hz), 7.50 (1H, s), 8.10 (1H, s) MS (ESI$^+$): m/z 356 (M+H)

EXAMPLE 36

Ethyl 5-(7-ethyl-2-methyl-4-phenylpyrrolo[1,2-b]pyridazin-3-yl)pentanoate

NMR (CDCl$_3$, δ): 1.23 (3H, t, J=7 Hz), 1.37 (3H, t, J=7 Hz), 1.40-1.60 (4H, m), 2.15 (2H, t, J=7 Hz), 2.41-2.48 (2H, m), 2.55 (3H, s), 3.02 (2H, q, J=7 Hz), 4.08 (2H, q, J=7 Hz), 5.88 (1H, d, J=4 Hz), 6.48 (1H, d, J=4 Hz), 7.31-7.34 (2H, m), 7.40-7.49 (3H, m) MS (ESI$^+$): m/z 365 (M+H)

EXAMPLE 37

Ethyl 5-[7-ethyl-2-methyl-4-(6-quinolinyl)pyrrolo[1,2-b]pyridazin-3-yl]pentanoate NMR (CDCl$_3$, δ): 1.18 (3H, t, J=7 Hz), 1.39 (3H, t, J=7 Hz), 1.39-1.55 (4H, m), 2.14 (2H, d, J=7 Hz), 2.44-2.55 (2H, m), 2.58 (3H, s), 3.03 (2H, q, J=7 Hz), 4.03 (2H, q, J=7 Hz), 5.86 (1H, d, J=4 Hz), 6.51 (1H, d, J=4 Hz), 7.45-7.52 (1H, m), 7.69 (1H, dd, J=2 Hz, 8 Hz), 7.84 (1H, d, J=2 Hz), 8.20 (2H, d, J=8 Hz), 9.00 (1H, m)

EXAMPLE 38

Ethyl 7-{4-[4-({[(benzyloxy)carbonyl]amino}sulfonyl)phenyl]-7-ethyl-2-methylpyrrolo[1,2-b]pyridazin-3-yl}heptanoate NMR (CDCl$_3$, δ): 1.12-1.23 (7H, m), 1.33-1.51 (7H, s), 2.17 (2H, t, J=7 Hz), 2.35 (2H, m), 2.56 (3H, s), 3.02 (2H, q, J=7 Hz), 4.11 (2H, q, J=7 Hz), 5.17 (2H, s), 5.78 (1H, d, J=5 Hz), 6.52 (1H, d, J=5 Hz), 7.29-7.38 (5H, m), 7.49 (2H, d, J=9 Hz), 7.87 (1H, s, br), 8.11 (2H, d, J=9 Hz) MS (ESI$^+$): m/z 606 (M+H) MS (ESI$^-$): m/z 604 (M−H)

EXAMPLE 39

2-{[4-(3-Chlorophenyl)-7-ethyl-2-methylpyrrolo[1,2-b]pyridazin-3-yl]methyl}-1,3-propanediol NMR (CDCl$_3$, δ): 1.26 (3H, t, J=7 Hz), 1.38 (3H, t, J=7 Hz), 1.64-1.82 (3H, m), 2.59 (3H, s), 3.02 (2H, q, J=7 Hz), 3.45 (2H, m), 3.63 (2H, m), 4.12 (2H, q, J=7 Hz), 5.93 (1H, d, J=5 Hz), 6.53 (1H, d, J=5 Hz), 7.28 (1H, m), 7.42-7.44 (3H, m)

EXAMPLE 40

Ethyl 5-{7-ethyl-2-methyl-4-[3-(methylsulfonyl)phenyl]pyrrolo[1,2-b]pyridazin-3-yl}pentanoate NMR (CDCl$_3$, δ): 1.22 (3H, t, J=8 Hz), 1.33-1.57 (7H, m), 2.18 (2H, t, J=8 Hz), 2.35-2.45 (2H, m), 2.56 (3H, s), 3.01 (2H, q, J=8 Hz), 3.12 (3H, s), 4.08 (2H, q, J=8 Hz), 5.80 (1H, d, J=5 Hz), 6.51 (1H, d, J=5 Hz), 7.64-7.74 (2H, m), 7.96 (1H, br s), 8.04 (1H, m) MS (ESI$^+$): m/z 443 (M+H)

EXAMPLE 41

Ethyl 5-[4-(2-chloro-4-pyridinyl)-7-ethyl-2-methylpyrrolo[1,2-b]pyridazin-3-yl]pentanoate NMR (CDCl$_3$, δ): 1.23 (3H, t, J=8 Hz), 1.30-1.62 (7H, m), 2.21 (2H, t, J=8 Hz), 2.35-2.45 (2H, m), 2.55 (3H, s), 3.00 (2H, q, J=8 Hz), 4.10 (2H, q, J=8 Hz), 5.85 (1H, d, J=5 Hz), 6.53 (1H, d, J=5 Hz), 7.24 (1H, dd, J=7, 1 Hz), 7.35 (1H, br s), 8.53 (1H, d, J=7 Hz) MS (ESI$^+$): m/z 400 (M+H)

EXAMPLE 42

Ethyl 5-[7-ethyl-2-methyl-4-(3-nitrophenyl)pyrrolo[1,2-b]pyridazin-3-yl]pentanoate NMR (CDCl$_3$, δ): 1.21 (3H, t, J=8 Hz), 1.34-1.59 (7H, m), 2.17 (2H, t, J=8 Hz), 2.37-2.47 (2H, m), 2.57 (3H, s), 3.01 (2H, q, J=8 Hz), 4.08 (2H, q, J=8 Hz), 5.81 (1H, d, J=5 Hz), 6.52 (1H, d, J=5 Hz), 7.64-7.74 (2H, m), 8.25 (1H, br s), 8.33 (1H, m) MS (ESI$^+$): m/z 410 (M+H)

EXAMPLE 43

Ethyl 4-(4-fluorophenyl)-2-methylpyrrolo[1,2-b]pyridazine-3-carboxylate

NMR (CDCl$_3$, δ): 0.98 (3H, t, J=8 Hz), 2.55 (3H, s), 4.05 (2H, q, J=8 Hz), 6.35 (1H, m), 6.81 (1H, m), 7.12-7.22 (2H, m), 7.41-7.50 (2H, m), 7.76 (1H, m) MS (ESI$^+$): m/z 359 (M+H)

EXAMPLE 44

4-(3-Butyl-7-ethyl-2-methylpyrrolo[1,2-b]pyridazin-4-yl)benzonitrile

NMR (CDCl$_3$, δ): 0.78 (3H, t, J=8 Hz), 1.12-1.43 (7H, m), 2.31-2.40 (2H, m), 2.56 (3H, s), 3.00 (2H, q, J=8 Hz), 5.79 (1H, d, J=5 Hz), 6.50 (1H, d, J=5 Hz), 7.47 (2H, d, J=8 Hz), 7.77 (2H, d, J=8 Hz) MS (ESI$^+$): m/z 318 (M+H)

EXAMPLE 45

Ethyl 5-[4-(5-bromo-3-pyridinyl)-7-ethyl-2-methylpyrrolo[1,2-b]pyridazin-3-yl]pentanoate NMR (CDCl$_3$, δ): 1.24 (3H, t, J=7 Hz), 1.37 (3H, t, J=7 Hz), 1.40-1.65 (4H, m), 2.21 (2H, t, J=7 Hz), 2.37-2.49 (2H, m), 2.56 (3H, s), 3.00 (2H, q, J=7 Hz), 4.10 (2H, q, J=7 Hz), 5.87 (1H, d, J=4 Hz), 6.53 (1H, d, J=4 Hz), 7.85 (1H, m), 8.53 (1H, d, J=2 Hz), 8.77 (1H, d, J=2 Hz) MS: (m/z) 444, 446 (M+H)

EXAMPLE 46

Ethyl 5-{4-(2-chloro-4-pyridinyl)-7-ethyl-2-[(methylthio)methyl]pyrrolo[1,2-b]pyridazin-3-yl}pentanoate NMR (CDCl$_3$, δ): 1.24 (3H, t, J=7 Hz), 1.36 (3H, t, J=7 Hz), 1.40-1.63 (4H, m), 2.18 (3H, s), 2.20 (2H, t, J=7 Hz), 2.48-2.58 (2H, m), 3.02 (2H, q, J=7 Hz), 3.81 (2H, s), 4.10 (2H, q, J=7 Hz), 5.89 (1H, d, J=4 Hz), 6.57 (1H, d, J=4 Hz), 7.27 (1H, m), 7.38 (1H, s), 8.53 (1H, d, J=4 Hz) MS: (m/z) 446 (M+H)

EXAMPLE 47

Ethyl 6-[4-(3-cyanophenyl)-7-ethyl-2-methylpyrrolo[1,2-b]pyridazin-3-yl]hexanoate NMR (CDCl$_3$, δ): 1.15-1.29 (5H, m), 1.32-1.61 (7H, m), 2.20 (2H, t, J=8 Hz), 2.33-2.43 (2H, m), 2.56 (3H, s), 3.01 (2H, q, J=8 Hz), 4.10 (2H, q, J=8 Hz), 5.79 (1H, d, J=5 Hz), 6.51 (1H, d, J=5 Hz), 7.57-7.67 (3H, m), 7.75 (1H, m) MS (ESI$^+$): m/z 404 (M+H)

EXAMPLE 48

Ethyl 5-[4-(6-chloro-2-pyridinyl)-7-ethyl-2-methylpyrrolo[1,2-b]pyridazin-3-yl]pentanoate NMR (CDCl$_3$, δ): 1.23 (3H, t, J=7 Hz), 1.36 (3H, t, J=7 Hz), 1.46-1.65 (4H, m), 2.22 (2H, t, J=7 Hz), 2.46-2.57 (2H, m), 2.54 (3H, s), 3.00 (2H, q, J=7 Hz), 4.09 (2H, q, J=7 Hz), 5.95 (1H, d, J=4 Hz), 6.51 (1H, d, J=4 Hz), 7.38-7.47 (2H, m), 7.80 (1H, t, J=8 Hz) MS (ESI$^+$): m/z 400

EXAMPLE 49

Ethyl 5-[7-ethyl-4-(3-methoxyphenyl)-2-methylpyrrolo[1,2-b]pyridazin-3-yl]pentanoate NMR (CDCl$_3$, δ): 1.23 (3H, t, J=7 Hz), 1.36 (3H, t, J=7 Hz), 1.40-1.62 (4H, m), 2.17 (2H, t, J=7 Hz), 2.43-2.52 (2H, m), 2.54 (3H, s), 3.00 (2H, q, J=7 Hz), 3.83 (3H, s), 4.08 (2H, q, J=7 Hz), 5.91 (1H, d, J=4 Hz), 6.49 (1H, d, J=4 Hz), 6.87-6.99 (3H, m), 7.37 (1H, t, J=8 Hz) MS (ESI$^+$): m/z 395

EXAMPLE 50

Ethyl 5-[4-(3,5-dichlorophenyl)-7-ethyl-2-methylpyrrolo[1,2-b]pyridazin-3-yl]pentanoate NMR (CDCl$_3$, δ): 1.23 (3H, t, J=7 Hz), 1.37 (3H, t, J=7 Hz), 1.39-1.52 (2H, m), 1.52-1.64 (2H, m), 2.22 (2H, t, J=7 Hz), 2.38-2.48 (2H, m), 2.54 (3H, s), 3.00 (2H, q, J=7 Hz), 4.10 (2H, q, J=7 Hz), 5.88 (1H, d, J=4 Hz), 6.51 (1H, d, J=4 Hz), 7.25 (2H, m), 7.45 (1H, m) MS (ESI$^+$): m/z 433

EXAMPLE 51

Ethyl 5-[4-(5-chloro-2-thienyl)-7-ethyl-2-methylpyrrolo[1,2-b]pyridazin-3-yl]pentanoate NMR (CDCl$_3$, δ): 1.25 (3H, t, J=7 Hz), 1.36 (3H, t, J=7 Hz), 1.46-1.58 (2H, m), 1.60-1.74 (2H, m), 2.28 (2H, t, J=7 Hz), 2.53 (3H, s), 2.56-2.66 (2H, m), 2.98 (2H, q, J=7 Hz), 4.12 (2H, q, J=7 Hz), 6.20 (1H, d, J=4 Hz), 6.53 (1H, d, J=4 Hz), 6.94 (1H, d, J=4 Hz), 6.98 (1H, d, J=4 Hz) MS (ESI$^+$): m/z 405

EXAMPLE 52

Ethyl 5-[7-ethyl-4-(3-fluorophenyl)-2-methylpyrrolo[1,2-b]pyridazin-3-yl]pentanoate NMR (CDCl$_3$, δ): 1.23 (3H, t, J=7 Hz), 1.39 (3H, t, J=7 Hz), 1.38-1.50 (2H, m), 150-1.63 (2H, m), 2.17 (2H, t, J=7 Hz), 2.39-2.48 (2H, m), 2.54 (3H, s), 3.03 (2H, q, J=7 Hz), 4.09 (2H, q, J=7 Hz), 5.88 (1H, d, J=4 Hz), 6.50 (1H, d, J=4 Hz), 7.03-7.16 (3H, m), 7.38-7.47 (1H, m) MS (ESI$^+$): m/z 383

EXAMPLE 53

Ethyl 5-[7-ethyl-2-methyl-4-(3-quinolinyl)pyrrolo[1,2-b]pyridazin-3-yl]pentanoate NMR (CDCl$_3$, δ): 1.18 (3H, t, J=7 Hz), 1.38 (3H, t, J=7 Hz), 1.40-1.60 (4H, m), 2.16 (2H, t, J=7 Hz), 2.44-2.56 (2H, m), 2.59 (3H, s), 3.04 (2H, q, J=7 Hz), 4.03 (2H, q, J=7 Hz), 5.89 (1H, d, J=4 Hz), 6.53 (1H, d, J=4 Hz), 7.62 (1H, t, J=8 Hz), 7.80 (1H, t, J=8 Hz), 7.90 (1H, d, J=8 Hz), 8.21 (2H, m), 8.90 (1H, d, J=2 Hz) MS (ESI$^+$): m/z 416

EXAMPLE 54

Ethyl 5-[7-ethyl-2-methyl-4-(4-pyridinyl)pyrrolo[1,2-b]pyridazin-3-yl]pentanoate NMR (CDCl$_3$, δ): 1.23 (3H, t, J=7 Hz), 1.38 (3H, t, J=7 Hz), 1.40-1.64 (4H, m), 2.19 (2H, t, J=7 Hz), 2.38-2.52 (2H, m), 2.55 (3H, s), 3.02 (2H, q, J=7 Hz), 4.09 (2H, q, J=7 Hz), 5.83 (1H, d, J=4 Hz), 6.51 (1H, d, J=4 Hz), 7.29 (2H, m), 8.72 (2H, m) MS (ESI$^+$): m/z 366

EXAMPLE 55

Ethyl 5-[7-ethyl-4-(3-methoxy-5-isoxazolyl)-2-methylpyrrolo[1,2-b]pyridazin-3-yl]pentanoate NMR (CDCl$_3$, δ): 1.25 (3H, t, J=7 Hz), 1.36 (3H, t, J=7 Hz), 1.55-1.82 (4H, m), 2.33 (2H, t, J=7 Hz), 2.55 (3H, s), 2.62-2.72 (2H, m), 2.99 (2H, q, J=7 Hz), 4.08 (3H, s), 4.12 (2H, q, J=7 Hz), 6.26 (1H, s), 6.34 (1H, d, J=4 Hz), 6.58 (1H, d, J=4 Hz)

EXAMPLE 56

Ethyl 5-[7-ethyl-2-methyl-4-(5-methyl-3-isoxazolyl)pyrrolo[1,2-b]pyridazin-3-yl]pentanoate NMR (CDCl$_3$, δ): 1.25 (3H, t, J=7 Hz), 1.36 (3H, t, J=7 Hz), 1.50-1.75 (4H, m), 2.29 (2H, t, J=7 Hz), 2.55 (6H, s), 2.56-2.65 (2H, m), 2.99 (2H, q, J=7 Hz), 4.11 (2H, q, J=7 Hz), 6.16 (1H, d, J=4 Hz), 6.22 (1H, s), 6.54 (1H, d, J=4 Hz) MS (ESI$^+$): m/z 370

EXAMPLE 57

Ethyl 5-[4-(2-chloro-4-pyridinyl)-7-ethyl-2-(methoxymethyl)pyrrolo[1,2-b]pyridazin-3-yl]pentanoate NMR (CDCl$_3$, δ): 1.23 (3H, t, J=7 Hz), 1.37 (3H, t, J=7 Hz), 1.36-1.63 (4H, m), 2.20 (2H, t, J=7 Hz), 2.48-2.63 (2H, m), 3.03 (2H, q, J=7 Hz), 3.45 (3H, s), 4.09 (2H, q, J=7 Hz), 4.62 (2H, s), 5.89 (1H, d, J=4 Hz), 6.60 (1H, d, J=4 Hz), 7.26 (1H, m), 7.37 (1H, s), 8.53 (1H, d, J=5 Hz) MS (ESI$^+$): m/z 430

EXAMPLE 58

Ethyl 5-[7-ethyl-2-(methoxymethyl)-4-(3-methoxyphenyl)pyrrolo[1,2-b]pyridazin-3-yl]pentanoate NMR (CDCl$_3$, δ): 1.22 (3H, t, J=7 Hz), 1.37 (3H, t, J=7 Hz), 1.40-1.63 (4H, m), 2.16 (2H, t, J=7 Hz), 2.54-2.65 (2H, m), 3.04 (2H, q, J=7 Hz), 3.45 (3H, s), 3.83 (3H, s), 4.08 (2H, q, J=7 Hz), 4.62 (2H, s), 5.96 (1H, d, J=4 Hz), 6.56 (1H, d, J=4 Hz), 6.87-7.00 (3H, m), 7.38 (1H, t, J=8 Hz) MS (ESI$^+$): m/z 425

EXAMPLE 59

Ethyl 5-[7-ethyl-2-(methoxymethyl)-4-(6-quinolinyl)pyrrolo[1,2-b]pyridazin-3-yl]pentanoate NMR (CDCl$_3$, δ): 1.17 (3H, t, J=7 Hz), 1.43 (3H, t, J=7 Hz), 1.36-1.58 (4H, m), 2.10 (2H, m), 2.56-2.68 (2H, m), 3.07 (2H, q, J=7 Hz), 3.48 (3H, s), 4.02 (2H, q, J=7 Hz), 4.66 (2H, s), 5.90 (1H, d, J=4 Hz), 6.56 (1H, d, J=4 Hz), 7.45-7.50 (1H, m), 7.72 (1H, dd, J=2 Hz, 8 Hz), 7.86 (1H, d, J=2 Hz), 8.16-8.24 (2H, m), 8.98 (1H, m)

EXAMPLE 60

Ethyl 5-[7-ethyl-2-(methoxymethyl)-4-(3-pyridinyl)pyrrolo[1,2-b]pyridazin-3-yl]pentanoate NMR (CDCl$_3$, δ): 1.22 (3H, t, J=7 Hz), 1.38 (3H, t, J=7 Hz), 1.40-1.60 (4H, m), 2.17 (2H, t, J=7 Hz), 2.52-2.64 (2H, m), 3.04 (2H, q, J=7 Hz), 3.46 (3H, s), 4.10 (2H, q, J=7 Hz), 4.63 (2H, s), 5.89 (1H, d, J=4 Hz), 6.58 (1H, d, J=4 Hz), 7.42 (1H, m), 7.71 (1H, m), 8.62 (1H, m), 8.70 (1H, m) MS (ESI$^+$): m/z 396

EXAMPLE 61

Ethyl 5-[4-(3-chlorophenyl)-7-ethyl-2-(methoxymethyl)pyrrolo[1,2-b]pyridazin-3-yl]pentanoate NMR (CDCl$_3$, δ): 1.23 (3H, t, J=7 Hz), 1.37 (3H, t, J=7 Hz), 1.40-1.58 (4H, m), 2.17 (2H, t, J=7 Hz), 2.51-2.62 (2H, m), 3.03 (2H, q, J=7 Hz), 3.45 (3H, s), 4.08 (2H, q, J=7 Hz), 4.61 (2H, s), 5.92 (1H, d, J=4 Hz), 6.56 (1H, d, J=4 Hz), 7.25 (1H, m), 7.37 (1H, s), 7.42 (2H, m)

EXAMPLE 62

Ethyl 5-[7-ethyl-2-methyl-4-(3-methylphenyl)pyrrolo[1,2-b]pyridazin-3-yl]pentanoate NMR (CDCl$_3$, δ): 1.23 (3H, t, J=7 Hz), 1.37 (3H, t, J=7 Hz), 1.40-1.60 (4H, m), 2.16 (2H, t, J=7 Hz), 2.40 (3H, s), 2.40-2.50 (2H, m), 2.54 (3H, s), 3.03 (2H, q, J=7 Hz), 4.08 (2H, q, J=7 Hz), 5.90 (1H, d, J=4 Hz), 6.49 (1H, d, J=4 Hz), 7.10-7.15 (2H, m), 7.24 (1H, m), 7.33 (1H, m) MS: (m/z) 379 (M+H)

EXAMPLE 65

Ethyl 5-[7-ethyl-2-(methoxymethyl)-4-(5-methyl-3-pyridinyl)pyrrolo[1,2-b]pyridazin-3-yl]pentanoate NMR (CDCl$_3$, δ): 1.23 (3H, t, J=7 Hz), 1.37 (3H, t, J=7 Hz), 1.40-1.60 (4H, m), 2.18 (2H, t, J=7 Hz), 2.42 (3H, s), 2.48-2.63 (2H, m), 3.05 (2H, q, J=7 Hz), 3.46 (3H, s), 4.08 (2H, q, J=7 Hz), 4.62 (2H, s), 5.90 (1H, d, J=4 Hz), 6.57 (1H, d, J=4 Hz), 7.51 (1H, s), 8.41 (1H, s), 8.53 (1H, s) MS (ESI$^+$): m/z 410

EXAMPLE 66

Ethyl 5-[4-(5-bromo-3-pyridinyl)-7-ethyl-2-methylpyrrolo[1,2-b]pyridazin-3-yl]pentanoate NMR (CDCl$_3$, δ): 1.24 (3H, t, J=7 Hz), 1.37 (3H, t, J=7 Hz), 1.40-1.65 (4H, m), 2.21 (2H, t, J=7 Hz), 2.37-2.49 (2H, m), 2.56 (3H, s), 3.00 (2H, q, J=7 Hz), 4.10 (2H, q, J=7 Hz), 5.87 (1H, d, J=4 Hz), 6.53 (1H, d, J=4 Hz), 7.85 (1H, m), 8.53 (1H, d, J=2 Hz), 8.77 (1H, d, J=2 Hz) MS (ESI$^+$): m/z 444, 446

EXAMPLE 67

Ethyl 5-[4-(5-bromo-3-pyridinyl)-7-ethyl-2-(methoxymethyl)pyrrolo[1,2-b]pyridazin-3-yl]pentanoate NMR (CDCl$_3$, δ): 1.23 (3H, t, J=7 Hz), 1.37 (3H, t, J=7 Hz), 1.40-1.63 (4H, m), 2.19 (2H, t, J=7 Hz), 2.50-2.66 (2H, m), 3.03 (2H, q, J=7 Hz), 3.46 (3H, s), 4.10 (2H, q, J=7 Hz), 4.62 (2H, s), 5.91 (1H, d, J=4 Hz), 6.60 (1H, d, J=4 Hz), 7.88 (1H, m), 8.55 (1H, d, J=2 Hz), 8.77 (1H, d, J=2 Hz) MS (ESI$^+$): m/z 474, 476

EXAMPLE 68

Ethyl 5-[4-(5,6-dichloro-3-pyridinyl)-7-ethyl-2-methylpyrrolo[1,2-b]pyridazin-3-yl]pentanoate NMR (CDCl$_3$, δ): 1.24 (3H, t, J=7 Hz), 1.37 (3H, t, J=7 Hz), 1.36-1.60 (4H, m), 2.23 (2H, t, J=7 Hz), 2.37-2.50 (2H, m), 2.55 (3H, s), 3.02 (2H, q, J=7 Hz), 4.12 (2H, q, J=7 Hz), 5.87 (1H, d, J=4 Hz), 6.53 (1H, d, J=4 Hz), 7.81 (1H, d, J=2 Hz), 8.30 (1H, d, J=2 Hz) MS (ESI$^+$): m/z 434

EXAMPLE 69

Ethyl 4-[7-ethyl-2-(methoxymethyl)-4-(5-methyl-3-pyridinyl)pyrrolo[1,2-b]pyridazin-3-yl]butanoate NMR (CDCl$_3$, δ): 1.37 (3H, t, J=7 Hz), 1.65-1.78 (2H, m), 2.16-2.25 (2H, m), 2.42 (3H, s), 2.53-2.65 (2H, m), 3.04 (2H, q, J=7 Hz), 3.46 (3H, s), 4.12 (2H, q, J=7 Hz), 4.67 (2H, m), 5.91 (1H, d, J=4 Hz), 6.58 (1H, d, J=4 Hz), 7.53 (1H, s), 8.43 (1H, s), 8.54 (1H, s) MS (ESI$^+$): m/z 396

EXAMPLE 70

Ethyl 3-[7-ethyl-2-(methoxymethyl)-4-(5-methyl-3-pyridinyl)pyrrolo[1,2-b]pyridazin-3-yl]propanoate NMR (CDCl$_3$, δ): 1.25 (3H, t, J=7 Hz), 1.37 (3H, t, J=7 Hz), 2.35-2.55 (2H, m), 2.42 (3H, s), 2.84-2.96 (2H, m), 3.04 (2H, q, J=7 Hz), 3.46 (3H, s), 4.08 (2H, q, J=7 Hz), 4.65 (2H, s), 5.91 (1H, d, J=4 Hz), 6.61 (1H, d, J=4 Hz), 7.51 (1H, s), 8.41 (1H, s), 8.52 (1H, s)

EXAMPLE 71

Ethyl 4-[7-ethyl-2-methyl-4-(5-methyl-3-pyridinyl)pyrrolo[1,2-b]pyridazin-3-yl]butanoate NMR (CDCl$_3$, δ): 1.20 (3H, t, J=7 Hz), 1.37 (3H, t, J=7 Hz), 1.66-1.82 (2H, m), 2.16-2.28 (2H, m), 2.42 (3H, s), 2.44-2.53 (2H, m), 2.59 (3H, s), 3.02 (2H, q, J=7 Hz), 4.12 (2H, q, J=7 Hz), 5.87 (1H, d, J=4 Hz), 6.53 (1H, d, J=4 Hz), 7.51 (1H, s), 8.41 (1H, d, J=2 Hz), 8.53 (1H, d, J=2 Hz) MS (ESI$^+$): m/z 366

EXAMPLE 72

Ethyl 3-[7-ethyl-2-methyl-4-(5-methyl-3-pyridinyl)pyrrolo[1,2-b]pyridazin-3-yl]propanoate NMR (CDCl$_3$, δ): 1.24 (3H, t, J=7 Hz), 1.37 (3H, t, J=7 Hz), 2.30-2.43 (2H, m), 2.42 (3H, s), 2.58 (3H, s), 2.76-2.86 (2H, m), 3.02 (2H, q, J=7 Hz), 4.10 (2H, q, J=7 Hz), 5.87 (1H, d, J=4 Hz), 6.53 (1H, d, J=4 Hz), 7.48 (1H, s), 8.40 (1H, d, J=2 Hz), 8.53 (1H, d, J=2 Hz) MS (ESI$^+$): m/z 352

EXAMPLE 73

Ethyl 3-[4-(5-bromo-3-pyridinyl)-7-ethyl-2-methylpyrrolo[1,2-b]pyridazin-3-yl]propanoate NMR (CDCl$_3$, δ): 1.21 (3H, t, J=7 Hz), 1.39 (2H, t, J=7 Hz), 2.35 (2H, t, J=7 Hz), 2.58 (3H, s), 2.74-2.83 (2H, m), 3.01 (2H, q, J=7 Hz), 4.08 (2H, q, J=7 Hz), 5.89 (1H, d, J=4 Hz), 6.55 (1H, d, J=4 Hz), 7.87 (1H, s), 8.53 (1H, s), 8.79 (1H, s) MS: (m/z) 416 (M$^+$), 418 (M$^+$–2), 85(bp)

EXAMPLE 74

Ethyl 5-[4-(3-cyanophenyl)-7-ethyl-2-(methoxymethyl)pyrrolo[1,2-b]pyridazin-3-yl]pentanoate NMR (CDCl$_3$, δ): 1.23 (3H, t, J=8 Hz), 1.32-1.55 (5H, m), 2.16 (2H, t, J=8 Hz), 2.46-2.57 (2H, m), 3.03 (2H, q, J=8 Hz), 3.46 (3H, s), 4.09 (1H, q, J=8 Hz), 4.62 (2H, s), 5.34 (1H, d, J=5 Hz), 6.57 (1H, d, J=5 Hz), 7.59-7.64 (2H, m), 7.68 (1H, br s), 7.75 (1H, m) MS (ESI$^+$): 420 (M+H)

EXAMPLE 75

Ethyl 5-[2-[(acetyloxy)methyl]-4-(5-bromo-3-pyridinyl)-7-ethylpyrrolo[1,2-b]pyridazin-3-yl]pentanoate NMR (CDCl$_3$, δ): 1.23 (3H, t, J=7 Hz), 1.34-1.55 (7H, m), 2.11-2.22 (5H, m), 2.47 (2H, m), 3.02 (2H, q, J=7 Hz), 4.09 (2H, q, J=7 Hz), 5.29 (2H, s), 5.94 (1H, d, J=5 Hz), 6.63 (1H, d, J=5 Hz), 7.88 (1H, m), 8.56 (1H, m), 8.79 (1H, m)

EXAMPLE 76

To a solution of ethyl 5-[4-(3-cyanophenyl)-7-ethyl-2-methylpyrrolo[1,2-b]pyridazin-3-yl]pentanoate (1.20 g) in ethanol (12 mL) was added 1N sodium hydroxide (4.62 mL) and was stirred at ambient temperature for 2 hours. The reaction mixture was acidified with 1N hydrogen chloride and was partitioned between ethyl acetate and water. The organic layer was washed with water and brine, dried over magnesium sulfate, and evaporated in vacuo. The residue was purified by flash silica gel chromatography (silica gel, 100 mL) eluted with hexane-ethyl acetate=3-1, 2-1, and 1-1 to give an yellow solid (846 mg). The solid was recrystallized from hexane-ethyl acetate (5-1) to give 5-[4-(3-cyanophenyl)-7-ethyl-2-methylpyrrolo[1,2-b]pyridazin-3-yl] pentanoic acid as a pale yellow crystals (795 mg, 71.4%).

5-[4-(3-Cyanophenyl)-7-ethyl-2-methylpyrrolo[1,2-b]pyridazin-3-yl]pentanoic acid mp: 109-110° C. NMR (CDCl3, δ): 1.33-1.60 (7H, m), 2.42 (2H, t, J=8 Hz), 2.34-2.48 (2H, m), 2.56 (3H, s), 3.01 (2H, q, J=8 Hz), 5.80 (1H, d, J=5 Hz), 6.52 (1H, d, J=5 Hz), 7.56-7.64 (2H, m), 7.66 (1H, br s), 7.76 (1H, m) MS (ESI$^+$): m/z 362 (M–H)

The following compounds were obtained in substantially the same manner as that of Example 76.

EXAMPLE 77

3-[4-(3-Chlorophenyl)-7-ethyl-2-phenylpyrrolo[1,2-b]pyridazin-3-yl]propanoic acid NMR (CDCl$_3$, δ): 1.36 (3H, t, J=7H), 1.56 (2H, m), 2.03 (2H, m), 2.79 (2H, m), 3.01 (2H, q, J=7 Hz), 6.01 (1H, d, J=5 Hz), 6.63 (1H, d, J=5 Hz), 7.27 (1H, m), 7.40-7.53 (8H, m)

EXAMPLE 78

5-{7-Ethyl-2-methyl-4-[3-(trifluoromethyl)phenyl]pyrrolo[1,2-b]pyridazin-3-yl}pentanoic acid NMR (CDCl$_3$, δ): 1.37 (3H, t, J=7 Hz), 1.40-1.62 (4H, m), 2.22 (2H, t, J=7 Hz), 2.38-2.46 (2H, m), 2.56 (3H, s), 3.02 (2H, q, J=7 Hz), 5.84 (1H, d, J=4 Hz), 6.51 (1H, d, J=4 Hz), 7.53-7.64 (3H, m), 7.72 (1H, d, J=8 Hz) MS (ESI$^+$): m/z 403 (M–H), 405 (M+H)

EXAMPLE 79

5-[7-Ethyl-2-methyl-4-(5-methyl-3-pyridinyl)pyrrolo[1,2-b]pyridazin-3-yl]pentanoic acid NMR (CDCl$_3$, δ): 1.37 (3H, t, J=7 Hz), 1.45-1.67 (4H, m), 2.22 (2H, t, J=7 Hz), 2.42 (3H, s), 2.35-2.48 (2H, m), 2.56 (3H, s), 3.02 (2H, q, J=7 Hz), 5.83 (1H, d, J=4 Hz), 6.51 (1H, d, J=4 Hz), 7.53 (1H, s), 8.39 (1H, s), 8.53 (1H, s) MS (ESI$^+$): m/z 352 (M+H)

EXAMPLE 80

5-[7-Ethyl-4-(3-methoxy-5-isoxazolyl)-2-(methoxymethyl)pyrrolo[1,2-b]pyridazin-3-yl]pentanoic acid NMR (CDCl$_3$, δ): 1.36 (3H, t, J=7 Hz), 1.58-1.83 (4H, m), 2.38 (2H, t, J=7 Hz), 2.74-2.85 (2H, m), 3.03 (2H, q, J=7 Hz), 3.43 (3H, s), 4.08 (3H, s), 4.62 (2H, s), 6.28 (1H, s), 6.41 (1H, d, J=4 Hz), 6.67 (1H, d, J=4 Hz) MS (ESI$^+$): m/z 386 (M−H), 388 (M+H)

EXAMPLE 81

5-{7-Ethyl-2-methyl-4-[3-(1,3-oxazol-5-yl)phenyl]pyrrolo[1,2-b]pyridazin-3-yl}pentanoic acid NMR (CDCl$_3$, δ): 1.38 (3H, t, J=7 Hz), 1.45-1.65 (4H, m), 2.21 (2H, t, J=7 Hz), 2.43-2.53 (2H, m), 2.56 (3H, s), 3.03 (2H, q, J=7 Hz), 5.89 (1H, d, J=4 Hz), 6.51 (1H, d, J=4 Hz), 7.32 (1H, d, J=8 Hz), 7.39 (1H, s), 7.53 (1H, t, J=8 Hz), 7.65 (1H, s), 7.73 (1H, d, J=8 Hz), 7.93 (1H, s) MS (ESI$^+$): m/z 402 (M−H), 404 (M+H)

EXAMPLE 82

5-[4-(3,4-Dichlorophenyl)-7-ethyl-2-methylpyrrolo[1,2-b]pyridazin-3-yl]pentanoic acid NMR (CDCl$_3$, δ): 1.37 (3H, t, J=7 Hz), 1.42-1.65 (4H, m), 2.27 (2H, t, J=7 Hz), 2.38-2.48 (2H, m), 2.54 (3H, s), 3.02 (2H, q, J=7 Hz), 5.87 (1H, d, J=4 Hz), 6.51 (1H, d, J=4 Hz), 7.19 (1H, dd, J=2 Hz, 8 Hz), 7.45 (1H, d, J=2 Hz), 7.56 (1H, d, J=8 Hz) MS (ESI$^+$): m/z 403 (M−H), 405 (M+H)

EXAMPLE 83

5-[4-(4-Chloro-2-pyridinyl)-7-ethyl-2-methylpyrrolo[1,2-b]pyridazin-3-yl]pentanoic acid NMR (CDCl$_3$, δ): 1.36 (3H, t, J=7 Hz), 1.47-1.66 (4H, m), 2.24 (2H, t, J=7 Hz), 1.45-2.56 (2H, m), 2.55 (3H, s), 3.00 (2H, q, J=7 Hz), 5.94 (1H, d, J=4 Hz), 6.53 (1H, d, J=4 Hz), 7.39 (1H, dd, J=2 Hz, 7 Hz), 7.53 (1H, d, J=2 Hz), 8.67 (1H, d, J=7 Hz) MS (ESI$^+$): m/z 372 (M+H)

EXAMPLE 84

5-[4-(5-Chloro-2-thienyl)-7-ethyl-2-(methoxymethyl)pyrrolo[1,2-b]pyridazin-3-yl]pentanoic acid NMR (CDCl$_3$, δ): 1.36 (3H, t, J=7 Hz), 1.52-1.74 (4H, m), 2.33 (2H, t, J=7 Hz), 2.69-2.78 (2H, m), 3.01 (2H, q, J=7 Hz), 3.44 (3H, s), 4.60 (2H, s), 6.25 (1H, d, J=4 Hz), 6.60 (1H, d, J=4 Hz), 6.97 (2H, m) MS (ESI$^+$): m/z 405 (M−H), 407 (M+H)

EXAMPLE 85

5-[7-Ethyl-4-(6-methoxy-2-pyrazinyl)-2-methylpyrrolo[1,2-b]pyridazin-3-yl]pentanoic acid NMR (CDCl$_3$, δ): 1.37 (3H, t, J=7 Hz), 1.55-1.69 (4H, m), 2.28 (2H, m), 2.52 (2H, m), 2.56 (3H, s), 3.03 (2H, q, J=7 Hz), 3.97 (3H, s), 6.03 (1H, d, J=4 Hz), 6.54 (1H, d, J=4 Hz), 8.30 (1H, s), 8.32 (1H, s) MS (ESI$^+$): m/z 369 (M+H)

EXAMPLE 86

5-[4-(1-Benzofuran-2-yl)-7-ethyl-2-methylpyrrolo[1,2-b]pyridazin-3-yl]pentanoic acid NMR (CDCl$_3$, δ): 1.39 (3H, t, J=7 Hz), 1.66-1.86 (4H, m), 2.34-2.47 (2H, m), 2.58 (3H, s), 2.69-2.85 (2H, m), 3.03 (2H, q, J=7 Hz), 6.47 (1H, d, J=4 Hz), 6.61 (1H, d, J=4 Hz), 7.16 (1H, s), 7.26-7.43 (2H, m), 7.57 (1H, d, J=8 Hz), 7.68 (1H, d, J=8 Hz)

EXAMPLE 87

5-[4-(1-Benzothien-2-yl)-7-ethyl-2-methylpyrrolo[1,2-b]pyridazin-3-yl]pentanoic acid NMR (CDCl$_3$, δ): 1.37 (3H, t, J=7 Hz), 1.53-1.73 (4H, m), 2.30 (2H, t, J=7 Hz), 2.56 (3H, s), 2.62-2.73 (2H, m), 3.02 (2H, q, J=7 Hz), 6.19 (1H, d, J=4 Hz), 6.53 (1H, d, J=4 Hz), 7.34-7.45 (3H, m), 7.79-7.93 (2H, m)

EXAMPLE 88

5-[7-Ethyl-2-methyl-4-(1,3-oxazol-5-yl)pyrrolo[1,2-b]pyridazin-3-yl]pentanoic acid NMR (CDCl$_3$, δ): 1.37 (3H, t, J=7 Hz), 1.57-1.70 (2H, m), 1.70-1.88 (2H, m), 2.43 (2H, t, J=7 Hz), 2.56 (3H, s), 2.66-2.75 (2H, m), 3.02 (2H, q, J=7 Hz), 6.41 (1H, d, J=4 Hz), 6.60 (1H, d, J=4 Hz), 7.52 (1H, s), 8.13 (1H, s) MS (ESI$^+$): m/z 328 (M+H)

EXAMPLE 89

5-(7-Ethyl-2-methyl-4-phenylpyrrolo[1,2-b]pyridazin-3-yl)pentanoic acid

NMR (CDCl$_3$, δ): 1.37 (3H, t, J=7 Hz), 1.40-1.62 (4H, m), 2.20 (2H, t, J=7 Hz), 2.43-2.52 (2H, m), 2.54 (3H, s), 3.01 (2H, q, J=7 Hz), 5.89 (1H, d, J=4 Hz), 6.48 (1H, d, J=4 Hz), 7.33 (2H, m), 7.38-7.52 (3H, m) MS (ESI$^+$): m/z 337 (M+H)

EXAMPLE 90

5-[7-Ethyl-2-methyl-4-(6-quinolinyl)pyrrolo[1,2-b]pyridazin-3-yl]pentanoic acid

NMR (CDCl$_3$, δ): 1.39 (3H, t, J=7 Hz), 1.47-1.61 (4H, m), 2.14-2.23 (2H, m), 2.44-2.55 (2H, m), 2.59 (3H, s), 3.05 (2H, q, J=7 Hz), 5.86 (1H, d, J=4 Hz), 6.51 (1H, d, J=4 Hz), 7.49 (1H, m), 7.73 (1H, dd, J=2 Hz, 8 Hz), 7.85 (1H, d, J=2 Hz), 8.23 (2H, m), 8.97 (1H, m) MS (ESI$^+$): m/z 386 (M−H), 388 (M+H)

EXAMPLE 91

7-{4-[4-(Aminosulfonyl)phenyl]-7-ethyl-2-methylpyrrolo[1,2-b]pyridazin-3-yl}heptanoic acid NMR (CDCl$_3$, δ): 0.98 (2H, m), 1.17-1.48 (9H, m), 2.27 (2H, t, J=7 Hz), 2.36 (2H, m), 2.56 (3H, s), 3.02 (2H, q, J=7 Hz), 5.06 (2H, s, br), 5.84 (1H, d, J=5 Hz), 6.52 (1H, d, J=5 Hz), 7.52 (2H, d, J=9 Hz), 8.04 (2H, d, J=9 Hz) MS (ESI$^+$): m/z 444 (M+H)

EXAMPLE 92

({[4-(3-Chlorophenyl)-7-ethyl-2-(2-furyl)pyrrolo[1,2-b]pyridazin-3-yl]carbonyl}amino)acetic acid NMR (CDCl$_3$, δ): 1.41 (3H, t, J=7 Hz), 3.07 (2H, q, J=7 Hz), 3.95 (2H, d, J=5 Hz), 6.02 (1H, t, br, 5 Hz), 6.37 (1H, d, J=5 Hz), 6.50 (1H, m), 6.75 (1H, d, J=5 Hz), 7.01 (1H, d, J=7 Hz), 7.37-7.45 (3H, m), 7.51 (1H, m), 7.55 (1H, m)

EXAMPLE 93

5-{7-Ethyl-2-methyl-4-[3-(methylsulfonyl)phenyl]pyrrolo[1,2-b]pyridazin-3-yl}pentanoic acid NMR (CDCl$_3$, δ): 1.30-1.59 (7H, m), 2.22 (2H, t, J=8 Hz), 2.33-2.49 (2H, m), 2.56 (3H, s), 3.01 (2H, q, J=8 Hz), 3.12 (3H, s), 5.80 (1H, d, J=5 Hz), 6.50 (1H, d, J=5 Hz), 7.63-7.74 (2H, m), 7.95 (1H, br s), 8.03 (1H, br d, J=8 Hz) MS (ESI$^+$): m/z 415 (M+H)

EXAMPLE 94

5-[4-(2-Chloro-4-pyridinyl)-7-ethyl-2-methylpyrrolo[1,2-b]pyridazin-3-yl]pentanoic acid mp: 139-140° C. NMR (CDCl$_3$, δ): 1.32-1.64 (7H, m), 2.28 (2H, t, J=8 Hz), 2.36-2.46 (2H, m), 2.55 (3H, s), 3.00 (2H, q, J=8 Hz), 5.85 (1H, d, J=5 Hz), 6.52 (1H, d, J=5 Hz), 7.24 (1H, br d, J=7 Hz), 7.36 (1H, br s), 8.53 (1H, d, J=7 Hz) MS (ESI$^+$): m/z 372 (M+H)

EXAMPLE 95

5-[7-Ethyl-2-methyl-4-(2-vinyl-4-pyridinyl)pyrrolo[1,2-b]pyridazin-3-yl]pentanoic acid NMR (CDCl$_3$, δ): 1.36 (3H, t, J=8 Hz), 1.40-1.62 (4H, m), 2.25 (2H, t, J=8 Hz), 2.35-2.47 (2H, m), 2.56 (3H, s), 3.00 (2H, q, J=8 Hz), 5.54 (1H, d, J=10 Hz), 5.86 (1H, d, J=5 Hz), 6.23 (1H, d, J=16 Hz), 6.51 (1H, d, J=5 Hz), 6.88 (1H, dd, J=16, 10 Hz), 7.20 (1H, dd, J=6, 1 Hz), 7.38 (1H, br s), 8.70 (1H, d, J=6 Hz)

EXAMPLE 96

5-[7-Ethyl-2-methyl-4-(3-nitrophenyl)pyrrolo[1,2-b]pyridazin-3-yl]pentanoic acid NMR (CDCl$_3$, δ): 1.37 (3H, t, J=8 Hz), 1.41-1.59 (4H, m), 2.23 (2H, t, J=8 Hz), 2.37-2.47 (2H, m), 2.57 (3H, s), 3.02 (2H, q, J=8 Hz), 5.81 (1H, d, J=5 Hz), 6.51 (1H, d, J=5 Hz), 7.63-7.74 (2H, m), 8.25 (1H, br s), 8.32 (1H, m)

EXAMPLE 97

{[7-Ethyl-4-(4-fluorophenyl)-2-isopropylpyrrolo[1,2-b]pyridazin-3-yl]methoxy}acetic acid NMR (CDCl$_3$, δ): 1.33-1.45 (9H, m), 3.04 (2H, q, J=8 Hz), 3.43 (1H, m), 4.01 (2H, s), 4.45 (2H, s), 6.09 (1H, d, J=5 Hz), 6.58 (1H, d, J=5 Hz), 7.13-7.22 (2H, m), 7.40-7.49 (2H, m)

EXAMPLE 98

5-[4-(5-Acetyl-3-pyridinyl)-7-ethyl-2-methylpyrrolo[1,2-b]pyridazin-3-yl]pentanoic acid NMR (CDCl$_3$, δ): 1.37 (3H, t, J=7 Hz), 1.43-1.63 (4H, m), 2.23 (2H, t, J=7 Hz), 2.35-2.48 (2H, m), 2.57 (3H, s), 2.69 (3H, s), 3.03 (2H, q, J=7 Hz), 5.80 (1H, d, J=4 Hz), 6.53 (1H, d, J=4 Hz), 8.26 (1H, m), 8.78 (1H, d, J=2 Hz), 9.23 (1H, d, J=2 Hz) MS: (m/z) 378 (M−H), 380 (M+H)

EXAMPLE 99

5-{4-(2-Chloro-4-pyridinyl)-7-ethyl-2-[(methylthio)methyl]pyrrolo[1,2-b]pyridazin-3-yl}pentanoic acid NMR (CDCl$_3$, δ): 1.36 (3H, t, J=7 Hz), 1.42-1.65 (4H, m), 2.18 (3H, s), 2.28 (2H, t, J=7 Hz), 2.48-2.60 (2H, m), 3.02 (2H, q, J=7 Hz), 3.81 (2H, s), 5.89 (1H, d, J=4 Hz), 6.57 (1H, d, J=4 Hz), 7.27 (1H, m), 7.38 (1H, s), 8.53 (1H, d, J=5 Hz) MS: (m/z) 416 (M−H), 418 (M+H)

EXAMPLE 100

5-{4-(2-Chloro-4-pyridinyl)-7-ethyl-2-[(methylsulfonyl)methyl]pyrrolo[1,2-b]pyridazin-3-yl}pentanoic acid NMR (CDCl$_3$, δ): 1.37 (3H, t, J=7 Hz), 1.45-1.65 (4H, m), 2.29 (2H, t, J=7 Hz), 2.56-2.67 (2H, m), 2.98 (2H, q, J=7 Hz), 3.13 (3H, s), 4.54 (2H, s), 5.98 (1H, d, J=4 Hz), 6.69 (1H, d, J=4 Hz), 7.27 (1H, m), 7.38 (1H, s), 8.56 (1H, d, J=5 Hz) MS: (m/z) 448 (M−H), 450 (M+H)

EXAMPLE 101

5-[4-(2-Chloro-4-pyridinyl)-7-ethyl-2-phenylpyrrolo[1,2-b]pyridazin-3-yl]pentanoic acid NMR (CDCl$_3$, δ): 1.03-1.45 (4H, m), 1.36 (3H, t, J=7 Hz), 1.97 (2H, t, J=7 Hz), 2.36-2.48 (2H, m), 3.02 (2H, q, J=7 Hz), 5.96 (1H, d, J=4 Hz), 6.64 (1H, d, J=4 Hz), 7.31 (1H, d, J=5 Hz), 7.39-7.53 (6H, m), 8.55 (1H, d, J=5 Hz)

EXAMPLE 102

5-[4-(6-Chloro-2-pyridinyl)-7-ethyl-2-methylpyrrolo-[1,2-b]pyridazin-3-yl]pentanoic acid NMR (CDCl$_3$, δ): 1.36 (3H, t, J=7 Hz), 1.56-1.73 (4H, m), 2.29 (2H, t, J=7 Hz), 2.46-2.56 (2H, m), 2.56 (3H, s), 3.02 (2H, q, J=7 Hz), 5.96 (1H, d, J=4 Hz), 6.53 (1H, d, J=4 Hz), 7.38-7.48 (2H, m), 7.78 (1H, t, J=8 Hz) MS (ESI$^+$): m/z 372 (M+H), MS (ESI$^-$): m/z 370

EXAMPLE 103

5-[7-Ethyl-4-(3-methoxyphenyl)-2-methylpyrrolo[1,2-b]pyridazin-3-yl]pentanoic acid NMR (CDCl$_3$, δ): 1.37 (3H, t, J=7 Hz), 1.46-1.63 (4H, m), 2.22 (2H, t, J=7 Hz), 2.44-2.53 (2H, m), 2.54 (3H, s), 3.01 (2H, q, J=7 Hz), 3.82 (3H, s), 5.92 (1H, d, J=4 Hz), 6.49 (1H, d, J=4 Hz), 6.87-7.01 (3H, m), 7.37 (1H, t, J=8 Hz) MS (ESI$^+$): m/z 367, MS (ESI$^-$): m/z 365

EXAMPLE 104

5-[4-(3,5-Dichlorophenyl)-7-ethyl-2-methylpyrrolo[1,2-b]pyridazin-3-yl]pentanoic acid NMR (CDCl$_3$, δ): 1.37 (3H, t, J=7 Hz), 1.42-1.53 (2H, m), 1.53-1.66 (2H, m), 2.27 (2H, t, J=7 Hz), 2.41-2.49 (2H, m), 2.54 (3H, s), 3.01 (2H, q, J=7 Hz), 5.88 (1H, d, J=4 Hz), 6.52 (1H, d, J=4 Hz), 7.26 (2H, m), 7.45 (1H, m) MS (ESI$^+$): m/z 405, MS (ESI$^-$): m/z 403

EXAMPLE 105

5-[4-(5-Chloro-2-thienyl)-7-ethyl-2-methylpyrrolo[1,2-b]pyridazin-3-yl]pentanoic acid NMR (CDCl$_3$, δ): 1.36 (3H, t, J=7 Hz), 1.48-1.62 (2H, m), 1.62-1.73 (2H, m), 2.34 (2H, t, J=7 Hz), 2.53 (3H, s), 2.58-2.67 (2H, m), 2.99 (2H, q, J=7 Hz), 6.20 (1H, d, J=4 Hz), 6.53 (1H, d, J=4 Hz), 6.94 (1H, d, J=4 Hz), 6.98 (1H, d, J=4 Hz) MS (ESI$^+$): m/z 377, MS (ESI$^-$): m/z 375

EXAMPLE 106

5-[7-Ethyl-4-(3-fluorophenyl)-2-methylpyrrolo[1,2-b]pyridazin-3-yl]pentanoic acid NMR (CDCl$_3$, δ): 1.37 (3H, t, J=7 Hz), 1.40-1.64 (4H, m), 2.23 (2H, t, J=7 Hz), 2.41-2.49 (2H, m), 2.55 (3H, s), 3.00 (2H, q, J=7 Hz), 5.88 (1H, d, J=4 Hz), 6.50 (1H, d, J=4 Hz), 7.03-7.16 (3H, m), 7.38-7.47 (1H, m) MS (ESI$^+$): m/z 355, MS (ESI$^-$): m/z 353

EXAMPLE 107

5-[7-Ethyl-2-methyl-4-(3-quinolinyl)pyrrolo[1,2-b]pyridazin-3-yl]pentanoic acid

NMR (CDCl$_3$, δ): 1.39 (3H, t, J=7 Hz), 1.47-1.65 (4H, m), 2.20-2.30 (2H, m), 2.45-2.53 (2H, m), 2.59 (3H, s), 3.05 (2H, q, J=7 Hz), 5.87 (1H, d, J=4 Hz), 6.53 (1H, d, J=4 Hz), 7.62 (1H, t, J=8 Hz), 7.79 (1H, t, J=8 Hz), 7.87 (1H, d, J=8 Hz), 8.21 (2H, m), 8.88 (1H, d, J=2 Hz) MS (ESI$^+$): m/z 388, MS (ESI$^-$): m/z 386

EXAMPLE 108

5-[7-Ethyl-2-methyl-4-(4-pyridinyl)pyrrolo[1,2-b]pyridazin-3-yl]pentanoic acid

NMR (CDCl$_3$, δ): 1.37 (3H, t, J=7 Hz), 1.40-1.70 (4H, m), 2.20-2.30 (2H, m), 2.37-2.53 (2H, m), 2.56 (3H, s), 3.01 (2H, q, J=7 Hz), 5.84 (1H, d, J=4 Hz), 6.51 (1H, d, J=4 Hz), 7.39 (2H, d, J=7 Hz), 8.74 (2H, d, J=7 Hz)

EXAMPLE 109

5-[7-Ethyl-4-(3-methoxy-5-isoxazolyl)-2-methylpyrrolo[1,2-b]pyridazin-3-yl]pentanoic acid NMR (CDCl$_3$, δ): 1.36 (3H, t, J=7 Hz), 1.57-1.84 (4H, m), 2.41 (2H, t, J=7 Hz), 2.55 (3H, s), 2.63-2.72 (2H, m), 3.02 (2H, q, J=7 Hz), 4.08 (3H, s), 6.27 (1H, s), 6.34 (1H, d, J=4 Hz), 6.57 (1H, d, J=4 Hz)

EXAMPLE 110

5-[7-Ethyl-4-(3-methoxyphenyl)-2-phenylpyrrolo[1,2-b]pyridazin-3-yl]pentanoic acid NMR (CDCl$_3$, δ): 1.06-1.33 (4H, m), 1.36 (3H, t, J=7 Hz), 1.91 (2H, t, J=7 Hz), 2.42-2.53 (2H, m), 3.01 (2H, q, J=7 Hz), 3.83 (3H, s), 6.03 (1H, d, J=4 Hz), 6.59 (1H, d, J=4 Hz), 6.93-7.02 (3H, m), 7.36-7.54 (6H, m) MS (ESI$^+$): m/z 429

EXAMPLE 111

5-[7-Ethyl-2-methyl-4-(5-methyl-3-isoxazolyl)pyrrolo[1,2-b]pyridazin-3-yl]pentanoic acid NMR (CDCl$_3$, δ): 1.36 (3H, t, J=7 Hz), 1.52-1.77 (4H, m), 2.35 (2H, t, J=7 Hz), 2.55 (6H, s), 2.56-2.67 (2H, m), 3.01 (2H, q, J=7 Hz), 6.16 (1H, d, J=4 Hz), 6.23 (1H, s), 6.54 (1H, d, J=4 Hz) MS (ESI$^+$): m/z 342, MS (ESI$^-$): m/z 340

EXAMPLE 112

5-[7-Ethyl-2-phenyl-4-(4-pyridinyl)pyrrolo[1,2-b]pyridazin-3-yl]pentanoic acid

NMR (CDCl$_3$, δ): 1.11-1.33 (4H, m), 1.36 (3H, t, J=7 Hz), 1.99 (2H, t, J=7 Hz), 2.38-2.50 (2H, m), 3.03 (2H, q, J=7 Hz), 5.94 (1H, d, J=4 Hz), 6.63 (1H, d, J=4 Hz), 7.38-7.56 (7H, m), 8.74 (2H, d, J=6 Hz)

EXAMPLE 113

5-[7-Ethyl-2-phenyl-4-(2-pyrazinyl)pyrrolo[1,2-b]pyridazin-3-yl]pentanoic acid

NMR (CDCl$_3$, δ): 1.10-1.33 (4H, m), 1.36 (3H, t, J=7 Hz), 1.95 (2H, t, J=7 Hz), 2.45-2.57 (2H, m), 3.02 (2H, q, J=7 Hz), 6.05 (1H, d, J=4 Hz), 6.66 (1H, d, J=4 Hz), 7.40-7.55 (5H, m), 8.67 (1H, d, J=3 Hz), 8.77 (1H, s), 8.85 (1H, s) MS (ESI$^+$): m/z 401, MS (ESI$^-$): m/z 399

EXAMPLE 114

5-[7-Ethyl-2-phenyl-4-(3-pyridinyl)pyrrolo[1,2-b]pyridazin-3-yl]pentanoic acid

NMR (CDCl$_3$, δ): 1.05-1.30 (4H, m), 1.36 (3H, t, J=7 Hz), 1.95 (2H, t, J=7 Hz), 2.35-2.48 (2H, m), 3.02 (2H, q, J=7 Hz), 5.94 (1H, d, J=4 Hz), 6.62 (1H, d, J=4 Hz), 7.40-7.55 (6H, m), 7.76-7.83 (1H, m), 8.65-8.72 (2H, m) MS (ESI$^+$): m/z 400, MS (ESI$^-$): m/z 398

EXAMPLE 115

5-[4-(2-Chloro-4-pyridinyl)-7-ethyl-2-(methoxymethyl)pyrrolo[1,2-b]pyridazin-3-yl]pentanoic acid NMR (CDCl$_3$, δ): 1.37 (3H, t, J=7 Hz), 1.42-1.64 (4H, m), 2.27 (2H, t, J=7 Hz), 2.48-2.62 (2H, m), 3.04 (2H, q, J=7 Hz), 3.45 (3H, s), 4.62 (2H, s), 5.90 (1H, d, J=4 Hz), 6.61 (1H, d, J=4 Hz), 7.27 (1H, m), 7.38 (1H, s), 8.53 (1H, d, J=5 Hz) MS (ESI$^+$): m/z 402

EXAMPLE 116

5-[7-Ethyl-2-(methoxymethyl)-4-(3-methoxyphenyl)pyrrolo[1,2-b]pyridazin-3-yl]pentanoic acid NMR (CDCl$_3$, δ): 1.37 (3H, t, J=7 Hz), 1.40-1.62 (4H, m), 2.19 (2H, t, J=7 Hz), 2.55-2.66 (2H, m), 3.03 (2H, q, J=7 Hz), 3.45 (3H, s), 3.82 (3H, s), 4.62 (2H, s), 5.96 (1H, d, J=4 Hz), 6.56 (1H, d, J=4 Hz), 6.87-7.00 (3H, m), 7.37 (1H, t, J=8 Hz) MS (ESI$^+$): m/z 397, MS (ESI$^-$): m/z 395

EXAMPLE 117

5-[4-(2-Chloro-4-pyridinyl)-7-ethyl-2-(2-thienyl)pyrrolo[1,2-b]pyridazin-3-yl]pentanoic acid NMR (CDCl$_3$, δ): 1.20-1.50 (4H, m), 1.38 (3H, t, J=7 Hz), 2.15 (2H, t, J=7 Hz), 2.55-2.68 (2H, m), 3.04 (2H, q, J=7 Hz), 5.93 (1H, d, J=4 Hz), 6.64 (1H, d, J=4 Hz), 7.13 (1H, t, J=5 Hz), 7.28 (1H, d, J=5 Hz), 7.35-7.47 (3H, m), 8.54 (1H, d, J=5 Hz) MS (ESI$^+$): m/z 440

EXAMPLE 118

5-[7-Ethyl-2-(methoxymethyl)-4-(6-quinolinyl)pyrrolo[1,2-b]pyridazin-3-yl]pentanoic acid NMR (CDCl$_3$, δ): 1.39 (3H, t, J=7 Hz), 1.45-1.60 (4H, m), 2.16 (2H, m), 2.55-2.75 (2H, m), 3.07 (2H, q, J=7 Hz), 3.47 (3H, s), 4.66 (2H, s), 5.89 (1H, d, J=4 Hz), 6.57 (1H, d, J=4 Hz), 7.45-7.53 (1H, m), 7.72 (1H, d, J=8 Hz), 7.86 (1H, s), 8.22 (2H, m), 8.94 (1H, m) MS (ESI$^+$): m/z 418, MS (ESI$^-$): m/z 416

EXAMPLE 119

5-[7-Ethyl-2-(methoxymethyl)-4-(3-pyridinyl)pyrrolo[1,2-b]pyridazin-3-yl]pentanoic acid NMR (CDCl$_3$, δ): 1.38 (3H, t, J=7 Hz), 1.45-1.64 (4H, m), 2.22 (2H, t, J=7 Hz), 2.48-2.68 (2H, m), 3.06 (2H, q, J=7 Hz), 3.46 (3H, s), 4.63 (2H, s), 5.89 (1H, d, J=4 Hz), 6.58 (1H, d, J=4 Hz), 7.48 (1H, m), 7.78 (1H, m), 8.62 (1H, m), 8.69 (1H, m) MS (ESI$^+$): m/z 368

EXAMPLE 120

5-[4-(3-Chlorophenyl)-7-ethyl-2-(methoxymethyl)pyrrolo[1,2-b]pyridazin-3-yl]pentanoic acid NMR (CDCl$_3$, δ): 1.37 (3H, t, J=7 Hz), 1.45-1.63 (4H, m), 2.23 (2H, t, J=7 Hz), 2.53-2.63 (2H, m), 3.04 (2H, q, J=7 Hz), 3.45 (3H, s), 4.63 (2H, s), 5.93 (1H, d, J=4 Hz), 6.58 (1H, d, J=4 Hz), 7.25 (1H, m), 7.36 (1H, s), 7.42 (2H, m)

EXAMPLE 121

5-[7-Ethyl-2-methyl-4-(3-methylphenyl)pyrrolo[1,2-b]pyridazin-3-yl]pentanoic acid NMR (CDCl$_3$, δ): 1.23-1.63 (4H, m), 1.37 (3H, t, J=7 Hz), 2.22 (2H, t, J=7 Hz), 2.40 (3H, s), 2.40-2.49 (2H, m), 2.54 (3H, s), 3.02 (2H, q, J=7 Hz), 5.89 (1H, d, J=4 Hz), 6.48 (1H, d, J=4 Hz), 7.10-7.14 (2H, m), 7.23-7.27 (1H, m), 7.32-7.38 (1H, m) MS (ESI$^+$): m/z 351

EXAMPLE 124

5-[7-Ethyl-2-(methoxymethyl)-4-(5-methyl-3-pyridinyl)pyrrolo[1,2-b]pyridazin-3-yl]pentanoic acid NMR (CDCl$_3$, δ): 1.37 (3H, t, J=7 Hz), 1.44-1.65 (4H, m), 2.16-2.26 (2H, m), 2.43 (3H, s), 2.47-2.69 (2H, m), 3.03 (2H, q, J=7 Hz), 3.45 (3H, s), 4.63 (2H, m), 5.88 (1H, d, J=4 Hz), 6.57 (1H, d, J=4 Hz), 7.56 (1H, s), 8.42 (1H, s), 8.53 (1H, s) MS (ESI$^+$): m/z 382, MS (ESI$^-$): m/z 380

EXAMPLE 125

5-[4-(5-Bromo-3-pyridinyl)-7-ethyl-2-methylpyrrolo[1,2-b]pyridazin-3-yl]pentanoic acid NMR (CDCl$_3$, δ): 1.37 (3H, t, J=7 Hz), 1.45-1.67 (4H, m), 2.27 (2H, t, J=7 Hz), 2.38-2.52 (2H, m), 2.56 (3H, s), 3.02 (2H, q, J=7 Hz), 5.87 (1H, d, J=4 Hz), 6.53 (1H, d, J=4 Hz), 7.88 (1H, m), 8.53 (1H, d, J=2 Hz), 8.77 (1H, d, J=2 Hz) MS (ESI$^+$): m/z 416, 418

EXAMPLE 126

5-[4-(5-Bromo-3-pyridinyl)-7-ethyl-2-(methoxymethyl)pyrrolo[1,2-b]pyridazin-3-yl]pentanoic acid NMR (CDCl$_3$, δ): 1.37 (3H, t, J=7 Hz), 1.45-1.65 (4H, m), 2.25 (2H, t, J=7 Hz), 2.49-2.68 (2H, m), 3.03 (2H, q, J=7 Hz), 3.45 (3H, s), 4.63 (2H, s), 5.91 (1H, d, J=4 Hz), 6.62 (1H, d, J=4 Hz), 7.89 (1H, m), 8.51 (1H, s), 8.79 (1H, m) MS (ESI$^+$): m/z 446, 448

EXAMPLE 127

5-[4-(5,6-Dichloro-3-pyridinyl)-7-ethyl-2-methylpyrrolo[1,2-b]pyridazin-3-yl]pentanoic acid NMR (CDCl$_3$, δ): 1.37 (3H, t, J=7 Hz), 1.43-1.68 (4H, m), 2.29 (2H, t, J=7 Hz), 2.38-2.52 (2H, m), 2.57 (3H, s), 3.02 (2H, q, J=7 Hz), 5.87 (1H, d, J=4 Hz), 6.53 (1H, d, J=4 Hz), 7.81 (1H, d, J=2 Hz), 8.31 (1H, d, J=2 Hz) MS (ESI$^+$): m/z 406, MS (ESI$^-$): m/z 404

EXAMPLE 128

5-[7-Ethyl-2-methyl-4-(5-vinyl-3-pyridinyl)pyrrolo[1,2-b]pyridazin-3-yl]pentanoic acid NMR (CDCl$_3$, δ): 1.37 (3H, t, J=7 Hz), 1.45-1.68 (4H, m), 2.23 (2H, t, J=7 Hz), 2.38-2.53 (2H, m), 2.56 (3H, s), 3.02 (2H, q, J=7 Hz), 5.46 (1H, d, J=1 Hz), 5.86 (1H, d, J=4 Hz), 5.89 (1H, d, J=17 Hz), 6.52 (1H, d, J=4 Hz), 6.72-6.83 (1H, dd, J=11 Hz, 17 Hz), 7.77 (1H, m), 8.47 (1H, d, J=2 Hz), 8.68 (1H, d, J=2 Hz) MS (ESI$^+$): m/z 364

EXAMPLE 129

5-[7-Ethyl-2-(methoxymethyl)-4-(5-vinyl-3-pyridinyl)pyrrolo[1,2-b]pyridazin-3-yl]pentanoic acid NMR (CDCl$_3$, δ): 1.37 (3H, t, J=7 Hz), 1.45-1.65 (4H, m), 2.22 (2H, t, J=7 Hz), 2.45-2.73 (2H, m), 3.04 (2H, q, J=7 Hz), 3.46 (3H, s), 4.63 (2H, m), 5.44 (1H, d, J=11 Hz), 5.87 (1H, d, J=18 Hz), 5.92 (1H, d, J=4 Hz), 6.57 (1H, d, J=4 Hz), 6.72-6.83 (1H, dd, J=11 Hz, 18 Hz), 7.78 (1H, s), 8.48 (1H, s), 8.68 (1H, s) MS (ESI$^+$): m/z 394 (M+H), MS (ESI$^-$): m/z 392

EXAMPLE 130

5-[4-(5-Acetyl-3-pyridinyl)-7-ethyl-2-(methoxymethyl)pyrrolo[1,2-b]pyridazin-3-yl]pentanoic acid NMR (CDCl$_3$, δ): 1.38 (3H, t, J=7 Hz), 1.44-1.60 (4H, m), 2.22 (2H, t, J=7 Hz), 2.50-2.63 (2H, m), 2.69 (3H, s), 3.02 (2H, q, J=7 Hz), 3.46 (3H, s), 4.64 (2H, s), 5.86 (1H, d, J=4 Hz), 6.59 (1H, d, J=4 Hz), 8.29 (1H, m), 8.79 (1H, d, J=2 Hz), 9.23 (1H, d, J=2 Hz) MS (ESI$^+$): m/z 410, MS (ESI$^-$): m/z 408

EXAMPLE 131

4-[7-Ethyl-2-(methoxymethyl)-4-(5-methyl-3-pyridinyl)pyrrolo[1,2-b]pyridazin-3-yl]butanoic acid NMR (CDCl$_3$, δ): 1.38 (3H, t, J=7 Hz), 1.70-1.87 (2H, m), 2.26 (2H, t, J=7 Hz), 2.45 (3H, s), 2.53-2.81 (2H, m), 3.06 (2H, q, J=7 Hz), 3.46 (3H, s), 4.66 (2H, m), 5.90 (1H, d, J=4 Hz), 6.59 (1H, d, J=4 Hz), 7.61 (1H, s), 8.43 (1H, s), 8.46 (1H, s) MS (ESI$^+$): m/z 368

EXAMPLE 132

3-[7-Ethyl-2-(methoxymethyl)-4-(5-methyl-3-pyridinyl)pyrrolo[1,2-b]pyridazin-3-yl]propanoic acid NMR (CDCl$_3$, δ): 1.37 (3H, t, J=7 Hz), 2.30-2.60 (2H, m), 2.42 (3H, s), 2.77-3.13 (2H, m), 3.05 (2H, q, J=7 Hz), 3.47 (3H, s), 4.66 (2H, s), 5.91 (1H, d, J=4 Hz), 6.60 (1H, d, J=4 Hz), 7.58 (1H, s), 8.42 (1H, s), 8.54 (1H, s) MS (ESI$^+$): m/z 354

EXAMPLE 133

4-[7-Ethyl-2-methyl-4-(5-methyl-3-pyridinyl)pyrrolo[1,2-b]pyridazin-3-yl]butanoic acid NMR (CDCl$_3$, δ): 1.37 (3H, t, J=7 Hz), 1.70-1.88 (2H, m), 2.22-2.32 (2H, m), 2.45 (3H, s), 2.50-2.62 (2H, m), 2.59 (3H, s), 3.02 (2H, q, J=7 Hz), 5.86 (1H, d, J=4 Hz), 6.53 (1H, d, J=4 Hz), 7.60 (1H, s), 8.42 (2H, m) MS (ESI$^+$): m/z 338, MS (ESI$^-$): m/z 336

EXAMPLE 134

3-[7-Ethyl-2-methyl-4-(5-methyl-3-pyridinyl)pyrrolo[1,2-b]pyridazin-3-yl]propanoic acid NMR (CDCl$_3$, δ): 1.37 (3H, t, J=7 Hz), 2.42 (3H, s), 2.40-2.53 (2H, m), 2.59 (3H, s), 2.82 (2H, t, J=7 Hz), 3.03 (2H, q, J=7 Hz), 5.86 (1H, d, J=4 Hz), 6.53 (1H, d, J=4 Hz), 7.57 (1H, s), 8.38 (1H, s), 8.52 (1H, s) MS (ESI$^+$): m/z 324, MS (ESI$^-$): m/z 322

EXAMPLE 135

3-[4-(5-Bromo-3-pyridinyl)-7-ethyl-2-methylpyrrolo[1,2-b]pyridazin-3-yl]propanoic acid mp: 181-182° C. NMR (CDCl$_3$, δ): 1.38(2H, t, J=7 Hz), 2.4(2H, t, J=7 Hz), 2.58(3H, s), 2.74-2.85(2H, m), 3.01(2H, q, J=7 Hz), 5.89(1H, d, J=4 Hz), 6.55(1H, d, J=4 Hz), 7.87(1H, s), 8.54(1H, s), 8.77(1H, s) MS: (m/z) 388 (M$^+$), 390(M$^+$+2), 114(bp)

EXAMPLE 136

5-[4-(3-Cyanophenyl)-7-ethyl-2-(methoxymethyl)pyrrolo[1,2-b]pyridazin-3-yl]pentanoic acid NNMR (CDCl$_3$, δ): 1.30-1.57 (5H, m), 2.21 (2H, t, J=8 Hz), 2.47-2.57 (2H, m), 3.03 (2H, q, J=8 Hz), 3.45 (3H, s), 4.62 (2H, s), 5.84 (1H, d, J=5 Hz), 6.57 (1H, d, J=5 Hz), 7.59-7.64 (2H, m), 7.68 (1H, br s), 7.75 (1H, m) MS (ESI$^+$): 392 (M+H)

EXAMPLE 136-2

5-[4-[3-(Aminocarbonyl)phenyl]-7-ethyl-2-(methoxymethyl)pyrrolo[1,2-b]pyridazin-3-yl]pentanoic acid NMR (CDCl$_3$, δ): 1.30-1.70 (5H, overlapped with H$_2$O), 2.20-2.50 (4H, m), 2.80-2.93 (2H, m), 3.03 (2H, q, J=8 Hz), 3.46 (3H, s), 4.54 (1H, d, J=10 Hz), 4.77 (1H, d, J=10 Hz), 5.80 (1H, d, J=5 Hz), 6.55 (1H, d, J=5 Hz), 7.43-7.50 (2H, m), 7.58 (1H, t, J=8 Hz), 7.77 (1H, br s), 7.88 (1H, br s), 7.99 (1H, br d, J=8 Hz) MS (ESI$^+$): 410 (M+H)

EXAMPLE 137

5-[4-(5-Bromo-3-pyridinyl)-7-ethyl-2-phenylpyrrolo[1,2-b]pyridazin-3-yl]pentanoic acid NMR (CDCl$_3$, δ): 1.06-1.26 (4H, m), 1.36 (3H, t, J=7 Hz), 1.94 (2H, t, J=7 Hz), 2.40 (2H, m), 2.99 (2H, q, J=7 Hz), 5.96 (1H, d, J=5 Hz), 6.63 (1H, d, J=5 Hz), 7.40-7.52 (5H, m), 7.93 (1H, s), 8.59 (1H, s), 8.77 (1H, s)

EXAMPLE 138

5-[7-Ethyl-4-(5-ethyl-3-pyridinyl)-2-phenylpyrrolo[1,2-b]pyridazin-3-yl]pentanoic acid NMR (CDCl$_3$, δ): 1.05-1.42 (10H, m), 1.92 (2H, m), 2.41 (2H, m), 2.75 (2H, q, J=7 Hz), 3.01 (2H, q, J=7 Hz), 5.93 (1H, d, J=5 Hz), 6.55 (1H, d, J=5 Hz), 7.37-7.54 (5H, m), 7.62 (1H, m), 8.45 (1H, m), 8.52 (1H, m)

EXAMPLE 139

5-[4-(5-Bromo-3-pyridinyl)-7-ethyl-2-(2-thienyl)pyrrolo[1,2-b]pyridazin-3-yl]pentanoic acid NMR (CDCl$_3$, δ): 1.25-1.48 (7H, m), 2.12 (2H, t, J=7 Hz), 2.62 (2H, m), 3.03 (2H, q, J=7 Hz), 5.93 (1H, d, J=5 Hz), 6.64 (1H, d, J=5 Hz), 7.14 (1H, m), 7.37 (1H, d, J=5 Hz), 7.43 (1H, d, J=5 Hz), 7.92 (1H, s) 8.58 (1H, m), 8.79 (1H, m) MS (ESI$^+$): m/z 484 (M+H)

EXAMPLE 140

5-[2-[(Benzyloxy)methyl]-4-(5-bromo-3-pyridinyl)-7-ethylpyrrolo[1,2-b]pyridazin-3-yl]pentanoic acid NMR (CDCl$_3$, δ): 1.23 (3H, t, J=7 Hz), 1.34-1.48 (5H, m), 2.09 (2H, m), 2.53 (2H, m), 3.04 (2H, q, J=7 Hz), 4.07 (2H, J=7 Hz), 4.65 (2H, s), 4.72 (2H, s), 5.90 (1H, d, J=5 Hz), 6.60 (1H, d, J=5 Hz), 7.29-7.38 (5H, m), 7.86 (1H, s), 8.54 (1H, m), 8.77 (1H, m)

EXAMPLE 141

5-(4-(5-Bromo-3-pyridinyl)-2-{[(4-cyanobenzyl)oxy]methyl}-7-ethylpyrrolo[1,2-b]pyridazin-3-yl)pentanoic acid NMR (CDCl$_3$, δ): 1.35-1.56 (7H, m), 2.18 (2H, m), 2.57 (2H, m), 3.03 (2H, q, J=7 Hz), 4.69 (2H, s), 4.74 (2H, s), 5.92 (1H, d, J=5 Hz), 6.62 (1H, d, J=5 Hz), 7.47 (2H, d, J=8 Hz), 7.64 (2H, d, J=8 Hz), 7.88 (1H, s), 8.54 (1H, m), 8.79 (1H, m)

EXAMPLE 142

5-[2-[(Benzylamino)methyl]-4-(5-bromo-3-pyridinyl)-7-ethylpyrrolo[1,2-b]pyridazin-3-yl]pentanoic acid NMR (CDCl$_3$, δ): 1.20-1.49 (7H, m), 2.17 (2H, m), 2.32 (2H, m), 3.04 (2H, q, J=7 Hz), 4.29 (4H, s), 5.94 (1H, d, J=5 Hz), 6.51 (1H, s, br), 6.12 (1H, d, J=5 Hz), 7.27-7.36 (3H, m), 7.48 (2H, m), 7.84 (1H, m), 8.49 (1H, m), 8.75 (1H, m)

EXAMPLE 143

5-[4-(5-Bromo-3-pyridinyl)-7-ethyl-2-(4-morpholinylmethyl)pyrrolo[1,2-b]pyridazin-3-yl]pentanoic acid NMR (CDCl$_3$, δ): 1.20-1.38 (5H, m), 1.49 (4H, m), 2.24 (2H, q, J=7 Hz), 2.59 (4H, m), 3.01 (2H, q, J=7 Hz), 3.70 (4H, m), 5.88 (1H, d, J=5 Hz), 6.55 (1H, d, J=5 Hz), 7.90 (1H, m), 8.55 81H, m), 8.78 (1H, m)

EXAMPLE 144

5-{4-[5-(Aminocarbonyl)-3-pyridinyl]-7-ethyl-2-methylpyrrolo[1,2-b]pyridazin-3-yl}pentanoic acid from ethyl 5-[4-(5-cyano-3-pyridinyl)-7-ethyl-2-methylpyrrolo[1,2-b]-pyridazin-3-yl]pentanoate NMR (CDCl$_3$, δ): 1.10-1.70 (4H, m), 1.37 (3H, t, J=7 Hz), 2.24-2.77 (4H, m), 2.59 (3H, s), 3.02 (2H, q, J=7 Hz), 5.77 (1H, d, J=4 Hz), 6.52 (1H, d, J=4 Hz), 7.57 (1H, br), 7.97 (1H, br), 8.07 (1H, s), 8.68 (1H, s), 9.18 (1H, s) MS (ESI$^+$): m/z 381

EXAMPLE 145

5-[4-[5-(Aminocarbonyl)-3-pyridinyl]-7-ethyl-2-(methoxymethyl)pyrrolo[1,2-b]pyridazin-3-yl]pentanoic acid NMR (CDCl$_3$, δ): 1.16-1.72 (4H, m), 1.37 (3H, t, J=7 Hz), 2.25-2.50 (3H, m), 2.83-2.97 (1H, m), 3.04 (2H, q, J=7 Hz), 3.47 (3H, s), 4.56 (1H, d, J=17 Hz), 4.77 (1H, d, J=17 Hz), 5.81 (1H, d, J=4 Hz), 6.58 (1H, d, J=4 Hz), 7.52 (1H, br), 7.82 (1H, br), 8.11 (1H, m), 8.70 (1H, d, J=2 Hz), 9.18 (1H, d, J=2 Hz) MS (ESI$^+$): m/z 411

EXAMPLE 146

To a solution of triethyl 4-phosphonocrotonate (2.13 g) in tetrahydrofuran (20 mL) was added dropwise lithium bis(trimethylsilyl)amide (1.1 mol/L solution in hexanes, 15 mL) at 2° C. under nitrogen, and the mixture was stirred at the same temperature for 30 minutes. To the mixture was added dropwise a solution of 4-(4-fluorophenyl)-2-isopropylpyrrolo[1,2-b]pyridazine-3-carbaldehyde (1.2 g) in tetrahydrofuran (20 mL). After being stirred for 3 hours at 2° C., the mixture was poured into saturated aqueous ammonium chloride, and the mixture was extracted with ethyl acetate. The organic layer was washed with water, brine, dried over anhydrous magnesium sulfate and concentrated. The residue was purified by silica gel column chromatography (eluent; 3% ethyl acetate in n-hexane) to give the title compound (1.06 g) as an yellow crystals.

Ethyl (2E,4E)-5-[4-(4-fluorophenyl)-2-isopropylpyrrolo[1,2-b]pyridazin-3-yl]-2,4-pentadienoate NMR (300 MHz, CDCl$_3$, δ): 1.28(3H, t, J=7 Hz), 1.35 (6H, d, J=7 Hz), 3.30(1H, quintet, J=7 Hz), 4.19(2H, quartet, J=7 Hz), 5.63(1H, d, J=16 Hz), 5.94(1H, dd, J=16, 11 Hz), 6.16(1H, dd, J=4.4, 1.5 Hz), 6.76(1H, dd, J=4.4, 2.6 Hz), 6.78(1H, d, J=16 Hz), 7.11-7.23(3H, m), 7.33-7.40(2H, m), 7.72(1H, dd, J=2.6, 1.5 Hz) MS (ESI$^+$): m/z 379 (M+H)

The following compounds were obtained in substantially the same manner as that of Example 146.

EXAMPLE 147

Ethyl (2E)-3-[7-chloro-4-(4-fluorophenyl)-2-isopropylpyrrolo[1,2-b]pyridazin-3-yl]-2-propenoate NMR (CDCl$_3$, δ): 1.25 (3H, t, J=7 Hz), 1.40 (6H, d, J=7 Hz), 3.38 (1H, m), 4.16 (2H, q, J=7 Hz), 5.57 (1H, d, J=15 Hz), 6.25 (1H, d, J=5 Hz), 6.74 (1H, d, J=5 Hz), 7.15 (1H, d, J=8.5 Hz), 7.29 (1H, d, J=85 Hz), 7.33 (1H, d, J=8.5 Hz), 7.35 (1H, d, J=85 Hz), 7.63 (1H, d, J=15 Hz) MS (ESI$^-$): m/z 385 (M–H)

EXAMPLE 148

(2E)-3-[7-Chloro-4-(4-fluorophenyl)-2-isopropylpyrrolo[1,2-b]pyridazin-3-yl]-2-propenenitrile NMR (CDCl$_3$, δ): 1.41 (6H, d, J=7 Hz), 3.28 (1H, m), 4.99 (1H, d, J=15 Hz), 6.24 (1H, d, J=5 Hz), 6.76 (1H, d, J=15 Hz), 7.17-7.27 (2H, m), 7.30-7.40 (3H, m) MS (ESI$^-$): m/z 340 (M+H)

EXAMPLE 149

To a solution of ethyl (2E,4E)-5-[4-(4-fluorophenyl)-2-isopropylpyrrolo[1,2-b]pyridazin-3-yl]-2,4-pentadienoate (300 mg) in tetrahydrofuran (3 mL) and acetic acid (1 mL) was added dropwise N-chlorosuccinimide (106 mg). The mixture was stirred at ambient temperature for 24 hours. The resulting mixture was concentrated and partitioned between saturated aqueous sodium hydrogencarbonate and ethyl acetate. The organic layer was washed with brine, dried over anhydrous magnesium sulfate, and concentrated. The residue was purified by silica gel column chromatography (eluent; 1% ethyl acetate in n-hexane) to give the title compound (110 mg) as an oil.

Ethyl (2E,4E)-5-[7-chloro-4-(4-fluorophenyl)-2-isopropylpyrrolo[1,2-b]pyridazin-3-yl]-2,4-pentadienoate NMR (300 MHz, CDCl$_3$, δ): 1.28(3H, t, J=7 Hz), 1.40 (6H, d, J=7 Hz), 3.33(1H, quintet, J=7 Hz), 4.19(2H, quartet, J=7 Hz), 5.64(1H, d, J=16 Hz), 5.94(1H, dd, J=16,11 Hz), 6.18(1H, d, J=4.4 Hz), 6.71(1H, d, J=4.4 Hz), 6.79(1H, d, J=16 Hz), 7.13-7.23(3H, m), 7.32-7.37(2H, m)

The following compounds were obtained in substantially the same manner as that of Example 149.

EXAMPLE 151

Ethyl 7-chloro-4-(2-chlorophenyl)-2-isopropylpyrrolo[1,2-b]pyridazine-3-carboxylate NMR (300 MHz, CDCl$_3$, δ): 0.89 (3H, t, J=75 Hz), 1.41 (6H, d, J=75 Hz), 3.41-3.56 (1H, m), 4.00 (2H, q, J=7.5 Hz), 6.16 (1H, d, J=5 Hz), 6.76 (1H, d, J=5 Hz), 7.25-7.53 (4H, m) MS (ES+): m/e 377.44

EXAMPLE 152

Ethyl 7-chloro-2-isopropyl-4-(2-naphthyl)pyrrolo[1,2-b]pyridazine-3-carboxylate

NMR (300 MHz, CDCl$_3$, δ): 0.78 (3H, t, J=75 Hz), 1.43 (6H, d, J=75 Hz), 3.29-3.41 (1H, m), 3.95 (2H, q, J=75 Hz), 6.40 (1H, d, J=5 Hz), 6.79 (1H, d, J=5 Hz), 7.50-7.60 (3H, m), 7.81-8.00 (4H, m)

EXAMPLE 153

To a solution of ethyl (2E,4E)-5-[7-chloro-4-(4-fluorophenyl)-2-isopropylpyrrolo[1,2-b]pyridazin-3-yl]-2,4-pentadienoate (82 mg) in ethanol (2 mL) was added 1N sodium hydroxide solution (0.5 mL), and the mixture was stirred at ambient temperature for 12 hours. The resulting mixture was concentrated in vacuo, and the residue was dissolved in water, acidified with 1N hydrochloric acid, and extracted with ethyl acetate. The organic layer was washed with water, brine, dried over anhydrous magnesium sulfate and concentrated. The residue was purified by silica gel column chromatography (eluent; 50% ethyl acetate in n-hexane) to give the title compound (14 mg) as a brown amorphous solid, which was recrystallized from aqueous ethanol.

(2E,4E)-5-[7-Chloro-4-(4-fluorophenyl)-2-isopropylpyrrolo[1,2-b]pyridazin-3-yl]-2,4-pentadienoic acid NMR (300 MHz, CDCl$_3$, δ): 1.40 (6H, d, J=7 Hz), 1.30-1.90 (1H, br), 3.34 (1H, quintet, J=7 Hz), 5.64 (1H, d, J=16 Hz), 5.98 (1H, dd, J=16,11 Hz), 6.19 (1H, d, J=4.4 Hz), 6.72 (1H, d, J=4.4 Hz), 6.84 (1H, d, J=16 Hz), 7.14-7.37 (5H, m) MS (ESI$^-$): m/z 383 (M−H)

EXAMPLE 154

To a mixture of ethyl 5-[4-(2-chloro-4-pyridinyl)-7-ethyl-2-(2-thienyl)pyrrolo[1,2-b]pyridazin-3-yl]pentanoate (130 mg) in toluene (5 mL) was added 28% sodium methylate methanol solution (536 mg) and the mixture was heated under reflux for 2 hours. The solution was acidified to pH 4 with 1N hydrochloric acid and extracted with chloroform. The organic layer was separated, dried over magnesium sulfate, and evaporated in vacuo. To the residue in ethanol (5 mL) was added 1N sodium hydroxide solution (1 mL) and the mixture was heated at 60° C. for 1 hour. The solution was acidified to pH 4 with 1N hydrochloric acid and extracted with chloroform. The organic layer was separated, washed with brine, dried over magnesium sulfate, and evaporated in vacuo. The residue was purified by silica gel column chromatography eluting with a mixture of hexane and ethyl acetate (1:1) to give 5-[7-ethyl-4-(2-methoxy-4-pyridinyl)-2-(2-thienyl)pyrrolo[1,2-b]pyridazin-3-yl]pentanoic acid as an yellow powder (50.0 mg).

5-[7-Ethyl-4-(2-methoxy-4-pyridinyl)-2-(2-thienyl)pyrrolo[1,2-b]pyridazin-3-yl]pentanoic acid NMR (CDCl$_3$, δ): 1.30-1.48 (4H, m), 1.38 (3H, t, J=7 Hz), 2.13 (2H, t, J=7 Hz), 2.58-2.69 (2H, m), 3.02 (2H, q, J=7 Hz), 4.02 (3H, s), 5.96 (1H, d, J=4 Hz), 6.61 (1H, d, J=4 Hz), 6.78 (1H, s), 6.90 (1H, d, J=5 Hz), 7.12 (1H, m), 7.34 (1H, m), 7.42 (1H, d, J=5 Hz), 8.29 (1H, d, J=5 Hz)

The following compounds were obtained in substantially the same manner as that of Example 154.

EXAMPLE 155

5-[7-Ethyl-4-(2-methoxy-4-pyridinyl)-2-methylpyrrolo[1,2-b]pyridazin-3-yl]pentanoic acid NMR (CDCl$_3$, δ): 1.31-1.64 (7H, m), 2.25 (2H, t, J=8 Hz), 2.43 (2H, br t, J=8 Hz), 2.54 (3H, s), 3.00 (2H, q, J=8 Hz), 4.04 (3H, s), 5.60 (1H, br s), 5.90 (1H, d, J=5 Hz), 6.51 (1H, d, J=5 Hz), 6.81 (1H, br s), 6.93 (1H, br d, J=7 Hz), 8.30 (1H, d, J=7 Hz) MS (ESI$^+$): m/z 368 (M+H)

EXAMPLE 155-2

5-[7-Ethyl-2-methyl-4-(2-oxo-1,2-dihydro-4-pyridinyl)pyrrolo[1,2-b]pyridazin-3-yl]pentanoic acid NMR (CDCl$_3$, δ): 1.29-1.67 (7H, m), 2.29 (2H, t, J=8 Hz), 2.35-2.60 (5H, m), 3.00 (2H, q, J=8 Hz), 5.94 (1H, d, J=5 Hz), 6.54 (1H, d, J=5 Hz), 6.64 (1H, br d, J=7 Hz), 6.84 (1H, br s), 7.70 (1H, br d, J=7 Hz) MS (ESI$^+$): m/z 354 (M+H)

The following compounds were obtained in substantially the same manner as that of Example 154.

EXAMPLE 156

5-[7-Ethyl-4-(2-methoxy-4-pyridinyl)-2-phenylpyrrolo[1,2-b]pyridazin-3-yl]pentanoic acid NMR (CDCl$_3$, δ): 1.08-1.30 (4H, m), 1.36 (3H, t, J=7 Hz), 1.95 (2H, t, J=7 Hz), 2.48-2.53 (2H, m), 3.03 (2H, q, J=7 Hz), 4.01 (3H, s), 6.02 (1H, d, J=4 Hz), 6.63 (1H, d, J=4 Hz), 6.82 (1H, s), 6.94 (1H, d, J=5 Hz), 7.42-7.54 (5H, m), 8.29 (1H, d, J=5 Hz) MS (ESI$^+$): m/z 430

EXAMPLE 157

5-[7-Ethyl-2-(methoxymethyl)-4-(2-methoxy-4-pyridinyl)pyrrolo[1,2-b]pyridazin-3-yl]pentanoic acid NMR (CDCl$_3$, δ): 1.37 (3H, t, J=7 Hz), 1.40-1.64 (4H, m), 2.24 (2H, t, J=7 Hz), 2.53-2.64 (2H, m), 3.03 (2H, q, J=7 Hz), 3.45 (3H, s), 4.01 (3H, s), 4.61 (2H, s), 5.94 (1H, d, J=4 Hz), 6.58 (1H, d, J=4 Hz), 6.77 (1H, s), 6.89 (1H, d, J=5 Hz), 8.28 (1H, d, J=5 Hz) MS (ESI$^+$): m/z 398, MS (ESI$^-$): m/z 396

EXAMPLE 158

To a solution of ethyl 5-[4-(2-chloro-4-pyridinyl)-7-ethyl-2-phenylpyrrolo[1,2-b]pyridazin-3-yl]pentanoate (120 mg) in toluene (5 mL) and tetrahydrofuran (10 mL) was added sodium thiomethoxide (91.0 mg) and the mixture was heated under reflux for 4 hours. The solution was acidified with 1N hydrochloric acid and extracted with chloroform. The organic layer was separated, washed with brine, dried over magnesium sulfate, and evaporated in vacuo. The residue was purified by silica gel column chromatography eluting with a mixture of hexane and ethyl acetate (10:1-3:1) to give 5-{7-ethyl-4-[2-(methylthio)-4-pyridinyl]-2-phenylpyrrolo-[1,2-b]pyridazin-3-yl}pentanoic acid as an yellow powder (85.0 mg).

5-{7-Ethyl-4-[2-(methylthio)-4-pyridinyl]-2-phenylpyrrolo[1,2-b]pyridazin-3-yl}pentanoic acid NMR (CDCl$_3$, δ): 1.07-1.17 (2H, m), 1.17-1.30 (2H, m), 1.36 (3H, t, J=7 Hz), 1.97 (2H, t, J=7 Hz), 2.38-2.48 (2H, m), 2.61 (3H, s), 3.02 (2H, q, J=7 Hz), 5.98 (1H, d, J=4 Hz), 6.63 (1H, d, J=4 Hz), 7.03 (1H, dd, J=1 Hz, 5 Hz), 7.25 (1H, m), 7.43-7.55 (5H, m), 8.57 (1H, d, J=5 Hz) MS (ESI$^+$): m/z 446 (M+H)

EXAMPLE 159

A mixture of 3-[(1-amino-5-ethyl-1H-pyrrol-2-yl)carbonyl]benzonitrile (3.00 g), ethyl 6-benzoylhexanoate (5.07 g), and trifluoromethanesulfonic acid (376 mg) in toluene (60 mL) was refluxed for 1 hour and 20 minutes with Dean-Stark equipment. The mixture was partitioned between ethyl acetate (60 mL) and water (60 mL), and the organic layer was washed with saturated sodium bicarbonate (60 mL) and brine (60 mL), dried over magnesium sulfate, and evaporated to give a dark colored oil. Flash silica gel column chromatography eluting with acetone=1-100 to 7-100 afforded ethyl 5-[4-(3-cyanophenyl)-7-ethyl-2-phenylpyrrolo-[1,2-b]pyridazin-3-yl]pentanoate as an orange oil (4.45 g, 78.6%).

Ethyl 5-[4-(3-cyanophenyl)-7-ethyl-2-phenylpyrrolo[1,2-b]pyridazin-3-yl]pentanoate NMR (CDCl$_3$, δ): 1.01-1.27 (7H, m), 1.36 (3H, t, J=7 Hz), 1.86 (2H, t, J=7 Hz), 2.40 (2H, m), 3.02 (2H, q, J=7 Hz), 4.02 (2H, q, J=7 Hz), 5.90 (1H, d, J=5 Hz), 6.61 (1H, d, J=5 Hz), 7.44-7.53 (5H, s), 7.60-7.69 (2H, m), 7.74-7.79 (2H, m)

The following compound was obtained in substantially the same manner as that of Example 159.

EXAMPLE 160

Ethyl 5-[4-(2-chloro-4-pyridinyl)-7-ethyl-2-(2-thienyl)pyrrolo[1,2-b]pyridazin-3-yl]pentanoate NMR (CDCl$_3$, δ): 1.21 (3H, t, J=7 Hz), 1.38 (3H, t, J=7 Hz), 1.25-1.48 (4H, m), 2.07 (2H, t, J=7 Hz), 2.57-2.68 (2H, m), 3.04 (2H, q, J=7 Hz), 4.12 (2H, q, J=7 Hz), 5.93 (1H, d, J=4 Hz), 6.64 (1H, d, J=4 Hz), 7.12 (1H, m), 7.28 (1H, dd, J=1 Hz, 5 Hz), 7.37 (1H, m), 7.41 (1H, s), 7.45 (1H, d, J=5 Hz), 8.55 (1H, d, J=5 Hz) MS: (m/z) 468 (M+H)

EXAMPLE 161

Ethyl 5-[4-(2-chloro-4-pyridinyl)-7-ethyl-2-phenylpyrrolo[1,2-b]pyridazin-3-yl]pentanoate NMR (CDCl$_3$, δ): 1.05-1.17 (2H, m), 1.19-1.30 (2H, m), 1.28 (3H, t, J=7 Hz), 1.36 (3H, t, J=7 Hz), 1.91 (2H, t, J=7 Hz), 2.38-2.48 (2H, m), 3.02 (2H, q, J=7 Hz), 4.12 (2H, q, J=7 Hz), 5.96 (1H, d, J=4 Hz), 6.64 (1H, d, J=4 Hz), 7.31 (1H, dd, J=2 Hz, 5 Hz), 7.41-7.54 (6H, m), 8.56 (1H, d, J=5 Hz) MS (ESI$^+$): m/z 462 (M+H)

EXAMPLE 162

Ethyl [4-(3-chlorophenyl)-7-ethyl-2-phenylpyrrolo[1,2-b]pyridazin-3-yl]acetate

NMR (CDCl$_3$, δ): 1.08 (3H, t, J=7 Hz), 1.37 (3H, t, J=7 Hz), 3.03 (2H, q, J=7 Hz), 3.36 (2H, s), 3.93 (2H, q, J=7 Hz), 6.09 (1H, d, J=5 Hz), 6.66 (1H, d, J=5 Hz), 7.33 (1H, m), 7.41-7.50 (8H, m) MS (ESI$^+$): m/z 419 (M+H)

EXAMPLE 163

Ethyl 4-(3-chlorophenyl)-7-ethyl-2-(2-furyl)pyrrolo[1,2-b]pyridazine-3-carboxylate NMR (CDCl$_3$, δ): 1.06 (3H, t, J=7 Hz), 1.41 (3H, t, J=7 Hz), 3.08 (2H, q, J=7 Hz), 4.09 (2H, q, J=7 Hz), 6.34 (1H, d, J=5 Hz), 6.53 (1H, m), 6.74 (1H, d, J=5 Hz), 6.97 (1H, m), 7.39-7.46 (3H, m), 7.52 (2H, m) MS (ESI$^+$): m/z 395 (M+H)

EXAMPLE 164

Ethyl 4-(3-chlorophenyl)-7-ethyl-2-(2-pyridinyl)pyrrolo[1,2-b]pyridazine-3-carboxylate NMR (CDCl$_3$, δ): 0.94 (3H, m), 1.41 (3H, m), 3.08 (2H, q, J=7 Hz), 3.11 (2H, m), 4.00 (2H, m), 6.36 (1H, m), 6.76 (1H, m), 7.26-7.55 (4H, m), 7.84 (1H, m), 8.15 (1H, m), 8.57 (1H, m) MS (ESI$^+$): m/z 406 (M+H)

EXAMPLE 165

Ethyl 5-[4-(3-cyanophenyl)-7-ethyl-2-(1,3-thiazol-2-yl)pyrrolo[1,2-b]pyridazin-3-yl]pentanoate NMR (CDCl$_3$, δ): 1.21 (3H, t, J=7 Hz), 1.33-1.50 (7H, m), 2.14 (2H, t, J=7 Hz), 2.46 (2H, m), 2.97 (2H, q, J=7 Hz), 3.06 (2H, q, J=7 Hz), 4.05 (2H, q, J=7 Hz), 5.88 (1H, d, J=5 Hz), 6.67 (1H, d, J=5 Hz), 7.43 (1H, d, J=3 Hz), 7.64-7.67 (2H, m), 7.70 (1H, m), 7.78 (1H, m), 7.93 (1H, d, J=3 Hz)

EXAMPLE 166

Methyl 5-[4-(3-cyanophenyl)-7-ethyl-2-(1-methyl-1H-pyrrol-2-yl)pyrrolo[1,2-b]pyridazin-3-yl]pentanoate NMR (CDCl$_3$, δ): 1.04 (2H, m), 1.21-1.41 (5H, m), 1.99 (2H, t, J=7 Hz), 2.46 (2H, m), 3.02 (2H, q, J=7 Hz), 3.60 (3H, s), 3.68 (3H, s), 5.89 (1H, d, J=5 Hz), 6.23 (1H, m), 6.35 (1H, m), 6.62 (1H, d, J=5 Hz), 6.76 (1H, m), 7.62-7.79 (4H, m)

EXAMPLE 167

Ethyl 3-[4-(3-chlorophenyl)-7-ethyl-2-phenylpyrrolo[1,2-b]pyridazin-3-yl]propanoate NMR (CDCl$_3$, δ): 1.08 (3H, t, J=7 Hz), 1.37 (3H, t, J=7 Hz), 2.02 (2H, m), 2.80 (2H, m), 3.02 (2H, q, J=7 Hz), 3.89 (2H, q, J=7 Hz), 6.01 (1H, d, J=5 Hz), 6.63 (1H, d, J=5 Hz), 7.31 (1H, m), 7.41-7.54 (8H, m)

EXAMPLE 168

Ethyl 5-[4-(3-cyanophenyl)-7-ethyl-2-(1,3-oxazol-5-yl)pyrrolo[1,2-b]pyridazin-3-yl]pentanoate NMR (CDCl$_3$, δ): 1.17-1.49 (10H, m), 2.08 (2H, t, J=7 Hz), 2.57 (2H, m), 3.03 (2H, q, J=7 Hz), 4.06 (2H, q, J=7 Hz), 5.91 (1H, d, J=5 Hz), 6.66 (1H, d J=5 Hz), 7.55 (1H, s), 7.62-7.68 (3H, m), 7.78 (1H, m), 8.04 (1H, s)

EXAMPLE 169

Ethyl 5-[7-ethyl-4-(3-methoxyphenyl)-2-phenylpyrrolo[1,2-b]pyridazin-3-yl]pentanoate NMR (CDCl$_3$, δ): 1.05-1.29 (4H, m), 1.18 (3H, t, J=7 Hz), 1.36 (3H, t, J=7 Hz), 1.86 (2H, t, J=7 Hz), 2.42-2.52 (2H, m), 3.02 (2H, q, J=7 Hz), 3.84 (3H, s), 4.02 (2H, q, J=7 Hz), 6.02 (1H, d, J=4 Hz), 6.60 (1H, d, J=4 Hz), 6.95-7.02 (3H, m), 7.36-7.56 (6H, m)

EXAMPLE 170

Ethyl 5-[7-ethyl-2-phenyl-4-(4-pyridinyl)pyrrolo[1,2-b]pyridazin-3-yl]pentanoate NMR (CDCl$_3$, δ): 1.04-1.29 (4H, m), 1.19 (3H, t, J=7 Hz), 1.36 (3H, t, J=7 Hz), 1.88 (2H, t, J=7 Hz), 2.38-2.48 (2H, m), 3.02 (2H, q, J=7 Hz), 4.04 (2H, q, J=7 Hz), 5.95 (1H, d, J=4 Hz), 6.62 (1H, d, J=4 Hz), 7.36 (2H, m), 7.42-7.54 (5H, m), 8.76 (2H, m)

EXAMPLE 171

Ethyl 5-[7-ethyl-2-phenyl-4-(2-pyrazinyl)pyrrolo[1,2-b]pyridazin-3-yl]pentanoate NMR (CDCl$_3$, δ): 1.10-1.32 (4H, m), 1.18 (3H, t, J=7 Hz), 1.36 (3H, t, J=7 Hz), 1.90 (2H, t, J=7 Hz), 2.45-2.55 (2H, m), 3.02 (2H, q, J=7 Hz), 4.02 (2H, q, J=7 Hz), 6.05 (1H, d, J=4 Hz), 6.66 (1H, d, J=4 Hz), 7.43-7.56 (5H, m), 8.66 (1H, m), 8.77 (1H, m), 8.86 (1H, m)

EXAMPLE 172

Ethyl 5-[7-ethyl-2-phenyl-4-(3-pyridinyl)pyrrolo[1,2-b]pyridazin-3-yl]pentanoate NMR (CDCl$_3$, δ): 1.04-1.30 (4H, m), 1.18 (3H, t, J=7 Hz), 1.37 (3H, t, J=7 Hz), 1.87 (2H, t, J=7 Hz), 2.38-2.50 (2H, m), 3.02 (2H, q, J=7 Hz), 4.01 (2H, q, J=7 Hz), 5.96 (1H, d, J=4 Hz), 6.63 (1H, d, J=4 Hz), 7.42-7.55 (6H, m), 7.77 (1H, m), 8.66-8.73 (2H, m)

EXAMPLE 173

Ethyl 5-[4-(5-bromo-3-pyridinyl)-7-ethyl-2-phenylpyrrolo[1,2-b]pyridazin-3-yl]pentanoate NMR (CDCl$_3$, δ): 1.12-1.28 (7H, m), 1.36 (3H, t, J=7 Hz), 1.89 (2H, t, J=7 Hz), 2.43 (2H, m), 3.01 (2H, m), 4.02 (2H, q, J=7 Hz), 5.97 (1H, d, J=5 Hz), 6.65 (1H, d, J=5 Hz), 7.43-7.55 (5H, m), 7.93 (1H, m), 8.61 (1H, m), 8.79 (1H, m)

EXAMPLE 174

Ethyl 5-[4-(5-bromo-3-pyridinyl)-7-ethyl-2-(2-thienyl)pyrrolo[1,2-b]pyridazin-3-yl]pentanoate NMR (CDCl$_3$, δ): 1.16-1.46 (10H, m), 1.57 (2H, t, J=7 Hz), 2.62 (2H, m), 2.30 (2H, m), 3.03 (2H, q, J=7 Hz), 4.05 (2H, q, J=7 Hz), 5.93 (1H, d, J=5 Hz), 6.63 (1H, d, J=5 Hz), 7.36 (1H, m), 7.44 (1H, m), 7.91 (1 H, m)

EXAMPLE 175

To a solution of ethyl 5-[4-(3-cyanophenyl)-7-ethyl-2-phenylpyrrolo[1,2-b]pyridazin-3-yl]pentanoate (1.00 g) in dimethylsulfoxide (20 mL) was added 1N sodium hydroxide (5.31 mL) over 1.5 hours. The reaction was quenched by adding 1N hydrochloric acid (6 mL) under an ice-bath. The mixture was partitioned between ethyl acetate (50 mL) and water (50 mL). The organic layer was washed with water (50×2 mL) and brine, dried over magnesium sulfate, and evaporated. Flash silica gel column chromatography eluting with ethyl acetate-hexane=1/3 to 1/1 afforded 5-[4-(3-cyanophenyl)-7-ethyl-2-phenylpyrrolo[1,2-b]pyridazin-3-yl]pentanoic acid as an yellow solid (668 mg).

5-[4-(3-Cyanophenyl)-7-ethyl-2-phenylpyrrolo[1,2-b]pyridazin-3-yl]pentanoic acid NMR (CDCl$_3$, δ): 1.03-1.25 (4H, m), 1.36 (3H, t, J=7 Hz), 1.93 (2H, t, J=7 Hz), 2.39 (2H, m), 3.02 (2H, q, J=7 Hz), 5.91(1H, d, J=5 Hz), 6.63 (1H, d, J=5 Hz), 7.26-7.53 (5H, s), 7.56-7.69 (2H, m), 7.72-7.79 (2H, m) MS (ESI$^+$): m/z 424 (M+H)

The following compounds were obtained in substantially the same manner as that of Example 175.

EXAMPLE 176

5-[4-(3-Cyanophenyl)-7-ethyl-2-(1,3-thiazol-2-yl)pyrrolo[1,2-b]pyridazin-3-yl]pentanoic acid NMR (CDCl$_3$, δ): 1.20-1.52 (7H, m), 2.19 (2H, m), 2.98 (2H, m), 3.04 (2H, q, J=7 Hz), 4.05 (2H, q, J=7 Hz), 5.38 (1H, d, J=5 Hz), 6.67 (1H, d, J=5 Hz), 7.43 (1H, d, J=3 Hz), 7.60-7.64 (2H, m), 7.67 (1H, m), 7.76 (1H, m), 7.92 (1H, d, J=3 Hz) MS (ESI$^+$): m/z 431 (M+H)

EXAMPLE 177

5-[4-(3-Cyanophenyl)-7-ethyl-2-(1-methyl-1H-pyrrol-2-yl)pyrrolo[1,2-b]pyridazin-3-yl]pentanoic acid NMR (CDCl$_3$, δ): 1.12 (2H, m), 1.23-1.41 (5H, m), 2.04 (2H, t, J=7 Hz), 2.48 (2H, m), 3.02 (2H, q, J=7 Hz), 3.68(3H, s), 5.90 (1H, d, J=5 Hz), 6.22 (1H, m), 6.35 (1H, m), 6.62 (1H, d, J=5 Hz), 6.75 (1H, m), 7.57-7.789 (4H, m) MS (ESI$^+$) m/z 427 (M+H)

EXAMPLE 178

5-[4-(3-Cyanophenyl)-7-ethyl-2-(1,3-oxazol-5-yl)pyrrolo[1,2-b]pyridazin-3-yl]pentanoic acid NMR (CDCl$_3$, δ): 1.31-1.49 (7H, m), 2.17 (2H, t, J=7 Hz), 2.57 (2H, m), 3.04 (2H, q, J=7 Hz), 5.42 (1H, d, J=5 Hz), 6.67 (1H, d, J=5 Hz), 7.56 (1H, s), 7.64 (2H, m), 7.67 (1H, s), 7.78 (1H, m), 8.07 (1H, s)

EXAMPLE 179

5-[4-(3-Cyanophenyl)-2-(3,5-dimethyl-4-isoxazolyl)-7-ethylpyrrolo[1,2-b]pyridazin-3-yl]pentanoic acid NMR (CDCl$_3$, δ): 1.04-1.30 (7H, m), 1.97 (2H, t, J=7 Hz), 2.26-2.35 (5H, m), 2.41 (3H, s), 3.00 (2H, q, J=7 Hz), 4.06 (2H, q, J=7 Hz), 5.97 (1H, d, J=5 Hz), 6.68 (1H, d, J=5 Hz), 7.61-7.68 (2H, m), 7.73 (1H, s), 7.79 (1H, m)

EXAMPLE 180

A solution of 3-[(1-amino-5-ethyl-1H-pyrrol-2-yl)carbonyl]benzonitrile (120 mg), 1-tert-butyl 7-ethyl 2-[(3,5-dimethyl-4-isoxazolyl)carbonyl]heptanedioate (203 mg), and toluenesulfonic acid monohydrate (3.76 mg) in toluene (1 mL) was refluxed for 1 hour.

Additional p-toluenesulfonic acid monohydrate (14.5 mg) was added, and the mixture was refluxed for 1 hour. The mixture was stirred further for 0.5 hour after adding trifluoromethanesulfonic acid (3.76 mg). The mixture was partitioned between ethyl acetate (20 mL) and saturated sodium bicarbonate (10 mL). The organic layer was washed with brine, dried over magnesium sulfate, and evaporated. Flash silica gel column chromatography eluting with ethyl acetate-hexane=1/40 to 2/5 afforded ethyl 5-[4-(3-cyanophenyl)-2-(3,5-dimethyl-4-isoxazolyl)-7-ethylpyrrolo-[1,2-b]pyridazin-3-yl]pentanoate as an yellow gum (75.7 mg, 19.1%).

Ethyl 5-[4-(3-cyanophenyl)-2-(3,5-dimethyl-4-isoxazolyl)-7-ethylpyrrolo[1,2-b]pyridazin-3-yl]pentanoate NMR (CDCl$_3$, δ): 1.04-1.30 (7H, m), 1.97 (2H, t, J=7 Hz), 2.26-2.35 (5H, m), 2.41 (3H, s), 3.00 (2H, q, J=7 Hz), 4.06 (2H, q, J=7 Hz), 5.97 (1H, d, J=5 Hz), 6.68 (1H, d, J=5 Hz), 7.61-7.68 (2H, m), 7.73 (1H, s), 7.79 (1H, m)

EXAMPLE 181

To a solution of N-[2-(3-cyanobenzoyl)-5-ethyl-1H-pyrrol-1-yl]-2-(methylsulfonyl)acetamide (2.70 g) in tetrahydrofuran (30 mL) was added sodium hydride (601 mg, 60% in oil) under an ice-bath. After stirring for 40 minutes, the reaction was quenched by adding 1N hydrochloric acid (15 mL). The mixture was extracted with ethyl acetate (50 mL), and the extract was washed with water (50×2 mL) and brine (50 mL), dried over magnesium sulfate, and evaporated to give a brownish yellow solid (3.36 g). The solid was triturated in diisopropyl ether (20 mL) to give 3-[7-ethyl-3-(methylsulfonyl)-2-oxo-1,2-dihydropyrrolo[1,2-b]pyridazin-4-yl]benzonitrile as an yellow powder (2.31 g, 90.1%).

3-[7-Ethyl-3-(methylsulfonyl)-2-oxo-1,2-dihydropyrrolo[1,2-b]pyridazin-4-yl]benzonitrile NMR (CDCl$_3$, δ): 1.37 (3H, t, J=7 Hz), 2.46-3.07 (5H, m), 6.81 (1H, d, J=5 Hz), 6.70 (1H, d, J=5 Hz), 7.60-7.69 (3H, m), 7.83 (1H, d, J=9 Hz)

The following compound was obtained in substantially the same manner as that of Example 181.

EXAMPLE 182

Ethyl 4-(4-cyanophenyl)-7-ethyl-2-oxo-1,2-dihydropyrrolo[1,2-b]pyridazine-3-carboxylate NMR (CDCl$_3$, δ): 0.78 (3H, t, J=7 Hz), 1.36 (3H, t, J=7 Hz), 3.02 (2H, q, J=7 Hz), 4.02 (2H, q, J=7 Hz), 6.15 (1H, d, J=5 Hz), 6.64 (1H, d, J=5 Hz), 7.42 (2H, d, J=9 Hz), 7.77 (2H, d, J=9 Hz), 11.74 (1H, s, br) MS (ESI$^+$): m/z 336 (M+H)

EXAMPLE 183

To a solution of 3-[7-ethyl-3-(methylsulfonyl)-2-oxo-1,2-dihydropyrrolo[1,2-b]pyridazin-4-yl]benzonitrile (1.30 g) and triethylamine (578 mg) in dichloromethane (18 mL) was added trifluoromethanesulfonic anhydride (1.61 g) under an ice-bath over 30 minutes (3 to 7° C.). After stirring for 0.5 hour, the reaction was quenched by adding water (100 mL). The mixture was partitioned between ethyl acetate (200 mL) containing chloroform (200 mL) and 1N hydrochloric acid (50 mL). An insoluble yellow solid was collected by filtration (0.542 g). The organic layer was washed with brine, dried over magnesium sulfate, and evaporated to give a dark yellow solid (1.27 g). Both the solid was combined, and triturated in diisopropyl ether (30 mL) to give 4-(3-cyanophenyl)-7-ethyl-3-(methylsulfonyl)pyrrolo[1,2-b]pyridazin-2-yl trifluoromethanesulfonate as a brownish yellow powder (1.67 g, 92.6%).

4-(3-Cyanophenyl)-7-ethyl-3-(methylsulfonyl)pyrrolo[1,2-b]pyridazin-2-yl trifluoromethanesulfonate NMR (CDCl$_3$, δ): 139 (3H, t, J=7 Hz), 3.02 (2H, q, J=7 Hz), 3.22 (3H, s), 6.40 (1H, d, J=5 Hz), 6.93 (1H, d, J=5 Hz), 7.63 (3H, m), 7.82 (1H, m)

EXAMPLE 184

A mixture of 4-(3-cyanophenyl)-7-ethyl-3-(methylsulfonyl)pyrrolo[1,2-b]pyridazin-2-yl trifluoromethanesulfonate (150 mg) and pyrrolidine (45.6 mg) in tetrahydrofuran (1 mL) was refluxed for 1.5 hours. The mixture was partitioned between ethyl acetate (20 mL) and 1N hydrochloric acid (10 mL). The organic extract was washed with brine, dried over magnesium sulfate, and evaporated to give a dark colored solid. Flash silica gel column chromatography eluting with ethyl acetate-hexane=1-4 to 1-2 afforded 3-[7-ethyl-3-(methylsulfonyl)-2-(1-pyrrolidinyl)-pyrrolo[1,2-b]pyridazin-4-yl]benzonitrile as an yellow oil, which was crystalyzed upon standing (112 mg, 89.6%).

3-[7-Ethyl-3-(methylsulfonyl)-2-(1-pyrrolidinyl)pyrrolo[1,2-b]pyridazin-4-yl]benzonitrile NMR (CDCl$_3$, δ): 1.38 (3H, t, J=7 Hz), 1.99 (4H, m), 3.99 (2H, q, J=7 Hz), 3.22 (3H, s), 3.42-3.70 (4H, m), 6.28 (1H, d, J=5 Hz), 6.68 (1H, d, J=5 Hz), 7.57 (1H, t, J=9 Hz), 7.69-7.78 (3H, m) MS (ESI$^+$): m/z 395 (M+H)

The following compounds were obtained in substantially the same manner as that of Example 184.

EXAMPLE 185

3-[2-(Dimethylamino)-7-ethyl-3-(methyl sulfonyl)pyrrolo[1,2-b]pyridazin-4-yl]benzonitrile NMR (CDCl$_3$, δ): 1.39 (3H, t, J=7 Hz), 2.97 (6H, s), 3.02 (2H, q, J=7 Hz), 3.26 (3H, s), 6.28 (1H, d, J=5 Hz), 6.69 (1H, d, J=5 Hz), 7.57 (1H, t, J=9 Hz), 7.66-7.79 (3H, m) MS (ESI$^+$): m/z 369 (M+H)

EXAMPLE 186

3-[7-Ethyl-2-[(2-methoxyethyl)amino]-3-(methylsulfonyl)pyrrolo[1,2-b]pyridazin-4-yl]benzonitrile NMR (CDCl$_3$, δ): 1.35 (3H, t, J=7 Hz), 2.96 (2H, q, J=7 Hz), 3.07 (3H, s), 3.43 (3H, s), 3.61-3.73 (4H, m), 5.96 (1H, d, J=5 Hz), 6.51 (1H, d, J=5 Hz), 6.75 (1H, m, br), 7.51-7.60 (3H, m), 7.74 (1H, m) MS (ESI$^+$): m/z 399 (M+H)

EXAMPLE 187

A mixture of ethyl 2-(4-fluorobenzoyl)-3-oxo-4-phenylbutanoate (1.4 g), 1H-pyrrol-1-amine (350 mg), and p-toluenesulfonic acid monohydrate (41 mg) in ethanol (10 ml) was refluxed for 5 hours. The mixture was partioned between ethyl acetate and water. The organic layer was separated, washed with brine, dried over magnesium sulfate, and evaporated. The residue was chromatographed on silica gel eluting with a mixture of ethyl acetate and hexane (1:4) to give ethyl 2-benzyl-4-(4-fluorophenyl)pyrrolo[1,2-b]pyridazine-3-carboxylate (828 mg) as an oil.

Ethyl 2-benzyl-4-(4-fluorophenyl)pyrrolo[1,2-b]pyridazine-3-carboxylate

NMR (CDCl$_3$, δ): 0.70 (3H, t, J=7 Hz), 3.71 (2H, q, J=7 Hz), 4.29 (2H, s), 6.37 (1H, dd, J=1, 4 Hz), 6.85 (1H, dd, J=2, 4 Hz), 7.10-7.30 (7H, m), 7.38-7.46 (2H, m), 7.83 (1H, dd, 1, 2 Hz)

EXAMPLE 188

To a solution of ethyl 2-benzyl-4-(4-fluorophenyl)pyrrolo[1,2-b]pyridazine-3-carboxylate (730 mg) in tetrahydrofuran (10 ml) was added N-chlorosuccinimide (260 mg) and the mixture was stirred at 20° C. for 2 hours. The mixture was partitioned between ethyl acetate and water. The organic layer was separated, washed with aqueous sodium thiosulfate, water and brine, dried over magnesium sulfate, and evaporated. The residue was purified by silica gel column chromatography eluting with a mixture of toluene and ethyl acetate (10:1) to give ethyl 2-benzyl-7-chloro-4-(4-fluorophenyl)pyrrolo[1,2-b]pyridazine-3-carboxylate (285 mg) as an yellow oil.

Ethyl 2-benzyl-7-chloro-4-(4-fluorophenyl)pyrrolo[1,2-b]pyridazine-3-carboxylate NMR (CDCl$_3$, δ): 0.69 (3H, t, J=7 Hz), 3.70 (2H, q, J=7 Hz), 4.37 (2H, s), 6.39 (1H, d, J=4 Hz), 6.82 (1H, d, J=4 Hz), 7.10-7.30 (7H, m), 7.35-7.45 (2H, m)

EXAMPLE 189

A mixture of ethyl 3-(4-fluorobenzoyl)-4-oxopentanoate (800 mg), 1H-pyrrol-1-amine (265 mg), and p-toluenesulfonic acid monohydrate (31 mg) in ethanol (5 ml) was refluxed for 5 hours. The mixture was partioned between ethyl acetate and water. The organic layer was separated, washed with brine, dried over magnesium sulfate, and evaporated. The residue was chromatographed on silica gel eluting with a mixture of ethyl acetate and hexane (1:4) to give ethyl[4-(4-fluorophenyl)-2-methylpyrrolo[1,2-b]pyridazin-3-yl]acetate (1.09 g) as an oil.

Ethyl [4-(4-fluorophenyl)-2-methylpyrrolo[1,2-b]pyridazin-3-yl]acetate

NMR (CDCl$_3$, δ): 1.25 (3H, t, J=7 Hz), 2.45 (3H, s), 3.45 (2H, s), 4.16 (2H, q, J=7 Hz), 6.03 (1H, dd, J=1, 4 Hz), 6.72 (1H, dd, J=2, 4 Hz), 7.17 (2H, dt, J=2, 7 Hz), 7.40 (2H, ddd, J=2, 5, 7 Hz), 7.68 (1H, dd, J=1, 2 Hz)

EXAMPLE 190

To a solution of ethyl[4-(4-fluorophenyl)-2-methylpyrrolo[1,2-b]pyridazin-3-yl]acetate (100 mg) in tetrahydrofuran (2 ml) was added N-chlorosuccinimide (43 mg) and the mixture was stirred at 20° C. for 2 hours. The mixture was partitioned between ethyl acetate and water. The organic layer was separated, washed with aqueous ethyl acetate, water and brine, dried over magnesium sulfate, and evaporated. The residue was purified by silica gel column chromatography eluting with a mixture of toluene and ethyl acetate (10:1) to give ethyl[7-chloro-4-(4-fluorophenyl)-2-methylpyrrolo[1,2-b]pyridazin-3-yl]acetate (34 mg) as an yellow oil.

Ethyl [7-chloro-4-(4-fluorophenyl)-2-methylpyrrolo[1,2-b]pyridazin-3-yl]acetate

NMR (CDCl$_3$, δ): 1.25 (3H, t, J=7 Hz), 2.54 (3H, s), 3.47 (2H, s), 4.16 (2H, q, J=7 Hz), 6.05 (1H, d, J=4 Hz), 6.68 (1H, d, J=4 Hz), 7.18 (2H, dt, J=2, 7 Hz), 7.38 (2H, ddd, J=2, 5, 7 Hz)

EXAMPLE 191

To a solution of ethyl[7-chloro-4-(4-fluorophenyl)-2-methylpyrrolo[1,2-b]pyridazin-3-yl]acetate (300 mg) in tetrahydrofuran (4 ml) was added 1N sodium hydroxide (1.7 ml), followed by methanol (2 ml). After standing at 20° C. overnight, the mixture was partitioned between 1N hydrochloric acid and ethyl acetate. The organic layer was separated, washed with water and brine, dried over magnesium sulfate, and evaporated. The residue was triturated with ether to give [7-chloro-4-(4-fluorophenyl)-2-methylpyrrolo[1,2-b]pyridazin-3-yl]acetic acid (250 mg) as an yellow powder.

[7-Chloro-4-(4-fluorophenyl)-2-methylpyrrolo[1,2-b]pyridazin-3-yl]acetic acid

NMR (CDCl$_3$, δ): 2.57 (3H, s), 3.54 (2H, s), 6.06 (1H, d, J=4 Hz), 6.69 (1H, d, J=4 Hz), 7.19 (2H, t, J=7 Hz), 7.38 (2H, dd, J=5, 7 Hz)

EXAMPLE 192

To a solution of [7-chloro-4-(4-fluorophenyl)-2-methylpyrrolo[1,2-b]pyridazin-3-yl]acetic acid (220 mg) in tetrahydrofuran (10 ml) was added 1,1'-carbonyldiimidazole (18 mg) and the mixture was stirred at 20° C. for 1 hour, then magnesium bis(3-ethoxy-3-oxo-propanoate) (109 mg) was added. After the mixture was stirred overnight at 20° C., magnesium bis(3-ethoxy-3-oxo-propanoate) (109 mg) was added. After stirring for 3 hours, the mixture was partitioned between 1N hydrochloric acid and ethyl acetate. The organic layer was separated, washed with water and brine, dried over magnesium sulfate, and evaporated. The residue was chromatographed on silica gel eluting with a mixture of ethyl acetate and hexane (1:5) to give the product (237 mg) as an oil, which was triturated with ethyl acetate and washed with isopropyl ether to give ethyl 4-[7-chloro-4-(4-fluorophenyl)-2-methylpyrrolo[1,2-b]pyridazin-3-yl]-3-oxobutanoate (212 mg) as an yellow powder.

Ethyl 4-[7-chloro-4-(4-fluorophenyl)-2-methylpyrrolo[1,2-b]pyridazin-3-yl]-3-oxobutanoate mp 116-118° C. NMR (CDCl$_3$, δ): 1.25 (3H, t, J=7 Hz), 2.46 (3H, s), 3.40 (2H, s), 3.75 (2H, s), 4.16 (2H, q, J=7 Hz), 6.04 (1H, d, J=4 Hz), 6.68 (1H, d, J=4 Hz), 7.20 (2H, t, J=7 Hz), 7.28 (2H, dd, J=5, 7 Hz)

EXAMPLE 193

To a solution of ethyl 4-[7-chloro-4-(4-fluorophenyl)-2-methylpyrrolo[1,2-b]pyridazin-3-yl]-3-oxo-butanoate (160 mg) in methanol (5 ml) was added sodium borohydride (23.4 mg) at 0° C. and the mixture was stirred at the same temperature for 1 hour. The mixture was partitioned between 1N hydrochloric acid and ethyl acetate. The organic layer was separated, washed with water and brine, dried over magnesium sulfate, and evaporated. The residue was purified by preparative thin-layer chromatography eluting with a mixture of ethyl acetate and hexane (1:3) and triturated with ethyl acetate to give ethyl 4-[7-chloro-4-(4-fluorophenyl)-2-methylpyrrolo[1,2-b]pyridazin-3-yl]-3-hydroxybutanoate (95 mg) as an yellow powder.

Ethyl 4-[7-chloro-4-(4-fluorophenyl)-2-methylpyrrolo[1,2-b]pyridazin-3-yl]-3-hydroxybutanoate NMR (CDCl$_3$, δ): 1.23 (3H, t, J=7 Hz), 2.18-2.38 (2H, m), 2.67 (3H, s), 2.70-2.85 (2H, m), 4.03 (1H, m), 4.09 (2H, q, J=7 Hz), 5.96 (1H, d, J=4 Hz), 6.65 (1H, d, J=4 Hz), 7.19 (2H, t, J=7 Hz), 7.30-7.45 (2H, m)

EXAMPLE 194

To a solution of ethyl 4-[7-chloro-4-(4-fluorophenyl)-2-methylpyrrolo[1,2-b]pyridazin-3-yl]-3-hydroxybutanoate (52 mg) in tetrahydrofuran (1 ml) was added 1N sodium hydroxide (0.27 ml), followed by methanol (1 ml). After standing at 20° C. overnight, the mixture was partitioned between 1N hydrochloric acid and ethyl acetate. The organic layer was separated, washed with water and brine, dried over magnesium sulfate, and evaporated to give 4-[7-chloro-4-(4-fluorophenyl)-2-methylpyrrolo[1,2-b]pyridazin-3-yl]-3-hydroxybutanoic acid (45 mg) as an yellow oil.

4-[7-Chloro-4-(4-fluorophenyl)-2-methylpyrrolo[1,2-b]pyridazin-3-yl]-3-hydroxybutanoic acid NMR (CDCl$_3$, δ): 2.125-2.45 (2H, m), 2.66 (3H, s), 2.70-2.88 (2H, m), 4.02 (1H, m), 5.97 (1H, d, J=4 Hz), 6.65 (1H, d, J=4 Hz), 7.20 (2H, t, J=7 Hz), 7.30-7.45 (2H, m)

EXAMPLE 195

A mixture of ethyl 7-(4-fluorobenzoyl)-8-oxononanoate (300 mg), (1-amino-5-ethyl-1H-pyrrol-2-yl)(4-fluorophenyl)methanone (216 mg), and p-toluenesulfonic acid monohydrate (35.4 mg) in ethanol (6 ml) was refluxed for 5 hours. The mixture was partioned between ethyl acetate and water. The organic layer was separated, washed with brine, dried over magnesium sulfate, and evaporated. The residue was chromatographed on silica gel eluting with a mixture of ethyl acetate and hexane (1:4) to give ethyl 6-[7-ethyl-2,4-bis(4-fluorophenyl)pyrrolo[1,2-b]pyridazin-3-yl]hexanoate (83 mg) and ethyl 6-[7-ethyl-4-(4-fluorophenyl)-2-methylpyrrolo[1,2-b]pyridazin-3-yl]hexanoate (40 mg) as an oil.

Ethyl 6-[7-ethyl-2,4-bis(4-fluorophenyl)pyrrolo[1,2-b]pyridazin-3-yl]hexanoate

NMR (CDCl$_3$, δ): 0.85-1.00 (2H, m), 1.00-1.10 (2H, m), 1.16-1.30 (2H, m), 1.21 (3H, t, J=7 Hz), 1.36 (3H, t, J=7 Hz), 2.00 (2H, t, J=7 Hz), 2.40 (2H, t, J=7 Hz), 3.01 (2H, q, J=7 Hz), 4.06 (2H, q, J=7 Hz), 5.97 (1H, d, J=4 Hz), 6.61 (1H, d, J=4 Hz), 7.12-7.24 (4H, m), 7.38 (2H, dd, J=5, 9 Hz), 7.50 (2H, dd, J=5, 9 Hz)

Ethyl 6-[7-ethyl-4-(4-fluorophenyl)-2-methylpyrrolo[1,2-b]pyridazin-3-yl]hexanoate NMR (CDCl$_3$, δ): 1.15-1.30 (2H, m), 1.23 (3H, t, J=7 Hz), 1.35-1.45 (2H, m), 1.37 (3H, t, J=7 Hz), 1.45-1.55 (2H, m), 2.18 (2H, t, J=7 Hz), 2.40 (2H, t, J=7 Hz), 2.54 (3H, s), 3.01 (2H, q, J=7 Hz), 4.10 (2H, q, J=7 Hz), 5.85 (1H, d, J=4 Hz), 6.49 (1H, d, J=4 Hz), 7.16 (2H, t, J=9 Hz), 7.32 (2H, dd, J=5, 9 Hz)

EXAMPLE 196

A mixture of (1-amino-5-ethyl-1H-pyrrol-2-yl)(4-fluorophenyl)methanone (500 mg), ethyl 8-acetyl-9-oxodecanoate (678 mg), and p-toluenesulfonic acid monohydrate (82 mg) in ethanol (5 ml) was refluxed for 2 hours. The mixture was partioned between ethyl acetate and 1N hydrochloric acid. The organic layer was separated, washed with water and brine, dried over magnesium sulfate, and evaporated. The residue was chromatographed on silica gel eluting with toluene to give ethyl 6-[7-ethyl-4-(4-fluorophenyl)-2-methylpyrrolo[1,2-eb]pyridazin-3-yl]hexanoate (130 mg) as an oil and [5-ethyl-1-({(1E)-1-[7-ethyl-4-(4-fluorophenyl)-2-methylpyrrolo[1,2-b]pyridazin-3-yl]ethylidene}amino)-1H-pyrrol-2-yl](4-fluorophenyl)methanone (70 mg) as an yellow crystal.

[5-Ethyl-1-({(1E)-1-[7-ethyl-4-(4-fluorophenyl)-2-methylpyrrolo[1,2-b]pyridazin-3-yl] ethylidene}amino)-1H-pyrrol-2-yl](4-fluorophenyl) methanone NMR (CDCl$_3$, δ): 1.13 (3H, t, J=7 Hz), 1.39 (3H, t, J=7 Hz), 1.80-2.00 (2H, m), 1.91 (3H, s), 2.86 (3H, s), 3.06 (2H, q, J=7 Hz), 5.97 (1H, d, J=4 Hz), 6.11 (1H, d, J=4 Hz), 6.62 (2H, t, J=4 Hz), 7.11 (4H, t, J=9 Hz), 7.48 (2H, dd, J=5, 9 Hz), 7.82 (2H, dd, J=5, 9 Hz)

Ethyl 6-[7-ethyl-4-(4-fluorophenyl)-2-methylpyrrolo[1,2-b]pyridazin-3-yl]hexanoate NMR (CDCl$_3$, δ): 1.15-1.30 (2H, m), 1.23 (3H, t, J=7 Hz), 1.35-1.45 (2H, m), 1.37 (3H, t, J=7 Hz), 1.45-1.55 (2H, m), 2.18 (2H, t, J=7 Hz), 2.40 (2H, t, J=7 Hz), 2.54 (3H, s), 3.01 (2H, q, J=7 Hz), 4.10 (2H, q, J=7 Hz), 5.85 (1H, d, J=4 Hz), 6.49 (1H, d, J=4 Hz), 7.16 (2H, t, J=9 Hz), 7.32 (2H, dd, J=5, 9 Hz)

EXAMPLE 197

A mixture of ethyl 7-(4-cyanobenzoyl)-8-oxononanoate (2.2 g), 2-ethyl-1H-pyrrol-1-amine (809 mg), and p-toluenesulfonic acid monohydrate (64 mg) in toluene (40 ml) was refluxed for 20 minutes. The mixture was partioned between ethyl acetate and 1N hydrochloric acid. The organic layer was separated, washed with water and brine, dried over magnesium sulfate, and evaporated. The residue was chromatographed on silica gel eluting with a mixture of ethyl acetate and hexane (1:5) to give the product, which was triturated with hexane to give ethyl 6-[4-(4-cyanophenyl)-7-ethyl-2-methylpyrrolo-[1,2-b]pyridazin-3-yl]hexanoate (2.21 g) as an yellow crystals.

Ethyl 6-[4-(4-cyanophenyl)-7-ethyl-2-methylpyrrolo[1,2-b]pyridazin-3-yl]hexanoate NMR (CDCl$_3$, δ): 1.15-1.25 (2H, m), 1.25 (3H, t, J=7 Hz), 1.30-1.45 (2H, m), 1.38 (3H, t, J=7 Hz), 1.45-1.65 (2H, m), 2.19 (2H, t, J=7 Hz), 2.38 (2H, t, J=7 Hz), 2.56 (3H, s), 3.02 (2H, q, J=7 Hz), 4.12 (2H, q, J=7 Hz), 5.80 (1H, d, J=4 Hz), 6.51 (1H, d, J=4 Hz), 7.48 (2H, t, J=9 Hz), 7.78 (2H, d, J=9 Hz)

EXAMPLE 198

To a solution of ethyl 6-[4-(4-cyanophenyl)-7-ethyl-2-methylpyrrolo[1,2-b]pyridazin-3-yl]hexanoate (15 g) in tetrahydrofuran (15 ml) was added 2N potassium hydroxide (7.4 ml), followed by methanol (7.4 ml). After stirring at 50° C. for 2 hours and 60° C. for 3 hours, the mixture was partitioned between 1N hydrochloric acid and ethyl acetate. The precipitates were filtered and washed with ethyl acetate. The organic layer and the washings were combined, washed with water and brine, dried over magnesium sulfate, and evaporated. The residue was triturated with ethyl acetate and the precipitates were filtered. The filtrate was purified by silica gel column chromatography eluting with a mixture of ethyl acetate and hexane (1:1) and triturated with isopropyl ether to give 6-[4-(4-cyanophenyl)-7-ethyl-2-methylpyrrolo[1,2-b]pyridazin-3-yl]hexanoic acid (650 mg) as an yellow crystals. The two precipitates were combined and recrystallized from ethyl acetate to give 6-{4-[4-(aminocarbonyl)phenyl]-7-ethyl-2-methylpyrrolo[1,2-b]pyridazin-3-yl}hexanoic acid (550 mg, 37.6%) as an yellow crystals.

6-[4-(4-Cyanophenyl)-7-ethyl-2-methylpyrrolo[1,2-b]pyridazin-3-yl]hexanoic acid

NMR (CDCl$_3$, δ): 1.15-1.30 (2H, m), 1.35-1.45 (2H, m), 1.38 (3H, t, J=7 Hz), 1.45-1.60 (2H, m), 2.26 (2H, t, J=7 Hz), 2.38 (2H, t, J=7 Hz), 2.56 (3H, s), 3.02 (2H, q, J=7 Hz), 5.80 (1H, d, J=4 Hz), 6.51 (1H, d, J=4 Hz), 7.48 (2H, t, J=9 Hz), 7.79 (2H, d, J=9 Hz)

6-{4-[4-(Aminocarbonyl)phenyl]-7-ethyl-2-methylpyrrolo[1,2-b]pyridazin-3-yl}hexanoic acid NMR (CDCl$_3$, δ): 1.1-1.20 (2H, m), 1.29 (3H, t, J=7 Hz), 1.30-1.45 (4H, m), 2.10 (2H, t, J=7 Hz), 2.37 (2H, t, J=7 Hz), 2.51 (3H, s), 2.92 (2H, q, J=7 Hz), 5.73 (1H, d, J=4 Hz), 6.51 (1H, d, J=4 Hz), 7.45 (2H, t, J=9 Hz), 7.47 (1H, s), 7.80 (2H, d, J=9 Hz), 8.09 (1H, s)

EXAMPLE 199

To a solution of 3-[(1-amino-5-ethyl-1H-pyrrol-2-yl)carbonyl]benzonitrile (200 mg) in toluene (6 mL) was added 2,4-pentanedione (837 mg) and p-toluenesulfonic acid monohydrate (32 mg) at ambient temperature. The reaction mixture was refluxed for 1 hour. The residue was purified by flash silica gel chromatography (silica gel, 80 mL) eluted with hexane-ethyl acetate=10-1 to give 3-(3-acetyl-7-ethyl-2-methylpyrrolo[1,2-b]pyridazin-4-yl)benzonitrile (63 mg, 24.8%) as an yellow solid.

3-(3-Acetyl-7-ethyl-2-methylpyrrolo[1,2-b]pyridazin-4-yl)benzonitrile

NMR (CDCl$_3$, δ): 1.39 (3H, t, J=8 Hz), 1.95 (3H, s), 2.50 (3H, s), 3.04 (2H, q, J=8 Hz), 6.27 (1H, d, J=5 Hz), 6.69 (1H, d, J=5 Hz), 7.59-7.72 (2H, m), 7.76-7.84 (2H, m) MS (ESI$^+$): m/z 304 (M+H)

EXAMPLE 200

To a solution of ethyl (2E)-3-[7-chloro-4-(4-fluorophenyl)-2-isopropylpyrrolo[1,2-b]pyridazin-3-yl]-2-propenoate (50 mg) in toluene was added dropwise 1.5 M diisobutylaluminum hydride (0.277 mL) in toluene (24 mL) in a dryice-acetone bath. After addition, the mixture was stirred for 2 hours (−10° C.). The reaction mixture was quenched with sodium, potassium-tartarate and was filtered through Celite. The organic layer was separated, dried over magnesium sulfate, and evaporated in vacuo. The residue was purified by flash silica gel chromatography (silica gel, 40 mL) eluted with hexane-ethyl acetate=10-1, 5-1, and 3-1 to give (2E)-3-[7-chloro-4-(4-fluorophenyl)-2-isopropylpyrrolo[1,2-b]pyridazin-3-yl]-2-propen-1-ol as an yellow solid (30 mg).

(2E)-3-[7-Chloro-4-(4-fluorophenyl)-2-isopropylpyrrolo[1,2-b]pyridazin-3-yl]-2-propen-1-ol NMR (CDCl$_3$, δ): 1.38 (6H, d, J=7 Hz), 3.31 (1H, m), 4.05-4.11 (2H, m), 5.48 (1H, dt, J=15, 6 Hz), 6.11 (1H, d, J=5 Hz), 6.45 (1H, d, J=15 Hz), 6.68 (1H, d, J=5 Hz), 7.08-7.18 (2H, m), 7.29-7.40 (2H, m) MS (ESI$^-$): m/z 345 (M+H)

The following compounds were obtained in substantially the same manner as that of Example 200.

EXAMPLE 201

[4-(4-Fluorophenyl)-2-methylpyrrolo[1,2-b]pyridazin-3-yl]methanol

NMR (CDCl$_3$, δ): 1.45 (1H, t, J=5 Hz), 2.65 (3H, s), 4.47 (2H, d, J=5 Hz), 6.13 (1H, m), 6.73 (1H, m), 7.14-7.28 (2H, m), 7.43-7.51 (2H, m), 7.70 (1H, m) MS (ESI$^+$): m/z 257 (M+H)

EXAMPLE 202

[7-Ethyl-4-(4-fluorophenyl)-2-isopropylpyrrolo[1,2-b]pyridazin-3-yl]methanol

NMR (CDCl$_3$, δ): 1.31-1.46 (10H, m), 3.04 (2H, q, J=8 Hz), 3.46 (1H, m), 4.49 (2H, d, J=5 Hz), 6.05 (1H, d, J=5 Hz), 6.56 (1H, d, J=5 Hz), 7.12-7.22 (2H, m), 7.41-7.50 (2H, m) MS (ESI$^+$): m/z 313 (M+H)

EXAMPLE 203

2-{[7-Ethyl-4-(4-fluorophenyl)-2-isopropylpyrrolo[1,2-b]pyridazin-3-yl]methoxy}ethanol NMR (CDCl$_3$, δ): 1.30-1.45 (9H, m), 3.04 (2H, q, J=8 Hz), 3.35 (1H, m), 3.46 (2H, t, J=6 Hz), 3.69 (2H, br t, J=8 Hz), 4.30 (2H, s), 6.07 (1H, d, J=5 Hz), 6.55 (1H, d, J=5 Hz), 7.11-7.22 (2H, m), 7.41-7.51 (2H, m) MS (ESI$^+$): m/z 357 (M+H)

EXAMPLE 204

To a solution of (2E)-3-[7-chloro-4-(4-fluorophenyl)-2-isopropylpyrrolo[1,2-b]pyridazin-3-yl]-2-propen-1-ol (30 mg) in N,N-dimethylformamide (1 mL) was added 60% sodium hydride in oil (3.8 mg) in an ice-water bath under nitrogen atmosphere. After 20 minutes, to the mixture was added methyl iodide (18.5 mg) at the temperature. After 15 minutes, the reaction mixture was stirred at ambient temperature for 5 hours. The reaction mixture was partitioned between ethyl acetate and water. The organic layer was washed with water three times and brine, dried over magnesium sulfate, and evaporated in vacuo. The residue was purified by p-TLC (hexane-ethyl acetate=10-1) to give 7-chloro-4-(4-fluorophenyl)-2-isopropyl-3-[(1E)-3-methoxy-1-propenyl]pyrrolo[1,2-b]pyridazine as a brown oil (35 mg, 10.2%).

7-Chloro-4-(4-fluorophenyl)-2-isopropyl-3-[(1E)-3-methoxy-1-propenyl]pyrrolo[1,2-b]pyridazine NMR (CDCl$_3$, δ): 1.38 (3H, t, J=7 Hz), 3.31 (1H, m), 4.05-4.11 (2H, m), 5.48 (1H, dt, J=15, 6 Hz), 6.11 (1H, d, J=5 Hz), 6.45 (1H, d, J=15 Hz), 6.68 (1H, d, J=5 Hz), 7.08-7.18 (2H, m), 7.29-7.40 (2H, m) MS (ESI$^-$): m/z 345 (M+H)

EXAMPLE 205

To dimethylsulfoxide (0.5 mL) was added 60% sodium hydride in oil (27 mg) and was heated at 60° C. for 40 minutes. To this mixture was added (3-carboxypropyl)(triphenyl)phosphonium bromide (124 mg) at ambient temperature and was stirred for 40 minutes. 7-Chloro-4-(4-fluorophenyl)-2-isopropylpyrrolo[1,2-b]pyridazine-3-carbaldehyde (40 mg) was added therein at ambient temperature. After 4 hours, the reaction mixture was acidified with 1N hydrogen chloride and was partitioned between ethyl acetate and water. The organic layer was washed with water three times and brine, dried over magnesium sulfate, and evaporated in vacuo. The residue was purified by p-TLC (hexane-ethyl acetate=1-1) to give (4E)-5-[7-chloro-4-(4-fluorophenyl)-2-isopropylpyrrolo[1,2-b]pyridazin-3-yl]-4-pentenoic acid as an yellow oil (21 mg, E:Z=16:1, 56.3%).

(4E)-5-[7-Chloro-4-(4-fluorophenyl)-2-isopropylpyrrolo[1,2-b]pyridazin-3-yl]-4-pentenoic acid NMR (CDCl$_3$, δ): 1.40 (6H, d, J=7 Hz), 2.20-2.37 (4H, m), 3.25 (1H, m), 5.30 (0.94H, dt, J=15, 7 Hz), 5.01 (0.06H, m), 6.09 (1H, d, J=5 Hz), 6.24 (0.94H, d, J=15 Hz), 6.84 (0.06H, d, J=10 Hz), 6.67 (0.94H, d, J=5 Hz), 6.70 (0.06H, d, J=5 Hz), 7.07-7.17 (2H, m), 7.26-7.35 (2H, m). MS (ESI$^-$): m/z 385 (M–H)

EXAMPLE 206

To a solution of 7-chloro-4-(4-fluorophenyl)-2-isopropylpyrrolo[1,2-b]pyridazine-3-carbaldehyde (40 mg) was added 1N sodium hydroxide (19.3 mg) and acetone (0.425 mL) at ambient temperature. After 8 hours, the reaction mixture was partitioned between ethyl acetate and water. The organic layer was washed with water and brine, dried over magnesium sulfate, and evaporated in vacuo. The residue was purified by p-TLC (hexane-ethyl acetate=5-1) to give (3E)-4-[7-chloro-4-(4-fluorophenyl)-2-isopropylpyrrolo[1,2-b]pyridazin-3-yl]-3-buten-2-one as an yellow solid (33 mg).

(3E)-4-[7-Chloro-4-(4-fluorophenyl)-2-isopropylpyrrolo[1,2-b]pyridazin-3-yl]-3-buten-2-one NMR (CDCl$_3$, δ): 1.40 (6H, d, J=7 Hz), 2.13 (3H, s), 3.38 (1H, m), 5.89(1H, d, J=15 Hz), 6.23 (1H, d, J=5 Hz), 6.75 (1H, d, J=5 Hz), 7.13-7.23 (2H, m), 7.30-7.39 (2H, m), 7.49 (1H, d, J=15 Hz)

EXAMPLE 207

A solution of ethyl 4-(4-fluorophenyl)-2-isopropylpyrrolo[1,2-b]pyridazine-3-carboxylate (100 mg) in tetrahydrofuran (1 mL) was purged with nitrogen gas under a dryice-acetone bath. To the mixture was added 2,2'-azobisisobutyronitrile (0.5 mg) was added to the mixture. After 5 minutes, was added 1,3-dibromo-5,5-dimethyl-2,4-imidazolidinedione (43.8 mg). The resulting mixture was stirred for 3 hours (–78 to –30° C.). Water (5 mL) was added, and the mixture was extracted with ethyl acetate. The organic extract was washed with brine, dried over anhydrous magnesium sulfate, and evaporated to give an yellow gum. Flash silica gel column chromatography eluting with toluene-hexane=1-5 to 2-3 afforded ethyl 7-bromo-4-(4-fluorophenyl)-2-isopropylpyrrolo[1,2-b]pyridazine-3-carboxylate product as an yellow gum (90.0 mg, 72.5%).

Ethyl 7-bromo-4-(4-fluorophenyl)-2-isopropylpyrrolo[1,2-b]pyridazine-3-carboxylate NMR (CDCl$_3$, δ): 0.98 (3H, t, J=7 Hz), 1.40 (6H, d, J=7 Hz), 3.31 (1H, septet, J=7 Hz), 4.05 (2H, q, J=7 Hz), 6.39 (1H, d, J=5 Hz), 6.87 (1H, d, J=5 Hz), 7.16 (2H, t, J=9 Hz), 7.45 (2H, dd, J=4 and 9 Hz) MS (ESI$^+$): m/z 405 (M+H)

EXAMPLE 208

A suspension of sodium hydride (74.4 mg) in dimethylsulfoxide (1.4 mL) was stirred for 1 hour at 60° C. The mixture was added to a solution of methyl triphenylphosphonium bromide (1.11 g) in dimethylsulfoxide (1.0 mL) at room temperature. After stirring for 0.5 hour, the mixture was added ethyl 4-(4-fluorophenyl)-7-formyl-2-isopropylpyrrolo[1,2-b]pyridazine-3-carboxylate (500 mg). After stirring for 15 hours, the mixture was partitioned between ethyl acetate (20 mL) and water (5 mL). The organic layer was washed with water and brine, dried over anhydrous magnesium sulfate, and evaporated to give an orange gum. Flash silica gel column chromatography eluting with ethyl acetate-hexane=1-7 to 3-1 afforded ethyl 4-(4-fluorophenyl)-2-isopropyl-7-vinylpyrrolo[1,2-b]pyridazine-3-carboxylate an yellow gum, which was solidified upon standing (36.1 mg, 72.6%).

Ethyl 4-(4-fluorophenyl)-2-isopropyl-7-vinylpyrrolo[1,2-b]pyridazine-3-carboxylate NMR (CDCl$_3$, δ): 0.97 (3H, t, J=7 Hz), 1.38 (6H, d, J=7 Hz), 3.32 (1H, septet, J=7 Hz), 4.03 (2H, q, J=7 Hz), 5.35 (1H, dd, J=2 and 12 Hz), 6.11 (1H, dd, J=2 and 18 Hz), 6.34 (1H, d, J=5 Hz), 6.99 (1H, d, J=5 Hz), 7.16 (1H, t, J=9 Hz), 7.25 (1H, dd, J=12 and 18 Hz), 7.45 (2H, d, J=4 and 9 Hz)

EXAMPLE 209

To a solution of ethyl 7-{4-[4-({[(benzyloxy)carbonyl]amino}sulfonyl)phenyl]-7-ethyl-2-methylpyrrolo[1,2-b]pyridazin-3-yl}heptanoate (169 mg) in ethanol (2 mL) was added 10% palladium on activated carbon (1.6 mg), and the mixture was stirred under hydrogen pressure (3 kg/cm2) for 2 hours. The resulting mixture was filtered through celite, and the filtrate was concentrated to give an yellow gum. Preparative silica gel thin layer chromatography eluting with ethyl acetate-hexane=1-1 afforded ethyl 7-{4-[4-(aminosulfonyl)phenyl]-7-ethyl-2-methylpyrrolo[1,2-b]pyridazin-3-yl}heptanoate as an yellow gum (76.8 mg, 58.4%).

Ethyl 7-{4-[4-(aminosulfonyl)phenyl]-7-ethyl-2-methylpyrrolo[1,2-b]pyridazin-3-yl}heptanoate NMR (CDCl$_3$, δ): 1.07-1.25 (7H, m), 1.30-1.46 (7H, m), 2.18 (2H, t, J=7 Hz), 2.36 (2H, m), 2.55 (3H, s), 3.00 (2H, q, J=7 Hz), 4.12 (2H, q, J=7 Hz), 5.21 (2H, s), 5.82 (1H, d, J=5 Hz), 6.50 (1H, d, J=5 Hz), 7.52 (2H, d, J=9 Hz), 8.05 (2H, d, J=9 Hz) MS (ESI$^+$): m/z 472 (M+H)

EXAMPLE 210

To a solution of ethyl 4-(4-cyanophenyl)-2-(2-ethoxy-2-oxoethyl)-7-ethylpyrrolo[1,2-b]pyridazine-3-carboxylate (77.9 mg) in ethanol (0.5 mL)-tetrahydrofuran (0.5 mL) was added 1N potassium hydroxide. The resulting solution was stirred for 2.5 hours at room temperature. The mixture was stirred for further 1 hour after adding 1N potassium hydroxide (0.04 mL). The reaction was quenched by adding 1N hydrochloric acid (0.23 mL). The volatile was evaporated off, and the resulting residue was partitioned between ethyl acetate (10 mL) and 1N hydrochloric acid (6 mL). The organic layer was washed with brine, dried, and evaporated to give [4-(4-cyanophenyl)-3-(ethoxycarbonyl)-7-ethylpyrrolo[1,2-b]pyridazin-2-yl]acetic acid as an yellow solid (67.7 mg, 93.4%).

[4-(4-Cyanophenyl)-3-(ethoxycarbonyl)-7-ethylpyrrolo[1,2-b]pyridazin-2-yl]acetic acid NMR (CDCl$_3$, δ): 0.84 (3H, t, J=7 Hz), 1.38 (3H, t, J=7 Hz), 3.05 (2H, q, J=7 Hz), 3.93 (2H, q, J=7 Hz), 4.18 (3H, s), 6.27 (1H, d, J=5 Hz), 6.74 (1H, d, J=5 Hz), 7.52 (2H, d, J=9 Hz), 7.76 (2H, d, J=9 Hz) MS (ESI$^+$): m/z 378 (M+H)

EXAMPLE 211

To a solution of ethyl 2-(2-amino-2-oxoethyl)-4-(4-cyanophenyl)-7-ethylpyrrolo[1,2-b]pyridazine-3-carboxylate (35.0 mg) in tetrahydrofuran (1 mL) was added 60% sodium hydride (4.50 mg) under an ice-bath. The resulting mixture was stirred for 1 hour. The reaction was quenched by adding 1N HCl (4 mL). The mixture was extracted with ethyl acetate (10 mL), and the organic layer was washed with water and brine, dried over magnesium sulfate, and evaporated. Preparative silica gel thin layer chromatography eluting with ethyl chloroform-methanol=10-1 afforded 4-(7-ethyl-1,3-dioxo-1,2,3,4-tetrahydropyrido[3,4-e]pyrrolo[1,2-b]-pyridazin-10-yl)benzonitrile as an yellow solid (3.86 mg, 12.6%).

4-(7-Ethyl-1,3-dioxo-1,2,3,4-tetrahydropyrido[3,4-e]pyrrolo[1,2-b]pyridazin-10-yl)benzonitrile NMR (CDCl$_3$, δ): 1.40 (3H, t, J=7 Hz), 3.08 (2H, q, J=7 Hz), 4.16 (3H, s), 6.38 (1H, d, J=5 Hz), 6.85 (1H, d, J=5 Hz), 7.46 (2H, d, J=9 Hz), 7.78 (2H, d, J=9 Hz), 7.92 (1H, s, br)

EXAMPLE 212

To methanol (1 mL) was added 60% sodium hydride (651 mg) at room temperature. Then, 4-(3-cyanophenyl)-7-ethyl-3-(methylsulfonyl)pyrrolo[1,2-b]pyridazin-2-yl trifluoromethanesulfonate (70.0 mg) was added to the mixture. The resulting mixture was stirred for 2 hours at room temperature and 1 hour at 50° C. The mixture was partitioned between ethyl acetate and water. The organic layer was washed with brine, dried over magnesium sulfate, and evaporated. Preparative silica gel thin layer chromatography eluting with ethyl acetate-hexane=1-1 afforded 3-[7-ethyl-2-methoxy-3-(methylsulfonyl)pyrrolo[1,2-b]pyridazin-4-yl]benzonitrile as an yellow solid (1.92 mg, 3.7%).

3-[7-Ethyl-2-methoxy-3-(methylsulfonyl)pyrrolo[1,2-b]pyridazin-4-yl]benzonitrile NMR (CDCl$_3$, δ): 1.38 (3H, t, J=7 Hz), 3.01 (2H, q, J=7 Hz), 3.24 (3H, s), 4.18 (3H, s), 6.12 (1H, d, J=5 Hz), 6.63 (1H, d, J=5 Hz), 7.53-7.64 (3H, m), 7.76 (1H, m)

EXAMPLE 213

To a solution of ethyl 4-(3-cyanophenyl)-7-ethyl-3-(methylsulfonyl)pyrrolo[1,2-b]pyridazine-2-carboxylate (92.6 mg) in tetrahydrofuran (1 mL) and ethanol (0.5 mL) was added 1N sodium hydroxide (0.349 mL). The resulting mixture was stirred for 3 hours at room temperature. The resulting mixture was stirred further for 40 minutes after adding 1N sodium hydroxide (0.1 mL). The mixture was stirred further for 1.5 hours after adding 1N sodium hydroxide (0.1 mL). The reaction was quenched by adding 1N hydrochloric acid (1 mL), and the mixture was partitioned between ethyl acetate (20 mL) and water (10 mL). The organic layer was washed with brine, dried over magnesium sulfate, and evaporated to give a red oil. Flash silica gel column chromatography eluting with ethyl acetate-hexane=1-1 afforded 3-(6-ethyl-1,1-dioxido-3-oxo-2,3-dihydropyrrolo[1,2-b]thieno[2,3-e]pyridazin-9-yl)benzonitrile as a red foam (52.4 mg, 64.0%).

3-(6-Ethyl-1,1-dioxido-3-oxo-2,3-dihydropyrrolo[1,2-b]thieno[2,3-e]pyridazin-9-yl)benzonitrile NMR (CDCl$_3$, δ): 1.45 (3H, t, J=7 Hz), 3.21, (3H, s), 4.28 (2H, s), 6.91 (1H, d, J=5 Hz), 7.26 (1H, d, J=5 Hz), 7.75 (1H, t, J=9 Hz), 7.91 (1H, d, J=9 Hz), 8.08-8.16 (2H, m) MS (ESI$^+$): m/z 352 (M+H)

EXAMPLE 214

To a solution of 3-(6-ethyl-1,1-dioxido-3-oxo-2,3-dihydropyrrolo[1,2-b]thieno[2,3-e]pyridazin-9-yl)benzonitrile (60.0 mg) in tetrahydrofuran (0.2 mL) was added 1 M solution of borane-tetrahydrofuran complex in tetrahydrofuran (0.487 mL) under an ice-bath. After stirring for 1 hour, the reaction was quenched by adding 1N hydrochloric acid (1 mL). The mixture was partitioned between ethyl acetate (20 mL) and water (10 mL), and the organic layer was washed with brine, dried, and evaporated to give 3-(6-ethyl-3-hydroxy-1,1-dioxido-2,3-dihydropyrrolo[1,2-b]thieno[2,3-e]pyridazin-9-yl)-benzonitrile as an yellow foam (576 mg, 99.8%).

3-(6-Ethyl-3-hydroxy-1,1-dioxido-2,3-dihydropyrrolo[1,2-b]thieno[2,3-e]pyridazin-9-yl)benzonitrile NMR (CDCl$_3$, δ): 1.45 (3H, t, J=7 Hz), 3.21, (3H, s), 4.28 (2H, s), 6.91 (1H, d, J=5 Hz), 7.26 (1H, d, J=5 Hz), 7.75 (1H, t, J=9 Hz), 7.91 (1H, d, J=9 Hz), 8.08-8.16 (2H, m)

EXAMPLE 215

To a solution of 3-(6-ethyl-3-hydroxy-1,1-dioxido-2,3-dihydropyrrolo[1,2-b]thieno[2,3-e]pyridazin-9-yl)benzonitrile (54.0 mg) in tetrahydrofuran (1 mL) was added 60% sodium hydride (6.69 mg) under an ice-bath. After stirring for 0.5 hour, methyl iodide (25.9 mg) was added, and the mixture was stirred for 3 hours 20 minutes at room temperature. The mixture was stirred for another 6 hours after adding methyl iodide (25.9 mg). The mixture was further stirred for 1 hour after adding 60% sodium hydride (3.0 mg) and methyl iodide (25.9 mg). The mixture was partitioned between ethyl acetate and 1N hydrochloric acid, and the organic layer was washed with brine, dried over magnesium sulfate, and evaporated to give an yellow oil. Preparative silica gel thin layer chromatography eluting with ethyl acetate-hexane=1-2 afforded 3-(6-ethyl-1,1-dioxidopyrrolo[1,2-b]thieno[2,3-e]pyridazin-9-yl)benzonitrile (5.9 mg, 10.5%, an yellow solid) and 3-(6-ethyl-3-methoxy-1,1-dioxido-2,3-dihydropyrrolo[1,2-b]thieno[2,3-e]pyridazin-9-yl)benzonitrile (16.8 mg, 30.0%, an orange gum).

3-(6-Ethyl-1,1-dioxidopyrrolo[1,2-b]thieno[2,3-e]pyridazin-9-yl)benzonitrile

NMR (CDCl$_3$, δ): 1.40 (3H, t, J=7 Hz), 3.07 (2H, q, J=7 Hz), 6.68 (1H, d, J=5 Hz), 6.82 (1H, d, J=5 Hz), 7.02 (1H, d, J=7 Hz), 7.37 (1H, d, J=7 Hz), 7.72 (1H, t, J=9 Hz), 7.87 (1H, d, J=9 Hz), 8.11-8.16 (2H, m)

3-(6-Ethyl-3-methoxy-1,1-dioxido-2,3-dihydropyrrolo[1,2-b]thieno[2,3-e]pyridazin-9-yl)benzonitrile NMR (CDCl$_3$, δ): 1.42 (3H, t, J=7 Hz), 3.12 (2H, q, J=7 Hz), 3.67 (3H, s), 3.73 (2H, m), 5.02 (1H, m), 6.74 (1H, d, J=5 Hz), 6.97 (1H, d, J=5 Hz), 7.70 (1H, t, J=9 Hz), 7.85 (1H, d, J=9 Hz), 8.04-8.13 (2H, m) MS (ESI$^+$): m/z 368 (M+H)

EXAMPLE 216

A mixture of 3-[(1-amino-5-ethyl-1H-pyrrol-2-yl)carbonyl]benzonitrile (1.00 g), ethyl 3-(methylsulfonyl)-2-oxopropanoate (1.34 g), and p-toluenesulfonic acid monohydrate (79.5 mg) in toluene (20 mL) was refluxed for 1 hour with Dean-Stark condenser. The volatile was removed in vacuo. Flash silica gel column chromatography eluting with ethyl acetate-hexane=1-10 to 9-15 afforded the intermediate imine (1.38 g, 67.7%) as an orange foam. The foam was dissolved in N-methylmorpholine (10 mL), and the solution was stirred for 1 hour at 130° C. The mixture was partitioned between ethyl acetate (50 mL) and water (30 mL). The organic layer was washed with water (30×2 mL) and brine, dried over magnesium sulfate, and evaporated to give a dark orange solid. The solid was triturated in diisopropyl ether (10 mL) to give 2-(trimethylsilyl)ethyl 4-(3-cyanophenyl)-7-ethyl-3-(methylsulfonyl)pyrrolo[1,2-b]pyridazine-2-carboxylate as an yellow powder (1.11 g, 67.7%).

2-(Trimethylsilyl)ethyl 4-(3-cyanophenyl)-7-ethyl-3-(methylsulfonyl)pyrrolo[1,2-b]pyridazine-2-carboxylate NMR (CDCl$_3$, δ): 0.12 (9H, s), 1.22 (2H, m), 1.39 (3H, t, J=7 Hz), 3.09 (2H, q, J=7 Hz), 3.23 (3H, s), 4.53 (2H, m), 6.30 (1H, d, J=5 Hz), 6.89 (1H, d, J=5 Hz), 7.50-7.67 (3H, m), 7.82 (1H, m) MS (ESI$^+$): m/z 470 (M+H)

The following compound was obtained in substantially the same manner as that of Example 216.

EXAMPLE 217

Ethyl 4-(3-cyanophenyl)-7-ethyl-3-(methylsulfonyl)pyrrolo[1,2-b]pyridazine-2-carboxylate NMR (CDCl$_3$, δ): 1.39 (3H, t, J=7 Hz), 1.47 (3H, t, J=7 Hz), 3.10 (2H, q, J=7 Hz), 3.21, (3H, s), 4.51 (2H, q, J=7 Hz), 6.30 (1H, d, J=5 Hz), 6.90 (1H, d, J=5 Hz), 7.61-7.67 (3H, m), 7.72 (1H, m)

EXAMPLE 218

A solution of 2-(trimethylsilyl)ethyl 4-(3-cyanophenyl)-7-ethyl-3-(methylsulfonyl)pyrrolo[1,2-b]pyridazine-2-carboxylate (1.09) in trifluoroacetic acid (5 mL) was stirred for 1.5 hours under an ice-bath. The reaction was quenched by adding water (20 mL). An yellow crystal was formed upon the addition, which was collected by filtration. The crystal was washed with water (5 mL) and hexane (3 mL) to give 4-(3-cyanophenyl)-7-ethyl-3-(methylsulfonyl)pyrrolo[1,2-b]pyridazine-2-carboxylic acid as an yellow crystal (756 mg, 88.2%).

4-(3-Cyanophenyl)-7-ethyl-3-(methylsulfonyl)pyrrolo[1,2-b]pyridazine-2-carboxylic acid NMR (CDCl$_3$, δ): 1.41 (2H, m), 3.10 (2H, q, J=7 Hz), 3.30 (3H, s), 6.36 (1H, d, J=5 Hz), 6.94 (1H, d, J=5 Hz), 7.53-7.67 (3H, m), 7.82 (1H, m) MS (ESI$^+$): m/z 370 (M+H)

EXAMPLE 219

A mixture of 4-(3-cyanophenyl)-7-ethyl-3-(methylsulfonyl)pyrrolo[1,2-b]pyridazine-2-carboxylic acid (40.0 mg), diemthylamine hydrochloride (12.4 mg), 1-(3-dimethylaminopropyl)-3-ethylcarbodiimide (25.2 mg), and 1-hydroxybenzotriazole (21.9 mg) in N,N-dimethylformamide (1 mL) was stirred for 3 hours at room temperature. The mixture was partitioned between ethyl acetate (20 mL) and 1N hydrochloric acid (10 mL). The organic layer was washed with water (10×3 mL), saturated sodium bicarbonate (10 mL), and brine, dried over magnesium sulfate, and evaporated to give 4-(3-cyanophenyl)-7-ethyl-N,N-dimethyl-3-(methylsulfonyl)pyrrolo[1,2-b]pyridazine-2-carboxamide as an yellow solid (43.4 mg, 101%).

4-(3-Cyanophenyl)-7-ethyl-N,N-dimethyl-3-(methylsulfonyl)pyrrolo[1,2-b]pyridazine-2-carboxamide NMR (CDCl$_3$, δ): 1.38 (2H, m), 3.07 (2H, q, J=7 Hz), 3.12 (3H, s), 3.18 (3H, s), 3.27 (3H, s), 6.27 (1H, d, J=5 Hz), 6.85 (1H, d, J=5 Hz), 7.57-7.67 (3H, m), 7.81 (1H, m) MS (ESI$^+$): m/z 397 (M+H)

EXAMPLE 220

A mixture of ethyl 4-(3-chlorophenyl)-7-ethyl-2-(2-furyl)pyrrolo[1,2-b]pyridazine-3-carboxylate (450 mg) and 85% potassium hydroxide (3.01 g) in a mixture of ethanol (3 mL) and water (2 mL) was refluxed for 25 hours. The reaction mixture was cooled under an ice-bath, and quenched by adding concentrated hydrochloric (5 mL). The mixture was partitioned between ethyl acetate (20 mL) and water (10 mL), and the organic layer was washed with brine, dried over magnesium sulfate, and evaporated to give an yellow solid (388 mg). The solid was triturated in hexane to give 4-(3-chlorophenyl)-7-ethyl-2-(2-furyl)pyrrolo[1,2-b]pyridazine-3-carboxylic acid as an yellow powder (361 mg, 86.4%).

4-(3-Chlorophenyl)-7-ethyl-2-(2-furyl)pyrrolo[1,2-b]pyridazine-3-carboxylic acid NMR (CDCl$_3$, δ): 1.41 (3H, t, J=7 Hz), 3.08 (2H, q, J=7 Hz), 6.37 (1H, d, J=5 Hz), 6.55 (1H, m), 6.76 (1H, d, J=5 Hz), 7.02 (1H, d, J=3 Hz), 7.40-7.55 (5H, m) MS (ESI$^+$): m/z 367 (M+H)

EXAMPLE 221

To a solution of 4-(3-chlorophenyl)-7-ethyl-2-(2-furyl)pyrrolo[1,2-b]pyridazine-3-carboxylic acid (358 mg) and N,N-dimethylformamide (1.39 mg) in dichloromethane (3 mL) was added oxalyl chloride (157 mg) at room temperature. After stirring for 30 minutes, the volatile was removed in vacuo, and the residue was azeotroped with toluene three times to afford 4-(3-chlorophenyl)-7-ethyl-2-(2-furyl)pyrrolo[1,2-b]pyridazine-3-carbonyl chloride as an yellow gum (396 mg, 106%).

4-(3-Chlorophenyl)-7-ethyl-2-(2-furyl)pyrrolo[1,2-b]pyridazine-3-carbonyl chloride NMR (CDCl$_3$, δ): 1.42 (3H, t, J=7 Hz), 3.10 (2H, q, J=7 Hz), 6.45 (1H, d, J=5 Hz), 6.59 (1H, m), 6.82 (1H, d, J=5 Hz), 7.06 (1H, d, J=7 Hz), 7.38-7.55 (4H, m), 7.63 (1H, m)

EXAMPLE 222

To a solution of methyl aminoacetate hydrochloride (26.1 mg) and triethylamine (42.0 mg) in dichloromethane (0.5 mL) was added a solution of 4-(3-chlorophenyl)-7-ethyl-2-(2-furyl)pyrrolo[1,2-b]pyridazine-3-carbonyl chloride (40.0 mg) in dichloromethane (0.5 mL) under an ice-bath. The mixture was partitioned between ethyl acetate (20 mL) and 1N hydrochloric acid (10 mL), and the organic layer was washed with brine (10 mL), dried over magnesium sulfate, and evaporated to give methyl ({[4-(3-chlorophenyl)-7-ethyl-2-(3-furyl)pyrrolo[1,2-b]pyridazin-3-yl]carbonyl}amino)acetate as an yellow gum (50.6 mg, 111%).

Methyl ({[4-(3-chlorophenyl)-7-ethyl-2-(3-furyl)pyrrolo[1,2-b]pyridazin-3-yl]carbonyl}amino)acetate NMR (CDCl$_3$, δ): 1.41 (3H, t, J=7 Hz), 3.10 (2H, q, J=7 Hz), 3.69 (3H, s), 3.95 (2H, d, J=5 Hz), 6.01 (1H, t, br, 5 Hz), 6.35 (1H, d, J=5 Hz), 6.51 (1H, m), 6.75 (1H, d, J=5 Hz), 7.01 (1H, d, J=7 Hz), 7.37-7.48 (3H, m), 7.53 (1H, m), 7.58 (1H, m) MS (ESI$^+$): m/z 438 (M+H)

The following compound was obtained in substantially the same manner as that of Example 222.

EXAMPLE 223

4-(3-Chlorophenyl)-7-ethyl-2-(2-furyl)-N,N-bis(2-hydroxyethyl)pyrrolo[1,2-b]pyridazine-3-carboxamide NMR (CDCl$_3$, δ): 1.42 (3H, t, J=7 Hz), 2.35-2.72 (4H, m), 3.08 (2H, d, J=5 Hz), 3.20-3.63 (4H, m), 3.82 (2H, m), 6.40 (1H, t, br, 5 Hz), 6.54 (1H, m), 6.75 (1H, d, J=5 Hz), 7.04 (1H, d, J=3 Hz), 7.40-7.48 (2H, m), 7.53-7.60 (2H, m), 7.71 (1H, m) MS (ESI$^+$): m/z 454 (M+H)

EXAMPLE 224

To a solution of 3-[4-(3-chlorophenyl)-7-ethyl-2-phenylpyrrolo[1,2-b]pyridazin-3-yl]propanoic acid (100 mg) in dioxane (0.5 mL) was added triethylamine (25.2 mg) followed by a solution of pivaloyl chloride (30.1 mg) in dioxane (0.5 mL). A white precipitate was formed. After stirring for 40 minutes at room temperature, the precipitate was removed by filtration, and washed with dioxane (2 mL). To the combined washing was added a solution of 2-aminoethanesulfonic acid (38.6 mg) in 1N sodium hydroxide (0.247 mL). The resulting mixture was stirred for 1 hour at room temperature. The mixture was partitioned between ethyl acetate (15 mL) and water (5 mL). The organic layer was washed with brine, dried over magnesium sulfate, and evaporated. Preparative silica gel thin layer chromatography eluting with chloroform-methanol=5-1 afforded 2-({3-[4-(3-chlorophenyl)-7-ethyl-2-phenylpyrrolo-[1,2-b]pyridazin-3-yl]propanoyl}amino)ethanesulfonic acid as an yellow solid (104 mg, 82.0%).

2-({3-[4-(3-Chlorophenyl)-7-ethyl-2-phenylpyrrolo[1,2-b]pyridazin-3-yl]propanoyl}amino)ethanesulfonic acid NMR (CDCl$_3$, δ): 1.27 (5H, m), 2.59 (4H, m), 2.90-3.14 (4H, m), 5.96 (1H, m), 6.06 (1H, m), 7.06-7.40 (9H, m)

EXAMPLE 225

A solution of 3-[4-(3-chlorophenyl)-7-ethyl-2-phenylpyrrolo[1,2-b]pyridazin-3-yl]propanoic acid (100 mg), (2R,3R,4S,5S,6R)-2-amino-3,5-bis[(2,2-dimethylpropanoyl)oxy]-6-{[(2,2-dimethylpropanoyl)oxy]methyl}tetrahydro-2H-pyran-4-yl pivalate (255 mg), 1-(3-dimethylaminopropyl)-3-ethylcarbodiimide (0.494 mmol), and 1-hydroxybenzotriazole (66.7 mg) in N,N-dimethylformamide (1 mL) was stirred for 1 hour at room temperature. The mixture was partitioned between ethyl acetate (20 mL) and 1N hydrochloric acid (10 mL). The organic layer was washed with water (10×3 mL), saturated sodium bicarbonate (10 mL), and brine, dried over magnesium sulfate, and evaporated to give an yellow foam (339 mg). Flash silica gel column chromatography eluting with ethyl acetate-hexane=1-10 to 2-5 afforded (2R,3R,4S,5S,6R)-2-({3-[4-(3-chlorophenyl)-7-ethyl-2-phenylpyrrolo[1,2-b]pyridazin-3-yl]propanoyl}amino)-3,5-bis[(2,2-dimethylpropanoyl)oxy]-6-{[(2,2-dimethylpropanoyl)oxy]methyl}tetrahydro-2H-pyran-4-yl pivalate an yellow foam (240 mg, 108%).

(2R,3R,4S,5S,6R)-2-({3-[4-(3-Chlorophenyl)-7-ethyl-2-phenylpyrrolo[1,2-b]pyridazin-3-yl]propanoyl}amino)-3,5-bis[(2,2-dimethylpropanoyl)oxy]-6-{[(2,2-dimethylpropanoyl)oxy]methyl}tetrahydro-2H-pyran-4-yl pivalate NMR (CDCl$_3$, δ): 0.97-1.26 (3H, m), 1.35 (3H, t, J=7 Hz), 1.83 (2H, m), 2.81 (2H, m), 3.01 (2H, q, J=7 Hz), 3.87-4.16 (3H, m), 4.90-5.27 (3H, m), 5.36-5.51 (2H, m), 6.01 (1H, d, J=5 Hz), 6.52 (1H, d, J=5 Hz), 7.29 (1H, m), 7.40-7.59 (8H, m)

EXAMPLE 226

To a solution of ethyl[4-(3-chlorophenyl)-7-ethyl-2-phenylpyrrolo[1,2-b]pyridazin-3-yl]acetate (114 mg) in tetrahydrofuran (2 mL) was added 1 M diisobutylaluminum hydride in toluene (0.816 mL) under an ice-bath. After stirring for 1 hour at room temperature, additional 1 M diisobutylaluminum hydride (0.41 mL) was added. The reaction was quenched by adding 1N hydrochloric acid (1 mL) after 1 hour. The mixture was partitioned between ethyl acetate (20 mL) and 1N hydrochloric acid (10 mL), and filtered through celite. The organic layer was washed with water (10 mL) and brine, dried over magnesium sulfate, and evaporated to give an yellow gum. Flash silica gel column chromatography eluting with ethyl acetate-hexane=1-20 to 2-50 afforded 2-[4-(3-chlorophenyl)-7-ethyl-2-phenylpyrrolo[1,2-b]pyridazin-3-yl]ethanol as an yellow oil, which was crystalyzed upon standing (107 mg, 104%).

2-[4-(3-Chlorophenyl)-7-ethyl-2-phenylpyrrolo[1,2-b]pyridazin-3-yl]ethanol

NMR (CDCl$_3$, δ): 1.37 (3H, t, J=7 Hz), 2.77 (2H, t, J=7 Hz), 3.01 (2H, q, J=7 Hz), 3.26 (2H, m), 3.26 (2H, m), 6.00 (1H, d, J=5 Hz), 6.63 (1H, d, J=5 Hz), 7.34 (1H, m), 7.41-7.55 (8H, m)

EXAMPLE 227

To a mixture of 2-[4-(3-chlorophenyl)-7-ethyl-2-phenylpyrrolo[1,2-b]pyridazin-3-yl]ethanol (105 mg), 2,3,4,6-tetra-O-acetyl-beta-D-galactosyl bromide (299 mg), silver carbonate (154 mg) in toluene (2 mL) was added silver triflate (3.58 mg) under an ice bath. After 40 minutes, 2,3,4,6-tetra-O-acetyl-beta-D-galactosyl bromide (114 mg), silver carbonate (229 mg) was added, and the mixture was stirred for 50 minutes. The mixture was further stirred for 50 minutes after adding 2,3,4,6-tetra-O-acetyl-beta-D-galactosyl bromide (114 mg), silver carbonate (154 mg). The mixture was filtered through celite, and the filtrate was partitioned between ethyl acetate and water. The organic layer was washed with brine, dried over magnesium sulfate, and evaporated to give an yellow gum. Flash silica gel column chromatography eluting with ethyl acetate-hexane=1-10 to 7/10 afforded (2R,3R,4S,5S,6R)-4,5-bis(acetyloxy)-6-[(acetyloxy)methyl]-2-{2-[4-(3-chlorophenyl)-7-ethyl-2-phenylpyrrolo[1,2-b]pyridazin-3-yl]ethoxy}tetrahydro-2H-pyran-3-yl acetate as an yellow gum (115 mg, 58.4%).

(2R,3R,4S,5S,6R)-4,5-bis(Acetyloxy)-6-[(acetyloxy)methyl]-2-{2-[4-(3-chlorophenyl)-7-ethyl-2-phenylpyrrolo[1,2-b]pyridazin-3-yl]ethoxy}tetrahydro-2H-pyran-3-yl acetate NMR (CDCl$_3$, δ): 1.35 (3H, t, J=7 Hz), 1.70 (3H, m), 1.94 (3H, s), 2.04 (3H, s), 2.11 (3H, s), 2.78 (2H, m), 3.01 (2H, q, J=7 Hz), 3.10 (1H, m), 3.46 (1H, m), 3.62 (1H, t, J=6 Hz), 3.79 (1H, d, J=8 Hz), 3.98 (2H, m), 4.83 (1H, dd, J=3 and 10 Hz), 4.97 (1H, dd, J=8 and 10 Hz), 5.28 (1H, d, J=3 Hz), 6.02 (1H, d, J=5 Hz), 6.64 (1H, d, J=5 Hz), 7.31 (1H, m), 7.41-7.56 (8H, m)

EXAMPLE 228

To a solution of (2R,3R,4S,5S,6R)-4,5-bis(acetyloxy)-6-[(acetyloxy)methyl]-2-{2-[4-(3-chlorophenyl)-7-ethyl-2-phenylpyrrolo[1,2-b]pyridazin-3-yl]ethoxy}tetrahydro-2H-pyran-3-yl acetate (113 mg) in methanol (2 mL) was added sodium methoxide (0.86 mg) at room temperature. After stirring for 2 hours, the solvent was evaporated off, and the mixture was partitioned between ethyl acetate (20 mL) and water (10 mL). The organic layer was washed with brine, dried over magnesium sulfate, and evaporated to give an yellow foam (77.3 mg). The foam was triturated in hexane to give (2R,3R,4S,5R,6R)-2-{2-[4-(3-chlorophenyl)-7-ethyl-2-phenylpyrrolo[1,2-b]pyridazin-3-yl]ethoxy}-6-(hydroxymethyl)tetrahydro-2H-pyran-3,4,5-triol as an yellow powder (48.3 mg, 89.7%).

(2R,3R,4S,5R,6R)-2-{2-[4-(3-Chlorophenyl)-7-ethyl-2-phenylpyrrolo[1,2-b]pyridazin-3-yl]ethoxy}-6-(hydroxymethyl)tetrahydro-2H-pyran-3,4,5-triol NMR (CDCl$_3$, δ): 1.36 (3H, t, J=7 Hz), 1.92 (1H, m), 2.06 (1H, m), 2.56 (1H, s, br), 2.76-2.92 (3H, m), 3.02 (2H, q, J=7 Hz), 3.24 (2H, m), 3.38-3.50 (3H, m), 3.63-3.84 (3H, m), 2.41 (1H, s, br), 6.01 (1H, d, J=5 Hz), 6.63 (1H, d, J=5 Hz), 7.32 (1H, m), 7.41-7.57 (8H, m)

The following compounds were obtained in substantially the same manner as that of Example 228.

EXAMPLE 229

3-[4-(3-Chlorophenyl)-7-ethyl-2-phenylpyrrolo[1,2-b]pyridazin-3-yl]-N-[(2R,3R,4S,5R,6R)-3,4,5-trihydroxy-6-(hydroxymethyl)tetrahydro-2H-pyran-2-yl]propanamide NMR (CDCl$_3$, δ): 1.38 (3H, t, J=7 Hz), 1.97 (2H, m), 2.83 (2H, m), 3.01 (2H, q, J=7 Hz), 3.31-3.52 (3H, m), 3.61-3.76 (2H, m), 3.88 (1H, m), 4.63 (1H, d, J=9 Hz), 6.01 (1H, d, J=5 Hz), 6.64 (1H, d, J=5 Hz), 7.34 (1H, m), 7.42-7.59 (8H, m)

EXAMPLE 230

Ethyl 5-[4-(5-bromo-3-pyridinyl)-7-ethyl-2-(hydroxymethyl)pyrrolo[1,2-b]pyridazin-3-yl]pentanoate from ethyl 5-[2-[(acetyloxy)methyl]-4-(5-bromo-3-pyridinyl)-7-ethylpyrrolo[1,2-b]pyridazin-3-yl]pentanoate NMR (CDCl$_3$, δ): 1.24 (3H, t, J=7 Hz), 1.34-1.50 (5H, m), 154 (2H, m), 2.19 (2H, t, J=7 Hz), 2.37 (2H, m), 3.02 (2H, q, J=7 Hz), 3.71 (1H, t, J=5 Hz), 4.10 (2H, q, J=7 Hz), 4.86 (2H, d, J=5 Hz), 5.97 (1H, d, J=5 Hz), 6.60 (1H, d, J=5 Hz), 7.88 (1H, m), 8.55 (1H, m), 8.79 (1H, m)

EXAMPLE 231

To a solution of 5-[4-(3-cyanophenyl)-7-ethyl-2-methylpyrrolo[1,2-b]pyridazin-3-yl]pentanoic acid (50 mg) in N,N-dimethylformamide (1 mL) was added 1,1'-carbonyldiimidazole (33.6 mg) at ambient temperature. After 1 hour stirring, to the mixture was added methanesulfonamide (19.7 mg) and 1,8-diazabicyclo[5.4.0]undec-7-ene (31.6 mg). The mixture was heated at 50° C. for 2 hours. The reaction mixture was partitioned between ethyl acetate and water. The aqueous layer was acidified with 1N hydrogen chloride and was extracted with ethyl acetate. The organic layer was washed with water 3 times and brine, dried over magnesium sulfate, and evaporated in vacuo to give an yellow solid. The residue was crystallized from IPE to give yellow solid (45 mg). The solid was recrystallized from ethanol to give N-{5-[4-(3-cyanophenyl)-7-ethyl-2-methylpyrrolo[1,2-b]pyridazin-3-yl]pentanoyl}methanesulfonamide (25 mg) as an yellow solid.

N-{5-[4-(3-Cyanophenyl)-7-ethyl-2-methylpyrrolo[1,2-b]pyridazin-3-yl]pentanoyl}methanesulfonamide NMR (CDCl$_3$, δ): 1.33-1.61 (7H, m), 2.21 (2H, t, J=8 Hz), 2.40 (2H, t, J=8 Hz), 2.55 (3H, s), 3.00 (2H, q, J=8 Hz), 3.29 (3H, s), 5.80 (1H, d, J=5 Hz), 6.52 (1H, d, J=5 Hz), 7.58-7.67 (3H, m), 7.76 (1H, m), 7.86 (1H, br s) MS (ESI$^+$): m/z 439 (M+H)

EXAMPLE 232

To a solution of ethyl 5-[4-(3-cyanophenyl)-7-ethyl-2-methylpyrrolo[1,2-b]pyridazin-3-yl]pentanoate (45 mg) in tetrahydrofuran (1 mL) was added lithium borohydride (5 mg) in an ice-water bath. Then the reaction mixture was stirred at ambient temperature. After 2 hours, another lithium borohydride (5 mg) was added therein and was stirred overnight. The reaction mixture was partitioned between ethyl acetate and water. The organic layer was washed with brine, dried over magnesium sulfate, and was evaporated in vacuo. The residue was purified by p-TLC (hexane-ethyl acetate=1-1) to give 3-[7-ethyl-3-(6-hydroxyhexyl)-2-methylpyrrolo[1,2-b]pyridazin-4-yl]benzonitrile (26 mg, 64.5%) as an yellow oil and 6-{4-[3-(aminomethyl)phenyl]-7-ethyl-2-methylpyrrolo[1,2-b]pyridazin-3-yl}-1-hexanol (13 mg, 31.9%) as a yellow solid.

3-[7-Ethyl-3-(6-hydroxyhexyl)-2-methylpyrrolo[1,2-b]pyridazin-4-yl]benzonitrile

NMR (CDCl$_3$, δ): 1.15-1.53 (11H, m), 2.32-2.41 (2H, m), 2.56 (3H, s), 3.01 (2H, q, J=8 Hz), 3.58 (2H, br t, J=8 Hz), 5.58 (1H, br t, J=8 Hz), 5.79 (1H, d, J=5 Hz), 6.51 (1H, d, J=5 Hz), 7.57-7.63 (2H, m), 7.65 (1H, br s), 7.75 (1H, m) MS (ESI$^+$): m/z 362 (M+H)

6-{4-[3-(Aminomethyl)phenyl]-7-ethyl-2-methylpyrrolo[1,2-b]pyridazin-3-yl}-1-hexanol NMR (CDCl$_3$, δ): 1.03-1.43 (11H, m), 2.41 (2H, t, J=8 Hz), 2.55 (3H, s), 3.01 (2H, q, J=8 Hz), 3.39-3.61 (2H, m), 3.88-4.04 (2H, m), 4.25 (2H, br s), 5.31 (1H, d, J=5 Hz), 6.49 (1H, d, J=5 Hz), 7.28-7.40 (3H, m), 7.51 (1H, t, J=8 Hz) MS (ESI$^+$): m/z 366 (M+H)

EXAMPLE 233

To a suspension of 6-{4-[4-(aminocarbonyl)phenyl]-7-ethyl-2-methylpyrrolo[1,2-b]pyridazin-3-yl}hexanoic acid (590 mg) in water (3 mL) was added 1N sodium hydroxide (15 mL) at ambient temperature. After 5 hours, the mixture became clear solution. The solution was filtered through membrane filter, washed with water (0.4 mL×3), and was freeze dried for 15 hours to give 6-{4-[4-(aminocarbonyl)phenyl]-7-ethyl-2-methylpyrrolo[1,2-b]pyridazin-3-yl}hexanoic acid sodium salt (612 mg, 98.2%) as a pale yellow powder.

6-{4-[4-(Aminocarbonyl)phenyl]-7-ethyl-2-methylpyrrolo[1,2-b]pyridazin-3-yl}hexanoic acid sodium salt NMR (DMSO-d$_6$, δ): 1.10-1.15 (2H, m), 1.20-1.40 (7H, m), 1.74 (2H, t, J=8 Hz), 2.25-2.38 (2H, m), 2.50 (3H, s), 2.91 (2H, q, J=8 Hz), 5.72 (1H, d, J=5 Hz), 6.50 (1H, d, J=5 Hz), 7.39-7.46 (3H, m), 7.97 (2H, d, J=8 Hz), 8.26 (1H, br s)

EXAMPLE 234

A solution of 5-[4-(3-cyanophenyl)-7-ethyl-2-methylpyrrolo[1,2-b]pyridazin-3-yl]pentanoic acid (100 mg), triethylamine (29.4 mg), and diphenylphosphoryl azide (79.9 mg) in tert-butanol (2 mL) was heated at 80° C. for 8 hours. The cooled reaction mixture was partitioned between ethyl acetate and water. The aqueous layer was extracted with ethyl acetate. The combined organic layer was washed with brine, dried over magnesium sulfate, and evaporated in vacuo. The residue was purified by p-TLC (hexane-ethyl acetate=3-1) to give tert-butyl 4-[4-(3-cyanophenyl)-7-ethyl-2-methylpyrrolo[1,2-b]pyridazin-3-yl]butylcarbamate (28 mg, 23.4%) as an yellow oil.

tert-Butyl 4-[4-(3-cyanophenyl)-7-ethyl-2-methylpyrrolo[1,2-b]pyridazin-3-yl]butylcarbamate NMR (CDCl$_3$, δ): 1.27-1.47 (14H, m), 2.34-2.45 (2H, m), 2.55 (3H, s), 2.91-3.02 (4H, m), 4.39 (1H, br s), 5.79 (1H, d, J=5 Hz), 6.51 (1H, d, J=5 Hz), 7.56-7.67 (3H, m), 7.75 (1H, m) MS (ESI$^+$): m/z 433 (M+H)

EXAMPLE 235

To tert-butyl 4-[4-(3-cyanophenyl)-7-ethyl-2-methylpyrrolo[1,2-b]pyridazin-3-yl]butylcarbamate (25 mg) was added 4N hydrogen chloride in ethyl acetate (1 mL) at ambient temperature. After 1 hour, the mixture was evaporated in vacuo. The residue was triturated with isopropyl ether to give 3-[3-(4-aminobutyl)-7-ethyl-2-methylpyrrolo[1,2-b]pyridazin-4-yl]benzonitrile hydrochloride as dark green amorphous (18 mg).

3-[3-(4-Aminobutyl)-7-ethyl-2-methylpyrrolo[1,2-b]pyridazin-4-yl]benzonitrile hydrochloride NMR (CDCl$_3$, δ): 1.27-1.47 (14H, m), 2.34-2.45 (2H, m), 2.55 (3H, s), 2.91-3.02 (4H, m), 4.39 (1H, br s), 5.79 (1H, d, J=5 Hz), 6.51 (1H, d, J=5 Hz), 7.56-7.67 (3H, m), 7.75 (1H, m) MS (ESI$^+$): m/z 333 (M+H)

EXAMPLE 236

To lithium chloride (16.5 mg) was added a solution of ethyl 5-[4-(2-chloro-4-pyridinyl)-7-ethyl-2-methylpyrrolo[1,2-b]pyridazin-3-yl]pentanoate (65 mg) and tributyl(vinyl)stannane (56.7 mg) in dioxane (1 mL) and tetrakis(triphenylphosphine)palladium(0) (1.9 mg). The mixture was refluxed. After 4 hours, tributyl(vinyl)stannane (50 mg) and tetrakis(triphenylphosphine)palladium(0) (1.9 mg) was added. After refluxed over night, the reaction mixture was quenched with potassium fluoride (1.8 mmol) in H$_2$O. The mixture was filtered through Celite and was washed with ethyl acetate. The organic layer was separated, washed with water and brine, dried over magnesium sulfate, and evaporated in vacuo. The residue was purified by flash silica gel chromatography (silica gel, 50 mL) eluted with hexane-ethyl acetate=5-1 and 3-1 to give ethyl 5-[7-ethyl-2-methyl-4-(2-vinyl-4-pyridinyl)pyrrolo[1,2-b]pyridazin-3-yl]pentanoate (18 mg, 28.3%) as an yellow oil.

Ethyl 5-[7-ethyl-2-methyl-4-(2-vinyl-4-pyridinyl)pyrrolo[1,2-b]pyridazin-3-yl]pentanoate NMR (CDCl$_3$, δ): 1.15-1.70 (10H, m), 2.18 (2H, t, J=8 Hz), 2.36-2.46 (2H, m), 2.55 (3H, s), 3.00 (2H, q, J=8 Hz), 4.08 (2H, q, J=8 Hz), 5.54 (1H, d, J=10 Hz), 5.86 (1H, d, J=5 Hz), 6.25 (1H, d, J=16 Hz), 6.51 (1H, d, J=5 Hz), 6.87 (1H, dd, J=16, 10 Hz), 7.16 (1H, dd, J=6, 1 Hz), 7.33 (1H, br s), 8.70 (1H, d, J=6 Hz) MS (ESI$^+$): m/z 392 (M+H)

The following compounds were obtained in substantially the same manner as that of Example 236.

EXAMPLE 237

Ethyl 5-{4-[5-(1-ethoxyvinyl)-3-pyridinyl]-7-ethyl-2-methylpyrrolo[1,2-b]pyridazin-3-yl}pentanoate NMR (CDCl$_3$, δ): 1.23 (3H, t, J=7 Hz), 1.37 (3H, t, J=7 Hz), 1.42 (3H, t, J=7 Hz), 1.40-1.60 (4H, m), 2.20 (2H, t, J=7 Hz), 2.38-2.52 (2H, m), 2.56 (3H, s), 3.03 (2H, q, J=7 Hz), 3.96 (2H, q, J=7 Hz), 4.09 (2H, q, J=7 Hz), 4.34 (1H, d, J=2 Hz), 4.76 (1H, d, J=2 Hz), 5.87 (1H, d, J=4 Hz), 6.52 (1H, d, J=4 Hz), 7.89 (1H, m), 8.53 (1H, d, J=2 Hz), 8.93 (1H, d, J=2 Hz) MS: (m/z) 436 (M+H)

EXAMPLE 238

Ethyl 5-[7-ethyl-2-methyl-4-(5-vinyl-3-pyridinyl)pyrrolo[1,2-b]pyridazin-3-yl]pentanoate NMR (CDCl$_3$, δ): 1.22 (3H, t, J=7 Hz), 1.37 (3H, t, J=7 Hz), 1.40-1.65 (4H, m), 2.18 (2H, t, J=7 Hz), 2.40-2.53 (2H, m), 2.56 (3H, s), 3.02 (2H, q, J=7 Hz), 4.08 (2H, q, J=7 Hz), 5.43 (1H, d, J=11 Hz), 5.88 (1H, d, J=4 Hz), 5.89 (1H, d, J=18 Hz), 6.52 (1H, d, J=4 Hz), 6.71-6.83 (1H, dd, J=11 Hz, 18 Hz), 7.73 (1H, m), 8.47 (1H, d, J=2 Hz), 8.68 (1H, d, J=2 Hz)

EXAMPLE 239

Ethyl 5-[7-ethyl-2-(methoxymethyl)-4-(5-vinyl-3-pyridinyl)pyrrolo[1,2-b]pyridazin-3-yl]pentanoate NMR (CDCl$_3$, δ): 1.22 (3H, t, J=7 Hz), 1.38 (3H, t, J=7 Hz), 1.40-1.60 (4H, m), 2.17 (2H, t, J=7 Hz), 2.52-2.65 (2H, m), 3.04 (2H, q, J=7 Hz), 3.46 (3H, s), 4.08 (2H, q, J=7 Hz), 4.63 (2H, s), 5.43 (1H, d, J=11 Hz), 5.88 (1H, d, J=18 Hz), 5.91 (1H, d, J=4 Hz), 6.58 (1H, d, J=4 Hz), 6.71-6.83 (1H, dd, J=11 Hz, 18 Hz), 7.75 (1H, m), 8.49 (1H, d, J=2 Hz), 8.71 (1H, d, J=2 Hz)

EXAMPLE 240

Ethyl 5-[4-[5-(1-ethoxyvinyl)-3-pyridinyl]-7-ethyl-2-(methoxymethyl)pyrrolo[1,2-b]pyridazin-3-yl]pentanoate NMR (CDCl$_3$, δ): 1.22 (3H, t, J=7 Hz), 1.37 (3H, t, J=7 Hz), 1.42 (3H, t, J=7 Hz), 1.40-1.63 (4H, m), 2.18 (2H, t, J=7 Hz), 2.51-2.63 (2H, m), 3.03 (2H, q, J=7 Hz), 3.47 (3H, s), 3.93 (2H, q, J=7 Hz), 4.12 (2H, q, J=7 Hz), 4.35 (1H, d, J=3 Hz), 4.63 (2H, s), 4.77 (1H, d, J=3 Hz), 5.92 (1H, d, J=4 Hz), 6.58 (1H, d, J=4 Hz), 7.92 (1H, m), 8.53 (1H, d, J=2 Hz), 8.93 (1H, d, J=2 Hz) MS (ESI$^+$): m/z 466

EXAMPLE 241

Ethyl 5-[7-ethyl-2-phenyl-4-(5-vinyl-3-pyridinyl)pyrrolo[1,2-b]pyridazin-3-yl]pentanoate NMR (CDCl$_3$, δ): 1.15-1.31 (7H, m), 1.37 (3H, t, J=7 Hz), 1.87 (2H, t, J=7 Hz), 2.43 (2H, m), 3.01 (2H, q, J=7 Hz), 3.98 (2H, q, J=7 Hz), 5.45 (1H, d, J=11 Hz), 5.88 (1H, d, J=18 Hz), 5.98 (1H, d, J=5 Hz), 6.62 (1H, d, J=5 Hz), 6.78 (1H, dd, J=11 and 18 Hz), 7.44-7.55 (5H, m), 7.81 (1H, m), 8.55 (1H, m), 8.72 (1H, m)

EXAMPLE 242

A solution of 5-[4-(2-chloro-4-pyridinyl)-7-ethyl-2-methylpyrrolo[1,2-b]pyridazin-3-yl]pentanoic acid (50 mg) in dioxane (15 mL) in a sealed tube was added 50% dimethylamine in water (15 mL). The mixture was heated at 175° C. overnight. The cooled reaction mixture was concentrated in vacuo. The residue was dissolved in water (1 mL) and the pH was adjusted to 7-8. The mixture was extracted with chloroform three times. The organic layer was dried over magnesium sulfate and evaporated in vacuo. The residue was purified by flash silica gel chromatography (silica gel, 50 mL) eluted with chloroform-ethyl acetate=1-1 and chloroform-methanol=20-1 to give yellow oil (43 mg). The oil was crystallized from isopropyl ether to give 5-{4-[2-(dimethylamino)-4-pyridinyl]-7-ethyl-2-methylpyrrolo[1,2-b]pyridazin-3-yl}pentanoic acid as an yellow solid (27 mg, 52.8%).

5-{4-[2-(Dimethylamino)-4-pyridinyl]-7-ethyl-2-methylpyrrolo[1,2-b]pyridazin-3-yl}pentanoic acid NMR (CDCl$_3$, δ): 1.36 (3H, t, J=8 Hz), 1.40-1.65 (4H, m), 2.25 (2H, t, J=8 Hz), 1.86-1.96 (2H, m), 2.55 (3H, s), 3.00

(2H, q, J=8 Hz), 4.08 (2H, q, J=8 Hz), 5.54 (1H, d, J=10 Hz), 5.86 (1H, d, J=5 Hz), 6.25 (1H, d, J=16 Hz), 6.51 (1H, d, J=5 Hz), 6.87 (1H, dd, J=16, 10 Hz), 7.16 (1H, dd, J=6, 1 Hz), 7.33 (1H, br s), 8.70 (1H, d, J=6 Hz)

EXAMPLE 243

To a suspension of 7-chloro-4-(4-fluorophenyl)-2-isopropylpyrrolo[1,2-b]pyridazine-3-carbaldehyde (40 mg) in ethanol (1 mL) was added 2-aminoethanol (11.8 mg), sodium cyanoborohydride (12.1 mg), and acetic acid (1 drop) in an ice-water bath. After 10 minutes, the mixture was stirred at ambient temperature. After 2 hours, sodium cyanoborohydride (11.8 mg) was added and the reaction mixture was acidified to pH4 with acetic acid (5 drops). After stirring overnight, the reaction mixture was partitioned between ethyl acetate and water. The organic layer was washed with saturated sodium bicarbonate, water, and brine, dried over magnesium sulfate, and evaporated in vacuo. The residue was purified by p-TLC (chloroform-methanol=10-1) to give 2-({[7-chloro-4-(4-fluorophenyl)-2-isopropylpyrrolo[1,2-b]pyridazin-3-yl]methyl}amino)ethanol as pale yellow oil (21 mg).

2-({[7-Chloro-4-(4-fluorophenyl)-2-isopropylpyrrolo[1,2-b]pyridazin-3-yl]methyl}amino)ethanol NMR (CDCl$_3$, δ): 1.43 (6H, d, J=7 Hz), 2.65 (2H, t, J=7 Hz), 3.42 (1H, m), 353 (2H, t, J=7 Hz), 3.59 (2H, s), 6.01 (1H, d, J=5 Hz), 6.77 (1H, d, J=5 Hz), 7.14-7.24 (2H, m), 7.35-7.44 (2H, m) MS (ESI$^+$): m/z 362 (M+H)

EXAMPLE 244

To a solution of [4-(4-fluorophenyl)-2-methylpyrrolo[1,2-b]pyridazin-3-yl]methanol (505 mg) and triethylamine (997 mg) in dichloromethane (4 mL) and dimethyl sulfoxide (2 mL) was added sulfur trioxide pyridine complex (941 mg) in an ice-water bath under nitrogen. After 30 minutes, the mixture was stirred at ambient temperature for 2 hours. The reaction mixture was concentrated to about ⅓ volume. The mixture was partitioned between ethyl acetate and water. The organic layer was washed with water three times and brine, dried over magnesium sulfate, and evaporated in vacuo. The residue was purified by flash silica gel chromatography (silica gel, 30 mL) eluted with hexane-chloroform=3-1 and 2-1 to give 4-(4-fluorophenyl)-2-methylpyrrolo[1,2-b]pyridazine-3-carbaldehyde as an yellow solid (340 mg, 67.9%).

4-(4-Fluorophenyl)-2-methylpyrrolo[1,2-b]pyridazine-3-carbaldehyde

NMR (CDCl$_3$, δ): 2.77 (3H, s), 6.50 (1H, m), 6.86 (1H, m), 7.20-7.30 (2H, m), 7.44-7.54 (2H, m), 8.89 (1H, br s), 9.79 (1H, s)

EXAMPLE 245

A mixture of ethyl 4-(4-fluorophenyl)-2-isopropyl-7-vinylpyrrolo[1,2-b]pyridazine-3-carboxylate (8.9 g) and 10% palladium on carbon (900 mg) in ethanol (180 mL) was stirred under hydrogen atomosphere (3.5 atm) at ambient temperature. After 10 hours, the mixture was stood overnight. To the mixture was added 10% palladium on carbon (900 mg) and was stirred under hydrogen atomosphere (35 atm) at ambient temperature. After 12 hours, the mixture was stood overnight. To the mixture was added 10% palladium on carbon (900 mg) and was stirred under hydrogen atomosphere (35 atm) at ambient temperature for 8 hours. The mixture was filtered through Celite. The filtrate was concentrated in vacuo to give ethyl 7-ethyl-4-(4-fluorophenyl)-2-isopropylpyrrolo[1,2-b]pyridazine-3-carboxylate as an yellow oil (9.0 g, 100.5%).

Ethyl 7-ethyl-4-(4-fluorophenyl)-2-isopropylpyrrolo[1,2-b]pyridazine-3-carboxylate NMR (CDCl$_3$, δ): 0.96 (3H, t, J=8 Hz), 1.38 (3H, t, J=8 Hz), 3.05 (2H, q, J=8 Hz), 4.01 (2H, q, J=8 Hz), 6.27 (1H, d, J=5 Hz), 6.64 (1H, d, J=5 Hz), 7.10-7.19 (2H, m), 7.41-7.49 (2H, m) MS (ESI$^+$): m/z 362 (M+H)

The following compounds were obtained in substantially the same manner as that of Example 245.

EXAMPLE 246

5-[7-Ethyl-4-(5-ethyl-3-pyridinyl)-2-methylpyrrolo[1,2-b]pyridazin-3-yl]pentanoic acid from 5-[7-ethyl-2-methyl-4-(5-vinyl-3-pyridinyl)pyrrolo[1,2-b]pyridazin-3-yl]pentanoic acid NMR (CDCl$_3$, δ): 1.30 (3H, t, J=7 Hz), 1.37 (3H, t, J=7 Hz), 1.45-1.65 (4H, m), 2.22 (2H, m), 2.35-2.50 (2H, m), 2.56 (3H, s), 2.75 (2H, q, J=7 Hz), 3.00 (2H, q, J=7 Hz), 5.84 (1H, d, J=4 Hz), 6.52 (1H, d, J=4 Hz), 7.57 (1H, s), 8.42 (1H, d, J=2 Hz), 8.53 (1H, d, J=2 Hz) MS (ESI$^+$): m/z 366 (M+H), MS (ESI$^-$): m/z 364

EXAMPLE 247

5-[7-Ethyl-4-(5-ethyl-3-pyridinyl)-2-(methoxymethyl)pyrrolo[1,2-b]pyridazin-3-yl]pentanoic acid NMR (CDCl$_3$, δ): 130 (3H, t, J=7 Hz), 1.37 (3H, t, J=7 Hz), 1.45-1.64 (4H, m), 2.17 (2H, m), 2.45-2.67 (2H, m), 2.73 (2H, q, J=7 Hz), 3.04 (2H, q, J=7 Hz), 3.45 (3H, s), 4.62 (2H, m), 5.89 (1H, d, J=4 Hz), 6.58 (1H, d, J=4 Hz), 7.59 (1H, s), 8.44 (1H, s), 8.54 (1H, s) MS (ESI$^+$): m/z 396

EXAMPLE 248

Ethyl 5-[7-ethyl-4-(5-ethyl-3-pyridinyl)-2-phenylpyrrolo[1,2-b]pyridazin-3-yl]pentanoate NMR (CDCl$_3$, δ): 1.04-1.23 (7H, m), 1.32 (3H, t, J=7 Hz), 1.37 (3H, t, J=7 Hz), 1.86 (2H, t, J=7 Hz), 2.42 (2H, m), 2.74 (2H, q, J=7 Hz), 3.01 (2H, q, J=7 Hz), 3.99 (2H, q, J=7 Hz), 5.97 (1H, d, J=5 Hz), 6.62 (1H, d, J=5 Hz), 7.45-7.53 (5H, m), 7.60 (1H, m), 8.50 (1H, m), 8.56 (1H, m)

EXAMPLE 249

To a solution of 3-(7-ethyl-2-neopentylpyrrolo[1,2-b]pyridazin-4-yl)benzamide (35 mg) in ethanol (1 mL) was added water (0.2 mL) and potassium hydroxide (68.9 mg) at ambient temperature. The reaction mixture was heated at 60° C. After 2 hours, potassium hydroxide (100 mg) was added. After 5 hours, potassium hydroxide (100 mg) was added. After 12 hours, the mixture was acidified with 1N hydrogen chloride. The precipitate was filtered, washed with water and ethyl acetate to give 3-(7-ethyl-2-neopentylpyrrolo-[1,2-b]pyridazin-4-yl)benzoic acid as an yellow solid (19 mg, 54.1%).

3-(7-Ethyl-2-neopentylpyrrolo[1,2-b]pyridazin-4-yl)benzoic acid

NMR (CDCl₃, δ): 1.05 (9H, s), 1.39 (3H, t, J=8 Hz), 2.69 (2H, s), 3.04 (2H, q, J=8 Hz), 6.42 (1H, s), 6.54 (1H, d, J=5 Hz), 6.65 (1H, d, J=5 Hz), 7.62 (1H, t, J=8 Hz), 7.97 (1H, d, J=8 Hz), 8.21 (1H, d, J=8 Hz), 8.46 (1H, br s) MS (ESI⁺): m/z 337 (M+H)

The following compound was obtained in substantially the same manner as that of Example 249.

EXAMPLE 250

3-[7-Ethyl-2-(2-furyl)pyrrolo[1,2-b]pyridazin-4-yl]benzoic acid

NMR (CDCl₃, δ): 1.44 (3H, t, J=8 Hz), 3.11 (2H, q, J=8 Hz), 6.56 (1H, m), 6.61 (1H, d, J=5 Hz), 6.72 (1H, d, J=5 Hz), 7.03 (1H, br s), 7.07 (1H, d, J=5 Hz), 7.55-7.69 (2H, m), 8.03 (1H, br d, J=8 Hz), 8.23 (1H, br d, J=8 Hz), 8.52 (1H, br s)

EXAMPLE 251

A solution of ethyl 5-{4-[5-(1-ethoxyvinyl)-3-pyridinyl]-7-ethyl-2-methylpyrrolo[1,2-b]pyridazin-3-yl}pentanoate (190 mg) in methanol (5 mL) and 1N hydrochloric acid (5 mL) was stirred at ambient temperature for 2 hours. The solution was diluted with brine and extracted with chloroform. The organic layer was separated, dried over magnesium sulfate, and evaporated in vacuo. The residue was purified by silica gel column chromatography eluting with a mixture of hexane and ethyl acetate (10:1-2:1) to give ethyl 5-[4-(5-acetyl-3-pyridinyl)-7-ethyl-2-methylpyrrolo[1,2-b]pyridazin-3-yl]pentanoate as an yellow oil (160 mg).

Ethyl 5-[4-(5-acetyl-3-pyridinyl)-7-ethyl-2-methylpyrrolo[1,2-b]pyridazin-3-yl]pentanoate NMR (CDCl₃, δ): 1.24 (3H, t, J=7 Hz), 1.38 (3H, t, J=7 Hz), 1.40-1.60 (4H, m), 2.19 (2H, t, J=7 Hz), 2.36-2.47 (2H, m), 2.57 (3H, s), 2.70 (3H, s), 3.02 (2H, q, J=7 Hz), 4.08 (2H, q, J=7 Hz), 5.81 (1H, d, J=4 Hz), 6.53 (1H, d, J=4 Hz), 8.23 (1H, m), 8.78 (1H, d, J=2 Hz), 9.23 (1H, d, J=2 Hz) MS: (m/z) 408 (M+H)

The following compound was obtained in substantially the same manner as that of Example 251.

EXAMPLE 252

Ethyl 5-[4-(5-acetyl-3-pyridinyl)-7-ethyl-2-(methoxymethyl)pyrrolo[1,2-b]pyridazin-3-yl]pentanoate NMR (CDCl₃, δ): 1.24 (3H, t, J=7 Hz), 1.38 (3H, t, J=7 Hz), 1.40-1.59 (4H, m), 2.17 (2H, t, J=7 Hz), 2.50-2.63 (2H, m), 2.70 (3H, s), 3.03 (2H, q, J=7 Hz), 3.46 (3H, s), 4.12 (2H, q, J=7 Hz), 4.63 (2H, s), 5.86 (1H, d, J=4 Hz), 6.59 (1H, d, J=4 Hz), 8.26 (1H, m), 8.79 (1H, d, J=2 Hz), 9.24 (1H, d, J=2 Hz) MS (ESI⁺): m/z 438

EXAMPLE 253

To a solution of ethyl 5-{4-(2-chloro-4-pyridinyl)-7-ethyl-2-[(methylthio)methyl]pyrrolo[1,2-b]pyridazin-3-yl}pentanoate (139 mg) in tetrahydrofuran (4 mL) and water (1 mL) was added oxone (287 mg) and the mixture was stirred at ambient temperature for 4 hours. The solution was diluted with water and extracted with ethyl acetate. The organic layer was separated, washed with saturated sodium bicarbonate solution, sodium thiosulfate solution and brine, dried over magnesium sulfate, and evaporated in vacuo. The residue was purified by silica gel column chromatography eluting with a mixture of hexane and ethyl acetate (10:1-1:1) to give ethyl 5-{4-(2-chloro-4-pyridinyl)-7-ethyl-2-[(methylsulfonyl)methyl]pyrrolo[1,2-b]pyridazin-3-yl}pentanoate as an yellow oil (124 mg).

Ethyl 5-{4-(2-chloro-4-pyridinyl)-7-ethyl-2-[(methylsulfonyl)methyl]pyrrolo[1,2-b]pyridazin-3-yl}pentanoate NMR (CDCl₃, δ): 1.24 (3H, t, J=7 Hz), 1.37 (3H, t, J=7 Hz), 1.40-1.63 (4H, m), 2.21 (2H, t, J=7 Hz), 2.57-2.68 (2H, m), 3.02 (2H, q, J=7 Hz), 3.12 (3H, s), 4.10 (2H, q, J=7 Hz), 4.53 (2H, s), 5.98 (1H, d, J=4 Hz), 6.68 (1H, d, J=4 Hz), 7.27 (1H, m), 7.38 (1H, s), 8.56 (1H, d, J=5 Hz)

EXAMPLE 254

A mixture of ethyl 5-[4-(5-bromo-3-pyridinyl)-7-ethyl-2-methylpyrrolo[1,2-b]pyridazin-3-yl]pentanoate (167 mg) and copper(I) cyanide (37 mg) in 1-methyl-2-pyrrolidinone (3 mL) was stirred at 170° C. for 4 hours. The mixture was partitioned between ethyl acetate and water. The organic layer was separated, washed with water and brine, dried over magnesium sulfate, and evaporated in vacuo. The residue was purified by silica gel column chromatography eluting with a mixture of hexane and ethyl acetate (20:1-5:1) to give ethyl 5-[4-(5-cyano-3-pyridinyl)-7-ethyl-2-methylpyrrolo[1,2-b]pyridazin-3-yl]pentanoate as an yellow oil (88 mg).

Ethyl 5-[4-(5-cyano-3-pyridinyl)-7-ethyl-2-methylpyrrolo[1,2-b]pyridazin-3-yl]pentanoate NMR (CDCl₃, δ): 124 (3H, t, J=7 Hz), 1.37 (3H, t, J=7 Hz), 1.40-1.62 (4H, m), 2.21 (2H, t, J=7 Hz), 2.35-2.47 (2H, m), 2.57 (3H, s), 3.02 (2H, q, J=7 Hz), 4.12 (2H, q, J=7 Hz), 5.79 (1H, d, J=4 Hz), 6.54 (1H, d, J=4 Hz), 7.98 (1H, m), 8.80 (1H, d, J=2 Hz), 8.97 (1H, d, J=2 Hz) MS (ESI⁺): m/z 391.

The following compounds were obtained in substantially the same manner as that of Example 254.

EXAMPLE 255

5-[4-(5-Cyano-3-pyridinyl)-7-ethyl-2-methylpyrrolo[1,2-b]pyridazin-3-yl]pentanoic acid NMR (CDCl₃, δ): 1.37 (3H, t, J=7 Hz), 1.40-1.67 (4H, m), 2.28 (2H, m), 2.37-2.47 (2H, m), 2.57 (3H, s), 3.01 (2H, q, J=7 Hz), 5.80 (1H, d, J=4 Hz), 6.55 (1H, d, J=4 Hz), 8.01 (1H, s), 8.81 (1H, br), 8.98 (1H, br)

EXAMPLE 256

Ethyl 5-[4-(5-cyano-3-pyridinyl)-7-ethyl-2-(methoxymethyl)pyrrolo[1,2-b]pyridazin-3-yl]pentanoate NMR (CDCl₃, δ): 1.23 (3H, t, J=7 Hz), 1.37 (3H, t, J=7 Hz), 1.40-1.60 (4H, m), 2.19 (2H, t, J=7 Hz), 2.49-2.60 (2H, m), 3.04 (2H, q, J=7 Hz), 3.46 (3H, s), 4.12 (2H, q, J=7 Hz), 4.63 (2H, s), 5.84 (1H, d, J=4 Hz), 6.63 (1H, d, J=4 Hz), 8.02 (1H, m), 8.83 (1H, d, J=2 Hz), 8.98 (1H, d, J=2 Hz)

EXAMPLE 257

5-[4-(5-Cyano-3-pyridinyl)-7-ethyl-2-(methoxymethyl)pyrrolo[1,2-b]pyridazin-3-yl]pentanoic acid NMR (CDCl$_3$, δ): 1.38 (3H, t, J=7 Hz), 1.40-1.65 (4H, m), 2.27 (2H, t, J=7 Hz), 2.48-2.64 (2H, m), 3.03 (2H, q, J=7 Hz), 3.46 (3H, s), 4.64 (2H, s), 5.84 (1H, d, J=4 Hz), 6.62 (1H, d, J=4 Hz), 8.03 (1H, s), 8.82 (1H, s), 8.97 (1H, s)

EXAMPLE 258

5-[4-(5-Cyano-3-pyridinyl)-7-ethyl-2-phenylpyrrolo[1,2-b]pyridazin-3-yl]pentanoic acid NMR (CDCl$_3$, δ): 1.06-1.24 (4H, m), 1.36 (3H, t, J=7 Hz), 1.94 (2H, t, J=7 Hz), 2.38 (2H, m), 2.99 (2H, q, J=7 Hz), 5.88 (1H, d, J=5 Hz), 6.64 (1H, d, J=5 Hz), 7.44-7.52 (5H, m), 8.06 (1H, s), 8.87 (1H, s), 8.98 (1H, s) MS (ESI$^+$): m/z 425 (M+H)

EXAMPLE 259

To a suspension of lithium aluminum hydride (98.8 mg) in tetrahydrofuran (10 mL) was added ethyl 5-[4-(3-chlorophenyl)-7-ethyl-2-phenylpyrrolo[1,2-b]pyridazin-3-yl]pentanoate (600 mg) in tetrahydrofuran (10 mL) under ice-water cooling and the mixture was stirred at 0° C. for 2 hours. The reaction was quenched with saturated potassium sodium tartrate solution and the insolubles were filtered off and washed with ethyl acetate. The filtrates were washed with brine, dried over magnesium sulfate, and evaporated in vacuo. The residue was purified by silica gel column chromatography eluting with a mixture of hexane and ethyl acetate (10:1-2:1) to give 5-[4-(3-chlorophenyl)-7-ethyl-2-phenylpyrrolo[1,2-b]pyridazin-3-yl]-1-pentanol as an yellow oil (478 mg).

5-[4-(3-Chlorophenyl)-7-ethyl-2-phenylpyrrolo[1,2-b]pyridazin-3-yl]-1-pentanol

NMR (CDCl$_3$, δ): 0.90-1.22 (6H, m), 1.27 (1H, t, J=7 Hz), 1.36 (3H, t, J=7 Hz), 2.37-2.47 (2H, m), 3.02 (2H, q, J=7 Hz), 3.29-3.41 (2H, m), 5.97 (1H, d, J=4 Hz), 6.61 (1H, d, J=4 Hz), 7.32 (1H, m), 7.40-7.55 (8H, m)

EXAMPLE 260

To a solution of 5-[4-(3-chlorophenyl)-7-ethyl-2-phenylpyrrolo[1,2-b]pyridazin-3-yl]-1-pentanol (63.0 mg) and triethylamine (22.8 mg) in dichloromethane (3 mL) was added methanesulfonyl chloride (18.9 mg) under ice-water cooling and the mixture was stirred at 0° C. for 1 hour. The solution was washed with brine, dried over magnesium sulfate, and evaporated in vacuo. The residue was added to sodium cyanide (14.7 mg) in dimethylformamide (2 mL) and the mixture was stirred at 60° C. for 5 hours. The mixture was partitioned between ethyl acetate and water. The organic layer was separated, washed with water and brine, dried over magnesium sulfate, and evaporated in vacuo. The residue was purified by silica gel column chromatography eluting with a mixture of hexane and ethyl acetate (20:1-5:1) to give 6-[4-(3-chlorophenyl)-7-ethyl-2-phenylpyrrolo[1,2-b]pyridazin-3-yl]hexanenitrile as an yellow oil (58.5 mg).

6-[4-(3-chlorophenyl)-7-ethyl-2-phenylpyrrolo[1,2-b]pyridazin-3-yl]hexanenitrile NMR (CDCl$_3$, δ): 1.00-1.15 (4H, m), 1.17-1.28 (2H, m), 1.36 (3H, t, J=7 Hz), 1.98 (2H, t, J=7 Hz), 2.38-2.47 (2H, m), 3.03 (2H, q, J=7 Hz), 5.99 (1H, d, J=4 Hz), 6.62 (1H, d, J=4 Hz), 7.32 (1H, m), 7.38-7.56 (8H, m) MS (ESI$^+$): m/z 428

EXAMPLE 261

A mixture of 5-[4-(3-chlorophenyl)-7-ethyl-2-phenylpyrrolo[1,2-b]pyridazin-3-yl]-1-pentanol (65 mg), trimethyloxonium tetrafluoroborate (27.5 mg) and 2,6-di-t-butyl-4-methylpyridine (47.8 mg) in 1,2-dichloroethane (3 mL) was stirred at ambient temperature for 4 hours. The solution was washed with water, 1N hydrochloric acid, water, saturated sodium bicarbonate solution and brine, dried over magnesium sulfate, and evaporated in vacuo. The residue was purified by silica gel column chromatography eluting with a mixture of hexane and ethyl acetate (20:1-5:1) to give 4-(3-chlorophenyl)-7-ethyl-3-(5-methoxypentyl)-2-phenylpyrrolo[1,2-b]pyridazine as an yellow oil (60 mg).

4-(3-chlorophenyl)-7-ethyl-3-(5-methoxypentyl)-2-phenylpyrrolo[1,2-b]pyridazine

NMR (CDCl$_3$, δ): 0.90-1.32 (6H, m), 1.36 (3H, t, J=7 Hz), 2.37-2.47 (2H, m), 3.03 (2H, q, J=7 Hz), 3.08 (2H, t, J=7 Hz), 3.31 (3H, s), 5.97 (1H, d, J=4 Hz), 6.61 (1H, d, J=4 Hz), 7.27-7.33 (1H, m), 7.38-7.53 (8H, m) MS (ESI$^+$): m/z 433

EXAMPLE 262

To a solution of 5-[4-(3-chlorophenyl)-7-ethyl-2-phenylpyrrolo[1,2-b]pyridazin-3-yl]-1-pentanol (55 mg) and triethylamine (19.9 mg) in dichloromethane (3 mL) was added methanesulfonyl chloride (165 mg) under ice-water cooling and the mixture was stirred at 0° C. for 1 hour. The solution was washed with brine, dried over magnesium sulfate, and evaporated in vacuo. To the residue in 1,2-dichloroethane (3 mL) was added 2 M dimethylamine in tetrahydrofuran (3 mL) and the mixture was stirred at 60° C. for 120 hours. The solution was diluted with chloroform, washed with brine, dried over magnesium sulfate, and evaporated in vacuo. The residue was purified by silica gel column chromatography eluting with a mixture of hexane and ethyl acetate (20:1-5:1) to give 5-[4-(3-chlorophenyl)-7-ethyl-2-phenylpyrrolo[1,2-b]pyridazin-3-yl]-N,N-dimethyl-1-pentanamine as an yellow oil (38 mg).

N-{5-[4-(3-Chlorophenyl)-7-ethyl-2-phenylpyrrolo[1,2-b]pyridazin-3-yl]pentyl}-N,N-dimethylamine NMR (CDCl$_3$, δ): 0.86-0.97 (2H, m), 1.02-1.15 (4H, m), 1.36 (3H, t, J=7 Hz), 1.97-2.04 (2H, m), 2.11 (6H, s), 2.37-2.47 (2H, m), 3.02 (2H, q, J=7 Hz), 5.97 (1H, d, J=4 Hz), 6.61 (1H, d, J=4 Hz), 7.31 (1H, m), 7.39-7.54 (8H, m) MS (ESI$^+$): m/z 446

EXAMPLE 263

To a stirred solution of 5-[4-(3-cyanophenyl)-7-ethyl-2-phenylpyrrolo[1,2-b]pyridazin-3-yl]pentanoic acid (60 mg) in dichloromethane (2 ml) was added 1-(3-dimethylaminopropyl)-3-ethylcarbodiimide hydrochloride (35.3 mg) and 2-aminopyridine (20 mg) and the reaction mixture was stirred for 10 minutes. 4-Dimethylaminopyridine (2 mg) was added and the reaction mixture was stirred at room temperature for 15 hours. The mixture was diluted with water and extracted with ethyl acetate. The organic layer was washed with water, brine, dried over anhydrous magnesium sulfate and concentrated in vacuo. The residue was purified by flash column chromatography on silica gel eluting with a mixture of ethyl acetate and n-hexane (1:2) to give 5-[4-(3-cyanophenyl)-7-ethyl-2-phenylpyrrolo[1,2-b]pyridazin-3-yl]-N-(2-pyridinyl)pentanamide (55.7 mg) as an yellow amorphous.

5-[4-(3-Cyanophenyl)-7-ethyl-2-phenylpyrrolo[1,2-b]pyridazin-3-yl]-N-(2-pyridinyl)pentanamide mp: 67-70° C. NMR (CDCl3, δ): 1.12 (2H, quintet, J=7 Hz), 1.30 (2H, quintet, J=7 Hz), 1.36 (3H, t, J=7 Hz), 1.95 (2H, t, J=7 Hz), 2.43 (2H, q, J=7 Hz), 3.02 (2H, q, J=7 Hz), 5.90 (1H, d, J=4 Hz), 6.62 (1H, d, J=4 Hz), 7.00-7.05 (1H, m), 7.43-7.54 (5H, m), 7.59-7.77 (6H, m), 8.11 (1H, d, J=7.5 Hz), 8.24 (1H, d, J=4 Hz) MS: (m/z) 499 (M+), 45 (bp)

The following compounds were obtained in substantially the same manner as that of Example 263.

EXAMPLE 264

5-[4-(3-Chlorophenyl)-7-ethyl-2-phenylpyrrolo[1,2-b]pyridazin-3-yl]-N-(2-pyridinyl)pentanamide NMR (CDCl$_3$, δ): 1.15 (2H, quintet, J=7 Hz), 1.24(2H, quintet, J=7 Hz), 1.36(3H, t, J=7 Hz), 1.91(2H, t, J=7 Hz), 2.45(2H, t, J=7 Hz), 3.00(2H, q, J=7 Hz), 5.97(1H, d, J=5 Hz), 6.60(1H, d, J=4 Hz), 7.00(1H, t, J=7 Hz), 7.30(1H, s), 7.38-7.53(7H, m), 7.65-7.73(2H, m), 8.11(1H, d, J=7 Hz), 8.25(1H, d, J=5 Hz) MS: (m/z) 509 (M$^+$+H), 74 (bp)

EXAMPLE 265

N-{5-[4-(3-Chlorophenyl)-7-ethyl-2-phenylpyrrolo[1,2-b]pyridazin-3-yl]pentanoyl}methanesulfonamide NMR (CDCl$_3$, δ): 1.08 (2H, quintet, J=7 Hz), 1.23 (2H, quintet, J=7 Hz), 1.36 (3H, t, J=7 Hz), 1.85 (2H, t, J=7 Hz), 2.44 (2H, t, J=7 Hz), 3.02 (2H, q, J=7 Hz), 3.21 (3H, s), 5.99 (1H, d, J=4 Hz), 6.62 (1H, d, J=4 Hz), 7.30-7.33 (1H, m), 7.43-7.55 (8H, m)

EXAMPLE 266

5-[4-(2-chloro-4-pyridinyl)-7-ethyl-2-phenylpyrrolo[1,2-b]pyridazin-3-yl]-N-(2-pyridinyl)pentanamide NMR (CDCl$_3$, δ): 1.12 (2H, quintet, J=7 Hz), 1.27 (2H, quintet, J=7 Hz), 1.36 (3H, t, J=7 Hz), 1.97 (2H, t, J=7 Hz), 2.45 (2H, t, J=7 Hz), 3.01 (2H, q, J=7 Hz), 5.95 (1H, d, J=5 Hz), 6.63 (1H, d, J=4 Hz), 7.01 (1H, t, J=7 Hz), 7.31 (1H, d, J=7 Hz), 7.41-7.53 (6H, m), 7.68 (1H, ddd, J=7, 7, 1 Hz), 7.77 (1H, s), 8.12 (1H, d, J=7.5 Hz), 8.24 (1H, d, J=5 Hz), 8.53 (1H, d, J=6 Hz) MS: (m/z) 510 (M++H), 80 (bp)

EXAMPLE 267

N-{5-[4-(5-Bromo-3-pyridinyl)-7-ethyl-2-methylpyrrolo[1,2-b]pyridazin-3-yl]pentanoyl}methanesulfonamide mp: 124-125° C. NMR (CDCl$_3$, δ): 1.37 (3H, t, J=7 Hz), 1.43-1.49 (2H, m), 1.55-1.65 (2H, m), 2.23 (2H, t, J=7 Hz), 2.34-2.48 (2H, m), 2.55 (3H, s), 3.01 (2H, q, J=7 Hz), 3.28 (3H, s), 5.87 (1H, d, J=4 Hz), 6.53 (1H, d, J=4 Hz), 7.09 (1H, s), 7.40 (1H, s), 8.53 (1H, s), 8.77 (1H, s) MS: (m/z) 493(M$^+$), 491 (M$^+$−2), 137 (bp)

EXAMPLE 268

To a solution of ethyl 5-[4-(5-bromo-3-pyridinyl)-7-ethyl-2-(hydroxymethyl)pyrrolo[1,2-b]pyridazin-3-yl]pentanoate (100.0 mg) and (bromomethyl)benzene (111 mg) in N,N-dimethylformamide (1 mL) was added 60% sodium hydride (17.4 mg) under an ice-bath. After stirring for 2.5 hour, the reaction was quenched by adding 1N hydrochloric acid (1 mL), and the mixture was partitioned between ethyl acetate (10 mL) and water (5 mL). The organic layer was washed with 1N hydrochloric acid (5 mL), water (5 mL, three times), and brine, dried over magnesium sulfate, and evaporated. Flash silica gel column chromatography eluting with ethyl acetate-hexane=1/40 to 20/40 afforded ethyl 5-[2-[(benzyloxy)methyl]-4-(5-bromo-3-pyridinyl)-7-ethylpyrrolo[1,2-b]pyridazin-3-yl]pentanoate as an yellow gum (47.7 mg, 39.9%).

Ethyl 5-[2-[(benzyloxy)methyl]-4-(5-bromo-3-pyridinyl)-7-ethylpyrrolo[1,2-b]pyridazin-3-yl]pentanoate NMR (CDCl$_3$, δ): 1.23 (3H, t, J=7 Hz), 1.34-1.48 (5H, m), 2.09 (2H, m), 2.53 (2H, m), 3.04 (2H, q, J=7 Hz), 4.07 (2H, J=7 Hz), 4.65 (2H, s), 4.72 (2H, s), 5.90 (1H, d, J=5 Hz), 6.60 (1H, d, J=5 Hz), 7.29-7.38 (5H, m), 7.86 (1H, s), 8.54 (1H, m), 8.77 (1H, m)

The following compound was obtained in substantially the same manner as that of Example 268.

EXAMPLE 269

Ethyl 5-(4-(5-bromo-3-pyridinyl)-2-{[(4-cyanobenzyl)oxy]methyl}-7-ethylpyrrolo[1,2-b]pyridazin-3-yl)pentanoate NMR (CDCl$_3$, δ): 1.23 (3H, J=7 Hz), 1.35-1.55 (7H, m), 2.12 (2H, t, J=7 Hz), 2.57 (2H, m), 3.02 (2H, q, J=7 Hz), 4.07 (2H, q, J=7 Hz), 4.49 (2H, s), 4.76 (2H, s), 5.93 (1H, d, J=7 Hz), 6.62 (1H, d, J=7 Hz), 7.48 (2H, d, J=8 Hz), 7.65 (2H, d, J=8 Hz), 7.86 (1H, m), 8.54 (1H, m), 8.78 (1H, m)

EXAMPLE 270

To a solution of ethyl 5-[4-(5-bromo-3-pyridinyl)-7-ethyl-2-(hydroxymethyl)pyrrolo[1,2-b]pyridazin-3-yl]pentanoate (200 mg) and triethylamine (65.9 mg) in dichloromethane (2 mL) was added methanesulfonyl chloride (54.7 mg) under an ice-bath. After stirring for 1 hour, the reaction was quenched by adding 1N hydrochloric acid (1 mL). The mixture was partitioned between ethyl acetate (20 mL) and 1N hydrochloric acid (5 mL). The organic layer was washed with saturated sodium bicarbonate and brine, dried over magnesium sulfate, and evaporated to give ethyl 5-(4-(5- bromo-3-pyridinyl)-7-ethyl-2-{[(methylsulfonyl)oxy]methyl}pyrrolo[1,2-b]pyridazin-3-yl)pentanoate as an yellow gum (247 mg).

Ethyl 5-(4-(5-bromo-3-pyridinyl)-7-ethyl-2-{[(methylsulfonyl)oxy]methyl}pyrrolo[1,2-b]pyridazin-3-yl)pentanoate NMR (CDCl$_3$, δ): 1.22 (3H, t, J=7 Hz), 1.34-1.65 (7H, m), 2.20 (2H, t, J=7 Hz), 2.55 (2H, m), 3.02 (2H, q, J=7 Hz), 3.15 (3H, s), 4.07 (2H, q, J=7 Hz), 5.42 (2H, s), 5.99 (1H, d, J=5 Hz), 6.68 (1H, d, J=5 Hz), 7.87 (1H, m), 8.54 (1H, m), 8.81 (1H, m)

EXAMPLE 271

A mixture of ethyl 5-(4-(5-bromo-3-pyridinyl)-7-ethyl-2-{[(methylsulfonyl)oxy]methyl}pyrrolo[1,2-b]pyridazin-3-yl)pentanoate (50.0 mg), benzylamine (29.8 mg) in dichloromethane (1 mL) was stirred for 20 hour at room temperature. The mixture was partitioned between ethyl acetate and water. The organic layer was washed with brine, dried, and evaporated. Preparative thin layer chromatography eluting with ethyl acetate-hexane=1:2 afforded ethyl 5-[2-[(benzylamino)methyl]-4-(5-bromo-3-pyridinyl)-7-ethylpyrrolo[1,2-b]pyridazin-3-yl]pentanoate as an yellow gum (19.1 mg).

Ethyl 5-[2-[(benzylamino)methyl]-4-(5-bromo-3-pyridinyl)-7-ethylpyrrolo[1,2-b]pyridazin-3-yl]pentanoate NMR (CDCl$_3$, δ): 1.23 (3H, t, J=7 Hz), 1.30-1.50 (7H, m), 2.13 (2H, t, J=7 Hz), 2.42 (2H, m), 3.03 (2H, q, J=7 Hz), 3.96 (4H, m), 4.09 (2H, q, J=7 Hz), 5.89 (1H, d, J=5 Hz), 6.57 (1H, d, J=5 Hz), 7.23-7.42 (5H, m), 7.86 (1H, m), 8.53 (1H, m), 8.77 (1H, m)

The following compound was obtained in substantially the same manner as that of Example 271.

EXAMPLE 272

Ethyl 5-[4-(5-bromo-3-pyridinyl)-7-ethyl-2-(4-morpholinylmethyl)pyrrolo[1,2-b]pyridazin-3-yl]pentanoate NMR (CDCl$_3$, δ): 1.23 (3H, t, J=7 Hz), 1.31-1.56 (7H, m), 2.19 (2H, t, J=7 Hz), 2.45-2.65 (6H, m), 3.02 (2H, q, J=7 Hz), 3.60-3.75 (6H, m), 4.09 (2H, q, J=7 Hz), 5.88 (1H, d, J=5 Hz), 6.57 (1H, d, J=5 Hz), 7.89 (1H, m), 8.55 (1H, m), 8.78 (1H, m)

EXAMPLE 273

To a solution of (7-chloro-4-(4-fluorophenyl)-2-isopropylpyrrolo[1,2-b]pyridazin-3-yl)methanol (40 mg) in N,N-dimethylformamide (1 mL) was added 40% sodium hydride in oil (55 mg) in an ice-water bath. After 20 minutes, to the mixture was added 2-bromoethyl acetate (31 mg) at the temperature. After 15 minutes, the reaction mixture was stirred at ambient temperature for 5 hours. The reaction mixture was partitioned between ethyl acetate and water. The organic layer was washed with water three times and brine, dried over magnesium sulfate, and evaporated in vacuo. The residue was purified by p-TLC (hexane-ethyl acetate=10-1) to give [7-chloro-4-(4-fluorophenyl)-2-isopropylpyrrolo[1,2-b]pyridazin-3-yl]methyl acetate as a pale yellow solid (42 mg).

[7-Chloro-4-(4-fluorophenyl)-2-isopropylpyrrolo[1,2-b]pyridazin-3-yl]methyl acetate NMR (CDCl$_3$, δ): 1.41 (6H, d, J=8 Hz), 2.06 (3H, s), 3.21 (1H, m), 4.92 (2H, s), 6.14 (1H, d, J=5 Hz), 6.72 (1H, d, J=5 Hz), 7.13-7.24 (2H, m), 7.34-7.43 (2H, m) MS (ESI$^+$): m/z 361 (M+H)

The following compound was obtained in substantially the same manner as that of Preparation 20.

EXAMPLE 274

Ethyl{[7-ethyl-4-(4-fluorophenyl)-2-isopropylpyrrolo[1,2-b]pyridazin-3-yl]methoxy}acetate NMR (CDCl$_3$, δ): 1.25 (3H, t, J=8 Hz), 1.30-1.45 (9H, m), 3.04 (2H, q, J=8 Hz), 3.51 (1H, m), 3.97 (2H, s), 4.15 (2H, q, J=8 Hz), 4.40 (2H, s), 6.06 (1H, d, J=5 Hz), 6.56 (1H, d, J=5 Hz), 7.11-7.22 (2H, m), 7.41-7.51 (2H, m) MS (ESI$^+$): m/z 399 (M+H)

The following compound was obtained in substantially the same manner as that of Preparation 276.

EXAMPLE 275

Ethyl 2-(2-amino-2-oxoethyl)-4-(4-cyanophenyl)-7-ethylpyrrolo[1,2-b]pyridazine-3-carboxylate NMR (CDCl$_3$, δ): 0.84 (3H, t, J=7 Hz), 1.38 (3H, t, J=7 Hz), 3.06 (2H, q, J=7 Hz), 3.96 (2H, q, J=7 Hz), 4.02 (3H, s), 5.41 (1H, s, br), 6.09 (1H, s, br), 6.28 (1H, d, J=5 Hz), 6.75 (1H, d, J=5 Hz), 7.53 (2H, d, J=9 Hz), 7.77 (2H, d, J=9 Hz) MS (ESI$^+$): m/z 753 (2M+H)

EXAMPLE 276

A mixture of 4-(3-cyanophenyl)-7-ethyl-3-(methylsulfonyl)pyrrolo[1,2-b]pyridazine-2-carboxylic acid (40.0 mg), pyrrolidine (10.8 mg), 1-(3-dimethylaminopropyl)-3-ethylcarbodiimide hydrochloride (31.1 mg), and 1-hydroxybenzotriazole (21.9 mg) in N,N-dimethylformamide (1 mL) was stirred for 6 hour at room temperature. The mixture was partitioned between ethyl acetate (20 mL) and 1N hydrochloric acid (10 mL). The organic layer was washed with water (10 mL) three times, saturated sodium bicarbonate (10 mL), and brine, dried, and evaporated to give 3-[7-ethyl-3-(methylsulfonyl)-2-(1-pyrrolidinylcarbonyl)pyrrolo[1,2-b]pyridazin-4-yl]benzonitrile as an yellow solid (35.6 mg).

3-[7-Ethyl-3-(methylsulfonyl)-2-(1-pyrrolidinylcarbonyl)pyrrolo[1,2-b]pyridazin-4-yl]benzonitrile NMR (CDCl$_3$, δ): 1.38 (2H, m), 1.99 (4H, m), 3.07 (2H, q, J=7 Hz), 3.23 (3H, s), 3.59 (2H, t, J=7 Hz), 3.68 (2H, t, J=7 Hz), 6.27 (1H, d, J=5 Hz), 6.83 (1H, d, J=5 Hz), 7.57-7.66 (3H, m), 7.79 (1H, m) MS (ESI$^+$): m/z 423 (M+H)

EXAMPLE 277

To a solution of 3-[7-ethyl-2-(2-furyl)pyrrolo[1,2-b]pyridazin-4-yl]benzoic acid (40 mg) in N,N-dimethylformamide (4 mL) was added 1-(3-dimethylaminopropyl)-3-ethylcarbodiimide hydrochloride (30 mg), 1-hydroxybenzotriazole (24 mg), and 2-aminoethanol (15 mg) at ambient temperature. After stirring overnight, the reaction mixture was partitioned between ethyl acetate and saturated sodium bicarbonate. The organic layer was washed with water 3 times and brine, dried over magnesium sulfate, and evaporated in vacuo. The residue was purified by flash silica gel column chromatography (silica gel, 40 mL) eluted with chloroform-methanol=50-1 and 20-1 to give an yellow solid (42 mg). The solid was triturated with isopropyl ether to give 3-[7-ethyl-2-(2-furyl)pyrrolo[1,2-b]pyridazin-4-yl]-N-(2-hydroxyethyl)benzamide as an yellow solid (35 mg).

3-[7-Ethyl-2-(2-furyl)pyrrolo[1,2-b]pyridazin-4-yl]-N-(2-hydroxyethyl)benzamide

NMR (CDCl$_3$, δ): 1.43 (3H, t, J=8 Hz), 2.39-2.49 (2H, m), 3.10 (2H, q, J=8 Hz), 3.60-3.74 (2H, m), 3.80-3.94 (2H, m), 6.53-6.86 (4H, m), 7.00 (1H, s), 6.61 (1H, d, J=5 Hz), 6.72 (1H, d, J=5 Hz), 7.03 (1H, br s), 7.07 (1H, d, J=5 Hz), 7.55-7.65 (2H, m), 7.86-7.97 (2H, m), 8.17 (1H, br s) MS (ESI$^+$): m/z 376 (M+H)

The following compounds were obtained in substantially the same manner as that of Example 283.

EXAMPLE 278

5-[4-(3-Cyanophenyl)-7-ethyl-2-phenylpyrrolo[1,2-b]pyridazin-3-yl]-N-methylpentanamide mp: 60° C. NMR (CDCl$_3$, δ): 1.02-1.12 (2H, m), 1.17-1.25 (2H, m), 1.36 (3H, t, J=7 Hz), 1.73 (2H, t, J=7 Hz), 2.40 (2H, t, J=7 Hz), 2.71 (3H, d, J=7 Hz), 3.03 (2H, q, J=7 Hz), 5.09 (1H, broad s), 5.90 (1H, d, J=4 Hz), 6.63 1H, d, J=4 Hz), 7.45-7.55 (5H, m), 7.60-7.78 (4H, m) MS: (m/z) 437 (M$^+$+H), 115 (bp)

EXAMPLE 279

4-(3-Chlorophenyl)-7-ethyl-3-[5-(4-morpholinyl)-5-oxopentyl]-2-phenylpyrrolo[1,2-b]pyridazine mp: 55-58° C. NMR (CDCl3, δ): 1.05-1.14 (2H, m), 1.17-1.23 (2H, m), 1.35 (3H, t, J=7 Hz), 1.84 (2H, t, J=7 Hz), 2.45 (2H, t, J=7 Hz), 3.02 (2H, q, J=7 Hz), 3.24 (2H, t, J=6 Hz), 3.50 (2H, t, J=6 Hz), 3.55-3.62 (4H, m), 5.99 (1H, d, J=4 Hz), 6.62 (1H, d, J=4 Hz), 7.30-7.35 (1H, m), 7.40-7.55 (8H, m) MS: (m/z) 502 (M$^+$+H), 115 (bp)

EXAMPLE 280

5-[4-(3-Chlorophenyl)-7-ethyl-2-phenylpyrrolo[1,2-b]pyridazin-3-yl]-N-methylpentanamide mp: 70-72° C. NMR (CDCl$_3$, δ): 1.06 (2H, quintet, J=7 Hz), 1.22 (2H, quintet, J=7 Hz), 1.36 (3H, t, J=7 Hz), 1.72 (2H, t, J=7 Hz), 2.43 (2H, t, J=7 Hz), 2.70 (3H, d, J=7 Hz), 3.03 (2H, q, J=7 Hz), 5.08 (1H, broad s), 5.99 (1H, d, J=4 Hz), 6.61 (1H, d, J=4 Hz), 7.29-7.33 (1H, m), 7.41-7.55 (8H, m) MS: (m/z) 446 (M$^+$+H), 115 (bp)

EXAMPLE 281

5-[4-(2-Chloro-4-pyridinyl)-7-ethyl-2-phenylpyrrolo[1,2-b]pyridazin-3-yl]-N-methylpentanamide NMR (CDCl$_3$, δ): 1.07 (2H, quintet, J=7 Hz), 1.23 (2H, quintet, J=7 Hz), 1.36(3H, t, J=7 Hz), 1.74 (2H, t, J=7 Hz), 2.41 (2H, t, J=7 Hz), 2.71 (3H, d, J=7 Hz), 3.02 (2H, q, J=7 Hz), 5.10 (1H, broad s), 5.95 (1H, d, J=4 Hz), 6.64 (1H, d, J=4 Hz), 7.31 (1H, d, J=7 Hz), 7.42 (1H, s), 7.46-7.52 (1H, m), 7.41-7.55 (1H, d, J=7 Hz) MS: (m/z) 447 (M$^+$+H), 115 (bp)

EXAMPLE 282

3-{7-Ethyl-3-[5-(4-morpholinyl)-5-oxopentyl]-2-phenylpyrrolo[1,2-b]pyridazin-4-yl}benzonitrile from 5-[4-(3-cyanophenyl)-7-ethyl-2-phenylpyrrolo[1,2-b]pyridazin-3-yl]pentanoic acid mp: 66-69° C. NMR (CDCl3, δ): 1.04-1.12 (2H, m), 1.17-1.23 (2H, m), 1.36 (3H, t, J=7 Hz), 1.84 (2H, t, J=7 Hz), 2.42 (2H, t, J=7 Hz), 3.03 (2H, q, J=7 Hz), 3.23 (2H, t, J=6 Hz), 3.50 (2H, t, J=6 Hz), 3.55-3.63 (4H, m), 5.90 (1H, d, J=4 Hz), 6.63 (1H, d, J=4 Hz), 7.43-7.55 (5H, m), 7.60-7.78 (4H, m) MS: (m/z) 493 (M$^+$+H), 126 (bp)

EXAMPLE 283

To a solution of 5-[4-(3-cyanophenyl)-7-ethyl-2-methylpyrrolo[1,2-b]pyridazin-3-yl]pentanoic acid (50 mg) in N,N-dimethylformamide (1 mL) was added 1-(3-dimethylaminopropyl)-3-ethylcarbodiimide hydrochloride (35 mg) and 1-hydroxybenzotriazole (28 mg) at ambient temperature. After 30 minutes, to the mixture was added morpholine (24 mg). After 5 hours, the reaction mixture was partitioned between ethyl acetate and saturated sodium bicarbonate. The organic layer was washed with water three times and brine, dried over magnesium sulfate, and evaporated in vacuo. The residue was purified by flash silica gel column chromatography (silica gel, 40 mL) eluted with hexane-ethyl acetate=3-1, 2-1, 1-1, 1-3, and 0-1 to give 3-{7-ethyl-2-methyl-3-[5-(4-morpholinyl)-5-oxopentyl]pyrrolo[1,2-b]pyridazin-4-yl}benzonitrile as an yellow gum (53 mg).

3-{7-Ethyl-2-methyl-3-[5-(4-morpholinyl)-5-oxopentyl]pyrrolo[1,2-b]pyridazin-4-yl}benzonitrile NMR (CDCl$_3$, δ): 1.15-1.61 (7H, m), 2.18 (2H, t, J=8 Hz), 2.41 (2H, t, J=8 Hz), 2.56 (3H, s), 3.00 (2H, q, J=8 Hz), 3.82 (2H, t, J=5 Hz), 3.51-3.68 (6H, m), 5.78 (1H, d, J=5 Hz), 6.50 (1H, d, J=5 Hz), 7.56-7.67 (3H, m), 7.74 (1H, m) MS (ESI$^+$): m/z 431 (M+H)

The following compound was obtained in substantially the same manner as that of Example 283.

EXAMPLE 284

5-[4-(3-Cyanophenyl)-7-ethyl-2-methylpyrrolo[1,2-b]pyridazin-3-yl]pentanamide

NMR (CDCl$_3$, δ): 1.31-1.61 (7H, m), 2.11 (2H, t, J=8 Hz), 2.40 (2H, t, J=8 Hz), 2.56 (3H, s), 3.00 (2H, q, J=8 Hz), 5.36 (2H, br s), 5.79 (1H, d, J=5 Hz), 6.50 (1H, d, J=5 Hz), 7.56-7.67 (3H, m), 7.75 (1H, m) MS (ESI$^+$): m/z 361 (M+H)

Preparation 178

To a suspension of 60% sodium hydride (8.79 g) in tetrahydrofuran (500 mL) was added cyclohexanol (10 g) and the mixture was stirred at 0° C. for 0.5 hour. To the mixture was added bromoacetic acid (13.9 g) under ice-water cooling and the mixture was heated under reflux for 2 hours. After adding water to the mixture and organic solvent was evaporated in vacuo. The aqueous solution was diluted with water, washed with ether, acidified with 1 N hydrochloric acid, and extracted with ether. The organic layer was separated, dried over magnesium sulfate, and evaporated in vacuo to give (cyclohexyloxy)acetic acid as colorless oil (133 g).

(cyclohexyloxy)acetic acid $^1$H NMR (CDCl$_3$) δ 1.18-1.47 (5H, m), 1.52-1.63 (1H, m), 1.72-1.85 (2H, m), 1.90-2.03 (2H, m), 3.36-3.47 (1H, m), 4.13 (2H, s).

The following compound(s) was (were) obtained in substantially the same manner as that of Preparation 178.

Preparation 179 isopropoxyacetic acid $^1$H NMR (CDCl$_3$) δ 1.24 (6H, d, J=7 Hz), 3.68-3.82 (1H, m), 4.11 (2H, s).

The following compound(s) was (were) obtained in substantially the same manner as that of Preparation 129 and Preparation 130.

Preparation 180 tert-butyl 4-(benzyloxy)-3-oxobutanoate $^1$H NMR (CDCl$_3$) δ 1.44 (9H, s), 3.45 (2H, s), 4.14 (2H, s), 4.60 (2H, s), 7.28-7.40 (5H, m).

Preparation 181 tert-butyl 4-(cyclohexyloxy)-3-oxobutanoate $^1$H NMR (CDCl$_3$) δ 1.18-1.43 (5H, m), 1.47 (9H, s), 1.53-1.63 (1H, m), 1.69-1.85 (2H, m), 1.87-1.97 (2H, m), 3.24-3.38 (1H, m), 3.46 (2H, s), 4.11 (2H, s).

Preparation 182 tert-butyl 4-isopropoxy-3-oxobutanoate $^1$H NMR (CDCl$_3$) δ 1.20 (6H, d, J=7 Hz), 1.47 (9H, s), 3.45 (2H, s), 3.60-3.70 (1H, m), 4.08 (2H, s).

The following compound(s) was (were) obtained in substantially the same manner as that of Preparation 159.

Preparation 183

1-tert-butyl 4-ethyl 2-acetylsuccinate $^1$H NMR (CDCl$_3$) δ 1.25 (3H, t, J=7 Hz), 1.47 (9H, s), 2.35 (3H, s), 3.08 (2H, m), 3.93 (1H, m), 4.12 (2H, q, J=7 Hz).

Preparation 184

1-tert-butyl 7-ethyl 2-[(benzyloxy)acetyl]heptanedioate $^1$H NMR (CDCl$_3$) δ 1.25 (3H, t, J=7 Hz), 1.30-1.50 (2H, m), 1.40 (9H, s), 1.56-1.72 (2H, m), 1.75-1.95 (2H, m), 2.28 (2H, t, J=7 Hz), 3.52 (1H, t, J=7 Hz), 4.11 (2H, q, J=7 Hz), 4.16 (2H, s), 4.59 (2H, s), 7.27-7.40 (5H, m).

Preparation 185

1-tert-butyl 5-ethyl 2-[(benzyloxy)acetyl]pentanedioate $^1$H NMR (CDCl$_3$) δ 1.25 (3H, t, J=7 Hz), 1.41 (9H, s), 2.10-2.23 (2H, m), 2.36 (2H, t, J=7 Hz), 3.66 (1H, t, J=7 Hz), 4.12 (2H, q, J=7 Hz), 4.18 (2H, s), 4.60 (2H, s), 7.26-7.38 (5H, m).

Preparation 186

1-tert-butyl 7-ethyl 2-[(cyclohexyloxy)acetyl]heptanedioate $^1$H NMR (CDCl$_3$) δ 1.25 (3H, t, J=7 Hz), 1.44 (9H, s), 1.15-1.92 (16H, m), 2.29 (2H, t, J=7 Hz), 3.24-3.38 (1H, m), 3.56 (1H, t, J=7 Hz), 4.12 (4H, m), Preparation 187

1-tert-butyl 7-ethyl 2-(isopropoxyacetyl)heptanedioate $^1$H NMR (CDCl$_3$) δ 1.20 (6H, d, J=7 Hz), 1.25 (3H, t, J=7 Hz), 1.25-1.45 (2H, m), 1.45 (9H, s), 1.60-1.72 (2H, m), 1.75-1.95 (2H, m), 2.29 (2H, t, J=7 Hz), 3.54 (1H, t, J=7 Hz), 3.60-3.68 (1H, m), 4.11 (2H, s), 4.12 (2H, q, J=7 Hz). MS (ESI$^+$): m/z 345.

The following compound(s) was (were) obtained in substantially the same manner as that of Preparation 20.

Preparation 188

1-tert-butyl 5-ethyl 2-[(cyclohexyloxy)acetyl]pentanedioate $^1$H NMR (CDCl$_3$) δ 1.26 (3H, t, J=7 Hz), 1.45 (9H, s), 1.18-1.62 (6H, m), 1.66-1.78 (2H, m), 1.84-1.98 (2H, m), 2.10-2.23 (2H, m), 2.38 (2H, t, J=7 Hz), 3.25-3.38 (1H, m), 3.69 (1H, t, J=7 Hz), 4.12 (2H, q, J=7 Hz), 4.15 (2H, s). MS (ESI$^+$): m/z 357.

Preparation 189

To a suspension of 60% sodium hydride (527 mg) in dimethylformamide (20 mL) was added 3,5-pyridinedicarboxylic acid (2.00 g) under ice-water cooling and the mixture was stirred at 0° C. for 1 hour. To the mixture was added (bromomethyl)benzene (2.05 g) and the mixture was stirred at 60° C. for 2 hours. The mixture was partitioned between ethyl acetate and water. The organic layer was washed with water and brine, dried over magnesium sulfate, and evaporated in vacuo. The residue was triturated with ethyl acetate to give 5-[(benzyloxy)carbonyl]nicotinic acid as a pale yellow powder (722 mg).

5-[(benzyloxy)carbonyl]nicotinic acid $^1$H NMR (DMSO-d$_6$) δ 5.42 (2H, s), 7.34-7.54 (5H, m), 8.63 (1H, m), 9.23-9.34 (2H, m).

The following compound(s) was (were) obtained in substantially the same manner as that of Preparation 24.

Preparation 190

1-tert-butyl 4-ethyl 2-acetyl-2-[(5-methyl-3-pyridinyl)carbonyl]succinate $^1$H NMR (CDCl$_3$) δ 1.23 (3H, t, J=7 Hz), 1.40 (9H, s), 2.38 (3H, s), 2.45 (3H, s), 3.20 (2H, m), 4.13 (2H, q, J=7 Hz), 7.88 (1H, s), 8.57 (1H, s), 8.74 (1H, s). MS (ESI$^+$): m/z 363.

Preparation 191 ethyl 2-[(5-methyl-3-pyridinyl)carbonyl]-3-oxobutanoate $^1$H NMR (CDCl$_3$) δ 0.96 (3H, t, J=7 Hz), 2.15 (3H, s), 2.45 (3H, s), 4.03 (2H, q, J=7 Hz), 4.12 (1H, t, J=7 Hz), 7.89 (1H, s), 8.54 (1H, s), 8.72 (1H, s). MS (ESI$^+$): m/z 250.

Preparation 192

1-tert-butyl 6-ethyl 2-acetyl-2-[(5-bromo-3-pyridinyl)carbonyl]hexanedioate $^1$H NMR (CDCl$_3$) δ 1.25 (3H, t, J=7 Hz), 1.36 (9H, s), 1.60-1.73(2H, m), 2.23-2.35 (2H, m), 2.38 (2H, t, J=7 Hz), 2.48 (3H, s), 4.12 (2H, q, J=7 Hz), 8.20 (1H, m), 8.78 (1H, m), 8.81 (1H, m).

Preparation 193

1-tert-butyl 5-ethyl 2-[(5-bromo-3-pyridinyl)carbonyl]-2-(methoxyacetyl)pentanedioate $^1$H NMR (CDCl$_3$) δ 1.25 (3H, t, J=7 Hz), 1.39 (9H, s), 2.40-2.47 (2H, m), 2.55-2.67 (2H, m), 3.36 (3H, s), 4.12 (2H, q, J=7 Hz), 4.27 (1H, d, J=17 Hz), 4.40 (1H, d, J=17 Hz), 8.21 (1H, m), 8.79 (1H, d, J=2 Hz), 8.82 (1H, d, J=2 Hz). MS (ESI$^+$): m/z 472 474.

Preparation 194

1-tert-butyl 7-ethyl 2-acetyl-2-({5-[(benzyloxy)carbonyl]-3-pyridinyl}carbonyl)heptanedioate $^1$H NMR (CDCl$_3$) δ 1.23 (3H, t, J=7 Hz), 1.20-1.40 (2H, m), 1.32 (9H, s), 1.65-1.76 (2H, m), 2.19-2.26 (2H, m), 2.32 (2H, t, J=7 Hz), 2.44 (3H, s), 4.12 (2H, q, J=7 Hz), 5.41 (2H, s), 7.35-7.48 (5H, m), 8.62 (1H, m), 9.07 (1H, d, J=2 Hz), 933 (1H, d, J=2 Hz). MS (ESI$^+$): m/z 526.

Preparation 195

1-tert-butyl 7-ethyl 2-[(benzyloxy)acetyl]-2-[(5-methyl-3-pyridinyl)carbonyl]heptanedioate $^1$H NMR (CDCl$_3$) δ 1.23 (3H, t, J=7 Hz), 1.20-1.46 (2H, m), 1.32 (9H, s), 1.60-1.74 (2H, m), 2.10-2.36 (4H, m), 2.35 (3H, s), 4.10 (2H, q, J=7 Hz), 4.38 (1H, d, J=18 Hz), 4.53 (1H, d, J=18 Hz), 4.54 (2H, m), 7.27-7.40 (5H, m), 7.79 (1H, m), 8.54 (1H, d, J=2 Hz), 8.72 (1H, d, J=2 Hz). MS (ESI$^+$): m/z 512.

Preparation 196

1-tert-butyl 5-ethyl 2-[(benzyloxy)acetyl]-2-[(5-methyl-3-pyridinyl)carbonyl]pentanedioate $^1$H NMR (CDCl$_3$) δ 1.26 (3H, t, J=7 Hz), 1.34 (9H, s), 2.35 (3H, s), 2.40-2.72 (4H, m), 4.12 (2H, q, J=7 Hz), 4.38 (1H, d, J=17 Hz), 4.50 (1H, d, J=17 Hz), 4.53 (2H, m), 7.25-7.38 (5H, m), 7.81 (1H, s), 8.54 (1H, s), 8.73 (1H, s). MS (ESI$^+$): m/z 484.

Preparation 197

1-tert-butyl 7-ethyl 2-[(cyclohexyloxy)acetyl]-2-[(5-methyl-3-pyridinyl)carbonyl]heptanedioate $^1$H NMR (CDCl$_3$) δ 1.25 (3H, t, J=7 Hz), 1.16-1.55 (10H, m), 1.37 (9H, s), 1.60-1.76 (2H, m), 1.78-1.90 (2H, m), 2.15-2.28 (2H, m), 2.31 (2H, t, J=7 Hz), 2.39 (3H, s), 3.17-3.29 (1H, m), 4.12 (2H, q, J=7 Hz), 4.34 (1H, d, J=18 Hz), 4.44 (1H, d, J=18 Hz), 7.86 (1H, s), 8.56 (1H, s), 8.76 (1H, s). MS (ESI$^+$): m/z 504.

Preparation 198

1-tert-butyl 7-ethyl 2-[(5-bromo-3-pyridinyl)carbonyl]-2-[(cyclohexyloxy)acetyl]heptanedioate $^1$H NMR (CDCl$_3$) δ 1.24 (3H, t, J=7 Hz), 1.39 (9H, s), 1.16-1.88 (14H, m), 2.15-2.40 (4H, m), 3.16-3.28 (1H, m), 4.10 (2H, q, J=7 Hz), 4.28 (1H, d, J=18 Hz), 4.38 (1H, d, J=18 Hz), 8.20 (1H, m), 8.78 (1H, d, J=2 Hz), 8.84 (1H, d, J=2 Hz). MS (ESI$^+$): m/z 568 570.

Preparation 199

1-tert-butyl 5-ethyl 2-[(cyclohexyloxy)acetyl]-2-[(5-methyl-3-pyridinyl)carbonyl]pentanedioate $^1$H NMR (CDCl$_3$) δ 1.24 (3H, t, J=7 Hz), 1.15-1.38 (4H, m), 1.39 (9H, s), 1.45-1.75 (4H, m), 1.76-1.93 (2H, m), 2.39 (3H, s), 2.45-2.75 (4H, m), 3.17-3.30 (1H, m), 4.12 (2H, q, J=7 Hz), 4.32 (1H, d, J=17 Hz), 4.41 (1H, d, J=17 Hz), 7.88 (1H, s), 8.55 (1H, s), 8.77 (1H, s). MS (ESI$^+$): m/z 476.

Preparation 200

1-tert-butyl 5-ethyl 2-[(5-bromo-3-pyridinyl)carbonyl]-2-[(cyclohexyloxy)acetyl]pentanedioate $^1$H NMR (CDCl$_3$) δ 1.26 (3H, t, J=7 Hz), 1.15-1.35 (4H, m), 1.40 (9H, s), 1.40-1.65 (2H, m), 1.65-1.75 (2H, m), 1.75-1.92 (2H, m), 2.35-2.85 (4H, m), 3.16-3.32 (1H, m), 4.12 (2H, q, J=7 Hz), 4.28 (1H, d, J=17 Hz), 4.35 (1H, d, J=17 Hz), 8.22 (1H, t, J=2 Hz), 8.78 (1H, d, J=2 Hz), 8.87 (1H, d, J=2 Hz). MS (ESI$^+$): m/z 540 542.

Preparation 201

1-tert-butyl 7-ethyl 2-(isopropoxyacetyl)-2-[(5-methyl-3-pyridinyl)carbonyl]heptanedioate $^1$H NMR (CDCl$_3$) δ 1.12 (6H, d, J=7 Hz), 1.23 (3H, t, J=7 Hz), 1.30-1.55 (2H, m), 1.37 (9H, s), 1.63-1.77 (2H, m), 2.19-2.28 (2H, m), 2.28 (2H, t, J=7 Hz), 2.39 (3H, s), 3.53-3.64 (1H, m), 4.10 (2H, q, J=7 Hz), 4.31 (1H, d, J=18 Hz), 4.42 (1H, d, J=18 Hz), 7.86 (1H, s), 8.55 (1H, s), 8.74 (1H, s). MS (ESI$^+$): m/z 464.

Preparation 202

1-tert-butyl 7-ethyl 2-[(5-bromo-3-pyridinyl)carbonyl]-2-(isopropoxyacetyl)heptanedioate $^1$H NMR (CDCl$_3$) δ 1.10 (6H, d, J=7 Hz), 1.24 (3H, t, J=7 Hz), 1.39 (9H, s), 1.18-1.48 (2H, m), 1.64-1.77 (2H, m), 2.18-2.37 (4H, m), 3.52-3.64 (1H, m), 4.12 (2H, q, J=7 Hz), 4.25 (1H, d, J=17 Hz), 4.36 (1H, d, J=17 Hz), 8.19 (1H, t, J=2 Hz), 8.77 (1H, d, J=2 Hz), 8.83 (1H, d, J=2 Hz). MS (ESI$^+$): m/z 528 530.

Preparation 203

1-tert-butyl 7-ethyl 2-[(acetyloxy)acetyl]-2-[(5-methyl-3-pyridinyl)carbonyl]heptanedioate $^1$H NMR (CDCl$_3$) δ 1.24 (3H, t, J=7 Hz), 1.33 (9H, s), 1.20-1.42 (2H, m), 1.63-1.74 (2H, m), 2.14 (3H, s), 2.27-2.38 (4H, m), 2.40 (3H, s), 4.10 (2H, q, J=7 Hz), 5.08 (1H, d, J=18 Hz), 5.36 (1H, d, J=18 Hz), 7.84 (1H, s), 8.56 (1H, s), 8.75 (1H, s). MS (ESI$^+$): m/z 464.

The following compound(s) was (were) obtained in substantially the same manner as that of Preparation 78.

Preparation 204 ethyl 3-[(5-methyl-3-pyridinyl)carbonyl]-4-oxopentanoate $^1$H NMR (CDCl$_3$) δ 1.23 (3H, t, J=7 Hz), 2.21 (3H, s), 2.44 (3H, s), 3.03 (2H, t, J=7 Hz), 4.12 (2H, q, J=7 Hz), 4.96 (1H, t, J=7 Hz), 8.08 (1H, s), 8.66 (1H, s), 9.03 (1H, s). MS (ESI$^+$): m/z 264.

Preparation 205 ethyl 5-[(5-bromo-3-pyridinyl)carbonyl]-6-oxoheptanoate $^1$H NMR (CDCl$_3$) δ 1.25 (3H, t, J=7 Hz), 1.60-1.78 (2H, m), 1.98-2.12 (2H, m), 2.20 (3H, s), 2.36 (2H, t, J=7 Hz), 4.12 (2H, q, J=7 Hz), 4.39 (1H, t, J=7 Hz), 8.38 (1H, m), 8.87 (1H, d, J=2 Hz), 9.08 (1H, d, J=2 Hz).

Preparation 206 ethyl 4-[(5-bromo-3-pyridinyl)carbonyl]-6-methoxy-5-oxohexanoate $^1$H NMR (CDCl$_3$) δ 1.25 (3H, t, J=7 Hz), 2.04-2.16 (1H, m), 2.20-2.34 (1H, m), 2.40-2.48 (2H, m), 3.22 (3H, s), 3.93 (1H, d, J=17 Hz), 4.00 (1H, d, J=17 Hz), 4.12 (2H, q, J=7 Hz), 4.85 (1H, m), 8.47 (1H, m), 8.88 (1H, s), 9.16 (1H, s). MS (ESI$^+$): m/z 372 374.

Preparation 207 benzyl 5-(2-acetyl-7-ethoxy-7-oxoheptanoyl)nicotinate $^1$H NMR (CDCl$_3$) δ 1.24 (3H, t, J=7 Hz), 1.30-1.43 (2H, m), 1.65-1.75 (2H, m), 1.93-2.15 (2H, m), 2.19 (3H, s), 2.29 (2H, t, J=7 Hz), 4.12 (2H, q, J=7 Hz), 4.44 (1H, t, J=7 Hz), 5.43 (2H, s), 7.35-7.50 (5H, m), 8.81 (1H, m), 9.28 (1H, d, J=2 Hz), 939 (1H, d, J=2 Hz). MS (ESI$^+$): m/z 426.

Preparation 208 ethyl 8-(benzyloxy)-6-[(5-methyl-3-pyridinyl)carbonyl]-7-oxooctanoate $^1$H NMR (CDCl$_3$) δ 1.22 (3H, t, J=7 Hz), 1.30-1.43 (2H, m), 1.60-1.69 (2H, m), 1.73-1.86 (1H, m), 1.95-2.08 (1H, m), 2.25 (2H, t, J=7 Hz), 2.34 (3H, s), 4.05 (2H, s), 4.07 (2H, q, J=7 Hz), 4.35-4.45 (2H, m), 4.69 (1H, t, J=7 Hz), 7.09 (2H, m), 7.17-7.25 (3H, m), 7.93 (1H, s), 8.58 (1H, d, J=2 Hz), 8.94 (1H, d, J=2 Hz). MS (ESI$^+$): m/z 412.

Preparation 209 ethyl 6-(benzyloxy)-4-[(5-methyl-3-pyridinyl)carbonyl]-5-oxohexanoate $^1$H NMR (CDCl$_3$) δ 1.23 (3H, t, J=7 Hz), 2.07-2.35 (2H, m), 2.34 (3H, s), 2.38-2.48 (2H, m), 4.05 (2H, s), 4.12 (2H, q, J=7 Hz), 4.34 (1H, d, J=17 Hz), 4.41 (1H, d, J=17 Hz), 4.90 (1H, m), 7.03 (2H, m), 7.15-7.25 (3H, m), 8.00 (1H, s), 8.57 (1H, s), 9.02 (1H, s). MS (ESI$^+$): m/z 384.

Preparation 210 ethyl 8-(cyclohexyloxy)-6-[(5-methyl-3-pyridinyl)carbonyl]-7-oxooctanoate $^1$H NMR (CDCl$_3$) δ 0.91-1.70 (12H, m), 1.23 (3H, t, J=7 Hz), 1.70-1.85 (2H, m), 1.96-2.04 (2H, m), 2.27 (2H, t, J=7 Hz), 2.43 (3H, s), 3.14-3.28 (1H, m), 4.00 (2H, s), 4.12 (2H, q, J=7 Hz), 4.76 (1H, t, J=7 Hz), 8.04 (1H, s), 8.62 (1H, s), 9.00 (1H, s). MS (ESI$^+$): m/z 404.

Preparation 211 ethyl 6-[(5-bromo-3-pyridinyl)carbonyl]-8-(cyclohexyloxy)-7-oxooctanoate $^1$H NMR (CDCl$_3$) δ 0.95-1.87 (14H, m), 1.23 (3H, t, J=7 Hz), 1.96-2.07 (2H, m), 2.28 (2H, t, J=7 Hz), 3.16-3.27 (1H, m), 3.96-4.07 (2H, m), 4.12 (2H, q, J=7 Hz), 4.72 (1H, t, J=7 Hz), 8.38 (1H, m), 8.87 (1H, d, J=2 Hz), 9.08 (1H, d, J=2 Hz). MS (ESI$^+$): m/z 468 470.

Preparation 212 ethyl 6-(cyclohexyloxy)-4-[(5-methyl-3-pyridinyl)carbonyl]-5-oxohexanoate $^1$H NMR (CDCl$_3$) δ 0.88-1.25 (5H, m), 1.24 (3H, t, J=7 Hz), 1.40-1.83 (5H, m), 2.04-2.14 (1H, m), 2.18-2.34 (1H, m), 2.42 (2H, m), 2.44 (3H, s), 3.13-3.27 (1H, m), 4.00 (2H, s), 4.12 (2H, q, J=7 Hz), 4.93 (1H, m), 8.13 (1H, s), 8.63 (1H, d, J=2 Hz), 9.07 (1H, d, J=2 Hz). MS (ESI$^+$): m/z 376.

Preparation 213 ethyl 4-[(5-bromo-3-pyridinyl)carbonyl]-6-(cyclohexyloxy)-5-oxohexanoate $^1$H NMR (CDCl$_3$) δ 0.88-1.85 (10H, m), 1.25 (3H, t, J=7 Hz), 2.02-2.14 (1H, m), 2.18-2.34 (1H, m), 2.40-2.50 (2H, m), 3.15-3.27 (1H, m), 3.97 (1H, d, J=17 Hz), 4.02 (1H, d, J=17 Hz), 4.13 (2H, q, J=7 Hz), 4.87-4.95 (1H, m), 8.48 (1H, t, J=2 Hz), 8.88 (1H, d, J=2 Hz), 9.19 (1H, d, J=2 Hz). MS (ESI$^+$): m/z 440 442.

Preparation 214 ethyl 8-isopropoxy-6-[(5-methyl-3-pyridinyl)carbonyl]-7-oxooctanoate $^1$H NMR (CDCl$_3$) δ 0.86 (3H, d, J=7 Hz), 1.02 (3H, d, J=7 Hz), 1.23 (3H, t, J=7 Hz), 1.30-1.48 (2H, m), 1.60-1.72 (2H, m), 1.72-1.88 (1H, m), 1.95-2.07 (1H, m), 2.27 (2H, t, J=7 Hz), 2.43 (3H, s), 3.44-3.54 (1H, m), 3.95 (1H, d, J=18 Hz), 4.03 (1H, d, J=18 Hz), 4.08 (2H, q, J=7 Hz), 4.73 (1H, t, J=7 Hz), 8.06 (1H, s), 8.63 (1H, s), 9.02 (1H, s). MS (ESI$^+$): m/z 364.

Preparation 215 ethyl 6-[(5-bromo-3-pyridinyl)carbonyl]-8-isopropoxy-7-oxooctanoate $^1$H NMR (CDCl$_3$) δ 0.88 (3H, d, J=7 Hz), 1.03 (3H, t, J=7 Hz), 1.23 (3H, t, J=7 Hz), 1.20-1.46 (2H, m), 1.58-1.72 (2H, m), 1.73-1.87 (1H, m), 1.95-2.07 (1H, m), 2.27 (2H, 1, J=7 Hz), 3.46-3.58 (1H, m), 3.94 (1H, d, J=17 Hz), 4.03 (1H, d, J=17 Hz), 4.10 (2H, q, J=7 Hz), 4.68 (1H, t, J=7 Hz), 8.40 (1H, t, J=2 Hz), 8.86 (1H, d, J=2 Hz), 9.08 (1H, d, J=2 Hz). MS (ESI$^+$): m/z 428 430.

Preparation 216 ethyl 8-(acetyloxy)-6-[(5-methyl-3-pyridinyl)carbonyl]-7-oxooctanoate $^1$H NMR (CDCl$_3$) δ 1.24 (3H, t, J=7 Hz), 1.37-1.47 (2H, m), 1.60-1.77 (2H, m), 2.01 (3H, s), 1.97-2.08 (2H, m), 2.29 (2H, t, J=7 Hz), 2.44 (3H, s), 4.10 (2H, q, J=7 Hz), 4.52 (1H, t, J=7 Hz), 4.68 (1H, d, J=18 Hz), 4.76 (1H, d, J=18 Hz), 8.04 (1H, s), 8.66 (1H, s), 8.98 (1H, s). MS (ESI$^+$): m/z 364.

The following compound(s) was (were) obtained in substantially the same manner as that of Example 21.

EXAMPLE 285 ethyl[7-ethyl-2-methyl-4-(5-methyl-3-pyridinyl)pyrrolo[1,2-b]pyridazin-3-yl]acetate $^1$H NMR (CDCl$_3$) δ 1.24 (3H, t, J=7 Hz), 1.38 (3H, t, J=7 Hz), 2.40 (3H, s), 2.50 (3H, s), 3.02 (2H, q, J=7 Hz), 3.44 (2H, s), 4.14 (2H, q, J=7 Hz), 5.98 (1H, d, J=4 Hz), 6.56 (1H, d, J=4 Hz), 7.55 (1H, s), 8.45 (1H, s), 8.54 (1H, s). MS (ESI$^+$): m/z 338.

EXAMPLE 286 ethyl 7-ethyl-2-methyl-4-(5-methyl-3-pyridinyl)pyrrolo[1,2-b]pyridazine-3-carboxylate $^1$H NMR (CDCl$_3$) δ 0.96 (3H, t, J=7 Hz), 1.38 (3H, t, J=7 Hz), 2.41 (3H, s), 2.61 (3H, s), 3.04 (2H, q, J=7 Hz), 4.05 (2H, q, J=7 Hz), 6.30 (1H, d, J=4 Hz), 6.67 (1H, d, J=4 Hz), 7.58 (1H, s), 8.48 (1H, d, J=2 Hz), 8.51 (1H, d, J=2 Hz). MS (ESI$^+$): m/z 324.

EXAMPLE 287 ethyl 4-[4-(5-bromo-3-pyridinyl)-7-ethyl-2-methylpyrrolo[1,2-b]pyridazin-3-yl]butanoate $^1$H NMR (CDCl$_3$) δ 10.21 (3H, t, J=7 Hz), 1.37 (3H, t, J=7 Hz), 1.67-1.78 (2H, m), 2.22 (3H, s), 2.42-2.54 (2H, m), 2.59 (3H, s), 3.01 (2H, q, J=7 Hz), 4.06 (2H, q, J=7 Hz), 5.87 (1H, d, J=4 Hz), 6.53 (1H, d, J=4 Hz), 7.87 (1H, m), 8.54 (1H, d, J=2 Hz), 8.77 (1H, d, J=2 Hz). MS (ESI$^+$): m/z 430 432.

EXAMPLE 288 ethyl 3-[4-(5-bromo-3-pyridinyl)-7-ethyl-2-(methoxymethyl)pyrrolo[1,2-b]pyridazin-3-yl]propanoate $^1$H NMR (CDCl$_3$) δ 1.20 (3H, t, J=7 Hz), 1.37 (3H, t, J=7 Hz), 2.42 (2H, t, J=7 Hz), 2.85-2.97 (2H, m), 3.06 (2H, q, J=7 Hz), 3.46 (3H, s), 4.08 (2H, q, J=7 Hz), 4.65 (2H, s), 5.94 (1H, d, J=4 Hz), 6.63 (1H, d, J=4 Hz), 7.87 (1H, m), 8.54 (1H, d, J=2 Hz), 8.78 (1H, d, J=2 Hz). MS (ESI$^+$): m/z 446 448.

EXAMPLE 289 ethyl 4-[2-[(acetyloxy)methyl]-4-(5-bromo-3-pyridinyl)-7-ethylpyrrolo[1,2-b]pyridazin-3-yl]butanoate $^1$H NMR (CDCl$_3$) δ 1.20 (3H, t, J=7 Hz), 1.37 (3H, t, J=7 Hz), 1.60-1.75 (2H, m), 2.17 (3H, s), 2.10-2.28 (2H, m), 2.45-2.60 (2H, m), 3.02 (2H, q, J=7 Hz), 4.05 (2H, q, J=7 Hz), 5.32 (2H, s), 5.95 (1H, d, J=4 Hz), 6.63 (1H, d, J=4 Hz), 7.88 (1H, m), 8.55 (1H, m), 8.78 (1H, m). MS (ESI$^+$): m/z 488 490.

EXAMPLE 290 benzyl 5-[3-(5-ethoxy-5-oxopentyl)-7-ethyl-2-methylpyrrolo[1,2-b]pyridazin-4-yl]nicotinate $^1$H NMR (CDCl$_3$) δ 1.24 (3H, t, J=7 Hz), 1.37 (3H, t, J=7 Hz), 1.33-1.60 (4H, m), 2.18 (2H, t, J=7 Hz), 2.35-2.47 (2H, m), 2.56 (3H, s), 3.03 (2H, q, J=7 Hz), 4.10 (2H, q, J=7 Hz), 5.42 (2H, s), 5.82 (1H, d, J=4 Hz), 6.53 (1H, d, J=4 Hz), 7.36-7.47 (5H, m), 8.33 (1H, m), 8.77 (1H, d, J=2 Hz), 933 (1H, d, J=2 Hz). MS (ESI$^+$): m/z 500.

EXAMPLE 291 ethyl 5-[2-[(benzyloxy)methyl]-7-ethyl-4-(5-methyl-3-pyridinyl)pyrrolo[1,2-b]pyridazin-3-yl]pentanoate $^1$H NMR (CDCl$_3$) δ 1.22 (3H, t, J=7 Hz), 1.38 (3H, t, J=7 Hz), 1.20-1.50 (4H, m), 2.06 (2H, t, J=7 Hz), 2.42 (3H, s), 2.47-2.63 (2H, m), 3.05 (2H, q, J=7 Hz), 4.08 (2H, q, J=7 Hz), 4.64 (2H, s), 4.73 (2H, s), 5.90 (1H, d, J=4 Hz), 6.58 (1H, d, J=4 Hz), 7.27-7.39 (5H, m), 7.51 (1H, s), 8.41 (1H, d, J=2 Hz), 8.53 (1H, d, J=2 Hz).

EXAMPLE 292 ethyl 3-[2-[(benzyloxy)methyl]-7-ethyl-4-(5-methyl-3-pyridinyl)pyrrolo[1,2-b]pyridazin-3-yl]propanoate $^1$H NMR (CDCl$_3$) δ 1.16 (3H, t, J=7 Hz), 1.38 (3H, t, J=7 Hz), 2.36 (2H, t, J=7 Hz), 2.42 (3H, s), 2.80-3.00 (2H, m), 3.06 (2H, q, J=7 Hz), 4.03 (2H, q, J=7 Hz), 4.65 (2H, s), 4.75 (2H, s), 5.92 (1H, d, J=2 Hz), 6.59 (1H, d, J=2 Hz), 7.26-7.38 (5H, m), 7.48 (1H, s), 8.40 (1H, d, J=2 Hz), 8.53 (1H, d, J=2 Hz). MS (ESI$^+$): m/z 458.

EXAMPLE 293 ethyl 5-[2-[(cyclohexyloxy)methyl]-7-ethyl-4-(5-methyl-3-pyridinyl)pyrrolo[1,2-b]pyridazin-3-yl]pentanoate $^1$H NMR (CDCl$_3$) δ 1.20-1.60 (10H, m), 1.25 (3H, t, J=7 Hz), 1.37 (3H, t, J=7 Hz), 1.70-1.83 (2H, m), 1.96-2.07 (2H, m), 2.15 (2H, t, J=7 Hz), 2.43 (3H, s), 2.53-2.68 (2H, m), 3.04 (2H, q, J=7 Hz), 3.42-3.53 (1H, m), 4.08 (2H, q, J=7 Hz), 4.69 (2H, s), 5.88 (1H, d, J=4 Hz), 6.55 (1H, d, J=4 Hz), 7.53 (1H, s), 8.42 (1H, d, J=2 Hz), 8.53 (1H, d, J=2 Hz).

EXAMPLE 294 ethyl 5-{4-(5-bromo-3-pyridinyl)-2-[(cyclohexyloxy)methyl]-7-ethylpyrrolo[1,2-b]pyridazin-3-yl}pentanoate $^1$H NMR (CDCl$_3$) δ 1.22-1.62 (10H, m), 1.23 (3H, t, J=7 Hz), 1.37 (3H, t, J=7 Hz), 1.73-1.86 (2H, m), 1.98-2.07 (2H, m), 2.18 (2H, t, J=7 Hz), 2.53-2.70 (2H, m), 3.03 (2H, q, J=7 Hz), 3.42-3.56 (1H, m), 4.12 (2H, q, J=7 Hz), 4.69 (2H, s), 5.88 (1H, d, J=4 Hz), 6.58 (1H, d, J=4 Hz), 7.88 (1H, m), 8.54 (1H, d, J=2 Hz), 8.77 (1H, d, J=2 Hz).

EXAMPLE 295 ethyl 3-[2-[(cyclohexyloxy)methyl]-7-ethyl-4-(5-methyl-3-pyridinyl)pyrrolo[1,2-b]pyridazin-3-yl]propanoate $^1$H NMR (CDCl$_3$) δ 1.19 (3H, t, J=7 Hz), 1.37 (3H, t, J=7 Hz), 1.16-1.45 (4H, m), 1.52-1.65 (2H, m), 1.73-1.83 (2H, m), 1.98-2.07 (2H, m), 2.35-2.47 (2H, m), 2.42 (3H, s), 2.84-2.98 (2H, m), 3.03 (2H, q, J=7 Hz), 3.45-3.56 (1H, m), 4.06 (2H, q, J=7 Hz), 4.71 (2H, s), 5.89 (1H, d, J=4 Hz), 6.58 (1H, d, J=4 Hz), 7.50 (1H, s), 8.42 (1H, s), 8.53 (1H, s). MS (ESI$^+$): m/z 450.

EXAMPLE 296 ethyl 3-{4-(5-bromo-3-pyridinyl)-2-[(cyclohexyloxy)methyl]-7-ethylpyrrolo[1,2-b]pyridazin-3-yl}propanoate $^1$H NMR (CDCl$_3$) δ 1.20 (3H, t, J=7 Hz), 1.37 (3H, t, J=7 Hz), 1.15-1.60 (6H, m), 1.73-1.85 (2H, m), 1.97-2.08 (2H, m), 2.45 (2H, t, J=7 Hz), 2.83-2.97 (2H, m), 3.05 (2H, q, J=7 Hz), 3.42-3.56 (1H, m), 4.08 (2H, q, J=7 Hz), 4.71 (2H, s), 5.90 (1H, d, J=4 Hz), 6.58 (1H, d, J=4 Hz), 7.86 (1H, t, J=2 Hz), 8.53 (1H, d, J=2 Hz), 8.77 (1H, d, J=2 Hz). MS (ESI$^+$): m/z 514 516.

EXAMPLE 297 ethyl 5-[7-ethyl-2-(isopropoxymethyl)-4-(5-methyl-3-pyridinyl)pyrrolo[1,2-b]pyridazin-3-yl]pentanoate $^1$H NMR (CDCl$_3$) δ 1.23 (3H, t, J=7 Hz), 1.26 (6H, d, J=7 Hz), 1.37 (3H, t, J=7 Hz), 1.38-1.62 (4H, m), 2.17 (2H, t, J=7 Hz), 2.43 (3H, s), 2.53-2.68 (2H, m), 3.03 (2H, q, J=7 Hz), 3.76-3.88 (1H, m), 4.08 (2H, q, J=7 Hz), 4.66 (2H, s), 5.88 (1H, d, J=4 Hz), 6.57 (1H, d, J=4 Hz), 7.52 (1H, s), 8.42 (1H, s), 8.53 (1H, s). MS (ESI$^+$): m/z 438.

EXAMPLE 298 ethyl 5-[4-(5-bromo-3-pyridinyl)-7-ethyl-2-(isopropoxymethyl)pyrrolo[1,2-b]pyridazin-3-yl]pentanoate $^1$H NMR (CDCl$_3$) δ 1.23 (3H, t, J=7 Hz), 1.25 (6H, d, J=7 Hz), 1.37 (3H, t, J=7 Hz), 1.37-1.64 (4H, m), 2.15 (2H, t, J=7 Hz), 2.54-2.72 (2H, m), 3.02 (2H, q, J=7 Hz), 3.75-3.87 (1H, m), 4.09 (2H, q, J=7 Hz), 4.66 (2H, s), 5.89 (1H, d, J=4 Hz), 6.58 (1H, d, J=4 Hz), 7.88 (1H, m), 8.55 (1H, d, J=2 Hz), 8.78 (1H, d, J=2 Hz). MS (ESI$^+$): m/z 502 504.

EXAMPLE 299 ethyl 5-[2-[(acetyloxy)methyl]-7-ethyl-4-(5-methyl-3-pyridinyl)pyrrolo[1,2-b]pyridazin-3-yl]pentanoate $^1$H NMR (CDCl$_3$) δ 1.23 (3H, t, J=7 Hz), 1.37 (3H, t, J=7 Hz), 1.30-158 (4H, m), 2.13 (2H, t, J=7 Hz), 2.18 (3H, s), 2.44 (3H, s), 2.40-2.55 (2H, m), 3.02 (2H, q, J=7 Hz), 4.08 (2H, q, J=7 Hz), 5.29 (2H, s), 5.93 (1H, d, J=4 Hz), 6.62 (1H, d, J=4 Hz), 7.52 (1H, s), 8.42 (1H, s), 8.53 (1H, s). MS (ESI$^+$): m/z 438.

The following compound(s) was (were) obtained in substantially the same manner as that of Example 236.

EXAMPLE 300 ethyl 4-{4-[5-(1-ethoxyvinyl)-3-pyridinyl]-7-ethyl-2-methylpyrrolo[1,2-b]pyridazin-3-yl}butanoate $^1$H NMR (CDCl$_3$) δ 1.24 (3H, t, J=7 Hz), 1.38 (3H, t, J=7 Hz), 1.41 (3H, t, J=7 Hz), 1.68-1.80 (2H, m), 2.22 (2H, t, J=7 Hz), 2.44-2.54 (2H, m), 2.59 (3H, s), 3.03 (2H, q, J=7 Hz), 3.95 (2H, q, J=7 Hz), 4.10 (2H, q, J=7 Hz), 4.36 (1H, d, J=3 Hz), 4.77 (1H, d, J=3 Hz), 5.88 (1H, d, J=4 Hz), 6.52 (1H, d, J=4 Hz), 7.92 (1H, m), 8.53 (1H, d, J=2 Hz), 8.93 (1H, d, J=2 Hz). MS (ESI$^+$): m/z 422.

EXAMPLE 301 ethyl 3-[4-[5-(1-ethoxyvinyl)-3-pyridinyl]-7-ethyl-2-(methoxymethyl)pyrrolo[1,2-b]pyridazin-3-yl]propanoate $^1$H NMR (CDCl$_3$) δ 1.19 (3H, 1, J=7 Hz), 1.26 (3H, t, J=7 Hz), 1.37 (3H, t, J=7 Hz), 2.42 (2H, t, J=7 Hz), 2.84-2.97 (2H, m), 3.07 (2H, q, J=7 Hz), 3.47 (3H, s), 3.97 (2H, q, J=7 Hz), 4.08 (2H, q, J=7 Hz), 4.36 (1H, d, J=3 Hz), 4.66 (2H, s), 4.77 (1H, d, J=3 Hz), 5.95 (1H, d, J=4 Hz), 6.61 (1H, d, J=4 Hz), 7.92 (1H, m), 8.54 (1H, d, J=2 Hz), 8.95 (1H, d, J=2 Hz). MS (ESI$^+$): m/z 438.

EXAMPLE 302 ethyl 3-[7-ethyl-2-(methoxymethyl)-4-(5-vinyl-3-pyridinyl)pyrrolo[1,2-b]pyridazin-3-yl]propanoate $^1$H NMR (CDCl$_3$) δ 1.18 (3H, t, J=7 Hz), 1.38 (3H, t, J=7 Hz), 2.40 (2H, t, J=7 Hz), 2.84-2.98 (2H, m), 3.03 (2H, q, J=7 Hz), 3.47 (3H, s), 4.04 (2H, q, J=7 Hz), 4.65 (2H, s), 5.46 (1H, d, J=11 Hz), 5.87 (1H, d, J=18 Hz), 5.94 (1H, d, J=4 Hz), 6.60 (1H, d, J=4 Hz), 6.72-6.83 (1H, dd, J=11 Hz, 18 Hz), 7.74 (1H, m), 8.49 (1H, d, J=2 Hz), 8.72 (1H, d, J=2 Hz). MS (ESI$^+$): m/z 394.

EXAMPLE 303 methyl 4-[7-ethyl-2-(methoxymethyl)-4-(5-vinyl-3-pyridinyl)pyrrolo[1,2-b]pyridazin-3-yl]butanoate $^1$H NMR (CDCl$_3$) δ 1.38 (3H, t, J=7 Hz), 1.65-1.78 (2H, m), 2.23 (2H, t, J=7 Hz), 2.54-2.70 (2H, m), 3.05 (2H, q, J=7 Hz), 3.47 (3H, s), 3.58 (3H, s), 4.67 (2H, s), 5.46 (1H, d, J=11 Hz), 5.88 (1H, d, J=18 Hz), 5.93 (1H, d, J=4 Hz), 6.58 (1H, d, J=4 Hz), 6.73-6.83 (1H, dd, J=11 Hz, 18 Hz), 7.77 (1H, m), 8.51 (1H, d, J=2 Hz), 8.71 (1H, d, J=2 Hz). MS (ESI$^+$): m/z 394.

EXAMPLE 304 methyl 4-[4-[5-(1-ethoxyvinyl)-3-pyridinyl]-7-ethyl-2-(methoxymethyl)pyrrolo[1,2-b]pyridazin-3-yl]butanoate $^1$H NMR (CDCl$_3$) δ 1.26 (3H, t, J=7 Hz), 1.38 (3H, t, J=7 Hz), 1.67-1.82 (2H, m), 2.22 (2H, t, J=7 Hz), 2.53-2.67 (2H, m), 3.04 (2H, q, J=7 Hz), 3.47 (3H, s), 3.58 (3H, s), 3.95 (2H, q, J=7 Hz), 4.34 (1H, d, J=2 Hz), 4.67 (2H, s), 4.77 (1H, d, J=2 Hz), 5.93 (1H, d, J=4 Hz), 6.59 (1H, d, J=4 Hz), 7.92 (1H, m), 8.54 (1H, d, J=2 Hz), 8.95 (1H, d, J=2 Hz). MS (ESI$^+$): m/z 438.

EXAMPLE 305 ethyl 3-{4-[5-(1-ethoxyvinyl)-3-pyridinyl]-7-ethyl-2-methylpyrrolo[1,2-b]pyridazin-3-yl}propanoate $^1$H NMR (CDCl$_3$) δ 1.19 (3H, t, J=7 Hz), 1.38 (3H, t, J=7 Hz), 1.44 (3H, t, J=7 Hz), 2.33-2.43 (2H, m), 2.58 (3H, s), 2.76-2.87 (2H, m), 3.03 (2H, q, J=7 Hz), 3.96 (2H, q, J=7 Hz), 4.06 (2H, q, J=7 Hz), 4.36 (1H, d; J=2 Hz), 4.77 (1H, d, J=2 Hz), 5.91 (1H, d, J=4 Hz), 6.54 (1H, d, J=4 Hz), 7.91 (1H, m), 8.53 (1H, d, J=2 Hz), 8.96 (1H, d, J=2 Hz). MS (ESI$^+$): m/z 408.

The following compound(s) was (were) obtained in substantially the same manner as that of Example 251.

EXAMPLE 306 ethyl 4-[4-(5-acetyl-3-pyridinyl)-7-ethyl-2-methylpyrrolo[1,2-b]pyridazin-3-yl]butanoate $^1$H NMR (CDCl$_3$) δ 1.19 (3H, t, J=7 Hz), 1.38 (3H, t, J=7 Hz), 1.66-1.82 (2H, m), 2.21 (2H, t, J=7 Hz), 2.41-2.51 (2H, m), 2.60 (3H, s), 2.69 (3H, s), 3.03 (2H, q, J=7 Hz), 4.03 (2H, q, J=7 Hz), 5.83 (1H, d, J=4 Hz), 6.53 (1H, d, J=4 Hz), 8.25 (1H, m), 8.79 (1H, d, J=2 Hz), 9.25 (1H, d, J=2 Hz). MS (ESI$^+$): m/z 394.

EXAMPLE 307 ethyl 3-[4-(5-acetyl-3-pyridinyl)-7-ethyl-2-(methoxymethyl)pyrrolo[1,2-b]pyridazin-3-yl]propanoate $^1$H NMR (CDCl$_3$) δ 1.18 (3H, t, J=7 Hz), 1.38 (3H, t, J=7 Hz), 2.41 (2H, t, J=7 Hz), 2.70 (3H, s), 2.83-2.96 (2H, m), 3.06 (2H, q, J=7 Hz), 3.47 (3H, s), 4.03 (2H, q, J=7 Hz), 4.66 (2H, s), 5.88 (1H, d, J=4 Hz), 6.61 (1H, d, J=4 Hz), 8.26 (1H, m), 8.79 (1H, d, J=2 Hz), 9.25 (1H, d, J=2 Hz).

EXAMPLE 308 methyl 4-[4-(5-acetyl-3-pyridinyl)-7-ethyl-2-(methoxymethyl)pyrrolo[1,2-b]pyridazin-3-yl]butanoate $^1$H NMR (CDCl$_3$) δ 1.38 (3H, t, J=7 Hz), 1.64-1.80 (2H, m), 2.20 (2H, t, J=7 Hz), 2.53-2.65 (2H, m), 2.70 (3H, s), 3.05 (2H, q, J=7 Hz), 3.47 (3H, s), 3.57 (3H, s), 4.67 (2H, s), 5.87 (1H, d, J=4 Hz), 6.60 (1H, d, J=4 Hz), 8.27 (1H, s), 8.81 (1H, d, J=2 Hz), 9.26 (1H, d, J=2 Hz). MS (ESI$^+$): m/z 410.

EXAMPLE 309 ethyl 3-[4-(5-acetyl-3-pyridinyl)-7-ethyl-2-methylpyrrolo[1,2-b]pyridazin-3-yl]propanoate $^1$H NMR (CDCl$_3$) δ 1.19 (3H, t, J=7 Hz), 1.38 (3H, t, J=7 Hz), 2.33-2.42 (2H, m), 2.59 (3H, s), 2.69 (3H, s), 2.75-2.83 (2H, m), 3.02 (2H, q, J=7 Hz), 4.05 (2H, q, J=7 Hz), 5.83 (1H, d, J=4 Hz), 6.53 (1H, d, J=4 Hz), 8.25 (1H, m), 8.78 (1H, d, J=2 Hz), 9.26(1H, d, J=2 Hz). MS (ESI$^+$): m/z 380.

EXAMPLE 310

A mixture of benzyl 5-[3-(5-ethoxy-5-oxopentyl)-7-ethyl-2-methylpyrrolo[1,2-b]pyridazin-4-yl]nicotinate (330 mg) and 10% palladium on carbon (33 mg) in methanol (10 mL) was stirred under 4 atm hydrogen atmosphere at ambient temperature for 2 hours. The catalysts were filtered off and washed with chloroform. The filtrates were evaporated in vacuo to give 5-[3-(5-ethoxy-5-oxopentyl)-7-ethyl-2-methylpyrrolo[1,2-b]pyridazin-4-yl]nicotinic acid as yellow oil (272 mg).

5-[3-(5-ethoxy-5-oxopentyl)-7-ethyl-2-methylpyrrolo[1,2-b]pyridazin-4-yl]nicotinic acid $^1$H NMR (CDCl$_3$) δ 1.21 (3H, t, J=7 Hz), 1.37 (3H, t, J=7 Hz), 1.35-1.63 (4H, m), 2.19 (2H, t, J=7 Hz), 2.38-2.49 (2H, m), 2.57 (3H, s), 3.03 (2H, q, J=7 Hz), 4.11 (2H, q, J=7 Hz), 5.85 (1H, d, J=4 Hz), 6.53 (1H, d, J=4 Hz), 8.40 (1H, m), 8.83 (1H, d, J=2 Hz), 937 (1H, d, J=2 Hz). MS (ESI$^-$): m/z 408, MS (ESI$^+$): m/z 410.

EXAMPLE 311

To a solution of 5-[3-(5-ethoxy-5-oxopentyl)-7-ethyl-2-methylpyrrolo[1,2-b]pyridazin-4-yl]nicotinic acid (235 mg) and triethylamine (87.1 mg) in t-butanol (10 mL) was added diphenylphosphoryl azide (237 mg) and the mixture was heated under reflux for 2 hours. After evaporation of solvent, the residue was partitioned between ethyl acetate and water. The organic layer was separated, washed with brine, dried over magnesium sulfate, and evaporated in vacuo. The residue was purified by silica gel column chromatography eluting with a mixture of hexane and ethyl acetate (20:1-2:1) to give ethyl 5-(4-{5-[(tert-butoxycarbonyl)amino]-3-pyridinyl}-7-ethyl-2-methylpyrrolo[1,2-b]pyridazin-3-yl)pentanoate as yellow oil (190 mg).

ethyl 5-(4-{5-[(tert-butoxycarbonyl)amino]-3-pyridinyl}-7-ethyl-2-methylpyrrolo[1,2-b]pyridazin-3-yl)pentanoate $^1$H NMR (CDCl$_3$) δ 1.24 (3H, t, J=7 Hz), 1.37 (3H, t, J=7 Hz), 1.42-1.67 (4H, m), 1.52 (9H, s), 2.19-2.28 (2H, m), 2.38-2.50 (2H, m), 2.55 (3H, s), 3.03 (2H, q, J=7 Hz), 4.12 (2H, q, J=7 Hz), 5.92 (1H, d, J=4 Hz), 6.53 (1H, d, J=4 Hz), 6.93 (1H, br), 7.87 (1H, s), 8.30 (1H, d, J=2 Hz), 8.70 (1H, d, J=2 Hz). MS (ESI$^+$): m/z 481.

EXAMPLE 312

A solution of ethyl 5-(4-{5-[(tert-butoxycarbonyl)amino]-3-pyridinyl}-7-ethyl-2-methylpyrrolo[1,2-b]pyridazin-3-yl)pentanoate (190 mg) in 2 N hydrogen chloride ethyl acetate solution (4 mL) was stirred at ambient temperature for 2 hours. After evaporation of solvent, the residue was partitioned between ethyl acetate and saturated sodium bicarbonate solution. The organic layer was separated, washed with brine, dried over magnesium sulfate, and evaporated in vacuo. The residue was purified by silica gel column chromatography eluting with a mixture of chloroform and methanol (100:1-20:1) to give ethyl 5-[4-(5-amino-3-pyridinyl)-7-ethyl-2-methylpyrrolo[1,2-b]pyridazin-3-yl]pentanoate as yellow oil (140 mg).

ethyl 5-[4-(5-amino-3-pyridinyl)-7-ethyl-2-methylpyrrolo[1,2-b]pyridazin-3-yl]pentanoate $^1$H NMR (CDCl$_3$) δ 1.24 (3H, t, J=7 Hz), 1.37 (3H, t, J=7 Hz), 1.40-1.65 (4H, m), 2.23 (2H, t, J=7 Hz), 2.45 (2H, t, J=7 Hz), 2.54 (3H, s), 3.03 (2H, q, J=7 Hz), 3.97 (2H, br), 4.12 (2H, q, J=7 Hz), 5.94 (1H, d, J=4 Hz), 6.53 (1H, d, J=4 Hz), 7.02 (1H, m), 8.02 (1H, d, J=2 Hz), 8.17 (1H, d, J=2 Hz). MS (ESI$^+$): m/z 381 (M+H).

EXAMPLE 313

To a solution of ethyl 5-[4-(5-amino-3-pyridinyl)-7-ethyl-2-methylpyrrolo[1,2-b]pyridazin-3-yl]pentanoate (55 mg), 37% formaldehyde solution (277 mg) and sodium cyanoborohydride (273 mg) in acetonitrile (1 mL) and methanol (1 mL) was added acetic acid (2 drops) and the mixture was stirred at ambient temperature for 2 hours. The solution was diluted with saturated sodium bicarbonate solution and extracted with chloroform. The organic layer was washed with brine, dried over magnesium sulfate, and evaporated in vacuo. The residue was purified by preparative silica gel column chromatography eluting with a mixture of chloroform and methanol (20:1) to give ethyl 5-{4-[5-(dimethylamino)-3-pyridinyl]-7-ethyl-2-methylpyrrolo[1,2-b]pyridazin-3-yl}pentanoate as yellow oil (365 mg).

ethyl 5-{4-[5-(dimethylamino)-3-pyridinyl]-7-ethyl-2-methylpyrrolo[1,2-b]pyridazin-3-yl}pentanoate $^1$H NMR (CDCl$_3$) δ 1.23 (3H, t, J=7 Hz), 1.37 (3H, t, J=7 Hz), 1.40-1.63 (4H, m), 2.19 (2H, t, J=7 Hz), 2.40-2.53 (2H, m), 2.55 (3H, s), 3.02 (6H, s), 3.03 (2H, q, J=7 Hz), 4.09 (2H, q, J=7 Hz), 5.93 (1H, d, J=4 Hz), 6.50 (1H, d, J=4 Hz), 6.96 (1H, m), 7.95 (1H, d, J=2 Hz), 8.20 (1H, d, J=2 Hz). MS (ESI$^+$): m/z 409.

The following compound(s) was (were) obtained in substantially the same manner as that of Example 245.

EXAMPLE 314

3-[7-ethyl-4-(5-ethyl-3-pyridinyl)-2-(methoxymethyl)pyrrolo[1,2-b]pyridazin-3-yl]propanoic acid $^1$H NMR (CDCl$_3$) δ 1.29 (3H, t, J=7 Hz), 1.37 (3H, t, J=7 Hz), 2.45-2.58 (2H, m), 2.73 (2H, q, J=7 Hz), 2.82-3.02 (2H, m), 3.03 (2H, q, J=7 Hz), 3.47 (3H, s), 4.67 (2H, s), 5.91 (1H, d, J=4 Hz), 6.59 (1H, d, J=4 Hz), 7.58 (1H, m), 8.43 (1H, d, J=2 Hz), 8.53 (1H, d, J=2 Hz). MS (ESI$^-$): m/z 366, MS (ESI$^+$): m/z 368.

EXAMPLE 315

4-[7-ethyl-4-(5-ethyl-3-pyridinyl)-2-(methoxymethyl)pyrrolo[1,2-b]pyridazin-3-yl]butanoic acid $^1$H NMR (CDCl$_3$) δ 1.31 (3H, t, J=7 Hz), 1.38 (3H, t, J=7 Hz), 1.69-1.85 (2H, m), 2.20-2.31 (2H, m), 2.52-2.75 (2H, m), 2.77 (2H, q, J=7 Hz), 3.06 (2H, q, J=7 Hz), 3.46 (3H, s), 4.60-4.80 (2H, m), 5.91 (1H, d, J=4 Hz), 6.58 (1H, d, J=4 Hz), 7.61 (1H, s), 8.44-8.53 (2H, m). MS (ESI$^+$): m/z 382.

The following compound(s) was (were) obtained in substantially the same manner as that of Example 228.

EXAMPLE 316 methyl 4-[4-(5-bromo-3-pyridinyl)-7-ethyl-2-(hydroxymethyl)pyrrolo[1,2-b]pyridazin-3-yl]butanoate $^1$H NMR (CDCl$_3$) δ 1.38 (3H, t, J=7 Hz), 1.65-1.79 (2H, m), 2.25 (2H, t, J=7 Hz), 2.39-2.53 (2H, m), 3.06 (2H, q, J=7 Hz), 3.61 (3H, s), 4.90 (2H, s), 5.96 (1H, d, J=4 Hz), 6.62 (1H, d, J=4 Hz), 7.88 (1H, m), 8.55 (1H, d, J=2 Hz), 8.79 (1H, d, J=2 Hz). MS (ESI$^+$): m/z 432 434.

EXAMPLE 317 ethyl 5-[7-ethyl-2-(hydroxymethyl)-4-(5-methyl-3-pyridinyl)pyrrolo[1,2-b]pyridazin-3-yl]pentanoate $^1$H NMR (CDCl$_3$) δ 1.23 (3H, t, J=7 Hz), 1.38 (3H, t, J=7 Hz), 1.35-1.60 (4H, m), 2.17 (2H, t, J=7 Hz), 2.35-2.45 (2H, m), 2.43 (3H, s), 3.04 (2H, q, J=7 Hz), 3.83 (1H, t, J=7 Hz), 4.10 (2H, q, J=7 Hz), 4.85 (2H, d, J=7 Hz), 5.96 (1H, d, J=4 Hz), 6.57 (1H, d, J=4 Hz), 7.50 (1H, s), 8.42 (1H, s), 8.54 (1H, s). MS (ESI$^+$): m/z 396.

The following compound(s) was (were) obtained in substantially the same manner as that of Example 268.

EXAMPLE 318 methyl 4-[4-(5-bromo-3-pyridinyl)-7-ethyl-2-(methoxymethyl)pyrrolo[1,2-b]pyridazin-3-yl]butanoate $^1$H NMR (CDCl$_3$) δ 1.37 (3H, t, J=7 Hz), 1.65-1.79 (2H, m), 2.24 (2H, t, J=7 Hz), 2.52-2.70 (2H, m), 3.04 (2H, q, J=7 Hz), 3.46 (3H, s), 3.60 (3H, s), 4.76 (2H, s), 5.93 (1H, d, J=4 Hz), 6.62 (1H, d, J=4 Hz), 7.88 (1H, m), 8.56 (1H, d, J=2 Hz), 8.79 (1H, d, J=2 Hz). MS (ESI$^+$): m/z 446 448.

EXAMPLE 319 ethyl 5-[2-[(2-tert-butoxy-2-oxoethoxy)methyl]-7-ethyl-4-(5-methyl-3-pyridinyl)pyrrolo[1,2-b]pyridazin-3-yl]pentanoate $^1$H NMR (CDCl$_3$) δ 1.24 (3H, t, J=7 Hz), 1.37 (3H, t, J=7 Hz), 1.30-1.60 (4H, m), 1.47 (9H, s), 2.17 (2H, t, J=7 Hz), 2.43 (3H, s), 2.58-2.72 (2H, m), 3.03 (2H, q, J=7 Hz), 4.08 (2H, s), 4.12 (2H, q, J=7 Hz), 4.81 (2H, s), 5.91 (1H, d, J=4 Hz), 6.58 (1H, d, J=4 Hz), 7.53 (1H, s), 8.43 (1H, s), 8.53 (1H, s). MS (ESI$^+$): m/z 510.

EXAMPLE 320 ethyl 5-[2-[(cyclopropylmethoxy)methyl]-7-ethyl-4-(5-methyl-3-pyridinyl)pyrrolo[1,2-b]pyridazin-3-yl]pentanoate $^1$H NMR (CDCl$_3$) δ 0.20-0.32 (2H, m), 0.53-0.63 (2H, m), 1.07-1.20 (1H, m), 1.22 (3H, t, J=7 Hz), 1.37 (3H, t, J=7 Hz), 1.40-1.60 (4H, m), 2.15 (2H, t, J=7 Hz), 2.43 (3H, s), 2.53-2.68 (2H, m), 3.02 (2H, q, J=7 Hz), 3.41 (2H, d, J=7 Hz), 4.08 (2H, q, J=7 Hz), 4.70 (2H, s), 5.89 (1H, d, J=4 Hz), 6.56 (1H, d, J=4 Hz), 7.52 (1H, s), 8.43 (1H, s), 8.53 (1H, s). MS (ESI$^+$): m/z 450.

EXAMPLE 321 ethyl 5-[2-[(cyclohexylmethoxy)methyl]-7-ethyl-4-(5-methyl-3-pyridinyl)pyrrolo[1,2-b]pyridazin-3-yl]pentanoate $^1$H NMR (CDCl$_3$) δ 0.88-1.05 (2H, m), 1.16-1.35 (4H, m), 1.25 (3H, t, J=7 Hz), 1.37 (3H, t, J=7 Hz), 1.38-1.59 (4H, m), 1.60-1.87 (5H, m), 2.16 (2H, t, J=7 Hz), 2.43 (3H, s), 2.54-2.67 (2H, m), 3.03 (2H, q, J=7 Hz), 3.35 (2H, d, J=7 Hz), 4.10 (2H, q, J=7 Hz), 4.64 (2H, s), 5.89 (1H, d, J=4 Hz), 6.56 (1H, d, J=4 Hz), 7.52 (1H, s), 8.43 (1H, d, J=2 Hz), 8.53 (1H, d, J=2 Hz). MS (ESI$^+$): m/z 492.

EXAMPLE 322 ethyl 5-{7-ethyl-4-(5-methyl-3-pyridinyl)-2-[(3-pyridinylmethoxy)methyl]pyrrolo[1,2-b]pyridazin-3-yl}pentanoate $^1$H NMR (CDCl$_3$) δ 1.22 (3H, t, J=7 Hz), 1.39 (3H, t, J=7 Hz), 1.35-1.54 (4H, m), 2.12 (2H, t, J=7 Hz), 2.43 (3H, s), 2.50-2.63 (2H, m), 3.03 (2H, q, J=7 Hz), 4.08 (2H, q, J=7 Hz), 4.66 (2H, s), 4.76 (2H, s), 5.92 (1H, d, J=4 Hz), 6.60 (1H, d, J=4 Hz), 7.28 (1H, m), 7.52 (1H, s), 7.72 (1H, d, J=8 Hz), 8.42 (1H, d, J=2 Hz), 8.54 (2H, m), 8.62 (1H, d, J=2 Hz). MS (ESI$^+$): m/z 487.

EXAMPLE 323 ethyl 5-{7-ethyl-4-(5-methyl-3-pyridinyl)-2-[(2-pyridinylmethoxy)methyl]pyrrolo[1,2-b]pyridazin-3-yl}pentanoate $^1$H NMR (CDCl$_3$) δ 1.21 (3H, t, J=7 Hz), 1.38 (3H, t, J=7 Hz), 1.36-1.54 (4H, m), 2.12 (2H, t, J=7 Hz), 2.42 (3H, s), 2.56-2.68 (2H, m), 3.03 (2H, q, J=7 Hz), 4.08 (2H, q, J=7 Hz), 4.77 (2H, s), 4.85 (2H, s), 5.92 (1H, d, J=4 Hz), 6.58 (1H, d, J=4 Hz), 7.22 (1H, m), 7.43-7.54 (2H, m), 7.66-7.74 (1H, m), 8.41 (1H, d, J=2 Hz), 8.54 (1H, d, J=2 Hz), 8.57 (1H, d, J=5 Hz). MS (ESI$^+$): m/z 487.

EXAMPLE 324 ethyl 5-{7-ethyl-4-(5-methyl-3-pyridinyl)-2-[(4-pyridinylmethoxy)methyl]pyrrolo[1,2-b]pyridazin-3-yl}pentanoate $^1$H NMR (CDCl$_3$) δ 1.22 (3H, t, J=7 Hz), 1.39 (3H, t, J=7 Hz), 1.38-1.57 (4H, m), 2.12 (2H, t, J=7 Hz), 2.43 (3H, s), 2.52-2.68 (2H, m), 3.05 (2H, q, J=7 Hz), 4.08 (2H, q, J=7 Hz), 4.66 (2H, s), 4.77 (2H, s), 5.93 (1H, d, J=4 Hz), 6.60 (1H, d, J=2 Hz), 7.28 (2H, d, J=7 Hz), 7.52 (1H, s), 8.42 (1H, d, J=2 Hz), 8.53 (1H, d, J=2 Hz), 858 (2H, d, J=7 Hz). MS (ESI$^+$): m/z 487.

EXAMPLE 325 ethyl 5-{7-ethyl-4-(5-methyl-3-pyridinyl)-2-[(2-pyrazinylmethoxy)methyl]pyrrolo[1,2-b]pyridazin-3-yl}pentanoate $^1$H NMR (CDCl$_3$) δ 1.22 (3H, t, J=7 Hz), 1.38 (3H, t, J=7 Hz), 1.38-1.57 (4H, m), 2.13 (2H, t, J=7 Hz), 2.43 (3H, s), 2.52-2.68 (2H, m), 3.03 (2H, q, J=7 Hz), 4.07 (2H, q, J=7 Hz), 4.82 (2H, s), 4.88 (2H, m), 5.92 (1H, d, J=4 Hz), 6.60 (1H, d, J=4 Hz), 7.52 (1H, s), 8.43 (1H, d, J=2 Hz), 8.48-8.57 (3H, m), 8.75 (1H, m). MS (ESI$^+$): m/z 488.

EXAMPLE 326 ethyl 5-[4-(3-cyanophenyl)-2-(ethoxymethyl)-7-ethylpyrrolo[1,2-b]pyridazin-3-yl]pentanoate $^1$H NMR (CDCl$_3$) δ 1.18-1.29 (6H, m), 1.34-1.53 (7H, m), 2.14 (2H, t, J=7 Hz), 2.52 (2H, m), 3.02 (2H, q, J=7 Hz), 3.53 (2H, q, J=7 Hz), 4.07 (2H, q, J=7 Hz), 4.66 (1H, s), 5.73 (1 J, d, J=5 Hz), 6.56 (1H, d, J=5 Hz), 7.60 (2H, m), 7.67 (1H, s), 7.75 (1H, m)

EXAMPLE 327 ethyl 5-[2-[(benzyloxy)methyl]-4-(3-cyanophenyl)-7-ethylpyrrolo[1,2-b]pyridazin-3-yl]pentanoate $^1$H NMR (CDCl$_3$) δ 1.22 (3H, t, J=7 Hz), 1.30-1.46 (7H, m), 2.06 (2H, t, J=7 Hz), 2.51 (2H, m), 3.02 (2H, q, J=7 Hz), 4.07 (2H, q, J=7 Hz), 4.64 (3H, s), 4.72 (3H, s), 5.83 (1H, d, J=5 Hz), 6.57 (1H, d, J=5 Hz), 7.25-7.38 (5H, m), 7.57 (2H, d, J=9 Hz), 7.65 (1H, s), 7.74 (1H, m).

EXAMPLE 328 methyl 4-({[4-(3-cyanophenyl)-3-(5-ethoxy-5-oxopentyl)-7-ethylpyrrolo[1,2-b]pyridazin-2-yl]methoxy}methyl)benzoate $^1$H NMR (CDCl$_3$) δ 1.22 (3H, t, J=7 Hz), 1.32-1.49 (7H, m), 2.01 (2H, t, J=7 Hz), 2.52 (2H, m), 3.02 (2H, t, J=7 Hz), 3.92 (3H, s), 4.07 (2H, t, J=7 Hz), 4.69 (2H, s), 4.75 (2H, s), 6.84 (1H, d, J=5 Hz), 6.59 (1H, d, J=5 Hz), 7.43 (2H, d, J=9 Hz), 7.60 (2H, m), 7.65 (1H, s), 7.75 (1H, m), 8.02 (2H, d, J=9 Hz).

EXAMPLE 329

A solution of ethyl 5-[2-[(2-tert-butoxy-2-oxoethoxy)methyl]-7-ethyl-4-(5-methyl-3-pyridinyl)pyrrolo[1,2-b]pyridazin-3-yl]pentanoate (60 mg) in trifluoroacetic acid (2 mL) was stirred at ambient temperature for 2 hours, and evaporated in vacuo to give {[3-(5-ethoxy-5-oxopentyl)-7-ethyl-4-(5-methyl-3-pyridinyl)pyrrolo[1,2-b]pyridazin-2-yl]methoxy}acetic acid as brown oil (55 mg).

{[3-(5-ethoxy-5-oxopentyl)-7-ethyl-4-(5-methyl-3-pyridinyl)pyrrolo[1,2-b]pyridazin-2-yl]methoxy}acetic acid $^1$H NMR (CDCl$_3$) δ 1.25 (3H, t, J=7 Hz), 1.37 (3H, t, J=7 Hz), 1.35-1.60 (4H, m), 2.23 (2H, t, J=7 Hz), 2.50-2.58 (2H, m), 2.67 (3H, s), 3.03 (2H, q, J=7 Hz), 4.08 (2H, q, J=7 Hz), 4.30 (2H, s), 4.87 (2H, s), 5.86 (1H, d, J=4 Hz), 6.67 (1H, d, J=4 Hz), 8.15 (1H, s), 8.69 (1H, s), 8.85 (1H, s). MS (ESI$^-$): m/z 452, MS (ESI$^+$): m/z 454.

EXAMPLE 330

To a solution of {[3-(5-ethoxy-5-oxopentyl)-7-ethyl-4-(5-methyl-3-pyridinyl)pyrrolo[1,2-b]pyridazin-2-yl]methoxy}acetic acid (55 mg), 1-ethyl-3-(3'-dimethylaminopropyl)carbodiimide hydrochloride (34.9 mg) and 1-hydroxybenotriazole (24.6 mg) in dimethylformamide (2 mL) was added morpholine (12.7 mg) and the mixture was stirred at ambient temperature for 1 hour. The mixture was partitioned between ethyl acetate and water. The organic layer was separated, washed with saturated sodium bicarbonate solution, water and brine, dried over magnesium sulfate, and evaporated in vacuo. The residue was purified by silica gel column chromatography eluting with a mixture of ethyl acetate and methanol (50:1-20:1) to give ethyl 5-(7-ethyl-4-(5-methyl-3-pyridinyl)-2-{[2-(4-morpholinyl)-2-oxoethoxy]methyl}pyrrolo[1,2-b]pyridazin-3-yl)pentanoate as yellow oil (50 mg).

ethyl 5-(7-ethyl-4-(5-methyl-3-pyridinyl)-2-{[2-(4-morpholinyl)-2-oxoethoxy]methyl}pyrrolo[1,2-b]pyridazin-3-yl)pentanoate $^1$H NMR (CDCl$_3$) δ 1.22 (3H, t, J=7 Hz), 1.37 (3H, t, J=7 Hz), 1.40-1.63 (4H, m), 2.15 (2H, t, J=7 Hz), 2.43 (3H, s), 2.54-2.68 (2H, m), 3.02 (2H, q, J=7 Hz), 3.48-357 (2H, m), 3.63-3.78 (6H, m), 4.08 (2H, q, J=7 Hz), 4.30 (2H, s), 4.78 (2H, s), 5.93 (H, d, J=4 Hz), 6.60 (1H, d, J=4 Hz), 7.52 (1H, s), 8.43 (1H, d, J=2 Hz), 8.54 (1H, d, J=2 Hz). MS (ESI$^+$): m/z 523.

The following compound(s) was (were) obtained in substantially the same manner as that of Example 330.

EXAMPLE 331 ethyl 5-[7-ethyl-2-{[2-(methylamino)-2-oxoethoxy]methyl}-4-(5-methyl-3-pyridinyl)pyrrolo[1,2-b]pyridazin-3-yl]pentanoate $^1$H NMR (CDCl$_3$) δ 1.23 (3H, t, J=7 Hz), 1.38 (3H, t, J=7 Hz), 1.38-1.62 (4H, m), 2.18 (2H, t, J=7 Hz), 2.44 (3H, s), 2.48-2.62 (2H, m), 2.88 (3H, d, J=7 Hz), 3.03 (2H, q, J=7 Hz), 4.11 (2H, q, J=7 Hz), 4.13 (2H, s), 4.77 (2H, s), 5.94 (1H, d, J=4 Hz), 6.63 (1H, d, J=4 Hz), 6.79 (1H, br), 753 (1H, s), 8.44 (1H, s), 8.56 (1H, s). MS (ESI$^+$): m/z 467.

The following compound(s) was (were) obtained in substantially the same manner as that of Example 271.

EXAMPLE 332 ethyl 5-[2-[(benzylamino)methyl]-7-ethyl-4-(5-methyl-3-pyridinyl)pyrrolo[1,2-b]pyridazin-3-yl]pentanoate $^1$H NMR (CDCl$_3$) δ 1.22 (3H, t, J=7 Hz), 1.38 (3H, t, J=7 Hz), 1.30-1.50 (2H, m), 1.60-1.85 (2H, m), 2.12 (2H, t, J=7 Hz), 2.30-2.45 (2H, m), 2.42 (3H, s), 3.03 (2H, q, J=7 Hz), 3.96 (2H, s), 3.98 (2H, s), 4.08 (2H, q, J=7 Hz), 5.87 (1H, d, J=4 Hz), 6.54 (1H, d, J=4 Hz), 7.27-7.43 (5H, m), 7.48 (1H, s), 8.38 (1H, d, J=2 Hz), 853 (1H, d, J=2 Hz). MS (ESI$^+$): m/z 485.

EXAMPLE 333

A mixture of ethyl 5-[7-ethyl-2-(hydroxymethyl)-4-(5-methyl-3-pyridinyl)pyrrolo[1,2-b]pyridazin-3-yl]pentanoate (100 mg), 1H-isoindole-1,3(2H) dione (44.6 mg) diisopropyl azodicarboxylate (76.7 mg) and triphenylphosphine (99.5 mg) in tetrahydrofuran (2 mL) was stirred at ambient temperature for 1 hour. After evaporation of solvent, the residue was purified by silica gel column chromatography eluting with a mixture of hexane and ethyl acetate (20:1-1:1) to give ethyl 5-[2-[(1,3-dioxo-1,3-dihydro-2H-isoindol-2-yl)methyl]-7-ethyl-4-(5-methyl-3-pyridinyl)pyrrolo[1,2-b]pyridazin-3-yl]pentanoate as yellow oil (107 mg).

ethyl 5-[2-[(1,3-dioxo-1,3-dihydro-2H-isoindol-2-yl)methyl]-7-ethyl-4-(5-methyl-3-pyridinyl)pyrrolo[1,2-b]pyridazin-3-yl]pentanoate $^1$H NMR (CDCl$_3$) δ 0.89 (3H, t, J=7 Hz), 1.26 (3H, t, J=7 Hz), 1.20-1.40 (2H, m), 1.53-1.75 (2H, m), 2.24 (2H, t, J=7 Hz), 2.44 (3H, s), 2.47 (2H, q, J=7 Hz), 2.50-2.64 (2H, m), 4.12 (2H, q, J=7 Hz), 5.10 (2H, s), 5.85 (1H, d, J=4 Hz), 6.43 (1H, d, J=4 Hz), 7.51 (1H, s), 7.78 (2H, m), 7.96 (2H, m), 8.43 (1H, s), 8.55 (1H, s). MS (ESI$^+$): m/z 525.

EXAMPLE 334

A mixture of ethyl 5-[2-[(1,3-dioxo-1,3-dihydro-2H-isoindol-2-yl)methyl]-7-ethyl-4-(5-methyl-3-pyridinyl)pyrrolo[1,2-b]pyridazin-3-yl]pentanoate (107 mg) and hydrazine monohydrate (51.1 mg) in ethanol (2 mL) was heated under reflux for 2 hours. After evaporation of solvent, the residue was partitioned between chloroform and saturated sodium bicarbonate solution. The organic layer was separated, washed with brine, dried over magnesium sulfate, and evaporated in vacuo to give ethyl 5-[2-(aminomethyl)-7-ethyl-4-(5-methyl-3-pyridinyl)pyrrolo[1,2-b]pyridazin-3-yl]pentanoate as yellow oil (67.6 mg).

ethyl 5-[2-(aminomethyl)-7-ethyl-4-(5-methyl-3-pyridinyl)pyrrolo[1,2-b]pyridazin-3-yl]pentanoate $^1$H NMR (CDCl$_3$) δ 1.23 (3H, t, J=7 Hz), 1.38 (3H, t, J=7 Hz), 1.38-1.62 (4H, m), 2.14 (2H, t, J=7 Hz), 2.42 (3H, s), 2.38-2.56 (2H, m), 3.04 (2H, q, J=7 Hz), 4.06 (2H, s), 4.08 (2H, q, J=7 Hz), 5.90 (1H, d, J=4 Hz), 6.55 (1H, d, J=4 Hz), 7.51 (1H, s), 8.41 (1H, s), 8.53 (1H, s). MS (ESI$^+$): m/z 395.

EXAMPLE 335

A mixture of ethyl 5-[2-(aminomethyl)-7-ethyl-4-(5-methyl-3-pyridinyl)pyrrolo[1,2-b]pyridazin-3-yl]pentanoate (67.6 mg) and acetic anhydride (19.2 mg) in dichloromethane (3 mL) was stirred at ambient temperature for 1 hour. The solution was diluted with chloroform, washed with saturated sodium bicarbonate solution and brine, dried over magnesium sulfate, and evaporated in vacuo. The residue was purified by preparative silica gel column chromatography eluting with a mixture of chloroform and methanol (20:1) to give ethyl 5-[2-[(acetylamino)methyl]-7-ethyl-4-(5-methyl-3-pyridinyl)pyrrolo[1,2-b]pyridazin-3-yl]pentanoate as yellow oil (70 mg).

ethyl 5-[2-[(acetylamino)methyl]-7-ethyl-4-(5-methyl-3-pyridinyl)pyrrolo[1,2-b]pyridazin-3-yl]pentanoate $^1$H NMR (CDCl$_3$) δ 1.22 (3H, t, J=7 Hz), 1.40 (3H, t, J=7 Hz), 1.40-1.63 (4H, m), 2.12 (2H, m), 2.15 (3H, s), 2.43 (3H, s), 2.40-2.53 (2H, m), 3.03 (2H, q, J=7 Hz), 4.10 (2H, q, J=7 Hz), 4.66 (2H, m), 5.94 (1H, d, J=4 Hz), 6.59 (1H, d, J=4 Hz), 6.85 (1H, br), 750 (1H, s), 8.40 (1H, d, J=2 Hz), 8.54 (1H, d, J=2 Hz). MS (ESI$^+$): m/z 437.

EXAMPLE 336

To a solution of ethyl 5-[2-(aminomethyl)-7-ethyl-4-(5-methyl-3-pyridinyl)pyrrolo[1,2-b]pyridazin-3-yl]pentanoate (80 mg) and pyridine (1 mL) in dichloromethane (2 mL) was added methanesulfonyl chloride (34.8 mg) under ice-water cooling and the mixture was stirred at ambient temperature for 1 hour. The solution was diluted with chloroform, washed with saturated sodium bicarbonate solution and brine, dried over magnesium sulfate, and evaporated in vacuo. The residue was purified by preparative silica gel column chromatography eluting with a mixture of chloroform and methanol (20:1) to give ethyl 5-(7-ethyl-4-(5-methyl-3-pyridinyl)-2-{[(methylsulfonyl)amino]methyl}pyrrolo[1,2-b]pyridazin-3-yl)pentanoate as yellow oil (62.8 mg)

ethyl 5-(7-ethyl-4-(5-methyl-3-pyridinyl)-2-{[(methylsulfonyl)amino]methyl}pyrrolo[1,2-b]pyridazin-3-yl)pentanoate $^1$H NMR (CDCl$_3$) δ 1.23 (3H, t, J=7 Hz), 1.39 (3H, t, J=7 Hz), 1.40-1.62 (4H, m), 2.19 (2H, t, J=7 Hz), 2.44 (3H, s), 2.38-2.51 (2H, m), 3.02 (2H, q, J=7 Hz), 3.06 (3H, s), 4.08 (2H, q, J=7 Hz), 4.58 (2H, s), 5.63 (1H, br), 5.97 (1H, d, J=4 Hz), 6.61 (1H, d, J=4 Hz), 7.50 (1H, s), 8.41 (1H, d, J=2 Hz), 8.54 (1H, d, J=2 Hz). MS (ESI$^+$): m/z 473.

EXAMPLE 337

A mixture of ethyl 5-[2-(aminomethyl)-7-ethyl-4-(5-methyl-3-pyridinyl)pyrrolo[1,2-b]pyridazin-3-yl]pentanoate (75 mg), benzoic acid (27.9 mg), 1-ethyl-3-(3'-dimethylaminopropyl)carbodiimide hydrochloride (54.7 mg) and 1-hydroxybenotriazole (385 mg) in dimethylformamide (2 mL) was stirred at ambient temperature for 2 hours. The mixture was partitioned between ethyl acetate and water. The organic layer was separated, washed with saturated sodium bicarbonate solution, water and brine, dried over magnesium sulfate, and evaporated in vacuo. The residue was purified by preparative silica gel column chromatography eluting with a mixture of chloroform and methanol (20:1) to give ethyl 5-[2-[(benzoylamino)methyl]-7-ethyl-4-(5-methyl-3-pyridinyl)pyrrolo[1,2-b]pyridazin-3-yl]pentanoate as yellow oil (60 mg).

ethyl 5-[2-[(benzoylamino)methyl]-7-ethyl-4-(5-methyl-3-pyridinyl)pyrrolo[1,2-b]pyridazin-3-yl]pentanoate $^1$H NMR (CDCl$_3$) δ 1.23 (3H, t, J=7 Hz), 1.42 (3H, t, J=7 Hz), 1.42-1.65 (4H, m), 2.17 (2H, t, J=7 Hz), 2.44 (3H, s), 2.44-2.58 (2H, m), 3.06 (2H, q, J=7 Hz), 4.08 (2H, q, J=7 Hz), 4.86 (2H, m), 5.96 (1H, d, J=4 Hz), 6.60 (1H, d, J=4 Hz), 7.46-7.59 (4H, m), 7.78 (1H, br), 7.91-7.97 (2H, m), 8.44 (1H, d, J=2 Hz), 8.56 (1H, d, J=2 Hz). MS (ESI$^+$): m/z 499.

The following compound(s) was (were) obtained in substantially the same manner as that of Example 337.

EXAMPLE 338 ethyl 5-(7-ethyl-4-(5-methyl-3-pyridinyl)-2-{[(2-pyrazinylcarbonyl)amino]methyl}pyrrolo[1,2-b]pyridazin-3-yl)pentanoate $^1$H NMR (CDCl$_3$) δ 1.23 (3H, t, J=7 Hz), 1.41 (3H, t, J=7 Hz), 1.42-1.64 (4H, m), 2.18 (2H, t, J=7 Hz), 2.44 (3H, s), 2.47-2.59 (2H, m), 3.08 (2H, q, J=7 Hz), 4.09 (2H, q, J=7 Hz), 4.89 (2H, d, J=7 Hz), 5.96 (1H, d, J=4 Hz), 6.60 (1H, d, J=4 Hz), 7.53 (1H, s), 8.43 (1H, d, J=2 Hz), 8.55 (1H, d, J=2 Hz), 8.62 (1H, m), 8.79 (1H, m), 9.15 (1H, br), 9.46 (1H, m). MS (ESI$^+$): m/z 501.

EXAMPLE 339

To a solution of ethyl 5-[2-(aminomethyl)-7-ethyl-4-(5-methyl-3-pyridinyl)pyrrolo[1,2-b]pyridazin-3-yl]pentanoate (80 mg) and pyridine (1 mL) in dichloromethane (2 mL) was added methyl chloridocarbonate (34.8 mg) under ice-water cooling and the mixture was stirred at ambient temperature for 2 hours.

After evaporation of solvent, the residue was partitioned between ethyl acetate and water. The organic layer was separated, washed with saturated sodium bicarbonate solution and brine, dried over magnesium sulfate, and evaporated in vacuo. The residue was purified by preparative silica gel column chromatography eluting with a mixture of chloroform and methanol (20:1) to give ethyl 5-[7-ethyl-2-{[(methoxycarbonyl)amino]methyl}-4-(5-methyl-3-pyridinyl)pyrrolo[1,2-b]pyridazin-3-yl]pentanoate as yellow oil (70 mg).

ethyl 5-[7-ethyl-2-{[(methoxycarbonyl)amino]methyl}-4-(5-methyl-3-pyridinyl)pyrrolo[1,2-b]pyridazin-3-yl]pentanoate $^1$H NMR (CDCl$_3$) δ 1.23 (3H, t, J=7 Hz), 1.39 (3H, t, J=7 Hz), 1.40-1.63 (4H, m), 2.19 (2H, t, J=7 Hz), 2.44 (3H, s), 2.40-2.55 (2H, m), 3.03 (2H, q, J=7 Hz), 3.07 (3H, s), 4.12 (2H, q, J=7 Hz), 4.57 (2H, m), 5.72 (1H, br), 5.97 (1H, d, J=4 Hz), 6.61 (1H, d, J=4 Hz), 7.51 (1H, s), 8.41 (1H, s), 8.56 (1H, s).

EXAMPLE 340

To a solution of ethyl 5-[4-(3-cyanophenyl)-7-ethyl-2-(hydroxymethyl)pyrrolo[1,2-b]pyridazin-3-yl]pentanoate (70.0 mg) and triethyl amine (185 mg) in dichloromethane (1 mL) was added methanesulfonyl chloride (20.9 mg) under an ice bath. After stirring for 1 hour, to the mixture was added 1-methylpiperazine (27.0 mg). The mixture was stirred for 0.5 hour under an ice bath and overnight at room temperature. The mixture was partitioned between ethyl acetate and water. The organic layer was washed with brine, dried over magnesium sulfate, and evaporated. Preparative silica gel thin layer chromatography (chloroform-methanol=20-1) afforded ethyl 5-{4-(5-bromo-3-pyridinyl)-7-ethyl-2-[(4-methyl-1-piperazinyl)methyl]pyrrolo[1,2-b]pyridazin-3-yl}pentanoate as an yellow gum (52.4 mg, 63.5%).

ethyl 5-{4-(5-bromo-3-pyridinyl)-7-ethyl-2-[(4-methyl-1-piperazinyl)methyl]pyrrolo[1,2-b]pyridazin-3-yl}pentanoate $^1$H NMR (CDCl$_3$): 1.23 (3H, t, J=7 Hz), 1.33-1.60 (7H, m), 2.16 (2H, t, J=7 Hz), 2.29 (3H, s), 2.34-2.65 (6H, m), 3.00 (2H, q, J=7 Hz), 3.54 (2H, s), 4.08 (2H, q, J=7 Hz), 5.86 (1H, d, J=5 Hz), 6.55 (1H, d, J=5 Hz 9, 7.87 (1H, m), 8.54 (1H, m), 8.77 (1H, m).

EXAMPLE 341

To a solution of ethyl 5-[4-(3-cyanophenyl)-7-ethyl-2-(hydroxymethyl)pyrrolo[1,2-b]pyridazin-3-yl]pentanoate (300 mg, 0.652 mmol) and tetrabromomethane (432 mg, 1.30 mmol) in tetrahydrofuran (3 mL) was added triphenylphosphine (308 mg, 1.17 mmol) over 40 minutes. The mixture was concentrated, and the residue was chromatographed on a flash silica gel column chromatography (ethyl acetate-hexane=1-8 to 1-5) to afford ethyl 5-[2-(bromomethyl)-4-(5-bromo-3-pyridinyl)-7-ethylpyrrolo[1,2-b]pyridazin-3-yl]pentanoate as an yellow gum (229 mg, 50.4%).

ethyl 5-[2-(bromomethyl)-4-(5-bromo-3-pyridinyl)-7-ethylpyrrolo[1,2-b]pyridazin-3-yl]pentanoate $^1$H NMR (CDCl$_3$) δ 1.23 (3H, t, J=7 Hz), 1.37 (3H, t, J=7 Hz), 1.41-1.50 (4H, m), 2.19 (2H, t, J=7 Hz), 2.58 (2H, m), 3.01 (2H, q, J=7 Hz), 4.08 (2H, q, J=7 Hz), 4.66 (2H, s), 5.94 (1H, d, J=5 Hz), 6.63 (1H, d, J=5 Hz), 7.88 (1H, m), 8.55 (1H, m), 8.79 (1H, m).

EXAMPLE 342

A mixture of ethyl 5-[2-(bromomethyl)-4-(5-bromo-3-pyridinyl)-7-ethylpyrrolo[1,2-b]pyridazin-3-yl]pentanoate (70.0 mg) and potassium cyanide (13.1 mg) in N,N-dimethylformamide (1 mL) was stirred for 28 hours at room temperature. The mixture was partitioned between ethyl acetate and water. The organic layer was washed with water (two times), brine, dried over magnesium sulfate, and evaporated to give ethyl 5-[4-(5-bromo-3-pyridinyl)-2-(cyanomethyl)-7-ethylpyrrolo[1,2-b]pyridazin-3-yl]pentanoate as an yellow gum (28.8 mg, 45.9%).

ethyl 5-[4-(5-bromo-3-pyridinyl)-2-(cyanomethyl)-7-ethylpyrrolo[1,2-b]pyridazin-3-yl]pentanoate $^1$H NMR (CDCl$_3$) δ 1.24 (3H, t, J=7 Hz), 1.46-1.65 (7H, m), 2.22 (2H, t, J=7 Hz), 2.48 (2H, m), 3.04 (2H, q, J=7 Hz), 3.98 (2H, s), 4.10 (2H, q, J=7 Hz), 5.98 (1H, d, J=5 Hz), 6.65 (1H, d, J=5 Hz), 7.88 (1H, m), 8.55 (1H, m), 8.81 (1H, m).

The following compound(s) was (were) obtained in substantially the same manner as that of Example 76.

EXAMPLE 343

[7-ethyl-2-methyl-4-(5-methyl-3-pyridinyl)pyrrolo[1,2-b]pyridazin-3-yl]acetic acid $^1$H NMR (CDCl$_3$) δ 1.36 (3H, t, J=7 Hz), 2.45 (3H, s), 2.56 (3H, s), 3.02 (2H, q, J=7 Hz), 3.28 (1H, d, J=17 Hz), 3.53 (1H, d, J=17 Hz), 5.91 (1H, d, J=4 Hz), 6.52 (1H, d, J=4 Hz), 7.71 (1H, s), 8.47 (1H, s), 8.59 (1H, s). MS (ESI$^-$): m/z 308, MS (ESI$^+$): m/z 310.

EXAMPLE 344

4-[4-(5-bromo-3-pyridinyl)-7-ethyl-2-methylpyrrolo[1,2-b]pyridazin-3-yl]butanoic acid $^1$H NMR (CDCl$_3$) δ 1.38 (3H, t, J=7 Hz), 1.65-1.85 (2H, m), 2.31 (2H, t, J=7 Hz), 2.45-2.63 (2H, m), 2.59 (3H, s), 3.03 (2H, q, J=7 Hz), 5.88 (1H, d, J=4 Hz), 6.53 (1H, d, J=4 Hz), 7.90 (1H, s), 8.53 (1H, s), 8.75 (1H, s). MS (ESI$^-$): m/z 400 402, MS (ESI$^+$): m/z 402 404.

EXAMPLE 345

4-[4-(5-acetyl-3-pyridinyl)-7-ethyl-2-methylpyrrolo[1,2-b]pyridazin-3-yl]butanoic acid $^1$H NMR (CDCl$_3$) δ 1.38 (3H, t, J=7 Hz), 1.68-1.82 (2H, m), 2.26 (2H, t, J=7 Hz), 2.45-2.58 (2H, m), 2.60 (3H, s), 2.70 (3H, s), 3.03 (2H, q, J=7 Hz), 5.83 (1H, d, J=4 Hz), 6.54 (1H, d, J=4 Hz), 8.28 (1H, m), 8.77 (1H, d, J=2 Hz), 9.19 (1H, d, J=2 Hz).

EXAMPLE 346

3-[4-(5-bromo-3-pyridinyl)-7-ethyl-2-(methoxymethyl)pyrrolo[1,2-b]pyridazin-3-yl]propanoic acid $^1$H NMR (CDCl$_3$) δ 1.37 (3H, t, J=7 Hz), 2.49 (2H, t, J=7 Hz), 2.80-3.00 (2H, m), 3.05 (2H, q, J=7 Hz), 3.46 (3H, s), 4.66 (2H, s), 5.94 (1H, d, J=4 Hz), 6.62 (1H, d, J=4 Hz), 7.88 (1H, s), 8.55 (1H, s), 8.77 (1H, s). MS (ESI$^-$): m/z 416 418, MS (ESI$^+$): m/z 418 420.

EXAMPLE 347

3-[4-(5-acetyl-3-pyridinyl)-7-ethyl-2-(methoxymethyl)pyrrolo[1,2-b]pyridazin-3-yl]propanoic acid $^1$H NMR (CDCl$_3$) δ 1.38 (3H, t, J=7 Hz), 2.48 (2H, t, J=7 Hz), 2.68 (3H, s), 2.85-2.97 (2H, m), 3.05 (2H, q, J=7 Hz), 3.47 (3H, s), 4.67 (2H, s), 5.88 (1H, d, J=4 Hz), 6.62 (1H, d, J=4 Hz), 8.27 (1H, m), 8.78 (1H, d, J=2 Hz), 9.23 (1H, d, J=2 Hz). MS (ESI$^-$): m/z 380, MS (ESI$^+$): m/z 382.

EXAMPLE 348

3-[7-ethyl-2-(methoxymethyl)-4-(5-vinyl-3-pyridinyl)pyrrolo[1,2-b]pyridazin-3-yl]propanoic acid $^1$H NMR (CDCl$_3$) δ 1.38 (3H, t, J=7 Hz), 2.46-2.58 (2H, m), 2.83-3.03 (2H, m), 3.05 (2H, q, J=7 Hz), 3.47 (3H, s), 4.68 (2H, s), 5.46 (1H, d, J=11 Hz), 5.88 (1H, d, J=18 Hz), 5.93 (1H, d, J=4 Hz), 6.60 (1H, d, J=4 Hz), 6.68-6.82 (1H, dd, J=11 Hz, 18 Hz), 7.78 (1H, m), 8.47 (1H, d, J=2 Hz), 8.68 (1H, d, J=2 Hz). MS (ESI$^-$): m/z 364, MS (ESI$^+$): m/z 366.

EXAMPLE 349

4-[4-(5-bromo-3-pyridinyl)-7-ethyl-2-(methoxymethyl)pyrrolo[1,2-b]pyridazin-3-yl]butanoic acid $^1$H NMR (CDCl$_3$) δ 1.37 (3H, t, J=7 Hz), 1.68-1.82 (2H, m), 2.29 (2H, t, J=7 Hz), 2.55-2.75 (2H, m), 3.04 (2H, q, J=7 Hz), 3.45 (3H, s), 4.64 (2H, s), 5.93 (1H, d, J=4 Hz), 6.61 (1H, d, J=4 Hz), 7.91 (1H, m), 8.56 (1H, d, J=2 Hz), 8.77 (1H, d, J=2 Hz). MS (ESI$^-$): m/z 430 432, MS (ESI$^+$): m/z 432 434.

EXAMPLE 350

4-[7-ethyl-2-(methoxymethyl)-4-(5-vinyl-3-pyridinyl)pyrrolo[1,2-b]pyridazin-3-yl]butanoic acid $^1$H NMR (CDCl$_3$) δ 1.38 (3H, t, J=7 Hz), 1.72-1.87 (2H, m), 2.26 (2H, t, J=7 Hz), 2.53-2.80 (2H, m), 3.06 (2H, q, J=7 Hz), 3.46 (3H, s), 4.68 (2H, m), 5.47 (1H, d, J=11 Hz), 5.88 (1H, d, J=18 Hz), 5.93 (1H, d, J=4 Hz), 6.59 (1H, d, J=4 Hz), 6.72-6.83 (1H, dd, J=11 Hz, 18 Hz), 7.81 (1H, m), 8.50 (1H, d, J=2 Hz), 8.63 (1H, d, J=2 Hz). MS (ESI$^-$): m/z 378, MS (ESI$^+$): m/z 380.

EXAMPLE 351

4-[4-(5-acetyl-3-pyridinyl)-7-ethyl-2-(methoxymethyl)pyrrolo[1,2-b]pyridazin-3-yl]butanoic acid $^1$H NMR (CDCl$_3$) δ 1.38 (3H, t, J=7 Hz), 1.66-1.83 (2H, m), 2.26 (2H, t, J=7 Hz), 2.55-2.70 (2H, m), 2.70 (3H, s), 3.05 (2H, q, J=7 Hz), 3.46 (3H, s), 4.67 (2H, s), 5.88 (1H, d, J=4 Hz), 6.62 (1H, d, J=4 Hz), 8.29 (1H, m), 8.80 (1H, d, J=2 Hz), 9.22 (1H, d, J=2 Hz). MS (ESI$^-$): m/z 394, MS (ESI$^+$): m/z 396.

EXAMPLE 352

5-[4-(5-amino-3-pyridinyl)-7-ethyl-2-methylpyrrolo[1,2-b]pyridazin-3-yl]pentanoic acid $^1$H NMR (CDCl$_3$) δ 1.34 (3H, t, J=7 Hz), 1.44-1.65 (4H, m), 2.16-2.32 (2H, m), 2.34-2.46 (2H, m), 2.53 (3H, s), 3.02 (2H, q, J=7 Hz), 5.06 (2H, br), 5.86 (1H, d, J=4 Hz), 5.98 (1H, d, J=4 Hz), 7.45 (1H, s), 7.84 (1H, s), 8.58 (1H, s). MS (ESI$^-$): m/z 351, MS (ESI$^+$): m/z 353.

EXAMPLE 353

5-{4-[5-(dimethylamino)-3-pyridinyl]-7-ethyl-2-methylpyrrolo[1,2-b]pyridazin-3-yl}pentanoic acid $^1$H NMR (CDCl$_3$) δ 1.37 (3H, t, J=7 Hz), 1.40-1.70 (4H, m), 2.23 (2H, m), 2.36-2.50 (2H, m), 2.56 (3H, s), 3.03 (2H, q, J=7 Hz), 3.06 (6H, s), 5.88 (1H, d, J=4 Hz), 6.53 (1H, d, J=4 Hz), 7.13 (1H, s), 7.90 (1H, s), 8.14 (1H, m). MS (ESI$^+$): m/z 381.

EXAMPLE 354

3-[4-(5-acetyl-3-pyridinyl)-7-ethyl-2-methylpyrrolo[1,2-b]pyridazin-3-yl]propanoic acid $^1$H NMR (CDCl$_3$) δ 1.37 (3H, t, J=7 Hz), 2.40-2.53 (2H, m), 2.60 (3H, s), 2.68 (3H, s), 2.83 (2H, t, J=7 Hz), 3.03 (2H, q, J=7 Hz), 5.83 (1H, d, J=4 Hz), 6.53 (1H, d, J=4 Hz), 8.27 (1H, m), 8.78 (1H, d, J=2 Hz), 9.22 (1H, d, J=2 Hz). MS (ESI$^-$): m/z 350, MS (ESI$^+$): m/z 352.

EXAMPLE 355

5-[2-[(benzyloxy)methyl]-7-ethyl-4-(5-methyl-3-pyridinyl)pyrrolo[1,2-b]pyridazin-3-yl]pentanoic acid $^1$H NMR (CDCl$_3$) δ 1.37 (3H, t, J=7 Hz), 1.35-1.55 (4H, m), 2.05-2.20 (2H, m), 2.42 (3H, s), 2.40-2.70 (2H, m), 3.03 (2H, q, J=7 Hz), 4.63 (2H, s), 4.74 (2H, m), 5.88 (1H, d, J=4 Hz), 6.58 (1H, d, J=4 Hz), 7.27-7.42 (5H, m), 7.53 (1H, s), 8.40 (1H, s), 8.53 (1H, s). MS (ESI$^+$): m/z 458.

EXAMPLE 356

3-[2-[(benzyloxy)methyl]-7-ethyl-4-(5-methyl-3-pyridinyl)pyrrolo[1,2-b]pyridazin-3-yl]propanoic acid $^1$H NMR (CDCl$_3$) δ 1.38 (3H, t, J=7 Hz), 2.40 (3H, s), 2.40-2.54 (2H, m), 2.80-3.08 (2H, m), 3.06 (2H, q, J=7 Hz), 4.65 (2H, s), 4.77 (2H, m), 5.89 (1H, d, J=4 Hz), 6.58 (1H, d, J=4 Hz), 7.26-7.42 (5H, m), 7.54 (1H, s), 8.39 (1H, d, J=2 Hz), 8.48 (1H, d, J=2 Hz). MS (ESI$^-$): m/z 428, MS (ESI$^+$): m/z 430.

EXAMPLE 357

5-[2-[(cyclohexyloxy)methyl]-7-ethyl-4-(5-methyl-3-pyridinyl)pyrrolo[1,2-b]pyridazin-3-yl]pentanoic acid $^1$H NMR (CDCl$_3$) δ 1.20-1.45 (6H, m), 1.36 (3H, t, J=7 Hz), 1.45-1.63 (4H, m), 1.70-1.83 (2H, m), 1.95-2.08 (2H, m), 2.14-2.28 (2H, m), 2.42 (3H, s), 2.46-2.60 (1H, m), 2.60-2.75 (1H, m), 3.03 (2H, q, J=7 Hz), 3.42-3.54 (1H, m), 4.72 (2H, m), 5.87 (1H, d, J=4 Hz), 6.54 (1H, d, J=4 Hz), 7.55 (1H, s), 8.41 (1H, s), 8.53 (1H, s). MS (ESI$^-$): m/z 448, MS (ESI$^+$): m/z 450.

EXAMPLE 358

5-{4-(5-bromo-3-pyridinyl)-2-[(cyclohexyloxy)methyl]-7-ethylpyrrolo[1,2-b]pyridazin-3-yl}pentanoic acid $^1$H NMR (CDCl$_3$) δ 1.18-1.60 (10H, m), 1.36 (3H, t, J=7 Hz), 1.70-1.80 (2H, m), 1.95-2.05 (2H, m), 2.22 (2H, t, J=7 Hz), 2.50-2.70 (2H, m), 3.03 (2H, q, J=7 Hz), 3.42-3.53 (1H, m), 4.68 (2H, s), 5.89 (1H, d, J=4 Hz), 6.58 (1H, d, J=4 Hz), 7.88 (1H, s), 8.54 (1H, d, J=2 Hz), 8.77 (1H, d, J=2 Hz). MS (ESI$^+$): m/z 514 516.

EXAMPLE 359

3-[2-[(cyclohexyloxy)methyl]-7-ethyl-4-(5-methyl-3-pyridinyl)pyrrolo[1,2-b]pyridazin-3-yl]propanoic acid $^1$H NMR (CDCl$_3$) δ 1.20-1.45 (5H, m), 1.37 (3H, t, J=7 Hz), 1.50-1.60 (1H, m), 1.72-1.84 (2H, m), 1.96-2.08 (2H, m), 2.42 (3H, s), 2.48-2.62 (2H, m), 2.80-3.10 (2H, m), 3.03 (2H, q, J=7 Hz), 3.44-3.66 (1H, m), 4.73 (2H, s), 5.88 (1H, d, J=4 Hz), 6.57 (1H, d, J=4 Hz), 7.55 (1H, s), 8.40 (1H, s), 8.51 (1H, s). MS (ESI$^+$): m/z 422.

EXAMPLE 360

3-{4-(5-bromo-3-pyridinyl)-2-[(cyclohexyloxy)methyl]-7-ethylpyrrolo[1,2-b]pyridazin-3-yl}propanoic acid $^1$H NMR (CDCl$_3$) δ 1.18-1.47 (5H, m), 1.37 (3H, t, J=7 Hz), 1.52-1.63 (1H, m), 1.72-1.85 (2H, m), 1.97-2.07 (2H, m), 2.48-2.62 (2H, m), 2.80-3.10 (2H, m), 3.03 (2H, q, J=7 Hz), 3.44-3.57 (1H, m), 4.73 (2H, s), 5.91 (1H, d, J=4 Hz), 6.61 (1H, d, J=4 Hz), 7.88 (1H, t, J=2 Hz), 8.55 (1H, d, J=2 Hz), 8.77 (1H, d, J=2 Hz). MS (ESI$^-$): m/z 484 486, MS (ESI$^+$): m/z 486 488.

EXAMPLE 361

5-[7-ethyl-2-(isopropoxymethyl)-4-(5-methyl-3-pyridinyl)pyrrolo[1,2-b]pyridazin-3-yl]pentanoic acid $^1$H NMR (CDCl$_3$) δ 1.25 (6H, d, J=7 Hz), 1.37 (3H, t, J=7 Hz), 1.44-1.63 (4H, m), 2.15-2.27 (2H, m), 2.43 (3H, s), 2.47-2.60 (1H, m), 2.60-2.73 (1H, m), 3.03 (2H, q, J=7 Hz), 3.75-3.87 (1H, m), 4.67 (2H, s), 5.87 (1H, d, J=4 Hz), 6.56 (1H, d, J=4 Hz), 7.55 (1H, s), 8.41 (1H, s), 8.53 (1H, s). MS (ESI⁻): m/z 408, MS (ESI⁺): m/z 410.

EXAMPLE 362

5-[4-(5-bromo-3-pyridinyl)-7-ethyl-2-(isopropoxymethyl)pyrrolo[1,2-b]pyridazin-3-yl]pentanoic acid ¹H NMR (CDCl₃) δ 1.25 (6H, d, J=7 Hz), 1.36 (3H, t, J=7 Hz), 1.45-1.65 (4H, m), 2.23 (2H, t, J=7 Hz), 2.50-2.60 (2H, m), 3.03 (2H, q, J=7 Hz), 3.75-3.85 (1H, m), 4.66 (2H, s), 5.89 (1H, d, J=4 Hz), 6.58 (1H, d, J=4 Hz), 7.89 (1H, m), 8.54 (1H, d, J=2 Hz), 8.77 (1H, d, J=2 Hz). MS (ESI⁺): m/z 474 476.

EXAMPLE 363

5-[7-ethyl-2-(hydroxymethyl)-4-(5-methyl-3-pyridinyl)pyrrolo[1,2-b]pyridazin-3-yl]pentanoic acid ¹H NMR (CDCl₃) δ 1.38 (3H, t, J=7 Hz), 1.40-1.65 (4H, m), 2.22 (2H, t, J=7 Hz), 2.33-2.45 (2H, m), 2.43 (3H, s), 3.03 (2H, q, J=7 Hz), 4.87 (2H, s), 5.94 (1H, d, J=4 Hz), 6.57 (1H, d, J=4 Hz), 7.56 (1H, s), 8.43 (1H, s), 8.54 (1H, s). MS (ESI⁻): m/z 366, MS (ESI⁺): m/z 368.

EXAMPLE 364

5-(7-ethyl-4-(5-methyl-3-pyridinyl)-2-{[2-(4-morpholinyl)-2-oxoethoxy]methyl}pyrrolo[1,2-b]pyridazin-3-yl)pentanoic acid ¹H NMR (CDCl₃) δ 1.37 (3H, t, J=7 Hz), 1.40-1.63 (4H, m), 2.22 (2H, t, J=7 Hz), 2.43 (3H, s), 2.50-2.72 (2H, m), 3.03 (2H, q, J=7 Hz), 3.51 (2H, m), 3.57-3.75 (6H, m), 4.32 (2H, s), 4.70-4.86 (2H, m), 5.90 (1H, d, J=4 Hz), 6.59 (1H, d, J=4 Hz), 7.53 (1H, s), 8.42 (1H, s), 8.53 (1H, s). MS (ESI⁻): m/z 493, MS (ESI⁺): m/z 495.

EXAMPLE 365

5-[7-ethyl-2-{[2-(methylamino)-2-oxoethoxy]methyl}-4-(5-methyl-3-pyridinyl)pyrrolo[1,2-b]pyridazin-3-yl]pentanoic acid ¹H NMR (CDCl₃) δ 1.37 (3H, t, J=7 Hz), 1.40-1.65 (4H, m), 2.22 (2H, t, J=7 Hz), 2.44 (3H, s), 2.45-2.64 (2H, m), 2.87 (3H, m), 3.03 (2H, q, J=7 Hz), 4.13 (2H, s), 4.74 (2H, m), 5.93 (1H, d, J=4 Hz), 6.60 (1H, d, J=4 Hz), 6.83 (1H, br), 7.57 (1H, s), 8.42 (1H, s), 8.53 (1H, s). MS (ESI⁻): m/z 437, MS (ESI⁺): m/z 439.

EXAMPLE 366

5-[2-[(cyclopropylmethoxy)methyl]-7-ethyl-4-(5-methyl-3-pyridinyl)pyrrolo[1,2-b]pyridazin-3-yl]pentanoic acid ¹H NMR (CDCl₃) δ 0.23-0.33 (2H, m), 0.55-0.64 (2H, m), 1.07-1.22 (1H, m), 1.36 (3H, t, J=7 Hz), 1.45-1.68 (4H, m), 2.19 (2H, t, J=7 Hz), 2.43 (3H, s), 2.50-2.75 (2H, m), 3.02 (2H, q, J=7 Hz), 3.40 (2H, d, J=7 Hz), 4.70 (2H, m), 5.87 (1H, d, J=4 Hz), 6.56 (1H, d, J=4 Hz), 7.57 (1H, s), 8.40 (1H, s), 8.54 (1H, s). MS (ESI⁺): m/z 422.

EXAMPLE 367

5-[2-[(cyclohexylmethoxy)methyl]-7-ethyl-4-(5-methyl-3-pyridinyl)pyrrolo[1,2-b]pyridazin-3-yl]pentanoic acid ¹H NMR (CDCl₃) δ 0.87-1.04 (2H, m), 1.10-1.82 (13H, m), 1.37 (3H, t, J=7 Hz), 2.18 (2H, t, J=7 Hz), 2.43 (3H, s), 2.47-2.72 (2H, m), 3.03 (2H, q, J=7 Hz), 3.33 (2H, d, J=7 Hz), 4.63 (2H, m), 5.87 (1H, d, J=4 Hz), 6.56 (1H, d, J=4 Hz), 7.56 (1H, s), 8.42 (1H, s), 8.53 (1H, s). MS (ESI⁻): m/z 462, MS (ESI⁺): m/z 464.

EXAMPLE 368

5-{7-ethyl-4-(5-methyl-3-pyridinyl)-2-[(3-pyridinylmethoxy)methyl]pyrrolo[1,2-b]pyridazin-3-yl}pentanoic acid ¹H NMR (CDCl₃) δ 1.38 (3H, t, J=7 Hz), 1.35-1.57 (4H, m), 2.13 (2H, t, J=7 Hz), 2.42 (3H, s), 2.47-2.66 (2H, m), 3.03 (2H, q, J=7 Hz), 4.68 (2H, s), 4.77 (2H, m), 5.90 (1H, d, J=4 Hz), 6.59 (1H, d, J=4 Hz), 7.28-7.36 (1H, m), 7.53 (1H, s), 7.73 (1H, d, J=8Hz), 8.41 (1H, d, J=2 Hz), 8.53 (2H, m), 8.63 (1H, s). MS (ESI⁻): m/z 457, MS (ESI⁺): m/z 459.

EXAMPLE 369

5-{7-ethyl-4-(5-methyl-3-pyridinyl)-2-[(2-pyridinylmethoxy)methyl]pyrrolo[1,2-b]pyridazin-3-yl}pentanoic acid ¹H NMR (CDCl₃) δ 1.37 (3H, t, J=7 Hz), 1.45-1.65 (4H, m), 2.23 (2H, t, J=7 Hz), 2.41 (3H, s), 2.48-2.74 (2H, m), 3.03 (2H, q, J=7 Hz), 4.80 (2H, s), 4.82 (2H, m), 5.88 (1H, d, J=4 Hz), 6.57 (1H, d, J=4 Hz), 7.26 (1H, m), 7.47-7.53 (2H, m), 7.69-7.77 (1H, m), 8.42 (1H, d, J=2 Hz), 8.50 (1H, d, J=2 Hz), 8.58 (1H, d, J=7 Hz). MS (ESI⁻): m/z 457, MS (ESI⁺): m/z 459.

EXAMPLE 370

5-{7-ethyl-4-(5-methyl-3-pyridinyl)-2-[(4-pyridinylmethoxy)methyl]pyrrolo[1,2-]pyridazin-3-yl}pentanoic acid ¹H NMR (CDCl₃) δ 1.38 (3H, t, J=7 Hz), 1.40-1.62 (4H, m), 2.16 (2H, t, J=7 Hz), 2.43 (3H, s), 2.48-2.71 (2H, m), 3.02 (2H, q, J=7 Hz), 4.68 (2H, s), 4.79 (2H, m), 5.91 (1H, d, J=4 Hz), 6.60 (1H, d, J=4 Hz), 7.32 (2H, d, J=7 Hz), 7.54 (1H, s), 8.42 (1H, d, J=2 Hz), 8.54 (1H, d, J=2 Hz), 8.55 (2H, d, J=7 Hz). MS (ESI⁻): m/z 457, MS (ESI⁺): m/z 459.

EXAMPLE 371

5-{7-ethyl-4-(5-methyl-3-pyridinyl)-2-[(2-pyrazinylmethoxy)methyl]pyrrolo[1,2-b]pyridazin-3-yl}pentanoic acid ¹H NMR (CDCl₃) δ 1.37 (3H, t, J=7 Hz), 1.45-1.62 (4H, m), 2.18 (2H, t, J=7 Hz), 2.43 (3H, s), 2.48-2.73 (2H, m), 3.03 (2H, q, J=7 Hz), 4.83 (2H, s), 4.88 (2H, m), 5.90 (1H, d, J=4 Hz), 6.59 (1H, d, J=4 Hz), 7.54 (1H, s), 8.42 (1H, s), 8.48-8.56 (3H, m), 8.76 (1H, s). MS (ESI⁻): m/z 458, MS (ESI⁺): m/z 460.

EXAMPLE 372

5-[2-[(benzylamino)methyl]-7-ethyl-4-(5-methyl-3-pyridinyl)pyrrolo[1,2-b]pyridazin-3-yl]pentanoic acid $^1$H NMR (DMSO-d$_6$) δ 1.33 (3H, t, J=7 Hz), 1.28-1.48 (4H, m), 2.03-2.13 (2H, m), 2.30-2.45 (2H, m), 2.40 (3H, s), 3.06 (2H, q, J=7 Hz), 4.37 (2H, s), 4.46 (2H, s), 5.92 (1H, d, J=4 Hz), 6.68 (1H, d, J=4 Hz), 7.40-7.52 (3H, m), 7.56-7.67 (3H, m), 8.36 (1H, d, J=2 Hz), 8.57 (1H, d, J=2 Hz). MS (ESI$^+$): m/z 457.

EXAMPLE 373

5-[2-[(acetylamino)methyl]-7-ethyl-4-(5-methyl-3-pyridinyl)pyrrolo[1,2-b]pyridazin-3-yl]pentanoic acid $^1$H NMR (CDCl$_3$) δ 1.40 (3H, t, J=7 Hz), 1.40-1.64 (4H, m), 2.16 (3H, s), 2.23 (2H, t, J=7 Hz), 2.35-2.50 (2H, m), 2.43 (3H, s), 3.03 (2H, q, J=7 Hz), 4.63-4.72 (2H, m), 5.92 (1H, d, J=4 Hz), 6.57 (1H, d, J=4 Hz), 6.88-6.97 (1H, br), 7.53 (1H, s), 8.41 (1H, s), 8.53 (1H, s). MS (ESI$^-$): m/z 407, MS (ESI$^+$): m/z 409.

EXAMPLE 374

5-(7-ethyl-4-(5-methyl-3-pyridinyl)-2-{[(methylsulfonyl)amino]methyl}pyrrolo[1,2-b]pyridazin-3-yl)pentanoic acid $^1$H NMR (CDCl$_3$) δ 1.38 (3H, t, J=7 Hz), 1.46-1.66 (4H, m), 2.23 (2H, t, J=7 Hz), 2.44 (3H, s), 2.39-2.53 (2H, m), 3.03 (2H, q, J=7 Hz), 3.05 (3H, s), 4.57 (2H, s), 5.72 (1H, br), 5.96 (1H, d, J=4 Hz), 6.61 (1H, d, J=4 Hz), 7.54 (1H, s), 8.41 (1H, d, J=2 Hz), 8.55 (1H, d, J=2 Hz). MS (ESI$^-$): m/z 443, MS (ESI$^+$): m/z 445.

EXAMPLE 375

5-[2-[(benzoylamino)methyl]-7-ethyl-4-(5-methyl-3-pyridinyl)pyrrolo[1,2-b]pyridazin-3-yl]pentanoic acid $^1$H NMR (CDCl$_3$) δ 1.42 (3H, t, J=7 Hz), 1.50-1.68 (4H, m), 2.25 (2H, t, J=7 Hz), 2.44 (3H, s), 2.40-2.60 (2H, m), 3.07 (2H, q, J=7 Hz), 4.89 (2H, m), 5.95 (1H, d, J=4 Hz), 6.61 (1H, d, J=4 Hz), 7.46-7.60 (4H, m), 7.83 (1H, br), 7.93 (2H, d, J=8 Hz), 8.44 (1H, d, J=2 Hz), 8.56 (1H, d, J=2 Hz). MS (ESI$^-$): m/z 469, MS (ESI$^+$): m/z 471.

EXAMPLE 376

5-(7-ethyl-4-(5-methyl-3-pyridinyl)-2-{[(2-pyrazinylcarbonyl)amino]methyl}pyrrolo[1,2-b]pyridazin-3-yl)pentanoic acid $^1$H NMR (CDCl$_3$) δ 1.41 (3H, t, J=7 Hz), 1.51-1.72 (4H, m), 2.24 (2H, t, J=7 Hz), 2.44 (3H, s), 2.45-2.58 (2H, m), 3.10 (2H, q, J=7 Hz), 4.90 (2H, m), 5.94 (1H, d, J=4 Hz), 6.59 (1H, d, J=4 Hz), 7.55 (1H, s), 8.43 (1H, s), 8.53 (1H, s), 8.62 (1H, m), 8.79 (1H, d, J=2 Hz), 9.20 (1H, br), 9.45 (1H, d, J=2 Hz). MS (ESI$^-$): m/z 471, MS (ESI$^+$): m/z 473.

EXAMPLE 377

5-[7-ethyl-2-{[(methoxycarbonyl)amino]methyl}-4-(5-methyl-3-pyridinyl)pyrrolo[1,2-b]pyridazin-3-yl] pentanoic acid $^1$H NMR (CDCl$_3$) δ 1.38 (3H, t, J=7 Hz), 1.45-1.65 (4H, m), 2.23 (2H, t, J=7 Hz), 2.40-2.53 (2H, m), 2.44 (3H, s), 3.02 (2H, q, J=7 Hz), 3.05 (3H, s), 4.58 (2H, s), 5.69 (1H, br), 5.96 (1H, d, J=4 Hz), 6.61 (1H, d, J=4 Hz), 7.53 (1H, s), 8.41 (1H, d, J=2 Hz), 8.54 (1H, d, J=2 Hz).

EXAMPLE 378

To a solution of ethyl 7-ethyl-2-methyl-4-(5-methyl-3-pyridinyl)pyrrolo[1,2-b]pyridazine-3-carboxylate (682 mg) in ethanol (20 mL) was added potassium hydroxide (5 g) solution (10 mL) and the mixture was heated under reflux for 1 hour. The solution was acidified with 1 N hydrochloric acid to pH 3-4 and diluted with brine, and extracted with chloroform twice. The organic layer was separated, dried over magnesium sulfate, and evaporated in vacuo. The crude product was triturated with ethyl acetate to give 7-ethyl-2-methyl-4-(5-methyl-3-pyridinyl)pyrrolo[1,2-b]pyridazine-3-carboxylic acid as a yellow powder (590 mg)

7-ethyl-2-methyl-4-(5-methyl-3-pyridinyl)pyrrolo[1,2-b]pyridazine-3-carboxylic acid $^1$H NMR (CDCl$_3$) δ 1.39 (3H, t, J=7 Hz), 2.44 (3H, s), 2.69 (3H, s), 3.05 (2H, q, J=7 Hz), 6.29 (1H, d, J=4 Hz), 6.67 (1H, d, J=4 Hz), 7.97 (1H, s), 8.41 (1H, s), 8.58 (1H, s). MS (ESI$^-$): m/z 294, MS (ESI$^+$): m/z 296.

The following compound(s) was (were) obtained in substantially the same manner as that of Example 175.

EXAMPLE 379

5-[4-(3-cyanophenyl)-2-(ethoxymethyl)-7-ethylpyrrolo[1,2-b]pyridazin-3-yl]pentanoic acid $^1$H NMR (CDCl$_3$) δ 1.25 (3H, t, J=7 Hz), 1.34-1.53 (7H, m), 2.20 (2H, t, J=7 Hz), 2.53 (2H, m), 3.03 (2H, q, J=7 Hz), 3.62 (2H, q, J=7 Hz), 4.66 (2H, s), 5.33 (1H, d, J=5 Hz), 6.57 (1H, d, J=5 Hz), 7.60 (2H, m), 7.66 (1H, s), 7.74 (1H, m)

EXAMPLE 380

5-[2-[(benzyloxy)methyl]-4-(3-cyanophenyl)-7-ethylpyrrolo[1,2-b]pyridazin-3-yl]pentanoic acid $^1$H NMR (CDCl$_3$) δ 1.30-1.46 (7H, m), 2.11 (2H, t, J=7 Hz), 2.50 (2H, m), 3.02 (2H, q, J=7 Hz), 4.64 (3H, s), 4.71 (3H, s), 5.83 (1H, d, J=5 Hz), 6.56 (1H, d, J=5 Hz), 7.25-7.34 (5H, m), 7.57 (2H, d, J=9 Hz), 7.65 (1H, s), 7.74 (1H, m). MS (ESI$^+$): m/z 468 (M+H)

EXAMPLE 381

4-({[3-(4-carboxybutyl)-4-(3-cyanophenyl)-7-ethylpyrrolo[1,2-b]pyridazin-2-yl]methoxy}methyl)benzoic acid $^1$H-NMR (CDCl$_3$) δ 1.05-1.43 (7H, m), 1.92 (2H, m), 2.31 (2H, m), 3.04 (2H, m), 4.65 (2H, s), 4.72 (2H, s), 5.82 (1H, m), 6.58 (1H, m), 7.46-7.77 (6H, m), 8.09 (2H, d, J=8 Hz). MS (ESI$^+$): m/z 510 (M−H)

EXAMPLE 381-2

4-({[4-[3-(carbamoyl)phenyl]-3-(4-carboxybutyl)-7-ethylpyrrolo[1,2-b]pyridazin-2-yl]methoxy}methyl)benzoic acid $^1$H-NMR (CDCl$_3$) δ 1.20-1.45 (7H, m), 2.03 (2H, m), 2.52 (2H, m), 3.03 (2H, q, J=7 Hz), 4.69 (2H, s), 4.73 (2H, s), 5.36 (1H, d, J=5 Hz), 6.57 (1H, d, J=5 Hz), 7.39-7.60 (4H, m), 7.77 (1H, s), 7.93 (1H, d, J=8 Hz), 7.98 (2H, d, J=8 Hz). MS (ESI$^+$): m/z 528 (M−H)

The following compound(s) was (were) obtained in substantially the same manner as that of Example 77.

EXAMPLE 382

5-{4-(5-bromo-3-pyridinyl)-7-ethyl-2-[(4-methyl-1-piperazinyl)methyl]pyrrolo[1,2-b]pyridazin-3-yl}pentanoic acid $^1$H NMR (CDCl$_3$) δ 1.34 (3H, t, J=7 Hz), 1.38-1.59 (4H, m), 2.22 (2H, m), 2.43-2.60 (5H, m), 2.83-3.04 (8H, m), 3.74 (3H, s), 5.88 (1H, d, J=5 Hz), 6.56 (1H, d, J=5 Hz), 7.87 (1H, m), 8.54 (1H, m), 8.76 (1H, m).

EXAMPLE 383

5-[4-(5-bromo-3-pyridinyl)-2-(cyanomethyl)-7-ethylpyrrolo[1,2-b]pyridazin-3-yl]pentanoic acid $^1$H NMR (CDCl$_3$) δ 1.35-1.60 (7H, m), 2.27 (2H, m), 2.46 (2H, m), 3.03 (2H, q, J=7 Hz), 3.98 (2H, s), 3.97 (1H, d, J=5 Hz), 6.65 (1H, d, J=5 Hz), 7.90 (1H, m), 8.54 (1H, s, br), 8.79 (1H, s, br).

EXAMPLE 384

5-[4-(5-bromo-3-pyridinyl)-7-ethyl-2-(hydroxymethyl)pyrrolo[1,2-b]pyridazin-3-yl]pentanoic acid $^1$H NMR (CDCl$_3$) δ 1.35-1.60 (7H, m), 2.22 (2H, t, J=7 Hz), 2.38 (2H, m), 3.02 (2H, q, J=7 Hz), 4.86 (2H, s), 5.95 (1H, d, J=5 Hz), 6.60 (1H, d, J=5 Hz), 7.88 (1H, m), 8.54 (1H, s, br), 8.79 (1H, s, br).

EXAMPLE 385

To a solution of 7-ethyl-2-methyl-4-(5-methyl-3-pyridinyl)pyrrolo[1,2-b]pyridazine-3-carboxylic acid (70 mg), 1-ethyl-3-(3'-dimethylaminopropyl)carbodiimide hydrochloride (68.2 mg) and 1-hydroxybenotriazole (48 mg) in dimethylformamide (2 mL) was added 2-aminoethanol (17.4 mg) and the mixture was stirred at ambient temperature for 1 hour. The mixture was partitioned between ethyl acetate and water. The organic layer was separated, washed with saturated sodium bicarbonate solution, water and brine, dried over magnesium sulfate, and evaporated in vacuo. The residue was purified by silica gel column chromatography eluting with a mixture of chloroform and methanol (50:1-10:1). The crude product was triturated with isopropylether to give 7-ethyl-N-(2-hydroxyethyl)-2-methyl-4-(5-methyl-3-pyridinyl)pyrrolo[1,2-b]pyridazine-3-carboxamide as a yellow powder (47 mg).

7-ethyl-N-(2-hydroxyethyl)-2-methyl-4-(5-methyl-3-pyridinyl)pyrrolo[1,2-b]pyridazine-3-carboxamide $^1$H NMR (CDCl$_3$) δ 1.38 (3H, t, J=7 Hz), 2.39 (3H, s), 2.57 (3H, s), 3.02 (2H, q, J=7 Hz), 3.33 (2H, m), 3.45 (2H, m), 6.03 (1H, br), 6.31 (1H, d, J=4 Hz), 6.66 (1H, d, J=4 Hz), 7.71 (1H, s), 8.47 (1H, s), 8.58 (1H, s). MS (ESI$^-$): m/z 337, MS (ESI$^+$): m/z 339.

The following compound(s) was (were) obtained in substantially the same manner as that of Example 385.

EXAMPLE 386

N-butyl-7-ethyl-2-methyl-4-(5-methyl-3-pyridinyl)pyrrolo[1,2-b]pyridazine-3-carboxamide $^1$H NMR (CDCl$_3$) δ 0.80 (3H, t, J=7 Hz), 0.96-1.08 (2H, m), 1.08-1.25 (2H, m), 1.38 (3H, t, J=7 Hz), 2.40 (3H, s), 2.56 (3H, s), 3.03 (2H, q, J=7 Hz), 3.16 (2H, m), 5.36 (1H, br), 6.31 (1H, d, J=4 Hz), 6.63 (1H, d, J=4 Hz), 7.69 (1H, s), 8.53 (1H, s), 8.62 (1H, s). MS (ESI$^+$): m/z 351.

EXAMPLE 387 ethyl 3-({[7-ethyl-2-methyl-4-(5-methyl-3-pyridinyl)pyrrolo[1,2-b]pyridazin-3-yl]carbonyl}amino)propanoate $^1$H NMR (CDCl$_3$) δ 1.24 (3H, t, J=7 Hz), 1.38 (3H, t, J=7 Hz), 2.21 (2H, t, J=7 Hz), 2.40 (3H, s), 2.55 (3H, s), 3.03 (2H, q, J=7 Hz), 3.43 (2H, q, J=7 Hz), 4.04 (2H, q, J=7 Hz), 6.08 (1H, br), 6.30 (1H, d, J=4 Hz), 6.65 (1H, d, J=4 Hz), 7.67 (1H, s), 8.50 (1H, d, J=1 Hz), 8.60 (1H, d, J=1 Hz). MS (ESI$^+$): m/z 395.

The following compound(s) was (were) obtained in substantially the same manner as that of Preparation 176.

EXAMPLE 388

4-(5-bromo-3-pyridinyl)-7-ethyl-2-methyl-3-[3-(4-morpholinyl)-3-oxopropyl]pyrrolo[1,2-b]pyridazine $^1$H NMR(CDCl$_3$) δ: $^1$H NMR(CDCl$_3$) δ: 1.37(3H, t, J=7 Hz), 2.41(2H, t, J=7 Hz), 2.60(3H, s), 2.72-2.82(2H, m), 3.01(2H, q, J=7 Hz), 3.19(2H, t, J=5 Hz), 3.55(4H, t, J=5 Hz), 3.63(2H, t, J=5 Hz), 5.89(1H, d, J=4 Hz), 6.55(1H, d, J=4 Hz), 7.87(1H, t, J=1 Hz), 8.54(1H, d, J=1 Hz), 8.77(1H, d, J=1 Hz) MS (m/z) 457(M$^+$), 459(M++2), 115(bp) mp. 178-180° C.

EXAMPLE 389

3-[4-(5-bromo-3-pyridinyl)-7-ethyl-2-methylpyrrolo[1,2-b]pyridazin-3-yl]-N-methylpropanamide $^1$H NMR(CDCl$_3$) δ: $^1$H NMR(CDCl$_3$) δ: 1.38(3H, t, J=7 Hz), 2.20(2H, t, J=7 Hz), 2.60(3H, s), 2.75(3H, d, J=6 Hz), 2.78-2.89(2H, m), 3.01(2H, q, J=7 Hz), 5.21-5.27(1H, m), 5.88(1H, d, J=4 Hz), 6.54(1H, d, J=4 Hz), 7.86(1H, t, J=1 Hz), 8.53(1H, d, J=1 Hz), 8.78(1H, d, J=1 Hz), MS (m/z) 401(M$^+$+1), 403(M$^+$+1), 115(bp) mp. 172-174° C.

The following compound(s) was (were) obtained in substantially the same manner as that of Example 263.

EXAMPLE 390

N-{3-[4-(5-bromo-3-pyridinyl)-7-ethyl-2-methylpyrrolo[1,2-b]pyridazin-3-yl]propanoyl}methanesulfonamide $^1$H NMR(CDCl$_3$) δ: 1.36(3H, t, J=7 Hz), 2.33-2.45(2H, m), 2.58(3H, s), 2.84-2.95(2H, m), 3.01(2H, q, J=7 Hz), 3.26(3H, s), 5.89(1H, d, J=4 Hz), 6.56(1H, d, J=4 Hz), 7.90(1H, s), 8.50(1H, s), 8.77(1H, s) MS (m/z) 465(M+, bp), 467(M$^+$–2, bp) mp. 196.5-197.5° C.

The following compound(s) was (were) obtained in substantially the same manner as that of Example 224.

EXAMPLE 391

2-[{3-[4-(3-chlorophenyl)-7-ethyl-2-phenylpyrrolo[1,2-b]pyridazin-3-yl]propanoyl}(methyl)amino]ethanesulfonic acid $^1$H NMR (CDCl$_3$) δ 1.32 (3H, t, J=7 Hz), 1.90 2H, m), 2.26 (3H, s), 2.57-2.2.78 (4H, m), 2.98 (2H, q, J=7 Hz), 3.31 (2H, m), 6.00 (1H, d, J=5 Hz), 6.61 (1H, d, J=5 Hz), 7.20-7.52 (5H, m).

The following compound(s) was (were) obtained in a similar manner to that of Preparation 20.

Preparation 217

1-tert-butyl 7-ethyl 2-(isobutoxyacetyl)heptanedioate $^1$H NMR (300 MHz, CDCl$_3$) δ 0.95 (6H, d, J=7 Hz), 1.27 (3H, t, J=7 Hz), 1.31-1.41 (2H, m), 1.46 (9H, s), 1.66 (2H, tt, J=7, 7 Hz), 1.75-1.98 (3H, m), 2.31 (2H, t, J=8 Hz), 3.26 (2H, d, J=7 Hz), 3.56 (1H, t, J=7 Hz), 4.06-4.17 (4H, m).

Preparation 218

1-tert-butyl 6-ethyl 2-(isobutoxyacetyl)hexanedioate $^1$H NMR (300 MHz, CDCl$_3$) δ 0.93 (6H, d, J=7 Hz), 1.25 (3H, t, J=7 Hz), 1.45 (9H, s), 1.59-1.69 (2H, m), 1.80-1.95 (3H, m), 2.32 (2H, t, J=7 Hz), 2.25 (2H, d, J=7 Hz), 3.57 (1H, t, J=7 Hz), 4.10 (2H, s), 4.12 (2H, q, J=7 Hz).

The following compound(s) was (were) obtained in a similar manner to that of Preparation 24.

Preparation 219

1-tert-butyl 6-ethyl 2-acetyl-2-(2-chloroisonicotinoyl)hexanedioate $^1$H NMR (CDCl$_3$) δ 1.26 (3H, t, J=7 Hz), 1.34 (9H, s), 1.60-1.73 (2H, m), 2.22-2.32 (2H, m), 2.39 (2H, t, J=7 Hz), 2.49 (3H, s), 4.12 (2H, q, J=7 Hz), 7.43 (1H, d, J=5 Hz), 7.57 (1H, s), 8.50 (1H, d, J=5 Hz). MS (ESI$^+$): m/z 412.

Preparation 220

1-tert-butyl 5-ethyl 2-acetyl-2-(2-chloroisonicotinoyl)pentanedioate $^1$H NMR (CDCl$_3$) δ 1.37 (3H, t, J=7 Hz), 1.72-1.84 (2H, m), 2.33 (2H, t, J=7 Hz), 2.47-2.57 (2H, m), 2.58 (3H, s), 3.03 (2H, q, J=7 Hz), 5.88 (1H, d, J=4 Hz), 6.53 (1H, d, J=4 Hz), 7.27 (1H, m), 7.38 (1H, s), 8.53 (1H, d, J=5 Hz). MS (ESI$^-$): m/z 356, MS (ESI$^+$): m/z 358.

Preparation 221

1-tert-butyl 7-ethyl 2-(2-chloroisonicotinoyl)-2-(phenylacetyl)heptanedioate $^1$H NMR (CDCl$_3$) δ 1.24 (3H, t, J=7 Hz), 1.35 (9H, s), 1.63-1.76 (2H, m), 2.22-2.37 (4H, m), 3.93 (1H, d, J=17 Hz), 4.12 (2H, q, J=7 Hz), 4.29 (1H, d, J=17 Hz), 7.22 (2H, d, J=8 Hz), 7.26-7.36 (4H, m), 7.50 (1H, s), 8.42 (1H, d, J=5 Hz). MS (ESI$^+$): m/z 502.

Preparation 222 tert-butyl 2-[2-(2-methoxy-2-oxoethoxy)ethyl]-2-[(5-methyl-3-pyridinyl)carbonyl]-3-oxobutanoate $^1$H NMR (CDCl$_3$) δ 1.33 (9H, s), 2.39 (3H, s), 2.47 (3H, s), 2.62 (2H, t, J=7 Hz), 3.66 (2H, m), 3.70 (3H, s), 3.90 (2H, s), 7.87 (1H, s), 8.56 (1H, s), 8.75 (1H, s). MS (ESI$^+$): m/z 394.

Preparation 223

1-tert-butyl 4-ethyl 2-acetyl-2-[(5-bromo-3-pyridinyl)carbonyl]succinate $^1$H NMR (CDCl$_3$) δ 1.27 (3H, t, J=7 Hz), 1.41 (9H, s), 2.45 (3H, s), 3.22 (2H, m), 4.12 (2H, q, J=7 Hz), 8.22 (1H, m), 8.80 (1H, m), 8.82 (1H, m). MS (ESI$^+$): m/z 428 430.

Preparation 224

1-tert-butyl 5-ethyl 2-[(acetyloxy)acetyl]-2-[(5-methyl-3-pyridinyl)carbonyl]pentanedioate $^1$H NMR (CDCl$_3$) δ 1.23 (3H, t, J=7 Hz), 1.35 (9H, s), 2.14 (3H, s), 2.40 (3H, s), 2.40-2.48 (2H, m), 2.62-2.70 (2H, m), 4.12 (2H, q, J=7 Hz), 5.12 (1H, d, J=18 Hz), 5.34 (1H, d, J=18 Hz), 7.85 (1H, s), 8.58 (1H, s), 8.78 (1H, s). MS (ESI$^+$): m/z 436.

Preparation 225

1-tert-butyl 6-ethyl 2-[(acetyloxy)acetyl]-2-[(5-methyl-3-pyridinyl)carbonyl]hexanedioate $^1$H NMR (CDCl$_3$) δ 1.24 (3H, t, J=7 Hz), 1.34 (9H, s), 1.60-1.75 (2H, m), 2.14 (3H, s), 2.26-2.39 (4H, m), 2.40 (3H, s), 4.12 (2H, q, J=7 Hz), 5.13 (1H, d, J=18 Hz), 5.40 (1H, d, J=18 Hz), 7.86 (1H, s), 8.57 (1H, s), 8.78 (1H, s). MS (ESI$^+$): m/z 450.

Preparation 226

1-tert-butyl 7-ethyl 2-[(acetyloxy)acetyl]-2-(3-cyanobenzoyl)heptanedioate $^1$H NMR (CDCl$_3$) δ 1.24 (3H, t, J=7 Hz), 1.32 (9H, s), 1.26-1.46 (2H, m), 1.66-1.77 (2H, m), 2.14 (3H, s), 2.26-2.38 (4H, m), 4.12 (2H, q, J=7 Hz), 5.06 (1H, d, J=18 Hz), 5.42 (1H, d, J=18 Hz), 7.57 (1H, t, J=8 Hz), 7.81 (1H, d, J=8 Hz), 7.92 (1H, d, J=8 Hz), 8.09 (1H, s).

Preparation 227

1-tert-butyl 6-ethyl 2-[(acetyloxy)acetyl]-2-[(5-bromo-3-pyridinyl)carbonyl]hexanedioate $^1$H NMR (CDCl$_3$) δ 1.25 (3H, t, J=7 Hz), 1.36 (9H, s), 1.60-1.74 (2H, m), 1.85-1.96 (2H, m), 2.14 (3H, s), 2.28-

2.42 (2H, m), 4.12 (2H, q, J=7 Hz), 5.12 (1H, d, J=17 Hz), 5.42 (1H, d, J=17 Hz), 8.23 (1H, m), 8.81 (1H, m), 8.83 (1H, m).

Preparation 228

1-tert-butyl 5-ethyl 2-[(acetyloxy)acetyl]-2-[(5-bromo-3-pyridinyl)carbonyl]pentanedioate $^1$H NMR (CDCl$_3$) δ 1.25 (3H, t, J=7 Hz), 1.37 (9H, s), 2.14 (3H, s), 2.41-2.51 (2H, m), 2.66 (2H, t, J=7 Hz), 4.13 (2H, q, J=7 Hz), 5.11 (1H, d, J=18 Hz), 5.33 (1H, d, J=18 Hz), 8.22 (1H, m), 8.82 (2H, m). MS (ESI$^+$): m/z 500 502.

Preparation 229

1-tert-butyl 5-ethyl 2-[(cyclohexylmethoxy)acetyl]-2-[(5-methyl-3-pyridinyl)carbonyl]pentanedioate $^1$H NMR (CDCl$_3$) δ 0.80-0.98 (2H, m), 1.00-1.32 (3H, m), 1.23 (3H, t, J=7 Hz), 1.38 (9H, s), 1.46-1.62 (6H, m), 2.39 (3H, s), 2.40-2.72 (4H, m), 3.19 (2H, d, J=7 Hz), 4.12 (2H, q, J=7 Hz), 4.31 (1H, d, J=17 Hz), 4.39 (1H, d, J=17 Hz), 7.88 (1H, s), 8.56 (1H, s), 8.77 (1H, s). MS (ESI$^+$): m/z 490.

Preparation 230

1-tert-butyl 5-ethyl 2-[(5-bromo-3-pyridinyl)carbonyl]-2-[(cyclohexylmethoxy)acetyl]pentanedioate $^1$H NMR (CDCl$_3$) δ 0.78-0.98 (2H, m), 1.10-1.33 (3H, m), 1.25 (3H, t, J=7 Hz), 1.40 (9H, s), 1.38-1.83 (6H, m), 2.35-2.75 (4H, m), 3.22 (2H, d, J=7 Hz), 4.12 (2H, q, J=7 Hz), 4.25 (1H, d, J=17 Hz), 4.37 (1H, d, J=17 Hz), 8.22 (1H, s), 8.78 (1H, s), 8.86 (1H, s). MS (ESI$^+$): m/z 554 556.

Preparation 231

1-tert-butyl 6-ethyl 2-[(5-bromo-3-pyridinyl)carbonyl]-2-[(cyclohexylmethoxy)acetyl]hexanedioate $^1$H NMR (CDCl$_3$) δ 0.80-0.97 (2H, m), 1.12-1.35 (3H, m), 1.25 (3H, t, J=7 Hz), 1.39 (9H, s), 1.46-1.80 (10H, m), 2.22-2.45 (2H, m), 3.20 (2H, d, J=7 Hz), 4.12 (2H, q, J=7 Hz), 4.30 (1H, d, J=17 Hz), 4.38 (1H, d, J=17 Hz), 8.22 (1H, s), 8.78 (1H, s), 8.85 (1H, s). MS (ESI$^+$): m/z 568 570.

Preparation 232

1-tert-butyl 6-ethyl 2-[(cyclopropylmethoxy)acetyl]-2-[(5-methyl-3-pyridinyl)carbonyl]hexanedioate $^1$H NMR (CDCl$_3$) δ 0.16-0.28 (2H, m), 0.48-0.59 (2H, m), 0.98-1.12 (1H, m), 1.24 (3H, t, J=7 Hz), 1.37 (9H, s), 1.55-1.80 (4H, m), 2.18-2.40 (2H, m), 2.39 (3H, s), 3.31 (2H, m), 4.12 (2H, q, J=7 Hz), 4.38 (1H, d, J=17 Hz), 4.53 (1H, d, J=17 Hz), 7.88 (1H, s), 8.55 (1H, d, J=2 Hz), 8.75 (1H, d, J=2 Hz). MS (ESI$^+$): m/z 462.

Preparation 233

1-tert-butyl 5-ethyl 2-[(cyclopropylmethoxy)acetyl]-2-[(5-methyl-3-pyridinyl)carbonyl]pentanedioate $^1$H NMR (CDCl$_3$) δ 0.15-0.23 (2H, m), 0.48-0.56 (2H, m), 0.95-1.10 (1H, m), 1.24 (3H, t, J=7 Hz), 1.39 (9H, s), 2.39 (3H, s), 2.40-2.68 (4H, m), 3.28 (2H, m), 4.12 (2H, q, J=7 Hz), 4.36 (1H, d, J=17 Hz), 4.48 (1H, d, J=17 Hz), 7.88 (1H, s), 8.55 (1H, s), 8.75 (1H, s). MS (ESI$^+$): m/z 448.

Preparation 234

1-tert-butyl 5-ethyl 2-[(5-bromo-3-pyridinyl)carbonyl]-2-[(2-methoxyethoxy)acetyl]pentanedioate $^1$H NMR (CDCl$_3$) δ 1.26 (3H, t, J=7 Hz), 1.46 (9H, s), 2.15-2.25 (2H, m), 2.42-2.72 (2H, m), 3.38 (3H, s), 3.48-3.72 (4H, m), 4.12 (2H, q, J=7 Hz), 4.43 (1H, d, J=17 Hz), 4.58 (1H, d, J=17 Hz), 8.22 (1H, s), 8.78 (1H, s), 8.82 (1H, s). MS (ESI$^+$): m/z 516 518.

Preparation 235 tert-butyl 2-[(5-bromo-3-pyridinyl)carbonyl]-3-oxobutanoate $^1$H NMR (CDCl$_3$) δ 1.22, 1.30 (9H, s), 2.22, 2.45 (3H, s), 7.96, 8.13 (1H, s), 8.66, 8.76-8.80 (2H, m).

Preparation 236

1-tert-butyl 6-ethyl 2-[(acetyloxy)acetyl]-2-[(5-chloro-3-pyridinyl)carbonyl]hexanedioate $^1$H NMR (300 MHz, CDCl$_3$) δ 1.25 (3H, t, J=7 Hz), 1.36 (9H, s), 1.63-1.71 (2H, m), 2.14 (3H, s), 2.27-2.40 (4H, m), 4.13 (2H, q, J=7 Hz), 5.11 (1H, d, J=18 Hz), 5.38 (1H, d, J=18 Hz), 8.07 (1H, dd, J=2 Hz), 8.71 (1H, d, J=2 Hz), 8.80 (1H, d, J=2 Hz).

Preparation 237

1-tert-butyl 7-ethyl 2-[(5-chloro-3-pyridinyl)carbonyl]-2-[(cyclopropylmethoxy)acetyl]heptanedioate $^1$H NMR (300 MHz, CDCl$_3$) δ 0.15-0.20 (2H, m), 0.49-0.58 (2H, m), 0.95-1.04 (1H, m), 1.24 (3H, t, J=7 Hz), 1.38 (9H, s), 1.68 (2H, tt, J=7, 7 Hz), 2.14-2.33 (4H, m), 3.26-3.29 (2H, m), 4.07-4.19 (4H, m), 4.31 (1H, d, J=17 Hz), 4.45 (1H, d, J=17 Hz), 8.05 (1H, dd, J=2 Hz), 8.68 (1H, d, J=2 Hz), 8.78 (1H, d, J=2 Hz).

Preparation 238

1-tert-butyl 6-ethyl 2-[(5-chloro-3-pyridinyl)carbonyl]-2-[(cyclopropylmethoxy)acetyl]hexanedioate $^1$H NMR (300 MHz, CDCl$_3$) δ 0.14-0.21 (2H, m), 0.49-0.55 (2H, m), 0.92-1.04 (1H, m), 1.25 (3H, t, J=7 Hz), 1.39 (9H, s), 1.62-1.74 (2H, m), 1.82-1.90 (2H, m), 2.21-2.33 (2H, m), 3.27-3.31 (2H, m), 4.12 (2H, q, J=7 Hz), 4.34 (1H, d, J=18 Hz), 4.46 (1H, d, J=18 Hz), 8.07 (1H, dd, J=2, 2 Hz), 8.68 (1H, d, J=2 Hz), 8.80 (1H, d, J=2 Hz).

Preparation 239

1-tert-butyl 7-ethyl 2-[(5-bromo-3-pyridinyl)carbonyl]-2-(isobutoxyacetyl)heptanedioate $^1$H NMR (300 MHz, CDCl$_3$) δ 0.85 (6H, d, J=7 Hz), 1.24 (3H, t, J=7 Hz), 1.38 (9H, s), 1.67 (2H, t, J=7 Hz), 1.75-1.93 (3H, m), 2.24-2.33 (4H, m), 3.17 (2H, d, J=7 Hz), 4.11 (2H, q, J=7 Hz), 4.28 (1H, d, J=17 Hz), 4.38 (1H, d, J=17 Hz), 8.20 (1H, dd, J=2, 2 Hz), 8.79 (1H, d, J=2 Hz), 8.84 (1H, d, J=2 Hz).

Preparation 240

1-tert-butyl 5-ethyl 2-[(5-chloro-3-pyridinyl)carbonyl]-2-(isobutoxyacetyl)pentanedioate $^1$H NMR (300 MHz, CDCl$_3$) δ 0.84 (6H, d, J=7 Hz), 1.24 (3H, t, J=7 Hz), 1.39 (9H, s), 1.80 (1H, qt, J=7 Hz), 2.34-2.71 (4H, m), 3.17 (2H, d, J=7 Hz), 4.12 (2H, q, J=7 Hz), 4.28 (1H, d, J=18 Hz), 4.36 (1H, d, J=18 Hz), 8.07 (1H, s), 8.69 (1H, s), 8.83 (1H, s).

Preparation 241

1-tert-butyl 5-ethyl 2-[(acetyloxy)acetyl]-2-(3-chlorobenzoyl)pentanedioate $^1$H NMR (300 MHz, CDCl$_3$) δ 1.24 (3H, t, J=7 Hz), 1.34 (9H, s), 2.14 (3H, s), 2.35-2.44 (2H, m), 2.60-2.68 (2H, m), 4.11 (2H, q, J=7 Hz), 5.11 (1H, d, J=18 Hz), 5.35 (1H, d, J=18 Hz), 7.38 (1H, dd, J=8, 8 Hz), 7.53 (1H, d, J=8 Hz), 7.60 (1H, d, J=8 Hz), 7.79 (1H, s).

Preparation 242

1-tert-butyl 6-ethyl 2-[(5-bromo-3-pyridinyl)carbonyl]-2-(isobutoxyacetyl)hexanedioate $^1$H NMR (300 MHz, CDCl$_3$) δ 0.85 (6H, d, J=7 Hz), 1.25 (3H, t, J=7 Hz), 1.39 (9H, s), 1.59-1.72 (2H, m), 1.80 (1H, qt, J=7, 7 Hz), 2.19-2.39 (4H, m), 3.18 (2H, d, J=7 Hz), 4.12 (2H, q, J=7 Hz), 4.31 (1H, d, J=17 Hz), 4.40 (1H, d, J=17 Hz), 8.22 (1H, dd, J=2, 2 Hz), 8.79 (1H, d, J=2 Hz), 8.85 (1H, d, J=2 Hz).

Preparation 243 tert-butyl 3-(5-bromo-3-pyridinyl)-2-[(5-bromo-3-pyridinyl)carbonyl]-3-oxopropanoate $^1$H NMR (CDCl$_3$) δ 1.05 (9H, s), 7.86 (2H, s), 8.46 (2H, s), 8.61 (2H, s). MS (ESI$^-$): m/z 481 483 485.

Preparation 244

1-tert-butyl 6-ethyl 2-[(acetyloxy)acetyl]-2-(3-chlorobenzoyl)hexanedioate $^1$H NMR (CDCl$_3$) δ 1.24 (3H, t, J=8 Hz), 1.33 (9H, s), 1.56-1.72 (2H, m), 2.15 (3H, s), 2.20-2.41 (4H, m), 4.11 (2H, q, J=8 Hz), 5.13 (1H, d, J=18 Hz), 5.40 (1H, d, J=18 Hz), 738(1H, t, J=8 Hz), 752(1H, br d, J=8 Hz), 7.60 (1H, br d, J=8 Hz), 7.79 (1H, br s).

Preparation 245 b 1-tert-butyl 7-ethyl 2-(methoxyacetyl)-2-[(5-methoxy-3-pyridinyl)carbonyl]heptanedioate $^1$H NMR (CDCl$_3$) δ 1.23 (3H, t, J=8 Hz), 1.27-1.43 (11H, m), 1.60-1.74 (2H, m), 2.15-2.34 (4H, m), 3.37 (3H, s), 3.90 (3H, s), 4.10 (2H, q, J=8 Hz), 4.35 (1H, d, J=18 Hz), 4.48 (1H, d, J=18 Hz), 7.58 (1H, m), 8.43 (1H, d, J=3 Hz), 8.50 (1H, d, J=1 Hz). MS (ESI$^+$): m/z 452 (M+H).

Preparation 246

1-tert-butyl 7-ethyl 2-acetyl-2-[(5-methoxy-3-pyridinyl)carbonyl]heptanedioate $^1$H NMR (CDCl$_3$) δ 1.24 (3H, t, J=8 Hz), 1.27-1.40 (11H, m), 1.60-1.74 (2H, m), 2.15-2.34 (4H, m), 2.44 (3H, s), 3.89 (3H, s), 4.10 (2H, q, J=8 Hz), 7.61 (1H, m), 8.43 (1H, d, J=3 Hz), 8.49 (1H, d, J=1 Hz). MS (ESI$^+$): m/z 422 (M+H).

Preparation 247

1-tert-butyl 5-ethyl 2-(methoxyacetyl)-2-[(5-methoxy-3-pyridinyl)carbonyl]pentanedioate $^1$H NMR (CDCl$_3$) δ 1.24 (3H, t, J=8 Hz), 1.38 (9H, s), 2.36-2.48 (2H, m), 2.53-2.67 (2H, m), 3.37 (3H, s), 3.90 (3H, s), 4.11 (2H, q, J=8 Hz), 4.33 (1H, d, J=18 Hz), 4.45 (1H, d, J=18 Hz), 7.59 (1H, m), 8.43 (1H, d, J=3 Hz), 8.51 (1H, d, J=1 Hz). MS (ESI$^+$): m/z 446 (M++Na).

Preparation 248

1-tert-butyl 6-ethyl 2-(methoxyacetyl)-2-[(5-methoxy-3-pyridinyl)carbonyl]hexanedioate $^1$H NMR (CDCl$_3$) δ 1.24 (3H, t, J=8 Hz), 1.37 (9H, s), 1.52-1.75 (2H, m), 2.18-2.39 (4H, m), 3.38 (3H, s), 3.90 (3H, s), 4.11 (2H, q, J=8 Hz), 4.37 (1H, d, J=18 Hz), 4.51 (1H, d, J=18 Hz), 7.60 (1H, m), 8.43 (1H, d, J=3 Hz), 8.50 (1H, d, J=1 Hz). MS (ESI$^+$): m/z 438 (M+H).

Preparation 249

1-tert-butyl 7-ethyl 2-(methoxyacetyl)-2-(5-pyrimidinylcarbonyl)heptanedioate $^1$H NMR (CDCl$_3$) δ 1.24 (3H, t, J=8 Hz), 1.30-1.44 (11H, m), 1.62-1.75 (2H, m), 2.16-2.35 (4H, m), 3.35 (3H, s), 4.11 (2H, q, J=8 Hz), 4.20 (1H, d, J=18 Hz), 4.33 (1H, d, J=18 Hz), 9.01 (2H, s), 9.31 (1H, s). MS (ESI$^+$): m/z 423 (M+H).

Preparation 250

1-tert-butyl 6-ethyl 2-[(5-chloro-3-pyridinyl)carbonyl]-2-(methoxyacetyl)hexanedioate $^1$H NMR (CDCl$_3$) δ 1.26 (3H, t, J=8 Hz), 1.39 (9H, s), 1.57-1.74 (2H, m), 1.78 (2H, br t, J=8 Hz), 2.23-2.41 (2H, m), 3.38 (3H, s), 4.14 (2H, q, J=8 Hz), 4.33 (1H, d, J=18 Hz), 4.45 (1H, d, J=18 Hz), 8.07 (1H, m), 8.71 (1H, br s), 8.80 (1H, br s). MS (ESI$^+$): m/z 442 (M+H).

Preparation 251

1-tert-butyl 5-ethyl 2-[(5-chloro-3-pyridinyl)carbonyl]-2-(methoxyacetyl)pentanedioate $^1$H NMR (CDCl$_3$) δ 1.25 (3H, t, J=8 Hz), 1.39 (9H, s), 2.37-2.48 (2H, m), 2.53-2.65 (2H, m), 3.36 (3H, s), 4.13 (2H, q, J=8 Hz), 4.26 (1H, d, J=18 Hz), 4.40 (1H, d, J=18 Hz), 8.06 (1H, br s), 8.70 (1H, br s), 8.80 (1H, br s). MS (ESI$^+$): m/z 428 (M+H).

Preparation 252

1-tert-butyl 7-ethyl 2-[(5-chloro-3-pyridinyl)carbonyl]-2-(methoxyacetyl)heptanedioate $^1$H NMR (CDCl$_3$) δ 1.24 (3H, t, J=8 Hz), 1.31-1.48 (11H, m), 1.55-1.75 (2H, m), 2.15-2.35 (4H, m), 3.36 (3H, s), 4.10 (2H, q, J=8 Hz), 4.27 (1H, d, J=18 Hz), 4.43 (1H, d, J=18 Hz), 8.03 (1H, t, J=2 Hz), 8.69 (1H, d, J=2 Hz), 8.77 (1H, d, J=2 Hz). MS (ESI$^+$): m/z 456 (M+H).

Preparation 253 methyl 4-(acetyloxy)-2-[(5-bromo-3-pyridinyl)carbonyl]-3-oxobutanoate $^1$H NMR (CDCl$_3$) δ 2.21 (3H, s), 3.58 (3H, br s), 4.87 (1H, br s), 5.19 (2H, br s), 7.98 (1H, br s), 8.58 (1H, br s), 8.79 (1H, br s). MS (ESI$^+$): m/z 358, 360 (M+H).

Preparation 254 tert-butyl 2-(2-{2-[2-(acetyloxy)ethoxy]ethoxy}ethyl)-2-[(5-methyl-3-pyridinyl)carbonyl]-3-oxobutanoate $^1$H-NMR (CDCl$_3$) δ 1.32 (9H, s), 2.07 (3H, s), 2.38 (3H, s), 2.45 (3H, s), 2.57 (2H, t, J=7 Hz), 3.43 (4H, m), 3.57 (4H, m), 4.16 (2H, m), 7.84 (1H, m), 8.53 (1H, m), 8.75 (1H, m).

Preparation 255

1-tert-butyl 6-ethyl 2-[(5-bromo-3-pyridinyl)carbonyl]-2-(methoxyacetyl)hexanedioate $^1$H NMR (CDCl$_3$) δ 1.26 (3H, t, J=7 Hz), 1.39 (9H, s), 1.55-1.75 (2H, m), 2.23-2.45 (4H, m), 3.38 (3H, s), 4.12 (2H, q, J=7 Hz), 4.34 (1H, d, J=18 Hz), 4.47 (1H, d, J=18 Hz), 8.22 (1H, m), 8.81 (1H, d, J=2 Hz), 8.83 (1H, d, J=2 Hz). MS (ESI$^+$): m/z 486 488.

Preparation 256 ethyl 2-(2-chloroisonicotinoyl)-3-oxobutanoate $^1$H NMR (CDCl$_3$) δ 0.91-1.00 (3H, m), 2.24 (1.2H, s), 2.48 (1.8H, s), 4.02 (1.2H, q, J=8 Hz), 4.10 (0.8H, q J=8 Hz), 7.24 (0.6H, m), 7.39 (0.6H, s), 7.45 (0.4H, m), 7.54 (1H, s), 8.49 (1H, m). MS (ESI$^+$): m/z 298 (M+H).

The following compound(s) was (were) obtained in a similar manner to that of Preparation 78.

Preparation 257 ethyl 5-(2-chloroisonicotinoyl)-6-oxoheptanoate $^1$H NMR (CDCl$_3$) δ 1.25 (3H, t, J=7 Hz), 1.60-1.73 (2H, m), 1.98-2.10 (2H, m), 2.20 (3H, s), 2.35 (2H, t, J=7 Hz), 4.12 (2H, q, J=7 Hz), 4.37 (1H, t, J=7 Hz), 7.67 (1H, d, J=5 Hz), 7.77 (1H, s), 8.59 (1H, d, J=5 Hz). MS (ESI$^+$): m/z 312.

Preparation 258 ethyl 4-(2-chloroisonicotinoyl)-5-oxohexanoate $^1$H NMR (CDCl$_3$) δ 1.26 (3H, t, J=7 Hz), 2.21 (3H, s), 2.22-2.35 (2H, m), 2.36-2.47 (2H, m), 4.12 (2H, q, J=7 Hz), 4.57 (1H, t, J=7 Hz), 7.76 (1H, dd, J=2 Hz, 5 Hz), 7.83 (1H, d, J=2 Hz), 8.61 (1H, d, J=5 Hz). MS (ESI$^+$): m/z 298.

Preparation 259 ethyl 6-(2-chloroisonicotinoyl)-7-oxo-8-phenyloctanoate $^1$H NMR (CDCl$_3$) δ 1.24 (3H, t, J=7 Hz), 1.20-1.38 (2H, m), 1.60-1.72 (2H, m), 1.95-2.06 (2H, m), 2.28 (2H, t, J=7 Hz), 3.71 (1H, d, J=17 Hz), 3.80 (1H, d, J=17 Hz), 4.12 (2H, q, J=7 Hz), 4.41 (1H, t, J=7 Hz), 7.10 (2H, m), 7.20-7.33 (4H, m), 7.39 (1H, s), 8.42 (1H, d, J=5 Hz).

Preparation 260 methyl ({3-[(5-methyl-3-pyridinyl)carbonyl]-4-oxopentyl}oxy)acetate $^1$H NMR (CDCl$_3$) δ 2.23 (3H, s), 2.23-2.40 (2H, m), 2.44 (3H, s), 3.58 (2H, m), 3.71 (3H, s), 4.02 (2H, s), 4.89 (1H, t, J=7 Hz), 8.12 (1H, s), 8.64 (1H, s), 9.07 (1H, s). MS (ESI$^+$): m/z 294.

Preparation 261 methyl(4-oxo-4-phenylbutoxy)acetate $^1$H NMR (CDCl$_3$) δ 2.04-2.16 (2H, m), 3.15 (2H, t, J=7 Hz), 3.64 (2H, t, J=7 Hz), 3.73 (3H, s), 4.09 (2H, s), 7.46 (2H, t, J=8 Hz), 7.56 (1H, t, J=8 Hz), 7.99 (2H, d, J=8 Hz). MS (ESI$^+$): m/z 237.

The following compound(s) was (were) obtained in a similar manner to that of Preparation 78.

Preparation 262 ethyl 3-[(5-bromo-3-pyridinyl)carbonyl]-4-oxopentanoate $^1$H NMR (CDCl$_3$) δ 1.24 (3H, t, J=7 Hz), 2.22 (3H, s), 2.97-3.17 (2H, m), 4.12 (2H, q, J=7 Hz), 4.91 (1H, m), 8.41 (1H, m), 8.88 (1H, m), 9.12 (1H, m). MS (ESI$^+$): m/z 328 330.

Preparation 263 ethyl 6-(acetyloxy)-4-[(5-methyl-3-pyridinyl)carbonyl]-5-oxohexanoate $^1$H NMR (CDCl$_3$) δ 1.25 (3H, t, J=7 Hz), 1.98 (3H, s), 2.23-2.34 (2H, m), 2.40-2.50 (2H, m), 2.45 (3H, s), 4.12 (2H, q, J=7 Hz), 4.69 (2H, m), 4.82 (1H, t, J=7 Hz), 8.14 (1H, s), 8.67 (1H, s), 9.07 (1H, s). MS (ESI$^+$): m/z 336.

Preparation 264 ethyl 7-(acetyloxy)-5-[(5-methyl-3-pyridinyl)carbonyl]-6-oxoheptanoate $^1$H NMR (CDCl$_3$) δ 1.25 (3H, t, J=7 Hz), 1.60-1.80 (2H, m), 2.02 (3H, s), 1.97-2.13 (2H, m), 2.35 (2H, t, J=7 Hz), 2.45 (3H, s), 4.12 (2H, q, J=7 Hz), 4.56 (1H, t, J=7 Hz), 4.69 (1H, d, J=17 Hz), 4.78 (1H, d, J=17 Hz), 8.06 (1H, s), 8.66 (1H, s), 9.00 (1H, s). MS (ESI$^+$): m/z 350.

Preparation 265 ethyl 8-(acetyloxy)-6-(3-cyanobenzoyl)-7-oxooctanoate $^1$H NMR (CDCl$_3$) δ 1.24 (3H, t, J=7 Hz), 1.35-1.50 (2H, m), 1.60-1.78 (2H, m), 2.04 (3H, s), 2.00-2.12 (2H, m), 2.29

(2H, t, J=7 Hz), 4.12 (2H, q, J=7 Hz), 4.49 (1H, t, J=7 Hz), 4.68 (1H, d, J=17 Hz), 4.75 (1H, d, J=17 Hz), 7.66 (1H, t, J=8 Hz), 7.88 (1H, d, J=8 Hz), 8.16 (1H, d, J=8 Hz), 8.26 (1H, s). MS (ESI$^-$): m/z 372.

Preparation 266 ethyl 7-(acetyloxy)-5-[(5-bromo-3-pyridinyl)carbonyl]-6-oxoheptanoate $^1$H NMR (CDCl$_3$) δ 1.25 (3H, t, J=7 Hz), 1.60-1.82 (2H, m), 2.04 (3H, s), 2.03-2.15 (2H, m), 2.35 (2H, t, J=7 Hz), 4.12 (2H, q, J=7 Hz), 4.51 (1H, t, J=7 Hz), 4.70 (1H, d, J=17 Hz), 4.75 (1H, d, J=17 Hz), 8.39 (1H, m), 8.88 (1H, s), 9.07 (1H, s). MS (ESI$^-$): m/z 414 416, MS (ESI$^+$): m/z 414 416.

Preparation 267 ethyl 6-(acetyloxy)-4-[(5-bromo-3-pyridinyl)carbonyl]-5-oxohexanoate $^1$H NMR (CDCl$_3$) δ 1.26 (3H, t, J=7 Hz), 2.00 (3H, s), 2.22-2.36 (2H, m), 2.43-2.53 (2H, m), 4.13 (2H, q, J=7 Hz), 4.70 (2H, m), 4.80 (1H, t, J=7 Hz), 8.48 (1H, s), 8.90 (1H, s), 9.19 (1H, s). MS (ESI$^+$): m/z 400 402.

Preparation 268 ethyl 6-(cyclohexylmethoxy)-4-[(5-methyl-3-pyridinyl)carbonyl]-5-oxohexanoate $^1$H NMR (CDCl$_3$) δ 0.60-0.82 (2H, m), 0.93-1.10 (3H, m), 1.12-1.65 (6H, m), 1.25 (3H, t, J=7 Hz), 2.07-2.17 (1H, m), 2.22-2.35 (1H, m), 2.42 (2H, m), 2.44 (3H, s), 3.05-3.23 (2H, m), 3.96 (2H, s), 4.12 (2H, q, J=7 Hz), 4.92 (1H, m), 8.16 (1H, s), 8.66 (1H, s), 9.08 (1H, s). MS (ESI$^+$): m/z 390.

Preparation 269 ethyl 4-[(5-bromo-3-pyridinyl)carbonyl]-6-(cyclohexylmethoxy)-5-oxohexanoate $^1$H NMR (CDCl$_3$) δ 0.63-0.84 (2H, m), 0.93-1.88 (3H, m), 1.25 (3H, t, J=7 Hz), 1.35-1.90 (6H, m), 2.02-2.14 (1H, m), 2.20-2.36 (1H, m), 2.44 (2H, t, J=7 Hz), 3.04-3.20 (2H, m), 3.95 (2H, s), 4.13 (2H, q, J=7 Hz), 4.854.93 (1H, m), 8.50 (1H, m), 8.88 (1H, d, J=2 Hz), 9.20 (1H, d, J=2 Hz). MS (ESI$^+$): m/z 454 456.

Preparation 270 ethyl 5-[(5-bromo-3-pyridinyl)carbonyl]-7-(cyclohexylmethoxy)-6-oxoheptanoate $^1$H NMR (300 MHz, CDCl$_3$) δ 0.75-0.86 (2H, m), 0.95-1.15 (3H, m), 1.24 (3H, t, J=7 Hz), 1.40-1.90 (10H, m), 2.36 (2H, t, J=7 Hz), 3.12 (2H, q, J=7 Hz), 3.97 (2H, s), 4.12 (2H, q, J=7 Hz), 4.71 (1H, t, J=7 Hz), 8.41 (1H, s), 8.88 (1H, s), 9.12 (1H, s). MS (ESI$^+$): m/z 468 470.

Preparation 271 ethyl 7-(cyclopropylmethoxy)-5-[(5-methyl-3-pyridinyl)carbonyl]-6-oxoheptanoate $^1$H NMR (CDCl$_3$) δ -0.08-0.00 (1H, m), 0.00-0.15 (1H, m), 0.28-0.49 (2H, m), 0.72-0.87 (1H, m), 1.23 (3H, t, J=7 Hz), 1.58-2.13 (4H, m), 2.32 (2H, t, J=7 Hz), 2.44 (3H, s), 3.10-3.26 (2H, m), 4.02 (2H, s), 4.12 (2H, q, J=7 Hz), 4.77 (1H, t, J=7 Hz), 8.07 (1H, s), 8.63 (1H, s), 9.03 (1H, s). MS (ESI$^+$): m/z 362.

Preparation 272 ethyl 6-(cyclopropylmethoxy)-4-[(5-methyl-3-pyridinyl)carbonyl]-5-oxohexanoate $^1$H NMR (CDCl$_3$) δ -0.08-0.00 (1H, m), 0.00-0.13 (1H, m), 0.23-0.47 (2H, m), 0.68-0.84 (1H, m), 1.24 (3H, t, J=7 Hz), 2.03-2.17 (1H, m), 2.22-2.36 (1H, m), 2.40 (2H, m), 2.44 (3H, s), 3.12 (2H, m), 3.98 (1H, d, J=17 Hz), 4.06 (1H, d, J=17 Hz), 4.12 (2H, q, J=7 Hz), 4.93 (1H, m), 8.12 (1H, s), 8.65 (1H, s), 9.08 (1H, s). MS (ESI$^+$): m/z 348.

Preparation 273 ethyl 4-[(5-bromo-3-pyridinyl)carbonyl]-6-(2-methoxyethoxy)-5-oxohexanoate $^1$H NMR (CDCl$_3$) δ 1.25 (3H, t, J=7 Hz), 1.90-2.37 (2H, m), 2.43 (2H, t, J=7 Hz), 3.18 (3H, s), 3.16-3.73 (4H, m), 4.06 (2H, q, J=7 Hz), 4.10-4.24 (2H, m), 4.86-4.93 (1H, m), 8.51 (1H, m), 8.87 (1H, d, J=2 Hz), 9.20 (1H, d, J=2 Hz). MS (ESI$^-$): m/z 414 416, MS (ESI$^+$): m/z 416 418.

Preparation 274

1-(5-bromo-3-pyridinyl)-1,3-butanedione $^1$H NMR (CDCl$_3$) δ 2.25 (3H, s), 6.18 (1H, s), 8.31 (1H, s), 8.78 (1H, s), 8.96 (1H, s). MS (ESI$^+$): m/z 242 244.

Preparation 275 ethyl 7-(acetyloxy)-5-[(5-chloro-3-pyridinyl)carbonyl]-6-oxoheptanoate $^1$H NMR (300 MHz, CDCl$_3$) δ 1.25 (3H, t, J=7 Hz), 1.60-1.70 (4H, m), 2.04 (3H, s), 2.35 (2H, t, J=6 Hz), 4.12 (2H, q, J=7 Hz), 4.52 (1H, t, J=7 Hz), 4.69 (1H, d, J=18 Hz), 4.78 (1H, d, J=18 Hz), 8.24 (1H, s), 8.78 (1H, s), 9.05 (1H, s).

Preparation 276 ethyl 6-[(5-chloro-3-pyridinyl)carbonyl]-8-(cyclopropylmethoxy)-7-oxooctanoate $^1$H NMR (300 MHz, CDCl$_3$) δ-0.09-0.11 (2H, m), 0.25-0.35 (1H, m), 0.37-0.46 (1H, m), 0.70-0.79 (1H, m), 1.24 (3H, t, J=7 Hz), 1.29-1.41 (2H, m), 1.64 (2H, t, J=7 Hz), 1.72-1.84 (1H, m), 1.96-2.08 (1H, m), 2.28 (2H, t, J=7 Hz), 3.12 (1H, dd, J=10, 7 Hz), 3.21 (1H, dd, J=10, 7 Hz), 3.97 (1H, d, J=12 Hz), 4.05 (1H, d, J=12 Hz), 4.11 (2H, q, J=7 Hz), 4.70 (1H, t, J=7 Hz), 8.26 (1H, dd, J=2, 2 Hz), 8.77 (1H, dd, J=2 Hz), 9.09 (1H, dd, J=2 Hz).

Preparation 277 ethyl 5-[(5-chloro-3-pyridinyl)carbonyl]-7-(cyclopropylmethoxy)-6-oxoheptanoate $^1$H NMR (300 MHz, CDCl$_3$) δ -0.07-0.09 (2H, m), 0.24-0.46 (2H, m), 0.68-0.79 (1H, m), 1.23 (3H, t, J=7 Hz), 1.47-1.84 (3H, m), 1.98-2.10 (1H, m), 2.33 (2H, t, J=7 Hz), 3.12 (1H, dd, J=10, 7 Hz), 3.21 (1H, dd, J=10, 7 Hz), 3.97 (1H, d, J=17 Hz), 4.06 (1H, d, J=17 Hz), 4.10 (2H, q, J=7 Hz), 4.73 (1H, t, J=6 Hz), 8.27 (1H, dd, J=2, 2 Hz), 8.77 (1H, d, J=2 Hz), 9.10 (1H, d, J=2 Hz).

Preparation 278 ethyl 6-[(5-bromo-3-pyridinyl)carbonyl]-8-isobutoxy-7-oxooctanoate $^1$H NMR (300 MHz, CDCl$_3$) δ 0.72 (3H, d, J=7 Hz), 0.77 (3H, d, J=7 Hz), 1.24 (3H, t, J=7 Hz), 1.30-1.42 (2H, m), 1.54-1.70 (3H, m), 1.75-1.87 (1H, m), 1.95-2.08 (1H, m), 2.28 (2H, t, J=8 Hz), 3.10 (1H, dd, J=9, 7 Hz), 3.14 (1H, dd, J=9, 7 Hz), 3.98 (2H, s), 4.11 (2H, q, J=7 Hz), 4.70 (1H, t, J=6 Hz), 8.39 (1H, dd, J=2 Hz), 8.87 (1H, d, J=2 Hz), 9.08 (1H, d, J=2 Hz).

Preparation 279 ethyl 4-[(5-chloro-3-pyridinyl)carbonyl]-6-isobutoxy-5-oxohexanoate $^1$H NMR (300 MHz, CDCl$_3$) δ 0.68 (3H, d, J=7 Hz), 0.72 (3H, d, J=7 Hz), 1.25 (3H, t, J=7 Hz), 1.52 (1H, qt, J=7, 7 Hz), 2.02-2.13 (1H, m), 2.20-2.32 (1H, m), 2.44 (2H, t, J=7 Hz), 3.07 (1H, dd, J=9, 7 Hz), 3.12 (1H, dd, J=9, 7 Hz), 3.98 (2H, s), 4.14 (2H, q, J=7 Hz), 4.90 (1H, d, J=9 Hz), 4.92 (1H, d, J=9 Hz), 8.34 (1H, dd, J=2 Hz), 8.78 (1H, d, J=2 Hz), 9.15 (1H, d, J=2 Hz).

Preparation 280 ethyl 6-(acetyloxy)-4-(3-chlorobenzoyl)-5-oxohexanoate $^1$H NMR (300 MHz, CDCl$_3$) δ 1.26 (3H, t, J=7 Hz), 1.95 (3H, s), 2.20-2.29 (2H, m), 2.41-2.47 (2H, m), 4.15 (2H, q, J=7 Hz), 4.64 (1H, d, J=17 Hz), 4.71 (1H, d, J=17 Hz), 4.78 (1H, t, J=6 Hz), 7.48 (1H, dd, J=8, 8 Hz), 7.60 (1H, d, J=8 Hz), 7.96 (1H, d, J=8 Hz), 8.04 (1H, s).

Preparation 281 ethyl 5-[(5-bromo-3-pyridinyl)carbonyl]-7-isobutoxy-6-oxoheptanoate $^1$H NMR (300 MHz, CDCl$_3$) δ 0.72 (3H, d, J=7 Hz), 0.77 (3H, d, J=7 Hz), 1.23 (3H, t, J=7 Hz), 1.61-1.73 (3H, m), 1.77-1.88 (1H, m), 1.98-2.10 (1H, m), 2.33 (2H, t, J=7 Hz), 3.10 (1H, dd, J=9, 7 Hz), 3.15 (1H, dd, J=9, 7 Hz), 3.99 (2H, s), 4.11 (2H, q, J=7 Hz), 4.73 (1H, t, J=7 Hz), 8.40 (1H, dd, J=2, 2 Hz), 8.87 (1H, d, J=2 Hz), 9.10 (1H, d, J=2 Hz).

Preparation 282

1,3-bis(5-bromo-3-pyridinyl)-1,3-propanedione $^1$H NMR (DMSO-d$_6$) δ 7.60 (1H, s), 8.78 (2H, s), 8.88 (2H, s), 9.30 (2H, s).

Preparation 283 ethyl 7-(acetyloxy)-5-(3-chlorobenzoyl)-6-oxoheptanoate $^1$H NMR (CDCl$_3$) δ 1.24 (3H, t, J=8 Hz), 1.57-1.75 (2H, m), 1.90-2.12 (5H, m), 2.34 (2H, t, J=8 Hz), 4.11 (2H, q, J=8 Hz), 4.52 (1H, t, J=8 Hz), 4.71 (2H, q, J=8 Hz), 4.65 (1H, d, J=16 Hz), 4.75 (1H, d, J=16 Hz), 7.43 (1H, t, J=8 Hz), 7.60 (1H, br d, J=8 Hz), 7.84 (1H, br d, J=8 Hz), 7.96 (1H, br s).

Preparation 284 ethyl 8-methoxy-6-[(5-methoxy-3-pyridinyl)carbonyl]-7-oxooctanoate $^1$H NMR (CDCl$_3$) δ 1.23 (3H, t, J=8 Hz), 1.27-1.43 (2H, m), 1.55-1.70 (2H, m), 1.84 (1H, m), 2.00 (1H, m), 2.27 (2H, d, J=8 Hz), 3.26 (3H, s), 3.92 (3H, s), 3.98 (2H, d, J=5 Hz), 4.10 (2H, q, J=8 Hz), 4.67 (1H, t, J=8 Hz), 7.71 (1H, m), 8.50 (1H, d, J=3 Hz), 8.78 (1H, br s). MS (ESI$^+$): m/z 352 (M+H).

Preparation 285 ethyl 6-[(5-methoxy-3-pyridinyl)carbonyl]-7-oxooctanoate $^1$H NMR (CDCl$_3$) δ 1.24 (3H, t, J=8 Hz), 1.27-1.41 (2H, m), 1.60-1.73 (2H, m), 1.90-2.14 (2H, m), 2.18 (3H, s), 2.24-2.84 (2H, m), 3.26 (3H, s), 3.92 (3H, s), 4.10 (2H, q, J=8 Hz), 4.40 (1H, t, J=8 Hz), 7.71 (1H, m), 8.51 (1H, d, J=3 Hz), 8.78 (1H, br s).

Preparation 286 ethyl 6-methoxy-4-[(5-methoxy-3-pyridinyl)carbonyl]-5-oxohexanoate $^1$H NMR (CDCl$_3$) δ 1.24 (3H, t, J=8 Hz), 2.10 (1H, m), 2.25 (1H, m), 2.38-2.47 (2H, m), 3.24 (3H, s), 3.94 (3H, s), 3.95 (1H, d, J=16 Hz), 4.00 (1H, d, J=16 Hz), 4.12 (2H, q, J=8 Hz), 4.38 (1H, m), 7.83 (1H, m), 8.52 (1H, d, J=3 Hz), 8.87 (1H, d, J=1 Hz). MS (ESI$^+$): m/z 346 (M++Na).

Preparation 287 ethyl 7-methoxy-5-[(5-methoxy-3-pyridinyl)carbonyl]-6-oxoheptanoate $^1$H NMR (CDCl$_3$) δ 1.23 (3H, t, J=8 Hz), 1.54-1.74 (2H, m), 1.84 (1H, m), 2.02 (1H, m), 2.32 (2H, d, J=8 Hz), 3.26 (3H, s), 3.92 (3H, s), 3.99 (2H, d, J=5 Hz), 4.10 (2H, q, J=8 Hz), 4.70 (1H, t, J=8 Hz), 7.71 (1H, m), 8.51 (1H, d, J=3 Hz), 8.79 (1H, br s). MS (ESI$^+$): m/z 338 (M+H).

Preparation 288 ethyl 8-methoxy-7-oxo-6-(5-pyrimidinylcarbonyl)octanoate $^1$H NMR (CDCl$_3$) δ 1.23 (3H, t, J=8 Hz), 1.25-1.45 (2H, m), 1.55-1.70 (2H, m), 1.81 (1H, m), 2.03 (1H, m), 2.28 (2H, t, J=8 Hz), 3.24 (3H, s), 3.92 (1H, d, J=18 Hz), 4.01 (1H, d, J=18 Hz), 4.10 (2H, q, J=8 Hz), 9.26 (2H, s), 9.40 (1H, s). MS (ESI$^+$): m/z 323 (M+H).

Preparation 289 ethyl 5-[(5-chloro-3-pyridinyl)carbonyl]-7-methoxy-6-oxoheptanoate $^1$H NMR (CDCl$_3$) δ 1.24 (3H, t, J=8 Hz), 1.52-1.74 (2H, m), 1.83 (1H, m), 2.02 (1H, m), 2.34-2.40 (2H, m), 3.25 (3H, s), 3.92 (1H, d, J=16 Hz), 4.01 (1H, d, J=16 Hz), 4.11 (2H, q, J=8 Hz), 4.68 (1H, t, J=8 Hz), 8.23 (1H, br s), 8.78 (1H, br s), 9.05 (1H, br s). MS (ESI$^+$): m/z 342 (M+H).

Preparation 290 ethyl 4-[(5-chloro-3-pyridinyl)carbonyl]-6-methoxy-5-oxohexanoate

¹H NMR (CDCl₃) δ 1.25 (3H, t, J=8 Hz), 2.09 (1H, m), 2.25 (1H, m), 2.38-2.49 (2H, m), 3.22 (3H, s), 3.91 (1H, d, J=18 Hz), 4.00 (1H, d, J=18 Hz), 4.14 (2H, q, J=8 Hz), 4.85 (1H, m), 8.33 (1H, br s), 8.78 (1H, br s), 9.14 (1H, br s). MS (ESI⁺): m/z 328 (M+H).

Preparation 291 ethyl 6-[(5-chloro-3-pyridinyl)carbonyl]-8-methoxy-7-oxooctanoate

¹H NMR (CDCl₃) δ 1.23 (3H, t, J=8 Hz), 1.27-1.43 (2H, m), 1.50-1.71 (2H, m), 1.82 (1H, m), 2.00 (1H, m), 2.27 (2H, d, J=8 Hz), 3.25 (3H, s), 3.92 (1H, d, J=16 Hz), 4.02 (1H, d, J=16 Hz), 4.10 (2H, q, J=8 Hz), 4.63 (1H, t, J=8 Hz), 8.23 (1H, br s), 8.78 (1H, br s), 9.03 (1H, br s). MS (ESI⁺): m/z 356 (M+H).

Preparation 292

2-[2-({3-[(5-methyl-3-pyridinyl)carbonyl]-4-oxopentyl}oxy)ethoxy]ethyl acetate trifluoroacetate ¹H-NMR (CDCl₃) δ 2.06 (3H, s), 2.28 (3H, s), 2.33 (2H, m), 2.65 (3H, s), 3.47-3.67 (8H, m), 4.17 (2H, m), 4.71 (1H, t, J=7 Hz), 8.66 (1H, m), 8.88 (11H, m), 9.31 (11H, m).

Preparation 293 ethyl 5-[(5-bromo-3-pyridinyl)carbonyl]-7-methoxy-6-oxoheptanoate

¹H NMR (CDCl₃) δ 1.23 (3H, t, J=7 Hz), 1.56-1.73 (2H, m), 1.77-1.92 (1H, m), 1.96-2.10 (1H, m), 2.32 (2H, t, J=7 Hz), 3.25 (3H, s), 3.92 (1H, d, J=17 Hz), 4.02 (1H, d, J=17 Hz), 4.12 (2H, q, J=7 Hz), 4.67 (1H, t, J=7 Hz), 8.39 (1H, m), 8.87 (1H, d, J=2 Hz), 9.09 (1H, d, J=2 Hz). MS (ESI⁺): m/z 386 388.

The following compound(s) was (were) obtained in a similar manner to that of Preparation 129 and 130.

Preparation 294 tert-butyl 3-oxo-4-phenylbutanoate

¹H NMR (CDCl₃) δ 1.46 (9H, s), 3.37 (2H, s), 3.82 (2H, s), 7.21 (2H, d, J=8 Hz), 7.25-7.37 (3H, m).

Preparation 295 tert-butyl 3-oxo-3-phenylpropanoate

¹H NMR (CDCl₃) δ 1.43 (9H, s), 3.81 (2H, s), 7.40-7.52 (2H, m), 7.56-7.63 (1H, m), 7.94 (2H, d, J=8 Hz).

Preparation 296 tert-butyl 4-(cyclohexylmethoxy)-3-oxobutanoate

¹H NMR (CDCl₃) δ 0.89-1.07 (2H, m), 1.13-1.40 (3H, m), 1.47 (9H, s), 1.60-1.83 (6H, m), 3.28 (2H, d, J=7 Hz), 3.45 (2H, s), 4.06 (2H, s).

Preparation 297 tert-butyl 4-(cyclopropylmethoxy)-3-oxobutanoate

¹H NMR (CDCl₃) δ 0.20-0.28 (2H, m), 0.55-0.64 (2H, m), 1.03-1.17 (1H, m), 1.47 (9H, s), 3.36 (2H, d, J=7 Hz), 3.45 (2H, s), 4.15 (2H, s).

Preparation 298 tert-butyl 4-(2-methoxyethoxy)-3-oxobutanoate

¹H NMR (CDCl₃) δ 1.47 (9H, s), 3.38 (3H, s), 3.44 (2H, s), 3.57 (2H, m), 3.70 (2H, m), 4.20 (2H, s).

Preparation 299 tert-butyl 4-isobutoxy-3-oxobutanoate

¹H NMR (300 MHz, CDCl₃) δ 0.93 (6H, d, J=7 Hz), 1.45 (9H, s), 1.91 (1H, qt, J=7, 7 Hz), 3.26 (2H, d, J=7 Hz), 3.45 (2H, s), 4.07 (2H, s).

Preparation 300 tert-butyl 3-(3-methyl-2-thienyl)-3-oxopropanoate

¹H-NMR (CDCl₃) δ 1.47 (9H, s), 2.57 (3H, s), 3.79 (2H, s), 6.96 (1H, d, J=5 Hz), 7.44 (1H, d, J=5 Hz).

Preparation 301 tert-butyl 3-(5-methyl-3-isoxazolyl)-3-oxopropanoate

¹H-NMR (CDCl₃) δ 1.475-1.57 (9H, m), 2.49 (3H, m), 3.95 (2H, s), 6.40 (1H, s).

The following compound(s) was (were) obtained in a similar manner to that of Preparation 132.

Preparation 302 ethyl (2E)-5-(3-cyanobenzoyl)-6-oxo-2-heptenoate

¹H-NMR (CDCl₃) δ 1.28 (3H, t, J=7 Hz), 2.20 (3H, s), 2.88 (2H, m), 4.16 (2H, q, J=7 Hz), 4.54 (1H, t, J=7 Hz), 5.88 (1H, d, J=16 Hz), 6.82 (1H, dt, J=7 and 16 Hz), 7.65 (1H, t, J=8 Hz), 7.89 (1H, d, J=8 Hz), 8.20 (1H, d, J=8 Hz), 8.27 (1H, s). MS (ESI⁺): m/z 300.14 (M+H)

Preparation 303

1-tert-butyl 7-ethyl 2-[(3-methyl-2-thienyl)carbonyl]heptanedioate

¹H-NMR (CDCl₃) δ 1.25 (3H, t, J=7 Hz), 1.35-1.51 (11H, m), 1.65 (2H, m), 1.96 (2H, m), 2.30 (2H, t, J=7 Hz), 2.58 (3H, s), 3.94 (1H, t, J=7 Hz), 4.12 (2H, q, J=7 Hz), 6.97 (1H, d, J=5 Hz), 7.44 (1H, d, J=5 Hz).

Preparation 304

1-tert-butyl 7-ethyl 2-[(5-methyl-3-isoxazolyl)carbonyl]heptanedioate

¹H-NMR (CDCl₃) δ 11.24 (3H, t, J=7 Hz), 1.39 (9H, s), 1.67 (2H, m), 1.98 (2H, m), 2.49 (3H, s), 4.10 (2H, q, J=7 Hz), 4.26 (1H, t, J=7 Hz), 6.37 (1H, s).

The following compound(s) was (were) obtained in a similar manner to that of Preparation 152.

Preparation 305 methyl 7-oxo-7-(2-thienyl)heptanoate $^1$H-NMR (CDCl$_3$) δ 1.41 (2H, m), 1.63-1.82 (4H, m), 2.33 (2H, t, J=7 Hz), 2.91 (2H, t, J=7 Hz), 3.67 (3H, s), 1.73 (1H, m), 7.62 (1H, m), 7.70 (1H, m).

The following compound(s) was (were) obtained in a similar manner to that of Preparation 153.

Preparation 306

5-methoxynicotinoyl chloride hydrochloride

Preparation 307

5-pyrimidinecarbonyl chloride hydrochloride

Preparation 308

5-chloronicotinoyl chloride hydrochloride

Preparation 309 methyl 2-bromo-4-(chlorocarbonyl)benzoate

The following compound(s) was (were) obtained in a similar manner to that of Preparation 159.

Preparation 310

1-tert-butyl 7-ethyl 2-(phenylacetyl)heptanedioate $^1$H NMR (CDCl$_3$) δ 1.24 (3H, t, J=7 Hz), 1.18-1.50 (2H, m), 1.46 (9H, s), 1.50-1.75 (2H, m), 1.75-1.88 (2H, m), 2.24 (2H, t, J=7 Hz), 3.47 (1H, t, J=7 Hz), 3.81 (2H, s), 4.10 (2H, q, J=7 Hz), 7.20 (2H, d, J=8 Hz), 7.25-7.37 (3H, m).

Preparation 311 tert-butyl 2-[2-(2-methoxy-2-oxoethoxy)ethyl]-3-oxobutanoate $^1$H NMR (CDCl$_3$) δ 1.46 (9H, s), 2.04-2.23 (2H, m), 2.29 (3H, s), 3.54 (2H, t, J=7 Hz), 3.69 (1H, t, J=7 Hz), 3.74 (3H, s), 4.04 (2H, s).

Preparation 312 tert-butyl 2-benzoyl-4-(2-methoxy-2-oxoethoxy)butanoate $^1$H NMR (CDCl$_3$) δ 1.34 (9H, s), 2.26-2.40 (2H, m), 3.55-3.67 (2H, m), 3.70 (3H, s), 4.04 (2H, s), 4.57 (1H, t, J=7 Hz), 7.47 (2H, t, J=8 Hz), 7.56 (1H, m), 8.01 (2H, d, J=8 Hz).

Preparation 313

1-tert-butyl 6-ethyl 2-[(acetyloxy)acetyl]hexanedioate $^1$H NMR (CDCl$_3$) δ 1.25 (3H, t, J=7 Hz), 1.48 (9H, s), 1.60-1.73 (2H, m), 1.82-1.95 (2H, m), 2.17 (3H, s), 2.32 (2H, t, J=7 Hz), 3.43 (1H, t, J=7 Hz), 4.12 (2H, q, J=7 Hz), 4.72 (1H, d, J=17 Hz), 4.83 (1H, d, J=17 Hz).

Preparation 314

1-tert-butyl 5-ethyl 2-[(cyclohexylmethoxy)acetyl]pentanedioate $^1$H NMR (CDCl$_3$) δ 0.85-1.06 (2H, m), 1.13-1.34 (3H, m), 1.26 (3H, t, J=7 Hz), 1.45 (9H, s), 1.60-1.85 (6H, m), 2.08-2.23 (2H, m), 2.36 (2H, t, J=7 Hz), 3.27 (2H, d, J=7 Hz), 3.67 (1H, t, J=7 Hz), 4.10 (2H, s), 4.12 (2H, q, J=7 Hz).

Preparation 315

1-tert-butyl 6-ethyl 2-[(cyclohexylmethoxy)acetyl]hexanedioate $^1$H NMR (CDCl$_3$) δ 0.88-1.06 (2H, m), 1.12-1.34 (3H, m), 1.25 (3H, t, J=7 Hz), 1.45 (9H, s), 1.54-1.94 (10H, m), 2.32 (2H, t, J=7 Hz), 3.27 (2H, d, J=7 Hz), 3.56 (1H, t, J=7 Hz), 4.09 (2H, s), 4.11 (2H, q, J=7 Hz). MS (ESI$^+$): m/z 385.

Preparation 316

1-tert-butyl 6-ethyl 2-[(cyclopropylmethoxy)acetyl]hexanedioate $^1$H NMR (CDCl$_3$) δ 0.22-0.33 (2H, m), 0.54-0.64 (2H, m), 1.04-1.18 (1H, m), 1.25 (3H, t, J=7 Hz), 1.45 (9H, s), 1.60-1.73 (2H, m), 1.83-1.95 (2H, m), 2.33 (2H, t, J=7 Hz), 3.33 (2H, d, J=7 Hz), 3.53 (1H, t, J=7 Hz), 4.12 (2H, q, J=7 Hz), 4.18 (2H, m). MS (ESI$^+$): m/z 343.

Preparation 317

1-tert-butyl 5-ethyl 2-[(cyclopropylmethoxy)acetyl]pentanedioate $^1$H NMR (CDCl$_3$) δ 0.20-0.35 (2H, m), 0.56-0.64 (2H, m), 1.04-1.16 (1H, m), 1.26 (3H, t, J=7 Hz), 1.45 (9H, s), 2.12-2.24 (2H, m), 2.38 (2H, t, J=7 Hz), 3.36 (2H, m), 3.65 (1H, t, J=7 Hz), 4.12 (2H, q, J=7 Hz), 4.19 (2H, s).

Preparation 318

1-tert-butyl 5-ethyl 2-[(2-methoxyethoxy)acetyl]pentanedioate $^1$H NMR (CDCl$_3$) δ 1.25 (3H, t, J=7 Hz), 1.46 (9H, s), 2.10-2.23 (2H, m), 2.38 (2H, t, J=7 Hz), 3.37 (3H, s), 3.60 (2H, m), 3.62 (1H, t, J=7 Hz), 3.70 (2H, m), 4.12 (2H, q, J=7 Hz), 4.23 (1H, d, J=17 Hz), 4.30 (1H, d, J=17 Hz). MS (ESI$^+$): m/z 333.

Preparation 319

1-tert-butyl 5-ethyl 2-(isobutoxyacetyl)pentanedioate $^1$H NMR (300 MHz, CDCl$_3$) δ 0.93 (6H, d, J=7 Hz), 1.26 (3H, t, J=7 Hz), 1.45 (9H, s), 1.91 (1H, qt, J=7, 7 Hz), 2.13 (2H, m), 2.37 (2H, t, J=7 Hz), 3.25 (2H, d, J=7 Hz), 3.67 (1H, t, J=7 Hz), 4.12 (2H, s), 4.13 (2H, q, J=7 Hz).

The following compound(s) was (were) obtained in a similar manner to that of Preparation 164.

Preparation 320 methyl 2-bromo-4-[(5-ethyl-1H-pyrrol-2-yl)carbonyl]benzoate $^1$H-NMR (CDCl$_3$) δ 1.32 (3H, t, J=7 Hz), 2.72 (2H, q, J=7 Hz), 3.97 (3H, s), 6.10 (1H, m), 6.77 (1H, m), 7.81 (1H, d, J=8 Hz), 7.85 (1H, d, J=8 Hz), 8.11 (1H, s), 9.32 (1H, s, br).

The following compound(s) was (were) obtained in a similar manner to that of Preparation 165.

Preparation 321 tert-butyl 2-(2-{2-[2-(acetyloxy)ethoxy]ethoxy}ethyl)-3-oxobutanoate $^1$H-NMR (CDCl$_3$) δ 1.46 (9H, s), 2.00-2.17 (5H, m), 2.25 (3H, s), 3.45-3.70 (10H, m), 4.22 (2H, m).

The following compound(s) was (were) obtained in a similar manner to that of Preparation 178.

Preparation 322

Isobutoxyacetic Acid $^1$H NMR (300 MHz, CDCl$_3$) δ 0.94 (6H, d, J=7 Hz), 1.93 (1H, qt, J=7, 7 Hz), 3.34 (2H, d, J=7 Hz), 4.12 (2H, s).

Preparation 323

To a suspension of 60% NaH (2.66 g) in DMF (20 mL) was added methyl hydroxyacetate (5.00 g) under ice-water cooling, and the mixture was stirred at 0° C. for 0.5 hour. To this was added 2-(2-bromoethoxy)tetrahydro-2H-pyran (12.8 g) under ice-water cooling, and the mixture was stirred at ambient temperature for 2 hours. The mixture was partitioned between AcOEt and water. The organic layer was separated, washed with water and brine, dried over MgSO$_4$, and evaporated in vacuo. The residue was purified by silica gel column chromatography eluting with a mixture of hexane and AcOEt (10:1-3:1) to give methyl [2-(tetrahydro-2H-pyran-2-yloxy)ethoxy]acetate pale yellow oil (445 g).

methyl[2-(tetrahydro-2H-pyran-2-yloxy)ethoxy]acetate $^1$H NMR (CDCl$_3$) δ 1.48-1.95 (6H, m), 3.46-3.57 (2H, m), 3.64-3.75 (2H, m), 3.76 (3H, s), 3.82-3.97 (2H, m), 4.20 (2H, s), 4.66 (1H, m).

Preparation 324

A mixture of methyl [2-(tetrahydro-2H-pyran-2-yloxy)ethoxy]acetate (1.07 g) and pyridinium p-toluenesulfonate (24.6 mg) in MeOH (10 mL) was heated under reflux for 2 hours. After evaporation of solvent, the residue was purified by silica gel column chromatography eluting with a mixture of hexane and AcOEt (10:1-1:3) to give methyl (2-hydroxyethoxy)acetate as colorless oil (555 mg).

methyl(2-hydroxyethoxy)acetate $^1$H NMR (CDCl$_3$) δ 3.69 (2H, m), 3.76 (2H, m), 3.78 (3H, s), 4.16 (2H, s).

Preparation 325

To solution of methyl(2-hydroxyethoxy)acetate (540 mg), imidazole (411 mg) and triphenylphosphine (1.37 g) in ether (2 mL) and CH$_3$CN (1 mL) was added iodine (1.43 g) under ice-water cooling and the mixture was stirred at 0° C. for 2 hours. After insolubles were filtered off, the filtrates were diluted with AcOEt, washed with aq Na$_2$SO$_3$ solution and brine, dried over MgSO$_4$, and evaporated in vacuo. The residue was purified by silica gel column chromatography eluting with a mixture of hexane and AcOEt (20:1-5:1) to give methyl(2-iodoethoxy)acetate as colorless oil (898 mg).

methyl(2-iodoethoxy)acetate $^1$H NMR (CDCl$_3$) δ 3.30 (2H, t, J=7 Hz), 3.77 (3H, s), 3.84 (2H, t, J=7 Hz), 4.17 (2H, s).

Preparation 326

To a suspension of 60% NaH (1.02 g) in THF (50 mL) was added tert-butyl 4-(acetyloxy)-3-oxobutanoate (5.00 g) under ice-water cooling and the mixture was stirred at 0° C. for 0.5 hour. To this added ethyl 3-iodopropanoate (5.54 g) and the mixture was stirred at 50° C. for 8 hours. The mixture was partitioned between AcOEt and water. The organic layer was separated, washed with brine, dried over MgSO$_4$, and evaporated in vacuo. The residue was purified by silica gel column chromatography eluting with a mixture of hexane and AcOEt (20:1-3:1) to give 1-tert-butyl 5-ethyl 2-[(acetyloxy)acetyl]pentanedioate as yellow oil (4.27 g).

1-tert-butyl 5-ethyl 2-[(acetyloxy)acetyl]pentanedioate $^1$H NMR (CDCl$_3$) δ 1.26 (3H, t, J=7 Hz), 1.46 (9H, s), 2.14-2.24 (2H, m), 2.17 (3H, s), 2.36 (2H, t, J=7 Hz), 3.60 (1H, t, J=7 Hz), 4.12 (2H, q, J=7 Hz), 4.73 (1H, d, J=18 Hz), 4.83 (1H, d, J=18 Hz).

Preparation 327

To a solution of benzyl 4-thiomorpholinecarboxylate (4.8 g) in methanol (30 mL) and H$_2$O (20 mL) was added oxone (16.2 g) under ice water cooling and the mixture was stirred at ambient temperature for 2 hours. The solution was evaporated in vacuo and partitioned between EtOAc and water. The aqueous layer was extracted with EtOAc. The combined organic layer was washed with water and brine, dried over MgSO$_4$ and evaporated in vacuo. The residue was purified by silica gel column chromatography eluting with a mixture of hexane and EtOAc to give benzyl 4-thiomorpholinecarboxylate 1,1-dioxide as a colorless solid (3.8 g).

benzyl 4-thiomorpholinecarboxylate 1,1-dioxide $^1$H NMR (300 MHz, CDCl$_3$) δ 3.02 (4H, br s), 4.01 (4H, t, J=5 Hz), 5.16 (2H, s), 7.33-7.40 (5H, m).

Preparation 328

To a solution of thiomorpholine (2 g) in 1N NaOH (11.6 mL) was added benzyl chloridocarbonate (1.66 mL) under ice water cooling and the mixture was stirred at ambient temperature for 2 hours. The solution was neutralized with 1N HCl and extracted with EtOAc twice. The combined organic layer was washed with water and brine, dried over MgSO$_4$ and evaporated in vacuo. The residue was purified by silica gel column chromatography to give benzyl 4-thiomorpholinecarboxylate as a colorless solid (4.8 g).

benzyl 4-thiomorpholinecarboxylate $^1$H NMR (300 MHz, CDCl$_3$) δ 2.59 (4H, br s), 3.77 (4H, t, J=5 Hz), 5.14 (2H, s), 7.30-7.41 (5H, m).

Preparation 329

To a solution of benzyl 4-thiomorpholinecarboxylate 1,1-dioxide (3.8 g) in methanol (32 mL) and 1,4-dioxane (8 mL) was added Palladium, 10 wt. % on activated carbon (380 mg) at ambient temperature. The mixture was stirred at ambient temperature for 4 hours under $H_2$ (3.4 atom). The mixture was filtered and evaporated in vacuo to give thiomorpholine 1,1-dioxide as a colorless solid (2.22 g).

thiomorpholine 1,1-dioxide $^1$H NMR (300 MHz, $CDCl_3$) δ 3.03 (4H, t, J=5 Hz), 3.33 (4H, t, J=5 Hz). MS (m/z) 1.36 (M+H).

Preparation 330

To a suspension of [(5-chloro-4-mercapto-6-methyl-3-pyridinyl)oxy]acetic acid (10 g) in dichloromethane (100 mL) was added Et3N (14 mL) in ice-MeOH bath. To this was added trifluoromethanesulfonic anhydride (14.3 mL) dropwise below 10° C. over 30 min. After 2 hours the mixture was partitioned between $CHCl_3$ and water. The aqueous layer was extracted with $CHCl_3$ twice. The combined organic layer was dried over $MgSO_4$ and evaporated in vacuo to give brown oil. The residue was purified by silica gel column chromatography (silica gel, 100 mL) eluted with hexane-EtOAc=15-1 and 10-1 to give 5-chloro-3-pyridinyl trifluoromethanesulfonate (15.8 g) as a pale brown oil.

5-chloro-3-pyridinyl trifluoromethanesulfonate $^1$H NMR (300 MHz, $CDCl_3$) δ 7.69 (1H, dd, J=4, 4 Hz), 8.52 (1H, d, J=4 Hz), 8.65 (1H, d, J=4 Hz).

Preparation 331

To ethanol (66 mL) and DMF (66 mL) was added Et3N (29.4 mL), 1,3-propanediylbis(diphenylphosphine) (3.48 g) and palladium acetate (1.9 g) in ice-water bath. To this was added 5-chloro-3-pyridinyl trifluoromethanesulfonate (22.1 g) at the temperature. The mixture was stirred at 50° C. for 4 hours under CO (1 atom). The mixture was partitioned between EtOAc and water. The aqueous layer was extracted with EtOAc. The combined organic layer was washed with water three times, dried over $MgSO_4$ and evaporated in vacuo. The residue was purified by silica gel column chromatography (silica gel, 200 mL) eluted with hexane-EtOAc=15-1 and 10-1 to give ethyl 5-chloronicotinate (105 g) as a pale brown oil.

ethyl 5-chloronicotinate $^1$H NMR (300 MHz, $CDCl_3$) δ 1.42 (3H, t, J=7 Hz), 4.43 (2H, q, J=7 Hz), 8.28 (1H, dd, J=3, 3 Hz), 8.74 (1H, d, J=3 Hz), 9.09 (1H, d, J=3 Hz).

Preparation 332

To 5-chloronicotinate (105 g) was added 1N NaOH (84.9 mL) at ambient temperature. The mixture was heated at 60° C. for 1 hour. The reaction mixture was adjusted to pH 4-5 with HCl. The precipitate was filtered to give 5-chloronicotinic acid (6.9 g) a colorless solid.

$^1$H NMR (300 MHz, DMSO-$d_6$) δ 8.30 (1H, dd, J=3 Hz), 8.88 (1H, d, J=3 Hz), 9.01 (1H, d, J=3 Hz), 1.38 (1H, br s).

5-chloronicotinic acid

H NMR (300 MHz, DMSO-$d_6$) δ 8.30 (1H, dd, J=3, 3 Hz), 8.88 (1H, d, J=3 Hz), 9.01 (1H, d, J=3 Hz), 1.38 (1H, br s).

The following compound(s) was (were) obtained in a similar manner to that of Preparation 332.

Preparation 333

5-methoxynicotinic acid $^1$H NMR (DMSO-$d_6$) δ 3.87 (3H, s), 7.73 (1H, m), 8.48 (1H, d, J=3 Hz), 8.65 (1H, d, J=1 Hz). MS (ESI$^+$): m/z 154 (M+H).

Preparation 334

5-pyrimidinecarboxylic acid $^1$H NMR (DMSO-$d_6$) δ 9.20 (2H, s), 9.37 (1H, s). MS (ESI$^+$): m/z 148 (M++Na).

Preparation 335

To a solution of diisopropylamine (5.41 g) in THF (30 mL) was added 1.5 M n-butyllithium hexane solution (35 mL) under dryice acetone cooling and the mixture was stirred at −78° C. for 10 minutes. To this was added tert-butyl acetate (5.87 g) under dryice acetone cooling and the mixture was stirred at −78° C. for 10 minutes and added dropwise to a solution of 5-bromonicotinic acid (3.00 g) and N,N-carbonyldiimidazole (2.65 g) in THF (30 mL) under dryice acetone cooling. The mixture was stirred at −78° C. for 0.5 hour. The mixture was partitioned between ethyl acetate and aq NH$_4$Cl solution. The organic layer was separated, washed with aq NaHCO$_3$ solution and brine, dried over MgSO$_4$, and evaporated in vacuo. The residue was triturated with isopropyl ether to give tert-butyl 3-(5-bromo-3-pyridinyl)-3-oxopropanoate as a colorless powder (3.71 g).

tert-butyl 3-(5-bromo-3-pyridinyl)-3-oxopropanoate

Enol form: $^1$H NMR (CDCl$_3$) δ 1.54 (9H, s), 5.62 (1H, s), 8.19 (1H, m), 8.72 (1H, d, J=2 Hz), 8.86 (1H, d, J=2 Hz). Keto form: $^1$H NMR (CDCl$_3$) δ 1.44 (9H, s), 3.90 (2H, s), 8.37 (1H, m), 8.86 (1H, d, J=2 Hz), 9.03 (1H, d, J=2 Hz). MS (ESI$^+$): m/z 300 302.

Preparation 336

To a suspension of NaH in DMF (50 mL) which was washed with hexane 3 times was added methyl 5-hydroxynicotinate (10.2 g) portionwise below 10° C. in an ice-water bath under nitrogen atmosphere. After 30 min, methyl iodide (4.56 mL) was added dropwise therein. The precipitate appeared and the mixture was hard to be stirred. DMF (30 mL) was added. After 20 min, the mixture was stirred at ambient temperature for 3 h. The reaction mixture was quenched with MeOH and was concentrated in vacuo. To the residue was added CHCl$_3$, sat. NaHCO$_3$, and brine. The organic layer was separated and the aqueous layer was extracted with CHCl$_3$. The combined organic layer was dried over MgSO$_4$ and was evaporated in vacuo. The residue was purified by flash silica gel chromatography (silica gel, 200 mL) eluted with hexane-AcOEt=5-1 and 3-1 to give methyl 5-methoxynicotinate (3.47 g) as a pale brown solid.

methyl 5-methoxynicotinate $^1$H NMR (CDCl$_3$) δ 3.91 (3H, s), 3.96 (3H, s), 7.76 (1H, m), 8.47 (1H, d, J=3 Hz), 8.83 (1H, d, J=1 Hz). MS (ESI$^+$): m/z 168 (M+H).

Preparation 337

To a solution of methyl 2-bromo-4-[(5-ethyl-1H-pyrrol-2-yl)carbonyl]benzoate (330 mg) in N,N-dimethylformamide (5 mL) was added 60% sodium hydride in oil (58.4 mg) in an ice-bath over 5 minutes. After stirring for 1 hour, (aminooxy)(diphenyl)phosphine oxide (340 mg) was added portionwise over 40 minutes. The resulting mixture was stirred for 1 hour in the bath. The reaction was quenched by adding water (10 mL). The mixture was partitioned between ethyl acetate and water. The organic layer was washed with water (two times) and brine, dried over magnesium sulfate, and evaporated. The residue was dissolved in ethyl acetatechexane (1-5), and to the solution was added silica gel. The mixture was filtered, and the filtrate was evaporated to give methyl 4-[(1-amino-5-ethyl-1H-pyrrol-2-yl)carbonyl]-2-bromobenzoate as an orange solid (310 mg).

methyl 4-[(1-amino-5-ethyl-1H-pyrrol-2-yl)carbonyl]-2-bromobenzoate $^1$H-NMR (CDCl$_3$) δ 1.29 (3H, t, J=7 Hz), 2.76 (2H, q, J=7 Hz), 3.97 (3H, s), 5.73 (2H, s, br), 5.93 (1H, d, J=5 Hz), 6.62 (1H, d, J=5 Hz), 7.73 (1H, d, J=8 Hz), 7.84 (1H, d, J=8 Hz), 8.02 (1H, s).

Preparation 338

To a solution of dimethyl 2-bromoterephthalate (1.04 g) in methanol (10 mL) was added 1 N sodium hydroxide (5.71 mL) at room temperature. After stirring for 1.5 hour, the reaction was quenched by adding 1 N hydrochloric acid (7 mL). White crystals were formed. Water (10 mL) was added to aid crystalyzation. The crystals were collected by filtration, washed with water, and dried in the air. 3-Bromo-4-(methoxycarbonyl)benzoic acid was obtained as white crystals (532 mg).

3-bromo-4-(methoxycarbonyl)benzoic acid $^1$H-NMR (DMSO-d$_6$) δ 3.89 (3H, s), 7.87 (1H, d, J=8 Hz), 8.01 (1H, d, J=8 Hz), 8.17 (1H, s).

Preparation 339

A mixture of 2-[2-(2-chloroethoxy)ethoxy]ethyl acetate (6.23 g) and sodium iodide (22.2 g) in acetone (60 mL) was refluxed for 4 hours. The mixture was further refluxed for 4 hours after adding sodium iodide (11.0 g). The solvent was evaporated off, and the residue was partitioned between EtOAc (50 mL) and water (50 mL). The aqueous layer was washed with 10% sodium thiosulfate and brine, dried over MgSO$_4$, and evaporated to give 2-[2-(2-iodoethoxy)ethoxy] ethyl acetate as a pale yellow oil (9.74 g).

2-[2-(2-iodoethoxy)ethoxy]ethyl acetate $^1$H-NMR (CDCl$_3$) δ 2.09 (3H, s), 3.27 (2H, t, J=7 Hz), 3.65-3.78 (8H, m), 4.24 (2H, m).

Preparation 340

A solution of 1-tert-butyl 7-ethyl 2-[(5-methyl-3-isoxazolyl)carbonyl]heptanedioate (126 mg) in trifluoroacetic acid (1 mL) was stirred for 1.5 hour at room temperature. The volatile was evaporated off, and azeotroped with toluene to give 7-ethoxy-2-[(5-methyl-3-isoxazolyl)carbonyl]-7-oxoheptanoic acid as a pale orange oil (106 mg).

7-ethoxy-2-[(5-methyl-3-isoxazolyl)carbonyl]-7-oxoheptanoic acid $^1$H-NMR (CDCl$_3$) δ 1.24 (3H, t, J=7 Hz), 1.41 (2H, m), 1.65 (2H, m), 2.02 (2H, m), 2.30 (2H, m), 2.50 (3H, s), 2.55 (1H, s, br), 4.10 (2H, q, J=7 Hz), 4.47 (1H, t, J=7 Hz), 6.40 (1H, s). MS (ESI$^+$): m/z 296.22 (M−H) and 593.52 (2M−H)

Preparation 341

To a suspension of dimethyl sulfone (5.43 g) in tetrahydrofuran (10 mL) was added 1.59 M n-butyl lithium (36.3 mL) in a dryice-acetone bath under a nitrogen atmosphere. After stirring for 0.5 hour, a solution of methyl methoxyacetate (2.00 g) in tetrahydrofuran (5 mL) was added. The resulting mixture was stirred for 2 hours in the bath and allowed to warm to room temperature over 2 hours. The mixture was partitioned between EtOAc and 4 N hydrochloric acid. The reaction was quenched by adding 4 N hydrochloric acid in EtOAc (15 mL). The mixture was partitioned between EtOAc (100 mL) and brine (100 mL). The aqueous layer was washed with EtOAc (100 mL, five times). The organic layer was combined, and the combined extracts were dried over MgSO$_4$, and evaporated. Flash silica gel column chromatography (EtOAc-hexane=50-200 to 300-100) afforded 2-(methylsulfonyl)-1-methoxyethanone as a colorless oil (2.24 g).

1-methoxy-3-(methylsulfonyl)acetone $^1$H-NMR (CDCl$_3$) δ 2.99 (3H, s), 3.08 (2H, s), 3.47 (3H, s), 4.19 (2H, s).

The following compound(s) was (were) obtained in a similar manner to that of Example 1.

EXAMPLE 392 ethyl 4-[3-bromo-4-(methoxycarbonyl)phenyl]-7-ethyl-2-methylpyrrolo[1,2-b]pyridazine-3-carboxylate $^1$H-NMR (CDCl$_3$) δ 0.98 (3H, t, J=7 Hz), 1.38 (3H, t, J=7 Hz), 2.61 (3H, s), 3.04 (2H, q, J=7 Hz), 3.98 (3H, s), 4.05 (2H, q, J=7 Hz), 6.29 (1H, d, J=5 Hz), 6.67 (1H, d, J=7 Hz), 7.44 (1H, d, J=8 Hz), 7.76 (1H, s), 7.89 (1H, d, J=8 Hz).

EXAMPLE 393

3-[7-ethyl-2-(methoxymethyl)-3-(methylsulfonyl)pyrrolo[1,2-b]pyridazin-4-yl]benzonitrile $^1$H-NMR (CDCl$_3$) δ 1.38 (3H, t, J=7 Hz), 2.98 (2H, q, J=7 Hz), 3.18 (3H, s), 3.45 (3H, s), 4.59 (2H, s), 6.25 (1H, d, J=5 Hz), 6.71 (1H, d, J=5 Hz), 7.65 (1H, t, J=8 Hz), 7.78 (1H, d, J=8 Hz), 7.94 (1H, d, J=8 Hz), 7.99 (1H, s). MS (ESI$^+$): m/z 370 (M+H)

The following compound(s) was (were) obtained in a similar manner to that of Example 16.

EXAMPLE 394

5-{4-[3-(aminocarbonyl)phenyl]-7-ethyl-2-phenylpyrrolo[1,2-b]pyridazin-3-yl}pentanoic acid $^1$H-NMR (CDCl$_3$) δ 1.02 (4H, m), 1.28 (3H, t, J=7 Hz), 1.70 (2H, m), 2.37 (2H, m), 2.92 (2H, q, J=7 Hz), 5.87 (1H, d, J=5 Hz), 6.66 (1H, d, J=5 Hz), 7.46-7.67 (5H, m), 7.96-8.08 (3H, m).

The following compound(s) was (were) obtained in a similar manner to that of Example 21.

EXAMPLE 395 ethyl 4-[4-(2-chloro-4-pyridinyl)-7-ethyl-2-methylpyrrolo[1,2-b]pyridazin-3-yl]butanoate $^1$H NMR (CDCl$_3$) δ 1.21 (3H, t, J=7 Hz), 1.37 (3H, t, J=7 Hz), 1.65-1.78 (2H, m), 2.22 (2H, t, J=7 Hz), 2.40-2.52 (2H, m), 2.58 (3H, s), 3.03 (2H, q, J=7 Hz), 4.05 (2H, q, J=7 Hz), 5.86 (1H, d, J=4 Hz), 6.53 (1H, d, J=4 Hz), 7.25 (1H, d, J=5 Hz), 7.36 (1H, s), 8.53 (1H, d, J=5 Hz). MS (ESI$^+$): m/z 386.

EXAMPLE 396 ethyl 3-[4-(2-chloro-4-pyridinyl)-7-ethyl-2-methylpyrrolo[1,2-b]pyridazin-3-yl]propanoate $^1$H NMR (CDCl$_3$) δ 1.24 (3H, t, J=7 Hz), 1.37 (3H, t, J=7 Hz), 2.30-2.39 (2H, m), 2.57 (3H, s), 2.74-2.83 (2H, m), 3.03 (2H, q, J=7 Hz), 4.12 (2H, q, J=7 Hz), 5.88 (1H, d, J=4 Hz), 6.55 (1H, d, J=4 Hz), 7.24 (1H, d, J=5 Hz), 7.35 (1H, s), 8.53 (1H, d, J=5 Hz). MS (ESI$^+$): m/z 372.

EXAMPLE 397 ethyl 5-[2-benzyl-4-(2-chloro-4-pyridinyl)-7-ethylpyrrolo[1,2-b]pyridazin-3-yl]pentanoate $^1$H NMR (CDCl$_3$) δ 1.23 (3H, t, J=7 Hz), 1.38 (3H, t, J=7 Hz), 1.30-1.50 (4H, m), 2.10 (2H, t, J=7 Hz), 2.23-2.35 (2H, m), 3.04 (2H, q, J=7 Hz), 4.09 (2H, q, J=7 Hz), 4.21 (2H, s), 5.88 (1H, d, J=4 Hz), 6.58 (1H, d, J=4 Hz), 7.14-7.32 (7H, m), 8.50 (1H, d, J=5 Hz).

EXAMPLE 398 methyl {2-[7-ethyl-2-methyl-4-(5-methyl-3-pyridinyl)pyrrolo[1,2-b]pyridazin-3-yl]ethoxy}acetate $^1$H NMR (CDCl$_3$) δ 1.37 (3H, t, J=7 Hz), 2.42 (3H, s), 2.61 (3H, s), 2.78-2.88 (2H, m), 3.03 (2H, q, J=7 Hz), 3.46-3.57 (2H, m), 3.71 (3H, s), 3.95 (2H, s), 5.87 (1H, d, J=4 Hz), 6.52 (1H, d, J=4 Hz), 7.54 (1H, s), 8.43 (1H, d, J=2 Hz), 8.53 (1H, d, J=2 Hz). MS (ESI$^+$): m/z 368.

EXAMPLE 399 ethyl[4-(5-bromo-3-pyridinyl)-7-ethyl-2-methylpyrrolo[1,2-b]pyridazin-3-yl]acetate $^1$H NMR (CDCl$_3$) δ 1.26 (3H, t, J=7 Hz), 1.38 (3H, t, J=7 Hz), 2.51 (3H, s), 3.03 (2H, q, J=7 Hz), 3.43 (2H, s), 4.12 (2H, q, J=7 Hz), 5.99 (1H, d, J=4 Hz), 6.58 (1H, d, J=4 Hz), 7.94 (1H, m), 8.58 (1H, d, J=2 Hz), 8.78 (1H, d, J=2 Hz). MS (ESI$^+$): m/z 402 404.

EXAMPLE 400 ethyl 3-[2-[(acetyloxy)methyl]-7-ethyl-4-(5-methyl-3-pyridinyl)pyrrolo[1,2-b]pyridazin-3-yl]propanoate $^1$H NMR (CDCl$_3$) δ 1.24 (3H, t, J=7 Hz), 1.37 (3H, t, J=7 Hz), 2.16 (3H, s), 2.32-2.42 (2H, m), 2.44 (3H, s), 2.77-2.90 (2H, m), 3.03 (2H, q, J=7 Hz), 4.12 (2H, q, J=7 Hz), 5.31 (2H, s), 5.96 (1H, d, J=4 Hz), 6.63 (1H, d, J=4 Hz), 7.53 (1H, s), 8.42 (1H, d, J=2 Hz), 8.55 (1H, s). MS (ESI$^+$): m/z 410.

EXAMPLE 401 ethyl 4-[2-[(acetyloxy)methyl]-7-ethyl-4-(5-methyl-3-pyridinyl)pyrrolo[1,2-b]pyridazin-3-yl]butanoate $^1$H NMR (CDCl$_3$) δ 1.25 (3H, t, J=7 Hz), 1.37 (3H, t, J=7 Hz), 1.64-1.78 (2H, m), 2.10-2.23 (2H, m), 2.17 (3H, s), 2.43 (3H, s), 2.43-2.58 (2H, m), 3.02 (2H, q, J=7 Hz), 4.12 (2H, q, J=7 Hz), 5.33 (2H, s), 5.93 (1H, d, J=4 Hz), 6.60 (1H, d, J=4 Hz), 7.53 (1H, s), 8.43 (1H, s), 8.55 (1H, s). MS (ESI$^+$): m/z 424.

EXAMPLE 402 ethyl 5-[2-[(acetyloxy)methyl]-4-(3-cyanophenyl)-7-ethylpyrrolo[1,2-b]pyridazin-3-yl]pentanoate $^1$H NMR (CDCl$_3$) δ 1.24 (3H, t, J=7 Hz), 1.37 (3H, t, J=7 Hz), 1.40-1.60 (4H, m), 2.16 (2H, t, J=7 Hz), 2.17 (3H, s), 2.40-2.52 (2H, m), 3.03 (2H, q, J=7 Hz), 4.12 (2H, q, J=7 Hz), 5.29 (2H, s), 5.88 (1H, d, J=4 Hz), 6.62 (1H, d, J=4 Hz), 7.60-7.68 (3H, m), 7.75-7.83 (1H, m). MS (ESI$^+$): m/z 448.

EXAMPLE 403 ethyl 4-[2-[(acetyloxy)methyl]-4-(5-bromo-3-pyridinyl)-7-ethylpyrrolo[1,2-b]pyridazin-3-yl]butanoate $^1$H NMR (CDCl$_3$) δ 1.22 (3H, t, J=7 Hz), 1.37 (3H, t, J=7 Hz), 1.65-1.82 (2H, m), 2.17 (3H, s), 2.21 (2H, t, J=7 Hz), 2.45-2.63 (2H, m), 3.02 (2H, q, J=7 Hz), 4.05 (2H, q, J=7 Hz), 5.33 (2H, s), 5.95 (1H, d, J=4 Hz), 6.63 (1H, d, J=4 Hz), 7.90 (1H, m), 8.57 (1H, d, J=2 Hz), 8.80 (1H, d, J=2 Hz). MS (ESI$^+$): m/z 488 490.

EXAMPLE 404 ethyl 3-[2-[(acetyloxy)methyl]-4-(5-bromo-3-pyridinyl)-7-ethylpyrrolo[1,2-b]pyridazin-3-yl]propanoate $^1$H NMR (CDCl$_3$) δ 1.23 (3H, t, J=7 Hz), 1.37 (3H, t, J=7 Hz), 2.16 (3H, s), 2.36 (2H, t, J=7 Hz), 2.77-2.95 (2H, m), 3.02 (2H, q, J=7 Hz), 4.06 (2H, q, J=7 Hz), 5.31 (2H, s), 5.96 (1H, d, J=4 Hz), 6.64 (1H, d, J=4 Hz), 7.88 (1H, s), 8.56 (1H, m), 8.80 (1H, m). MS (ESI$^+$): m/z 474 476.

EXAMPLE 405 ethyl 3-[2-[(cyclohexylmethoxy)methyl]-7-ethyl-4-(5-methyl-3-pyridinyl)pyrrolo[1,2-b]pyridazin-3-yl]propanoate $^1$H NMR (CDCl$_3$) δ 0.88-1.06 (2H, m), 1.19 (3H, t, J=7 Hz), 1.15-1.36 (3H, m), 1.37 (3H, t, J=7 Hz), 1.58-1.85 (6H, m), 2.42 (2H, m), 2.43 (3H, s), 2.83-2.97 (2H, m), 3.05 (2H, q, J=7 Hz), 3.38 (2H, d, J=7 Hz), 4.06 (2H, q, J=7 Hz), 4.66 (2H, s), 5.91 (1H, d, J=4 Hz), 6.58 (1H, d, J=4 Hz), 7.52 (1H, s), 8.42 (1H, d, J=2 Hz), 8.54 (1H, d, J=2 Hz).

EXAMPLE 406 ethyl 3-{4-(5-bromo-3-pyridinyl)-2-[(cyclohexylmethoxy)methyl]-7-ethylpyrrolo[1,2-b]pyridazin-3-yl}propanoate $^1$H NMR (CDCl$_3$) δ 0.85-1.06 (2H, m), 1.20 (3H, t, J=7 Hz), 1.37 (3H, t, J=7 Hz), 1.16-1.46 (3H, m), 1.55-1.84 (6H, m), 2.43 (2H, t, J=7 Hz), 2.82-3.00 (2H, m), 3.06 (2H, q, J=7 Hz), 3.37 (2H, d, J=7 Hz), 4.06 (2H, q, J=7 Hz), 4.66 (2H, s), 5.93 (1H, d, J=4 Hz), 6.62 (1H, d, J=4 Hz), 7.87 (1H, m), 8.55 (1H, d, J=2 Hz), 8.78 (1H, d, J=2 Hz). MS (ESI+): m/z 528 530.

EXAMPLE 407 ethyl 4-{4-(5-bromo-3-pyridinyl)-2-[(cyclohexyl-methoxy)methyl]-7-ethylpyrrolo[1,2-b]pyridazin-3-yl}butanoate $^1$H NMR (CDCl$_3$) δ 0.87-1.06 (2H, m), 1.21 (3H, t, J=7 Hz), 1.37 (3H, t, J=7 Hz), 1.16-1.46 (3H, m), 1.50-1.85 (8H, m), 2.23 (2H, t, J=7 Hz), 2.55-2.75 (2H, m), 3.04 (2H, q, J=7 Hz), 3.38 (2H, d, J=7 Hz), 4.08 (2H, q, J=7 Hz), 4.67 (2H, s), 5.92 (1H, d, J=4 Hz), 6.60 (1H, d, J=4 Hz), 7.89 (1H, m), 8.56 (1H, d, J=2 Hz), 8.79 (1H, d, J=2 Hz). MS (ESI+): m/z 542 544.

EXAMPLE 408 ethyl 4-[2-[(cyclopropylmethoxy)methyl]-7-ethyl-4-(5-methyl-3-pyridinyl)pyrrolo[1,2-b]pyridazin-3-yl]butanoate $^1$H NMR (CDCl$_3$) δ 0.22-0.32 (2H, m), 0.53-0.65 (2H, m), 1.10-1.20 (1H, m), 1.19 (3H, t, J=7 Hz), 1.37 (3H, t, J=7 Hz), 1.65-1.80 (2H, m), 2.14-2.30 (2H, m), 2.43 (3H, s), 2.57-2.74 (2H, m), 3.05 (2H, q, J=7 Hz), 3.43 (2H, d, J=7 Hz), 4.03 (2H, q, J=7 Hz), 4.74 (2H, s), 5.90 (1H, d, J=4 Hz), 6.57 (1H, d, J=4 Hz), 7.53 (1H, s), 8.43 (1H, s), 8.54 (1H, s). MS (ESI+): m/z 436.

EXAMPLE 409 ethyl 3-[2-[(cyclopropylmethoxy)methyl]-7-ethyl-4-(5-methyl-3-pyridinyl)pyrrolo[1,2-b]pyridazin-3-yl]propanoate $^1$H NMR (CDCl$_3$) δ 0.22-0.32 (2H, m), 0.54-0.63 (2H, m), 1.10-1.20 (1H, m), 1.21 (3H, t, J=7 Hz), 1.37 (3H, t, J=7 Hz), 2.40-2.50 (2H, m), 2.43 (3H, s), 2.86-2.98 (2H, m), 3.05 (2H, q, J=7 Hz), 3.42 (2H, d, J=7 Hz), 4.06 (2H, q, J=7 Hz), 4.71 (2H, s), 5.92 (1H, d, J=4 Hz), 6.60 (1H, d, J=4 Hz), 7.52 (1H, s), 8.42 (1H, s), 8.54 (1H, s). MS (ESI+): m/z 422.

EXAMPLE 410 ethyl 3-{4-(5-bromo-3-pyridinyl)-7-ethyl-2-[(2-methoxyethoxy)methyl]pyrrolo[1,2-b]pyridazin-3-yl}propanoate $^1$H NMR (CDCl$_3$) δ 1.20 (3H, t, J=7 Hz), 1.37 (3H, t, J=7 Hz), 2.44 (2H, t, J=7 Hz), 2.82-2.98 (2H, m), 3.05 (2H, q, J=7 Hz), 3.38 (3H, s), 3.58 (2H, m), 3.76 (2H, m), 4.05 (2H, q, J=7 Hz), 4.76 (2H, s), 5.93 (1H, d, J=4 Hz), 6.62 (1H, d, J=4 Hz), 7.87 (1H, m), 8.54 (1H, s), 8.79 (1H, s). MS (ESI+): m/z 490 492.

EXAMPLE 411

4-(5-bromo-3-pyridinyl)-7-ethyl-2-methylpyrrolo[1,2-b]pyridazine $^1$H NMR (CDCl$_3$) δ 1.39 (3H, t, J=7 Hz), 2.54 (3H, s), 3.04 (2H, q, J=7 Hz), 6.39 (1H, s), 6.51 (1H, d, J=4 Hz), 6.67 (1H, d, J=4 Hz), 8.17 (1H, m), 8.76 (1H, d, J=2 Hz), 8.86 (1H, d, J=2 Hz). MS (ESI+): m/z 316 318.

EXAMPLE 412 ethyl 4-[2-[(acetyloxy)methyl]-4-(5-chloro-3-pyridinyl)-7-ethylpyrrolo[1,2-b]pyridazin-3-yl]butanoate $^1$H NMR (300 MHz, CDCl$_3$) δ 1.20 (3H, t, J=7 Hz), 1.37 (3H, t, J=7 Hz), 1.70 (2H, tt, J=7, 7 Hz), 2.17 (3H, s), 2.20 (2H, t, J=7 Hz), 2.45-2.54 (2H, m), 3.02 (2H, q, J=7 Hz), 4.04 (2H, q, J=7 Hz), 5.33 (2H, s), 5.94 (1H, d, J=4 Hz), 6.63 (1H, d, J=4 Hz), 7.74 (1H, dd, J=2, 2 Hz), 8.53 (1H, d, J=2 Hz), 8.70 (1H, d, J=2 Hz).

EXAMPLE 413 ethyl 5-{4-(5-chloro-3-pyridinyl)-2-[(cyclopropyl-methoxy)methyl]-7-ethylpyrrolo[1,2-b]pyridazin-3-yl}pentanoate $^1$H NMR (300 MHz, CDCl$_3$) δ 0.23-0.26 (2H, m), 0.54-0.59 (2H, m), 1.07-1.16 (1H, m), 1.23 (3H, t, J=7 Hz), 1.37 (3H, t, J=7 Hz), 1.41-1.56 (4H, m), 2.17 (2H, t, J=7 Hz), 2.53-2.64 (2H, m), 3.03 (2H, q, J=7 Hz), 3.41 (2H, d, J=7 Hz), 4.09 (2H, q, J=7 Hz), 4.70 (2H, s), 5.90 (1H, d, J=5 Hz), 6.58 (1H, d, J=5 Hz), 7.72 (1H, s), 8.51 (1H, s), 8.68 (1H, s).

EXAMPLE 414 ethyl 4-{4-(5-chloro-3-pyridinyl)-2-[(cyclopropyl-methoxy)methyl]-7-ethylpyrrolo[1,2-b]pyridazin-3-yl}butanoate $^1$H NMR (300 MHz, CDCl$_3$) δ 0.24 (2H, dt, J=7, 7 Hz), 0.56 (2H, dt, J=7, 7 Hz), 1.07-1.15 (1H, m), 1.20 (3H, t, J=7 Hz), 1.37 (3H, t, J=7 Hz), 1.72 (2H, tt, J=7, 7 Hz), 2.21 (2H, t, J=7 Hz), 2.55-2.66 (2H, m), 3.02 (2H, q, J=7 Hz), 3.43 (2H, d, J=7 Hz), 4.04 (2H, q, J=7 Hz), 4.73 (2H, s), 5.91 (1H, d, J=5 Hz), 6.59 (1H, d, J=5 Hz), 7.74 (1H, dd, J=2, 2 Hz), 8.52 (1H, d, J=2 Hz), 8.68 (1H, d, J=2 Hz).

EXAMPLE 415 ethyl 5-[4-(5-bromo-3-pyridinyl)-7-ethyl-2-(isobu-toxymethyl)pyrrolo[1,2-b]pyridazin-3-yl]pentanoate $^1$H NMR (300 MHz, CDCl$_3$) δ 0.92 (6H, d, J=7 Hz), 1.26 (3H, t, J=7 Hz), 1.34 (3H, t, J=7 Hz), 1.38-1.56 (4H, m), 1.92 (1H, qt, J=7, 7 Hz), 2.15 (2H, t, J=7 Hz), 2.51-2.63 (2H, m), 3.03 (2H, q, J=7 Hz), 3.33 (2H, d, J=7 Hz), 4.09 (2H, q, J=7 Hz), 4.65 (2H, s), 5.90 (1H, d, J=7 Hz), 6.59 (1H, d, J=7 Hz), 7.88 (1H, dd, J=2, 2 Hz), 8.55 (1H, d, J=2 Hz), 8.77 (1H, d, J=2 Hz).

EXAMPLE 416 ethyl 3-[4-(5-chloro-3-pyridinyl)-7-ethyl-2-(isobu-toxymethyl)pyrrolo[1,2-b]pyridazin-3-yl]propanoate $^1$H NMR (300 MHz, CDCl$_3$) δ 0.92 (6H, d, J=7 Hz), 1.19 (3H, t, J=7 Hz), 1.37 (3H, t, J=7 Hz), 1.91 (1H, qt, J=7, 7 Hz), 2.41 (2H, t, J=8 Hz), 2.84-2.94 (2H, m), 3.03 (2H, q, J=7 Hz), 3.35 (2H, d, J=7H), 4.05 (2H, q, J=7 Hz), 4.68 (2H, s), 5.92 (1H, d, J=4 Hz), 6.61 (1H, d, J=4 Hz), 7.72 (1H, dd, J=2, 2 Hz), 8.51 (1H, d, J=2 Hz), 8.69 (1H, d, J=2 Hz).

EXAMPLE 417 ethyl 3-[2-[(acetyloxy)methyl]-4-(3-chlorophenyl)-7-ethylpyrrolo[1,2-b]pyridazin-3-yl]propanoate $^1$H NMR (300 MHz, CDCl$_3$) δ 1.19 (3H, t, J=7 Hz), 1.36 (3H, t, J=7 Hz), 2.15 (3H, s), 2.33 (2H, t, J=8 Hz), 2.82 (2H, t, J=8 Hz), 3.02 (2H, q, J=7 Hz), 4.06 (2H, q, J=7 Hz), 5.31 (2H, s), 5.97 (1H, d, J=4 Hz), 6.61 (1H, d, J=4 Hz), 7.23-7.26 (1H, m), 7.37 (1H, s), 7.44-7.46 (2H, m).

EXAMPLE 418 ethyl 4-[4-(5-bromo-3-pyridinyl)-7-ethyl-2-(isobutoxymethyl)pyrrolo[1,2-b]pyridazin-3-yl]butanoate $^1$H NMR (300 MHz, CDCl$_3$) δ 0.92 (6H, d, J=7 Hz), 1.20 (3H, t, J=7 Hz), 1.37 (3H, t, J=7 Hz), 1.71 (2H, tt, J=8, 8 Hz), 1.91 (1H, qt, J=7, 7 Hz), 2.20 (2H, t, J=8 Hz), 2.56-2.66 (2H, m), 3.03 (2H, q, J=7 Hz), 3.34 (2H, d, J=7 Hz), 4.05 (2H, q, J=7 Hz), 4.69 (2H, s), 5.91 (1H, d, J=5 Hz), 6.60 (1H, d, J=5 Hz), 7.89 (1H, s), 8.56 (1H, d, J=2 Hz), 8.78 (1H, d, J=2 Hz).

EXAMPLE 419

2,4-bis(5-bromo-3-pyridinyl)-7-ethylpyrrolo[1,2-b]pyridazine $^1$H NMR (CDCl$_3$) δ 1.45 (3H, t, J=7 Hz), 3.14 (2H, q, J=7 Hz), 6.66 (1H, d, J=4 Hz), 6.86 (1H, d, J=4 Hz), 6.91 (1H, s), 8.23 (1H, m), 8.48 (1H, m), 8.77 (1H, m), 8.83 (1H, m), 8.94 (1H, d, J=2 Hz), 9.18 (1H, d, J=2 Hz).

EXAMPLE 420 ethyl 4-[2-[(acetyloxy)methyl]-4-(3-chlorophenyl)-7-ethylpyrrolo[1,2-b]pyridazin-3-yl]butanoate $^1$H NMR (CDCl$_3$) δ 1.19 (3H, t, J=8 Hz), 1.34 (3H, t, J=8 Hz), 1.63-1.76 (2H, m), 2.10-2.22 (5H, m), 2.45-2.55 (2H, m), 3.01 (2H, q, J=8 Hz), 4.04 (2H, q, J=8 Hz), 5.32 (2H, s), 5.95 (1H, d, J=5 Hz), 6.59 (1H, d, J=5 Hz), 7.21-7.29 (1H, overlapped with CDCl$_3$), 7.36 (1H, br s), 7.38-7.46 (2H, m). MS (ESI$^+$): m/z 443 (M+H).

EXAMPLE 421 ethyl 5-[7-ethyl-2-(methoxymethyl)-4-(5-methoxy-3-pyridinyl)pyrrolo[1,2-b]pyridazin-3-yl]pentanoate $^1$H NMR (CDCl$_3$) δ 1.23 (3H, t, J=8 Hz), 1.33-1.60 (7H, m), 1.55-1.70 (2H, m), 2.17 (2H, t, J=8 Hz), 2.46-2.64 (2H, m), 3.04 (2H, d, J=8 Hz), 3.46 (3H, s), 3.90 (3H, s), 4.09 (2H, q, J=8 Hz), 4.62 (2H, s), 5.93 (1H, d, J=5 Hz), 6.59 (1H, d, J=5 Hz), 7.23 (1H, m), 8.22 (1H, d, J=1 Hz), 8.40 (1H, d, J=3 Hz). MS (ESI$^+$): m/z 426 (M+H).

EXAMPLE 422 ethyl 5-[7-ethyl-4-(5-methoxy-3-pyridinyl)-2-methylpyrrolo[1,2-b]pyridazin-3-yl]pentanoate $^1$H NMR (CDCl$_3$) δ 1.23 (3H, t, J=8 Hz), 1.33-1.62 (7H, m), 2.18 (2H, t, J=8 Hz), 2.38-2.49 (2H, m), 2.56 (3H, s), 3.01 (2H, q, J=8 Hz), 3.90 (3H, s), 4.08 (2H, q, J=8 Hz), 5.89 (1H, d, J=5 Hz), 6.51 (1H, d, J=5 Hz), 7.21 (1H, m), 8.21 (1H, d, J=1 Hz), 8.40 (1H, d, J=3 Hz). MS (ESI$^+$): m/z 396 (M+H).

EXAMPLE 423 ethyl 3-[7-ethyl-2-(methoxymethyl)-4-(5-methoxy-3-pyridinyl)pyrrolo[1,2-b]pyridazin-3-yl]propanoate $^1$H NMR (CDCl$_3$) δ 1.20 (3H, t, J=8 Hz), 1.38 (3H, t, J=8 Hz), 2.40 (2H, t, J=8 Hz), 2.81-2.96 (2H, m), 3.04 (2H, d, J=8 Hz), 3.47 (3H, s), 3.90 (3H, s), 4.05 (2H, q, J=8 Hz), 4.65 (2H, s), 5.96 (1H, d, J=5 Hz), 6.60 (1H, d, J=5 Hz), 7.21 (1H, m), 8.23 (1H, br s), 8.40 (1H, d, J=3 Hz). MS (ESI$^+$): m/z 398 (M+H).

EXAMPLE 424 ethyl 4-[7-ethyl-2-(methoxymethyl)-4-(5-methoxy-3-pyridinyl)pyrrolo[1,2-b]pyridazin-3-yl]butanoate $^1$H NMR (CDCl$_3$) δ 1.20 (3H, t, J=8 Hz), 1.38 (3H, t, J=8 Hz), 1.64-1.79 (2H, m), 2.14-2.24 (2H, m), 2.53-2.66 (2H, m), 3.04 (2H, d, J=8 Hz), 3.47 (3H, s), 3.90 (3H, s), 4.04 (2H, q, J=8 Hz), 4.67 (2H, br s), 5.94 (1H, d, J=5 Hz), 6.59 (1H, d, J=5 Hz), 7.23 (1H, m), 8.22 (1H, d, J=1 Hz), 8.40 (1H, d, J=3 Hz). MS (ESI$^+$): m/z 412 (M+H).

EXAMPLE 425 ethyl 5-[7-ethyl-2-(methoxymethyl)-4-(5-pyrimidinyl)pyrrolo[1,2-b]pyridazin-3-yl]pentanoate $^1$H NMR (CDCl$_3$) δ 1.23 (3H, t, J=8 Hz), 1.30-1.62 (7H, m), 2.19 (2H, t, J=8 Hz), 2.46-2.60 (2H, m), 3.04 (2H, d, J=8 Hz), 3.47 (3H, s), 3.90 (3H, s), 4.09 (2H, q, J=8 Hz), 4.63 (2H, s), 5.90 (1H, d, J=5 Hz), 6.61 (1H, d, J=5 Hz), 8.80 (2H, s), 9.34 (1H, s). MS (ESI$^+$): m/z 397 (M+H).

EXAMPLE 426 ethyl 4-[4-(5-chloro-3-pyridinyl)-7-ethyl-2-(methoxymethyl)pyrrolo[1,2-b]pyridazin-3-yl]butanoate $^1$H NMR (CDCl$_3$) δ 1.21 (3H, t, J=8 Hz), 1.37 (3H, t, J=8 Hz), 1.62-1.76 (2H, m), 2.21 (2H, t, J=8 Hz), 2.49-2.67 (2H, m), 3.04 (2H, d, J=8 Hz), 3.46 (3H, s), 4.06 (2H, q, J=8 Hz), 4.67 (2H, br s), 5.92 (1H, d, J=5 Hz), 6.61 (1H, d, J=5 Hz), 7.74 (1H, m), 8.53 (1H, d, J=1 Hz), 8.69 (1H, d, J=2 Hz). MS (ESI$^+$): m/z 414 (M−H).

EXAMPLE 427 ethyl 3-[4-(5-chloro-3-pyridinyl)-7-ethyl-2-(methoxymethyl)pyrrolo[1,2-b]pyridazin-3-yl]propanoate $^1$H NMR (CDCl$_3$) δ 1.20 (3H, t, J=8 Hz), 1.38 (3H, t, J=8 Hz), 2.40 (2H, t, J=8 Hz), 2.82-2.94 (2H, m), 3.04 (2H, d, J=8 Hz), 3.47 (3H, s), 4.06 (2H, q, J=8 Hz), 4.65 (2H, s), 5.93 (1H, d, J=5 Hz), 6.67 (1H, d, J=5 Hz), 7.73 (1H, br s), 8.51 (1H, br s), 8.70 (1H, br s). MS (ESI$^+$): m/z 402 (M+H).

EXAMPLE 428 ethyl 5-[4-(5-chloro-3-pyridinyl)-7-ethyl-2-(methoxymethyl)pyrrolo[1,2-b]pyridazin-3-yl]pentanoate $^1$H NMR (CDCl$_3$) δ 1.23 (3H, t, J=8 Hz), 1.34-1.60 (7H, m), 2.19 (2H, t, J=8 Hz), 2.47-2.64 (2H, m), 3.04 (2H, d, J=8 Hz), 3.46 (3H, s), 4.10 (2H, q, J=8 Hz), 4.62 (2H, s), 5.90

(1H, d, J=5 Hz), 6.60 (1H, d, J=5 Hz), 7.73 (1H, m), 8.51 (1H, br s), 8.68 (1H, br s). MS (ESI⁺): m/z 426 (M+H).

EXAMPLE 429 methyl 2-[(acetyloxy)methyl]-4-(5-bromo-3-pyridinyl)-7-ethylpyrrolo[1,2-b]pyridazine-3-carboxylate mp 122-123 deg.

¹H NMR (CDCl₃) δ 1.38 (3H, t, J=8 Hz), 2.12 (3H, s), 3.06 (2H, t, J=8 Hz), 3.61 (3H, s), 5.43 (2H, s), 6.37 (1H, d, J=5 Hz), 6.78 (1H, d, J=5 Hz), 7.93 (1H, t, J=1 Hz), 8.57 (1H, d, J=1 Hz), 8.78 (1H, d, J=1 Hz). MS (ESI⁺): m/z 432, 434 (M+H).

EXAMPLE 430

2-(2-{2-[7-ethyl-2-methyl-4-(5-methyl-3-pyridinyl)pyrrolo[1,2-b]pyridazin-3-yl]ethoxy}ethoxy)ethyl acetate ¹H-NMR (CDCl₃) δ 1.37 (3H, t, J=7 Hz), 2.05 (3H, s), 2.42 (3H, s), 2.59 (3H, s), 2.75 (2H, m), 3.00 (2H, q, J=7 Hz), 3.39-3.48 (4H, m), 3.54 (2H, m), 3.63 (2H, m), 4.16 (2H, m), 5.86 (1H, d, J=5 Hz), 6.52 (1H, d, J=5 Hz), 7.50 (1H, m), 8.43 (1H, m), 8.52 (1H, m).

EXAMPLE 431 ethyl (2E)-4-[4-(3-cyanophenyl)-7-ethyl-2-methylpyrrolo[1,2-b]pyridazin-3-yl]-2-butenoate ¹H-NMR (CDCl₃) δ 1.27 (3H, t, J=7 Hz), 1.36 (3H, t, J=7 Hz), 2.49 (3H, s), 3.02 (2H, q, J=7 Hz), 3.30 (2H, m), 4.16 (2H, q, J=7 Hz), 5.58 (1H, d, J=16 Hz), 5.90 (1H, d, J=5 Hz), 6.56 (1H, d, J=5 Hz), 6.97 (1H, dt, J=7 and 16 Hz), 7.58 (2H, m), 7.65 (1H, s), 7.75 (1H, m).

EXAMPLE 432 ethyl 4-[4-(5-bromo-3-pyridinyl)-7-ethyl-2-(methoxymethyl)pyrrolo[1,2-b]pyridazin-3-yl]butanoate ¹H NMR (300 MHz, CDCl₃) δ 1.23 (3H, t, J=7 Hz), 1.37 (3H, t, J=7 Hz), 1.65-1.78 (2H, m), 2.23 (2H, t, J=7 Hz), 2.54-2.72 (2H, m), 3.04 (2H, q, J=7 Hz), 3.46 (3H, s), 4.06 (2H, q, J=7 Hz), 4.66 (2H, s), 5.93 (1H, d, J=4 Hz), 6.62 (1H, d, J=4 Hz), 7.89 (1H, m), 8.55 (1H, d, J=2 Hz), 8.77 (1H, d, J=2 Hz). MS (ESI⁺): m/z 460 462.

EXAMPLE 433 ethyl 4-(2-chloro-4-pyridinyl)-7-ethyl-2-methylpyrrolo[1,2-b]pyridazine-3-carboxylate ¹H NMR (CDCl₃) δ 0.99 (3H, t, J=8 Hz), 1.38 (3H, t, J=8 Hz), 2.63 (3H, s), 3.05 (2H, q, J=8 Hz), 4.07(2H, q, J=8 Hz), 6.27 (1H, d, J=5 Hz), 6.70 (1H, d, J=5 Hz), 7.30 (1H, dd, J=5, 1 Hz), 7.41 (1H, br s), 8.49 (1H, d, J=5 Hz). MS (ESI⁺): m/z 344 (M+H).

The following compound(s) was (were) obtained in a similar manner to that of Example 76.

EXAMPLE 434

4-[4-(2-chloro-4-pyridinyl)-7-ethyl-2-methylpyrrolo[1,2-b]pyridazin-3-yl]butanoic acid ¹H NMR (CDCl₃) δ 1.37 (3H, t, J=7 Hz), 1.72-1.84 (2H, m), 2.33 (2H, t, J=7 Hz), 2.47-2.57 (2H, m), 2.58 (3H, s), 3.03 (2H, q, J=7 Hz), 5.88 (1H, d, J=4 Hz), 6.53 (1H, d, J=4 Hz), 7.27 (1H, m), 7.38 (1H, s), 8.53 (1H, d, J=5 Hz). MS (ESI⁻): m/z 356, MS (ESI⁺): m/z 358.

EXAMPLE 435

3-[4-(2-chloro-4-pyridinyl)-7-ethyl-2-methylpyrrolo[1,2-b]pyridazin-3-yl]propanoic acid ¹H NMR (CDCl₃) δ 1.37 (3H, t, J=7 Hz), 2.36-2.47 (2H, m), 2.58 (3H, s), 2.76-2.88 (2H, m), 3.03 (2H, q, J=7 Hz), 5.89 (1H, d, J=4 Hz), 6.55 (1H, d, J=4 Hz), 7.25 (1H, d, J=5 Hz), 7.35 (1H, s), 8.53 (1H, d, J=5 Hz).

EXAMPLE 436

4-[4-(2-chloro-4-pyridinyl)-7-ethyl-2-phenylpyrrolo[1,2-b]pyridazin-3-yl]butanoic acid ¹H NMR (CDCl₃) δ 1.24 (3H, t, J=7 Hz), 1.30-1.42 (2H, m), 1.35 (9H, s), 1.63-1.76 (2H, m), 2.22-2.37 (4H, m), 3.93 (1H, d, J=17 Hz), 4.12 (2H, q, J=7 Hz), 4.29 (1H, d, J=17 Hz), 7.22 (2H, d, J=8 Hz), 7.26-7.36 (4H, m), 7.50 (1H, s), 8.42 (1H, d, J=5 Hz). MS (ESI⁻): m/z 418, MS (ESI⁺): m/z 420.

EXAMPLE 437

3-[4-(2-chloro-4-pyridinyl)-7-ethyl-2-phenylpyrrolo[1,2-b]pyridazin-3-yl]propanoic acid ¹H NMR (CDCl₃) δ 1.36 (3H, t, J=7 Hz), 2.06 (2H, t, J=7 Hz), 2.78 (2H, t, J=7 Hz), 3.04 (2H, q, J=7 Hz), 5.99 (1H, d, J=4 Hz), 6.67 (1H, d, J=4 Hz), 7.28 (1H, d, J=5 Hz), 7.41 (1H, s), 7.45-7.55 (5H, m), 8.53 (1H, d, J=5 Hz). MS (ESI⁻): m/z 404, MS (ESI⁺): m/z 406.

EXAMPLE 438

5-[2-benzyl-4-(2-chloro-4-pyridinyl)-7-ethylpyrrolo[1,2-b]pyridazin-3-yl]pentanoic acid ¹H NMR (CDCl₃) δ 1.16-1.32 (2H, m), 1.39 (3H, t, J=7 Hz), 1.38-1.53 (2H, m), 2.15 (2H, t, J=7 Hz), 2.30-2.40 (2H, m), 3.06 (2H, q, J=7 Hz), 4.21 (2H, s), 5.88 (1H, d, J=4 Hz), 6.58 (1H, d, J=4 Hz), 7.18-7.35 (7H, m), 8.49 (1H, d, J=5 Hz). MS (ESI⁻): m/z 446, MS (ESI⁺): m/z 448.

EXAMPLE 439

{2-[7-ethyl-2-methyl-4-(5-methyl-3-pyridinyl)pyrrolo[1,2-b]pyridazin-3-yl]ethoxy}acetic acid ¹H NMR (CDCl₃) δ 1.37 (3H, t, J=7 Hz), 2.44 (3H, s), 2.59 (3H, s), 2.74-2.92 (2H, m), 3.02 (2H, q, J=7 Hz), 3.54-3.66 (2H, m), 3.93 (2H, m), 5.82 (1H, d, J=4 Hz), 6.53 (1H, d, J=4 Hz), 7.63 (1H, s), 8.52 (1H, s), 8.56 (1H, s).

EXAMPLE 440

{2-[4-(2-chloro-4-pyridinyl)-7-ethyl-2-phenylpyrrolo[1,2-b]pyridazin-3-yl]ethoxy}acetic acid ¹H NMR (CDCl₃) δ 1.37 (3H, t, J=7 Hz), 2.80 (2H, t, J=7 Hz), 3.03 (2H, q, J=7 Hz), 3.20 (2H, t, J=7 Hz), 3.72 (3H, s), 6.01 (1H, d, J=4 Hz), 6.67 (1H, d, J=4 Hz), 7.42 (1H, d, J=5 Hz), 7.45-7.60 (6H, m), 8.57 (1H, d, J=5 Hz).

EXAMPLE 441

[4-(5-bromo-3-pyridinyl)-7-ethyl-2-methylpyrrolo[1,2-b]pyridazin-3-yl]acetic acid ¹H NMR (CDCl₃) δ 1.37 (3H, t, J=7 Hz), 2.55 (3H, s), 2.97-3.10 (2H, m), 3.30-3.62 (2H, m), 5.97 (1H, m), 6.57 (1H, m), 8.03 (1H, s), 8.69 (1H, s), 8.77 (1H, s). MS (ESI⁺): m/z 374 376.

EXAMPLE 442

3-{7-ethyl-4-(5-methyl-3-pyridinyl)-2-[(4-pyridinylmethoxy)methyl]pyrrolo[1,2-b]pyridazin-3-yl}propanoic acid ¹H NMR (CDCl₃) δ 1.38 (3H, t, J=7 Hz), 2.33-2.50 (2H, m), 2.42 (3H, s), 2.80-3.00 (2H, m), 3.06 (2H, q, J=7 Hz), 4.72 (2H, s), 4.83 (2H, s), 5.92 (1H, d, J=4 Hz), 6.62 (1H, d, J=4 Hz), 7.36 (2H, d, J=7 Hz), 7.55 (1H, s), 8.41 (1H, s), 8.44 (2H, d, J=7 Hz), 8.53 (1H, s). MS (ESI⁺): m/z 429 431.

EXAMPLE 443

3-{7-ethyl-4-(5-methyl-3-pyridinyl)-2-[(2-pyrazinylmethoxy)methyl]pyrrolo[1,2-b]pyridazin-3-yl}propanoic acid ¹H NMR (CDCl₃) δ 1.38 (3H, t, J=7 Hz), 2.42 (3H, s), 2.40-2.55 (2H, m), 2.83-3.12 (2H, m), 3.03 (2H, q, J=7 Hz), 4.84 (2H, s), 4.91 (2H, m), 5.92 (1H, d, J=4 Hz), 6.61 (1H, d, J=4 Hz), 7.57 (1H, s), 8.42 (1H, s), 8.48-8.55 (3H, m), 8.76 (1H, s). MS (ESI⁺): m/z 432.

EXAMPLE 444

3-{7-ethyl-4-(5-methyl-3-pyridinyl)-2-[(2-pyridinylmethoxy)methyl]pyrrolo[1,2-b]pyridazin-3-yl}propanoic acid ¹H NMR (CDCl₃) δ 1.37 (3H, t, J=7 Hz), 2.43 (3H, s), 2.50-2.60 (2H, m), 2.88-3.05 (2H, m), 3.03 (2H, q, J=7 Hz), 4.81 (2H, s), 4.87 (2H, s), 5.82 (1H, d, J=4 Hz), 6.58 (1H, d, J=4 Hz), 7.27 (1H, m), 7.48 (1H, d, J=8 Hz), 7.56 (1H, s), 7.77 (1H, t, J=8 Hz), 8.43 (1H, s), 8.54 (2H, m).

EXAMPLE 445

4-{7-ethyl-4-(5-methyl-3-pyridinyl)-2-[(4-pyridinylmethoxy)methyl]pyrrolo[1,2-b]pyridazin-3-yl}butanoic acid ¹H NMR (CDCl₃) δ 1.40 (3H, t, J=7 Hz), 1.70-1.85 (2H, m), 2.16-2.31 (2H, m), 2.44 (3H, s), 2.53-2.83 (2H, m), 3.05 (2H, q, J=7 Hz), 4.72 (2H, s), 4.83-4.98 (2H, m), 5.92 (1H, d, J=4 Hz), 6.62 (1H, d, J=4 Hz), 7.30 (2H, d, J=7 Hz), 7.57 (1H, s), 8.38-8.55 (4H, m). MS (ESI⁻): m/z 443, MS (ESI⁺): m/z 445.

EXAMPLE 446

5-{4-(5-bromo-3-pyridinyl)-7-ethyl-2-[(4-pyridinylmethoxy)methyl]pyrrolo[1,2-b]pyridazin-3-yl}pentanoic acid ¹H NMR (CDCl₃) δ 1.38 (3H, t, J=7 Hz), 1.40-1.63 (4H, m), 2.20 (2H, t, J=7 Hz), 2.52-2.68 (2H, m), 3.04 (2H, q, J=7 Hz), 4.69 (2H, s), 4.78 (2H, s), 5.93 (1H, d, J=4 Hz), 6.63 (1H, d, J=4 Hz), 7.35 (2H, d, J=6 Hz), 7.88 (1H, m), 8.54 (2H, d, J=6 Hz), 8.55 (1H, m), 8.79 (1H, m).

EXAMPLE 447

5-{4-(5-bromo-3-pyridinyl)-7-ethyl-2-[(3-pyridinylmethoxy)methyl]pyrrolo[1,2-b]pyridazin-3-yl}pentanoic acid ¹H NMR (CDCl₃) δ 1.38 (3H, t, J=7 Hz), 1.40-1.62 (4H, m), 2.17 (2H, t, J=7 Hz), 2.50-2.67 (2H, m), 3.04 (2H, q, J=7 Hz), 4.69 (2H, s), 4.76 (2H, s), 5.92 (1H, d, J=4 Hz), 6.61 (1H, d, J=4 Hz), 7.32-7.38 (1H, m), 7.77 (1H, d, J=8 Hz), 7.88 (1H, m), 8.55 (2H, m), 8.65 (1H, m), 8.78 (1H, m). MS (ESI⁻): m/z 521 523, MS (ESI⁺): m/z 523 525.

EXAMPLE 448

5-{4-(5-bromo-3-pyridinyl)-7-ethyl-2-[(2-pyridinylmethoxy)methyl]pyrrolo[1,2-b]pyridazin-3-yl}pentanoic acid ¹H NMR (CDCl₃) δ 1.37 (3H, t, J=7 Hz), 1.48-1.67 (4H, m), 2.26 (2H, t, J=7 Hz), 2.53-2.75 (2H, m), 3.03 (2H, q, J=7 Hz), 4.82 (2H, s), 4.83 (2H, s), 5.90 (1H, d, J=4 Hz), 6.61 (1H, d, J=4 Hz), 7.26-7.34 (1H, m), 7.53 (1H, d, J=8 Hz), 7.75-7.83 (1H, m), 7.87 (1H, m), 8.55 (1H, d, J=2 Hz), 8.62 (1H, m), 8.77 (1H, d, J=2 Hz). MS (ESI⁺): m/z 523 525.

EXAMPLE 449

5-{4-(5-bromo-3-pyridinyl)-7-ethyl-2-[(2-pyrazinylmethoxy)methyl]pyrrolo[1,2-b]pyridazin-3-yl}pentanoic acid ¹H NMR (CDCl₃) δ 1.38 (3H, t, J=7 Hz), 1.45-1.64 (4H, m), 2.23 (2H, t, J=7 Hz), 2.53-2.72 (2H, m), 3.03 (2H, q, J=7 Hz), 4.83 (2H, s), 4.87 (2H, s), 5.93 (1H, d, J=4 Hz), 6.63 (1H, d, J=4 Hz), 7.88 (1H, m), 8.53 (3H, m), 8.77 (2H, m). MS (ESI⁻): m/z 522 524, MS (ESI⁺): m/z 524 526.

EXAMPLE 450

4-{4-(5-bromo-3-pyridinyl)-7-ethyl-2-[(4-pyridinylmethoxy)methyl]pyrrolo[1,2-b]pyridazin-3-yl}butanoic acid ¹H NMR (CDCl₃) δ 1.39 (3H, t, J=7 Hz), 1.69-1.84 (2H, m), 2.27 (2H, t, J=7 Hz), 2.56-2.80 (2H, m), 3.02 (2H, q, J=7 Hz), 4.73 (2H, s), 4.92 (2H, m), 5.94 (1H, d, J=4 Hz), 6.63 (1H, d, J=4 Hz), 7.31 (2H, d, J=6 Hz), 7.90 (1H, m), 8.46 (2H, d, J=6 Hz), 8.57 (1H, d, J=2 Hz), 8.78 (1H, d, J=2 Hz). MS (ESI⁻): m/z 507 509, MS (ESI⁺): m/z 509 511.

EXAMPLE 451

4-{4-(5-bromo-3-pyridinyl)-7-ethyl-2-[(3-pyridinyl-methoxy)methyl]pyrrolo[1,2-b]pyridazin-3-yl}butanoic acid ¹H NMR (CDCl₃) δ 1.38 (3H, t, J=7 Hz), 1.66-1.83 (2H, m), 2.26 (2H, t, J=7 Hz), 2.53-2.77 (2H, m), 3.04 (2H, q, J=7 Hz), 4.71 (2H, s), 4.86 (2H, m), 5.92 (1H, d, J=4 Hz), 6.62 (1H, d, J=4 Hz), 7.33 (1H, m), 7.78 (1H, d, J=8 Hz), 7.90 (1H, m), 8.50 (1H, m), 8.56 (1H, d, J=2 Hz), 8.60 (1H, s), 8.78 (1H, d, J=2 Hz). MS (ESI⁺): m/z 509 511.

EXAMPLE 452

4-{4-(5-bromo-3-pyridinyl)-7-ethyl-2-[(2-pyridinyl-methoxy)methyl]pyrrolo[1,2-b]pyridazin-3-yl}butanoic acid ¹H NMR (CDCl₃) δ 1.37 (3H, t, J=7 Hz), 1.70-1.85 (2H, m), 2.23-2.34 (2H, m), 2.57-2.76 (2H, m), 3.03 (2H, q, J=7 Hz), 4.81 (2H, s), 4.90 (2H, m), 5.91 (1H, d, J=4 Hz), 6.62 (1H, d, J=4 Hz), 7.28 (1H, m), 7.49 (1H, d, J=7 Hz), 7.77 (1H, t, J=8 Hz), 7.88 (1H, m), 8.55 (1H, d, J=2 Hz), 8.57 (1H, m), 8.74 (1H, d, J=2 Hz). MS (ESI⁺): m/z 509 511.

EXAMPLE 453

4-{4-(5-bromo-3-pyridinyl)-2-[(cyclopropyl-methoxy)methyl]-7-ethylpyrrolo[1,2-b]pyridazin-3-yl}butanoic acid ¹H NMR (CDCl₃) δ 0.22 (2H, m), 0.57 (2H, m), 1.07-1.22 (1H, m), 1.37 (3H, t, J=7 Hz), 1.72-1.87 (2H, m), 2.28 (2H, t, J=7 Hz), 2.58-2.77 (2H, m), 3.03 (2H, q, J=7 Hz), 3.41 (2H, d, J=7 Hz), 4.72 (2H, s), 5.92 (1H, d, J=4 Hz), 6.60 (1H, d, J=4 Hz), 7.93 (1H, m), 8.56 (1H, d, J=2 Hz), 8.77 (1H, d, J=2 Hz). MS (ESI⁻): m/z 470 472, MS (ESI⁺): m/z 472 474.

EXAMPLE 454

4-{4-(5-bromo-3-pyridinyl)-7-ethyl-2-[(2-pyrazinyl-methoxy)methyl]pyrrolo[1,2-b]pyridazin-3-yl}butanoic acid ¹H NMR (CDCl₃) δ 1.38 (3H, t, J=7 Hz), 1.68-1.83 (2H, m), 2.27 (2H, t, J=7 Hz), 2.56-2.78 (2H, m), 3.03 (2H, q, J=7 Hz), 4.84 (2H, s), 4.92 (2H, m), 5.94 (1H, d, J=4 Hz), 6.63 (1H, d, J=4 Hz), 7.91 (1H, m), 8.51 (2H, m), 8.56 (1H, d, J=2 Hz), 8.76 (2H, m). MS (ESI⁻): m/z 508 510, MS (ESI⁺): m/z 510 512.

EXAMPLE 455

3-{4-(5-bromo-3-pyridinyl)-7-ethyl-2-[(4-pyridinyl-methoxy)methyl]pyrrolo[1,2-b]pyridazin-3-yl}propanoic acid ¹H NMR (CDCl₃) δ 1.39 (3H, t, J=7 Hz), 2.38 (2H, t, J=7 Hz), 2.83-2.98 (2H, m), 3.07 (2H, q, J=7 Hz), 4.74 (2H, s), 4.83 (2H, s), 5.95 (1H, d, J=4 Hz), 6.65 (1H, d, J=4 Hz), 7.38 (2H, d, J=6 Hz), 7.88 (1H, s), 8.43 (2H, d, J=6 Hz), 8.55 (1H, s), 8.78 (1H, s). MS (ESI⁻): m/z 493 495, MS (ESI⁺): m/z 495 497.

EXAMPLE 456

4-{4-(5-bromo-3-pyridinyl)-7-ethyl-2-[(2-hydroxy-ethoxy)methyl]pyrrolo[1,2-b]pyridazin-3-yl}butanoic acid ¹H NMR (CDCl₃) δ 1.37 (3H, t, J=7 Hz), 1.68-1.83 (2H, m), 2.28 (2H, t, J=7 Hz), 2.53-2.76 (2H, m), 3.02 (2H, q, J=7 Hz), 3.75 (2H, m), 3.79 (2H, m), 4.78 (2H, s), 5.93 (1H, d, J=4 Hz), 6.63 (1H, d, J=4 Hz), 7.90 (1H, s), 8.56 (1H, s), 8.78 (1H, s). MS (ESI⁻): m/z 460 462, MS (ESI⁺): m/z 462 464.

EXAMPLE 457

3-[2-[(cyclohexylmethoxy)methyl]-7-ethyl-4-(5-methyl-3-pyridinyl)pyrrolo[1,2-b]pyridazin-3-yl]propanoic acid ¹H NMR (CDCl₃) δ 0.88-1.06 (2H, m), 1.10-1.36 (3H, m), 1.37 (3H, t, J=7 Hz), 1.58-1.85 (6H, m), 2.42 (3H, s), 2.48-2.60 (2H, m), 2.80-3.02 (2H, m), 3.04 (2H, q, J=7 Hz), 3.39 (2H, d, J=7 Hz), 4.67 (2H, m), 5.89 (1H, d, J=4 Hz), 6.58 (1H, d, J=4 Hz), 7.57 (1H, s), 8.42 (1H, s), 8.53 (1H, s). MS (ESI⁻): m/z 434, MS (ESI⁺): m/z 436.

EXAMPLE 458

3-{4-(5-bromo-3-pyridinyl)-2-[(cyclohexylmethoxy)methyl]-7-ethylpyrrolo[1,2-b]pyridazin-3-yl}propanoic acid ¹H NMR (CDCl₃) δ 0.88-1.05 (2H, m), 1.10-1.36 (3H, m), 1.37 (3H, t, J=7 Hz), 1.56-1.83 (6H, m), 2.51 (2H, t, J=7 Hz), 2.80-3.07 (2H, m), 3.06 (2H, q, J=7 Hz), 3.37 (2H, d, J=7 Hz), 4.67 (2H, s), 5.93 (1H, d, J=4 Hz), 6.63 (1H, d, J=4 Hz), 7.89 (1H, m), 8.55 (1H, s), 8.79 (1H, s). MS (ESI⁻): m/z 498 500, MS (ESI⁺): m/z 500 502.

EXAMPLE 459

4-{4-(5-bromo-3-pyridinyl)-2-[(cyclohexylmethoxy)methyl]-7-ethylpyrrolo[1,2-b]pyridazin-3-yl}butanoic acid ¹H NMR (CDCl₃) δ 0.86-1.03 (2H, m), 1.10-1.35 (3H, m), 1.37 (3H, t, J=7 Hz), 1.60-1.82 (8H, m), 2.28 (2H, t, J=7 Hz), 2.55-2.76 (2H, m), 3.05 (2H, q, J=7 Hz), 3.36 (2H, d, J=7 Hz), 4.67 (2H, s), 5.92 (1H, d, J=4 Hz), 6.62 (1H, d, J=4 Hz), 7.91 (1H, m), 8.55 (1H, d, J=2 Hz), 8.76 (1H, d, J=2 Hz). MS (ESI⁻): m/z 512 514, MS (ESI⁺): m/z 514 516.

EXAMPLE 460

4-[2-[(cyclopropylmethoxy)methyl]-7-ethyl-4-(5-methyl-3-pyridinyl)pyrrolo[1,2-b]pyridazin-3-yl]butanoic acid ¹H NMR (CDCl₃) δ 0.22-0.32 (2H, m), 0.55-0.63 (2H, m), 1.10-1.22 (1H, m), 1.37 (3H, t, J=7 Hz), 1.73-1.86 (2H, m), 2.20-2.35 (2H, m), 2.46 (3H, s), 2.55-2.86 (2H, m), 3.04 (2H, q, J=7 Hz), 3.43 (2H, d, J=7 Hz), 4.70-4.85 (2H, m), 5.88 (1H, d, J=4 Hz), 6.57 (1H, d, J=4 Hz), 7.62 (1H, s), 8.42 (1H, s), 8.46 (1H, s). MS (ESI⁺): m/z 408.

EXAMPLE 461

3-[2-[(cyclopropylmethoxy)methyl]-7-ethyl-4-(5-methyl-3-pyridinyl)pyrrolo[1,2-b]pyridazin-3-yl]propanoic acid $^1$H NMR (CDCl$_3$) δ 0.23-0.35 (2H, m), 0.54-0.65 (2H, m), 1.08-1.24 (1H, m), 1.37 (3H, t, J=7 Hz), 2.43 (3H, s), 2.50-2.65 (2H, m), 2.70-3.05 (2H, m), 3.04 (2H, q, J=7 Hz), 3.44 (2H, d, J=7 Hz), 4.74 (2H, s), 5.89 (1H, d, J=4 Hz), 6.58 (1H, d, J=4 Hz), 7.56 (1H, s), 8.42 (1H, s), 8.53 (1H, s). MS (ESI$^-$): m/z 392, MS (ESI$^+$): m/z 394.

EXAMPLE 462

3-{4-(5-bromo-3-pyridinyl)-7-ethyl-2-[(2-methoxyethoxy)methyl]pyrrolo[1,2-b]pyridazin-3-yl}propanoic acid $^1$H NMR (CDCl$_3$) δ 1.37 (3H, t, J=7 Hz), 2.48-2.62 (2H, m), 2.83-3.02 (2H, m), 3.02 (2H, q, J=7 Hz), 3.37 (3H, s), 3.60 (2H, m), 3.73 (2H, m), 4.75 (2H, s), 5.92 (1H, d, J=4 Hz), 6.61 (1H, d, J=4 Hz), 7.89 (1H, m), 8.55 (1H, d, J=2 Hz), 8.78 (1H, d, J=2 Hz). MS (ESI$^-$): m/z 460 462, MS (ESI$^+$): m/z 462 464.

EXAMPLE 463

5-(4-(5-bromo-3-pyridinyl)-7-ethyl-2-{[(4-morpholinylcarbonyl)oxy]methyl}pyrrolo[1,2-b]pyridazin-3-yl)pentanoic acid $^1$H NMR (CDCl$_3$) δ 1.37 (3H, t, J=7 Hz), 1.35-1.65 (4H, m), 2.23 (2H, t, J=7 Hz), 2.40-2.56 (2H, m), 3.02 (2H, q, J=7 Hz), 3.48-3.57 (4H, m), 3.60-3.78 (4H, m), 5.33 (2H, s), 5.93 (1H, d, J=4 Hz), 6.62 (1H, d, J=4 Hz), 7.89 (1H, m), 8.56 (1H, d, J=2 Hz), 8.79 (1H, d, J=2 Hz).

EXAMPLE 464

5-[4-(5-bromo-3-pyridinyl)-2-({[(dimethylamino)carbonyl]oxy}methyl)-7-ethylpyrrolo[1,2-b]pyridazin-3-yl]pentanoic acid $^1$H NMR (CDCl$_3$) δ 1.36 (3H, t, J=7 Hz), 1.45-1.65 (4H, m), 2.22 (2H, t, J=7 Hz), 2.42-2.57 (2H, m), 2.97 (6H, s), 3.03 (2H, q, J=7 Hz), 5.30 (2H, s), 5.93 (1H, d, J=4 Hz), 6.62 (1H, d, J=4 Hz), 7.89 (1H, s), 8.54 (1H, s), 8.78 (1H, s). MS (ESI$^+$): m/z 503 505.

EXAMPLE 465

5-(4-(5-bromo-3-pyridinyl)-7-ethyl-2-{[(1-pyrrolidinylcarbonyl)oxy]methyl}pyrrolo[1,2-b]pyridazin-3-yl)pentanoic acid $^1$H NMR (CDCl$_3$) δ 1.36 (3H, t, J=7 Hz), 1.40-1.63 (4H, m), 1.82-1.97 (4H, m), 2.23 (2H, t, J=7 Hz), 2.43-2.58 (2H, m), 3.03 (2H, q, J=7 Hz), 3.37-3.52 (4H, m), 5.31 (2H, s), 5.93 (1H, d, J=4 Hz), 6.60 (1H, d, J=4 Hz), 7.88 (1H, m), 8.54 (1H, d, J=2 Hz), 8.78 (1H, d, J=2 Hz). MS (ESI$^-$): m/z 527 529, MS (ESI$^+$): m/z 529 531.

EXAMPLE 466

5-{4-(5-bromo-3-pyridinyl)-7-ethyl-2-[({[methyl(phenyl)amino]carbonyl}oxy)methyl]pyrrolo[1,2-b]pyridazin-3-yl}pentanoic acid $^1$H NMR (CDCl$_3$) δ 1.38 (3H, t, J=7 Hz), 1.40-1.58 (4H, m), 2.18 (2H, t, J=7 Hz), 2.32-2.53 (2H, m), 3.04 (2H, q, J=7 Hz), 3.37 (3H, s), 5.36 (2H, s), 5.92 (1H, d, J=4 Hz), 6.63 (1H, d, J=4 Hz), 7.16-7.40 (5H, m), 7.87 (1H, s), 8.52 (1H, s), 8.79 (1H, s).

EXAMPLE 467

4-(4-(5-bromo-3-pyridinyl)-7-ethyl-2-{[(4-morpholinylcarbonyl)oxy]methyl}pyrrolo[1,2-b]pyridazin-3-yl)butanoic acid $^1$H NMR (CDCl$_3$) δ 1.37 (3H, t, J=7 Hz), 1.65-1.84 (2H, m), 2.27 (2H, t, J=7 Hz), 2.45-2.68 (2H, m), 3.04 (2H, q, J=7 Hz), 3.53 (4H, m), 3.69 (4H, m), 5.36 (2H, s), 5.95 (1H, d, J=4 Hz), 6.63 (1H, d, J=4 Hz), 7.91 (1H, m), 8.55 (1H, d, J=2 Hz), 8.78 (1H, d, J=2 Hz).

EXAMPLE 468

4-[4-(5-bromo-3-pyridinyl)-2-({[(dimethylamino)carbonyl]oxy}methyl)-7-ethylpyrrolo[1,2-b]pyridazin-3-yl]butanoic acid $^1$H NMR (CDCl$_3$) δ 1.36 (3H, t, J=7 Hz), 1.66-1.82 (2H, m), 2.27 (2H, t, J=7 Hz), 2.46-2.68 (2H, m), 2.97 (6H, s), 3.04 (2H, q, J=7 Hz), 5.33 (2H, s), 5.94 (1H, d, J=4 Hz), 6.62 (1H, d, J=4 Hz), 7.92 (1H, m), 8.56 (1H, d, J=2 Hz), 8.78 (1H, d, J=2 Hz).

EXAMPLE 469

3-[4-(5-bromo-3-pyridinyl)-2-({[(dimethylamino)carbonyl]oxy}methyl)-7-ethylpyrrolo[1,2-b]pyridazin-3-yl]propanoic acid $^1$H NMR (CDCl$_3$) δ 1.36 (3H, t, J=7 Hz), 2.45 (2H, t, J=7 Hz), 2.82-2.96 (2H, m), 2.97 (6H, s), 3.03 (2H, q, J=7 Hz), 5.33 (2H, s), 5.96 (1H, d, J=4 Hz), 6.63 (1H, d, J=4 Hz), 7.89 (1H, m), 8.55 (1H, d, J=2 Hz), 8.78 (1H, d, J=2 Hz). MS (ESI$^-$): m/z 473 475, MS (ESI$^+$): m/z 475 477.

EXAMPLE 470

5-{4-(5-bromo-3-pyridinyl)-2-[(1,1-dioxido-4-thiomorpholinyl)methyl]-7-ethylpyrrolo[1,2-b]pyridazin-3-yl}pentanoic acid $^1$H NMR (300 MHz, CDCl$_3$) δ 1.36 (3H, t, J=7 Hz), 1.42-1.56 (4H, m), 2.26 (2H, t, J=7 Hz), 2.48-2.61 (2H, m), 3.01 (2H, q, J=7 Hz), 3.10 (4H, t, J=6 Hz), 3.19 (4H, t, J=6 Hz), 3.85 (2H, s), 5.92 (1H, d, J=4 Hz), 6.61 (1H, d, J=4 Hz), 7.89 (1H, dd, J=2, 2 Hz), 8.56 (1H, d, J=2 Hz), 8.78 (1H, d, J=2 Hz). MS (m/z) 550 (M+H).

EXAMPLE 471

5-[4-(5-bromo-3-pyridinyl)-7-ethyl-2-(4-thiomorpholinylmethyl)pyrrolo[1,2-b]pyridazin-3-yl]pentanoic acid $^1$H NMR (300 MHz, CDCl$_3$) δ 1.37 (3H, t, J=7 Hz), 1.43-1.58 (4H, m), 2.24 (2H, t, J=7 Hz), 2.49-2.61 (2H, m), 2.66 (4H, t, J=4 Hz), 2.86 (4H, t, J=4 Hz), 3.02 (2H, q, J=7 Hz), 3.68 (2H, s), 5.89 (1H, d, J=5 Hz), 6.58 (1H, d, J=5 Hz), 7.90 (1H, s), 8.56 (1H, s), 8.79 (1H, s). MS (m/z) 518 (M+H).

EXAMPLE 472

5-(4-(5-bromo-3-pyridinyl)-7-ethyl-2-{[4-(2-hydroxyethyl)-1-piperazinyl]methyl}pyrrolo[1,2-b]pyridazin-3-yl)pentanoic acid $^1$H NMR (300 MHz, CDCl$_3$) δ 1.34 (3H, t, J=7 Hz), 1.41-1.57 (4H, m), 2.21 (2H, t, J=6 Hz), 2.43-2.57 (2H, m), 2.80-2.84 (4H, m), 2.91-3.00 (6H, m), 3.65 (2H, s), 3.83 (2H, m), 5.88 (1H, d, J=5 Hz), 6.57 (1H, d, J=5 Hz), 7.88 (1H, s), 8.55 (1H, s), 8.77 (1H, s). MS (m/z) 545 (M+H).

EXAMPLE 473

4-[4-(5-chloro-3-pyridinyl)-7-ethyl-2-(4-thiomorpholinylmethyl)pyrrolo[1,2-b]pyridazin-3-yl]butanoic acid $^1$H NMR (300 MHz, CDCl$_3$) δ 1.37 (3H, t, J=7 Hz), 1.72 (2H, tt, J=7, 7 Hz), 2.26 (2H, t, J=7 Hz), 2.53-2.68 (6H, m), 2.87-2.90 (4H, m), 3.02 (2H, q, J=7 Hz), 3.72 (2H, s), 5.91 (1H, d, J=4 Hz), 6.59 (1H, d, J=4 Hz), 7.78 (1H, dd, J=2, 2 Hz), 8.52 (1H, d, J=2 Hz), 8.68 (1H, d, J=2 Hz). MS (m/z) 460 (M+H).

EXAMPLE 474

4-{4-(5-chloro-3-pyridinyl)-7-ethyl-2-[(4-pyridinylmethoxy)methyl]pyrrolo[1,2-b]pyridazin-3-yl}butanoic acid $^1$H NMR (300 MHz, CDCl$_3$) δ 1.38 (3H, t, J=7 Hz), 1.73 (2H, tt, J=7, 7 Hz), 2.25 (2H, t, J=7 Hz), 2.57-2.73 (2H, m), 3.04 (2H, q, J=7 Hz), 4.72 (2H, s), 4.89 (2H, s), 5.93 (1H, d, J=5 Hz), 6.63 (1H, d, J=5 Hz), 7.31 (2H, d, J=6 Hz), 7.76 (1H, dd, J=2, 2 Hz), 8.46 (2H, d, J=6 Hz), 8.53 (1H, d, J=2 Hz), 8.67 (1H, d, J=2 Hz). MS (m/z) 465 (M+H).

EXAMPLE 475

4-[4-(5-chloro-3-pyridinyl)-7-ethyl-2-(4-morpholinylmethyl)pyrrolo[1,2-b]pyridazin-3-yl]butanoic acid $^1$H NMR (300 MHz, CDCl$_3$) δ 1.37 (3H, t, J=7 Hz), 1.73 (2H, tt, J=7, 7 Hz), 2.26 (2H, t, J=7 Hz), 2.54-2.72 (6H, m), 3.03 (2H, q, J=7 Hz), 3.66-3.73 (6H, m), 5.90 (1H, d, J=4 Hz), 6.59 (1H, d, J=4 Hz), 7.79 (1H, s), 8.53 (1H, s), 8.67 (1H, s). MS (m/z) 443 (M+H).

EXAMPLE 476

5-{4-(5-chloro-3-pyridinyl)-2-[(cyclopropylmethoxy)methyl]-7-ethylpyrrolo[1,2-b]pyridazin-3-yl}pentanoic acid $^1$H NMR (300 MHz, CDCl$_3$) δ 0.24 (2H, dt, J=7, 7 Hz), 0.57 (2H, dt, J=7, 7 Hz), 1.07-1.17 (1H, m), 1.38 (3H, t, J=7 Hz), 1.45-1.61 (4H, m), 2.23 (2H, t, J=7 Hz), 2.52-2.66 (2H, m), 3.02 (2H, q, J=7 Hz), 3.41 (2H, d, J=7 Hz), 4.70 (2H, s), 5.90 (1H, d, J=4 Hz), 6.59 (1H, d, J=4 Hz), 7.74 (1H, dd, J=2, 2 Hz), 8.52 (1H, d, J=2 Hz), 8.68 (1H, d, J=2 Hz). MS (m/z) 442 (M+H).

EXAMPLE 477

4-{4-(5-chloro-3-pyridinyl)-2-[(cyclopropylmethoxy)methyl]-7-ethylpyrrolo[1,2-b]pyridazin-3-yl}butanoic acid $^1$H NMR (300 MHz, CDCl$_3$) δ 0.23 (2H, dt, J=6, 6 Hz), 0.56 (2H, dt, J=6, 6 Hz), 1.05-1.17 (1H, m), 1.37 (3H, t, J=7 Hz), 1.75 (2H, tt, J=7, 7 Hz), 2.28 (2H, t, J=7 Hz), 2.57-2.70 (2H, m), 3.03 (2H, q, J=7 Hz), 3.42 (2H, d, J=7 Hz), 4.73 (2H, s), 5.91 (1H, d, J=5 Hz), 6.60 (1H, d, J=5 Hz), 7.77 (1H, dd, J=2, 2 Hz), 8.52 (1H, d, J=2 Hz), 8.66 (1H, d, J=2 Hz). MS (m/z) 428 (M+H).

EXAMPLE 478

5-[4-(5-bromo-3-pyridinyl)-7-ethyl-2-(isobutoxymethyl)pyrrolo[1,2-b]pyridazin-3-yl]pentanoic acid $^1$H NMR (300 MHz, CDCl$_3$) δ 0.93 (6H, d, J=7 Hz), 1.37 (3H, t, J=7 Hz), 1.42-1.59 (4H, m), 1.92 (1H, qt, J=7, 7 Hz), 2.24 (2H, t, J=7 Hz), 2.48-2.69 (2H, m), 3.03 (2H, q, J=7 Hz), 3.33 (2H, d, J=7 Hz), 4.66 (2H, s), 5.91 (1H, d, J=4 Hz), 6.60 (1H, d, J=4 Hz), 7.90 (1H, dd, J=2, 2 Hz), 8.56 (1H, d, J=2 Hz), 8.77 (1H, d, J=2 Hz). MS (m/z) 489 (M+H).

EXAMPLE 479

3-[4-(5-chloro-3-pyridinyl)-7-ethyl-2-(isobutoxymethyl)pyrrolo[1,2-b]pyridazin-3-yl]propanoic acid $^1$H NMR (300 MHz, CDCl$_3$) δ 0.92 (6H, d, J=7 Hz), 1.37 (3H, t, J=7 Hz), 1.91 (1H, qt, J=7, 7 Hz), 2.49 (2H, t, J=8 Hz), 2.82-2.98 (2H, m), 3.03 (2H, q, J=7 Hz), 3.35 (2H, d, J=7 Hz), 4.69 (2H, s), 5.92 (1H, d, J=4 Hz), 6.61 (1H, d, J=4 Hz), 7.72 (1H, dd, J=2, 2 Hz), 851 (1H, d, J=2 Hz), 8.69 (1H, d, J=2 Hz). MS (m/z) 416 (M+H).

EXAMPLE 480

3-[4-(5-bromo-3-pyridinyl)-7-ethyl-2-(4-morpholinylmethyl)pyrrolo[1,2-b]pyridazin-3-yl]propanoic acid $^1$H NMR (300 MHz, CDCl$_3$) δ 1.36 (3H, t, J=7 Hz), 2.55 (2H, t, J=8 Hz), 2.66 (4H, br s), 2.79-2.97 (2H, m), 3.02 (2H, q, J=7 Hz), 3.70-3.74 (6H, m), 5.92 (1H, d, J=4 Hz), 6.61 (1H, d, J=4 Hz), 7.90 (1H, dd, J=2, 2 Hz), 8.55 (1H, d, J=2 Hz), 8.79 (1H, d, J=2 Hz). MS (m/z) 474 (M+H).

EXAMPLE 481

4-[4-(5-bromo-3-pyridinyl)-7-ethyl-2-(4-morpholinylmethyl)pyrrolo[1,2-b]pyridazin-3-yl]butanoic acid $^1$H NMR (300 MHz, CDCl$_3$) δ 1.36 (3H, t, J=7 Hz), 1.73 (2H, tt, J=7, 7 Hz), 2.26 (2H, t, J=7 Hz), 2.57-2.70 (6H, m), 3.02 (2H, q, J=7 Hz), 3.69 (6H, m), 5.90 (1H, d, J=4 Hz), 6.58 (1H, d, J=4 Hz), 7.93 (1H, dd, J=2, 2 Hz), 8.57 (1H, d, J=2 Hz), 8.77(1H, d, J=2 Hz). MS (m/z) 488 (M+H).

EXAMPLE 482

4-{4-(5-chloro-3-pyridinyl)-2-[(cyclopropylamino)methyl]-7-ethylpyrrolo[1,2-b]pyridazin-3-yl}butanoic acid $^1$H NMR (300 MHz, CDCl$_3$) δ 0.54-0.60 (2H, m), 0.74-0.79 (2H, m), 1.38 (3H, t, J=7 Hz), 1.65 (2H, tt, J=6, 6 Hz), 2.21 (2H, t, J=6 Hz), 2.45-2.55 (2H, m), 3.03 (2H, q, J=7 Hz), 4.30 (2H, s), 5.04 (1H, br s), 5.93 (1H, d, J=5 Hz), 6.60 (1H, d, J=5 Hz), 7.73 (1H, dd, J=2, 2 Hz), 8.52 (1H, d, J=2 Hz), 8.69(1H, d, J=2 Hz). MS (m/z) 413 (M+H).

EXAMPLE 483

5-(4-(5-bromo-3-pyridinyl)-7-ethyl-2-{[(2-phenoxyethyl)amino]methyl}pyrrolo[1,2-b]pyridazin-3-yl)pentanoic acid $^1$H NMR (300 MHz, CDCl$_3$) δ 1.36 (3H, t, J=7 Hz), 1.42-1.56 (4H, m), 2.22 (2H, br s), 2.34-2.48 (2H, m), 3.03 (2H, q, J=7 Hz), 3.38-3.43 (2H, br s), 4.23-4.50 (4H, m), 5.93 (1H, d, J=4 Hz), 6.60 (1H, d, J=4 Hz), 6.89-6.97 (3H, m), 7.23-7.30 (2H, m), 7.85 (1H, s), 8.52 (1H, s), 8.78 (1H, s). MS (m/z) 552 (M+H).

EXAMPLE 484

5-(4-(5-bromo-3-pyridinyl)-7-ethyl-2-{[(2-hydroxyethyl)(methyl)amino]methyl}pyrrolo[1,2-b]pyridazin-3-yl)pentanoic acid $^1$H NMR (300 MHz, CDCl$_3$) δ 1.36 (3H, t, J=7 Hz), 1.34-1.54 (4H, m), 2.15-2.26 (2H, m), 2.33-2.52 (2H, m), 2.98 (2H, q, J=7 Hz), 3.16 (3H, s), 3.59-3.72 (2H, m), 3.99-4.10 (2H, m), 4.70 (2H, s), 5.94 (1H, d, J=4 Hz), 6.59 (1H, d, J=4 Hz), 7.85 (1H, s), 8.51 (1H, s), 8.73 (1H, s). MS (m/z) 490 (M+H).

EXAMPLE 485

5-[4-(5-bromo-3-pyridinyl)-7-ethyl-2-(1-piperidinylmethyl)pyrrolo[1,2-b]pyridazin-3-yl]pentanoic acid $^1$H NMR (300 MHz, CDCl$_3$) δ 1.36 (3H, t, J=7 Hz), 1.39-1.51 (6H, m), 1.62-1.71 (4H, m), 2.19 (2H, t, J=6 Hz), 2.52-2.65 (2H, m), 2.78-2.91 (4H, m), 3.10 (2H, q, J=7 Hz), 3.65 (2H, s), 5.89 (1H, d, J=5 Hz), 6.58 (1H, d, J=5 Hz), 7.88 (1H, s), 8.55 (1H, s), 8.76 (1H, s). MS (m/z) 500 (M+H).

EXAMPLE 486

3-[4-(5-bromo-3-pyridinyl)-7-ethyl-2-(4-thiomorpholinylmethyl)pyrrolo[1,2-b]pyridazin-3-yl]propanoic acid $^1$H NMR (300 MHz, CDCl$_3$) δ 1.37 (3H, t, J=7 Hz), 2.52 (2H, t, J=8 Hz), 2.68 (4H, t, J=5 Hz), 2.81-2.95 (6H, m), 3.02 (2H, q, J=7 Hz), 3.74 (2H, s), 5.92 (1H, d, J=5 Hz), 6.61 (1H, d, J=5 Hz), 7.89 (1H, dd, J=2, 2 Hz), 8.55 (1H, d, J=2 Hz), 8.79 (1H, d, J=2 Hz). MS (m/z) 490 (M+H).

EXAMPLE 487

3-(4-(5-bromo-3-pyridinyl)-7-ethyl-2-{[4-(2-hydroxyethyl)-1-piperazinyl]methyl}pyrrolo[1,2-b]pyridazin-3-yl)propanoic acid $^1$H NMR (300 MHz, DMSO-d$_6$) δ 1.32 (3H, t, J=7 Hz), 2.40-2.56 (12H, m), 2.58-2.65 (2H, m), 2.94 (2H, q, J=7 Hz), 3.52 (2H, t, J=5 Hz), 3.67 (2H, s), 5.83 (1H, d, J=5 Hz), 6.62 (1H, d, J=5 Hz), 8.25 (1H, dd, J=2, 2 Hz), 8.63 (1H, d, J=2 Hz), 8.86 (1H, d, J=2 Hz). MS (m/z) 517 (M+H).

EXAMPLE 488

4-[4-(5-bromo-3-pyridinyl)-7-ethyl-2-(isobutoxymethyl)pyrrolo[1,2-b]pyridazin-3-yl]butanoic acid $^1$H NMR (300 MHz, CDCl$_3$) δ 0.91 (6H, d, J=7 Hz), 1.37 (3H, t, J=7 Hz), 1.74 (2H, tt, J=8, 8 Hz), 1.91 (1H, qt, J=7, 7 Hz), 2.27 (2H, t, J=8 Hz), 2.56-2.73 (2H, m), 3.03 (2H, q, J=7 Hz), 3.33 (2H, d, J=7 Hz), 4.68 (2H, s), 5.92 (1H, d, J=5 Hz), 6.60 (1H, d, J=5 Hz), 7.92 (1H, dd, J=7, 7 Hz), 8.56 (1H, d, J=2 Hz), 8.77 (1H, d, J=2 Hz). MS (m/z) 475 (M+H).

EXAMPLE 489

5-[2-{[2-(benzylamino)-2-oxoethoxy]methyl}-7-ethyl-4-(5-methyl-3-pyridinyl)pyrrolo[1,2-b]pyridazin-3-yl]pentanoic acid $^1$H NMR (CDCl$_3$) δ 1.33 (3H, t, J=7 Hz), 1.39-1.60 (4H, m), 2.15 (2H, t, J=7 Hz), 2.42 (3H, s), 2.40-2.58 (2H, m), 2.95 (2H, q, J=7 Hz), 4.19 (2H, s), 4.50 (2H, d, J=7 Hz), 4.75 (2H, m), 5.91 (1H, d, J=4 Hz), 6.59 (1H, d, J=4 Hz), 7.07 (1H, br), 7.22-7.34 (5H, m), 7.54 (1H, s), 8.40 (1H, s), 8.53 (1H, s). MS (ESI$^-$): m/z 513, MS (ESI$^+$): m/z 515.

EXAMPLE 490

5-(7-ethyl-4-(5-methyl-3-pyridinyl)-2-{[(phenylsulfonyl)amino]methyl}pyrrolo[1,2-b]pyridazin-3-yl)pentanoic acid $^1$H NMR (CDCl$_3$) δ 1.36 (3H, t, J=7 Hz), 1.23-1.60 (4H, m), 2.19 (2H, t, J=7 Hz), 2.28-2.46 (2H, m), 2.42 (3H, s), 2.97 (2H, q, J=7 Hz), 4.37 (2H, m), 5.89 (1H, d, J=4 Hz), 5.90 (1H, m), 6.57 (1H, d, J=4 Hz), 7.42-7.53 (4H, m), 7.90 (2H, d, J=8 Hz), 8.34 (1H, s), 8.53 (1H, s). MS (ESI$^-$): m/z 505, MS (ESI$^+$): m/z 507.

EXAMPLE 491

5-[4-(5-bromo-3-pyridinyl)-7-ethyl-2-(1-pyrrolidinylmethyl)pyrrolo[1,2-b]pyridazin-3-yl]pentanoic acid $^1$H NMR (300 MHz, CDCl$_3$) δ 1.35 (3H, t, J=7 Hz), 1.39-1.57 (4H, m), 1.79-1.88 (4H, m), 2.18 (2H, t, J=7 Hz), 2.84-2.89 (6H, m), 3.00 (2H, q, J=7 Hz), 3.89-4.02 (2H, m), 5.88 (1H, d, J=5 Hz), 6.56 (1H, d, J=5 Hz), 7.87 (1H, s), 8.55 (1H, s), 8.75 (1H, s). MS (m/z) 486 (M+H).

EXAMPLE 492

3-[4-(3-chlorophenyl)-7-ethyl-2-(methoxymethyl)pyrrolo[1,2-b]pyridazin-3-yl]propanoic acid $^1$H NMR (CDCl$_3$) δ 1.37 (3H, t, J=8 Hz), 2.39-2.48 (2H, m), 2.83-2.94 (2H, m), 3.03 (2H, q, J=8 Hz), 3.45 (3H, s), 4.65 (2H, s), 5.95 (1H, d, J=5 Hz), 6.60 (1H, d, J=5 Hz), 7.24 (1H, m), 7.35 (1H, br s), 7.40-7.46 (2H, m). MS (ESI$^+$): m/z 373 (M+H).

EXAMPLE 493

4-[4-(3-chlorophenyl)-7-ethyl-2-(methoxymethyl)pyrrolo[1,2-b]pyridazin-3-yl]butanoic acid $^1$H NMR (CDCl$_3$) δ 1.37 (3H, t, J=8 Hz), 1.64-1.78 (2H, m), 2.24 (2H, t, J=8 Hz), 2.56-2.66 (2H, m), 3.04 (2H, q, J=8 Hz), 3.45 (3H, s), 4.65 (2H, s), 5.94 (1H, d, J=5 Hz), 6.59 (1H, d, J=5 Hz), 7.21-7.29 (1H, overlapped with CDCl$_3$), 7.36 (1H, br s), 7.39-7.46 (2H, m). MS (ESI$^+$): m/z 387 (M+H).

EXAMPLE 494

5-{4-(5-bromo-3-pyridinyl)-7-ethyl-2-[(4-phenyl-1-piperazinyl)methyl]pyrrolo[1,2-b]pyridazin-3-yl}pentanoic acid $^1$H NMR (300 MHz, CDCl$_3$) δ 1.37 (3H, t, J=7 Hz), 1.41-1.61 (4H, m), 2.22 (2H, t, J=7 Hz), 2.49-2.67 (2H, m), 2.76 (4H, t, J=5 Hz), 3.03 (2H, q, J=7 Hz), 3.20 (4H, t, J=5 Hz), 3.73 (2H, s), 5.89 (1H, d, J=5 Hz), 6.58 (1H, d, J=5 Hz), 6.85 (1H, dd, J=8, 8 Hz), 6.93 (2H, J=8 Hz), 7.25 (2H, J=8 Hz), 7.90 (1H, dd, J=2, 2 Hz), 8.56 (1H, d, J=2 Hz), 8.77 (1H, d, J=2 Hz).

EXAMPLE 495

5-(4-(5-bromo-3-pyridinyl)-7-ethyl-2-{[(2-methoxyethyl)amino]methyl}pyrrolo[1,2-b]pyridazin-3-yl)pentanoic acid $^1$H NMR (300 MHz, CDCl$_3$) δ 1.28 (3H, t, J=7 Hz), 1.32-1.43 (4H, m), 2.03-2.17 (2H, m), 2.23-2.41 (2H, m), 2.49-2.88 (2H, m), 2.98 (2H, q, J=7 Hz), 3.37 (3H, s), 3.89-3.99 (2H, m), 4.51 (2H, s), 5.91 (1H, d, J=5 Hz), 6.57 (1H, d, J=5 Hz), 7.82 (1H, s), 8.47 (1H, s), 8.72 (1H, s).

EXAMPLE 496

5-[7-ethyl-2-(methoxymethyl)-4-(5-methoxy-3-pyridinyl)pyrrolo[1,2-b]pyridazin-3-yl]pentanoic acid mp 111-112° C. $^1$H NMR (CDCl$_3$) δ 1.37 (3H, t, J=8 Hz), 1.41-1.60 (4H, m), 2.21 (2H, br t, J=8 Hz), 2.30-2.70 (2H, m), 3.04 (2H, d, J=8 Hz), 3.46 (3H, s), 3.90 (3H, s), 4.63 (2H, br d, J=5 Hz), 5.92 (1H, d, J=5 Hz), 6.58 (2H, d, J=8 Hz), 7.25 (1H, m), 8.22 (1H, d, J=1 Hz), 8.40 (1H, d, J=3 Hz). MS (ESI$^+$): m/z 398 (M+H).

EXAMPLE 497

5-[7-ethyl-4-(5-methoxy-3-pyridinyl)-2-methylpyrrolo[1,2-b]pyridazin-3-yl]pentanoic acid mp 133-134° C. $^1$H NMR (CDCl$_3$) δ 1.37 (3H, t, J=8 Hz), 1.40-1.62 (7H, m), 2.24 (2H, t, J=8 Hz), 2.35-2.49 (2H, m), 2.56 (3H, s), 3.01 (2H, q, J=8 Hz), 3.89 (3H, s), 5.87 (1H, d, J=5 Hz), 6.51 (1H, d, J=5 Hz), 7.23 (1H, m), 8.20 (1H, d, J=1 Hz), 8.39 (1H, d, J=3 Hz). MS (ESI$^+$): m/z 369 (M+H).

EXAMPLE 498

3-[7-ethyl-2-(methoxymethyl)-4-(5-methoxy-3-pyridinyl)pyrrolo[1,2-b]pyridazin-3-yl]propanoic acid mp 164-165° C. $^1$H NMR (CDCl$_3$) δ 1.37 (3H, t, J=8 Hz), 2.44-2.54 (2H, m), 2.80-3.00 (2H, m), 3.04 (2H, d, J=8 Hz), 3.47 (3H, s), 3.89 (3H, s), 4.66 (2H, br s), 5.95 (1H, d, J=5 Hz), 6.60 (1H, d, J=5 Hz), 7.25 (1H, m), 8.22 (1H, d, J=1 Hz), 8.38 (1H, d, J=3 Hz). MS (ESI$^+$): m/z 370 (M+H).

EXAMPLE 499

4-[7-ethyl-2-(methoxymethyl)-4-(5-methoxy-3-pyridinyl)pyrrolo[1,2-b]pyridazin-3-yl]butanoic acid mp 140-141° C. $^1$H NMR (CDCl$_3$) δ 1.38 (3H, t, J=8 Hz), 1.68-1.82 (2H, m), 2.25 (2H, t, J=8 Hz), 2.52-2.75 (2H, m), 3.04 (2H, d, J=8 Hz), 3.46 (3H, s), 3.92 (3H, s), 4.65 (2H, br d, J=7 Hz), 5.94 (1H, d, J=5 Hz), 6.59 (1H, d, J=5 Hz), 7.29 (1H, m), 8.23 (1H, d, J=1 Hz), 8.37 (1H, d, J=3 Hz). MS (ESI$^+$): m/z 384 (M+H).

EXAMPLE 500

5-[7-ethyl-2-(methoxymethyl)-4-(5-pyrimidinyl)pyrrolo[1,2-b]pyridazin-3-yl]pentanoic acid $^1$H NMR (CDCl$_3$) δ 1.38 (3H, t, J=8 Hz), 1.40-1.64 (4H, m), 2.25 (2H, t, J=8 Hz), 2.49-2.61 (2H, m), 3.04 (2H, d, J=8 Hz), 3.47 (3H, s), 4.65 (2H, s), 5.91 (1H, d, J=5 Hz), 6.62 (1H, d, J=5 Hz), 8.82 (2H, s), 9.32 (H, s). MS (ESI$^+$): m/z 369 (M+H).

EXAMPLE 501

4-[4-(5-chloro-3-pyridinyl)-7-ethyl-2-(methoxymethyl)pyrrolo[1,2-b]pyridazin-3-yl]butanoic acid mp 112-113° C. $^1$H NMR (CDCl$_3$) δ 1.38 (3H, t, J=8 Hz), 1.66-1.79 (2H, m), 2.28 (2H, t, J=8 Hz), 2.52-2.71 (2H, m), 3.05 (2H, d, J=8 Hz), 3.46 (3H, s), 4.66 (2H, br s) 5.92 (1H, d, J=5 Hz), 6.61 (1H, d, J=5 Hz), 7.77 (1H, m), 8.53 (1H, d, J=1 Hz), 8.67 (1H, d, J=2 Hz). MS (ESI$^+$): m/z 388 (M+H).

EXAMPLE 502

3-[4-(5-chloro-3-pyridinyl)-7-ethyl-2-(methoxymethyl)pyrrolo[1,2-b]pyridazin-3-yl]propanoic acid mp 159-160° C. $^1$H NMR (CDCl$_3$) δ 1.38 (3H, t, J=8 Hz), 2.47 (2H, br t, J=8 Hz), 2.79-2.98 (2H, m), 3.04 (2H, d, J=8 Hz), 3.47 (3H, s), 4.66 (2H, s), 5.93 (1H, d, J=5 Hz), 6.67 (1H, d, J=5 Hz), 7.74 (1H, m), 8.51 (1H, d, J=1 Hz), 8.68 (1H, d, J=3 Hz). MS (ESI$^+$): m/z 374, 376 (M+H).

EXAMPLE 503

5-[4-(5-chloro-3-pyridinyl)-7-ethyl-2-(methoxymethyl)pyrrolo[1,2-b]pyridazin-3-yl]pentanoic acid mp 118-119° C. $^1$H NMR (CDCl$_3$) δ 1.37 (3H, t, J=8 Hz), 1.40-1.62 (7H, m), 2.24 (2H, t, J=8 Hz), 2.45-2.64 (2H, m), 3.04 (2H, d, J=8 Hz), 3.45 (3H, s), 4.63 (2H, s), 5.91 (1H, d, J=5 Hz), 6.60 (1H, d, J=5 Hz), 7.74 (1H, m), 8.51 (1H, d, J=1 Hz), 8.67 (1H, d, J=2 Hz). MS (ESI$^+$): m/z 402, 404 (M+H).

EXAMPLE 504

4-[4-(5-bromo-3-pyridinyl)-7-ethyl-2-(4H-1,2,4-triazol-4-ylmethyl)pyrrolo[1,2-b]pyridazin-3-yl]butanoic acid $^1$H-NMR (CDCl$_3$) δ 1.36 (3H, t, J=7 Hz), 1.60 (2H, m), 2.32 (2H, m), 2.46 (2H, m), 3.01 (2H, q, J=7 Hz), 5.75 (2H, m), 5.97 (1H, d, J=5 Hz), 6.66 (1H, d, J=5 Hz), 7.87 (1H, m), 7.97 (1H, s), 8.53 (1H, s), 8.65 (1H, s), 8.69 (1H, s).

EXAMPLE 505

4-{4-(5-bromo-3-pyridinyl)-2-[(cyclopropylamino)methyl]-7-ethylpyrrolo[1,2-b]pyridazin-3-yl}butanoic acid $^1$H-NMR (CDCl$_3$) δ 0.56 (2H, m), 0.75 (2H, m), 1.38 (3H, t, J=7 Hz), 1.65 (2H, m), 2.21 (2H, m), 2.50 (2H, m), 3.01 (2H, q, J=7 Hz), 3.27 (3H, br), 4.29 (2H, s), 5.93 (1H, d, J=5 Hz), 6.60 (1H, d, J=5 Hz), 7.98 (1H, m), 8.55 (1H, m), 8.78 (1H, m). MS (ESI$^+$) m/z: 457 and 459 (M+H)

EXAMPLE 506

4-{4-(5-bromo-3-pyridinyl)-7-ethyl-2-[(2-oxo-1,3-oxazolidin-3-yl)methyl]pyrrolo[1,2-b]pyridazin-3-yl}butanoic acid $^1$H-NMR (CDCl$_3$) δ 1.37 (3H, t, J=7 Hz), 1.68 (2H, m), 2.31 (2H, m), 2.53 (2H, m), 2.98 (2H, q, J=7 Hz), 3.77 (2H, m), 4.42 (2H, t, J=7 Hz), 4.67 (2H, m), 5.94 (1H, d, J=5 Hz), 6.63 (1H, d, J=5 Hz), 7.89(1H, m), 8.55 (1H, m), 8.78 (1H, m).

EXAMPLE 507

2-bromo-4-[3-(ethoxycarbonyl)-7-ethyl-2-methylpyrrolo[1,2-b]pyridazin-4-yl]benzoic acid $^1$H-NMR (CDCl$_3$) δ 1.00 (3H, t, J=7 Hz), 1.38 (3H, t, J=7 Hz), 2.62 (3H, s), 3.04 (2H, q, J=7 Hz), 4.06 (2H, q, J=7 Hz), 6.29 (1H, d, J=5 Hz), 6.68 (1H, d, J=5 Hz), 7.49 (2H, dd, J=2 and 8 Hz), 7.82 (1H, d, J=2 Hz), 8.07 (1H, d, J=8 Hz). MS (ESI$^+$) m/z: 431 and 433 (M+H)

EXAMPLE 508

5-[4-(3-cyanophenyl)-7-ethyl-2-(phenoxymethyl)pyrrolo[1,2-b]pyridazin-3-yl]pentanoic acid $^1$H-NMR (CDCl$_3$) δ 1.25-1.49 (7H, m), 2.15 (2H, m), 2.54 (2H, m), 3.02 (2H, q, J=7 Hz), 5.23 (2H, s), 5.86 (1H, d, J=5 Hz), 6.60 (1H, d, J=5 Hz), 6.98 (1H, t, J=8 Hz), 7.06 (2H, d, J=8 Hz), 7.28 (2H, t, J=8 Hz), 7.60 (2H, m), 7.67 (1H, s), 7.77 (1H, m).

EXAMPLE 509

5-[4-(3-cyanophenyl)-7-ethyl-2-(3-methyl-2-thienyl)pyrrolo[1,2-b]pyridazin-3-yl]pentanoic acid $^1$H-NMR (CDCl$_3$) δ 1.14-1.28 (4H, m), 1.37 (3H, t, J=7 Hz), 2.01 (2H, t, J=7 Hz), 2.23 (3H, s), 2.40 (2H, m), 3.02 (2H, q, J=7 Hz), 5.92 (1 J, d, J=5 Hz) (6.64 (1H, d, J=5 Hz), 6.94 (1 J, d, J=5 Hz), 7.33 (1H, d, J=5 Hz), 7.57-7.66 (2H, m), 7.73-7.76 (2H, m).

EXAMPLE 510

(2E)-4-[4-(3-cyanophenyl)-7-ethyl-2-methylpyrrolo[1,2-b]pyridazin-3-yl]-2-butenoic acid $^1$H-NMR (CDCl$_3$) δ 1.38 (3H, t, J=7 Hz), 2.55 (3H, s), 3.03 (2H, q, J=7 Hz), 3.09 (2H, d, J=7 Hz), 5.45 (1H, dt, J=7 and 16 Hz), 6.05 (1H, d, J=5 Hz), 6.25 (1H, d, J=16 Hz), 6.57 (1H, d, J=5 Hz), 7.55 (1H, t, J=8 Hz), 7.66+–7.72 (3H, m). MS (ESI$^+$): m/z 345 (M+H)

EXAMPLE 511

4-[4-(5-bromo-3-pyridinyl)-7-ethyl-2-(methoxymethyl)pyrrolo[1,2-b]pyridazin-3-yl]butanoic acid $^1$H NMR (CDCl$_3$) δ 1.37 (3H, t, J=7 Hz), 1.68-1.84 (2H, m), 2.28 (2H, t, J=7 Hz), 2.56-2.74 (2H, m), 3.03 (2H, q, J=7 Hz), 3.46 (3H, s), 4.66 (2H, s), 5.93 (1H, d, J=4 Hz), 6.62 (1H, d, J=4 Hz), 7.92 (1H, m), 8.57 (1H, d, J=2 Hz), 8.78 (1H, d, J=2 Hz). MS (ESI$^-$): m/z 430 432, MS (ESI$^+$): m/z 432 434.

The following compound(s) was (were) obtained in a similar manner to that of Example 159.

EXAMPLE 512 ethyl 4-[4-(2-chloro-4-pyridinyl)-7-ethyl-2-phenylpyrrolo[1,2-b]pyridazin-3-yl]butanoate $^1$H NMR (CDCl$_3$) δ 1.26 (3H, t, J=7 Hz), 1.36 (3H, t, J=7 Hz), 1.35-1.45 (2H, m), 1.88 (2H, t, J=7 Hz), 2.43-2.55 (2H, m), 3.03 (2H, q, J=7 Hz), 4.12 (2H, q, J=7 Hz), 5.98 (1H, d, J=4 Hz), 6.65 (1H, d, J=4 Hz), 7.33 (1H, d, J=5 Hz), 7.42-7.55 (6H, m), 8.55 (1H, d, J=5 Hz). MS (ESI$^+$): m/z 448.

EXAMPLE 513 ethyl 3-[4-(2-chloro-4-pyridinyl)-7-ethyl-2-phenylpyrrolo[1,2-b]pyridazin-3-yl]propanoate $^1$H NMR (CDCl$_3$) δ 1.09 (3H, t, J=7 Hz), 1.36 (3H, t, J=7 Hz), 1.98-2.08 (2H, m), 2.75-2.85 (2H, m), 3.03 (2H, q, J=7 Hz), 3.92 (2H, q, J=7 Hz), 6.00 (1H, d, J=4 Hz), 6.67 (1H, d, J=4 Hz), 7.32 (1H, d, J=5 Hz), 7.42 (1H, s), 7.43-7.57 (5H, m), 8.55 (1H, d, J=5 Hz). MS (ESI$^+$): m/z 434.

EXAMPLE 514 methyl {2-[4-(2-chloro-4-pyridinyl)-7-ethyl-2-phenylpyrrolo[1,2-b]pyridazin-3-yl]ethoxy}acetate $^1$H NMR (CDCl$_3$) δ 1.36 (3H, t, J=7 Hz), 2.73-2.85 (2H, t, J=7 Hz), 3.03 (2H, t, J=7 Hz), 3.15 (2H, t, J=7 Hz), 3.74 (2H, s), 4.09 (3H, s), 6.02 (1H, d, J=4 Hz), 6.67 (1H, d, J=4 Hz), 7.39 (1H, m), 7.42-7.60 (6H, m), 8.53 (1H, d, J=5 Hz). MS (ESI$^+$): m/z 450.

EXAMPLE 515 ethyl 5-[4-(3-cyanophenyl)-7-ethyl-2-(3-methyl-2-thienyl)pyrrolo[1,2-b]pyridazin-3-yl]pentanoate $^1$H-NMR (CDCl$_3$) δ 1.09-1.26 (7H, m), 1.36 (3H, t, J=7 Hz), 1.93 (2H, t, J=7 Hz), 2.23 (3H, s), 2.39 (2H, m), 3.03 (2H, q, J=7 Hz), 4.03 (2H, q, J=7 Hz), 5.93 (1H, d, J=5 Hz), 6.64 (1H, d, J=7 Hz), 6.96 (1H, d, J=5 Hz), 7.33 (1H, d, J=5 Hz), 7.60-7.67 (2H, m), 7.72-7.79 (2H, m).

EXAMPLE 516 methyl 5-[4-(3-cyanophenyl)-7-ethyl-2-(2-thienyl)pyrrolo[1,2-b]pyridazin-3-yl]pentanoate $^1$H-NMR (CDCl$_3$) δ 1.21-1.47 (7H, m), 2.04 (2H, t, J=7 Hz), 2.60 (2H, m), 3.05 (2H, q, J=7 Hz), 3.61 (3H, s), 5.37 (1H, d, J=5 Hz), 6.63 (1H, d, J=5 Hz), 7.13 (1H, m), 7.36 (1H, m), 7.44 (1H, m), 7.62-7.78 (4H, m).

EXAMPLE 517 ethyl 3-[4-(3-cyanophenyl)-7-ethyl-2-phenylpyrrolo[1,2-b]pyridazin-3-yl]propanoate $^1$H-NMR (CDCl$_3$) δ 1.08 (3H, t, J=7 Hz), 1.37 (3H, t, J=7 Hz), 1.98 (2H, m), 2.75 (2H, m), 3.02 (2H, q, J=7 Hz), 3.89 (2H, q, J=7 Hz), 5.93 (1H, d, J=5 Hz), 6.63 (1H, d, J=5 Hz), 7.41-7.55 (5H, m), 7.57-7.78 (4H, m). MS (ESI$^+$): m/z 424 (M+H)

EXAMPLE 518 ethyl 5-[4-(3-chlorophenyl)-7-ethyl-2-phenylpyrrolo[1,2-b]pyridazin-3-yl]pentanoate $^1$H-NMR (CDCl$_3$) δ 1.02-1.25 (7H, m), 1.37 (3H, t, J=7 Hz), 1.88 (2H, t, J=7 Hz), 2.43 (2H, m), 3.01 (2H, q, J=7 Hz), 4.00 (2H, q, J=7 Hz), 5.96 (1H, d, J=5 Hz), 6.60 (1H, d, J=5 Hz), 7.29 (1H, m), 7.37-7.54 (8H, m). MS (ESI$^+$): m/z 461

EXAMPLE 519

4-(5-bromo-3-pyridinyl)-7-ethyl-2-phenylpyrrolo[1,2-b]pyridazine-3-carbonitrile $^1$H NMR (CDCl$_3$) δ 1.42 (3H, t, J=8 Hz), 3.12 (2H, t, J=8 Hz), 6.65 (1H, d, J=5 Hz), 6.94 (1H, d, J=5 Hz), 7.51-7.59 (3H, m), 7.83-7.91 (2H, m), 8.19 (1H, m), 8.85-8.92 (2H, m). MS (ESI$^+$): m/z 403, 405 (M+H).

The following compound(s) was (were) obtained in a similar manner to that of Example 175.

EXAMPLE 520

5-{4-(3-cyanophenyl)-7-ethyl-2-[(4-pyridinylmethoxy)methyl]pyrrolo[1,2-b]pyridazin-3-yl}pentanoic acid $^1$H NMR (CDCl$_3$) δ 1.38 (3H, t, J=7 Hz), 1.36-1.57 (4H, m), 2.16 (2H, t, J=7 Hz), 2.51-2.62 (2H, m), 3.03 (2H, q, J=7 Hz), 4.69 (2H, s), 4.78 (2H, s), 5.87 (1H, d, J=4 Hz), 6.61 (1H, d, J=4 Hz), 7.35 (2H, d, J=5 Hz), 7.61 (2H, d, J=5 Hz), 7.67 (1H, s), 7.77 (1H, m), 8.54 (2H, d, J=5 Hz). MS (ESI$^-$): m/z 467, MS (ESI$^+$): m/z 469.

EXAMPLE 521

5-{4-[3-(aminocarbonyl)phenyl]-7-ethyl-2-[(4-pyridinylmethoxy)methyl]pyrrolo[1,2-b]pyridazin-3-yl}pentanoic acid $^1$H NMR (CDCl$_3$) δ 1.38 (3H, t, J=7 Hz), 1.47-1.68 (4H, m), 2.15-2.40 (2H, m), 2.40-2.56 (1H, m), 2.82-2.96 (1H, m), 3.05 (2H, q, J=7 Hz), 4.68 (2H, s), 4.72 (1H, d, J=17 Hz), 4.93 (1H, d, J=17 Hz), 5.83 (1H, d, J=4 Hz), 6.58 (1H, d, J=4 Hz), 7.31 (2H, d, J=5 Hz), 7.39 (1H, br), 7.45 (1H, d, J=8 Hz), 7.58 (1H, t, J=8 Hz), 7.69 (1H, br), 7.77 (1H, br), 7.98 (1H, d, J=8 Hz), 8.57 (2H, d, J=5 Hz). MS (ESI$^-$): m/z 485, MS (ESI$^+$): m/z 487.

EXAMPLE 522

5-{4-(3-cyanophenyl)-7-ethyl-2-[(2-pyrazinylmethoxy)methyl]pyrrolo[1,2-b]pyridazin-3-yl}pentanoic acid $^1$H NMR (CDCl$_3$) δ 1.38 (3H, t, J=7 Hz), 1.30-1.57 (4H, m), 2.18 (2H, m), 2.48-2.65 (2H, m), 3.03 (2H, q, J=7 Hz), 4.83 (2H, s), 4.85 (2H, s), 5.86 (1H, d, J=4 Hz), 6.58 (1H, d, J=4 Hz), 7.61 (2H, d, J=5 Hz), 7.68 (1H, s), 7.77 (1H, m), 8.53 (2H, d, J=5 Hz), 8.76 (1H, s). MS (ESI$^-$): m/z 468, MS (ESI$^+$): m/z 470.

EXAMPLE 523

5-{4-(3-cyanophenyl)-7-ethyl-2-[(3-pyridinylmethoxy)methyl]pyrrolo[1,2-b]pyridazin-3-yl}pentanoic acid $^1$H NMR (CDCl$_3$) δ 1.38 (3H, t, J=7 Hz), 1.38-1.57 (4H, m), 2.15 (2H, t, J=7 Hz), 2.49-2.62 (2H, m), 3.04 (2H, q, J=7 Hz), 4.69 (2H, s), 4.76 (2H, s), 5.85 (1H, d, J=4 Hz), 6.61 (1H, d, J=4 Hz), 7.33 (1H, m), 7.62 (2H, m), 7.67 (1H, s), 7.73-7.82 (2H, m), 8.53 (1H, d, J=5 Hz), 8.67 (1H, s). MS (ESI$^-$): m/z 467, MS (ESI$^+$): m/z 469.

EXAMPLE 524

5-[4-(3-cyanophenyl)-7-ethyl-2-(5-methyl-3-isoxazolyl)pyrrolo[1,2-b]pyridazin-3-yl]pentanoic acid $^1$H-NMR (CDCl$_3$) δ 1.34-1.52 (7H, m), 2.17 (2H, t, J=7 Hz), 2.53 (3H, s), 2.77 (2H, m), 3.03 (2H, q, J=7 Hz), 5.89 (1H, d, J=5 Hz), 6.54 (1H, s), 6.67 (1H, d, J=5 Hz), 7.63 (2H, m), 7.68 (1H, s), 7.78 (1H, m).

EXAMPLE 525

5-[4-(3-cyanophenyl)-7-ethyl-2-(2-thienyl)pyrrolo[1,2-b]pyridazin-3-yl]pentanoic acid $^1$H-NMR (CDCl$_3$) δ 1.23-1.42 (7H, m), 2.07 (2H, t, J=7 Hz), 2.58 (2H, m), 3.03 (2H, q, J=7 Hz), 5.87 (1H, d, J=5 hz), 6.56 (1H, d, J=5 Hz), 7.13 (1H, m), 7.36 (1H, m), 7.43 (1H, d, J=5 Hz), 7.62 (2H, m), 7.70 (1H, s), 7.76 (1H, m).

EXAMPLE 526

3-[4-(3-cyanophenyl)-7-ethyl-2-phenylpyrrolo[1,2-b]pyridazin-3-yl]propanoic acid $^1$H-NMR (CDCl$_3$) δ 1.36 (3H, t, J=7 Hz), 1.99 (2H, m), 2.75 (2H, m), 3.00 (2H, q, J=7 Hz), 5.93 (1H, d, J=5 Hz), 6.63 (1H, d, J=5 Hz), 7.42-7.55 (5H, m), 7.57-7.78 (4H, m).

EXAMPLE 527

5-[4-(3-chlorophenyl)-7-ethyl-2-phenylpyrrolo[1,2-b]pyridazin-3-yl]pentanoic acid $^1$H-NMR (CDCl$_3$) δ 1.03-1.25 (4H, m), 1.36 (3H, t, J=7 Hz), 1.90 (2H, t, J=7 Hz), 2.41 (2H, m), 3.00 (2H, q, J=7 Hz), 5.97 (1H, d, J=5 Hz), 6.59 (1H, d, J=5 Hz), 7.28 (1H, m), 7.35-7.54 (8H, m). MS (ESI$^+$): m/z 433 (M+H)

The following compound(s) was (were) obtained in a similar manner to that of Example 180.

EXAMPLE 528 ethyl 5-[4-(3-cyanophenyl)-7-ethyl-2-(5-methyl-3-isoxazolyl)pyrrolo[1,2-b]pyridazin-3-yl]pentanoate $^1$H-NMR (CDCl$_3$) δ 1.22 (3H, t, J=7 Hz), 1.32-1.46 (5H, m), 1.72 (2H, m), 2.10 (2H, t, J=7 Hz), 2.54 (3H, s), 2.78 (2H, m), 3.03 (2H, q, J=7 Hz), 4.06 (2H, q, J=7 Hz), 5.89 (1H, d, J=5 Hz), 6.54 (1H, s), 6.66 (1H, d, J=5 Hz), 7.62 (2H, m), 7.67 (1H, s), 7.77 (1H, m).

The following compound(s) was (were) obtained in a similar manner to that of Preparation 176.

EXAMPLE 529 ethyl 4-[4-(aminocarbonyl)-3-bromophenyl]-7-ethyl-2-methylpyrrolo[1,2-b]pyridazine-3-carboxylate $^1$H-NMR (CDCl$_3$) δ 1.03 (3H, t, J=7 Hz), 1.37 (3H, t, J=7 Hz), 2.60 (3H, s), 3.03 (2H, q, J=7 Hz), 4.07 (2H, q, J=7 Hz), 5.83 (1H, s, br), 6.19 (1H, s, br), 6.28 (1H, d, J=5 Hz), 6.67 (1H, d, J=5 Hz), 7.46 (1H, d, J=8 Hz), 7.72 (1H, s), 7.77 (1H, d, J=8 Hz).

The following compound(s) was (were) obtained in a similar manner to that of Example 184.

EXAMPLE 530

3-[2-(cyclopentylamino)-7-ethyl-3-(methylsulfonyl)pyrrolo[1,2-b]pyridazin-4-yl]benzonitrile $^1$H-NMR (CDCl$_3$) δ 1.36 (3H, t, J=7 Hz), 1.51-1.80 (6H, m), 2.15 (2H, m), 2.96 (2H, q, J=7 Hz), 3.05 (3H, s), 4.27 (1H, m), 5.94 (1H, d, J=5 Hz), 6.47-6.53 (2H, m), 7.53-7.59 (3H, m), 7.74 (1H, m).

EXAMPLE 531

3-[7-ethyl-2-(methylamino)-3-(methylsulfonyl)pyrrolo[1,2-b]pyridazin-4-yl]benzonitrile $^1$H-NMR (CDCl$_3$) δ 1.37 (3H, t, J=7 Hz), 2.94-3.07 (8H, m), 5.95 (1H, d, J=5 Hz), 6.50 (2H, m), 7.54-7.59 (3H, m), 7.74 (1H, m).

The following compound(s) was (were) obtained in a similar manner to that of Example 225.

EXAMPLE 532

(2R,3R,4S,5S,6R)-2-({3-[4-(5-bromo-3-pyridinyl)-7-ethyl-2-(methoxymethyl)pyrrolo[1,2-b]pyridazin-3-yl]propanoyl}amino)-6-{1[(2,2-dimethylpropanoyl)oxy]methyl}tetrahydro-2H-pyran-3,4,5-triyl tris(2,2-dimethylpropanoate)

$^1$H-NMR (CDCl$_3$) δ 1.07 (9H, s), 1.11 (9H, s), 1.16 (9H, s), 1.18 (9H, s), 1.37 (3H, t, J=7 Hz), 2.23 (2H, m), 2.84 (2H, m), 3.03 (2H, q, J=7 Hz), 3.48 (3H, s), 3.91-4.21 (3H, m), 4.62-4.67 (2H, m), 5.00-5.26 (3H, m), 5.43 (2H, m), 5.91 (1H, d, J=5 Hz), 6.55 (1H, m, br), 6.62 (1H, d, J=5 Hz), 7.84 (1H, m), 8.51 (1H, m), 8.77 (1H, m).

The following compound(s) was (were) obtained in a similar manner to that of Example 226.

EXAMPLE 533

[4-(3-chlorophenyl)-7-ethyl-2-(2-furyl)pyrrolo[1,2-b]pyridazin-3-yl]methanol $^1$H-NMR (CDCl$_3$) δ 1.40 (3H, t, J=7 Hz), 2.53 (1H, t, J=7 Hz), 3.07 (2H, q, J=7 Hz), 4.48 (2H, m), 6.23 (1H, d, J=5 Hz), 6.62 (1H, m), 6.71 (1H, d, J=5 Hz), 7.10 (1H, d, J=5 Hz), 7.46-7.52 (3H, m), 7.61 (1H, m), 7.64 (1H, m).

EXAMPLE 534

[4-(2-chloro-4-pyridinyl)-7-ethyl-2-methylpyrrolo[1,2-b]pyridazin-3-yl]methanol $^1$H NMR (CDCl$_3$) δ 1.38 (3H, t, J=8 Hz), 3.05 (2H, q, J=8 Hz), 3.45-3.55 (4H, m), 4.40 (2H, br d, J=7 Hz), 4.77 (2H, br s), 6.22 (1H, d, J=5 Hz), 6.70 (1H, d, J=5 Hz), 8.11 (1H, m), 8.74 (1H, br s), 8.80 (1H, d, J=2 Hz). MS (ESI$^+$): m/z 302 (M+H).

The following compound(s) was (were) obtained in a similar manner to that of Example 227.

EXAMPLE 535

(2R,3S,4S,5R,6R)-2-[(acetyloxy)methyl]-6-({5-[4-(3-cyanophenyl)-7-ethyl-2-phenylpyrrolo[1,2-b]pyridazin-3-yl]pentyl}oxy)tetrahydro-2H-pyran-3,4,5-triyl triacetate $^1$H-NMR (CDCl$_3$) δ 0.82-1.18 (6H, m), 1.37 (3H, t, J=7 Hz), 1.92-2.17 (14H, m), 2.35 (2H, m), 3.01 (2H, q, J=7 Hz), 3.16 (1H, m), 3.62 (1H, m), 3.85 (1H, m), 4.11 (2H, m), 4.10 (2H, m), 4.30 (1H, d, J=8.1 Hz), 4.96 (1H, m), 5.11 (1H, m), 5.35 (1H, m), 5.90 (1H, d, J=5 Hz), 6.62 (1H, d, J=5 Hz), 7.44-7.53 (5H, m), 7.60-7.80 (4H, m).

The following compound(s) was (were) obtained in a similar manner to that of Example 228.

EXAMPLE 536 ethyl 3-[7-ethyl-2-(hydroxymethyl)-4-(5-methyl-3-pyridinyl)pyrrolo[1,2-b]pyridazin-3-yl]propanoate $^1$H NMR (CDCl$_3$) δ 1.19 (3H, t, J=7 Hz), 1.39 (3H, t, J=7 Hz), 2.33 (2H, t, J=7 Hz), 2.43 (3H, s), 2.70-2.82 (2H, m), 3.04 (2H, q, J=7 Hz), 3.71 (1H, t, J=5 Hz), 4.05 (2H, q, J=7 Hz), 4.89 (2H, d, J=5 Hz), 5.98 (1H, d, J=4 Hz), 6.61 (1H, d, J=4 Hz), 7.52 (1H, s), 8.42 (1H, d, J=2 Hz), 8.56 (1H, d, J=2 Hz). MS (ESI$^+$): m/z 368.

EXAMPLE 537 ethyl 4-[7-ethyl-2-(hydroxymethyl)-4-(5-methyl-3-pyridinyl)pyrrolo[1,2-b]pyridazin-3-yl]butanoate $^1$H NMR (CDCl$_3$) δ 1.24 (3H, t, J=7 Hz), 1.39 (3H, t, J=7 Hz), 1.62-1.78 (2H, m), 2.16-2.28 (2H, m), 2.36-2.53 (2H, m), 2.44 (3H, s), 3.06 (2H, q, J=7 Hz), 3.86 (1H, t, J=7 Hz), 4.12 (2H, q, J=7 Hz), 4.90 (2H, m), 5.96 (1H, d, J=4 Hz), 6.60 (1H, d, J=4 Hz), 7.53 (1H, s), 8.44 (1H, s), 8.56 (1H, s). MS (ESI$^+$): m/z 382.

EXAMPLE 538 ethyl 5-[4-(3-cyanophenyl)-7-ethyl-2-(hydroxymethyl)pyrrolo[1,2-b]pyridazin-3-yl]pentanoate $^1$H NMR (CDCl$_3$) δ 1.26 (3H, t, J=7 Hz), 1.39 (3H, t, J=7 Hz), 1.46-1.65 (4H, m), 2.16 (2H, t, J=7 Hz), 2.32-2.44 (2H, m), 3.04 (2H, q, J=7 Hz), 4.12 (2H, q, J=7 Hz), 4.86 (2H, s), 5.91 (1H, d, J=4 Hz), 6.60 (1H, d, J=4 Hz), 7.58-7.68 (3H, m), 7.75-7.82 (1H, m). MS (ESI$^+$): m/z 406.

EXAMPLE 539 ethyl 4-[4-(5-bromo-3-pyridinyl)-7-ethyl-2-(hydroxymethyl)pyrrolo[1,2-b]pyridazin-3-yl]butanoate $^1$H NMR (CDCl$_3$) δ 1.25 (3H, t, J=7 Hz), 1.38 (3H, t, J=7 Hz), 1.64-1.79 (2H, m), 2.23 (2H, t, J=7 Hz), 2.42-2.53 (2H, m), 3.04 (2H, q, J=7 Hz), 4.10 (2H, q, J=7 Hz), 4.91 (2H, s), 5.97 (1H, d, J=4 Hz), 6.62 (1H, d, J=4 Hz), 7.89 (1H, m), 8.56 (1H, d, J=2 Hz), 8.80 (1H, d, J=2 Hz). MS (ESI$^+$): m/z 446 448.

EXAMPLE 540 ethyl 3-[4-(5-bromo-3-pyridinyl)-7-ethyl-2-(hydroxymethyl)pyrrolo[1,2-b]pyridazin-3-yl]propanoate $^1$H NMR (CDCl$_3$) δ 1.20 (3H, t, J=7 Hz), 1.38 (3H, t, J=7 Hz), 2.32 (2H, m), 2.68-2.90 (2H, m), 3.03 (2H, q, J=7 Hz), 4.10 (2H, m), 4.89 (2H, s), 6.03 (1H, m), 6.65 (1H, m), 7.90 (1H, m), 8.58 (1H, m), 8.83 (1H, m). MS (ESI$^+$): m/z 432 434.

EXAMPLE 541 ethyl 4-[4-(5-chloro-3-pyridinyl)-7-ethyl-2-(hydroxymethyl)pyrrolo[1,2-b]pyridazin-3-yl]butanoate $^1$H NMR (300 MHz, CDCl$_3$) δ 1.22 (3H, t, J=7 Hz), 1.38 (3H, t, J=7 Hz), 1.67 (2H, tt, J=7, 7 Hz), 2.20 (2H, t, J=7 Hz), 2.37-2.79 (2H, m), 3.04 (2H, q, J=7 Hz), 3.77 (1H, t, J=4 Hz), 4.07 (2H, q, J=7 Hz), 4.91 (2H, d, J=4 Hz), 5.96 (1H, d, J=4 Hz), 6.61 (1H, d, J=4 Hz), 7.73 (1H, dd, J=2, 2 Hz), 8.52 (1H, d, J=2 Hz), 8.70 (1H, d, J=2 Hz).

EXAMPLE 542 ethyl 3-[4-(3-chlorophenyl)-7-ethyl-2-(hydroxymethyl)pyrrolo[1,2-b]pyridazin-3-yl]propanoate $^1$H NMR (300 MHz, CDCl$_3$) δ 1.20 (3H, t, J=7 Hz), 1.38 (3H, t, J=7 Hz), 2.31 (2H, t, J=8 Hz), 2.85 (2H, t, J=8 Hz), 3.04 (2H, q, J=7 Hz), 3.69-3.75 (1H, br s), 4.06 (2H, q, J=7 Hz), 4.88 (2H, s), 6.00 (1H, d, J=4 Hz), 6.59 (1H, d, J=4 Hz), 7.23-7.26 (1H, m), 7.36 (1H, s), 7.44-7.46 (2H, m).

EXAMPLE 543 ethyl 4-[4-(3-chlorophenyl)-7-ethyl-2-(hydroxymethyl)pyrrolo[1,2-b]pyridazin-3-yl]butanoate $^1$H NMR (CDCl$_3$) δ 1.21 (3H, t, J=8 Hz), 1.38 (3H, t, J=8 Hz), 1.57 (3H, s), 1.59-1.74 (2H, m), 2.20 (2H, t, J=8 Hz), 2.37-2.47 (2H, m), 3.03 (2H, q, J=8 Hz), 3.84 (1H, t, J=5 Hz), 4.06 (2H, q, J=8 Hz), 4.39 (2H, d, J=5 Hz), 5.32 (2H, s), 5.96 (1H, d, J=5 Hz), 6.56 (1H, d, J=5 Hz), 7.21-7.29 (1H, overlappled with CDCl$_3$), 736 (1H, br s), 7.39-7.47 (2H, m).

EXAMPLE 544

9-(5-bromo-3-pyridinyl)-6-ethyl-1H,3H-furo[3,4-e]pyrrolo[1,2-b]pyridazin-1-one $^1$H NMR (CDCl$_3$) δ 1.42 (3H, t, J=8 Hz), 3.11 (2H, q, J=8 Hz), 5.32 (2H, s), 6.87 (1H, d, J=5 Hz), 6.99 (1H, d, J=5 Hz), 8.20 (1H, m), 8.83-8.87 (2H, m). MS (ESI$^+$): m/z 358, 360 (M+H).

4-(5-bromo-3-pyridinyl)-7-ethyl-2-(hydroxymethyl)pyrrolo[1,2-b]pyridazine-3-carboxylic acid $^1$H NMR (CDCl$_3$-CD3OD) δ 1.40 (3H, t, J=8 Hz), 3.09 (2H, q, J=8 Hz), 4.93 (2H, s), 6.34 (1H, d, J=5 Hz), 6.79 (1H, d, J=5 Hz), 7.96 (1H, m), 8.55 (1H, br s), 8.73 (1H, br s). MS (ESI$^+$): m/z 376, 378 (M+H).

EXAMPLE 545

3-[4-(5-bromo-3-pyridinyl)-7-ethyl-2-(methoxymethyl)pyrrolo[1,2-b]pyridazin-3-yl]-N-[(2R,3R,4S,5R,6R)-3,4,5-trihydroxy-6-(hydroxymethyl)tetrahydro-2H-pyran-2-yl]propanamide $^1$H-NMR (DMSO-$d_6$) δ 1.30 (3H, t, J=7 Hz), 2.21 (1H, m), 2.96 (2H, q, J=7 Hz), 3.25-3.45 (8H, m), 3.66 (1H, m), 4.40 (1H, m), 4.55-4.67 (5H, m), 4.75 (1H, m), 5.85 (1H, d, J=5 Hz), 6.66 (1H, d, J=5 Hz), 8.23 (1H, m), 8.33 (1H, d, br, J=7 Hz), 8.61 (1H, m), 8.84 (1H, m).

EXAMPLE 546

3-[7-ethyl-2-phenyl-3-(5-{[(2R,3R,4S,5R,6R)-3,4,5-trihydroxy-6-(hydroxymethyl)tetrahydro-2H-pyran-2-yl]oxy}pentyl)pyrrolo[1,2-b]pyridazin-4-yl]benzonitrile $^1$H-NMR (CDCl$_3$) δ 0.85-1.38 (6H, m), 1.46 (3H, t, J=7 Hz), 2.13 (2H, m), 2.38 (2H, m), 2.65 (1H, m), 2.73 (1H, m), 3.02 (2H, q, J=7 Hz), 3.23 (1H, m), 3.48-3.70 (4H, m), 3.804.01 (3H, m), 4.13 (1H, m), 5.90 (1H, d, J=5 Hz), 6.63 (1H, d, J=5 Hz), 7.42-7.55 (5H, m), 7.60-7.79 (4H, m).

The following compound(s) was (were) obtained in a similar manner to that of Example 235.

EXAMPLE 547

N-(2-aminoethyl)-3-[4-(5-bromo-3-pyridinyl)-7-ethyl-2-(methoxymethyl)pyrrolo[1,2-b]pyridazin-3-yl]propanamide $^1$H-NMR (CDCl$_3$) δ 1.37 (3H, t, J=7 Hz), 2.29 (2H, m), 2.72-3.07 (6H, m), 333 (2H, q, J=7 Hz), 3.49 (3H, s), 4.68 (2H, s), 5.93 (1H, d, J=5 Hz), 6.06 (1H, m, br), 6.62 (1H, d, J=5 Hz), 7.89 (1H, m), 8.55 (1H, m), 8.77 (1H, m). MS (ESI$^+$) m/z: 460 and 462 (M+H)

The following compound(s) was (were) obtained in a similar manner to that of Example 268.

EXAMPLE 548 ethyl 3-{7-ethyl-4-(5-methyl-3-pyridinyl)-2-[(4-pyridinylmethoxy)methyl]pyrrolo[1,2-b]pyridazin-3-yl}propanoate $^1$H NMR (CDCl$_3$) δ 1.15 (3H, t, J=7 Hz), 1.38 (3H, t, J=7 Hz), 2.37 (2H, t, J=7 Hz), 2.43 (3H, s), 2.86-3.01 (2H, m), 3.03 (2H, q, J=7 Hz), 3.99 (2H, q, J=7 Hz), 4.68 (2H, s), 4.81 (2H, s), 5.95 (1H, d, J=4 Hz), 6.62 (1H, d, J=4 Hz), 7.27 (2H, d, J=7 Hz), 7.51 (1H, s), 8.43 (1H, s), 8.56 (1H, s), 8.57 (2H, d, J=7 Hz). MS (ESI$^+$): m/z 459.

EXAMPLE 549 ethyl 3-{7-ethyl-4-(5-methyl-3-pyridinyl)-2-[(2-pyrazinylmethoxy)methyl]pyrrolo[1,2-b]pyridazin-3-yl}propanoate $^1$H NMR (CDCl$_3$) δ 1.16 (3H, t, J=7 Hz), 1.38 (3H, t, J=7 Hz), 2.39 (2H, t, J=7 Hz), 2.43 (3H, s), 2.88-3.03 (2H, m), 3.04 (2H, q, J=7 Hz), 4.01 (2H, q, J=7 Hz), 4.83 (2H, s), 4.90 (2H, s), 5.94 (1H, d, J=4 Hz), 6.63 (1H, d, J=4 Hz), 7.53 (1H, s), 8.42 (1H, m), 8.48-8.55 (3H, m), 8.76 (1H, s). MS (ESI$^+$): m/z 460.

EXAMPLE 550 ethyl 3-{7-ethyl-4-(5-methyl-3-pyridinyl)-2-[(2-pyridinylmethoxy)methyl]pyrrolo[1,2-b]pyridazin-3-yl}propanoate $^1$H NMR (CDCl$_3$) δ 1.15 (3H, t, J=7 Hz), 1.38 (3H, t, J=7 Hz), 2.40 (2H, t, J=7 Hz), 2.42 (3H, s), 2.88-3.00 (2H, m), 3.03 (2H, q, J=7 Hz), 3.99 (2H, q, J=7 Hz), 4.79 (2H, s), 4.86 (2H, s), 5.92 (1H, d, J=4 Hz), 6.60 (1H, d, J=4 Hz), 7.16-7.23 (1H, m), 7.45-7.53 (2H, m), 7.68 (1H, m), 8.42 (1H, m), 8.53 (2H, m). MS (ESI$^+$): m/z 459.

EXAMPLE 551 ethyl 4-{7-ethyl-4-(5-methyl-3-pyridinyl)-2-[(4-pyridinylmethoxy)methyl]pyrrolo[1,2-b]pyridazin-3-yl}butanoate $^1$H NMR (CDCl$_3$) δ 1.18 (3H, t, J=7 Hz), 1.38 (3H, t, J=7 Hz), 1.60-1.80 (2H, m), 2.13-2.25 (2H, m), 2.43 (3H, s), 2.53-2.76 (2H, m), 3.03 (2H, q, J=7 Hz), 4.03 (2H, q, J=7 Hz), 4.68 (2H, s), 4.83 (2H, s), 5.92 (1H, d, J=4 Hz), 6.61 (1H, d, J=4 Hz), 7.27 (2H, d, J=5 Hz), 7.53 (1H, s), 8.42 (1H, s), 8.53 (1H, s), 8.55 (2H, d, J=5 Hz). MS (ESI$^+$): m/z 473.

EXAMPLE 552 ethyl 5-{4-(3-cyanophenyl)-7-ethyl-2-[(4-pyridinylmethoxy)methyl]pyrrolo[1,2-b]pyridazin-3-yl}pentanoate $^1$H NMR (CDCl$_3$) δ 1.22 (3H, t, J=7 Hz), 1.38 (3H, t, J=7 Hz), 1.35-1.57 (4H, m), 2.11 (2H, t, J=7 Hz), 2.53-2.65 (2H, m), 3.03 (2H, q, J=7 Hz), 4.03 (2H, q, J=7 Hz), 4.67 (2H, s), 4.78 (2H, s), 5.87 (1H, d, J=4 Hz), 6.61 (1H, d, J=4 Hz), 7.28 (2H, d, J=5 Hz), 7.61 (2H, m), 7.66 (1H, s), 7.78 (1H, m), 8.58 (2H, d, J=5 Hz). MS (ESI$^+$): m/z 497.

EXAMPLE 553 ethyl 5-{4-(3-cyanophenyl)-7-ethyl-2-[(2-pyrazinylmethoxy)methyl]pyrrolo[1,2-b]pyridazin-3-yl}pentanoate $^1$H NMR (CDCl$_3$) δ 1.22 (3H, t, J=7 Hz), 1.38 (3H, t, J=7 Hz), 1.35-1.58 (4H, m), 2.11 (2H, t, J=7 Hz), 2.55-2.65 (2H, m), 3.03 (2H, q, J=7 Hz), 4.10 (2H, q, J=7 Hz), 4.82 (2H, s), 4.86 (2H, s), 5.86 (1H, d, J=4 Hz), 6.60 (1H, d, J=4 Hz), 7.62 (2H, m), 7.67 (1H, s), 7.78 (1H, m), 8.51 (2H, m), 8.74 (1H, s). MS (ESI$^+$): m/z 498.

EXAMPLE 554 ethyl 5-{4-(3-cyanophenyl)-7-ethyl-2-[(3-pyridinylmethoxy)methyl]pyrrolo[1,2-b]pyridazin-3-yl}pentanoate $^1$H NMR (CDCl$_3$) δ 1.22 (3H, t, J=7 Hz), 1.39 (3H, t, J=7 Hz), 1.32-1.66 (4H, m), 2.10 (2H, t, J=7 Hz), 2.48-2.60 (2H, m), 3.03 (2H, q, J=7 Hz), 4.08 (2H, q, J=7 Hz), 4.66 (2H, s), 4.75 (2H, s), 5.86 (1H, d, J=4 Hz), 6.61 (1H, d, J=4 Hz), 7.28 (1H, m), 7.58-7.63 (2H, m), 7.66 (1H, s), 7.66-7.80 (2H, m), 8.54 (1H, m), 8.62 (1H, m). MS (ESI$^+$): m/z 497.

EXAMPLE 555 ethyl 5-{4-(5-bromo-3-pyridinyl)-7-ethyl-2-[(4-pyridinylmethoxy)methyl]pyrrolo[1,2-b]pyridazin-3-yl}pentanoate $^1$H NMR (CDCl$_3$) δ 1.23 (3H, t, J=7 Hz), 1.38 (3H, t, J=7 Hz), 1.40-1.62 (4H, m), 2.16 (2H, t, J=7 Hz), 2.53-2.71 (2H, m), 3.05 (2H, q, J=7 Hz), 4.09 (2H, q, J=7 Hz), 4.67 (2H, s), 4.78 (2H, s), 5.93 (1H, d, J=4 Hz), 6.63 (1H, d, J=4 Hz), 7.31 (2H, d, J=5 Hz), 7.88 (1H, m), 8.56 (1H, d, J=2 Hz), 8.58 (2H, d, J=5 Hz), 8.79 (1H, d, J=2 Hz).

EXAMPLE 556 ethyl 5-{4-(5-bromo-3-pyridinyl)-7-ethyl-2-[(3-pyridinylmethoxy)methyl]pyrrolo[1,2-b]pyridazin-3-yl}pentanoate $^1$H NMR (CDCl$_3$) δ 1.23 (3H, t, J=7 Hz), 1.40 (3H, t, J=7 Hz), 1.30-1.60 (4H, m), 2.15 (2H, t, J=7 Hz), 2.50-2.68 (2H, m), 3.06 (2H, q, J=7 Hz), 4.12 (2H, q, J=7 Hz), 4.68 (2H, s), 4.78 (2H, s), 5.95 (1H, m), 6.63 (1H, m), 7.24-7.38 (1H, m), 7.75 (1H, m), 7.89 (1H, m), 8.58 (2H, s), 8.64 (1H, s), 8.80 (1H, s). MS (ESI$^+$): m/z 551 553.

EXAMPLE 557 ethyl 5-{4-(5-bromo-3-pyridinyl)-7-ethyl-2-[(2-pyridinylmethoxy)methyl]pyrrolo[1,2-b]pyridazin-3-yl}pentanoate $^1$H NMR (CDCl$_3$) δ 1.24 (3H, t, J=7 Hz), 1.37 (3H, t, J=7 Hz), 1.40-1.58 (4H, m), 2.12 (2H, t, J=7 Hz), 2.53-2.68 (2H, m), 3.03 (2H, q, J=7 Hz), 4.10 (2H, q, J=7 Hz), 4.78 (2H, s), 4.84 (2H, s), 5.92 (1H, d, J=4 Hz), 6.62 (1H, d, J=4 Hz), 7.22 (1H, m), 7.48 (1H, d, J=8 Hz), 7.68-7.75 (1H, m), 7.88 (1H, m), 8.57 (2H, m), 8.78 (1H, d, J=2 Hz).

EXAMPLE 558 ethyl 5-{4-(5-bromo-3-pyridinyl)-7-ethyl-2-[(2-pyrazinylmethoxy)methyl]pyrrolo[1,2-b]pyridazin-3-yl}pentanoate $^1$H NMR (CDCl$_3$) δ 1.22 (3H, t, J=7 Hz), 1.38 (3H, t, J=7 Hz), 1.40-1.62 (4H, m), 2.15 (2H, t, J=7 Hz), 2.53-2.72 (2H, m), 3.05 (2H, q, J=7 Hz), 4.08 (2H, q, J=7 Hz), 4.82 (2H, s), 4.86 (2H, s), 5.94 (1H, d, J=4 Hz), 6.63 (1H, d, J=4 Hz), 7.88 (1H, m), 8.52 (2H, m), 8.55 (1H, d, J=2 Hz), 8.74 (1H, m), 8.79 (1H, d, J=2 Hz). MS (ESI$^+$): m/z 552 554.

EXAMPLE 559 ethyl 4-{4-(5-bromo-3-pyridinyl)-7-ethyl-2-[(4-pyridinylmethoxy)methyl]pyrrolo[1,2-b]pyridazin-3-yl}butanoate $^1$H NMR (CDCl$_3$) δ 1.19 (3H, t, J=7 Hz), 1.38 (3H, t, J=7 Hz), 1.60-1.80 (2H, m), 2.22 (2H, t, J=7 Hz), 2.55-2.74 (2H, m), 3.05 (2H, q, J=7 Hz), 4.06 (2H, q, J=7 Hz), 4.69 (2H, s), 4.83 (2H, s), 5.96 (1H, d, J=4 Hz), 6.63 (1H, d, J=4 Hz), 7.30 (2H, d, J=6 Hz), 7.88 (1H, m), 8.56 (2H, d, J=6 Hz), 8.57 (1H, m), 8.80 (1H, m). MS (ESI$^+$): m/z 537 539.

EXAMPLE 560 ethyl 4-{4-(5-bromo-3-pyridinyl)-7-ethyl-2-[(3-pyridinylmethoxy)methyl]pyrrolo[1,2-b]pyridazin-3-yl}butanoate $^1$H NMR (CDCl$_3$) δ 1.26 (3H, t, J=7 Hz), 1.38 (3H, t, J=7 Hz), 1.55-1.82 (2H, m), 2.18 (2H, t, J=7 Hz), 2.52-2.72 (2H, m), 3.05 (2H, q, J=7 Hz), 4.05 (2H, q, J=7 Hz), 4.68 (2H, s), 4.83 (2H, s), 5.94 (1H, d, J=4 Hz), 6.63 (1H, d, J=4 Hz), 7.28 (1H, m), 7.73 (1H, d, J=8 Hz), 7.88 (1H, m), 8.54 (2H, m), 8.62 (1H, s), 8.79 (1H, s)

EXAMPLE 561 ethyl 4-{4-(5-bromo-3-pyridinyl)-7-ethyl-2-[(2-pyridinylmethoxy)methyl]pyrrolo[1,2-b]pyridazin-3-yl}butanoate $^1$H NMR (CDCl$_3$) δ 1.26 (3H, t, J=7 Hz), 1.38 (3H, t, J=7 Hz), 1.63-1.82 (2H, m), 2.18 (2H, t, J=7 Hz), 2.55-2.75 (2H, m), 3.06 (2H, q, J=7 Hz), 4.00 (2H, q, J=7 Hz), 4.80 (2H, s), 4.88 (2H, s), 5.93 (1H, d, J=4 Hz), 6.62 (1H, d, J=4 Hz), 7.22 (1H, m), 7.48 (1H, d, J=8 Hz), 7.71 (1H, t, J=8 Hz), 7.89 (1H, m), 8.55 (2H, m), 8.78 (1H, d, J=2 Hz). MS (ESI$^+$): m/z 537 539.

EXAMPLE 562 ethyl 4-{4-(5-bromo-3-pyridinyl)-2-[(cyclopropylmethoxy)methyl]-7-ethylpyrrolo[1,2-b]pyridazin-3-yl}butanoate $^1$H NMR (CDCl$_3$) δ 0.25 (2H, m), 0.60 (2H, m), 1.08-1.22 (1H, m), 1.22 (3H, t, J=7 Hz), 1.37 (3H, t, J=7 Hz), 1.69-1.82 (2H, m), 2.21 (2H, t, J=7 Hz), 2.56-2.72 (2H, m), 3.03 (2H, q, J=7 Hz), 3.42 (2H, d, J=7 Hz), 4.04 (2H, q, J=7 Hz), 4.73 (2H, s), 5.91 (1H, d, J=4 Hz), 6.59 (1H, d, J=4 Hz), 7.89 (1H, m), 8.56 (1H, d, J=2 Hz), 8.79 (1H, d, J=2 Hz). MS (ESI$^+$): m/z 500 502.

EXAMPLE 563 ethyl 4-{4-(5-bromo-3-pyridinyl)-7-ethyl-2-[(2-pyrazinylmethoxy)methyl]pyrrolo[1,2-b]pyridazin-3-yl}butanoate $^1$H NMR (CDCl$_3$) δ 1.19 (3H, t, J=7 Hz), 1.38 (3H, t, J=7 Hz), 1.70-1.82 (2H, m), 2.23 (2H, t, J=7 Hz), 2.56-2.76 (2H, m), 3.06 (2H, q, J=7 Hz), 4.04 (2H, q, J=7 Hz), 4.84 (2H, s), 4.95 (2H, m), 5.94 (1H, d, J=4 Hz), 6.63 (1H, d, J=4 Hz), 7.89 (1H, m), 8.50 (2H, m), 8.56 (1H, s), 8.74 (1H, s), 8.79 (1H, m). MS (ESI$^+$): m/z 538 540.

EXAMPLE 564 ethyl 3-{4-(5-bromo-3-pyridinyl)-7-ethyl-2-[(4-pyridinylmethoxy)methyl]pyrrolo[1,2-b]pyridazin-3-yl}propanoate $^1$H NMR (CDCl$_3$) δ 1.16 (3H, t, J=7 Hz), 1.38 (3H, t, J=7 Hz), 2.41 (2H, t, J=7 Hz), 2.85-3.07 (2H, m), 3.06 (2H, q, J=7 Hz), 4.02 (2H, q, J=7 Hz), 4.68 (2H, s), 4.81 (2H, s), 5.95 (1H, d, J=4 Hz), 6.65 (1H, d, J=4 Hz), 7.31 (2H, d, J=6 Hz), 7.87 (1H, m), 8.55 (1H, m), 8.56 (2H, d, J=6 Hz), 8.79 (1H, d, J=2 Hz). MS (ESI$^+$): m/z 523 525.

EXAMPLE 565 ethyl 4-(4-(5-bromo-3-pyridinyl)-7-ethyl-2-{[2-(tetrahydro-2H-pyran-2-yloxy)ethoxy]methyl}pyrrolo[1,2-b]pyridazin-3-yl)butanoate $^1$H NMR (CDCl$_3$) δ 1.20 (3H, t, J=7 Hz), 1.37 (3H, t, J=7 Hz), 1.46-1.93 (8H, m), 2.21 (2H, t, J=7 Hz), 2.55-2.76 (2H, m), 3.02 (2H, q, J=7 Hz), 3.46-3.56 (1H, m), 3.60-3.68 (1H, m), 3.74-3.82 (2H, m), 3.83-3.96 (2H, m), 4.03 (2H, q, J=7 Hz), 4.63 (1H, m), 4.77 (2H, s), 5.91 (1H, d, J=4 Hz), 6.60 (1H, d, J=4 Hz), 7.89 (1H, m), 8.56 (1H, d, J=2 Hz), 8.78 (1H, d, J=2 Hz).

EXAMPLE 566 ethyl 4-{4-(5-chloro-3-pyridinyl)-7-ethyl-2-[(4-pyridinylmethoxy)methyl]pyrrolo[1,2-b]pyridazin-3-yl}butanoate $^1$H NMR (300 MHz, CDCl$_3$) δ 1.19 (3H, t, J=7 Hz), 1.38 (3H, t, J=7 Hz), 1.70 (2H, t, J=7 Hz), 2.19 (2H, t, J=7 Hz), 2.55-2.67 (2H, m), 3.04 (2H, q, J=7 Hz), 4.03 (2H, q, J=7 Hz), 4.69 (2H, s), 4.83 (2H, s), 5.94 (1H, d, J=5 Hz), 6.63(1H, d, J=5 Hz), 7.29 (2H, d, J=6 Hz), 7.73 (1H, dd, J=2, 2 Hz), 8.52 (1H, d, J=2 Hz), 8.58 (2H, d, J=6 Hz), 8.69 (1H, d, J=2 Hz).

EXAMPLE 567 ethyl 3-[4-(3-chlorophenyl)-7-ethyl-2-(methoxymethyl)pyrrolo[1,2-b]pyridazin-3-yl]propanoate $^1$H NMR (CDCl$_3$) δ 1.20 (3H, t, J=8 Hz), 1.37 (3H, t, J=8 Hz), 2.33-2.44 (2H, m), 2.84-2.94 (2H, m), 3.03 (2H, q, J=8 Hz), 3.45 (3H, s), 4.05 (2H, q, J=8 Hz), 4.64 (2H, s), 5.94 (1H, d, J=5 Hz), 6.58 (1H, d, J=5 Hz), 7.21-7.29 (1H, overlappled with CDCl$_3$), 7.36 (1H, br s), 7.38-7.46 (2H, m).

EXAMPLE 568 ethyl 4-[4-(3-chlorophenyl)-7-ethyl-2-(methoxymethyl)pyrrolo[1,2-b]pyridazin-3-yl]butanoate $^1$H NMR (CDCl$_3$) δ 1.20 (3H, t, J=8 Hz), 1.37 (3H, t, J=8 Hz), 1.62-1.78 (2H, m), 2.14-2.28 (2H, m), 2.53-2.66 (2H, m), 3.04 (2H, q, J=8 Hz), 3.46 (3H, s), 4.04 (2H, q, J=8 Hz), 4.65 (2H, s), 5.93 (1H, d, J=5 Hz), 6.58 (1H, d, J=5 Hz), 7.21-7.29 (1H, overlappled with CDCl$_3$), 7.36 (1H, br s), 7.39-7.46 (2H, m).

The following compound(s) was (were) obtained in a similar manner to that of Example 272.

EXAMPLE 569 ethyl 5-{4-(5-bromo-3-pyridinyl)-2-[(1,1-dioxido-4-thiomorpholinyl)methyl]-7-ethylpyrrolo[1,2-b]pyridazin-3-yl}pentanoate $^1$H NMR (300 MHz, CDCl$_3$) δ 1.23 (3H, t, J=7 Hz), 1.36 (3H, t, J=7 Hz), 1.39-1.53 (4H, m), 2.19 (2H, t, J=7 Hz), 2.50-2.61 (2H, m), 3.00 (2H, q, J=7 Hz), 3.10 (4H, t, J=6 Hz), 3.21 (4H, t, J=6 Hz), 3.85 (2H, s), 4.10 (2H, q, J=7 Hz), 5.92 (1H, d, J=4 Hz), 6.61 (1H, d, J=4 Hz), 7.88 (1H, dd, J=2, 2 Hz), 8.55 (1H, d, J=2 Hz), 8.80 (1H, d, J=2 Hz).

EXAMPLE 570 ethyl 5-[4-(5-bromo-3-pyridinyl)-7-ethyl-2-(4-thiomorpholinylmethyl)pyrrolo[1,2-b]pyridazin-3-yl]pentanoate $^1$H NMR (300 MHz, CDCl$_3$) δ 1.23 (3H, t, J=7 Hz), 1.37 (3H, t, J=7 Hz), 1.41-1.54 (4H, m), 2.19 (2H, t, J=7 Hz), 2.50-2.61 (2H, m), 2.66 (4H, t, J=4 Hz), 2.85 (4H, t, J=4 Hz), 3.01 (2H, q, J=7 Hz), 3.67 (2H, s), 4.10 (2H, q, J=7H), 5.88 (H, d, J=5 Hz), 6.57 (1H, d, J=5 Hz), 7.88 (1H, dd, J=2, 2 Hz), 8.55 (1H, d, J=2 Hz), 8.79 (1H, d, J=2 Hz).

EXAMPLE 571 ethyl 5-(4-(5-bromo-3-pyridinyl)-7-ethyl-2-{[4-(2-hydroxyethyl)-1-piperazinyl]methyl}pyrrolo[1,2-b]pyridazin-3-yl)pentanoate $^1$H NMR (300 MHz, CDCl$_3$) δ 1.23 (3H, t, J=7 Hz), 1.36 (3H, t, J=7 Hz), 1.40-1.55 (4H, m), 2.18 (2H, t, J=7 Hz), 2.48-2.66 (12H, m), 3.02 (2H, q, J=7 Hz), 3.61 (2H, t, J=5 Hz), 3.66 (2H, s), 4.10 (2H, q, J=7 Hz), 5.88 (1H, d, J=4 Hz), 6.57 (1H, d, J=4 Hz), 7.88 (1H, dd, J=2, 2 Hz), 8.55 (1H, d, J=2 Hz), 8.78 (1H, d, J=2 Hz).

EXAMPLE 572 ethyl 4-[4-(5-chloro-3-pyridinyl)-7-ethyl-2-(4-thiomorpholinylmethyl)pyrrolo[1,2-b]pyridazin-3-yl]butanoate $^1$H NMR (300 MHz, CDCl$_3$) δ 1.21 (3H, t, J=7 Hz), 1.37 (3H, t, J=7 Hz), 1.70 (2H, t, J=7, 7 Hz), 2.19 (2H, t, J=7 Hz), 2.50-2.67 (6H, m), 2.86 (4H, t, J=5 Hz), 3.02 (2H, q, J=7 Hz), 3.70 (2H, s), 4.05 (2H, q, J=5 Hz), 5.89 (1H, d, J=4 Hz), 6.58 (1H, d, J=4 Hz), 7.74 (1H, dd, J=2, 2 Hz), 8.52 (1H, d, J=2 Hz), 8.68 (1H, d, J=2 Hz).

EXAMPLE 573 ethyl 4-[4-(5-chloro-3-pyridinyl)-7-ethyl-2-(4-morpholinylmethyl)pyrrolo[1,2-b]pyridazin-3-yl]butanoate $^1$H NMR (300 MHz, CDCl$_3$) δ 1.21 (3H, t, J=7 Hz), 1.37 (3H, t, J=7 Hz), 1.72 (2H, tt, J=7, 7 Hz), 2.20 (2H, t, J=7 Hz), 2.56-2.69 (6H, m), 3.02 (2H, q, J=7 Hz), 3.68-3.71 (6H, m), 4.05 (2H, q, J=7 Hz) 5.89 (1H, d, J=4 Hz), 6.58 (1H, d, J=4 Hz), 7.74 (1H, dd, J=2, 2 Hz), 8.53 (1H, d, J=2 Hz), 8.69 (1H, d, J=2 Hz).

EXAMPLE 574 ethyl 3-[4-(5-bromo-3-pyridinyl)-7-ethyl-2-(4-morpholinylmethyl)pyrrolo[1,2-b]pyridazin-3-yl]propanoate $^1$H NMR (300 MHz, CDCl$_3$) δ 1.21 (3H, t, J=7 Hz), 1.34 (3H, t, J=7 Hz), 2.47-2.54 (2H, m), 2.59 (4H, t, J=5 Hz), 2.81-2.95 (2H, m), 3.02 (2H, q, J=7 Hz), 3.67 (4H, t, J=5 Hz), 3.69 (2H, s), 4.07 (2H, q, J=7 Hz), 5.90 (1H, d, J=4 Hz), 6.59 (1H, d, J=4 Hz), 7.88 (1H, dd, J=2, 2 Hz), 8.55 (1H, d, J=2 Hz), 8.79 (1H, d, J=2 Hz).

EXAMPLE 575 ethyl 4-[4-(5-bromo-3-pyridinyl)-7-ethyl-2-(4-morpholinylmethyl)pyrrolo[1,2-b]pyridazin-3-yl]butanoate $^1$H NMR (300 MHz, CDCl$_3$) δ 1.21 (3H, t, J=7 Hz), 1.36 (3H, t, J=7 Hz), 1.73 (2H, tt, J=7, 7 Hz), 2.20 (2H, t, J=7 Hz), 2.55-2.69 (6H, m), 3.02 (2H, q, J=7 Hz), 3.69 (4H, t, J=5 Hz), 4.05 (2H, q, J=7 Hz), 5.89 (1H, d, J=4 Hz), 6.58 (1H, d, J=4 Hz), 7.89 (1H, dd, J=2, 2 Hz), 8.57 (1H, d, J=2 Hz), 8.79 (1H, d, J=2 Hz).

EXAMPLE 576 ethyl 4-{4-(5-chloro-3-pyridinyl)-2-[(cyclopropylamino)methyl]-7-ethylpyrrolo[1,2-b]pyridazin-3-yl}butanoate $^1$H NMR (300 MHz, CDCl$_3$) δ 0.46-0.52 (4H, m), 1.21 (3H, t, J=7 Hz), 1.38 (3H, t, J=7 Hz), 1.71 (2H, tt, J=8, 8 Hz), 2.21 (2H, t, J=8 Hz), 2.32-2.39 (1H, m), 2.45-2.54 (2H, m), 3.04 (2H, q, J=7 Hz), 4.06 (2H, q, J=7 Hz), 4.07 (2H, s), 5.89 (1H, d, J=4 Hz), 6.57 (1H, d, J=4 Hz), 7.72 (1H, dd, J=2, 2 Hz), 8.50 (1H, d, J=2 Hz), 8.68 (1H, d, J=2 Hz).

EXAMPLE 577 ethyl 5-(4-(5-bromo-3-pyridinyl)-7-ethyl-2-{[(2-phenoxyethyl)amino]methyl}pyrrolo[1,2-b]pyridazin-3-yl)pentanoate $^1$H NMR (300 MHz, CDCl$_3$) δ 1.23 (3H, t, J=7 Hz), 1.37 (3H, t, J=7 Hz), 1.40-1.56 (4H, m), 2.18 (2H, t, J=8 Hz), 2.41-2.52 (2H, m), 3.04 (2H, q, J=7 Hz), 3.19 (2H, t, J=5 Hz), 4.07 (2H, s), 4.09 (2H, q, J=7 Hz), 4.17 (2H, t, J=5 Hz), 5.90 (1H, d, J=4 Hz), 6.57 (1H, d, J=4 Hz), 6.92-6.98 (3H, m), 7.29-7.32 (2H, m), 7.86 (1H, dd, J=2, 2 Hz), 8.54 (1H, d, J=2 Hz), 8.78 (1H, d, J=2 Hz).

EXAMPLE 578 ethyl 5-(4-(5-bromo-3-pyridinyl)-7-ethyl-2-{[(2-hydroxyethyl)(methyl)amino]methyl}pyrrolo[1,2-b]pyridazin-3-yl)pentanoate $^1$H NMR (300 MHz, CDCl$_3$) δ 1.23 (3H, t, J=7 Hz), 1.37 (3H, t, J=7 Hz), 1.42-1.63 (4H, m), 2.20 (2H, t, J=8 Hz), 2.38 (3H, s), 2.53-2.64 (2H, m), 2.75 (2H, t, J=5 Hz), 3.02 (2H, q, J=7 Hz), 3.66 (2H, t, J=5 Hz), 3.77 (2H, s), 4.10 (2H, q, J=7 Hz), 5.90 (1H, d, J=4 Hz), 6.59 (1H, d, J=4 Hz), 7.88 (1H, dd, J=2, 2 Hz), 8.55 (1H, d, J=2 Hz), 8.78 (1H, d, J=2 Hz).

EXAMPLE 579 ethyl 5-[4-(5-bromo-3-pyridinyl)-7-ethyl-2-(1-piperidinylmethyl)pyrrolo[1,2-b]pyridazin-3-yl]pentanoate 15 $^1$H NMR (300 MHz, CDCl$_3$) δ 1.23 (3H, t, J=7 Hz), 1.36 (3H, t, J=7 Hz), 1.42-1.58 (6H, m), 1.69 (4H, tt, J=5, 5 Hz), 2.18 (2H, t, J=8 Hz), 2.53-2.64 (2H, m), 3.02 (2H, q, J=7 Hz), 3.19 (4H, t, J=5 Hz), 3.60 (2H, s), 4.07 (2H, q, J=7 Hz), 5.86 (1H, d, J=5 Hz), 6.54 (1H, d, J=5 Hz), 7.89 (1H, dd, J=2, 2 Hz), 8.56 (1H, d, J=2 Hz), 8.75 (1H, d, J=2 Hz).

EXAMPLE 580 ethyl 3-[4-(5-bromo-3-pyridinyl)-7-ethyl-2-(4-thiomorpholinylmethyl)pyrrolo[1,2-b]pyridazin-3-yl]propanoate $^1$H NMR (300 MHz, CDCl$_3$) δ 1.23 (3H, t, J=7 Hz), 1.37 (3H, t, J=7 Hz), 2.46 (2H, t, J=8 Hz), 2.64 (4H, t, J=5 Hz), 2.86 (6H, m), 3.02 (2H, q, J=7 Hz), 3.69 (2H, s), 4.06 (2H, q, J=7 Hz), 5.91 (1H, d, J=5 Hz), 6.60 (1H, d, J=5 Hz), 7.88 (1H, dd, J=2, 2 Hz), 856(1H, d, J=2 Hz), 8.80(1H, d, J=2 Hz).

EXAMPLE 581 ethyl 3-(4-(5-bromo-3-pyridinyl)-7-ethyl-2-{[4-(2-hydroxyethyl)-1-piperazinyl]methyl}pyrrolo[1,2-b]pyridazin-3-yl)propanoate $^1$H NMR (300 MHz, CDCl$_3$) δ 1.21 (3H, t, J=7 Hz), 1.37 (3H, t, J=7 Hz), 2.46-2.63 (12H, m), 2.80-2.94 (2H, m), 3.03 (2H, q, J=7 Hz), 3.61 (2H, t, J=5 Hz), 3.70 (2H, s), 4.08 (2H, q, J=7 Hz), 5.90 (1H, d, J=5 Hz), 6.59 (1H, d, J=5 Hz), 7.88 (1H, dd, J=2, 2 Hz), 8.56 (1H, d, J=2 Hz), 8.79 (1H, d, J=2 Hz).

EXAMPLE 582 ethyl 5-[4-(5-bromo-3-pyridinyl)-7-ethyl-2-(1-pyrrolidinylmethyl)pyrrolo[1,2-b]pyridazin-3-yl]pentanoate $^1$H NMR (300 MHz, CDCl$_3$) δ 1.23 (3H, t, J=7 Hz), 1.37 (3H, t, J=7 Hz), 1.40-1.55 (4H, m), 1.75-1.80 (4H, m), 2.19 (2H, t, J=7 Hz), 2.54-2.66 (6H, m), 3.02 (2H, q, J=7 Hz), 3.76-3.81 (2H, m), 4.10 (2H, q, J=7 Hz), 5.87 (1H, d, J=5 Hz), 6.55 (1H, d, J=5 Hz), 7.89 (1H, dd, J=2, 2 Hz), 8.56 (1H, d, J=2 Hz), 8.77 (1H, d, J=2 Hz).

EXAMPLE 583 ethyl 5-{4-(5-bromo-3-pyridinyl)-7-ethyl-2-[(4-phenyl-1-piperazinyl)methyl]pyrrolo[1,2-b]pyridazin-3-yl}pentanoate $^1$H NMR (300 MHz, CDCl$_3$) δ 1.21 (3H, t, J=7 Hz), 1.38 (3H, t, J=7 Hz), 1.41-1.54 (4H, m), 2.17 (2H, t, J=7 Hz), 2.53-2.68 (2H, m), 2.75 (2H, t, J=5 Hz), 3.03 (2H, q, J=7 Hz), 3.19 (4H, t, J=5 Hz), 3.73 (2H, s), 4.07 (2H, q, J=7 Hz), 5.89 (1H, d, J=5 Hz), 6.58 (H, d, J=5 Hz), 6.85 (1H, dd, J=8, 8 Hz), 6.93 (2H, J=2.08 Hz), 7.25 (2H, J=8 Hz), 7.89 (1H, dd, J=2, 2 Hz), 8.56 (1H, d, J=2 Hz), 8.78 (1H, d, J=2 Hz).

EXAMPLE 584 ethyl 5-(4-(5-bromo-3-pyridinyl)-7-ethyl-2-{[(2-methoxyethyl)amino]methyl}pyrrolo[1,2-b]pyridazin-3-yl)pentanoate $^1$H NMR (300 MHz, CDCl$_3$) δ 1.23 (3H, t, J=7 Hz), 1.37 (3H, t, J=7 Hz), 1.41-1.60 (4H, m), 2.19 (2H, t, J=7 Hz), 2.43-2.52 (2H, m), 2.96 (2H, t, J=5 Hz), 3.03 (2H, q, J=7 Hz), 3.40 (3H, s), 3.58 (2H, t, J=5 Hz), 3.99 (2H, s), 4.10 (2H, q, J=7 Hz), 5.89 (1H, d, J=5 Hz), 6.56 (1H, d, J=5 Hz), 7.87 (1H, dd, J=2, 2 Hz), 8.54 (1H, d, J=2 Hz), 8.78 (1H, d, J=2 Hz).

The following compound(s) was (were) obtained in a similar manner to that of Example 385.

EXAMPLE 585

3-[4-(5-bromo-3-pyridinyl)-7-ethyl-2-(methoxymethyl)pyrrolo[1,2-b]pyridazin-3-yl]-N-[2-hydroxy-1,1-bis(hydroxymethyl)ethyl]propanamide $^1$H-NMR (CDCl$_3$) δ 1.37 (3H, 1, J=7 Hz), 2.25-3.10 (6H, m), 3.49 (3H, s), 3.58 (4H, m), 3.81 (2H, m), 4.55 (2H, s), 5.97 (1H, d, J=5 Hz), 6.54 (1H, s), 6.64 (1H, d, J=5 Hz), 7.93 (1H, m), 8.52 (1H, m), 8.78 (1H, m).

EXAMPLE 586 tert-butyl [2-({3-[4-(5-bromo-3-pyridinyl)-7-ethyl-2-(methoxymethyl)pyrrolo[1,2-b]pyridazin-3-yl]propanoyl}amino)ethyl]carbamate $^1$H-NMR (CDCl$_3$) δ 1.37 (3H, t, J=7 Hz), 1.43 (9H, s), 2.26 (2H, m), 2.88 (2H, m), 3.04 (2H, q, J=7 Hz), 3.20 (2H, m), 3.28 (2H, m), 3.48 (3H, s), 4.67 (2H, s), 4.85 (1H, s, br), 5.93 (1H, d, J=5 Hz), 6.20 (1H, s, br), 6.63 (1H, d, J=5 Hz), 7.88 (1H, m), 8.53 (1H, m), 8.79 (1H, m).

The following compound(s) was (were) obtained in a similar manner to that of Example 330.

EXAMPLE 587 ethyl 5-[2-{[2-(benzylamino)-2-oxoethoxy]methyl}-7-ethyl-4-(5-methyl-3-pyridinyl)pyrrolo[1,2-b]pyridazin-3-yl]pentanoate $^1$H NMR (CDCl$_3$) δ 1.22 (3H, t, J=7 Hz), 1.34 (3H, t, J=7 Hz), 1.33-1.55 (4H, m), 2.12 (2H, t, J=7 Hz), 2.43 (3H, s), 2.40-2.56 (2H, m), 2.96 (2H, q, J=7 Hz), 4.07 (2H, q, J=7 Hz), 4.19 (2H, s), 4.52 (2H, d, J=7 Hz), 4.76 (2H, s), 5.93 (1H, d, J=4 Hz), 6.59 (1H, d, J=4 Hz), 7.06 (1H, br), 7.23-7.38 (5H, m), 7.49 (1H, s), 8.40 (1H, s), 8.54 (1H, s). MS (ESI$^+$): m/z 543.

The following compound(s) was (were) obtained in a similar manner to that of Example 333.

EXAMPLE 588 ethyl 4-[4-(5-bromo-3-pyridinyl)-7-ethyl-2-(4H-1,2,4-triazol-4-ylmethyl)pyrrolo[1,2-b]pyridazin-3-yl]butanoate $^1$H-NMR (CDCl$_3$) δ 1.22-1.34 (6H, m), 1.67 (2H, m), 2.23 (2H, m), 2.51 (2H, m), 2.98 (2H, q, J=7 Hz), 4.21 (2H, q, J=7 Hz), 5.67 (2H, m), 5.97 (1H, d, J=5 Hz), 6.63 (1H, d, J=5 Hz), 7.85 (1H, m), 7.96 (1H, s), 8.34 (1H, s), 8.53 (1H, m), 8.79 (1H, m).

The following compound(s) was (were) obtained in a similar manner to that of Example 336.

EXAMPLE 589 ethyl 5-(7-ethyl-4-(5-methyl-3-pyridinyl)-2-{[(phenylsulfonyl)amino]methyl}pyrrolo[1,2-b]pyridazin-3-yl)pentanoate $^1$H NMR (CDCl$_3$) δ 1.23 (3H, t, J=7 Hz), 1.37 (3H, t, J=7 Hz), 1.26-1.57 (4H, m), 2.16 (2H, t, J=7 Hz), 2.33-2.46 (2H, m), 2.42 (3H, s), 2.98 (2H, q, J=7 Hz), 4.11 (2H, q, J=7 Hz), 4.38 (2H, m), 5.91 (1H, br), 5.92 (1H, d, J=4 Hz), 6.58 (1H, d, J=4 Hz), 7.43-7.55 (4H, m), 7.93 (2H, d, J=8 Hz), 8.33 (1H, d, J=2 Hz), 8.54 (1H, d, J=2 Hz). MS (ESI$^+$): m/z 535.

The following compound(s) was (were) obtained in a similar manner to that of Example 340.

EXAMPLE 590 ethyl 4-{4-(5-bromo-3-pyridinyl)-2-[(cyclopropylamino)methyl]-7-ethylpyrrolo[1,2-b]pyridazin-3-yl}butanoate $^1$H-NMR (CDCl$_3$) δ 0.48 (4H, m), 1.19 (3H, t, J=7 Hz), 1.37 (3H, t, J=7 Hz), 1.70 (2H, t, J=7 Hz), 2.22 (2H, m), 2.50 (2H, m), 2.95-3.07 (3H, m), 3.96-4.12 (4H, m), 5.90 (1H, d, J=5 Hz), 6.57 (1H, d, J=5 Hz), 7.88 (1H, m), 8.54 (1H, m), 8.77(1H, m).

EXAMPLE 591

To a suspension of LiAlH4 (113 mg) in THF (10 mL) was added ethyl[4-(5-bromo-3-pyridinyl)-7-ethyl-2-methylpyrrolo[1,2-b]pyridazin-3-yl]acetate (600 mg) under ice-water cooling and the mixture was stirred at 0° C. for 2 hours. To the mixture was added potassium sodium tartrate solution and the insolubles were filtered off. After evaporation of solvent, the residue was partitioned between AcOEt and water. The organic layer was separated, washed with brine, dried over MgSO$_4$, and evaporated in vacuo. The residue was purified by silica gel column chromatography eluting with a mixture of hexane and AcOEt (5:1-1:1) to give 2-[4-(5-bromo-3-pyridinyl)-7-ethyl-2-methylpyrrolo[1,2-b]pyridazin-3-yl]ethanol as yellow oil (246 mg).

2-[4-(5-bromo-3-pyridinyl)-7-ethyl-2-methylpyrrolo[1,2-b]pyridazin-3-yl]ethanol $^1$H NMR (CDCl$_3$) δ 1.37 (3H, t, J=7 Hz), 2.60 (3H, s), 2.72-2.84 (2H, m), 3.03 (2H, q, J=7 Hz), 3.65 (2H, t, J=7 Hz), 5.89 (1H, d, J=4 Hz), 6.55 (1H, d, J=4 Hz), 7.91 (1H, t, J=2 Hz), 8.56 (1H, d, J=2 Hz), 8.76 (1H, d, J=2 Hz). MS (ESI$^+$): m/z 360 362.

EXAMPLE 592

A mixture of 3-[4-(5-bromo-3-pyridinyl)-7-ethyl-2-methylpyrrolo[1,2-b]pyridazin-3-yl]propanoic acid (1.07 g), diphenylphosphoryl azide (1.14 g) and Et3N (0.576 mL) in BuOH (30 mL) was heated under reflux for 2 hours. After evaporation of solvent, the residue was partitioned between AcOEt and water. The organic layer was separated, washed with aq NaHCO$_3$ solution and brine, dried over MgSO$_4$, and evaporated in vacuo. The residue was purified by silica gel column chromatography eluting with a mixture of hexane and AcOEt (20:1-3:1) to give tert-butyl {2-[4-(5-bromo-3-pyridinyl)-7-ethyl-2-methylpyrrolo[1,2-b]pyridazin-3-yl]ethyl}carbamate as yellow oil (450 mg).

tert-butyl {2-[4-(5-bromo-3-pyridinyl)-7-ethyl-2-methylpyrrolo[1,2-b]pyridazin-3-yl]ethyl}carbamate $^1$H NMR (CDCl$_3$) δ 1.37 (9H, s), 1.37 (3H, t, J=7 Hz), 2.64 (3H, s), 2.62-2.75 (2H, m), 3.03 (2H, q, J=7 Hz), 3.10-3.27 (2H, m), 4.40-4.52 (1H, m), 5.89 (1H, d, J=4 Hz), 6.55 (1H, d, J=4 Hz), 7.89 (1H, m), 8.53 (1H, m), 8.77 (1H, m).

EXAMPLE 593

To a suspension of 60% NaH (74 mg) in DMF (3 mL) was added ethyl 3-[4-(5-bromo-3-pyridinyl)-7-ethyl-2-(hydroxymethyl)pyrrolo[1,2-b]pyridazin-3-yl]propanoate (200 mg) under ice-water cooling, and the mixture was stirred at 0° C. for 0.5 hour. To this was added 3-(bromomethyl)pyridine hydrobromide (234 mg) under ice-water cooling, and the mixture was stirred at ambient temperature for 2 hours. The mixture was partitioned between AcOEt and water. The aqueous layer was separated, acidified to pH 3-4 with HCl and extracted with AcOEt. The organic layer was washed with water and brine, dried over MgSO$_4$, and evaporated in vacuo. The residue was purified by silica gel column chromatography eluting with a mixture of CHCl$_3$ and MeOH (100:1-20:1) to give 3-{4-(5-bromo-3-pyridinyl)-7-ethyl-2-[(3-pyridinylmethoxy)methyl]pyrrolo[1,2-b]pyridazin-3-yl}propanoic acid as a yellow powder (110 mg).

3-{4-(5-bromo-3-pyridinyl)-7-ethyl-2-[(3-pyridinylmethoxy)methyl]pyrrolo[1,2-b]pyridazin-3-yl}propanoic acid $^1$H NMR (CDCl$_3$) δ 1.39 (3H, t, J=7 Hz), 2.41 (2H, t, J=7 Hz), 2.80-2.98 (2H, m), 3.04 (2H, q, J=7 Hz), 4.70 (2H, s), 4.83 (2H, s), 5.93 (1H, d, J=4 Hz), 6.63 (1H, d, J=4 Hz), 7.32-7.38 (1H, m), 7.81 (1H, d, J=8 Hz), 7.87 (1H, m), 8.52 (1H, d, J=8 Hz), 8.53 (1H, d, J=2 Hz), 8.63 (1H, s), 8.77 (1H, d, J=2 Hz).

The following compound(s) was (were) obtained in a similar manner to that of Example 593.

EXAMPLE 594

4-{4-(5-bromo-3-pyridinyl)-7-ethyl-2-[(2-methoxyethoxy)methyl]pyrrolo[1,2-b]pyridazin-3-yl}butanoic acid $^1$H NMR (CDCl$_3$) δ 1.37 (3H, t, J=7 Hz), 1.72-1.83 (2H, m), 2.28 (2H, t, J=7 Hz), 2.60-2.77 (2H, m), 3.03 (2H, q, J=7 Hz), 3.39 (3H, s), 3.62 (2H, m), 3.77 (2H, m), 4.75 (2H, s), 5.93 (1H, d, J=4 Hz), 6.62 (1H, d, J=4 Hz), 7.92 (1H, m), 8.56 (1H, d, J=2 Hz), 8.77 (1H, d, J=2 Hz). MS (ESI$^-$): m/z 474 476, MS (ESI$^+$): m/z 476 478.

EXAMPLE 595

3-{4-(5-bromo-3-pyridinyl)-7-ethyl-2-[(2-pyridinylmethoxy)methyl]pyrrolo[1,2-b]pyridazin-3-yl}propanoic acid $^1$H NMR (CDCl$_3$) δ 1.38 (3H, t, J=7 Hz), 2.48-2.62 (2H, m), 2.98-3.10 (2H, m), 3.05 (2H, q, J=7 Hz), 4.82 (2H, s), 4.88 (2H, s), 5.94 (1H, d, J=4 Hz), 6.63 (1H, d, J=4 Hz), 7.27 (1H, m), 7.48 (1H, d, J=8 Hz), 7.77 (1H, t, J=8 Hz), 7.90 (1H, m), 8.56 (2H, m), 8.80 (1H, m). MS (ESI$^+$): m/z 495 497.

EXAMPLE 596

3-{4-(5-bromo-3-pyridinyl)-2-[(cyclopropylmethoxy)methyl]-7-ethylpyrrolo[1,2-b]pyridazin-3-yl}propanoic acid $^1$H NMR (CDCl$_3$) δ 0.25 (2H, m), 0.58 (2H, m), 1.12 (1H, m), 1.37 (3H, t, J=7 Hz), 2.40-2.63 (2H, m), 2.85-3.05 (2H, m), 3.02 (2H, q, J=7 Hz), 3.42 (2H, d, J=7 Hz), 4.73 (2H, s), 5.93 (1H, d, J=4 Hz), 6.63 (1H, d, J=4 Hz), 7.89 (1H, m), 8.55 (1H, d, J=2 Hz), 8.77 (1H, d, J=2 Hz). MS (ESI$^-$): m/z 456 458, MS (ESI$^+$): m/z 458 460.

EXAMPLE 597

3-{4-(5-bromo-3-pyridinyl)-7-ethyl-2-[(2-pyrazinylmethoxy)methyl]pyrrolo[1,2-b]pyridazin-3-yl}propanoic acid $^1$H NMR (CDCl$_3$) δ 1.38 (3H, t, J=7 Hz), 2.48 (2H, t, J=7 Hz), 2.85-3.09 (2H, m), 3.06 (2H, q, J=7 Hz), 4.84 (2H, s), 4.92 (2H, s), 5.96 (1H, d, J=4 Hz), 6.65 (1H, d, J=4 Hz), 7.90 (1H, m), 8.48-8.62 (3H, m), 8.77 (2H, m).

EXAMPLE 598

A mixture of ethyl 4-(4-(5-bromo-3-pyridinyl)-7-ethyl-2-{[2-(tetrahydro-2H-pyran-2-yloxy)ethoxy]methyl}pyrrolo[1,2-b]pyridazin-3-yl)butanoate (89 mg) and pyridinium p-toluenesulfonate (0.8 mg) in MeOH (5 mL) was heated under reflux for 2 hours. After evaporation of solvent, the residue was purified by silica gel column chromatography eluting with a mixture of hexane and AcOEt (10:1-1:1) to give ethyl 4-{4-(5-bromo-3-pyridinyl)-7-ethyl-2-[(2-hydroxyethoxy)methyl]pyrrolo[1,2-b]pyridazin-3-yl}butanoate as yellow oil (69 mg).

ethyl 4-{4-(5-bromo-3-pyridinyl)-7-ethyl-2-[(2-hydroxyethoxy)methyl]pyrrolo[1,2-b]pyridazin-3-yl}butanoate $^1$H NMR (CDCl$_3$) δ 1.22 (3H, t, J=7 Hz), 1.37 (3H, t, J=7 Hz), 1.69-1.84 (2H, m), 2.22 (2H, t, J=7 Hz), 2.53-2.72 (2H, m), 3.03 (2H, q, J=7 Hz), 3.76 (2H, m), 3.83 (2H, m), 4.07 (2H, q, J=7 Hz), 4.79 (2H, s), 5.93 (1H, d, J=4 Hz), 6.61 (1H, d, J=4 Hz), 7.89 (1H, m), 8.56 (1H, d, J=2 Hz), 8.79 (1H, d, J=2 Hz). MS (ESI$^+$): m/z 490 492.

EXAMPLE 599

To a suspension of 60% NaH (695 mg) in DMF (3 mL) was added ethyl 5-[4-(5-bromo-3-pyridinyl)-7-ethyl-2-(hydroxymethyl)pyrrolo[1,2-b]pyridazin-3-yl]pentanoate (200 mg) under ice-water cooling and the mixture was stirred at 0° C. for 0.5 hour. To this was added 4-morpholinecarbonyl chloride (659 mg) and the mixture was stirred at ambient temperature for 15 hours. The mixture was partitioned between AcOEt and water. The organic layer was separated, washed with water and brine, dried over MgSO$_4$, and evaporated in vacuo. The residue was purified by silica gel column chromatography eluting with a mixture of hexane and AcOEt (20:1-1:1) to give [4-(5-bromo-3-pyridinyl)-3-(5-ethoxy-5-oxopentyl)-7-ethylpyrrolo[1,2-b]pyridazin-2-yl]methyl 4-morpholinecarboxylate as yellow oil (75 mg).

[4-(5-bromo-3-pyridinyl)-3-(5-ethoxy-5-oxopentyl)-7-ethylpyrrolo[1,2-b]pyridazin-2-yl]methyl 4-morpholinecarboxylate $^1$H NMR (CDCl$_3$) δ 1.23 (3H, t, J=7 Hz), 1.37 (3H, t, J=7 Hz), 1.40-1.60 (4H, m), 2.18 (2H, t, J=7 Hz), 2.42-2.54 (2H, m), 3.03 (2H, q, J=7 Hz), 3.53-3.57 (4H, m), 3.63-3.78 (4H, m), 4.09 (2H, q, J=7 Hz), 5.33 (2H, s), 5.93 (1H, d, J=4 Hz), 6.62 (1H, d, J=4 Hz), 7.87 (1H, m), 8.54 (1H, d, J=2 Hz), 8.78 (1H, d, J=2 Hz). MS (ESI$^+$): m/z 573 575.

The following compound(s) was (were) obtained in a similar manner to that of Example 599.

EXAMPLE 600 ethyl 5-[4-(5-bromo-3-pyridinyl)-2-({[(dimethylamino)carbonyl]oxy}methyl)-7-ethylpyrrolo[1,2-b]pyridazin-3-yl]pentanoate $^1$H NMR (CDCl$_3$) δ 1.23 (3H, t, J=7 Hz), 1.36 (3H, t, J=7 Hz), 1.35-1.60 (4H, m), 2.17 (2H, t, J=7 Hz), 2.44-2.57 (2H, m), 2.98 (6H, s), 3.03 (2H, q, J=7 Hz), 4.09 (2H, q, J=7 Hz), 5.30 (2H, s), 5.93 (1H, d, J=4 Hz), 6.61 (1H, d, J=4 Hz), 7.87 (1H, m), 8.54 (1H, d, J=2 Hz), 8.78 (1H, d, J=2 Hz). MS (ESI$^+$): m/z 531 533.

EXAMPLE 601

[4-(5-bromo-3-pyridinyl)-3-(5-ethoxy-5-oxopentyl)-7-ethylpyrrolo[1,2-b]pyridazin-2-yl]methyl 1-pyrrolidinecarboxylate $^1$H NMR (CDCl$_3$) δ 1.23 (3H, t, J=7 Hz), 1.36 (3H, t, J=7 Hz), 1.38-1.60 (4H, m), 1.86-1.98 (4H, m), 2.17 (2H, t, J=7 Hz), 2.44-2.57 (2H, m), 3.03 (2H, q, J=7 Hz), 3.36-3.52 (4H, m), 4.11 (2H, q, J=7 Hz), 5.32 (2H, s), 5.92 (1H, d, J=4 Hz), 6.61 (1H, d, J=4 Hz), 7.87 (1H, m), 8.55 (1H, d, J=2 Hz), 8.78 (1H, d, J=2 Hz).

EXAMPLE 602 ethyl 5-{4-(5-bromo-3-pyridinyl)-7-ethyl-2-[({[methyl(phenyl)amino]carbonyl}oxy)methyl]pyrrolo[1,2-b]pyridazin-3-yl}pentanoate $^1$H NMR (CDCl$_3$) δ 1.20 (3H, t, J=7 Hz), 1.37 (3H, t, J=7 Hz), 1.32-1.57 (4H, m), 2.13 (2H, t, J=7 Hz), 2.33-2.48 (2H, m), 3.03 (2H, q, J=7 Hz), 3.38 (3H, s), 4.08 (2H, q, J=7 Hz), 5.34 (2H, s), 5.92 (1H, d, J=4 Hz), 6.60 (1H, d, J=4 Hz), 7.20-7.38 (5H, m), 7.83 (1H, s), 8.49 (1H, s), 8.77 (1H, s).

EXAMPLE 603

[4-(5-bromo-3-pyridinyl)-3-(4-ethoxy-4-oxobutyl)-7-ethylpyrrolo[1,2-b]pyridazin-2-yl]methyl 4-morpholinecarboxylate $^1$H NMR (CDCl$_3$) δ 1.20 (3H, t, J=7 Hz), 1.37 (3H, t, J=7 Hz), 1.63-1.80 (2H, m), 2.22 (2H, t, J=7 Hz), 2.44-2.65 (2H, m), 3.03 (2H, q, J=7 Hz), 3.54 (4H, m), 3.68 (4H, m), 4.05 (2H, q, J=7 Hz), δ 37 (2H, s), 5.94 (1H, d, J=4 Hz), 6.62 (1H, d, J=4 Hz), 7.87 (1H, m), 8.55 (1H, d, J=2 Hz), 8.78 (1H, d, J=2 Hz). MS (ESI$^+$): m/z 559 561.

EXAMPLE 604 ethyl 4-[4-(5-bromo-3-pyridinyl)-2-({[(dimethylamino)carbonyl]oxy}methyl)-7-ethylpyrrolo[1,2-b]pyridazin-3-yl]butanoate $^1$H NMR (CDCl$_3$) δ 1.20 (3H, t, J=7 Hz), 1.36 (3H, t, J=7 Hz), 1.66-1.79 (2H, m), 2.20 (2H, t, J=7 Hz), 2.46-2.62 (2H, m), 2.97 (6H, s), 3.03 (2H, q, J=7 Hz), 4.04 (2H, q, J=7 Hz), 5.34 (2H, s), 5.93 (1H, d, J=4 Hz), 6.63 (1H, d, J=4 Hz), 7.89 (1H, m), 8.56 (1H, d, J=2 Hz), 8.78 (1H, d, J=2 Hz). MS (ESI$^+$): m/z 517 519.

EXAMPLE 605 ethyl 3-[4-(5-bromo-3-pyridinyl)-2-({[(dimethylamino)carbonyl]oxy}methyl)-7-ethylpyrrolo[1,2-b]pyridazin-3-yl]propanoate $^1$H NMR (CDCl$_3$) δ 1.20 (3H, t, J=7 Hz), 1.36 (3H, t, J=7 Hz), 2.37 (2H, t, J=7 Hz), 2.82-2.93 (2H, m), 2.97 (6H, s), 3.03 (2H, q, J=7 Hz), 4.05 (2H, q, J=7 Hz), 5.32 (2H, s), 5.96 (1H, d, J=4 Hz), 6.63 (1H, d, J=4 Hz), 7.88 (1H, m), 8.54 (1H, d, J=2 Hz), 8.78 (1H, d, J=2 Hz).

EXAMPLE 606

To a solution of sodium hydride (93.1 mg) in DMF (4 mL) was added ethyl 3-[4-(3-chlorophenyl)-7-ethyl-2-(hydroxymethyl)pyrrolo[1,2-b]pyridazin-3-yl]propanoate (150 mg) under ice water cooling and the mixture was stirred at this temperature for 1 hour. To this was added 4-(bromomethyl)pyridine hydrobromide (196 mg) and the mixture was stirred for 1 hour at ambient temperature. The reaction was quenched by adding water. The mixture was extracted with CHCl$_3$. The organic layer was washed with water and brine, dried over MgSO$_4$ and evaporated in vacuo. The residue was purified by silica gel column chromatography eluting with a mixture of CHCl$_3$-MeOH=30-1 to give 3-{4-(3-chlorophenyl)-7-ethyl-2-[(4-pyridinylmethoxy)methyl]pyrrolo[1,2-b]pyridazin-3-yl}propanoic acid (18 mg) as a yellow solid.

3-{4-(3-chlorophenyl)-7-ethyl-2-[(4-pyridinylmethoxy)methyl]pyrrolo[1,2-b]pyridazin-3-yl}propanoic acid $^1$H NMR (300 MHz, CDCl$_3$) δ 1.39 (3H, t, J=7 Hz), 2.33 (2H, t, J=7 Hz), 2.84-2.91 (2H, m), 3.04 (2H, q, J=7 Hz), 4.73 (2H, s), 4.82 (2H, s), 5.96 (1H, d, J=5 Hz), 6.62 (1H, d, J=5 Hz), 7.23-7.26 (1H, m), 7.36-7.38 (3H, m), 7.42-7.44 (2H, m), 8.41 (2H, d, J=5 Hz). MS (m/z) 450 (M+H).

The following compound(s) was (were) obtained in a similar manner to that of Example 606.

EXAMPLE 607

3-{4-(3-chlorophenyl)-7-ethyl-2-[(3-pyridinylmethoxy)methyl]pyrrolo[1,2-b]pyridazin-3-yl}propanoic acid $^1$H NMR (300 MHz, CDCl$_3$) δ 1.39 (3H, t, J=7 Hz), 2.32-2.38 (2H, m), 2.84-2.92 (2H, m), 3.04 (2H, q, J=7 Hz), 4.70 (2H, s), 4.82 (2H, s), 5.94 (1H, d, J=5 Hz), 6.60 (1H, d, J=5 Hz), 7.21-7.24 (1H, m), 7.31-7.36 (2H, m), 7.40-7.42 (2H, m), 7.80 (2H, d, J=8 Hz), 8.51 (1H, d, J=5 Hz), 8.64 (1H, s).

EXAMPLE 608

3-{4-(3-chlorophenyl)-7-ethyl-2-[(2-pyrazinylmethoxy)methyl]pyrrolo[1,2-b]pyridazin-3-yl}propanoic acid $^1$H NMR (300 MHz, CDCl$_3$) δ 1.38 (3H, t, J=7 Hz), 2.42 (2H, t, J=7 Hz), 2.91-2.97 (2H, m), 3.03 (2H, q, J=7 Hz), 4.83 (2H, s), 4.90 (2H, s), 5.96 (2H, d, J=5 Hz), 6.62 (2H, d, J=5 Hz), 7.23-7.26 (1H, m), 7.36 (1H, s), 7.43-7.44 (2H, m), 8.51-8.53 (2H, m), 8.75 (1H, s).

EXAMPLE 609

A solution of 5-[7-ethyl-2-methyl-4-(2-vinyl-4-pyridinyl)pyrrolo[1,2-b]pyridazin-3-yl]pentanoic acid (15 mg) in MeOH was added 10% Pd/C (2 mg). The mixture was stirred under hydrogen atomosphere (1 atm) for 6 h. The reaction mixture was filtered through Celite and the filtrate was concentrated in vacuo. The residue was triturated with hexane to give 5-[7-ethyl-4-(2-ethyl-4-pyridinyl)-2-methylpyrrolo[1,2-b]pyridazin-3-yl]pentanoic acid (14 mg) as an yellow solid.

5-[7-ethyl-4-(2-ethyl-4-pyridinyl)-2-methylpyrrolo[1,2-b]pyridazin-3-yl]pentanoic acid $^1$H NMR (CDCl$_3$) δ 1.29-1.64 (10H, m), 2.18-2.30 (2H, m), 2.45-2.48 (2H, m), 2.56 (3H, s), 2.91-3.06 (4H, m), 5.84 (1H, d, J=5 Hz), 6.53 (1H, d, J=16 Hz), 6.51 (1H, d, J=5 Hz), 7.25-7.32 (2H, m), 8.69 (1H, br s).

EXAMPLE 610

To a solution of ethyl 4-[4-(5-bromo-3-pyridinyl)-7-ethyl-2-(hydroxymethyl)pyrrolo[1,2-b]pyridazin-3-yl]butanoate (70.0 mg) in toluene (1 mL) was added tributylphosphine (0.098 mL), 1,3-oxazolidin-2-one (34.1 mg) in that order in an ice bath. After stirring for 5 minutes, to the mixture was added 1,1'-(azodicarbonyl)dipiperidine (98.9 mg). The mixture was stirred for 10 minutes in the bath, and 8 hours at room temperature. Hexane (5 mL) was added, and the mixture was filtered. The filtrate was evaporated. Preparative thin layer chromatography (ethyl acetate-hexane=1-1) afforded ethyl 4-{4-(5-bromo-3-pyridinyl)-7-ethyl-2-[(2-oxo-1,3-oxazolidin-3-yl)methyl]pyrrolo[1,2-b]pyridazin-3-yl}butanoate as an yellow gum (25.0 mg).

ethyl 4-{4-(5-bromo-3-pyridinyl)-7-ethyl-2-[(2-oxo-1,3-oxazolidin-3-yl)methyl]pyrrolo[1,2-b]pyridazin-3-yl}butanoate $^1$H-NMR (CDCl$_3$) δ 1.20 (3H, t, J=7 Hz), 1.369 (3H, t, J=7 Hz), 1.65 (3H, t, J=7 Hz), 2.25 (2H, t, J=7 Hz), 2.51 (2H, m), 2.99 (2H, q, J=7 Hz), 3.79 (2H, t, J=7 Hz), 4.04 (2H, q, J=7 Hz), 4.43 (2H, t, J=7 Hz), 4.69 (2H, m), 5.95 (1H, d, J=5 Hz), 6.61 (1H, d, J=5 Hz), 7.87 (1H, m), 8.55 (1H, m), 8.80 (1H, m).

EXAMPLE 611

To a solution of 2-bromo-4-[3-(ethoxycarbonyl)-7-ethyl-2-methylpyrrolo[1,2-b]pyridazin-4-yl]benzoic acid (50.0 mg) in tetrahydrofuran (1 mL) was added a solution of 1 M borane-tetrahydrofuran complex (0.348 mL) in an ice bath. After stirring for 2 hours at room temperature, additional solution of the borane-tetrahydrofuran complex (0.348 mL) was added. The mixture was stirred for 15 hours at room temperature. The mixture was partitioned between ethyl acetate and 1 N hydrochloric acid. The organic layer was washed with water, saturated sodium bicarbonate, and brine, dried over magnesium sulfate, and evaporated to give ethyl 4-[3-bromo-4-(hydroxymethyl)phenyl]-7-ethyl-2-methylpyrrolo[1,2-b]pyridazine-3-carboxylate as an yellow oil (54.2 mg).

ethyl 4-[3-bromo-4-(hydroxymethyl)phenyl]-7-ethyl-2-methylpyrrolo[1,2-b]pyridazine-3-carboxylate $^1$H-NMR (CDCl$_3$) δ 0.99 (3H, t, J=7 Hz), 1.38 (3H, t, J=7 Hz), 2.59 (3H, s), 3.03 (2H, q, J=7 Hz), 4.07 (2H, q, J=7 Hz), 4.82 (2H, s), 6.33 (1H, d, J=5 Hz), 6.66 (1H, d, J=5 Hz), 7.44 (1H, d, J=8 Hz), 7.58 (1H, d, J=8 Hz), 7.67 (1H, s).

EXAMPLE 612

To a solution of 2-(2-{2-[7-ethyl-2-methyl-4-(5-methyl-3-pyridinyl)pyrrolo[1,2-b]pyridazin-3-yl]ethoxy}ethoxy) ethyl acetate (62.0 mg) in methanol (1 mL) was added potassium carbonate (22.2 mg). After stirring for 1.5 hour, The solvent was evaporated off. Preparative thin layer chromatography (CHCl$_3$-MeOH=20-1) afforded the desired product as an yellow gum (54.1 mg). The gum was dissolved in 1 N HCl (1 mL), and the solution was lyophilized to give a dark green gum, which was crystalyzed upon standing. The crystal was triturated in diisopropyl ether to give 2-(2-{2-[7-ethyl-2-methyl-4-(5-methyl-3-pyridinyl)pyrrolo[1,2-b]pyridazin-3-yl]ethoxy}ethoxy)ethanol hydrochloride as an yellow powder (403 mg).

2-(2-{2-[7-ethyl-2-methyl-4-(5-methyl-3-pyridinyl)pyrrolo[1,2-b]pyridazin-3-yl]ethoxy}ethoxy)ethanol hydrochloride $^1$H-NMR (DMSO-d$_6$): 1.29 (3H, t, J=7 Hz), 2.51 (3H, s), 2.56 (3H, s), 2.62 (2H, m), 2.94 (2H, q, J=7 Hz), 3.30-3.47 (10H, m), 5.84 (1H, d, J=5 Hz), 6.59 (1H, d, J=5 Hz), 8.26 (1H, m), 8.77 (1H, m), 8.85 (1H, m).

EXAMPLE 613

A mixture of ethyl 5-[2-(bromomethyl)-4-(3-cyanophenyl)-7-ethylpyrrolo[1,2-b]pyridazin-3-yl]pentanoate (70.0 mg), phenol (21.1 mg), and pottassium carbonate (31.0 mg) in N,N-dimethylformamide was stirred for 25 hours at room temperature. The mixture was partitioned between ethyl acetate and 1 N hydrochloric acid. The organic layer was washed with water, saturated sodium bicarbonate, and brine, dried over magnesium sulfate, and evaporated to give ethyl 5-[4-(3-cyanophenyl)-7-ethyl-2-(phenoxymethyl)pyrrolo[1,2-b]pyridazin-3-yl]pentanoate as an yellow gum (775 mg, 108%).

ethyl 5-[4-(3-cyanophenyl)-7-ethyl-2-(phenoxymethyl)pyrrolo[1,2-b]pyridazin-3-yl]pentanoate $^1$H-NMR (CDCl$_3$) δ 1.21 (3H, t, J=7 Hz), 1.35-1.53 (7H, m), 2.07 (2H, m), 2.54 (2H, m), 3.03 (2H, q, J=7 Hz), 4.05 (2H, q, J=7 Hz), 5.24 (2H, s), 5.86 (1H, d, J=5 Hz), 6.65 (1H, d, J=5 Hz), 6.80-7.01 (3H, m), 7.03 (2H, d, J=9 Hz), 7.32 (2H, t, J=9 Hz), 7.55-7.63 (2H, m), 7.67 (1H, s), 7.76 (1H, m). MS (ESI$^+$): m/z 482 (M+H)

EXAMPLE 614

A mixture of 4-(3-cyanophenyl)-7-ethyl-3-(methylsulfonyl)pyrrolo[1,2-b]pyridazin-2-yl trifluoromethanesulfonate (50.0 mg), 3-furylboronic acid (23.6 mg), dichlorobis(triphenylphosphine)palladium (3.71 mg), and 2 N sodium carbonate (44.8 mg in 0.2 mL of water) in dioxane was stirred for 20 minutes at 85° C. The mixture was partitioned between EtOAc and water, and the organic layer was washed with brine, dried, and evaporated. Preparative thin layer chromatography (EtOAc-hexane=1-1) afforded 3-[7-ethyl-2-(2-furyl)-3-(methylsulfonyl)pyrrolo[1,2-b]pyridazin-4-yl]benzonitrile as an orange solid (11.5 mg).

3-[7-ethyl-2-(2-furyl)-3-(methylsulfonyl)pyrrolo[1,2-b]pyridazin-4-yl]benzonitrile $^1$H-NMR (CDCl$_3$) δ 1.40 (3H, t, J=7 Hz), 3.10 (2H, q, J=7 Hz), 3.20 (3H, s), 6.30 (1H, d, J=5 Hz), 6.63 (1H, m), 6.87 (1H, d, J=5 Hz), 6.95 (1H, m), 7.60-7.73 (4H, m), 8.79 (1H, m).

EXAMPLE 615

To a solution of 5-[4-(3-cyanophenyl)-7-ethyl-2-phenylpyrrolo[1,2-b]pyridazin-3-yl]pentanoic acid (100 mg) in tetrahydrofurane (1 mL) was added 1 M borane-tetrahydrofurane comples (0.708 mL) in an ice bath under a nitrogen atmosphere. The mixture was stirred for 4 hours in the bath and 1 hour at room temperature. The reaction was quenched by adding 1 N hydrochloric acid (1 mL). The mixture was partitioned between EtOAc (10 mL) and 1 N hydrochloric acid (5 mL). The organic layer was washed with water and brine, dried over magnesium sulfate, and evaporated. Preparative thin layer chromatography eluting with acetone-hexane=1-2 afforded 3-[7-ethyl-3-(5-hydroxypentyl)-2-phenylpyrrolo[1,2-b]pyridazin-4-yl]benzonitrile as an yellow gum (104 mg).

3-[7-ethyl-3-(5-hydroxypentyl)-2-phenylpyrrolo[1,2-b]pyridazin-4-yl]benzonitrile $^1$H-NMR (CDCl$_3$) δ 0.98-1.17 (6H, m), 1.36 (3H, t, J=7 Hz), 2.38 (2H, m), 2.58 (2H, m), 3.34 (2H, m), 5.89 (1H, d, J=5 Hz), 6.62 (1H, d, J=5 Hz), 7.45-7.53 (5H, m), 7.55-7.67 (4H, m). MS (ESI$^+$): m/z 410 (M+H)

The following compound(s) was (were) obtained in a similar manner to that of Preparation 24.

Preparation 343 ethyl 2-[(5-bromo-3-pyridinyl)carbonyl]-4-methoxy-3-oxobutanoate $^1$H NMR (CDCl$_3$) δ 0.96-1.10 (3H, m), 3.23 (1.5H, s), 3.49 (1.5H, s), 4.00-4.34 (4H, m), 4.57 (1H, s), 8.00 (0.15H, br s), 8.23 (0.15H, br s), 8.60-8.91 (2H, m).

Preparation 344

1-tert-butyl 8-ethyl 2-acetyl-2-[(6-cyano-3-pyridinyl)carbonyl]octanedioate $^1$H NMR (CDCl$_3$) δ 1.22-1.46 (16H, m), 1.55-1.70 (2H, m), 2.17-2.34 (4H, m), 2.48 (3H, s), 4.14 (2H, q, J=8 Hz), 7.77 (1H, br d, J=8 Hz), 8.17 (1H, dd, J=8, 2 Hz), 8.97 (1H, d, J=2 Hz).

The following compound(s) was (were) obtained in a similar manner to that of Preparation 78.

Preparation 345 ethyl 7-[(6-cyano-3-pyridinyl)carbonyl]-8-oxononanoate $^1$H NMR (CDCl$_3$) δ 1.20-1.45 (7H, m), 1.52-1.70 (2H, m), 1.92-2.14 (2H, m), 2.17-2.39 (5H, m), 4.11 (2H, q, J=8 Hz), 4.40 (1H, t, J=8 Hz), 7.84 (1H, br d, J=8 Hz), 8.39 (1H, m), 9.23 (1H, br s).

The following compound(s) was (were) obtained in a similar manner to that of Preparation 130.

Preparation 346 ethyl 4-methoxy-3-oxobutanoate $^1$H NMR (CDCl$_3$) δ 1.28 (3H, t, J=8 Hz), 3.42 (3H, s), 3.51 (2H, s), 4.09 (2H, s), 4.20 (2H, q, J=8 Hz).

The following compound(s) was (were) obtained in a similar manner to that of Preparation 338.

Preparation 347 benzyl 3-[(1-amino-5-ethyl-1H-pyrrol-2-yl)carbonyl]-5-bromobenzoate $^1$H-NMR (CDCl$_3$) δ 1.28 (3H, t, J=7 Hz), 2.75 (2H, q, J=7 Hz), 5.37 (2H, s), 5.73 (2H, s), 5.94 (1H, d, J=5 Hz), 6.66 (1H, d, J=5 Hz), 7.35-7.48 (5H, m), 7.99 (1H, s), 8.33 (1H, s), 8.38 (1H, s).

The following compound(s) was (were) obtained in a similar manner to that of Preparation 321.

Preparation 348 benzyl 3-bromo-5-[(5-ethyl-1H-pyrrol-2-yl)carbonyl]benzoate $^1$H-NMR (CDCl$_3$) δ 1.29 (3H, t, J=7 Hz), 2.72 (2H, q, J=7 Hz), 5.37 (2H, s), 6.09 (1H, m), 6.78 (1H, m), 7.33-7.45 (5H, m), 8.15 (1H, s), 8.33 (1H, s), 8.45 (1H, s).

The following compound(s) was (were) obtained in a similar manner to that of Preparation 310.

Preparation 349 benzyl 3-bromo-5-(chlorocarbonyl)benzoate

Preparation 350

To a solution of benzyl 3-bromo-5-iodobenzoate (1.00 g) in THF (10 mL) was added 0.76 M isopropyl magnesium bromide (3.16 mL) in an ice bath under a nitrogen atmosphere. After stirring for 0.5 hour, the mixture was poured onto dryice. The mixture was warmed to room temperature over 1 hour. The mixture was partitioned between EtOAc and 1 N HCl. The organic layer was washed with brine, dried over MgSO$_4$, and evaporated. Flash silica gel column chromatography (chloroform-methanol=50-0 to 50-2) afforded 3-benzyloxycarbonyl-5-bromobenzoic acid as a white solid (273 mg).

3-[(benzyloxy)carbonyl]-5-bromobenzoic acid $^1$H-NMR (DMSO-d$_6$) δ 5.39 (2H, s), 7.30-7.52 (5H, m), 8.29 (2H, s), 8.43 (1H, s).

Preparation 351

A mixture of 3-bromo-5-iodobenzoic acid (5.00 g) and N,N-dimethylformamide (0.059 mL) in dichloromethane (50 mL) was added oxalyl chloride (1.47 mL) in an ice bath under a nitrogen atmosphere. After stirring for 1 hour, the volatile was evaporated off. The residue was dissolved in dichloromethane (50 mL), and to the solution was added bensyl alcohol (1.82 g) followed by triethyl amine (3.2 mL) in the ice bath. The mixture was stirred for 2 hours at room temperature. The mixture was partitioned between EtOAc and water. The organic layer was washed with water (two times), satd. NaHCO$_3$, and brine, dried over MgSO$_4$ and evaporated. Flash silica gel column chromatography (EtOAc-hexanes=1/200 to 20/200) afforded benzyl 3-bromo-5-iodobenzoate as white crystals (5.95 g).

benzyl 3-bromo-5-iodobenzoate $^1$H-NMR (CDCl$_3$) δ 5.35 (3H, s), 7.35-7.68 (5H, m), 8.04 (1H, s), 8.16 (1H, m), 8.30 (1H, s).

The following compound(s) was (were) obtained in a similar manner to that of Example 1.

EXAMPLE 615 benzyl 3-bromo-5-[7-ethyl-2-methyl-3-(methylsulfonyl)pyrrolo[1,2-b]pyridazin-4-yl]benzoate $^1$H-NMR (CDCl$_3$) δ 1.38 (3H, t, J=7 Hz), 2.88 (3H, s), 3.05 (3H, s), 3.06 (2H, q, J=7 Hz), 5.35 (2H, s), 6.15 (1H, d, J=5 Hz), 6.72 (1H, d, J=5 Hz), 7.33-7.45 (5H, m), 7.68 (1H, m), 7.94 (1H, m), 8.28 (1H, m).

EXAMPLE 616

4-(3-cyanophenyl)-7-ethyl-2-phenylpyrrolo[1,2-b]pyridazine-3-carbonitrile $^1$H NMR (CDCl$_3$) δ 1.42 (3H, t, J=8 Hz), 3.12 (2H, q, J=8 Hz), 6.60 (1H, d, J=5 Hz), 6.92 (1H, d, J=5 Hz), 7.50-7.58 (3H, m), 7.73 (1H, t, J=8 Hz), 7.82-7.91 (3H, m), 7.93-8.01 (2H, m).

EXAMPLE 617

2-tert-butyl-4-(3-chlorophenyl)-7-ethylpyrrolo[1,2-b]pyridazine-3-carbonitrile $^1$H NMR (CDCl$_3$) δ 1.38 (3H, t, J=8 Hz), 1.60 (9H, s), 3.05 (2H, q, J=8 Hz), 6.48 (1H, d, J=5 Hz), 6.77 (1H, d, J=5 Hz), 7.45-7.54 (3H, m), 7.60 (1H, br s).

The following compound(s) was (were) obtained in a similar manner to that of reparation 78.

EXAMPLE 618 ethyl 6-[4-(6-cyano-3-pyridinyl)-7-ethyl-2-methylpyrrolo[1,2-b]pyridazin-3-yl]hexanoate $^1$H NMR (CDCl$_3$) δ 1.15-1.64 (12H, m), 2.21 (1H, t, J=8 Hz), 2.32-2.44 (2H, m), 2.56 (3H, s), 3.01 (2H, q, J=8 Hz), 4.10 (2H, q, J=8 Hz), 5.79 (1H, d, J=5 Hz), 6.54 (1H, d, J=5 Hz), 7.85 (1H, br s), 8.30 (1H, br d, J=8 Hz), 8.72 (1H, br s). MS (ESI$^+$): m/z 405 (M+H).

The following compound(s) was (were) obtained in a similar manner to that of Example 21.

EXAMPLE 619 ethyl 4-(5-bromo-3-pyridinyl)-7-ethyl-2-(methoxymethyl)pyrrolo[1,2-b]pyridazine-3-carboxylate $^1$H NMR (CDCl$_3$) δ 1.04 (3H, t, J=8 Hz), 1.38 (3H, t, J=8 Hz), 3.06 (2H, q, J=8 Hz), 3.39 (3H, s), 4.10 (2H, q, J=8 Hz), 4.76 (2H, s), 6.33 (1H, d, J=5 Hz), 6.74 (1H, d, J=5 Hz), 7.96 (1H, br s), 8.61 (1H, br s), 8.78 (1H, d, J=2 Hz). MS (ESI$^+$): m/z 418, 420 (M+H).

The following compound(s) was (were) obtained in a similar manner to that of Example 76.

EXAMPLE 620

3-bromo-5-[7-ethyl-2-methyl-3-(methylsulfonyl)pyrrolo[1,2-b]pyridazin-4-yl]benzoic acid $^1$H-NMR (CDCl$_3$+CD3OD) δ 1.38 (3H, t, J=7 Hz), 2.86 (3H, s), 3.05 (3H, s), 3.06 (2H, q, J=7 Hz), 6.19 (1H, d, J=5 Hz), 6.71 (1H, d, J=5 Hz), 7.53 (1H, s), 7.90 (1H, s), 8.23 (1H, s).

EXAMPLE 621

(2E)-3-[4-(5-bromo-3-pyridinyl)-7-ethyl-2-(methoxymethyl)pyrrolo[1,2-b]pyridazin-3-yl]acrylic acid $^1$H NMR (CDCl$_3$) δ 1.39 (3H, t, J=8 Hz), 3.07 (2H, q, J=8 Hz), 3.51 (3H, s), 4.65 (2H, s), 5.96 (1H, d, J=15 Hz), 6.27 (1H, d, J=5 Hz), 6.74 (1H, d, J=5 Hz), 7.68 (1H, d, J=15 Hz), 7.93 (1H, m), 8.57 (1H, d, J=1 Hz), 8.70 (1H, d, J=2 Hz). MS (ESI$^+$): m/z 416, 418 (M+H).

EXAMPLE 622

6-[4-(6-cyano-3-pyridinyl)-7-ethyl-2-methylpyrrolo[1,2-b]pyridazin-3-yl]hexanoic acid $^1$H NMR (CDCl$_3$) δ 1.15-1.69 (9H, m), 1.90-2.50 (4H, m), 2.56 (3H, s), 3.01 (2H, q, J=8 Hz), 5.80 (1H, d, J=5 Hz), 6.51 (1H, d, J=5 Hz), 7.84 (1H, dd, J=8, 2 Hz), 8.28 (1H, d, J=8 Hz), 8.51 (1H, d, J=2 Hz). MS (ESI$^+$): m/z 377 (M+H).

EXAMPLE 622-2

6-{4-[6-(aminocarbonyl)-3-pyridinyl]-7-ethyl-2-methylpyrrolo[1,2-b]pyridazin-3-yl}hexanoic acid $^1$H NMR (CDCl$_3$) δ 1.16-1.51 (9H, m), 2.10-2.24 (2H, m), 2.35-2.47 (2H, m), 2.58 (3H, s), 3.01 (2H, q, J=8 Hz), 5.85 (1H, d, J=5 Hz), 6.54 (1H, d, J=5 Hz), 7.22 (1H, br s), 7.90 (1H, dd, J=8, 1 Hz), 8.01 (1H, br s), 8.34 (1H, d, J=8 Hz), 8.61 (1H, d, J=1 Hz). MS (ESI$^+$): m/z 395 (M+H).

The following compound(s) was (were) obtained in a similar manner to that of Example 147.

EXAMPLE 623 ethyl (2E)-3-[4-(5-bromo-3-pyridinyl)-7-ethyl-2-(methoxymethyl)pyrrolo[1,2-b]pyridazin-3-yl]acrylate $^1$H NMR (CDCl$_3$) δ 1.27 (3H, t, J=8 Hz), 1.39 (3H, t, J=8 Hz), 3.06 (2H, q, J=8 Hz), 3.51 (3H, s), 4.17 (2H, q, J=8 Hz), 4.64 (2H, s), 5.97 (1H, d, J=15 Hz), 6.24 (1H, d, J=5 Hz), 6.73 (1H, d, J=5 Hz), 7.51 (1H, d, J=15 Hz), 7.91 (1H, br s), 8.57 (1H, br s), 8.70 (1H, br s). MS (ESI$^+$): m/z 444, 446 (M+H).

The following compound(s) was (were) obtained in a similar manner to that of Example 200.

EXAMPLE 624

[4-(5-bromo-3-pyridinyl)-7-ethyl-2-(methoxymethyl)pyrrolo[1,2-b]pyridazin-3-yl]methanol $^1$H NMR (CDCl$_3$) δ 1.38 (3H, t, J=8 Hz), 3.05 (2H, q, J=8 Hz), 3.45-3.55 (4H, m), 4.40 (2H, br d, J=7 Hz), 4.77 (2H, br s), 6.22 (1H, d, J=5 Hz), 6.70 (1H, d, J=5 Hz), 8.11 (1H, m), 8.74 (1H, br s), 8.80 (1H, d, J=2 Hz). MS (ESI$^+$): m/z 376, 378 (M+H).

The following compound(s) was (were) obtained in a similar manner to that of Example 205.

EXAMPLE 625

(4E)-5-[4-(2-chloro-4-pyridinyl)-7-ethyl-2-methylpyrrolo[1,2-b]pyridazin-3-yl]4-pentenoic acid $^1$H NMR (CDCl$_3$) δ 1.37 (3H, t, J=8 Hz), 2.26-2.43 (4H, m), 2.50 (3H, s), 3.01 (2H, q, J=8 Hz), 5.40 (1H, dt, J=15, 7 Hz), 6.05 (1H, d, J=5 Hz), 6.20 (1H, d, J=15 Hz), 6.56 (1H, d, J=5 Hz), 7.28 (1H, br d, J=5 Hz), 7.39 (1H, br s), 8.47 (1H, br d, J=5 Hz). MS (ESI$^+$): m/z 370 (M+H).

EXAMPLE 625-2

(4Z)-5-[4-(2-chloro-4-pyridinyl)-7-ethyl-2-methylpyrrolo[1,2-b]pyridazin-3-yl]-4-pentenoic acid $^1$H NMR (CDCl$_3$) δ 1.39 (3H, t, J=8 Hz), 1.87-2.00 (2H, m), 2.12 (2H, t, J=8 Hz), 2.42 (3H, s), 3.03 (2H, q, J=8 Hz), 5.58 (1H, dt, J=10, 8 Hz), 6.17 (1H, d, J=5 Hz), 6.26 (1H, br d, J=10 Hz), 6.60 (1H, d, J=5 Hz), 7.35 (1H, br d, J=5 Hz), 7.44 (1H, br s), 8.48 (1H, br d, J=5 Hz). MS (ESI$^+$): m/z 370 (M+H).

The following compound(s) was (were) obtained in a similar manner to that of Example 220.

EXAMPLE 626

4-(5-bromo-3-pyridinyl)-7-ethyl-2-(methoxymethyl)pyrrolo[1,2-b]pyridazine-3-carboxylic acid $^1$H NMR (CDCl$_3$) δ 1.39 (3H, t, J=8 Hz), 3.06 (2H, q, J=8 Hz), 3.44 (3H, s), 4.82 (2H, s), 6.36 (1H, d, J=5 Hz), 6.77 (1H, d, J=5 Hz), 8.09 (1H, br s), 8.65 (1H, br s), 8.72 (1H, br s). MS (ESI$^+$): m/z 390, 392 (M+H).

EXAMPLE 627

4-(2-chloro-4-pyridinyl)-7-ethyl-2-methylpyrrolo[1,2-b]pyridazine-3-carboxylic acid $^1$H NMR (CDCl$_3$) δ 1.38 (3H, t, J=8 Hz), 2.70 (3H, s), 3.06 (2H, q, J=8 Hz), 6.26 (1H, d, J=5 Hz), 6.72 (1H, d, J=5 Hz), 7.32 (1H, dd, J=5, 1 Hz), 7.43 (1H, br s), 8.50 (1H, d, J=5 Hz). MS (ESI$^+$): m/z 316 (M+H).

The following compound(s) was (were) obtained in a similar manner to that of Example 244.

EXAMPLE 628

4-(2-chloro-4-pyridinyl)-7-ethyl-2-methylpyrrolo[1,2-b]pyridazine-3-carbaldehyde $^1$H NMR (CDCl$_3$) δ 1.39 (3H, t, J=8 Hz), 2.81 (3H, s), 3.09 (2H, q, J=8 Hz), 6.43 (1H, d, J=5 Hz), 6.78 (1H, d, J=5 Hz), 7.34 (1H, br d, J=5 Hz), 7.46 (1H, br s), 8.56 (1H, d, J=5 Hz), 9.76 (1H, s). MS (ESI$^+$): m/z 300 (M+H).

EXAMPLE 629

4-(5-bromo-3-pyridinyl)-7-ethyl-2-(methoxymethyl)pyrrolo[1,2-b]pyridazine-3-carbaldehyde $^1$H NMR (CDCl$_3$) δ 1.41 (3H, t, J=8 Hz), 3.14 (2H, q, J=8 Hz), 3.55 (3H, s), 4.94 (2H, s), 6.50 (1H, d, J=5 Hz), 6.84 (1H, d, J=5 Hz), 7.95 (1H, br s), 8.12 (1H, br s), 8.84 (1H, br s), 9.85 (1H, s). MS (ESI$^+$): m/z 374, 376 (M+H).

EXAMPLE 630

A solution of phosphorus oxychloride (241 mg, 1.57 mmol) in N,N-dimethylformamide (4 mL) was stirred for 10 min at room temperature. The resulting mixture was cooled to 0° C., and a solution of ethyl 4-(4-fluorophenyl)-2-isopropylpyrrolo[1,2-b]pyridazine-3-carboxylate (428 mg, 1.31 mmol) in N,N-dimethylformamide (0.7 mL) was added. The resulting mixture was warmed to 50° C., and stirred for 45 min. Since the starting material was remained, a solution of phosphorus oxychloride (621 mg, 0.67 mmol) in N,N-dimethylformamide (0.2 mL) was added, and the mixture was stirred for 15 min. The resulting mixture was poured into ice-cooled water (10 mL), and extracted with ethyl acetate (30 mL). The organic layer was washed with water and saturated sodium bicarbonate. All the aqueous layer was extracted with ethyl acetate. The combined organic extract was washed with brine, dried over anhydrous magnesium sulfate, and evaporated to give a blue oil. Flash silica gel column chromatography eluting with ethyl acetate-hexane=1-20 to 1-10 afforded ethyl 4-(4-fluorophenyl)-7-formyl-2-isopropylpyrrolo[1,2-b]pyridazine-3-carboxylate as an yellow oil, which was crystalized upon standing (360 mg, 77.5%).

$^1$H-NMR (CDCl$_3$) δ 1.02 (3H, t, J=7 Hz), 1.41 (6H, d, J=7 Hz), 3.29 (1H, septet, J=7 Hz), 4.10 (2H, q, J=7 Hz), 6.42 (1H, d, J=5 Hz), 7.20 (2H, t, J=9 Hz), 7.45-7.51 (3H, m), 10.56 (1H, s). MS (ESI$^+$): m/z 355 (M+H)

EXAMPLE 631

To a solution of N,N-dimethylacetamide (80.1 mg, 0.919 mmol) in dichloroethane (1 mL) was added phosphorus oxychloride (141 mg, 0.919 mmol) in dichloroethane (0.5 mL) at 0° C. After stirring for 0.5 h, a solution of ethyl 4-(4-fluorophenyl)-2-isopropylpyrrolo[1,2-b]pyridazine-3-carboxylate (200 mg, 0.613 mmol) in dichloroethane (0.5 mL) was added. The resulting mixture was stirred for 3 days at room temperature. The mixture was partitioned between ethyl acetate (30 mL) and water (5 mL), and the organic layer was washed with saturated sodium bicarbonate, brine, dried over anhydrous magnesium sulfate, and evaporated to give an orange gum. Flash silica gel column chromatography eluting with ethyl acetate-hexane=1-20 to 1-10 afforded ethyl 7-acetyl-4-(4-fluorophenyl)-2-isopropylpyrrolo[1,2-b]pyridazine-3-carboxylate as an yellow gum (144 mg, 63.8%).

$^1$H-NMR (CDCl$_3$) δ 1.00 (3H, t, J=7 Hz), 1.41 (6H, d, J=7 Hz), 2.88 (3H, s), 3.09 (1H, septet, J=7 Hz), 4.09 (2H, q, J=7 Hz), 6.40 (1H, d, J=5 Hz), 7.19 (2H, t, J=9 Hz), 7.46 (2H, dd, J=3 and 9 Hz), 7.57 (2H, d, J=7 Hz). MS (ESI$^+$): m/z 369 (M+H)

EXAMPLE 632

A solution of ethyl 4-(4-fluorophenyl)-7-formyl-2-isopropylpyrrolo[1,2-b]pyridazine-3-carboxylate (100 mg, 0.282 mmol) and sodium borohydride (10.7 mg, 0.282 mmol) in ethanol (1 mL) was stirred for 0.5 h under an ice bath. The mixture was partitioned between ethyl acetate (10 mL) and water (5 mL), and the organic layer was washed with brine, dried over anhydrous magnesium sulfate, and evaporated to give ethyl 4-(4-fluorophenyl)-7-hydroxymethyl-2-isopropylpyrrolo[1,2-b]pyridazine-3-carboxylate as an yellow gum (89.1 mg, 89.1%).

$^1$H-NMR (CDCl$_3$) δ 0.97 (3H, t, J=7 Hz), 1.37 (6H, J=7 Hz), 3.25-3.37 (2H, m), 4.04 (2H, q, J=7 Hz), 5.06 (1H, d, J=7 Hz), 6.32 (1H, d, J=5 Hz), 6.78 (1H, d, J=5 Hz), 7.19 (2H, t, J=9 Hz), 7.46 (2H, d, J=4 and 9 Hz).

EXAMPLE 633

To a solution of ethyl 4-(4-fluorophenyl)-2-isopropylpyrrolo[1,2-b]pyridazine-3-carboxylate (80.0 mg, 0.245 mmol) and N,N-dimethylaminopyridine (29.9 mg, 0.245 mmol) in N,N-dimethylformamide (0.5 mL) was added 3,7-dinitro-5-(trifluoromethyl)dibenzo[b,d]thiophenium trifluoromethanesulfonate (120 mg, 0.245 mmol) at −20° C. The resulting mixture was stirred for 45 min at 0° C. and 12 h at room temperature. Water (5 mL) and ethyl acetate (10 mL) were added, and the resulting mixture was filtered. The organic layer was washed with brine, dried over anhydrous magnesium sulfate, and evaporated to give a brown gum. Flash silica gel column chromatography eluting with toluene-hexane=1-5 to 4-5 afforded ethyl 4-(4-fluorophenyl)-2-isopropyl-7-trifluoromethylpyrrolo[1,2-b]pyridazine-3-carboxylate product as an yellow gum (46.7 mg, 48.3%).

$^1$H-NMR (CDCl$_3$) δ 1.00 (3H, t, J=7 Hz), 1.38 (6H, d, J=7 Hz), 3.26 (1H, septet, J=7 Hz), 4.08 (2H, q, J=7 Hz), 6.33 (1H, d, J=5 Hz), 7.12 (H, d, J=5 Hz), 7.19 (2H, t, J=9 Hz), 7.47 (2H, d, J=4 and 9 Hz). MS (ESI$^+$): m/z 395 (M+H)

EXAMPLE 634

A solution of ethyl 4-(4-fluorophenyl)-7-formyl-2-isopropylpyrrolo[1,2-b]pyridazine-3-carboxylate (200 mg, 0.564 mmol), hydroxylamine hydrochloride (51.0 mg, 0.734 mmol), and sodium formate (69.1 mg, 1.02 mmol) in formic acid (2 mL) were refluxed for 2 h. The mixture was evaporated to give a green gum. The gum was partitioned between ethyl acetate (10 mL) and saturated sodium bicarbonate (5 mL). The organic layer was washed with brine, dried over anhydrous magnesium sulfate, and evaporated to give a green gum. Flash silica gel column chromatography eluting with ethyl acetate-hexane=1-10 to 1-8 gave ethyl 7-cyano-4-(4-fluorophenyl)-2-isopropylpyrrolo[1,2-b]pyridazine-3-carboxylate as an yellow crystal (144 mg, 72.6%).

$^1$H-NMR (CDCl$_3$) δ 1.01 (3H, t, J=7 Hz), 1.41 (6H, d, J=7 Hz), 3.26 (1H, septet, J=7 Hz), 4.09 (2H, q, J=7 Hz), 6.36 (1H, d, J=5 Hz), 7.20 (2H, t, J=9 Hz), 7.28 (1H, d, J=5 Hz), 7.47 (2H, d, J=4 and 9 Hz). MS (ESI$^+$): m/z 398 (M+HCOOH+H)

EXAMPLE 635

A solution of ethyl 7-cyano-4-(4-fluorophenyl)-2-isopropylpyrrolo[1,2-b]pyridazine-3-carboxylate (70.4 mg, 0.200 mmol) in sulfuric acid (1 mL) was stirred for 50 min at 70° C. The solution was partitioned between ethyl acetate and water. The organic layer was washed with brine, dried over anhydrous magnesium sulfate, and evaporated to give a brown gum. Preparative silica gel thin layer chromatography eluting with ethyl acetate-hexane=1-1 afforded ethyl 7-aminocarbonyl-4-(4-fluorophenyl)-2-isopropylpyrrolo[1,2-b]pyridazine-3-carboxylate as an orange solid (5.2 mg, 7.0%).

$^1$H-NMR (CDCl$_3$) δ 0.99 (3H, t, J=7 Hz), 1.41 (6H, d, J=7 Hz), 3.41 (1H, septet, J=7 Hz), 4.08 (2H, q, J=7 Hz), 5.93 (1H, br s), 6.46 (1H, d, J=5 Hz), 7.45 (2H, t, J=9 Hz), 7.28 (1H, d, J=5 Hz), 8.90 (1H, br s).

EXAMPLE 636

To a mixture of ethyl 4-(4-fluorophenyl)-2-isopropylpyrrolo[1,2-b]pyridazine-3-carboxylate (100 mg, 0.306 mmol) and ammonium thiocyanate (28.0 mg, 0.368 mmol) in methanol (100 mL) was added cerium ammonium nitrate (386 mg, 0.705 mmol) under an ice bath. The mixture was stirred for 30 min. The mixture was stirred for additional 10 min after adding ammonium thiocyanate (8.2 mg, 0.107 mmol). Water (5 mL) was added, and the mixture was extracted with ethyl acetate (20 mL). The organic extract was washed with brine, dried over anhydrous magnesium sulfate, and evaporated to give a deep green gum. Flash silica gel column chromatography eluting with ethyl acetate-hexane=1-10 to 3-20 afforded ethyl ethyl 4-(4-fluorophenyl)-2-isopropyl-7-thiocyanatopyrrolo[1,2-b]pyridazine-3-carboxylate as an yellow gum (89.6 mg, 82.3%).

$^1$H-NMR (CDCl$_3$) δ 1.01 (3H, t, J=7 Hz), 1.46 (6H, d, J=7 Hz), 3.36 (1H, septet, J=7 Hz), 4.08 (2H, q, J=7 Hz), 6.23 (1H, d, J=5 Hz), 7.14-7.22 (3H, m), 7.16 (2H, t, J=9 Hz), 7.46 (2H, dd, J=4 and 9 Hz).

EXAMPLE 637

To a solution of ethyl 4-(4-fluorophenyl)-2-isopropyl-7-thiocyanatopyrrolo[1,2-b]pyridazine-3-carboxylate (77.7 mg, 0.219 mmol) in methanol (0.7 mL) was added 85% potassium hydroxide (0.3 mg, 0.004 mmol) at room temperature. After stirring for 5 min, the mixture was partitioned between ethyl acetate (20 mL) and water (5 mL). The organic layer was washed with brine, dried over anhydrous magnesium sulfate, and evaporated to give an yellow gum. Preparative silica gel thin layer chromatography eluting with ethyl acetate-hexane=1-7 afforded ethyl 4-(4-fluorophenyl)-2-isopropyl-7-(methylthio)pyrrolo[1,2-b]pyridazine-3-carboxylate as an yellow gum (35.9 mg, 44.1%).

$^1$H-NMR (CDCl$_3$) δ 0.98 (3H, t, J=7 Hz), 1.41 (6H, d, J=7 Hz), 2.52 (3H, s), 3.32 (1H, septet, J=7 Hz), 4.05 (2H, q, J=7 Hz), 6.35 (1H, d, J=5 Hz), 6.89 (1H, d, J=5 Hz), 7.16 (2H, t, J=9 Hz), 7.44 (2H, d, J=4 and 9 Hz). MS (ESI$^+$): m/z 373 (M+H)

The following compound(s) was (were) obtained in a similar manner to that of Example 1

EXAMPLE 638

3-(9-ethyl-3-methoxy-5,6-dihydrobenzo[f]pyrrolo[1,2-b]cinnolin-12-yl)benzonitrile $^1$H NMR (CDCl$_3$) δ 1.41 (3H, t, J=8 Hz), 2.91-3.11 (6H, m), 3.78 (3H, s), 6.09 (1H, d, J=5 Hz), 6.38 (1H, dd, J=8, 3 Hz), 6.52 (1H, d, J=8 Hz), 6.59 (1H, d, J=5 Hz), 6.77 (1H, br s), 7.56 (1H, t, J=8 Hz), 7.67 (1H, br d, J=8 Hz), 7.70-7.77 (2H, m).

EXAMPLE 639

4-(3-ethyl-6H-indeno[1,2-e]pyrrolo[1,2-b]pyridazin-11-yl)benzonitrile $^1$H NMR (CDCl$_3$) δ 1.43 (3H, t, J=8 Hz), 3.09 (2H, q, J=8 Hz), 4.11 (3H, s), 6.14 (1H, d, J=5 Hz), 6.64 (1H, d, J=5 Hz), 6.71 (1H, d, J=8 Hz), 7.07 (1H, t, J=8 Hz), 7.20-7.30 (1H, overlapped with CDCl$_3$), 7.49 (1H, d, J=8 Hz), 7.69 (2H, d, J=8 Hz), 7.88 (2H, d, J=8 Hz). MS (ESI$^+$): m/z 336 (M+H).

The following compound(s) was (were) obtained in a similar manner to that of Preparation 24.

Preparation 352 ethyl 4-methoxy-2-[(5-methyl-3-pyridinyl)carbonyl]-3-oxobutanoate $^1$H NMR (CDCl$_3$) δ 0.97, 1.26 (3H, t, J=7 Hz), 2.40 (3H, s), 3.24, 3.35, 3.49 (3H, s), 3.98-4.20 (2H, m), 4.11, 4.20, 4.54 (2H, s), 5.70 (1H, s), 7.67, 7.92, 8.02, 8.50-8.66, 8.77, 8.89 (3H, m).

Preparation 353 ethyl 2-[(5-chloro-3-pyridinyl)carbonyl]-4-methoxy-3-oxobutanoate $^1$H NMR (CDCl$_3$) δ 1.00, 1.06, 1.28, 1.35 (3H, t, J=7 Hz), 3.23, 3.43, 3.49 (3H, s), 4.05-4.33 (2H, m), 4.56 (2H, s), 7.85, 8.05, 8.22, 8.29, 8.58-8.82, 8.85, 9.01, 9.10 (3H, m).

The following compound(s) was (were) obtained in a similar manner to that of Preparation 176.

Preparation 354 tert-butyl 3-bromo-5-({1-[(cyanoacetyl)amino]-5-ethyl-1H-pyrrol-2-yl}carbonyl)benzoate $^1$H-NMR (CDCl$_3$) δ 1.29 (34H, t, J=7 Hz), 1.60 (9H, s), 2.61 (2H, q, J=7 Hz), 3.64 (2H, s), 6.00 (1H, m), 6.80 (1H, m), 8.03 (1H, m), 8.26 (1H, m), 8.28 (1H, m).

Preparation 355 tert-butyl 3-bromo-5-[(5-ethyl-1-{[(methylsulfonyl)acetyl]amino}-1H-pyrrol-2-yl)carbonyl]benzoate $^1$H-NMR (CDCl$_3$) δ 1.29 (3H, t, J=7 Hz), 1.60 (9H, s), 2.60 (2H, q, J=7 Hz), 2.92 (3H, s), 4.04 (2H, s), 6.11 (1H, m), 6.78 (1H, m), 8.03 (1H, m), 8.25 (1H, m), 8.27 (1H, m).

The following compound(s) was (were) obtained in a similar manner to that of Preparation 153.

Preparation 356 tert-butyl 3-bromo-5-(chlorocarbonyl)benzoate

The following compound(s) was (were) obtained in a similar manner to that of Preparation 164.

Preparation 357 tert-butyl 3-bromo-5-[(5-ethyl-1H-pyrrol-2-yl)carbonyl]benzoate $^1$H-NMR (CDCl$_3$) δ 1.32 (3H, t, J=7 Hz), 1.61 (9H, s), 2.74 (2H, q, J=7 Hz), 6.10 (1H, m), 6.80 (1H, m), 8.13 (1H, m), 8.26 (1H, m), 8.39 (1H, m), 934 (1H, s, br).

The following compound(s) was (were) obtained in a similar manner to that of Preparation 338.

Preparation 358 tert-butyl 3-[(1-amino-5-ethyl-1H-pyrrol-2-yl)carbonyl]-5-bromobenzoate $^1$H-NMR (CDCl$_3$) δ 1.29 (3H, t, J=7 Hz), 1.61 (9H, s), 2.76 (2H, q, J=7 Hz), 5.74 (2H, s, br), 5.93 (1H, d, J=5 Hz), 6.63 (1H, d, J=5 Hz), 8.05 (1H, m), 8.25 (1H, m), 8.29 (1H, m).

Preparation 359

To a solution of tert-butyl 3-bromo-5-iodobenzoate (4.00 g) in tetrahydrofuran (30 mL) was added 0.76 M isopropylmagnesium bromide (13.7 mL) in an ice-methanol bath under a nitrogen atmosphere. After stirring for 0.5 hour, the mixture was poured onto dryice. The mixture was warmed to room temperature over 1 hour. The mixture was partitioned between EtOAc and 1 N hydrochloric acid. The organic layer was back extracted with 1 N sodium hydroxide (two times). The extract was acidified by adding concentrated hydrochloric acid, and extracted with chloroform (two times). The organic extract was washed with brine, dried over MgSO$_4$, and evaporated to give 3-bromo-5-(tert-butoxycarbonyl)benzoic acid as a pale brown solid (529 mg).

3-bromo-5-(tert-butoxycarbonyl)benzoic acid $^1$H-NMR (DMSO-d$_6$) δ 1.57 (9H, s), 8.21 (1H, s), 8.25 (1H, s), 8.37 (1H, s).

Preparation 360

To a vigirously stirred suspension of powdered MgSO$_4$ (7.36 g) in dichloromethane (50 mL) was added sulfuric acid (0.758 mL) at room temperature. After stirring for 15 minutes, to the mixture was added 3-bromo-5-iodobenzoic acid (5.00 g) followed by tert-butanol (7.31 mL). The mixture was stirred for 3 days at room temperature. The mixture was partitioned between EtOAc and water. The organic layer was washed with satd. NaHCO$_3$ and brine, dried over MgSO$_4$, and evaporated to give tert-butyl 3-bromo-5-iodobenzoate as pale purple crystals (4.44 g).

tert-butyl 3-bromo-5-iodobenzoate $^1$H-NMR (CDCl$_3$) δ 1.58 (9H, s), 8.00 (1H, m), 8.06 (1H, m), 8.22 (1H, m).

Preparation 361

To a suspension of lithium (316 mg) in ether (10 mL) was added cyclopropylbromide (250 g) in ether (10 mL) over 20 min in a methanol-ice bath under a nitrogen atmosphere. The mixture was stirred for 0.5 hour in an ice bath. The mixture was cooled in a dryice-acetone bath. To the mixture was added a solution of triisopropoxyborane (5.05 g) in tetrahydrofuran (5 mL) over 15 minutes. The mixture was allowed to warm to room temperature over 2 hours. The reaction was quenched by adding hydrochloric acid. The organic solvent was evaporated off, and the residual solution was extracted with ether (30 mL, five times). The combined extract was dried over MgSO$_4$, and evaporated to give a white solid (968 mg). The solid was triturated in cold hexanes to give cyclopropylboronic acid as a white powder (789 mg).

cyclopropylboronic acid

¹H-NMR (DMSO-d₆) δ −0.40 (1H, m), 0.32 (2H, m), 0.39 (2H, m), 7.28 (2H, s).

The following compound(s) was (were) obtained in a similar manner to that of Example 21.

EXAMPLE 640 ethyl 7-ethyl-2-(methoxymethyl)-4-(5-methyl-3-pyridinyl)pyrrolo[1,2-b]pyridazine-3-carboxylate ¹H NMR (CDCl₃) δ 0.99 (3H, t, J=7 Hz), 1.38 (3H, t, J=7 Hz), 2.41 (3H, s), 3.06 (2H, q, J=7 Hz), 3.38 (3H, s), 4.06 (2H, q, J=7 Hz), 4.75 (2H, s), 6.33 (1H, d, J=4 Hz), 6.71 (1H, d, J=4 Hz), 7.61 (1H, s), 8.52 (1H, d, J=2 Hz), 8.54 (1H, d, J=2 Hz). MS (ESI⁺): m/z 354.

EXAMPLE 641 ethyl 4-(5-chloro-3-pyridinyl)-7-ethyl-2-(methoxymethyl)pyrrolo[1,2-b]pyridazine-3-carboxylate ¹H NMR (300 MHz, CDCl₃) δ 1.04 (3H, t, J=7 Hz), 1.38 (3H, t, J=7 Hz), 3.06 (2H, q, J=7 Hz), 3.39 (3H, s), 4.09 (2H, q, J=7 Hz), 4.76 (2H, s), 6.33 (1H, d, J=4 Hz), 6.75 (1H, d, J=4 Hz), 7.81 (1H, dd, J=2, 2 Hz), 8.57 (1H, d, J=2 Hz), 8.68 (1H, d, J=2 Hz). MS (m/z) 374 (M+1).

The following compound(s) was (were) obtained in a similar manner to that of Example 0.76.

EXAMPLE 642

(2E)-3-[7-ethyl-2-(methoxymethyl)-4-(5-methyl-3-pyridinyl)pyrrolo[1,2-b]pyridazin-3-yl]acrylic acid ¹H NMR (CDCl₃) δ 1.39 (3H, t, J=7 Hz), 2.43 (3H, s), 3.07 (2H, q, J=7 Hz), 3.51 (3H, s), 4.65 (2H, s), 5.97 (1H, d, J=16 Hz), 6.27 (1H, d, J=4 Hz), 6.71 (1H, d, J=4 Hz), 7.61 (1H, s), 7.72 (1H, d, J=16 Hz), 8.46 (1H, d, J=2 Hz), 8.57 (1H, d, J=2 Hz). MS (ESI⁺): m/z 352.

EXAMPLE 643

(2E)-3-[4-(5-chloro-3-pyridinyl)-7-ethyl-2-(methoxymethyl)pyrrolo[1,2-b]pyridazin-3-yl]acrylic acid ¹H NMR (300 MHz, CDCl₃) δ 1.39 (3H, t, J=7 Hz), 3.07 (2H, q, J=7 Hz), 3.51 (3H, s), 4.65 (2H, s), 5.97 (1H, d, J=16 Hz), 6.27 (1H, d, J=4 Hz), 6.75 (1H, d, J=4 Hz), 7.69 (1H, d, J=16 Hz), 7.78 (1H, dd, J=2, 2 Hz), 8.54 (1H, d, J=2 Hz), 8.71 (1H, d, J=2 Hz). MS (m/z) 400 (M+1).

EXAMPLE 644

4-[4-(5-cyclopropyl-3-pyridinyl)-7-ethyl-2-(methoxymethyl)pyrrolo[1,2-b]pyridazin-3-yl]butanoic acid ¹H-NMR (CDCl₃) δ 0.78 (2H, m), 1.10 (2H, m), 1.37 (3H, t, J=7 Hz), 1.73 (2H, m), 1.98 (1H, m), 2.23 (2H, m), 2.62 (2H, m), 3.02 (2H, q, J=7 Hz 9, 3.46 (3H, s), 4.65 (2H, q, J=7 Hz), 5.88 (1H, d, J=5 Hz), 6.57 (1H, d, J=5 Hz), 7.36 (1H, m), 8.41 (1H, m), 8.47 (1H, m).

EXAMPLE 645

5-[4-(5-cyclopropyl-3-pyridinyl)-7-ethyl-2-(methoxymethyl)pyrrolo[1,2-b]pyridazin-3-yl]pentanoic acid ¹H-NMR (CDCl₃) δ 0.75 (2H, m), 1.08 (2H, m), 1.37 (3H, t, J=7 Hz), 1.40-1.57 (4H, m), 1.96 (1H, m), 2.18 (2H, m), 2.51 (2H, m), 3.02 (2H, q, J=7 Hz), 3.45 (3H, s), 4.61 (2H, m), 5.87 (1H, d, J=5 Hz), 6.56 (1H, d, J=5 Hz), 7.34 (1H, m), 8.39 (1H, m), 8.50 (1H, m).

EXAMPLE 646

3-[4-(5-cyclopropyl-3-pyridinyl)-7-ethyl-2-(methoxymethyl)pyrrolo[1,2-b]pyridazin-3-yl]propanoic acid ¹H-NMR (DMSO-d₆) δ 0.76 (2H, m), 1.08 (2H, m), 1.37 (3H, t, J=7 Hz), 1.95 (1H, m), 2.48 (2H, m), 2.87 (2H, m), 3.02 (2H, q, J=7 Hz), 3.47 (3H, s), 4.66 (2H, m), 5.90 (1H, d, J=5 Hz), 6.59 (1H, d, J=5 Hz), 7.35 (1H, m), 8.40 (1H, m), 8.48 (1H, m).

EXAMPLE 647

5-[4-(2-chloro-4-pyridinyl)-7-ethyl-2-methylpyrrolo[1,2-b]pyridazin-3-yl]-5-oxopentanoic acid ¹H NMR (CDCl₃) δ 1.38 (3H, t, J=8 Hz), 1.73-1.85 (2H, m), 2.26 (2H, t, J=8 Hz), 2.36 (2H, t, J=8 Hz), 2.46 (3H, s), 3.04 (2H, q, J=8 Hz), 6.33 (1H, d, J=5 Hz), 6.70 (1H, d, J=5 Hz), 7.34 (1H, br d), 7.45 (1H, br s), 8.53 (1H, d, J=6 Hz).

EXAMPLE 648

(2E)-3-[4-(2-chloro-4-pyridinyl)-7-ethyl-2-methylpyrrolo[1,2-b]pyridazin-3-yl]acrylic acid ¹H NMR (CDCl₃) δ 1.38 (3H, t, J=8 Hz), 2.67 (3H, s), 3.05 (2H, q, J=8 Hz), 5.79 (1H, d, J=15 Hz), 6.19 (1H, d, J=5 Hz), 6.67 (1H, d, J=5 Hz), 7.24-7.29 (1H, overlappled with CDCl₃), 7.40 (1H, br s), 7.51 (1H, d, J=15 Hz), 8.55 (1H, d, J=5 Hz).

The following compound(s) was (were) obtained in a similar manner to that of Example 146.

EXAMPLE 649 ethyl (2E)-3-[4-(2-chloro-4-pyridinyl)-7-ethyl-2-methylpyrrolo[1,2-b]pyridazin-3-yl]acrylate ¹H NMR (CDCl₃) δ 1.27 (3H, t, J=8 Hz), 1.38 (3H, t, J=8 Hz), 2.65 (3H, s), 3.04 (2H, q, J=8 Hz), 4.17 (2H, q, J=8 Hz), 5.76 (1H, d, J=15 Hz), 6.16 (1H, d, J=5 Hz), 6.65 (1H, d, J=5 Hz), 7.24-7.29 (1H, overlappled with CDCl₃), 7.40 (1H, br s), 7.53 (1H, d, J=15 Hz), 8.53 (1H, d, J=5 Hz). MS (ESI⁺): m/z 370 (M+H).

The following compound(s) was (were) obtained in a similar manner to that of Example 181.

EXAMPLE 650 tert-butyl 3-bromo-5-(3-cyano-7-ethyl-2-oxo-1,2-dihydropyrrolo[1,2-b]pyridazin-4-yl)benzoate $^1$H-NMR (CDCl$_3$) δ 1.36 (3H, t, J=7 Hz), 2.94 (2H, q, J=7 Hz), 6.57 (1H, d, J=5 Hz), 6.72 (1H, d, J=5 Hz), 7.94 (1H, m), 8.20 (1H, m), 8.38 (1H, m).

EXAMPLE 651 tert-butyl 3-bromo-5-[7-ethyl-3-(methylsulfonyl)-2-oxo-1,2-dihydropyrrolo[1,2-b]pyridazin-4-yl]benzoate $^1$H-NMR (CDCl$_3$) δ 1.35 (3H, t, J=7 Hz), 3.02 (2H, q, J=7 Hz), 3.06 (3H, s), 6.24 (1H, d, J=5 Hz), 6.70 (1H, d, J=5 Hz), 7.23 (1H, m), 7.94 (1H, m), 8.25 (1H, m).

The following compound(s) was (were) obtained in a similar manner to that of Example 183.

EXAMPLE 652 tert-butyl 3-bromo-5-(3-cyano-7-ethyl-2-{[(trifluoromethyl)sulfonyl]oxy}pyrrolo[1,2-b]pyridazin-4-yl)benzoate $^1$H-NMR (CDCl$_3$) δ 1.39 (3H, t, J=7 Hz), 1.61 (9H, s), 3.02 (2H, q, J=7 Hz), 6.81 (1H, d, J=5 Hz), 7.00 (1H, d, J=5 Hz), 7.96 (1H, m), 8.21 (1H, m), 8.33 (1H, m).

EXAMPLE 653 tert-butyl 3-bromo-5-(7-ethyl-3-(methylsulfonyl)-2-{[(trifluoromethyl)sulfonyl]oxy}pyrrolo[1,2-b]pyridazin-4-yl)benzoate $^1$H-NMR (CDCl$_3$) δ 1.38 (3H, t, J=7 Hz), 1.59 (9H, s), 3.01 (2H, q, J=7 Hz), 3.22 (3H, s), 6.46 (1H, d, J=5 Hz), 7.12 (1H, d, J=5 Hz), 7.67 (1H, m), 7.90 (1H, m), 8.23 (1H, m).

The following compound(s) was (were) obtained in a similar manner to that of Example 184.

EXAMPLE 654 tert-butyl 3-bromo-5-[3-cyano-7-ethyl-2-(1-pyrrolidinyl)pyrrolo[1,2-b]pyridazin-4-yl]benzoate $^1$H-NMR (CDCl$_3$) δ 1.35 (3H, t, J=7 Hz), 1.60 (9H, s), 2.01 (4H, m), 2.93 (2H, q, J=7 Hz), 3.73 (4H, m), 6.32 (1H, d, J=5 Hz), 6.58 (1H, d, J=7 Hz), 7.86 (1H, m), 8.12 (1H, m), 8.24 (1H, m).

EXAMPLE 655 tert-butyl 3-bromo-5-[7-ethyl-3-(methylsulfonyl)-2-(1-pyrrolidinyl)pyrrolo[1,2-b]pyridazin-4-yl]benzoate $^1$H-NMR (CDCl$_3$) δ 1.37 (3H, t, J=7 Hz), 1.58 (9H, s), 1.99 (4H, m), 2.98 (2H, q, J=7 Hz), 3.21 (3H, s), 3.52 (4H, m), 6.30 (1H, d, J=5 Hz), 6.66 (1H, d, J=5 Hz), 7.76 (1H, m), 8.00 (1H, m), 8.19 (1H, m).

The following compound(s) was (were) obtained in a similar manner to that of Example 147.

EXAMPLE 656 ethyl (2E)-3-[4-(5-chloro-3-pyridinyl)-7-ethyl-2-(methoxymethyl)pyrrolo[1,2-b]pyridazin-3-yl]acrylate $^1$H NMR (300 MHz, CDCl$_3$) δ 1.27 (3H, t, J=7 Hz), 1.39 (3H, t, J=7 Hz), 3.07 (2H, q, J=7 Hz), 3.51 (3H, s), 4.18 (2H, q, J=7 Hz), 4.64 (2H, s), 5.97 (1H, d, J=16 Hz), 6.24 (1H, d, J=4 Hz), 6.72 (1H, d, J=4 Hz), 7.61 (1H, d, J=16 Hz), 7.76 (1H, dd, J=2, 2 Hz), 8.54 (1H, d, J=2 Hz), 8.68 (1H, d, J=2 Hz).

The following compound(s) was (were) obtained in a similar manner to that of Example 205.

EXAMPLE 657

(4E)-5-[4-(5-chloro-3-pyridinyl)-7-ethyl-2-(methoxymethyl)pyrrolo[1,2-b]pyridazin-3-yl]-4-pentenoic acid $^1$H NMR (300 MHz, CDCl$_3$) δ 1.38 (3H, t, J=7 Hz), 2.25-2.41 (4H, m), 3.05 (2H, q, J=7 Hz), 3.50 (3H, s), 4.57 (2H, s), 5.53 (1H, dd, J=16, 7 Hz), 6.13 (1H, d, J=4 Hz), 6.36 (1H, d, J=16 Hz), 6.65 (1H, d, J=4 Hz), 7.80 (1H, s), 8.54 (1H, br s), 8.62 (1H, br s). MS (m/z) 400 (M+1).

The following compound(s) was (were) obtained in a similar manner to that of Preparation 153.

EXAMPLE 658

4-(2-chloro-4-pyridinyl)-7-ethyl-2-methylpyrrolo[1,2-b]pyridazine-3-carbonyl chloride The following compound(s) was (were) obtained in a similar manner to that of Example 244.

EXAMPLE 659

7-ethyl-2-(methoxymethyl)-4-(5-methyl-3-pyridinyl)pyrrolo[1,2-b]pyridazine-3-carbaldehyde $^1$H NMR (CDCl$_3$) δ 1.40 (3H, t, J=7 Hz), 2.45 (3H, s), 3.12 (2H, q, J=7 Hz), 3.56 (3H, s), 4.96 (2H, s), 6.51 (1H, d, J=4 Hz), 6.80 (1H, d, J=4 Hz), 7.62 (1H, s), 8.54 (1H, s), 8.61 (1H, s), 9.79 (1H, s). MS (ESI$^+$): m/z 310.

EXAMPLE 660

4-(5-chloro-3-pyridinyl)-7-ethyl-2-(methoxymethyl)pyrrolo[1,2-b]pyridazine-3-carbaldehyde $^1$H NMR (300 MHz, CDCl$_3$) δ 1.41 (3H, t, J=7 Hz), 3.12 (2H, q, J=7 Hz), 3.54 (3H, s), 4.94 (2H, s), 6.50 (1H, d, J=4 Hz), 6.84 (1H, d, J=4 Hz), 7.81 (1 (H, dd, J=2, 2 Hz), 8.59 (1H, d, J=2 Hz), 8.74 (1H, d, J=2 Hz), 9.85 (1H, s).

The following compound(s) was (were) obtained in a similar manner to that of Example 533.

EXAMPLE 661

[7-ethyl-2-(methoxymethyl)-4-(5-methyl-3-pyridinyl)pyrrolo[1,2-b]pyridazin-3-yl]methanol $^1$H NMR (CDCl$_3$) δ 1.38 (3H, t, J=7 Hz), 2.43 (3H, s), 3.05 (2H, q, J=7 Hz), 3.52 (3H, s), 4.37-4.51 (2H, br), 4.66-4.78 (2H, br), 6.20 (1H, d, J=4 Hz), 6.67 (1H, d, J=4 Hz), 7.75 (1H, s), 8.54 (1H, s), 8.60 (1H, s). MS (ESI$^+$): m/z 312.

EXAMPLE 662

[4-(5-chloro-3-pyridinyl)-7-ethyl-2-(methoxymethyl)pyrrolo[1,2-b]pyridazin-3-yl]methanol $^1$H NMR (300 MHz, CDCl$_3$) δ 1.38 (3H, t, J=7 Hz), 3.05 (2H, q, J=7 Hz), 3.53 (3H, s), 4.41 (2H, d, J=6 Hz), 4.77 (2H, s), 6.22 (1H, d, J=4 Hz), 6.70 (1H, d, J=4 Hz), 7.97 (1H, dd, J=2, 2 Hz), 8.69-8.71 (2H, m). MS (m/z) 332 (M+1).

EXAMPLE 663

A mixture of 7-ethyl-2-(methoxymethyl)-4-(5-methyl-3-pyridinyl)pyrrolo[1,2-b]pyridazine-3-carbaldehyde (48 mg) and ethyl (triphenylphosphoranylidene)acetate (56.8 mg) in THF (3 mL) was stirred at ambient temperature for 2 hours. After evaporation of solvent, the residue was purified by silica gel column chromatography eluting with a mixture of hexane and AcOEt (5:1-2:1) to give ethyl (2E)-3-[7-ethyl-2-(methoxymethyl)-4-(5-methyl-3-pyridinyl)pyrrolo[1,2-b]pyridazin-3-yl]acrylate as a yellow powder (30 mg).

ethyl (2E)-3-[7-ethyl-2-(methoxymethyl)-4-(5-methyl-3-pyridinyl)pyrrolo[1,2-b]pyridazin-3-yl]acrylate $^1$H NMR (CDCl$_3$) δ 1.26 (3H, t, J=7 Hz), 1.39 (3H, t, J=7 Hz), 2.42 (3H, s), 3.07 (2H, q, J=7 Hz), 3.51 (3H, s), 4.12 (2H, q, J=7 Hz), 4.64 (2H, s), 5.97 (1H, d, J=16 Hz), 6.24 (1H, d, J=4 Hz), 6.70 (1H, d, J=4 Hz), 7.55 (1H, s), 7.63 (1H, d, J=16 Hz), 8.47 (1H, d, J=2 Hz), 8.55 (1H, d, J=2 Hz). MS (ESI$^+$): m/z 380.

EXAMPLE 664

To a mixture of ethyl 4-[4-(5-bromo-3-pyridinyl)-7-ethyl-2-(methoxymethyl)pyrrolo[1,2-b]pyridazin-3-yl]butanoate (75.0 mg), cyclopropylboronic acid (18.2 mg), tricyclohexylphosphine (457 mg), and potassium phosphate (104 mg) in toluene-water (1 mL-0.2 mL) was added palladium acetate (1.83 mg). The mixture was stirred for 2 hours at 100° C. The mixture was partitioned between EtOAc and water. The organic layer was washed with brine, dried over MgSO$_4$, and evaporated. Preparative silicagel thin layer chromatography (EtOAc-hexanes=1-3) afforded ethyl 4-[4-(5-cyclopropyl-3-pyridinyl)-7-ethyl-2-(methoxymethyl)pyrrolo[1,2-b]pyridazin-3-yl]butanoateas an yellow gum (60.9 mg).

ethyl 4-[4-(5-cyclopropyl-3-pyridinyl)-7-ethyl-2-(methoxymethyl)pyrrolo[1,2-b]pyridazin-3-yl]butanoate $^1$H-NMR (CDCl$_3$) δ 0.76 (2H, m), 1.07 (2H, m), 1.20 (3H, t, J=7 Hz), 1.37 (3H, t, J=7 Hz), 1.68 (2H, m), 1.96 (1H, m), 2.17 (2H, m), 2.56 (2H, m), 3.02 (2H, q, J=7 Hz), 3.46 (3H, s), 4.03 (2H, q, J=7 Hz), 4.65 (2H, m), 5.90 (1H, d, J=5 Hz), 6.57 (1H, d, J=5 Hz), 7.30 (1H, m), 8.40 (1H, m), 8.51 (1H, m).

The following compound(s) was (were) obtained in a similar manner to that of Example 664.

EXAMPLE 665 ethyl 5-[4-(5-cyclopropyl-3-pyridinyl)-7-ethyl-2-(methoxymethyl)pyrrolo[1,2-b]pyridazin-3-yl]pentanoate $^1$H-NMR (CDCl$_3$) δ 0.76 (2H, m), 1.08 (2H, m), 1.23 (3H, t, J=7 Hz), 1.35-1.57 (7H, m), 1.96 (1H, m), 2.16 (2H, t, J=7 Hz), 2.53 (2H, m), 3.03 (2H, q, J=7 Hz), 3.46 (3H, s), 4.08 (2H, q, J=7 Hz), 4.62 (2H, s), 5.89 (1H, d, J=5 Hz), 6.56 (1H, d, J=5 Hz), 7.29 (1H, m), 8.40 (1H, m), 8.52 (1H, m).

EXAMPLE 666 ethyl 3-[4-(5-cyclopropyl-3-pyridinyl)-7-ethyl-2-(methoxymethyl)pyrrolo[1,2-b]pyridazin-3-yl]propanoate $^1$H-NMR (CDCl$_3$) δ 0.76 (2H, m), 1.08 (2H, m), 1.19 (3H, t, J=7 Hz), 1.37 (3H, t, J=7 Hz), 1.97 (1H, m), 2.38 (2H, m), 2.85 (2H, m), 3.02 (2H, q, J=7 Hz), 3.46 (3H, s), 4.04 (2H, q, J=7 Hz), 4.64 (2H, s), 5.92 (1H, d, J=5 Hz), 6.59 (1H, d, J=5 Hz), 7.29 (1H, m), 8.40 (1H, m), 8.53 (1H, m).

EXAMPLE 667 tert-butyl 3-[3-cyano-7-ethyl-2-(1-pyrrolidinyl)pyrrolo[1,2-b]pyridazin-4-yl]-5-cyclopropylbenzoate $^1$H-NMR (CDCl$_3$) δ 0.81 (2H, m), 1.03 (2H, m), 1.35 (3H, t, J=7 Hz), 1.59 (9H, s), 1.94-2.08 (5H, m), 2.94 (2H, q, J=7 Hz), 3.68-3.77 (4H, m), 6.35 (1H, j, J=5 Hz), 6.55 (1H, d, J=5 Hz), 7.43 (1H, s), 7.84 (1H, s), 7.97 (1H, s).

EXAMPLE 668

A solution of tert-butyl 3-bromo-5-[3-cyano-7-ethyl-2-(1-pyrrolidinyl)pyrrolo[1,2-b]pyridazin-4-yl]benzoate (16.0 mg) in trifluoroacetic acid (0.5 mL) was stirred for 0.5 hour at room temperature. The reaction was quenched by adding water. The mixture was neutralized by adding NaOH (pH=3). The mixture was extracted with EtOAc. The extract was washed with brine, dried over MgSO$_4$, and evaporated to give a greenish yellow solid. The solid was triturated in hexanes-CHCl$_3$ (2-1) to afford 3-bromo-5-[3-cyano-7-ethyl-2-(1-pyrrolidinyl)pyrrolo[1,2-b]pyridazin-4-yl]benzoic acid as an yellow powder (10.8 mg).

3-bromo-5-[3-cyano-7-ethyl-2-(1-pyrrolidinyl)pyrrolo[1,2-b]pyridazin-4-yl]benzoic acid $^1$H-NMR (CDCl$_3$+CD$_3$OD) δ 1.36 (3H, t, J=7 Hz), 2.01 (4H, m), 2.94 (2H, q, J=7 Hz), 3.72 (4H, m), 636 (1H, d, J=5 Hz), 6.60 (1H, d, J=5 Hz), 7.92 (1H, s), 8.23 (1H, m), 8.35 (1H, m).

The following compound(s) was (were) obtained in a similar manner to that of Example 668.

EXAMPLE 669

3-[3-cyano-7-ethyl-2-(1-pyrrolidinyl)pyrrolo[1,2-b]pyridazin-4-yl]-5-cyclopropylbenzoic acid ¹H-NMR (CDCl₃+CD₃OD) δ 0.81 (2H, m), 1.05 (2H, m), 1.35 (3H, t, J=7 Hz), 2.01 (5H, m), 2.94 (2H, q, J=7 Hz), 7.73 (4H, m), 637 (1H, d, J=5 Hz), 6.57 (1H, d, J=5 Hz), 6.98 (1H, s), 7.90 (1H, s), 8.08 (1H, s).

EXAMPLE 670

3-bromo-5-[7-ethyl-3-(methylsulfonyl)-2-(1-pyrrolidinyl)pyrrolo[1,2-b]pyridazin-4-yl]benzoic acid ¹H-NMR (CDCl₃+CD3OD) δ 1.37 (3H, t, J=7 Hz), 1.98 (4H, m), 2.99 (2H, q, J=7 Hz), 3.20 (3H, s), 3.56 (4H, m), 6.32 (1H, d, J=5 Hz), 6.67 (1H, d, J=5 Hz), 7.80 (1H, m), 8.08 (1H, m), 8.30 (1H, m).

EXAMPLE 671

To a 3-necked frask containing Zn—Cu couple was added a solution of ethyl 4-iodobutanoate (369 mg) in toluene (3 mL) and N,N-dimethylacetamide (0.2 mL) at ambient temperature under N₂. The mixture was stirred at the temperature for 1 h and then at 60° C. for 3 h. A suspension of tetrakis(triphenylphosphine)palladium (44 mg) in toluene (0.5 mL) was added and stirred for 5 min. After removal of an oil bath, the mixture was cooled in an ice-water bath. To this mixture was added a solution of 4-(2-chloro-4-pyridinyl)-7-ethyl-2-methylpyrrolo[1,2-b]pyridazine-3-carbonyl chloride (212 mg) in DCM (1 mL) dropwise. After 10 min, the reaction mixture was stirred at ambient temperature for 2 h. The reaction mixture was partitioned between AcOEt and H₂O. The organic layer was washed with sat. NaHCO₃ and brine, dried over MgSO₄, and evaporated in vacuo. The residue was purified by flash silica gel chromatography (silica gel, 80 mL) eluted with hexane-AcOEt=10-1 and 5-1 to give ethyl 5-[4-(2-chloro-4-pyridinyl)-7-ethyl-2-methylpyrrolo[1,2-b]pyridazin-3-yl]-5-oxopentanoate as yellow amorphous (143 mg).

ethyl 5-[4-(2-chloro-4-pyridinyl)-7-ethyl-2-methylpyrrolo[1,2-b]pyridazin-3-yl]-5-oxopentanoate ¹H NMR (CDCl₃) δ 1.23 (3H, t, J=8 Hz), 1.38 (3H, t, J=8 Hz), 1.71-1.84 (2H, m), 2.17 (3H, t, J=8 Hz), 2.32 (3H, t, J=8 Hz), 2.46 (3H, s), 3.04 (2H, q, J=8 Hz), 4.06 (2H, q, J=8 Hz), 6.32 (1H, d, J=5 Hz), 6.70 (1H, d, J=5 Hz), 7.32 (1H, dd, J=5, 1), 7.46 (1H, br s), 8.53 (1H, d, J=5 Hz).

EXAMPLE 672

To a solution of 5-[4-(2-chloro-4-pyridinyl)-7-ethyl-2-methylpyrrolo[1,2-b]pyridazin-3-yl]-5-oxopentanoic acid (47 mg) in EtOH (1 mL) was added sodium borohydride (5 mg) in an ice-water bath under N₂. After 10 min, the mixture was stirred at ambient temperature. After 1 h, another odium borohydride (5 mg) was added. After 2 h, the reaction mixture was partitioned between CHCl₃ and H₂O. The aqueous layer was extracted with CHCl₃ twice. The combined organic layer was dried over MgSO₄ and evaporated in vacuo. The residue was purified by p-TLC (CHCl₃-MeOH=10-1) to give 5-[4-(2-chloro-4-pyridinyl)-7-ethyl-2-methylpyrrolo[1,2-b]pyridazin-3-yl]-5-hydroxypentanoic acid as yellow amorphous (28 mg).

5-[4-(2-chloro-4-pyridinyl)-7-ethyl-2-methylpyrrolo[1,2-b]pyridazin-3-yl]-5-hydroxypentanoic acid ¹H NMR (CDCl₃) δ 1.36 (3H, t, J=8 Hz), 1.46-1.83 (3H, m), 1.95 (1H, m), 2.70 (3H, br s), 3.01 (2H, q, J=8 Hz), 4.63 (1H, m), 5.85 (1H, m), 6.55 (1H, d, J=5 Hz), 7.18-7.29 (1H, overlapped with CDCl₃), 7.34 (1H, d, J=2 Hz), 8.49 (1H, d, J=5 Hz).

The invention claimed is:

1. A compound of the formula I or a pharmaceutically acceptable salt thereof, or a prodrug thereof:

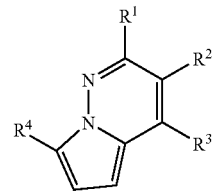

wherein

R¹ is (1) a mono- or di(lower)alkylamino,
  (2) a phenyl,
  (3) a saturated or unsaturated 5 to 6 membered heteromonocyclic group selected from the group consisting of a pyrrolidinyl, a pyrrolyl, an oxazolyl, an isooxazolyl, a thiazolyl, a furanyl, a thienyl, and a pyridinyl, or
  (4) a lower alkyl optionally substituted by (i) a lower alkoxy or (ii) a saturated 5- or 6-membered heteromonocyclic group selected from the group consisting of a piperazinyl and a morpholinyl, wherein the lower alkoxy is optionally substituted by a cyclo(lower)alkyl or a pyridinyl, R² is R⁷ or -A²-R⁷,
wherein A² is —(CH2)n- or —(CH═CH)m-
wherein n is an integer which may range from 2 to 6, and m is an integer of 1 to 2, and R⁷ is a hydrogen, a lower alkyl sulfonyl, a carboxy, an esterified carboxy or a pyridinyl, R³ is (1) a phenyl optionally substituted by a lower alkyl, a cyclo(lower)alkyl, a lower alkoxy, a halogen, a cyano, or a carbamoyl; or
  (2) a quinolinyl; or a pyridinyl substituted by a lower alkyl, a cyclo(lower)alkyl, a lower alkoxy, a carbamoyl or a halogen, and R⁴ is ethyl.

2. The compound of claim 1, wherein

R¹ is a phenyl, a pyrrolyl, an isooxazolyl, a furanyl, a thienyl, a lower alkyl optionally substituted by a lower alkoxy, a piperazinyl or a morpholinyl, wherein a lower alkoxy is optionally substituted by a cyclo(lower)alkyl or a pyridinyl, R² is —(CH2)n-R⁷, wherein n is an integer which may range from 2 to 5, and R⁷ is a carboxy or an esterified carboxy, and R³ is (1) a phenyl optionally substituted by a lower alkyl, a cyclo(lower)alkyl, a lower alkoxy, a halogen, a cyano, or a carbamoyl; or (2) a pyridinyl substituted by a lower alkyl, a cyclo(lower)alkyl, a lower alkoxy, a carbamoyl or a halogen.

3. A process for preparing a compound of claim 1 comprising:

(1) reacting a compound (II) of formula

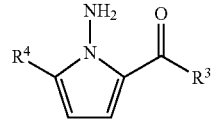

wherein $R^3$ and $R^4$ are as defined in claim 1 or a salt thereof with a compound (III) of formula

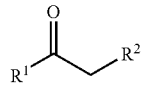

wherein $R^1$ and $R^2$ are as defined in claim 1 or a salt thereof to obtain a compound (I) of formula

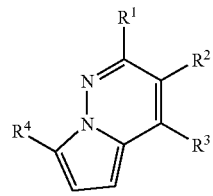

wherein $R^1$, $R^2$, $R^3$, and $R^4$ are as defined in claim 1 or a salt thereof, or (2) reacting a compound (V) of formula

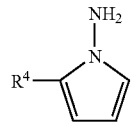

wherein $R^4$ is as defined in claim 1 or a salt thereof with a compound (VI) of formula

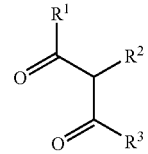

wherein $R^1$, $R^2$ and $R^3$ are as defined in claim 1 or a salt thereof to obtain a compound (I) of formula

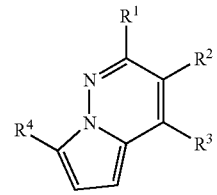

wherein $R^1$, $R^2$, $R^3$ and $R^4$ are as defined in claim 1 or a salt thereof.

4. A pharmaceutical composition comprising:
a compound of claim 1 in admixture with a pharmaceutically acceptable carrier.

5. A method for treating, in a subject, asthma, chronic obstructive pulmonary disease (COPD), fibrotic disease, acute and fulminant hepatitis, hepatic steatosis (alcoholic or non-alcoholic steatohepatitis), chronic (viral or non-viral) hepatitis, hepatic cirrhosis, autoimmune hepatitis, autoimmune inflammatory bowel disease, atopic dermatitis, the method comprising:
administering a therapeutically effective amount, or a prophylactically effective amount, of the compound of claim 1 to the subject.

* * * * *